(12) United States Patent
Leonard et al.

(10) Patent No.: US 10,201,546 B2
(45) Date of Patent: Feb. 12, 2019

(54) QUINOLINYL MODULATORS OF RORγT

(71) Applicant: Janssen Pharmaceutica NV, Beerse (BE)

(72) Inventors: Kristi A. Leonard, Lansdale, PA (US); Kent Barbay, Sunnybrook, PA (US); James P. Edwards, San Diego, CA (US); Kevin D. Kreutter, Plainsboro, NJ (US); David A. Kummer, San Diego, CA (US); Umar Maharoof, North Wales, PA (US); Rachel Nishimura, San Diego, CA (US); Maud Urbanski, Flemington, NJ (US); Hariharan Venkatesan, San Diego, CA (US); Aihua Wang, Jamison, PA (US); Ronald L. Wolin, San Diego, CA (US); Craig R. Woods, San Diego, CA (US); Anne Fourie, San Diego, CA (US); Xiaohua Xue, San Diego, CA (US); Maxwell D. Cummings, Ambler, PA (US); Kelly McClure, Ramona, CA (US); Virginia Tanis, Vista, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/447,917

(22) Filed: Mar. 2, 2017

(65) Prior Publication Data
US 2017/0182056 A1 Jun. 29, 2017

Related U.S. Application Data

(62) Division of application No. 14/513,426, filed on Oct. 14, 2014, now Pat. No. 9,624,225.

(60) Provisional application No. 61/890,889, filed on Oct. 15, 2013.

(51) Int. Cl.
| | |
|---|---|
| *A61K 31/5377* | (2006.01) |
| *C07D 487/04* | (2006.01) |
| *A61K 31/4985* | (2006.01) |
| *A61K 31/496* | (2006.01) |
| *A61K 31/506* | (2006.01) |
| *A61K 31/4709* | (2006.01) |
| *C07D 401/14* | (2006.01) |
| *A61K 45/06* | (2006.01) |
| *C07D 405/14* | (2006.01) |
| *C07D 401/06* | (2006.01) |
| *C07D 413/14* | (2006.01) |
| *C07D 417/14* | (2006.01) |
| *C07D 409/14* | (2006.01) |
| *A61K 31/5365* | (2006.01) |

(52) U.S. Cl.
CPC ...... *A61K 31/5377* (2013.01); *A61K 31/4709* (2013.01); *A61K 31/496* (2013.01); *A61K 31/4985* (2013.01); *A61K 31/506* (2013.01); *A61K 31/5365* (2013.01); *A61K 45/06* (2013.01); *C07D 401/06* (2013.01); *C07D 401/14* (2013.01); *C07D 405/14* (2013.01); *C07D 409/14* (2013.01); *C07D 413/14* (2013.01); *C07D 417/14* (2013.01); *C07D 487/04* (2013.01)

(58) Field of Classification Search
CPC .................................................. A61K 31/5377
USPC ..................................................... 514/210.18
See application file for complete search history.

(56) References Cited

U.S. PATENT DOCUMENTS

| | | | |
|---|---|---|---|
| 3,472,859 A | 10/1969 | Lesher | |
| 4,656,283 A | 4/1987 | Doehner, Jr. | |
| 4,710,507 A | 12/1987 | Campbell et al. | |
| 4,910,327 A | 3/1990 | Doehner, Jr. | |
| 4,927,926 A | 5/1990 | Corominas et al. | |

(Continued)

FOREIGN PATENT DOCUMENTS

| | | |
|---|---|---|
| CN | 101143845 | 3/2008 |
| CN | 101899011 | 12/2010 |

(Continued)

OTHER PUBLICATIONS

Cyr et al. Bioorganic & Medicinal Chemistry Letters, 26 (2016) 4387-4393.*

(Continued)

*Primary Examiner* — Nizal S Chandrakumar
(74) *Attorney, Agent, or Firm* — Yuriy P. Stercho

(57) ABSTRACT

The present invention comprises compounds of Formula I.

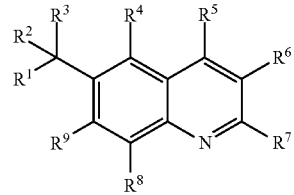

Formula I wherein:
$R^1$, $R^2$, $R^3$, $R^4$, $R^5$, $R^6$, $R^7$, $R^8$, and $R^9$ are defined in the specification.
The invention also comprises a method of treating or ameliorating a syndrome, disorder or disease, wherein said syndrome, disorder or disease is rheumatoid arthritis or psoriasis. The invention also comprises a method of modulating RORγt activity in a mammal by administration of a therapeutically effective amount of at least one compound of claim 1.

18 Claims, No Drawings
Specification includes a Sequence Listing.

(56) References Cited

U.S. PATENT DOCUMENTS

| | | | |
|---|---|---|---|
| 5,409,930 A | 4/1995 | Spada et al. | |
| 5,780,634 A | 7/1998 | Inoue et al. | |
| 6,248,739 B1 | 6/2001 | Turner et al. | |
| 6,451,812 B1 | 9/2002 | End et al. | |
| 6,624,159 B2 | 9/2003 | Anderson et al. | |
| 6,686,356 B2 | 2/2004 | Strohbach et al. | |
| 6,743,805 B2 | 6/2004 | End et al. | |
| 7,053,105 B2 | 5/2006 | Angibaud et al. | |
| 7,652,014 B2 | 1/2010 | Mabire et al. | |
| 7,902,225 B2 | 3/2011 | Guillemont et al. | |
| 8,017,606 B2 | 9/2011 | Andries et al. | |
| 8,389,739 B1 | 3/2013 | Thacher et al. | |
| 9,156,837 B2 | 10/2015 | Yamamoto et al. | |
| 9,221,804 B2 * | 12/2015 | Leonard | C07D 413/06 |
| 9,284,308 B2 * | 3/2016 | Leonard | C07D 417/14 |
| 9,290,476 B2 * | 3/2016 | Leonard | C07D 413/14 |
| 9,303,015 B2 | 4/2016 | Leonard et al. | |
| 9,309,222 B2 | 4/2016 | Leonard et al. | |
| 9,328,095 B2 | 5/2016 | Leonard et al. | |
| 9,346,782 B2 | 5/2016 | Leonard et al. | |
| 9,403,816 B2 | 8/2016 | Leonard et al. | |
| 9,624,225 B2 | 4/2017 | Leonard et al. | |
| 2003/0166675 A1 | 9/2003 | Yang | |
| 2005/0131014 A1 | 6/2005 | Wyeth | |
| 2007/0072844 A1 | 3/2007 | Jones et al. | |
| 2008/0188521 A1 | 8/2008 | Grimm et al. | |
| 2009/0197859 A1 | 8/2009 | Collantes et al. | |
| 2009/0286829 A1 | 11/2009 | Heidelbaugh et al. | |
| 2010/0311760 A1 | 12/2010 | de Vicente Fidalgo et al. | |
| 2011/0124870 A1 | 5/2011 | Guillemont et al. | |
| 2012/0322837 A1 | 12/2012 | Maeba et al. | |
| 2016/0136149 A1 | 5/2016 | Leonard et al. | |
| 2016/0279122 A1 | 9/2016 | Leonard et al. | |

FOREIGN PATENT DOCUMENTS

| | | | |
|---|---|---|---|
| EP | 371564 A2 | 6/1990 | |
| EP | 709377 A1 | 5/1996 | |
| EP | 1106612 A1 | 6/2001 | |
| EP | 2368886 A1 | 9/2011 | |
| EP | 2487159 | 8/2012 | |
| GB | 2095668 A | 10/1982 | |
| JP | 48026772 | 4/1973 | |
| JP | S48-026772 | 4/1973 | |
| JP | H6-507643 | 9/1994 | |
| JP | 2000169451 A | 6/2000 | |
| WO | WO 1992/20642 | 11/1992 | |
| WO | WO 199718208 A1 | 5/1997 | |
| WO | WO 1997021701 A1 | 6/1997 | |
| WO | WO 199744339 A1 | 11/1997 | |
| WO | WO 199855124 A1 | 12/1998 | |
| WO | WO 1998055124 A1 | 12/1998 | |
| WO | WO 199932450 A1 | 7/1999 | |
| WO | WO 9950660 A1 | 10/1999 | |
| WO | WO 2000001386 A1 | 1/2000 | |
| WO | WO 2000001411 A1 | 1/2000 | |
| WO | WO 2000001714 A1 | 1/2000 | |
| WO | WO 2000039082 A2 | 7/2000 | |
| WO | WO 2000040561 A1 | 7/2000 | |
| WO | WO 2000040563 A1 | 7/2000 | |
| WO | WO 2000047574 A1 | 8/2000 | |
| WO | WO 2001056552 A2 | 8/2001 | |
| WO | WO 2001062234 A2 | 8/2001 | |
| WO | WO 2001064194 A2 | 9/2001 | |
| WO | WO 2001064195 A2 | 9/2001 | |
| WO | WO 2001064196 A2 | 9/2001 | |
| WO | WO 2001064197 A2 | 9/2001 | |
| WO | WO 2001064198 A2 | 9/2001 | |
| WO | WO 2001064199 A2 | 9/2001 | |
| WO | WO 2001064217 A2 | 9/2001 | |
| WO | WO 2001064218 A2 | 9/2001 | |
| WO | WO 2001064226 A2 | 9/2001 | |
| WO | WO 2001064246 A2 | 9/2001 | |
| WO | WO 2001064252 A2 | 9/2001 | |
| WO | WO 2002002558 A1 | 1/2002 | |
| WO | WO 2002004445 A1 | 1/2002 | |
| WO | WO 2002004462 A1 | 1/2002 | |
| WO | WO 2002024682 A1 | 3/2002 | |
| WO | WO 2002024686 A2 | 3/2002 | |
| WO | WO 2002024687 A1 | 3/2002 | |
| WO | WO 2002028837 A1 | 4/2002 | |
| WO | WO 2002043733 A1 | 6/2002 | |
| WO | WO 2002051835 A1 | 7/2002 | |
| WO | WO 2002064142 A1 | 8/2002 | |
| WO | WO 2002070487 A1 | 9/2002 | |
| WO | WO 2002085364 A1 | 10/2002 | |
| WO | WO 2003000705 | 1/2003 | |
| WO | WO 2003053971 A1 | 7/2003 | |
| WO | WO 2003053972 A1 | 7/2003 | |
| WO | WO 2003082350 A2 | 10/2003 | |
| WO | WO 2004019932 A1 | 3/2004 | |
| WO | WO 2004024693 A1 | 3/2004 | |
| WO | WO 2004/037792 | 5/2004 | |
| WO | WO 2004037792 A2 | 5/2004 | |
| WO | WO 2005/037834 | 4/2005 | |
| WO | WO 2005054201 A1 | 6/2005 | |
| WO | WO 2005054210 A1 | 6/2005 | |
| WO | WO 2005058843 A1 | 6/2005 | |
| WO | WO 2005070430 A1 | 8/2005 | |
| WO | WO 2005075428 A1 | 8/2005 | |
| WO | WO 2006003146 A1 | 1/2006 | |
| WO | WO 2006013896 A1 | 2/2006 | |
| WO | WO 2006025683 | 3/2006 | |
| WO | WO 2006052718 A2 | 5/2006 | |
| WO | WO 2007014940 A2 | 2/2007 | |
| WO | WO 2007014941 A2 | 2/2007 | |
| WO | WO 2007088978 A1 | 8/2007 | |
| WO | WO 2008/003703 | 1/2008 | |
| WO | WO 2008051805 A2 | 5/2008 | |
| WO | WO 2008068267 A1 | 6/2008 | |
| WO | WO 2008/103277 | 8/2008 | |
| WO | WO 2008098104 A8 | 8/2008 | |
| WO | WO 2008112525 A2 | 9/2008 | |
| WO | WO 2008144767 A1 | 11/2008 | |
| WO | WO 2009/032667 | 3/2009 | |
| WO | WO 2009091735 A1 | 7/2009 | |
| WO | WO 2009140138 A1 | 11/2009 | |
| WO | WO 2009/147187 | 12/2009 | |
| WO | WO 2010/059602 | 5/2010 | |
| WO | WO 2010068296 A1 | 6/2010 | |
| WO | WO 2010127208 A1 | 11/2010 | |
| WO | WO 2010151740 A4 | 12/2010 | |
| WO | WO 2011020861 A1 | 2/2011 | |
| WO | WO 2011112264 A1 | 9/2011 | |
| WO | WO 2011130707 A2 | 10/2011 | |
| WO | WO 2012/064744 | 5/2012 | |
| WO | WO 2012064744 A2 | 5/2012 | |
| WO | WO 2012/106995 | 8/2012 | |
| WO | WO 2012116137 A2 | 8/2012 | |
| WO | WO 2012158784 A2 | 11/2012 | |
| WO | WO 2013/018695 | 2/2013 | |
| WO | WO 2013/019682 | 2/2013 | |
| WO | WO 2013061074 A1 | 5/2013 | |
| WO | WO 2013064231 A1 | 5/2013 | |
| WO | WO 2013079223 A1 | 6/2013 | |

OTHER PUBLICATIONS

Hueber et al. Sci Transl Med (2010), 2, 5272.*
Codarri, Nature Immunology, Jun. 2011, vol. 12(6), p. 560-568.*
Freshney (Culture of Animal Cells, A Manual of Basic Technique, Alan R. Liss, Inc., 1983, New York, p. 4.*
Spits et al. Annual Review of Immunology (2012), 30, 647-675.*
Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.s.
U.S. Appl. No. 15/069,030, Leonard et al.
Database Registry [Online] v/Chemical Abstracts Service, Columbus, Ohio, US; Dec. 9, 2008 (Dec. 9, 2008), XP002769955, Database accession No. 1082399-35-6 * compound with registry No. 1082399-35-6 *.

(56) References Cited

OTHER PUBLICATIONS

Database Registry [Online] Chemical Abstracts Service, Columbus, Ohio, US; Dec. 4, 2011 (Dec. 4, 2011), XP002769956, Database accession No. 1347913-41-0 *compound with registry No. 1347913-41-0 *.
Database Registry [Online] Chemical Abstracts Service, Columbus, Ohio, US; Dec. 2, 2011 (Dec. 2, 2011), XP002769957, Database accession No. 1347391-03-0 *compound with registry No. 1347391-03-0 *.
Database Registry [Online] Chemical Abstracts Service, Columbus, Ohio, US; Dec. 10, 2008 (Dec. 10, 2008), XP002769958, Database accession No. 1082562-72-8 *compound with registry No. 1082562-72-8 *.
Abdul-Ahad P, (Trends in dehydrogenase inhibitory potencies of some quinolones, using quantum chemical indices), European Journal of Medicinal Chemistry (1982), 17(4), 301-6.
Aghera V, (Synthesis, spectral and microbial studies of some novel quinoline derivatives via Vilsmeier-Haack reagent) Journal; (online computer file) URL: http://www.arkat-usa.org/get-file/25177/.
Baker B, (Irreversible enzyme inhibitors. 191. Hydrophobic bonding to some dehydrogenases by 6-, 7-, or 8-substituted-4-hydroxyquinoline-3-carboxylic acids), Journal of Medicinal Chemistry (1972), 15(3), 235-7.
Barczyk A, (Interleukin-17 in sputum correlates with airway hyperresponsiveness to methacholine), Respir Med (2003), 97(6), 726-733.
Bink A, (A fungicidal piperazine-1-carboxamidine induces mitochondrial fission-dependent apoptosis in yeast), FEMS Yeast Research (2010), 10(7), 812-818.
Bowes J, (The genetics of psoriatic arthritis: lessons from genomewide association studies), Discov Med (2010), 10(52), 177-83.
Codarri, et al., "RORγt Drives Production of the Cytokine GM-CSF in helper T cells, which is essential for the effector Phase of Autoimmune Neuroinflammation" Nature Immunology, vol. 12(6), Jun. 2011, pp. 560-568.
Cua, D (Interleukin-23 rather than interleukin-12 is the critical cytokine for autoimmune inflammation of the brain), Nature (2003), 421(6924), 744-748.
Dong C, (Diversification of T-helper-cell lineages: finding the family root of IL-17-producing cells), Nat Rev Immunol (2006), 6(4), 329-333.
Dorwald F. A. "SLIDE Reactions in Organic Synthesis", 2005, Wiley: VCH, Weinheim p. IX of Preface p. 1-15.
Fujino S, (Increased expression of interleukin 17 in inflammatory bowel disease) Gut (2003), 52(1), 65-70.
Gao W, (Clean and Convienient One-Pot Synthesis of 4-Hydroxycoumarin and 4-Hydroxy-2-Quinolone Derivatives), Synthetic Communications (2010) 40, 732-738.
Garber K, (Psoriasis: from bed to bench and back), Nat Biotech (2011), 29, 563-566.
Gazouli, M, (NOD2/CARD15, ATG16L1 and IL23R gene polymorphisms and childhood-onset of Crohn's disease) World J. Gastroenterol (2010) 16(14), 1753-8.
Gore T, (Synthesis of substituted 6,6'-biquinolines from ethyl ethoxymethyleneacetoacetate), Indian Journal of Chemistry (1965), 3(2), 90-1.
Hirao I, (Studies on the synthesis of quinoline compounds. I. Syntheses of 3,3'-dicarboxy-1,1'-diethyl-4,4'-dioxo-1,1',4,4'-tetrahydrobiquinolines), Memoirs of the Kyushu Institute of Technology, Engineering (1984), 14,13-16.
Hueber W, (Effects of AIN457, a fully human antibody to interleukin-17A, on psoriasis, rheumatoid arthritis, and uveitis), Sci Transl Med (2010), 2, 5272.
Inada T, (One-step synthesis of ethyl quinaldates by Lewis acid-catalyzed three-component coupling reaction of aromatic amines, aliphatic aldehydes, and ethyl glyoxylate), Heterocycles (2005), 66, 611-619.
Ivanov II B, (The orphan nuclear receptor RORgammat directs the differentiation program of proinflammatory IL-17+ T helper cells), Cell (2006), 126(6), 1121-33.

Kamenecka T, (Synthetic modulators of the retinoic acid receptor-related orphan receptors), Med Chem Commun (2013), 4, 764-776.
Knochel P, (Preparation of Polyfunctional Ketones by a Cobalt(II) Mediated Carbonylation of Organozinc Reagents), Tetrahedron Letters (1995), 36(46), 8411-8414.
Kochi Y, (A regulatory variant in CCR6 is associated with rheumatoid arthritis susceptibility), Nat Genet (2010), 42(6), 515-9.
Kolls J, (Interleukin-17 family members and inflammation), Immunity (2004), 21(4), 467-476.
Korn T, (IL-17 and Th17 Cells), Annual Reviews of Immunology (2009), 27, 485-517.
Krueger J, (IL-17A is essential for cell activation and inflammatory gene circuits in subjects with psoriasis) J Allergy Clin Immunol (2012), 130(1), 145-154.
Langrish C, (IL-23 drives a pathogenic T cell population that induces autoimmune inflammation), J Exp Med (2005), 201(2), 233-240.
Leonardi C, (Anti-interleukin-17 monoclonal antibody ixekizumab in chronic plaque psoriasis), N Engl J Med (2012), 366(13), 1190-1199.
Lock C, (Gene-microarray analysis of multiple sclerosis lesions yields new targets validated in autoimmune encephalomyelitis) Nat Med (2002), 8(5), 500-8.
Madrid P, et al. (Synthesis of ring-substituted 4-aminoquinolines and evaluation of their antimalarial activities), Bioorganic & Medicinal Chemistry Letters (2005), 15, 1015-1018.
Mao D, (Synthesis and Na+/H+ Exchanger-1 Inhibitory Activity of Substituted (Quinolinecarbonyl)guanidine Derivatives), Chemistry & Biodiversity (2009), 6(10), 1727-1736.
McKenzie B, (Understanding the IL-23-IL-17 immune pathway), Trends Immunol (2006), 27(1), 17-23.
Moriarty R, Organic Reactions (2001), 57, 327-415.
Nieman J, (Modifications of C-2 on the pyrroloquinoline template aimed at the development of potent herpes virus antivirals with improved aqueous solubility), Bioorganic & Medicinal Chemistry Letters (2010), 20(10), 3039-3042.
Nunez C, (IL23R: a susceptibility locus for celiac disease and multiple sclerosis?) Genes Immun (2008), 9(4), 289-93.
Osborne A, (Further studies of regioselective alkoxydehalogenation of 2,4-dichloroquinolines, 2,6-dichloropyridine and 2,4-dichloronitrobenzene), J Chem Research (S) (2002), 4.
Osborne A, (Regioselective Al koxydehalogenation of 2,4-Di halogenoquinolines and a Reinvestigation of the Bromination of 2-Methoxyquinoline), J Chem Soc Perkin Trans 1 (1993), 181-184.
Papp K, (Brodalumab, an anti-interleukin-17-receptor antibody for psoriasis), N Engl J Med (2012), 366(13), 1181-1189.
Pongratz E, et al., (Ylide von Heterocyclen, VIII Reaktionen von Iodonium-Yliden mit Säuren), Monatshefte fur Chemie (1984) 115(2), 231-242.
Ramachary D, (A novel and green protocol for two-carbon homologation: a direct amino acid/K2CO3-catalyzed four-component reaction of aldehydes, active methylenes, Hantzsch esters and alkyl halides), Tetrahedron Letters (2006) 47, 651-656.
Ramachary D, (Development of Pharmaceutical Drugs, Drug Intermediates and Ingredients by Using Direct Organo-Click Reactions), Eur. J. Org. Chem. (2008), 975-993.
Sato M, (Quinolone Carboxylic Acids as a Novel Monoketo Acid Class of Human Immunodeficiency Virus Type 1 Integrase Inhibitors), Journal of Medicinal Chemistry (2009), 52(15), 4869-4882.
Stamp L, (Interleukin-17: the missing link between T-cell accumulation and effector cell actions in rheumatoid arthritis), Immunol Cell Biol (2004), 82(1), 1-9.
STN Search Report Mar. 12, 2015, RN 1347913-41-0.
Tanis S, (The design and development of 2-aryl-2-hydroxyethylamine substituted 1H,7H-pyrido[1,2,3-de]quinoxaline-6-carboxamides as inhibitors of human cytomegalovirus polymerase), Bioorganic & Medicinal Chemistry Letters (2010), 20(6), 1994-2000.
Tonel G, (Cutting edge: A critical functional role for IL-23 in psoriasis), J Immunol (2010), 185(10), 5688-5691.
Venkatesh, et al. "Role of the Development Scientist in Compound Lead Selection and Optimization", J. Pharm. Sci. vol. 89, No. 2, pp. 145-154 2000.

(56) References Cited

OTHER PUBLICATIONS

Yen D, (IL-23 is essential for T cell-mediated colitis and promotes inflammation via IL-17 and IL-6), J Clin Invest (2006), 116(5), 1310-1316.
Zelenin A, (Reaction of polyfluoro carbonyl compounds with 1,2,3,4-tetrahydroquinoline), Izvestiya Akademii Nauk SSSR, Seriya Khimicheskaya (1986), (9), 2074-80 Abstract Only.
International Search Report—PCT/US2013/065007, dated Jan. 7, 2014.
International Search Report—PCT/US2013/065013, dated Dec. 16, 2013.
International Search Report—PCT/US2013/065026, dated Feb. 21, 2014.
International Search Report—PCT/US2013/065031, dated Dec. 13, 2013.
International Search Report—PCT/US2013/065040, dated Dec. 16, 2013.
International Search Report—PCT/US2013/065048, dated Dec. 3, 2013.
International Search Report—PCT/US2014/060372, dated Mar. 27, 2015.
International Search Report—PCT/US2014/060375, dated Mar. 26, 2015.
International Search Report—PCT/US2013/065053, dated Jan. 7, 2014.
Arebro et al., J. Allergy Clin Immunol, Mar. 2016, vol. 137, No. 3, pp. 960-963.
Dolff et al., Clinical Immunology (2011) 141, 197-204.
Feagan et al., N Engl J Med 2016;375:1946-60.
Fitzpatrick, Leo Robert. Ror-gamma T inhibition as a Pharmacological Approach for Inflammatory Bowel Disease, Medical Research Archives, [S.I.], v. 2, n. 2, Aug. 2015. ISSN 2375-1924. Available at: <https://journals.ke-i.org/index.php/mra/article/view/334.
Hodgson et al., PharmacoEconomics (2018) 36:387-398.
Innovimmune: ROR Gamma Inhibitor (INV-17) Tested in Lupus Model. 2015 Eular Congress News. https://static1.squarespace.com/static/577aff0015d5db17f97d2d57/t/584f44f9725e254d6b032644/1481590043630/150611_INV-17+Lupus+Thursday_EULAR_2015+small+size.pdf.
Jethwa et al., Clinical and Experimental Immunology, 183: 30-36, 2015.
McGinley et al., Journal of Autoimmunity 87 (2018) 97e108.
Mease et al., N Engl J Med 2014;370:2295-306.
Poddubnyy et al., Ann Rheum Dis 2014;0:1-7.
Qian et al., Clin. Invest. (2012) 2(4), 417-421.
Sandborn et al., N Engl J Med 2012;367:1519-28.
Shanahan F., Lancet, 2002; 359: 62-69.
Silva et al., Biomarkers Journal, 2015, vol. 1, No. 1:6, pp. 1-6.
Wang et al., Eur. J. Immunol. 2016. 46: 1343-1350.
Weitz et al., Expert Opin. Biol. Ther. (2014) 14(4):515-526.
Withers et al., Nature Medicine, vol. 22, No. 3, Mar. 2016, pp. 319-325.
Yang et al., Mediators of Inflammation, vol. 2016, Article ID 6470364, pp. 1-7.
Database Registry, Dec. 9, 2008, RN 1082474_85_8, Retrieved from STN international [online], retrieved on May 29, 2018.

\* cited by examiner

QUINOLINYL MODULATORS OF RORγT

CROSS-REFERENCE TO RELATED APPLICATIONS

This application is a divisional of U.S. application Ser. No. 14/513,426, filed on Oct. 14, 2014, which claims priority from provisional U.S. Application No. 61/890,889, filed on Oct. 15, 2013, which are all incorporated herein by reference.

FIELD OF THE INVENTION

The invention is directed to substituted quinoline compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of $CD4^+$ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23.). RORγt-deficient mice are healthy and reproduce normally, but have shown impaired Th17 cell differentiation in vitro, a significantly reduced Th17 cell population in vivo, and decreased susceptibility to EAE (Ivanov, II, B. S. McKenzie, et al. (2006). "The orphan nuclear receptor RORgammat directs the differentiation program of proinflammatory IL-17+T helper cells." Cell 126(6): 1121-33.). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8; Langrish, C. L., Y. Chen, et al. (2005). "IL-23 drives a pathogenic T cell population that induces autoimmune inflammation." J Exp Med 201(2): 233-40; Yen, D., J. Cheung, et al. (2006). "IL-23 is essential for T cell-mediated colitis and promotes inflammation via IL-17 and IL-6." J Clin Invest 116(5): 1310-6.). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33; Fujino, S., A. Andoh, et al. (2003). "Increased expression of interleukin 17 in inflammatory bowel disease." Gut 52(1): 65-70; Lock, C., G. Hermans, et al. (2002). "Gene-microarray analysis of multiple sclerosis lesions yields new targets validated in autoimmune encephalomyelitis." Nat Med 8(5): 500-8; Krueger, J. G., S. Fretzin, et al. "IL-17A is essential for cell activation and inflammatory gene circuits in subjects with psoriasis." J Allergy Clin Immunol 130(1): 145-154 e9.). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8., Nunez, C., B. Dema, et al. (2008). "IL23R: a susceptibility locus for celiac disease and multiple sclerosis?" Genes Immun 9(4): 289-93; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet 42(6): 515-9.).

Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. A., "Brodalumab, an anti-interleukin-17-receptor antibody for psoriasis." N Engl J Med 2012 366(13): 1181-9; Leonardi, C., R. Matheson, et al. "Anti-interleukin-17 monoclonal antibody ixekizumab in chronic plaque psoriasis." N Engl J Med 366(13): 1190-9.). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk, N. S., Chu, D. S., Callanan, D., Nguyen, Q. D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.).

All the above evidence supports inhibition of the Th17 pathway by modulating RORγt activity as an effective strategy for the treatment of immune-mediated inflammatory diseases.

SUMMARY OF THE INVENTION

The present invention comprises compounds of Formula I.

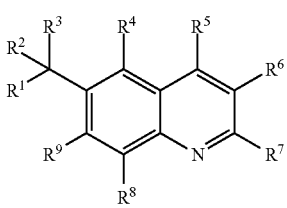

Formula I

R¹ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, quinazolinyl, cinnolinyl, benzothiazolyl, indazolyl, tetrahydropyranyl, tetrahydrofuranyl, furanyl, phenyl, oxazolyl, isoxazolyl, thiophenyl, benzoxazolyl, benzimidazolyl, indolyl, thiadiazolyl, oxadiazolyl or quinolinyl; wherein said azetidinyl, pyridyl, pyridyl-N-oxide, pyrazinyl, pyrimidinyl, pyridazyl, piperidinyl, quinazolinyl, cinnolinyl, benzothiazolyl, indazolyl, imidazolyl, phenyl, thiophenyl, benzoxazolyl, benzimidazolyl, indolyl, quinolinyl, and pyrazolyl are optionally substituted with C(O)$C_{(1-4)}$alkyl, C(O)NH$_2$, C(O)NHC$_{(1-2)}$alkyl, C(O)N(C$_{(1-2)}$alkyl)$_2$, NHC(O)C$_{(1-4)}$alkyl, NHSO$_2$C$_{(1-4)}$alkyl, C$_{(1-4)}$ alkyl, CF$_3$, CH$_2$CF$_3$, Cl, F, —CN, OC$_{(1-4)}$alkyl, N(C$_{(1-4)}$alkyl)$_2$, —(CH$_2$)$_3$OCH$_3$, SC$_{(1-4)}$alkyl, OH, CO$_2$H, CO$_2$C$_{(1-4)}$alkyl, C(O)CF$_3$, SO$_2$CF$_3$, OCF$_3$, OCHF$_2$, SO$_2$CH$_3$, SO$_2$NH$_2$, SO$_2$NHC$_{(1-2)}$alkyl, SO$_2$N(C$_{(1-2)}$alkyl)$_2$, C(O)NHSO$_2$CH$_3$, or OCH$_2$OCH$_3$; and optionally substituted with up to two additional substituents independently selected from the group consisting of Cl, C$_{(1-2)}$alkyl, SCH$_3$, OC$_{(1-2)}$alkyl, CF$_3$, —CN, and F; and wherein said triazolyl, oxazolyl, isoxazolyl, pyrrolyl, and thiazolyl are optionally substituted with up to two substituents independently selected from the group consisting of SO$_2$CH$_3$, SO$_2$NH$_2$, C(O)NH$_2$, —CN, OC$_{(1-2)}$alkyl, (CH$_2$)$_{(2-3)}$OCH$_3$, SCH$_3$, CF$_3$, F, Cl, and C$_{(1-2)}$alkyl; and said thiadiazolyl and oxadiazolyl are optionally substituted with C$_{(1-2)}$alkyl; and said pyridyl, pyridyl-N-oxide, pyrimidinyl, pyridazyl, and pyrazinyl are optionally substituted with up to three additional substituents independently selected from the group consisting of C(O)NHC$_{(1-2)}$alkyl, C(O)N(C$_{(1-2)}$alkyl)$_2$, NHC(O)C$_{(1-4)}$alkyl, NHSO$_2$C$_{(1-4)}$alkyl, C(O)CF$_3$, SO$_2$CF$_3$, SO$_2$NHC$_{(1-2)}$alkyl, SO$_2$N(C$_{(1-2)}$alkyl)$_2$, C(O)NHSO$_2$CH$_3$, SO$_2$CH$_3$, SO$_2$NH$_2$, C(O)NH$_2$, —CN, OC$_{(1-4)}$alkyl, (CH$_2$)$_{(2-3)}$OCH$_3$ (including —(CH$_2$)$_3$OCH$_3$), SC$_{(1-4)}$alkyl, CF$_3$, F, Cl, and C$_{(1-4)}$ alkyl;

R² is H, C$_{(1-6)}$alkyl, —C≡CH, triazolyl, pyridyl, pyridyl-N-oxide, pyrazolyl, pyrimidinyl, oxazolyl, isoxazolyl, azetidin-3-yl, N-acetyl-azetidin-3-yl, N-methylsulfonyl-azetidin-3-yl, N-Boc-azetidin-3-yl, N-methyl-azetidin-3-yl, N-acetamidyl-azetidin-3-yl, N-acetyl piperidinyl, 1-H-piperidinyl, N-Boc-piperidinyl, N—C$_{(1-3)}$alkyl-piperidinyl, N-methylsulfonyl-piperidinyl, thiazolyl, pyridazyl, pyrazinyl, 1-(3-methoxypropyl)-imidazolyl, thiadiazolyl, oxadiazolyl, or imidazolyl; wherein said imidazolyl is optionally substituted with up to three additional substituents independently selected from the group consisting of C$_{(1-2)}$alkyl, SCH$_3$, OC$_{(1-2)}$alkyl, CF$_3$, —CN, F, and Cl; and said pyridyl, pyridyl-N-oxide, pyrimidinyl, pyridazyl, and pyrazinyl, are optionally substituted with up to three additional substituents independently selected from the group consisting of SO$_2$CH$_3$, SO$_2$NH$_2$, C(O)NH$_2$, —CN, OC$_{(1-2)}$alkyl, (CH$_2$)$_{(2-3)}$OCH$_3$, SCH$_3$, CF$_3$, F, Cl, and C$_{(1-2)}$alkyl; and said triazolyl, thiazolyl, oxazolyl and isoxazolyl are optionally substituted with up to two substituents independently selected from the group consisting of SO$_2$CH$_3$, SO$_2$NH$_2$, C(O)NH$_2$, —CN, OC$_{(1-2)}$alkyl, (CH$_2$)$_{(2-3)}$OCH$_3$, SCH$_3$, CF$_3$, F, Cl, and C$_{(1-2)}$alkyl; and said thiadiazolyl and oxadiazolyl are optionally substituted with C$_{(1-2)}$alkyl; and said pyrazolyl is optionally substituted with up to three CH$_3$ groups;

R³ is H, OH, OCH$_3$, or NH$_2$;

R⁴ is H, or F;

R⁵ is H, Cl, —CN, CF$_3$, SC$_{(1-4)}$alkyl, OC$_{(1-4)}$alkyl, OH, C$_{(1-4)}$alkyl, N(CH$_3$)OCH$_3$, NH(C$_{(1-4)}$ alkyl), N(C$_{(1-4)}$alkyl)$_2$, 4-hydroxy-piperidinyl, azetidin-1-yl, or fur-2-yl; provided that R⁵ is not H if R⁷ is OCH$_3$;

R⁶ is C$_{(1-4)}$alkyl-Q, OC$_{(1-4)}$alkyl-Q, NA³A⁴, NHC$_{(1-4)}$alkylQ, NHCOC$_{(1-4)}$alkylQ, C(O)NA³A⁴, CO$_2$C(CH$_3$)$_3$, O-tetrahydropyranyl, O—(N-methyl)-piperidinyl, O—C$_{(3-6)}$cycloalkyl, O—(N-methyl)-pyrrolidinyl, O—(N-methyl)-azetidinyl, O—(N-methyl)-aziridinyl, cyclopropyl, cyclobutyl, oxetanyl, pyrrolidinyl, cyclopentyl, tetrahydrofuranyl, cyclohexyl, 1-methyl-1,2,3,6-tetrahydropyridin-4-yl, piperidinyl, or tetrahydropyranyl; wherein said cyclopropyl, cyclobutyl, cyclopentyl, pyrrolidinyl, piperidinyl, tetrahydropyranyl, and cyclohexyl are optionally substituted with F, C(O)C$_{(1-3)}$alkyl, OC(O)C$_{(1-4)}$alkyl, and C$_{(1-4)}$alkyl, and up to one additional fluorine atom; provided that R⁶ is not CH$_2$-phenyl, CH$_2$-pyridinyl, CH$_2$-pyrimidinyl, CH$_2$-pyrazinyl, nor CH$_2$-pyridazyl;

Q is H, CF$_3$, OH, SO$_2$CH$_3$, —CN, NA³A⁴, CO$_2$C$_{(1-4)}$alkyl, OC$_{(1-4)}$alkyl, cyclopropyl, cyclobutyl, oxetanyl, cyclopentyl, tetrahydrofuranyl, pyrazolyl, isoxazolyl, imidazolyl, triazolyl, oxazolyl, thiazolyl, pyrrolidinyl, cyclohexyl, piperidinyl, tetrahydropyranyl, 1,1-dioxo-tetrahydrothiopyran-4-yl, tetrahydrothiopyran-4-yl, phenyl, pyridinyl, pyrimidinyl, pyrazinyl, or pyridazyl; wherein said cyclopropyl, cyclobutyl, cyclopentyl, pyrrolidinyl, piperidinyl, tetrahydropyranyl, and cyclohexyl are optionally substituted with F, C(O)C$_{(1-3)}$alkyl, CO$_2$C(CH$_3$)$_3$, and C$_{(1-4)}$alkyl, and up to one additional fluorine atom; and said pyrazolyl, isoxazolyl, imidazolyl, triazolyl, oxazolyl, and thiazolyl are all optionally substituted with one or two CH$_3$ groups; and said oxetanyl is optionally substituted with CH$_3$;

wherein

A³ is H, or C$_{(1-4)}$alkyl;

A⁴ is H, C$_{(1-4)}$alkyl, CH$_2$-cyclopropyl, cyclopropyl, C$_{(1-3)}$alkylCF$_3$, CH$_2$CH$_2$OCH$_2$CF$_3$, C(O)C$_{(1-2)}$alkylCF$_3$,

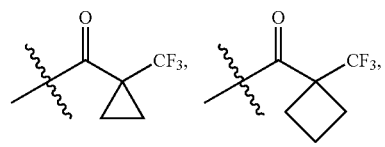 [SMILES: *C(=O)C1(C(F)(F)F)CC1 ; *C(=O)C1(C(F)(F)F)CCC1]

or C$_{(0-1)}$alkyl-trifluoromethyl-cyclohexyl, or A³ and A⁴ may be taken together with their attached nitrogen to form a ring selected from the group consisting of:

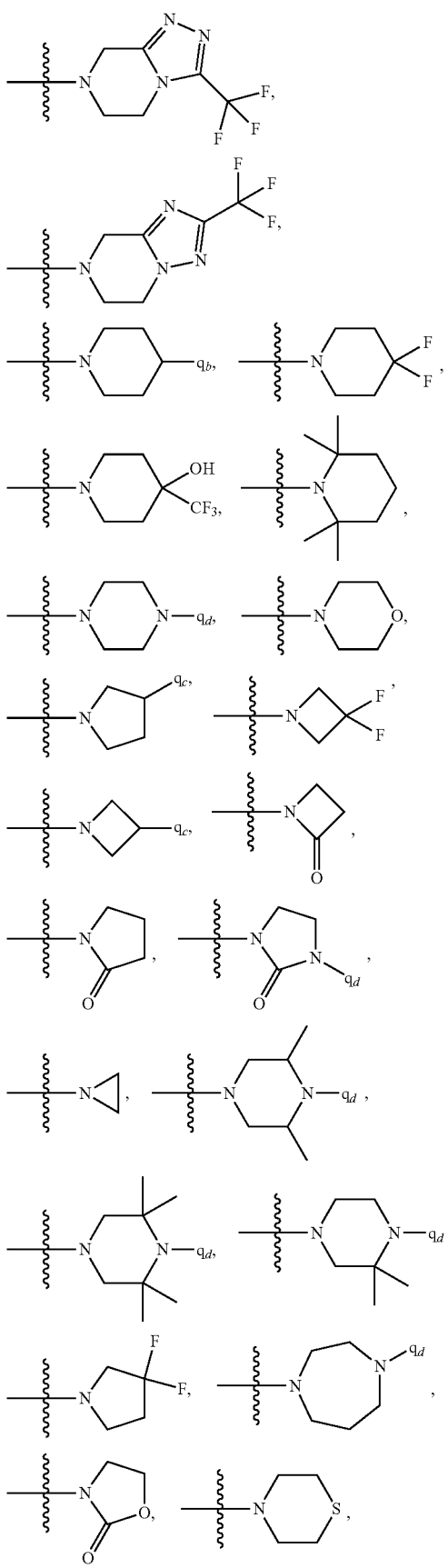

wherein
- $q_b$ is H, F, $CF_3$, $SO_2CH_3$, $OC_{(1-4)}$alkyl, pyrazol-1-yl, 3-trifluoromethyl-pyrazol-1-yl, imidazol-1-yl, or triazolyl;
- $q_c$ is H, F, $CF_3$, $OC_{(1-4)}$alkyl, or OH;
- $q_d$ is H, $CH_2CF_3$, $C_{(1-4)}$alkyl, $C(O)C_{(1-4)}$alkyl, phenyl, $CO_2C(CH_3)_3$, $SO_2C_{(1-4)}$alkyl, $CH_2CH_2CF_3$, $CH_2$-cyclopropyl, $CH_2$-phenyl, or $C_{(3-6)}$cycloalkyl;

provided that if $R^6$ is $OCH_2$-Q, then Q may not be OH, nor $NA^3A^4$;

$R^7$ is H, Cl, —CN, $C_{(1-4)}$alkyl, cyclopropyl, cyclobutyl, $OC_{(1-4)}$alkyl$CF_3$, $OCF_3$, $OCHF_2$, $OCH_2CH_2OC_{(1-4)}$alkyl, $CF_3$, $SCH_3$, $C_{(1-4)}$alkyl$NA^1A^2$ (including $CH_2NA^1A^2$), $CH_2OC_{(2-3)}$alkyl$NA^1A^2$, $NA^1A^2$, $C(O)NA^1A^2$, $CH_2NHC_{(2-3)}$alkyl$NA^1A^2$, $CH_2N(CH_3)C_{(2-3)}$alkyl$NA^1A^2$, $NHC_{(2-3)}$alkyl$NA^1A^2$, $N(CH_3)C_{(2-4)}$alkyl$NA^1A^2$, $OC_{(2-4)}$alkyl$NA^1A^2$, $OC_{(1-4)}$alkyl, $OCH_2$-(1-methyl)-imidazol-2-yl, thiophenyl, furyl, pyrazolyl, imidazolyl, pyridyl, pyridazyl, pyrazinyl, pyrimidinyl, indazolyl, phenyl, or wherein said phenyl, thiophenyl, furyl, pyrazolyl, imidazolyl, pyridyl, pyridazyl, pyrazinyl, pyrimidinyl, and indazolyl are optionally substituted with up to three substituents independently selected from the group consisting of F, Cl, $CH_3$, $CF_3$, and $OCH_3$;

$A^1$ is H, or $C_{(1-4)}$alkyl;

$A^2$ is H, $C_{(1-4)}$alkyl, $C_{(1-4)}$alkyl$OC_{(1-4)}$alkyl, $C_{(1-4)}$alkylOH, $C(O)C_{(1-4)}$alkyl, or $OC_{(1-4)}$alkyl; or $A^1$ and $A^2$ may be taken together with their attached nitrogen to form a ring selected from the group consisting of:

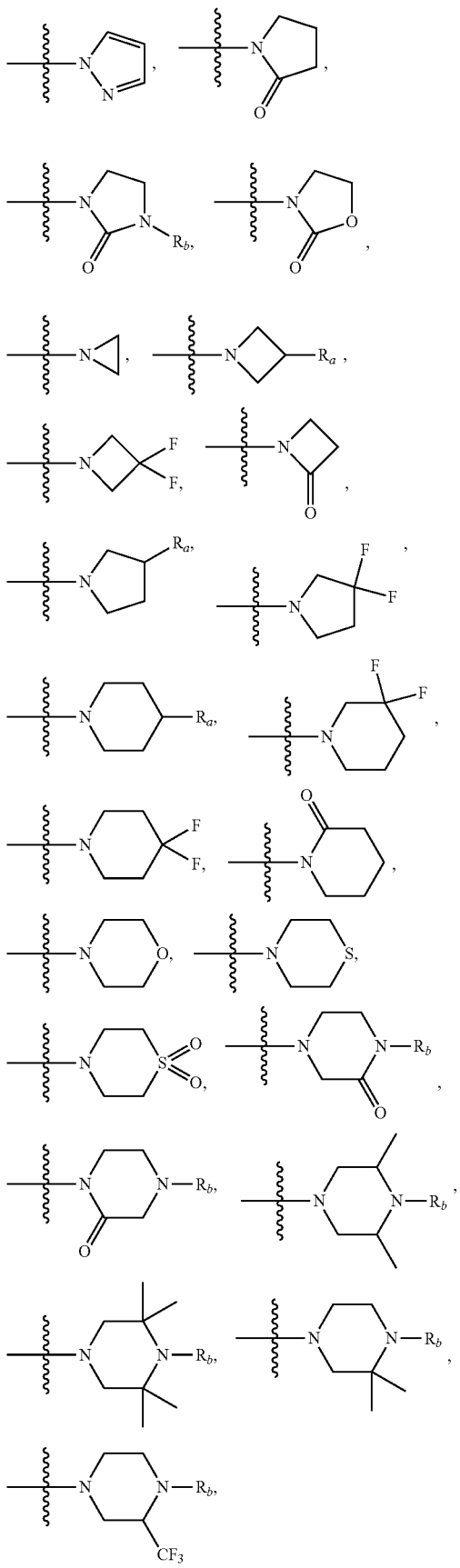
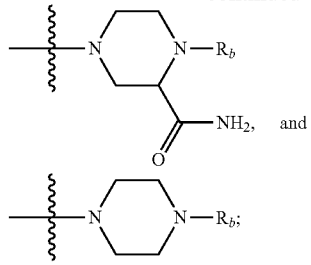
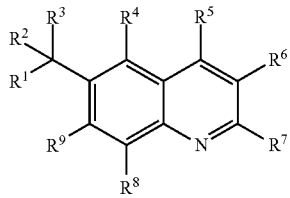

$R_a$ is H, $OC_{(1-4)}$alkyl, $CH_2OH$, $NH(CH_3)$, $N(CH_3)_2$, $NH_2$, $CH_3$, F, $CF_3$, $SO_2CH_3$, or OH;

$R_b$ is H, $CO_2C(CH_3)_3$, $C_{(1-4)}$alkyl, $C(O)C_{(1-4)}$alkyl, $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;

$R^8$ is H, $C_{(1-3)}$alkyl (including $CH_3$), $OC_{(1-3)}$alkyl (including $OCH_3$) $CF_3$, $NH_2$, $NHCH_3$, —CN, or F;

$R^9$ is H, or F;

and pharmaceutically acceptable salts thereof.

DETAILED DESCRIPTION OF THE INVENTION

The present invention comprises compounds of Formula I.

Formula I $R^1$ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, quinazolinyl, cinnolinyl, benzothiazolyl, indazolyl, tetrahydropyranyl, tetrahydrofuranyl, furanyl, phenyl, oxazolyl, isoxazolyl, thiophenyl, benzoxazolyl, benzimidazolyl, indolyl, thiadiazolyl, oxadiazolyl or quinolinyl; wherein said azetidinyl, pyridyl, pyridyl-N-oxide, pyrazinyl, pyrimidinyl, pyridazyl, piperidinyl, quinazolinyl, cinnolinyl, benzothiazolyl, indazolyl, imidazolyl, phenyl, thiophenyl, benzoxazolyl, benzimidazolyl, indolyl, quinolinyl, and pyrazolyl are optionally substituted with $C(O)C_{(1-4)}$alkyl, $C(O)NH_2$, $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C_{(1-4)}$ alkyl, $CF_3$, $CH_2CF_3$, Cl, F, —CN, $OC_{(1-4)}$alkyl, $N(C_{(1-4)}$alkyl$)_2$, —$(CH_2)_3OCH_3$, $SC_{(1-4)}$alkyl, OH, $CO_2H$, $CO_2C_{(1-4)}$alkyl, $C(O)CF_3$, $SO_2CF_3$, $OCF_3$, $OCHF_2$, $SO_2CH_3$, $SO_2NH_2$, $SO_2NHC_{(1-2)}$alkyl, $SO_2N(C_{(1-2)}$alkyl$)_2$, $C(O)NHSO_2CH_3$, or $OCH_2OCH_3$; and optionally substituted with up to two additional substituents independently selected from the group consisting of Cl, $C_{(1-2)}$alkyl, $SCH_3$, $OC_{(1-2)}$alkyl, $CF_3$, —CN, and F; and wherein said triazolyl, oxazolyl, isoxazolyl, pyrrolyl, and thiazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said thiadiazolyl and oxadiazolyl are optionally substituted with $C_{(1-2)}$alkyl; and said pyridyl, pyridyl-N-oxide, pyrimidinyl, pyridazyl, and pyrazinyl are optionally substituted with up to three additional substituents independently selected from the group consisting of $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C(O)CF_3$, $SO_2CF_3$, $SO_2NHC_{(1-2)}$alkyl, $SO_2N(C_{(1-2)}$alkyl$)_2$, $C(O)NHSO_2CH_3$, $SO_2CH_3$, $SO_2NH_2$, $C(O)NH_2$, —CN, $OC_{(1-4)}$alkyl, $(CH_2)_{(2-3)}OCH_3$ (including —$(CH_2)_3OCH_3$), $SC_{(1-4)}$alkyl, $CF_3$, F, Cl, and $C_{(1-4)}$alkyl;

$R^2$ is H, $C_{(1-6)}$alkyl, —C≡CH, triazolyl, pyridyl, pyridyl-N-oxide, pyrazolyl, pyrimidinyl, oxazolyl, isoxazolyl, azetidin-3-yl, N-acetyl-azetidin-3-yl, N-methylsulfonyl-azetidin-3-yl, N-Boc-azetidin-3-yl, N-methyl-azetidin-3-yl, N-acetamidyl-azetidin-3-yl, N-acetyl piperidinyl, 1-H-piperidinyl, N-Boc-piperidinyl, N—$C_{(1-3)}$alkyl-piperidinyl, N-methylsulfonyl-piperidinyl, thiazolyl, pyridazyl, pyrazinyl, 1-(3-methoxypropyl)-imidazolyl, thiadiazolyl, oxadiazolyl, or imidazolyl; wherein said imidazolyl is optionally substituted with up to three additional substituents independently selected from the group consisting of $C_{(1-2)}$alkyl, $SCH_3$, $OC_{(1-2)}$alkyl, $CF_3$, —CN, F, and Cl; and said pyridyl, pyridyl-N-oxide, pyrimidinyl, pyridazyl, and pyrazinyl, are optionally substituted with up to three additional substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said triazolyl, thiazolyl, oxazolyl and isoxazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said thiadiazolyl and oxadiazolyl are optionally substituted with $C_{(1-2)}$alkyl; and said pyrazolyl is optionally substituted with up to three $CH_3$ groups;

$R^3$ is H, OH, $OCH_3$, or $NH_2$;

$R^4$ is H, or F;

$R^5$ is H, Cl, —CN, $CF_3$, $SC_{(1-4)}$alkyl, $OC_{(1-4)}$alkyl, OH, $C_{(1-4)}$alkyl, $N(CH_3)OCH_3$, $NH(C_{(1-4)}$ alkyl), $N(C_{(1-4)}$alkyl$)_2$, 4-hydroxy-piperidinyl, azetidin-1-yl, or fur-2-yl; provided that $R^5$ is not H if $R^7$ is $OCH_3$;

$R^6$ is $C_{(1-4)}$alkyl-Q, $OC_{(1-4)}$alkyl-Q, $NA^3A^4$, $NHC_{(1-4)}$alkylQ, $NHCOC_{(1-4)}$alkylQ, $C(O)NA^3A^4$, $C(O)OC_{(1-4)}$alkyl, O-tetrahydropyranyl, O—(N-methyl)-piperidinyl, O—$C_{(3-6)}$cycloalkyl, O—(N-methyl)-pyrrolidinyl, O—(N-methyl)-azetidinyl, O—(N-methyl)-aziridinyl, cyclopropyl, cyclobutyl, oxetanyl, pyrrolidinyl, cyclopentyl, tetrahydrofuranyl, cyclohexyl, 1-methyl-1,2,3,6-tetrahydropyridin-4-yl, piperidinyl, or tetrahydropyranyl; wherein said cyclopropyl, cyclobutyl, cyclopentyl, pyrrolidinyl, piperidinyl, tetrahydropyranyl, and cyclohexyl are optionally substituted with F, $C(O)C_{(1-3)}$alkyl, $CO_2C(CH_3)_3$, and $C_{(1-4)}$alkyl, and up to one additional fluorine atom; provided that $R^6$ is not $CH_2$-phenyl, $CH_2$-pyridinyl, $CH_2$-pyrimidinyl, $CH_2$-pyrazinyl, nor $CH_2$-pyridazyl;

Q is H, $CF_3$, OH, $SO_2CH_3$, —CN, $NA^3A^4$, $CO_2C_{(1-4)}$alkyl, $OC_{(1-4)}$alkyl, cyclopropyl, cyclobutyl, oxetanyl, cyclopentyl, tetrahydrofuranyl, pyrazolyl, isoxazolyl, imidazolyl, triazolyl, oxazolyl, thiazolyl, pyrrolidinyl, cyclohexyl, piperidinyl, tetrahydropyranyl, 1,1-dioxo-tetrahydrothiopyran-4-yl, tetrahydrothiopyran-4-yl, phenyl, pyridinyl, pyrimidinyl, pyrazinyl, or pyridazyl;

wherein said cyclopropyl, cyclobutyl, cyclopentyl, pyrrolidinyl, piperidinyl, tetrahydropyranyl, and cyclohexyl are optionally substituted with F, $C(O)C_{(1-3)}$ alkyl, $CO_2C(CH_3)_3$, and $C_{(1-4)}$alkyl, and up to one additional fluorine atom; and said pyrazolyl, isoxazolyl, imidazolyl, triazolyl, oxazolyl, and thiazolyl are all optionally substituted with one or two $CH_3$ groups; and said oxetanyl is optionally substituted with $CH_3$;

wherein $A^3$ is H, or $C_{(1-4)}$alkyl;

$A^4$ is H, $C_{(1-4)}$alkyl, $CH_2$-cyclopropyl, cyclopropyl, $C_{(1-3)}$alkyl$CF_3$, $CH_2CH_2OCH_2CF_3$, $C(O)C_{(1-2)}$ alkyCF$_3$,

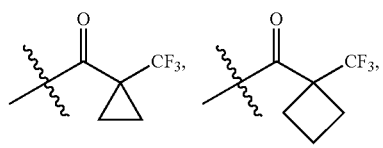 [SMILES: *C(=O)C1(C(F)(F)F)CC1 ; *C(=O)C1(C(F)(F)F)CCC1]

or $C_{(0-1)}$alkyl-trifluoromethyl-cyclohexyl, or $A^3$ and $A^4$ may be taken together with their attached nitrogen to form a ring selected from the group consisting of:

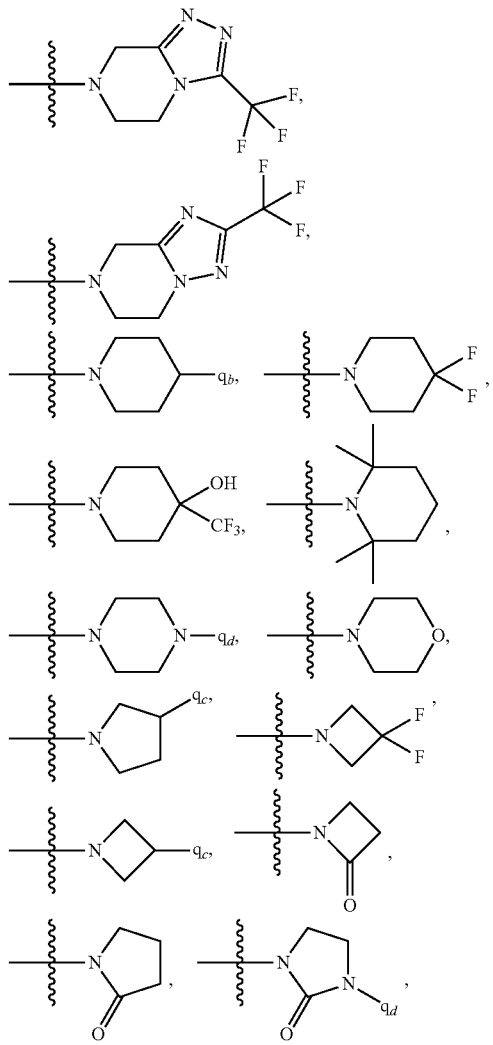

-continued

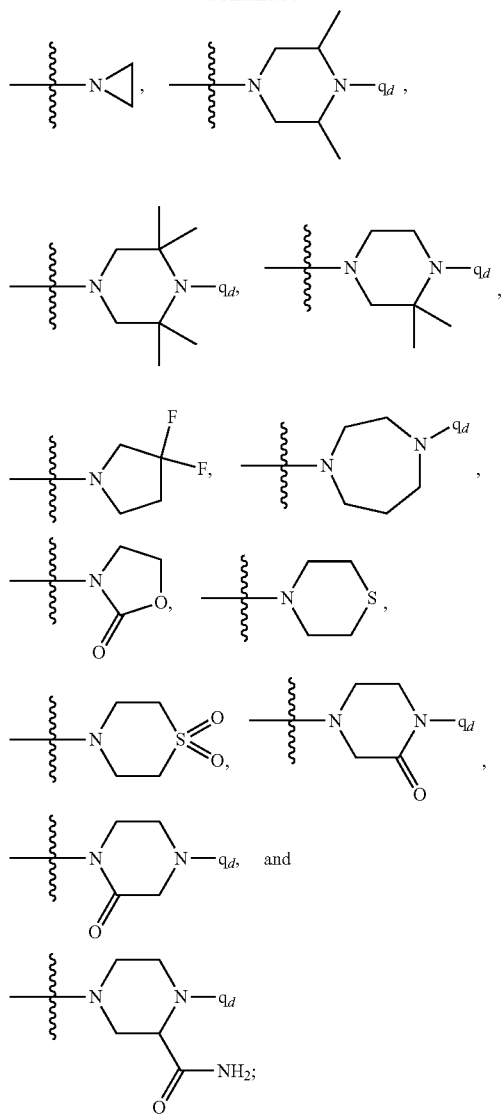

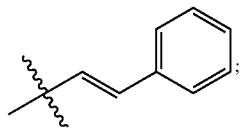 [SMILES: */C=C/c1ccccc1]

wherein
- $q_b$ is H, F, $CF_3$, $SO_2CH_3$, $OC_{(1-4)}$alkyl, pyrazol-1-yl, or 3-trifluoromethyl-pyrazol-1-yl, imidazol-1-yl, or triazolyl;
- $q_c$ is H, F, $CF_3$, $OC_{(1-4)}$alkyl, or OH;
- $q_d$ is H, $CH_2CF_3$, $C_{(1-4)}$alkyl, $C(O)C_{(1-4)}$alkyl, phenyl, $CO_2C(CH_3)_3$, $SO_2C_{(1-4)}$alkyl, $CH_2CH_2CF_3$, $CH_2$-cyclopropyl, $CH_2$-phenyl, or $C_{(3-6)}$cycloalkyl; provided that if $R^6$ is $OCH_2$-Q, then Q may not be OH, nor $NA^3A^4$;
- $R^7$ is H, Cl, —CN, $C_{(1-4)}$alkyl, cyclopropyl, cyclobutyl, $OC_{(1-4)}$alkyl$CF_3$, $OCF_3$, $OCHF_2$, $OCH_2CH_2OC_{(1-4)}$alkyl, $CF_3$, $SCH_3$, $C_{(1-4)}$alkyl$NA^1A^2$ (including $CH_2NA^1A^2$), $CH_2OC_{(2-3)}$alkyl$NA^1A^2$, $NA^1A^2$, $C(O)NA^1A^2$, $CH_2NHC_{(2-3)}$alkyl$NA^1A^2$, $CH_2N(CH_3)C_{(2-3)}$alkyl$NA^1A^2$, $NHC_{(2-3)}$alkyl$NA^1A^2$, $N(CH_3)C_{(2-4)}$alkyl$NA^1A^2$, $OC_{(2-4)}$alkyl$NA^1A^2$, $OC_{(1-4)}$alkyl, $OCH_2$-(1-methyl)-imidazol-2-yl, thiophenyl, furyl, pyrazolyl, imidazolyl, pyridyl, pyridazyl, pyrazinyl, pyrimidinyl, indazolyl, phenyl, or wherein said phenyl, thiophenyl, furyl, pyrazolyl, imidazolyl, pyridyl, pyridazyl, pyrazinyl, pyrimidinyl, and indazolyl are optionally substituted with up to three substituents independently selected from the group consisting of F, Cl, $CH_3$, $CF_3$, and $OCH_3$;

$A^1$ is H, or $C_{(1-4)}$alkyl;

$A^2$ is H, $C_{(1-4)}$alkyl, $C_{(1-4)}$alkyl$OC_{(1-4)}$alkyl, $C_{(1-4)}$alkylOH, $C(O)C_{(1-4)}$alkyl, or $OC_{(1-4)}$alkyl; or $A^1$ and $A^2$ may be taken together with their attached nitrogen to form a ring selected from the group consisting of:

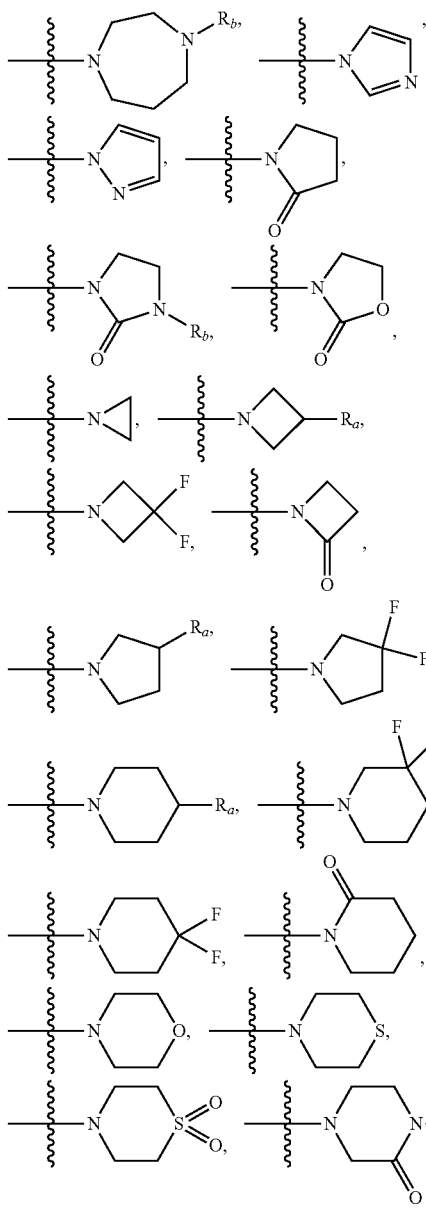

-continued

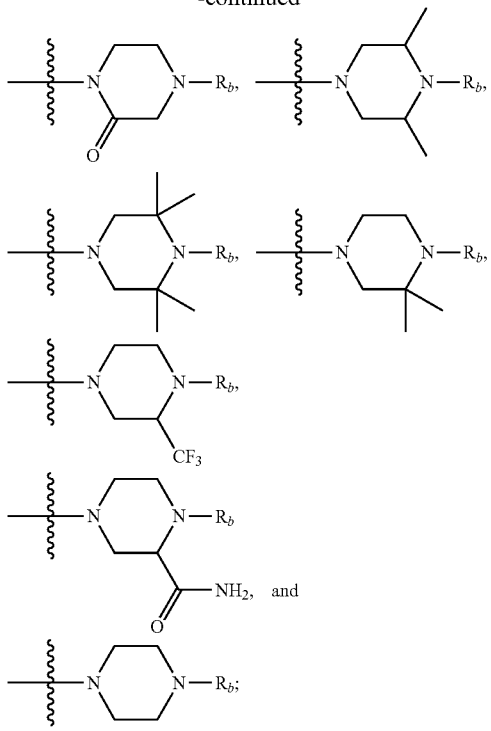

$R_a$ is H, $OC_{(1-4)}$alkyl, $CH_2OH$, $NH(CH_3)$, $N(CH_3)_2$, $NH_2$, $CH_3$, F, $CF_3$, $SO_2CH_3$, or OH;

$R_b$ is H, $CO_2C(CH_3)_3$, $C_{(1-4)}$alkyl, $C(O)C_{(1-4)}$alkyl, $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;

$R^8$ is H, $C_{(1-3)}$alkyl (including $CH_3$), $OC_{(1-3)}$alkyl (including $OCH_3$) $CF_3$, $NH_2$, $NHCH_3$, —CN, or F;

$R^9$ is H, or F;

and pharmaceutically acceptable salts thereof;

In another embodiment of the invention:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said pyridyl, pyridyl N-oxide, piperidinyl, imidazolyl, phenyl, thiophenyl, benzoxazolyl, pyrazolyl, pyrazinyl, pyrimidinyl, pyridazyl, or quinolinyl are optionally substituted with $C(O)C_{(1-4)}$alkyl, $C(O)NH_2$, $C_{(1-4)}$alkyl, $CF_3$, $CH_2CF_3$, Cl, F, —CN, $OC_{(1-4)}$alkyl, $N(C_{(1-4)}$alkyl$)_2$, —$(CH_2)_3OCH_3$, $SC_{(1-4)}$alkyl, OH, $CO_2H$, $CO_2C_{(1-4)}$alkyl, $OCF_3$, $OCHF_2$, $SO_2CH_3$, $SO_2NH_2$, or $OCH_2OCH_3$; and optionally substituted with up to two additional substituents independently selected from the group consisting of Cl, $C_{(1-2)}$alkyl (including $CH_3$), $SCH_3$, $OC_{(1-2)}$alkyl (including $OCH_3$), $CF_3$, —CN, and F; and wherein said triazolyl, oxazolyl, isoxazolyl, pyrrolyl, and thiazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl (including $CH_3$); and said pyridyl, and pyridyl-N-oxide are optionally substituted with up to three additional substituents independently selected from the group consisting of $SO_2CH_3$, $SO_2NH_2$, $C(O)NH_2$, —CN, $OC_{(1-4)}$ alkyl, $(CH_2)_{(2-3)}OCH_3$ (including —$(CH_2)_3OCH_3$), $SC_{(1-4)}$alkyl, $CF_3$, F, Cl, and $C_{(1-4)}$alkyl;

$R^2$ is H, $C_{(1-6)}$alkyl (including $C_{(1-4)}$alkyl), —C≡CH, 1-methyl triazolyl, pyridyl, pyridyl-N-oxide, 1-methyl pyrazolyl, pyrimidinyl, oxazolyl, isoxazolyl, azetidin-3-yl, N-acetyl-azetidin-3-yl, N-methylsulfonyl-azetidin-3-yl, N-Boc-azetidin-3-yl, N-acetyl piperidinyl, 1-H-piperidinyl, N-Boc-piperidinyl, N—$C_{(1-3)}$alkyl-piperidinyl (including N—$C_{(1-2)}$alkyl-piperidinyl), N-methyl sulfonyl-piperidinyl, thiazolyl, pyridazyl, pyrazinyl, 1-(3-methoxypropyl)-imidazolyl, or 1-$C_{(1-2)}$ alkyl imidazolyl; wherein said 1-$C_{(1-2)}$alkyl imidazolyl is optionally substituted with up to two additional substituents independently selected from the group consisting of $C_{(1-2)}$alkyl (including $CH_3$), $SCH_3$, $OC_{(1-2)}$alkyl, $CF_3$, —CN, F, and Cl; and said pyridyl, and pyridyl-N-oxide are optionally substituted with up to three additional substituents independently selected from the group consisting of $SO_2CH_3$, $SO_2NH_2$, $C(O)NH_2$, —CN, $OC_{(1-2)}$alkyl (including $OCH_3$), $(CH_2)_{(2-3)}OCH_3$, $SCH_3$, $CF_3$, F, Cl, and $C_{(1-2)}$alkyl (including $CH_3$); and said thiazolyl, oxazolyl and isoxazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl (including $CH_3$); and said 1-methyl pyrazolyl is optionally substituted with up to two additional $CH_3$ groups;

$R^3$ is H, OH, $OCH_3$, or $NH_2$;

$R^4$ is H, or F;

$R^5$ is H, Cl, —CN, $CF_3$, $SC_{(1-4)}$alkyl, $OC_{(1-4)}$alkyl, OH, $C_{(1-4)}$alkyl, $N(CH_3)OCH_3$, $NH(C_{(1-4)}$ alkyl), $N(C_{(1-4)}$ alkyl$)_2$, 4-hydroxy-piperidinyl, azetidin-1-yl, or fur-2-yl; provided that $R^5$ is not H if $R^7$ is $OCH_3$;

$R^6$ is $C_{(1-4)}$alkyl-Q, $OC_{(1-4)}$alkyl-Q, $C(O)NA^3A^4$, $C(O)OC_{(1-4)}$alkyl, O-tetrahydropyranyl, O—(N-methyl)-piperidinyl, cyclopropyl, cyclobutyl, pyrrolidinyl, cyclopentyl, tetrahydrofuranyl, cyclohexyl, 1-methyl-1,2,3,6-tetrahydropyridin-4-yl, piperidinyl, or tetrahydropyranyl; wherein said cyclopropyl, cyclobutyl, cyclopentyl, pyrrolidinyl, piperidinyl, tetrahydropyranyl, and cyclohexyl are optionally substituted with F, $C(O)C_{(1-3)}$alkyl, $CO_2C(CH_3)_3$, and $C_{(1-4)}$alkyl, and up to one additional fluorine atom; provided that $R^6$ is not $CH_2$-phenyl, $CH_2$-pyridinyl, $CH_2$-pyrimidinyl, $CH_2$-pyrazinyl, nor $CH_2$-pyridazyl;

Q is H, $CF_3$, OH, $SO_2CH_3$, —CN, $NA^3A^4$, $OC_{(1-4)}$alkyl, cyclopropyl, cyclobutyl, oxetanyl, cyclopentyl, tetrahydrofuranyl, pyrazolyl, isoxazolyl, imidazolyl, triazolyl, oxazolyl, thiazolyl, pyrrolidinyl, cyclohexyl, piperidinyl, tetrahydropyranyl, 1,1-dioxo-tetrahydrothiopyran-4-yl, tetrahydrothiopyran-4-yl, phenyl, pyridinyl, pyrimidinyl, pyrazinyl, or pyridazyl; wherein said cyclopropyl, cyclobutyl, cyclopentyl, pyrrolidinyl, piperidinyl, tetrahydropyranyl, and cyclohexyl are optionally substituted with F, $C(O)C_{(1-3)}$alkyl (including $C(O)CH_3$), $CO_2C(CH_3)_3$, and $C_{(1-4)}$alkyl, and up to one additional fluorine atom; and said pyrazolyl, isoxazolyl, imidazolyl, triazolyl, oxazolyl, and thiazolyl are all optionally substituted with one or two $CH_3$ groups; and said oxetanyl is optionally substituted with $CH_3$;

wherein $A^3$ is H, or $C_{(1-4)}$alkyl;

$A^4$ is H, $C_{(1-4)}$alkyl, $CH_2$-cyclopropyl, cyclopropyl, $C_{(1-3)}$alkyl$CF_3$, $CH_2CH_2OCH_2CF_3$, $C(O)C_{(1-2)}$alkyl$CF_3$,

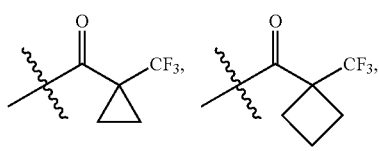 [SMILES: *C(=O)C1(C(F)(F)F)CC1 ; *C(=O)C1(C(F)(F)F)CCC1]

or C_{(0-1)}alkyl-trifluoromethyl-cyclohexyl, or $A^3$ and $A^4$ may be taken together with their attached nitrogen to form a ring selected from the group consisting of:

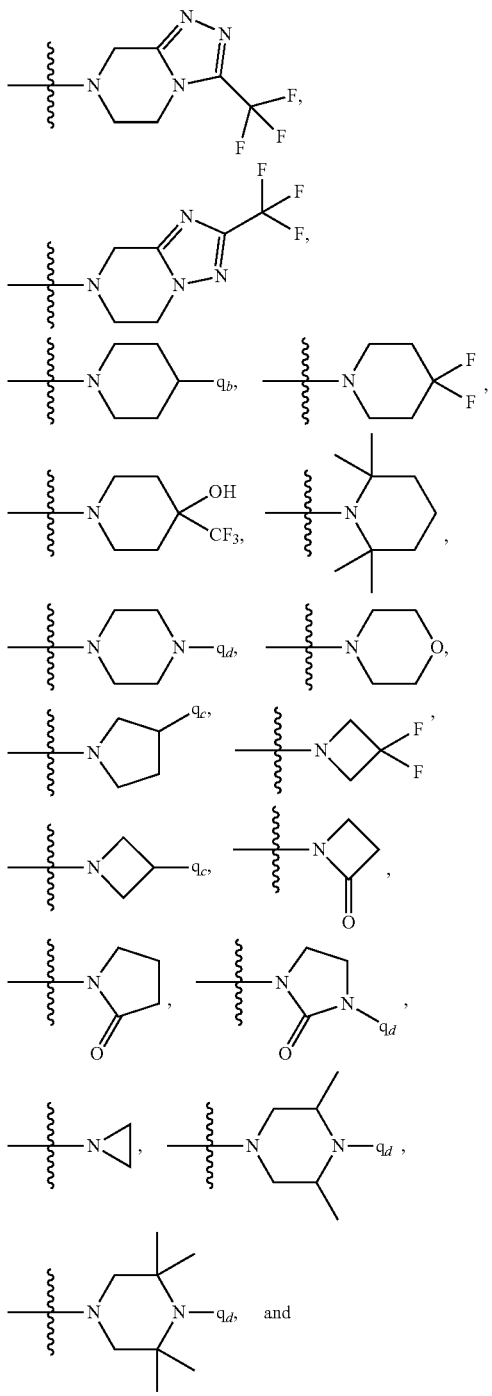

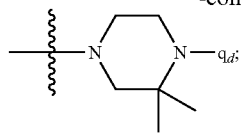

wherein $q_b$ is H, F, $CF_3$, $SO_2CH_3$, $OC_{(1-4)}$alkyl, pyrazol-1-yl, or 3-trifluoromethyl-pyrazol-1-yl, imidazol-1-yl, or triazolyl;

$q_c$ is H, F, $CF_3$, $OC_{(1-4)}$alkyl, or OH;

$q_d$ is H, $CH_2CF_3$, $C_{(1-4)}$alkyl, $C(O)C_{(1-4)}$alkyl (including $C(O)CH_3$), or phenyl; provided that if $R^6$ is $OCH_2$-Q, then Q may not be OH, nor $NA^3A^4$;

$R^7$ is H, Cl, —CN, $C_{(1-4)}$alkyl, cyclopropyl, $OC_{(1-4)}$alkylCF_3, $OCH_2CH_2OC_{(1-4)}$alkyl, $CF_3$, $SCH_3$, $CH_2NA^1A^2$, $CH_2OC_{(2-3)}$alkyl$NA^1A^2$, $NA^1A^2$, $C(O)NA^1A^2$, $N(CH_3)C_{(2-4)}$alkyl$NA^1A^2$, $OC_{(2-4)}$alkyl$NA^1A^2$, $OC_{(1-4)}$alkyl, $OCH_2$-(1-methyl)-imidazol-2-yl, furyl, pyrazolyl, imidazolyl, pyridyl, pyridazyl, pyrazinyl, pyrimidinyl, thiophenyl, 1-methyl-indazolyl, phenyl, or

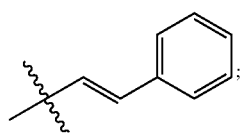

wherein said imidazolyl or pyrazolyl is optionally substituted with one $CH_3$ group;

$A^1$ is H, or $C_{(1-4)}$alkyl;

$A^2$ is H, $C_{(1-4)}$alkyl, $C_{(1-4)}$alkyl$OC_{(1-4)}$alkyl, $C_{(1-4)}$alkylOH, $C(O)C_{(1-4)}$alkyl, or $OC_{(1-4)}$alkyl; or $A^1$ and $A^2$ may be taken together with their attached nitrogen to form a ring selected from the group consisting of:

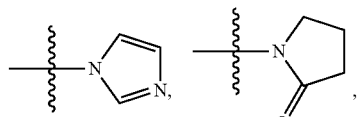

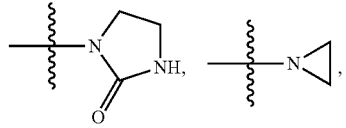

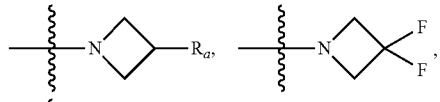

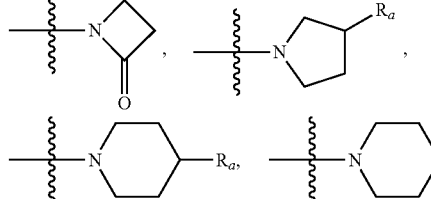

-continued

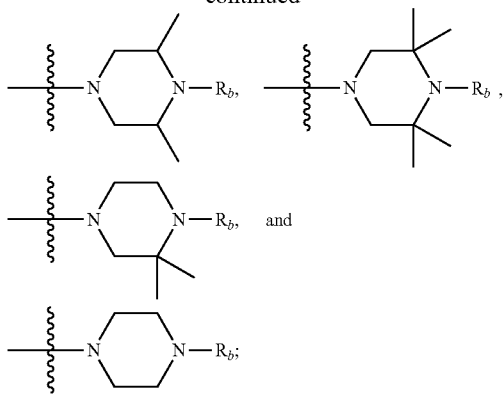

$R_a$ is H, $OC_{(1-4)}$alkyl, $CH_2OH$, $NH(CH_3)$, $N(CH_3)_2$, $NH_2$, $CH_3$, F, or OH;

$R_b$ is H, $CO_2C(CH_3)_3$, $C_{(1-4)}$alkyl, $C(O)C_{(1-4)}$alkyl (including $C(O)CH_3$), $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;

$R^8$ is H, $CH_3$, $OCH_3$, or F;

$R^9$ is H, or F;

and pharmaceutically acceptable salts thereof;

In another embodiment of the invention:

$R^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $C(O)$ $C_{(1-4)}$alkyl (including $C(O)CH_3$), $C(O)NH_2$, $C_{(1-4)}$alkyl (including $CH_3$, and $CH_2CH_3$), $CF_3$, $CH_2CF_3$, Cl, F, —CN, $OC_{(1-4)}$alkyl (including $OCH_3$), $N(C_{(1-4)}$alkyl$)_2$ (including $N(CH_3)_2$), —$(CH_2)_3OCH_3$, $SC_{(1-4)}$alkyl (including $SCH_3$), OH, $CO_2H$, $CO_2C_{(1-4)}$alkyl (including $CO_2C(CH_3)_3$), $OCF_3$, $OCHF_2$, $SO_2CH_3$, $SO_2NH_2$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups;

$R^2$ is H, $C_{(1-4)}$alkyl, —C≡CH, 1-methyl-triazolyl, pyridyl, pyridyl-N-oxide, 1-methyl-pyrazolyl, pyrimidinyl, pyrazinyl, oxazolyl, isoxazolyl, N-acetyl-azetidin-3-yl, N-methylsulfonyl-azetidin-3-yl, N-Boc-azetidin-3-yl, N-acetyl piperidinyl, 1-H-piperidinyl, N-Boc-piperidinyl, N—$C_{(1-2)}$alkyl-piperidinyl, N-methylsulfonyl-piperidinyl, thiazolyl, pyridazyl, 1-(3-methoxypropyl)-imidazolyl, or 1-$C_{(1-2)}$alkyl-imidazolyl; wherein said 1-$C_{(1-2)}$alkyl imidazolyl is optionally substituted with up to two additional $CH_3$ groups, or one substituent selected from the group consisting of $SCH_3$, and Cl; and said pyridyl, and pyridyl-N-oxide are optionally substituted with up to two substitutents independently selected from the group consisting of $SO_2CH_3$, $SO_2NH_2$, $C(O)NH_2$, —CN, $OCH_3$, $CF_3$, Cl, and $CH_3$; and said thiazolyl, oxazolyl and isoxazolyl are optionally substituted with up to two $CH_3$ groups; and said 1-methyl pyrazolyl is optionally substituted with up to two additional $CH_3$ groups;

$R^3$ is H, OH, $OCH_3$, or $NH_2$;

$R^4$ is H, or F;

$R^5$ is H, Cl, —CN, $CF_3$, $SC_{(1-4)}$alkyl (including $SCH_3$), $OC_{(1-4)}$alkyl (including $OC_{(1-3)}$alkyl) OH, $C_{(1-4)}$alkyl, $N(CH_3)OCH_3$, $NH(C_{(1-4)}$alkyl) (including $NH(C_{(1-2)}$alkyl)), $N(C_{(1-4)}$alkyl$)_2$ (including $N(C_{(1-2)}$alkyl$)_2$), 4-hydroxy-piperidinyl, azetidin-1-yl, or fur-2-yl; provided that $R^5$ is not H if $R^7$ is $OCH_3$;

$R^6$ is $C_{(1-4)}$alkyl-Q, $OC_{(1-4)}$alkyl-Q, $C(O)NA^3A^4$, $C(O)$ $OC_{(1-4)}$alkyl, O-tetrahydropyranyl, O—(N-methyl)-piperidinyl, cyclopropyl, cyclobutyl, pyrrolidinyl, cyclopentyl, tetrahydrofuranyl, cyclohexyl, 1-methyl-1,2,3,6-tetrahydropyridin-4-yl, piperidinyl, or tetrahydropyranyl; wherein said cyclopropyl, cyclobutyl, cyclopentyl, pyrrolidinyl, piperidinyl, tetrahydropyranyl, and cyclohexyl are optionally substituted with F, $CO_2C(CH_3)_3$, and $C_{(1-4)}$alkyl (including $CH_3$), and up to one additional fluorine atom; provided that $R^6$ is not $CH_2$-phenyl, $CH_2$-pyridinyl, nor $CH_2$-pyrimidinyl;

Q is H, $CF_3$, OH, $SO_2CH_3$, —CN, $NA^3A^4$, $OC_{(1-4)}$alkyl, cyclopropyl, cyclobutyl, oxetanyl, cyclopentyl, tetrahydrofuranyl, pyrazolyl, isoxazolyl, imidazolyl, triazolyl, oxazolyl, thiazolyl, pyrrolidinyl, cyclohexyl, piperidinyl, tetrahydropyranyl, 1,1-dioxo-tetrahydrothiopyran-4-yl, tetrahydrothiopyran-4-yl, phenyl, pyridinyl, or pyrimidinyl; wherein said cyclopropyl, cyclobutyl, cyclopentyl, pyrrolidinyl, piperidinyl, tetrahydropyranyl, and cyclohexyl are optionally substituted with F, $C(O)CH_3$, $CO_2C(CH_3)_3$, and $C_{(1-4)}$ alkyl (including $CH_3$), and up to one additional fluorine atom; and said pyrazolyl, isoxazolyl, imidazolyl, triazolyl, oxazolyl, and thiazolyl are all optionally substituted with one or two $CH_3$ groups; and said oxetanyl is optionally substituted with $CH_3$;

wherein $A^3$ is H, or $C_{(1-4)}$alkyl;

$A^4$ is H, $C_{(1-4)}$alkyl, $CH_2$-cyclopropyl, cyclopropyl, $C_{(1-3)}$alkyl$CF_3$, $CH_2CH_2OCH_2CF_3$, $C(O)C_{(1-2)}$alkyl$CF_3$,

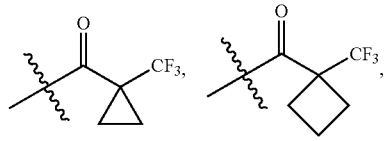 [SMILES: *C(=O)C1(C(F)(F)F)CC1 ; *C(=O)C1(C(F)(F)F)CCC1]

or $C_{(0-1)}$alkyl-trifluoromethyl-cyclohexyl, or $A^3$ and $A^4$ may be taken together with their attached nitrogen to form a ring selected from the group consisting of:

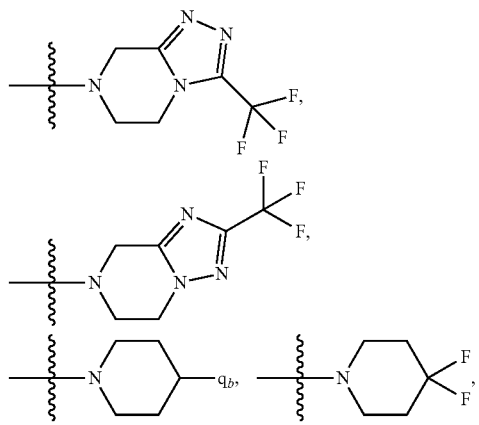

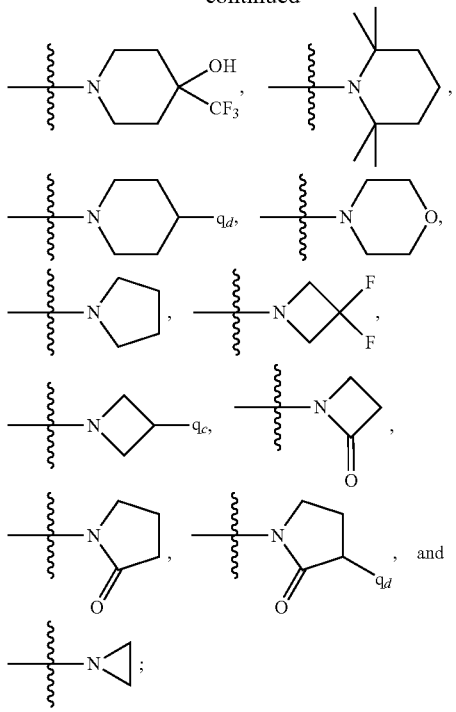

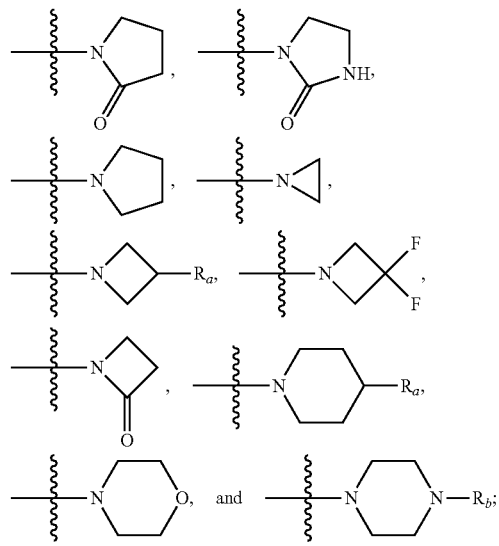

wherein $q_b$ is H, F, CF$_3$, SO$_2$CH$_3$, OC$_{(1-4)}$alkyl (including OCH$_3$), pyrazol-1-yl, 3-trifluoromethyl-pyrazol-1-yl, imidazol-1-yl, or triazolyl;

$q_c$ is H, F, CF$_3$, OC$_{(1-4)}$alkyl, or OH;

$q_d$ is H, CH$_2$CF$_3$, C$_{(1-4)}$alkyl, C(O)CH$_3$, or phenyl; provided that if R$^6$ is OCH$_2$-Q, then Q may not be OH, nor NA$^3$A$^4$;

R$^7$ is H, Cl, —CN, C$_{(1-4)}$alkyl, cyclopropyl, OC$_{(1-4)}$alkylCF$_3$ (including OCH$_2$CF$_3$), OCH$_2$CH$_2$OC$_{(1-4)}$alkyl (including OCH$_2$CH$_2$OCH$_3$), CF$_3$, SCH$_3$, NA$^1$A$^2$, C(O)NA$^1$A$^2$ (including C(O)NHCH$_3$), N(CH$_3$)C$_{(2-4)}$alkylNA$^1$A$^2$ (including N(CH$_3$)CH$_2$CH$_2$NA$^1$A$^2$), OC$_{(2-4)}$alkylNA$^1$A$^2$ (including OCH$_2$CH$_2$NA$^1$A$^2$), OC$_{(1-4)}$alkyl (including OC$_{(1-3)}$alkyl), OCH$_2$-(1-methyl)-imidazol-2-yl, imidazolyl, furyl, pyrazolyl, pyridyl, pyrimidinyl, thiophenyl, 1-methyl-indazolyl, phenyl, or

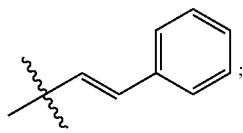 [SMILES: */C=C/c1ccccc1]

wherein said imidazolyl or pyrazolyl is optionally substituted with one CH$_3$ group;

A$^1$ is H, or C$_{(1-4)}$alkyl;

A$^2$ is H, C$_{(1-4)}$alkyl, C$_{(1-4)}$alkylOC$_{(1-4)}$alkyl, C$_{(1-4)}$alkylOH, C(O)C$_{(1-4)}$alkyl (including C(O)C$_{(1-2)}$alkyl), or OC$_{(1-4)}$alkyl (including OCH$_3$); or A$^1$ and A$^2$ may be taken together with their attached nitrogen to form a ring selected from the group consisting of:

R$_a$ is H, F, OC$_{(1-4)}$alkyl (including OCH$_3$), or OH;
R$_b$ is C$_{(1-4)}$alkyl (including CH$_3$), C(O)CH$_3$, or phenyl;
R$^8$ is H, CH$_3$, OCH$_3$, or F;
R$^9$ is H, or F;
and pharmaceutically acceptable salts thereof;

In another embodiment of the invention:

R$^1$ is pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with SO$_2$CH$_3$, C(O)CH$_3$, C(O)NH$_2$, CH$_3$, CH$_2$CH$_3$, CF$_3$, Cl, F, —CN, OCH$_3$, N(CH$_3$)$_2$, —(CH$_2$)$_3$OCH$_3$, SCH$_3$, OH, CO$_2$H, CO$_2$C(CH$_3$)$_3$, or OCH$_2$OCH$_3$; and optionally substituted with up to two additional substituents independently selected from the group consisting of Cl, OCH$_3$, and CH$_3$; and wherein said triazolyl, oxazolyl, isoxazolyl, and thiazolyl are optionally substituted with one or two CH$_3$ groups;

R$^2$ is H, C$_{(1-4)}$alkyl (including CH$_3$), —C≡CH, 1-methyl-1,2,3-triazolyl, pyridyl, pyridyl-N-oxide, 1-methyl-pyrazol-4-yl, pyrimidin-5-yl, pyridazyl, pyrazin-2-yl, isoxazolyl, N-acetyl-azetidin-3-yl, N-methylsulfonyl-azetidin-3-yl, N-Boc-azetidin-3-yl, N-acetyl piperidinyl, N-methylsulfonyl-piperidinyl, 1-H-piperidinyl, N-Boc-piperidinyl, N—C$_{(1-2)}$alkyl-piperidinyl, thiazol-5-yl, 1-(3-methoxypropyl)-imidazol-5-yl, or 1-C$_{(1-2)}$alkyl imidazol-5-yl (including 1-ethyl imidazol-5-yl and 1-methyl imidazol-5-yl); wherein said 1-C$_{(1-2)}$alkyl-imidazol-5-yl (including 1-methyl imidazol-5-yl) is optionally substituted with up to two additional CH$_3$ groups, or one substituent selected from the group consisting of SCH$_3$, and Cl; and said pyridyl, and pyridyl-N-oxide are optionally substituted with up to two substituents independently selected from the group consisting of C(O)NH$_2$, —CN, OCH$_3$, CF$_3$, Cl, and CH$_3$; and said thiazol-5-yl, and said isoxazolyl are optionally substituted with up to two CH$_3$ groups; and said 1-methyl pyrazol-4-yl is optionally substituted with up to two additional CH$_3$ groups;

R$^3$ is H, OH, OCH$_3$, or NH$_2$;
R$^4$ is H, or F;

R⁵ is H, Cl, —CN, CF₃, SCH₃, OC₍₁₋₃₎alkyl, OH, C₍₁₋₄₎ alkyl (including C₍₁₋₂₎alkyl), N(CH₃)OCH₃, NH(C₍₁₋₂₎ alkyl), N(C₍₁₋₂₎alkyl)₂, 4-hydroxy-piperidinyl, azetidin-1-yl, or fur-2-yl; provided that R⁵ is not H if R⁷ is OCH₃;

R⁶ is C₍₁₋₄₎alkyl-Q, OC₍₁₋₄₎alkyl-Q, C(O)NA³A⁴, C(O)OC₍₁₋₄₎alkyl, O-tetrahydropyranyl, O—(N-methyl)-piperidinyl, cyclopropyl, cyclobutyl, pyrrolidinyl, cyclopentyl, tetrahydrofuranyl, cyclohexyl, 1-methyl-1,2,3,6-tetrahydropyridin-4-yl, piperidinyl, or tetrahydropyran-4-yl; wherein said cyclopropyl, cyclobutyl, cyclopentyl, pyrrolidinyl, piperidinyl, and cyclohexyl are optionally substituted with F, CO₂C(CH₃)₃, and CH₃, and up to one additional fluorine atom; provided that R⁶ is not CH₂-phenyl, CH₂-pyridinyl, nor CH₂-pyrimidinyl;

Q is H, CF₃, OH, SO₂CH₃, —CN, NA³A⁴, OC₍₁₋₄₎alkyl, cyclopropyl, cyclobutyl, oxetanyl, cyclopentyl, tetrahydrofuranyl, 1,3-dimethyl-pyrazol-5-yl, 3,5-dimethyl-isoxazol-4-yl, thiazol-2-yl, pyrrolidinyl, cyclohexyl, piperidinyl, tetrahydropyran-4-yl, 1,1-dioxotetrahydrothiopyran-4-yl, tetrahydrothiopyran-4-yl, phenyl, pyridin-3-yl, or pyrimidin-2-yl; wherein said cyclopropyl, cyclobutyl, cyclopentyl, pyrrolidinyl, piperidinyl, and cyclohexyl are optionally substituted with F, C(O)CH₃, CO₂C(CH₃)₃, and CH₃, and up to one additional fluorine atom; and said oxetanyl is optionally substituted with CH₃;

wherein

A³ is H, or C₍₁₋₄₎alkyl (including CH₃);

A⁴ is H, C₍₁₋₄₎alkyl (including CH₃), CH₂-cyclopropyl, cyclopropyl, C₍₁₋₃₎alkylCF₃, CH₂CH₂OCH₂CF₃, C(O)C₍₁₋₂₎alkylCF₃,

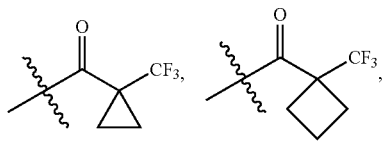 [SMILES: *C(=O)C1(C(F)(F)F)CC1 ; *C(=O)C1(C(F)(F)F)CCC1]

or C₍₀₋₁₎alkyl-trifluoromethyl-cyclohexyl, or

A³ and A⁴ may be taken together with their attached nitrogen to form a ring selected from the group consisting of:

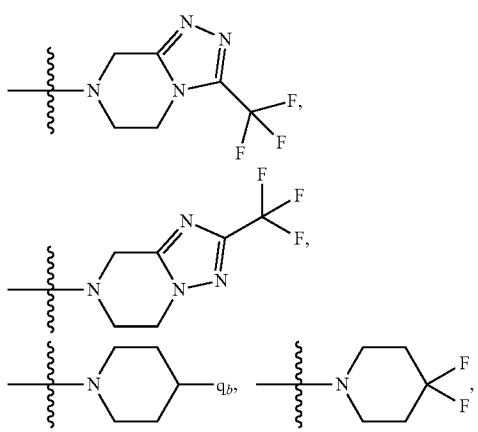

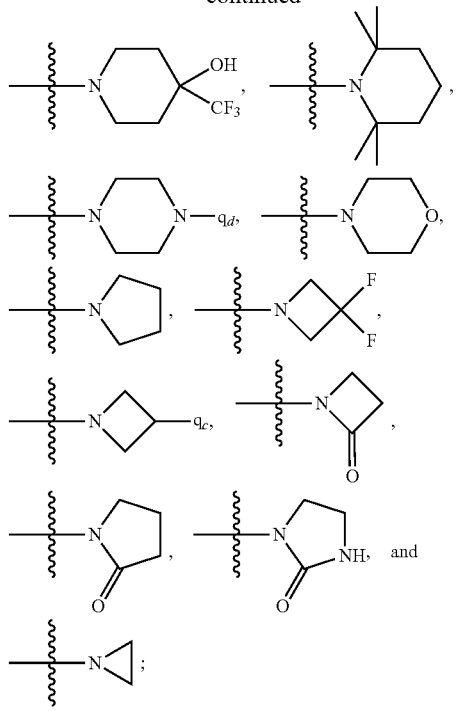

wherein q_b is H, F, CF₃, SO₂CH₃, OCH₃, pyrazol-1-yl, 3-trifluoromethyl-pyrazol-1-yl, or imidazol-1-yl;

q_c is H, F, or CF₃, q_d is CH₂CF₃; provided that if R⁶ is OCH₂-Q, then Q may not be OH, nor NA³A⁴;

R⁷ is H, Cl, —CN, C₍₁₋₄₎alkyl, cyclopropyl, OCH₂CF₃, OCH₂CH₂OCH₃, CF₃, SCH₃, NA¹A², C(O)NHCH₃, N(CH₃)CH₂CH₂NA¹A², OCH₂CH₂NA¹A², OC₍₁₋₃₎alkyl (including OC₍₁₋₂₎alkyl), OCH₂-(1-methyl)-imidazol-2-yl, imidazol-2-yl, pyrazol-4-yl, pyrid-3-yl, pyrimidin-5-yl, thiophen-3-yl, 1-methyl-indazol-5-yl, 1-methyl-indazol-6-yl, fur-2-yl, phenyl, or

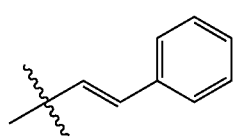 [SMILES: */C=C/c1ccccc1]

wherein said imidazol-2-yl or pyrazol-4-yl are optionally substituted with one CH₃ group;

A¹ is H, or C₍₁₋₄₎alkyl (including C₍₁₋₂₎alkyl);

A² is H, C₍₁₋₄₎alkyl (including C₍₁₋₂₎alkyl), C₍₁₋₄₎alkyl OC₍₁₋₄₎alkyl (including CH₂CH₂OCH₃), C₍₁₋₄₎alkylOH, C(O)C₍₁₋₂₎alkyl, or OCH₃; or A¹ and A² may be taken together with their attached nitrogen to form a ring selected from the group consisting of:

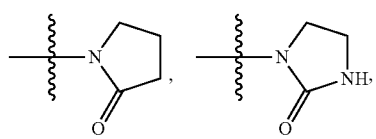

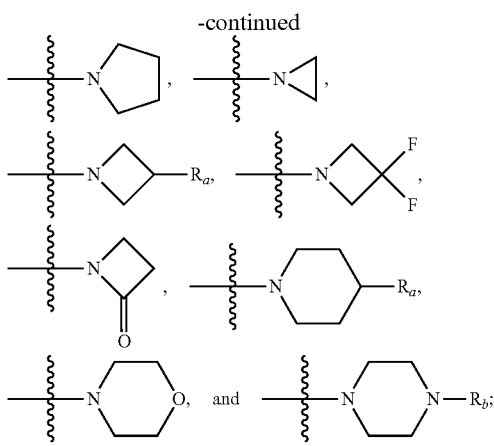

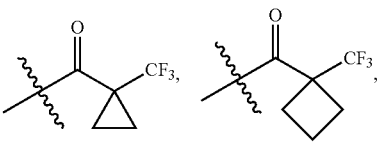 [SMILES: *C(=O)C1(C(F)(F)F)CC1 ; *C(=O)C1(C(F)(F)F)CCC1]

$R_a$ is H, F, OCH$_3$, or OH;
$R_b$ is CH$_3$, or phenyl;
$R^8$ is H, CH$_3$, OCH$_3$, or F;
$R^9$ is H, or F;
and pharmaceutically acceptable salts thereof;
In another embodiment of the invention
$R^1$ is imidazolyl, pyrimidinyl, triazolyl, tetrahydropyranyl, thiazolyl, pyridyl, piperidinyl, phenyl, or oxazolyl; wherein said piperidinyl, pyridyl, imidazolyl, and phenyl are optionally substituted with SO$_2$CH$_3$, C(O)CH$_3$, CH$_3$, CF$_3$, Cl, F, —CN, OCH$_3$, or N(CH$_3$)$_2$; and optionally substituted with up to one additional group independently selected from the group consisting of Cl, OCH$_3$, and CH$_3$; and wherein said triazolyl, oxazolyl, and thiazolyl are optionally substituted with one or two CH$_3$ groups;
$R^2$ is H, CH$_3$, —C≡CH, 1-methyl-1,2,3-triazol-5-yl, pyrid-3-yl, 2-trifluoromethyl-pyrid-4-yl, 1-methyl-pyrazol-4-yl, 1,3,5-trimethyl-pyrazol-4-yl, thiazol-5-yl, N-acetyl-azetidin-3-yl, N-methylsulfonyl-azetidin-3-yl, N-Boc-azetidin-3-yl, N-acetyl-piperidin-4-yl, N-Boc-piperidin-4-yl, 1-H-piperidin-4-yl, N-methylsulfonyl-piperidin-4-yl, 1,2-dimethyl-imidazol-5-yl, or 1-methyl-imidazol-5-yl;
$R^3$ is OH;
$R^4$ is H;
$R^5$ is H, Cl, —CN, CF$_3$, C$_{(1-2)}$alkyl, OH, N(CH$_3$)OCH$_3$, OCH$_3$, azetidin-1-yl, or fur-2-yl; provided that $R^5$ is not H if $R^7$ is OCH$_3$;
$R^6$ is C$_{(1-4)}$alkyl-Q, OC$_{(1-4)}$alkyl-Q, C(O)NA$^3$A$^4$, C(O)OC$_{(1-4)}$alkyl, O-tetrahydropyranyl, O—(N-methyl)-piperidinyl, cyclopentyl, cyclohexyl, 1-methyl-1,2,3,6-tetrahydropyridin-4-yl, or tetrahydropyran-4-yl; provided that $R^6$ is not CH$_2$-phenyl, CH$_2$-pyridinyl, nor CH$_2$-pyrimidinyl;
Q is H, CF$_3$, OH, SO$_2$CH$_3$, NA$^3$A$^4$, OC$_{(1-4)}$alkyl, cyclopropyl, 1-methyl-cyclopropyl, oxetanyl, 3-methyl-oxetanyl, tetrahydrofuranyl, 1,3-dimethyl-pyrazol-5-yl, 3,5-dimethyl-isoxazol-4-yl, thiazol-2-yl, N-methyl-pyrrolidin-2-yl, cyclohexyl, N-acetyl-piperidin-4-yl, N-Boc-piperidin-4-yl, 1-H-piperidin-4-yl, tetrahydropyran-4-yl, 1,1-dioxo-tetrahydrothiopyran-4-yl, tetrahydrothiopyran-4-yl, phenyl, pyridin-3-yl, or pyrimidin-2-yl; wherein said cyclopropyl, and said cyclohexyl are optionally substituted with up to two fluorine atoms;

wherein
$A^3$ is H, or CH$_3$;
$A^4$ is CH$_3$, CH$_2$-cyclopropyl, cyclopropyl, C$_{(1-3)}$alkylCF$_3$, CH$_2$CH$_2$OCH$_2$CF$_3$, C(O)C$_{(1-2)}$alkylCF$_3$,

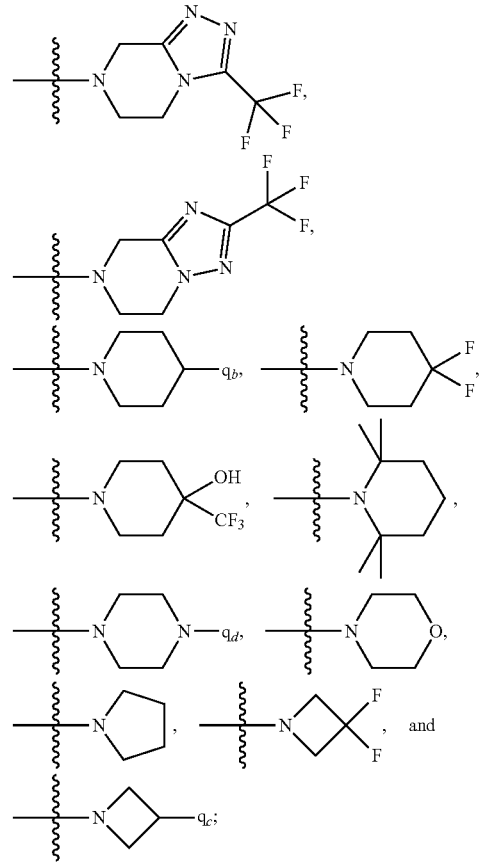

or C$_{(0-1)}$alkyl-trifluoromethyl-cyclohexyl, or A$^3$ and A$^4$ may be taken together with their attached nitrogen to form a ring selected from the group consisting of:

wherein
$q_b$ is H, F, CF$_3$, SO$_2$CH$_3$, pyrazol-1-yl, or 3-trifluoromethyl-pyrazol-1-yl;
$q_c$ is H, F, or CF$_3$,
$q_d$ is CH$_2$CF$_3$;
provided that if $R^6$ is OCH$_2$-Q, then Q may not be OH, nor NA$^3$A$^4$;
$R^7$ is Cl, —CN, CF$_3$, C$_{(1-4)}$alkyl, cyclopropyl, NA$^1$A$^2$, C(O)NHCH$_3$, OCH$_2$CH$_2$OCH$_3$, 1-methyl imidazol-2-yl, 1-methyl pyrazol-4-yl, OC$_{(1-2)}$alkyl (including OCH$_3$), pyrimidin-5-yl, thiophen-3-yl, 1-methyl-indazol-5-yl, 1-methyl-indazol-6-yl, fur-2-yl, phenyl, or

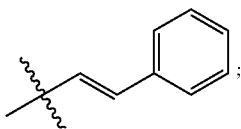 [SMILES: */C=C/c1ccccc1]

A[1] is C$_{(1-2)}$alkyl;
A[2] is C$_{(1-2)}$alkyl, CH$_2$CH$_2$OCH$_3$, or OCH$_3$; or A[1] and A[2] may be taken together with their attached nitrogen to form a ring which is:

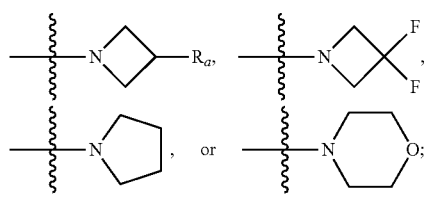

R$_a$ is H, OH, OCH$_3$, F;
R[8] is H, CH$_3$, OCH$_3$, or F;
R[9] is H;
and pharmaceutically acceptable salts thereof.

In another embodiment of the invention
R[1] is imidazolyl, triazolyl, tetrahydropyranyl, thiazolyl, pyridyl, or phenyl; wherein said pyridyl, imidazolyl, and phenyl are optionally substituted with one substituent selected from the group consisting of CH$_3$, CF$_3$, Cl, and —CN; and optionally substituted with up to one additional CH$_3$; and wherein said triazolyl, and thiazolyl are optionally substituted with one or two CH$_3$ groups;
R[2] is H, CH$_3$, 1-methyl-1,2,3-triazol-5-yl, pyrid-3-yl, 2-trifluoromethyl-pyrid-4-yl, 1,3,5-trimethyl-pyrazol-4-yl, N-acetyl-azetidin-3-yl, N-methylsulfonyl-azetidin-3-yl, N-Boc-azetidin-3-yl, N-acetyl-piperidin-4-yl, N-Boc-piperidin-4-yl, 1-H-piperidin-4-yl, N-methylsulfonyl-piperidin-4-yl, 1,2-dimethyl-imidazol-5-yl, or 1-methyl-imidazol-5-yl;
R[3] is OH;
R[4] is H;
R[5] is H, Cl, —CN, CF$_3$, C$_{(1-2)}$alkyl, OCH$_3$, azetidin-1-yl, or fur-2-yl; provided that R[5] is not H if R[7] is OCH$_3$;
R[6] is C$_{(1-4)}$alkyl-Q, OC$_{(1-4)}$alkyl-Q, C(O)NA$^3$A$^4$, C(O)OC$_{(1-4)}$alkyl, O-tetrahydropyranyl, O—(N-methyl)-piperidinyl, cyclopentyl, cyclohexyl, 1-methyl-1,2,3,6-tetrahydropyridin-4-yl, or tetrahydropyran-4-yl; provided that R[6] is not CH$_2$-phenyl, CH$_2$-pyridinyl, nor CH$_2$-pyrimidinyl;
Q is H, CF$_3$, OH, SO$_2$CH$_3$, NA$^3$A$^4$, OC$_{(1-4)}$alkyl, cyclopropyl, 1-methyl-cyclopropyl, oxetanyl, 3-methyl-oxetanyl, tetrahydrofuranyl, 1,3-dimethyl-pyrazol-5-yl, 3,5-dimethyl-isoxazol-4-yl, thiazol-2-yl, N-methyl-pyrrolidin-2-yl, cyclohexyl, N-acetyl-piperidin-4-yl, N-Boc-piperidin-4-yl, 1-H-piperidin-4-yl, tetrahydropyran-4-yl, 1,1-dioxo-tetrahydrothiopyran-4-yl, tetrahydrothiopyran-4-yl, phenyl, pyridin-3-yl, or pyrimidin-2-yl; wherein said cyclopropyl, and said cyclohexyl are optionally substituted with up to two fluorine atoms;
wherein
A[3] is H, or CH$_3$;
A[4] is CH$_3$, CH$_2$-cyclopropyl, cyclopropyl, C$_{(1-3)}$alkylCF$_3$, CH$_2$CH$_2$OCH$_2$CF$_3$, C(O)C$_{(1-2)}$alkylCF$_3$,

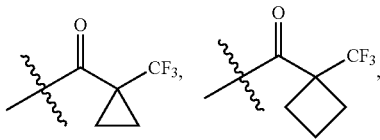 [SMILES: *C(=O)C1(C(F)(F)F)CC1 ; *C(=O)C1(C(F)(F)F)CCC1]

C$_{(0-1)}$alkyl-trifluoromethyl-cyclohexyl, or A[3] and A[4] may be taken together with their attached nitrogen to form a ring selected from the group consisting of:

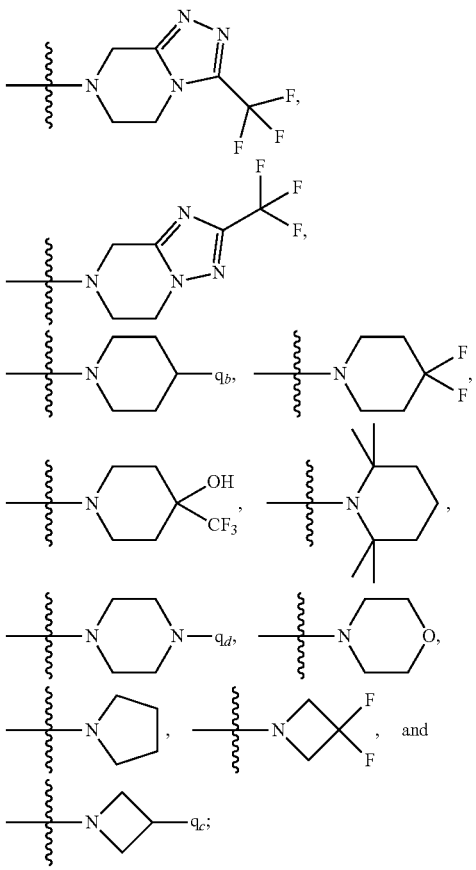

wherein
q$_b$ is H, F, CF$_3$, SO$_2$CH$_3$, pyrazol-1-yl, or 3-trifluoromethyl-pyrazol-1-yl;
q$_c$ is H, F, or CF$_3$,
q$_d$ is CH$_2$CF$_3$;
provided that if R[6] is OCH$_2$-Q, then Q may not be OH, nor NA$^3$A$^4$;
R[7] is Cl, CF$_3$, CH$_2$CH$_3$, cyclopropyl, OCH$_3$, pyrimidin-5-yl, thiophen-3-yl, 1-methyl-indazol-5-yl, 1-methyl-indazol-6-yl, fur-2-yl, azetidin-1-yl, phenyl, or

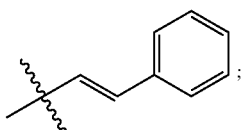 [SMILES: */C=C/c1ccccc1]

R[8] is H, or CH$_3$;
R[9] is H;
and pharmaceutically acceptable salts thereof.

Another embodiment of the invention is a compound selected from the group consisting of:
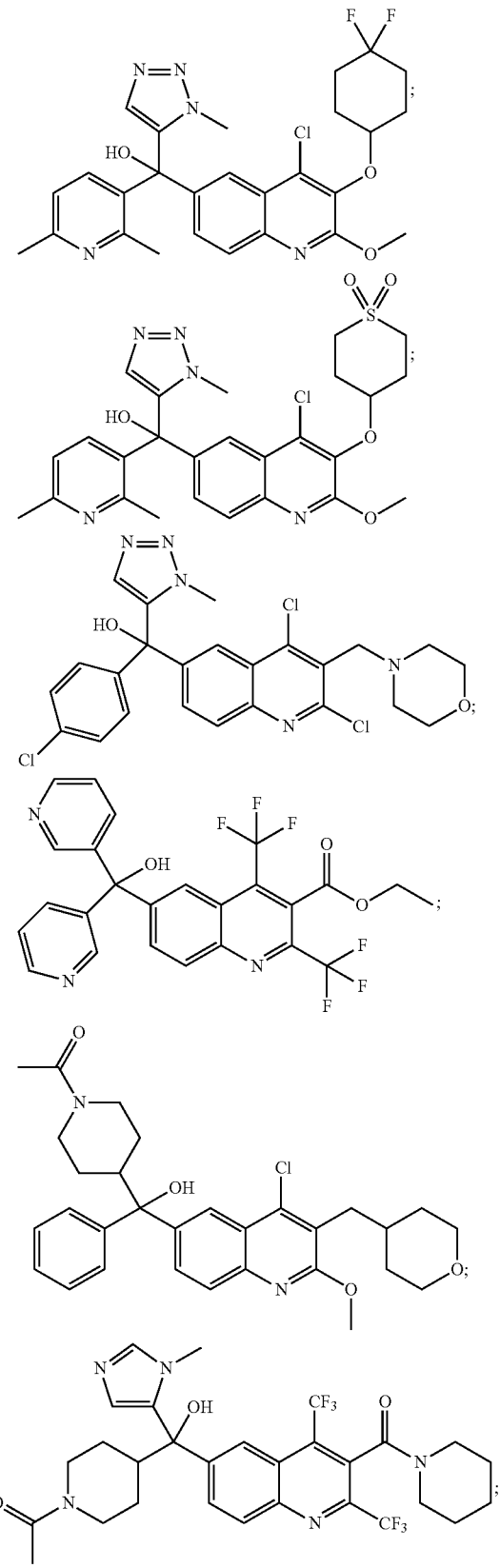
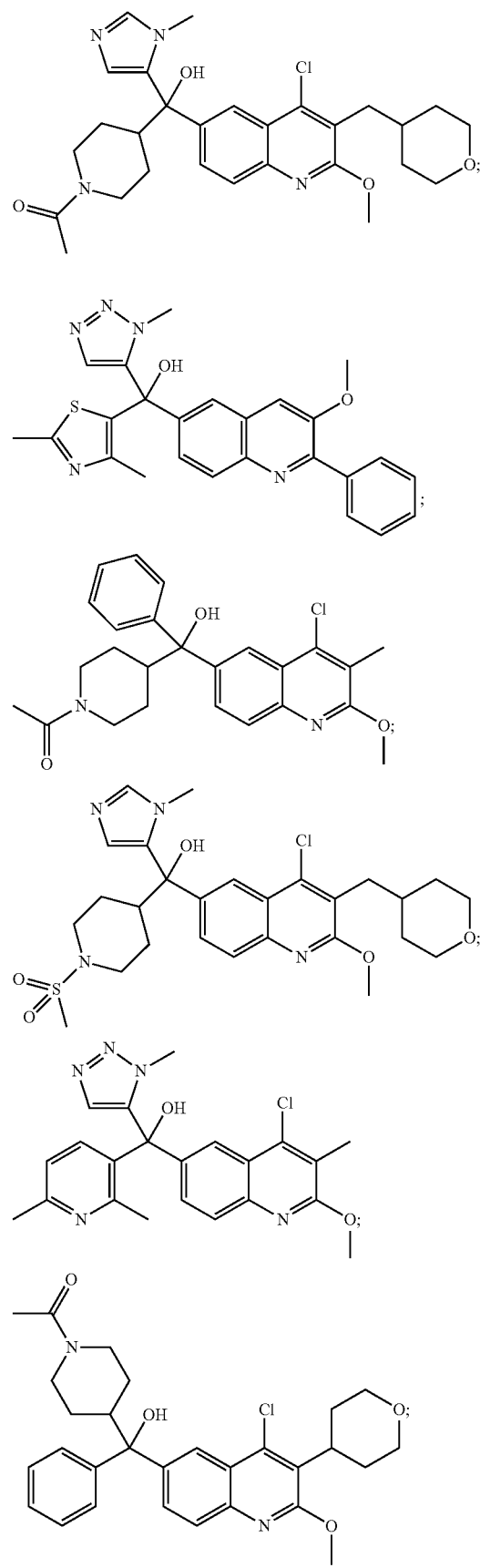

-continued
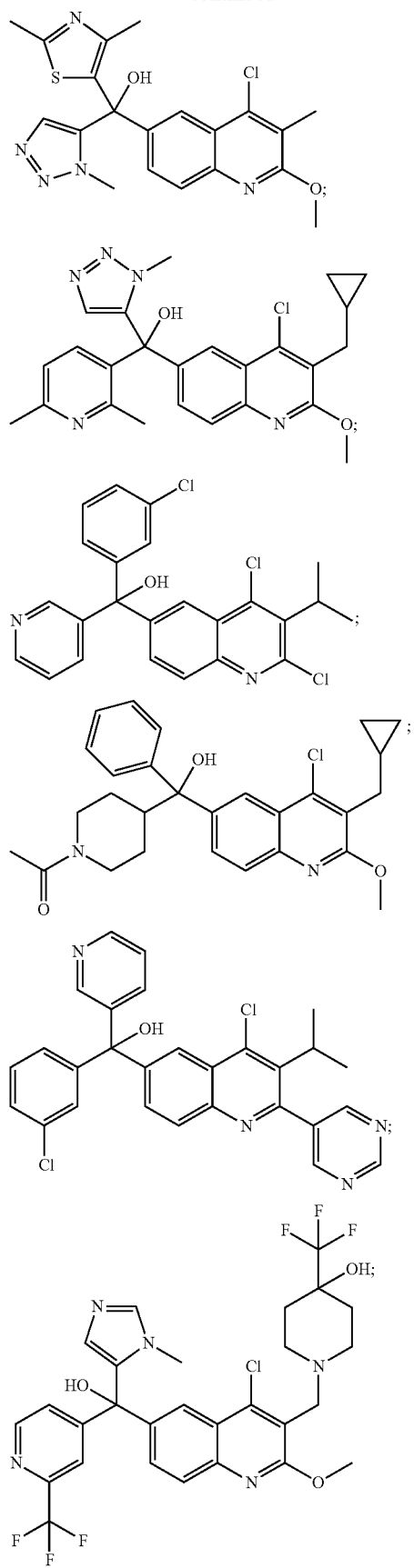
-continued
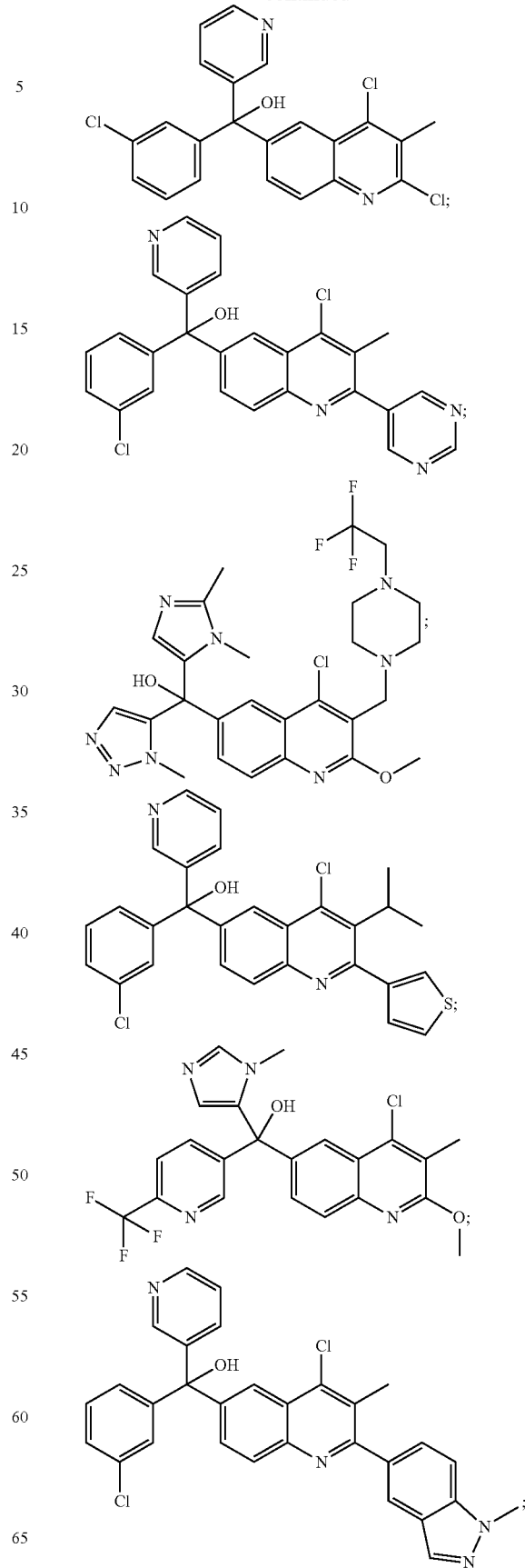

31
-continued
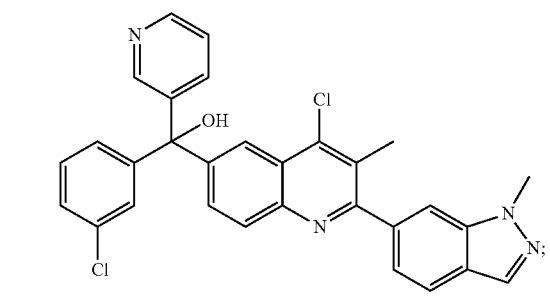
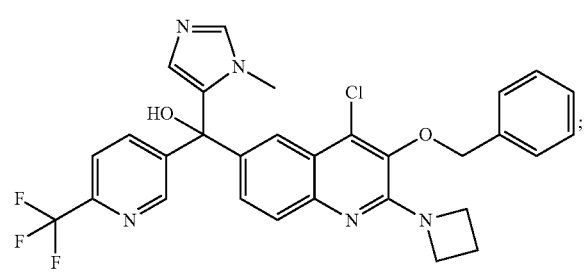
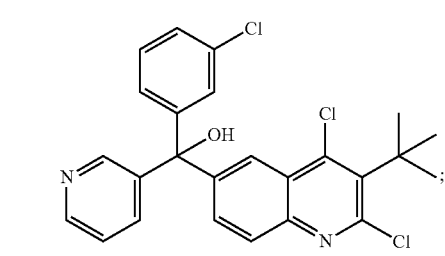
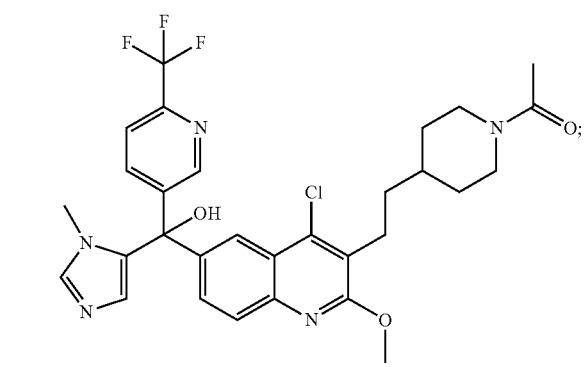
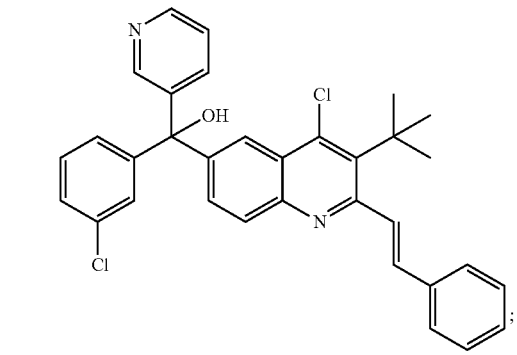
32
-continued
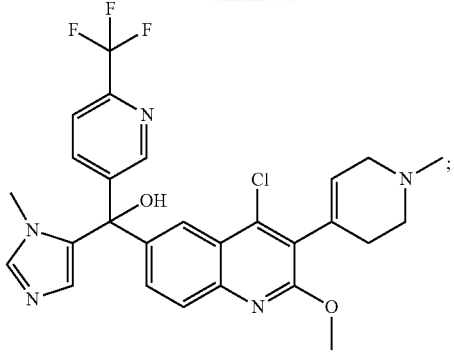
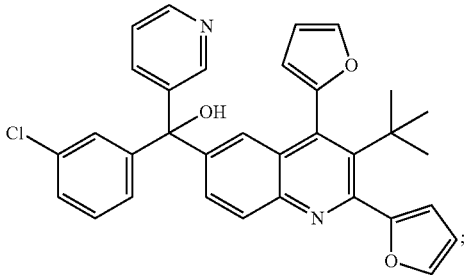
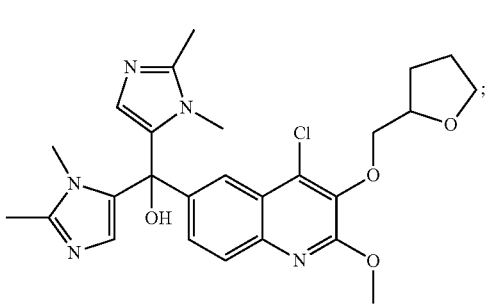
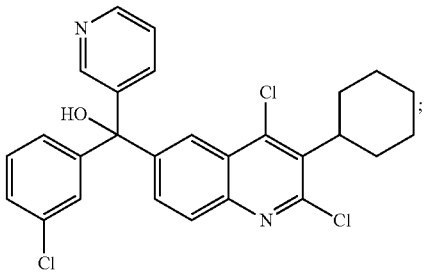
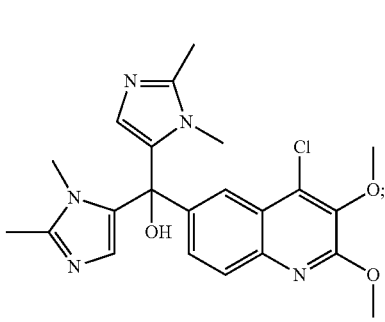

33
-continued
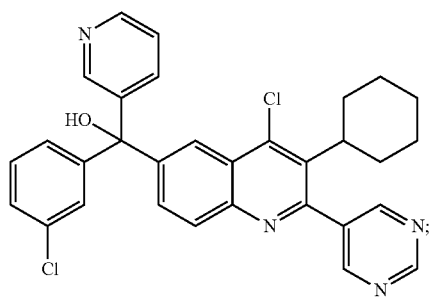
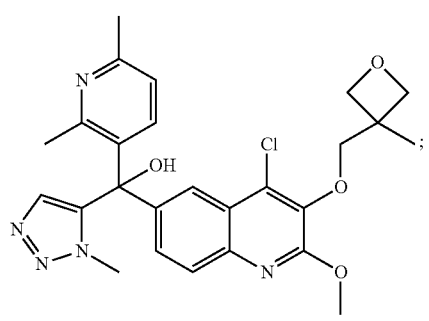
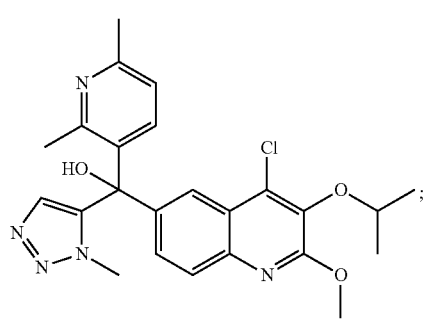
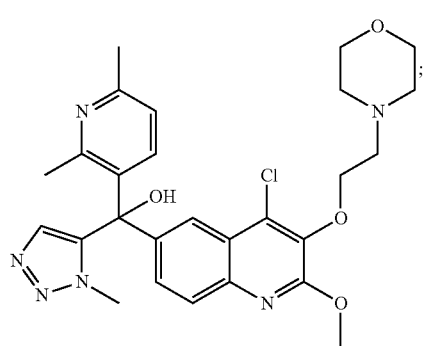
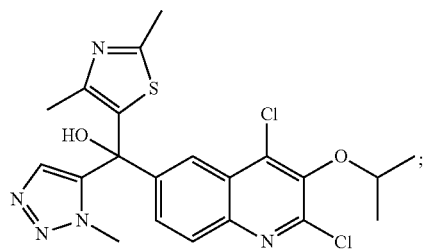
34
-continued
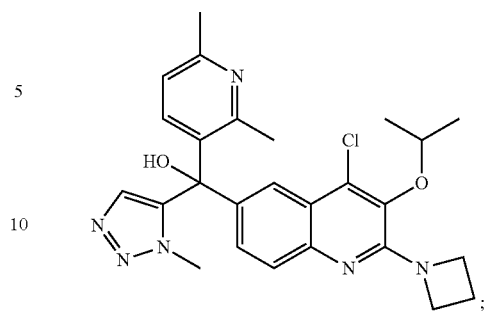
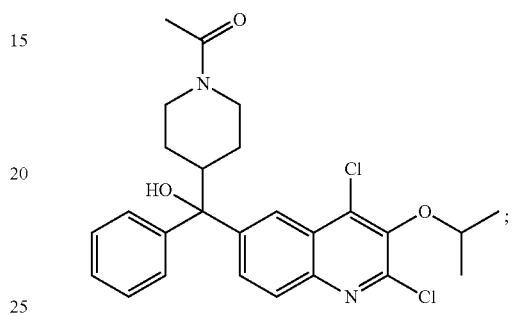
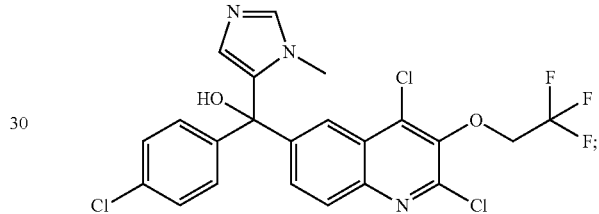
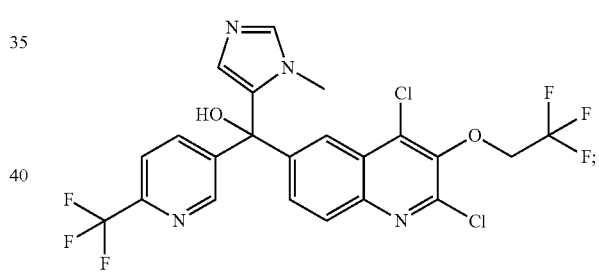
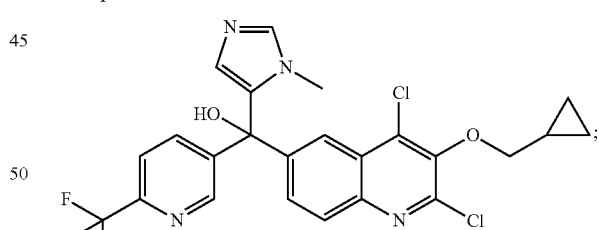
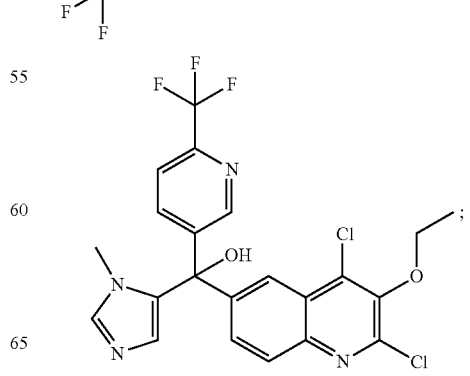

35
-continued
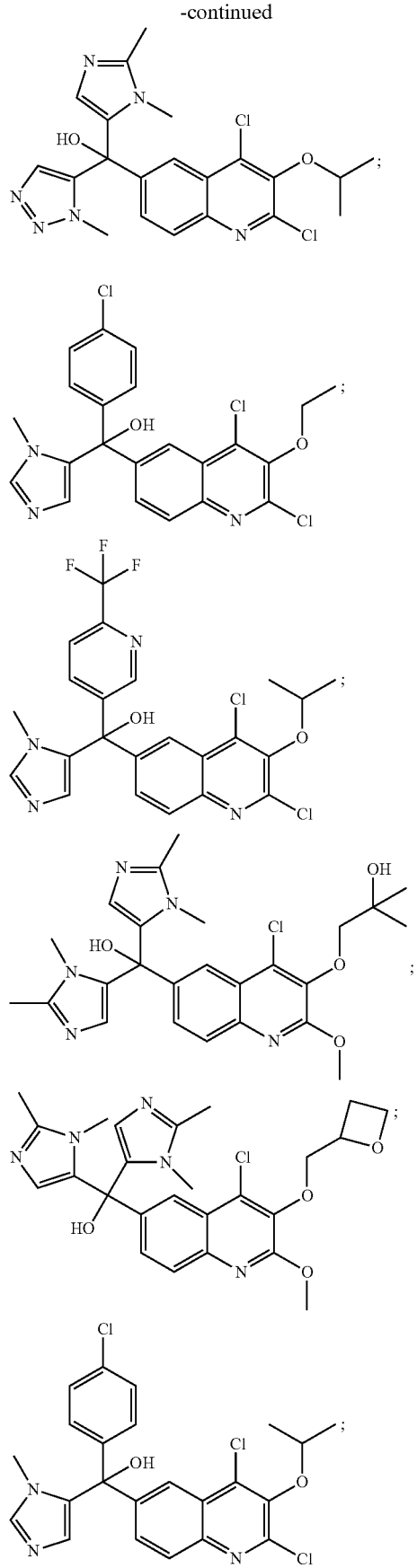
36
-continued
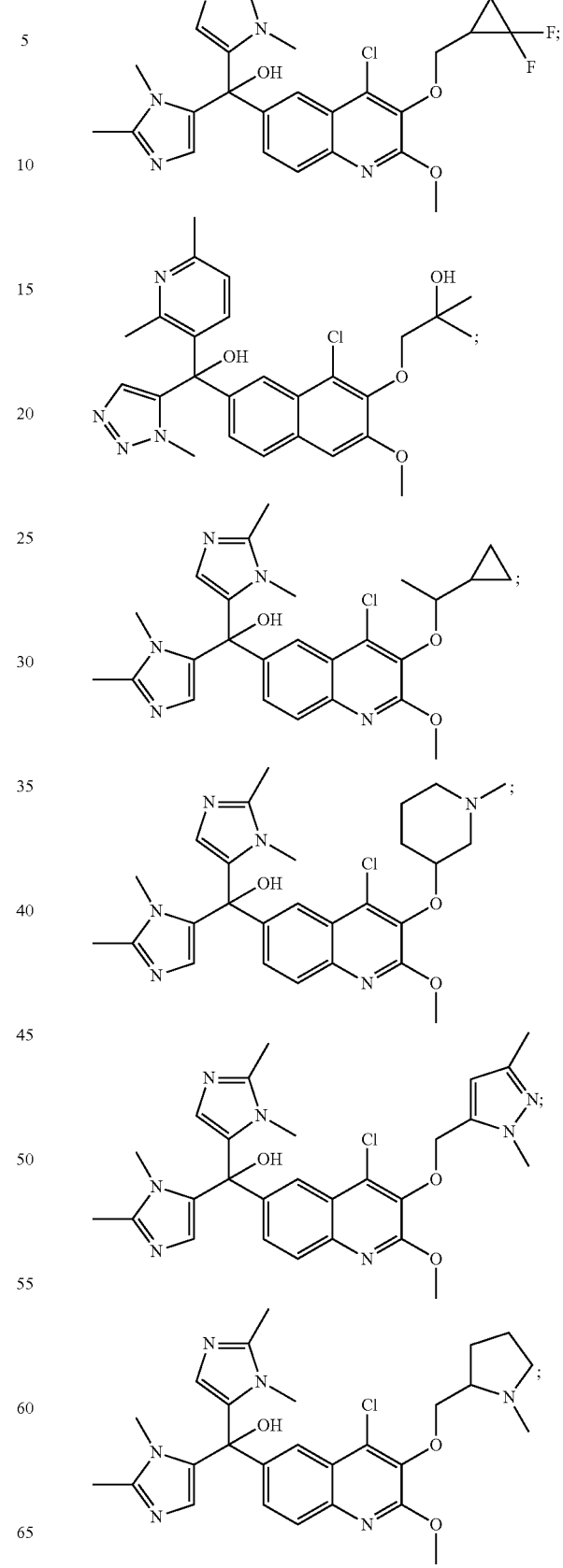

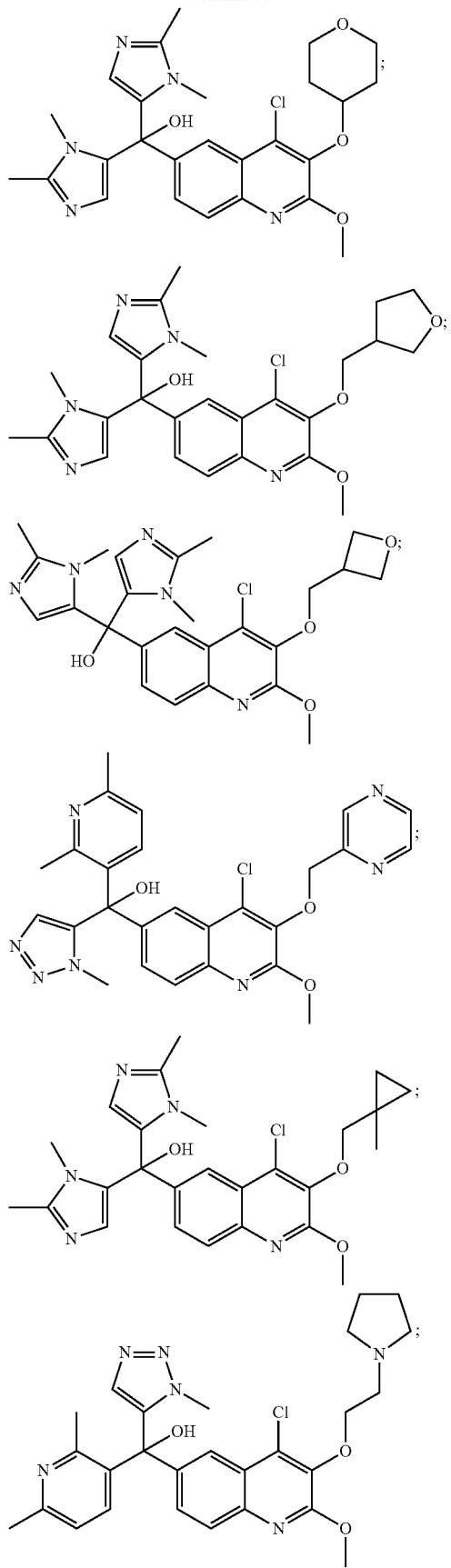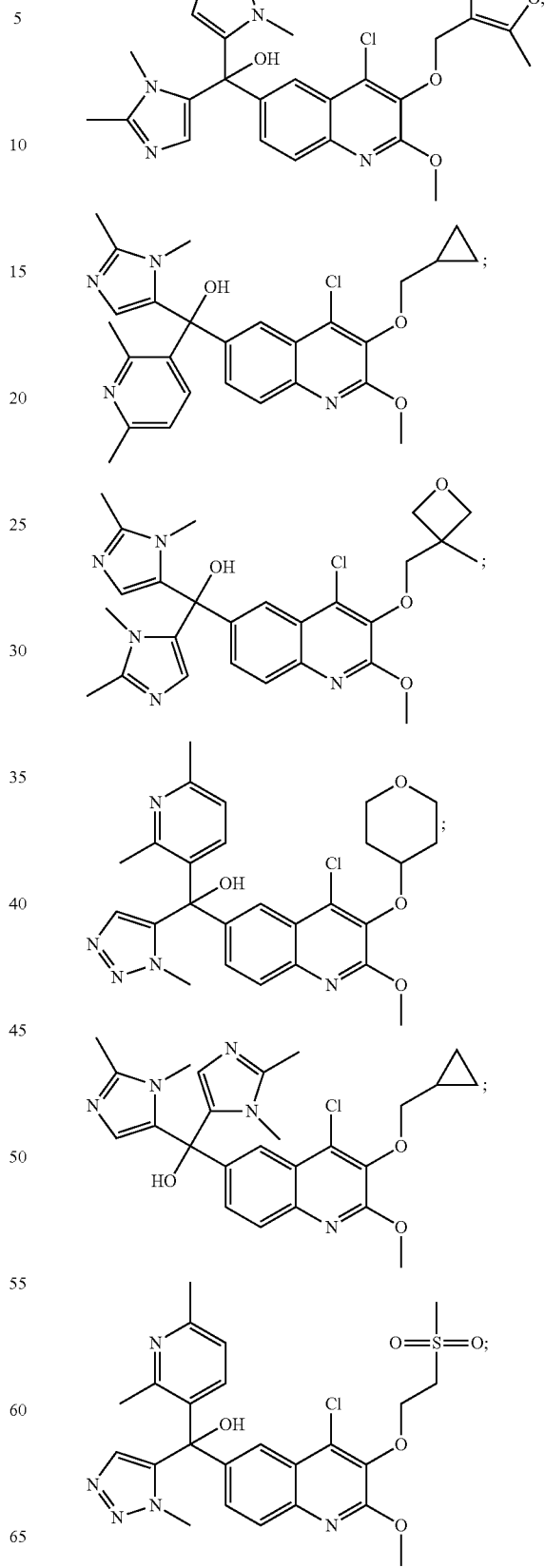

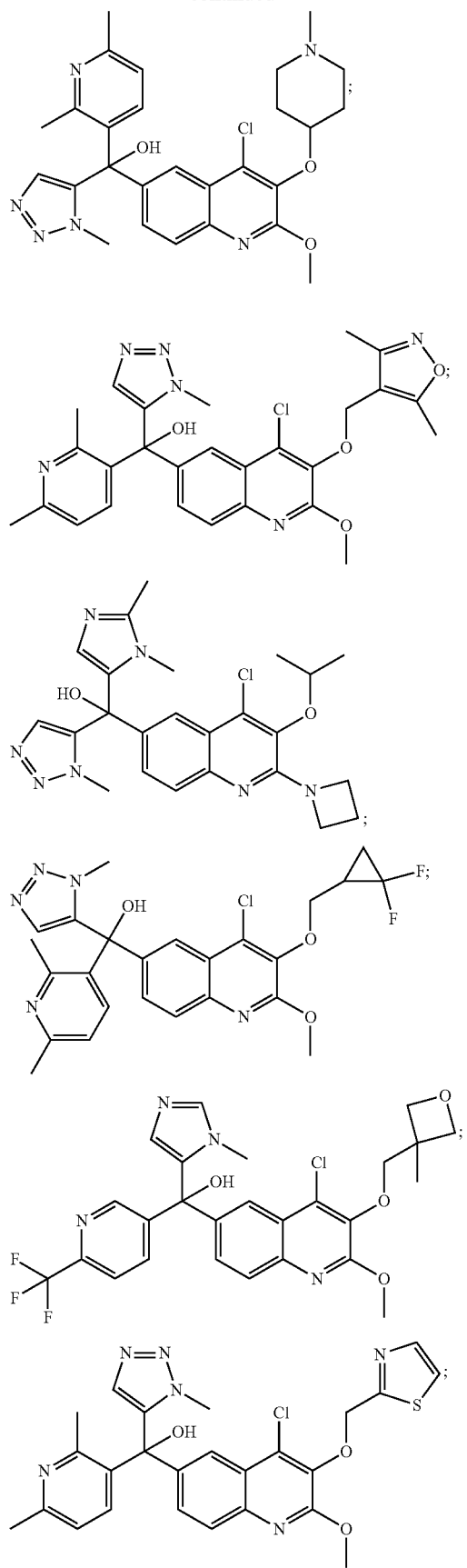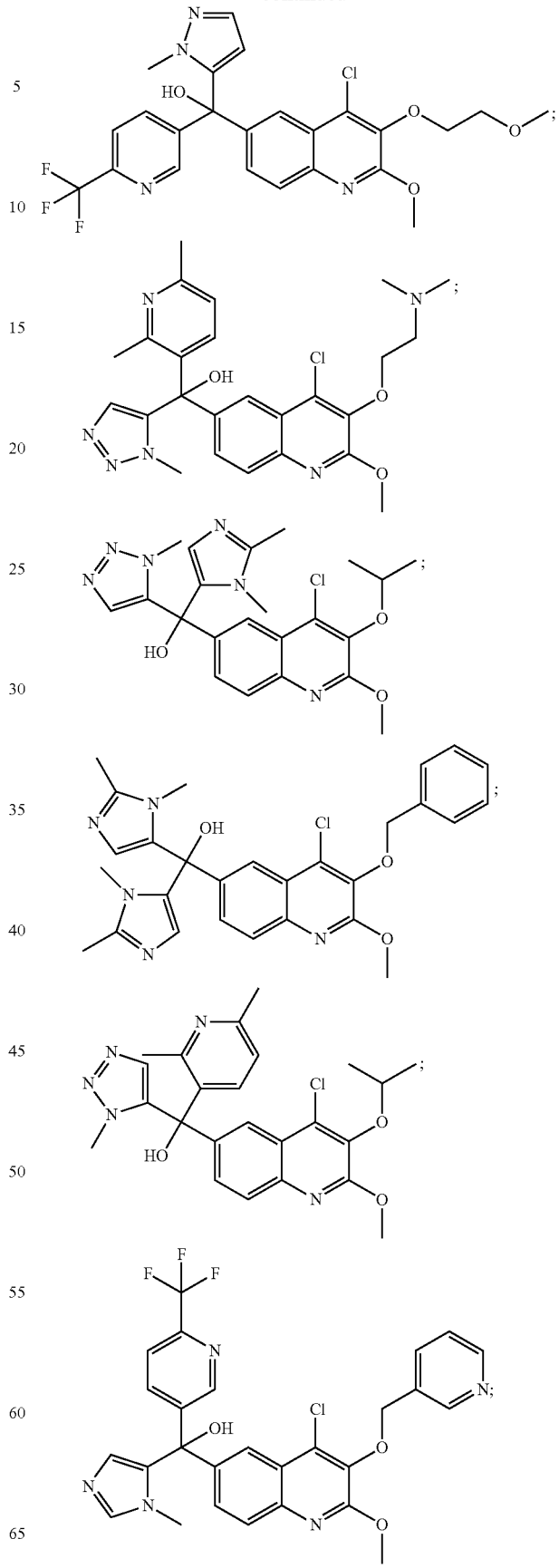

-continued
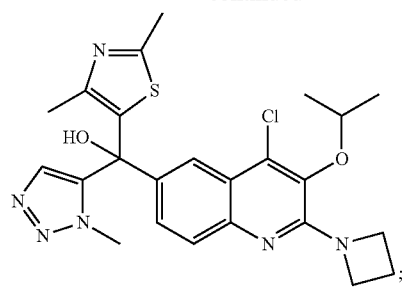
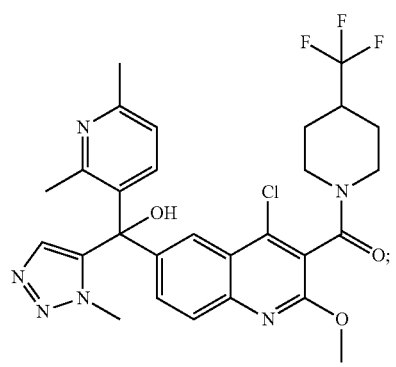
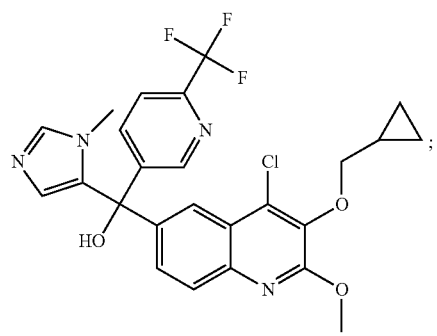
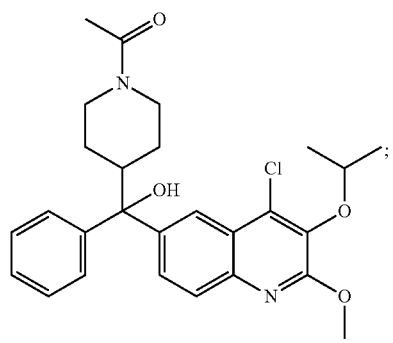
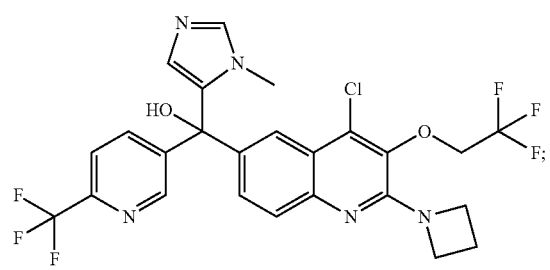
-continued
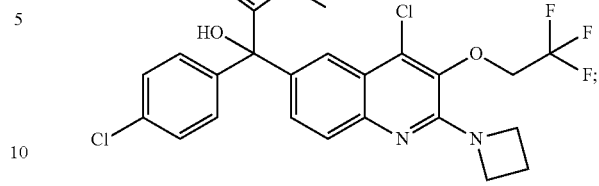
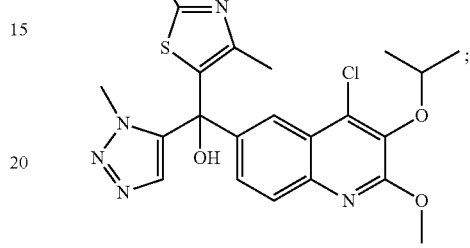
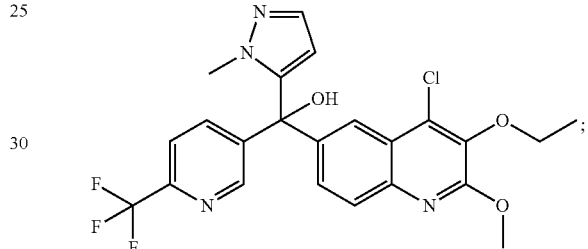
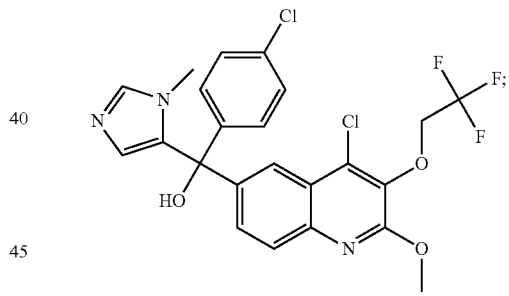
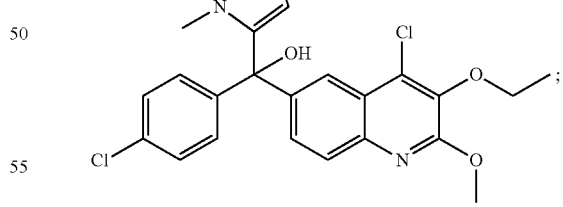
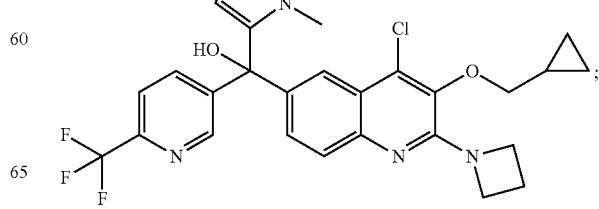

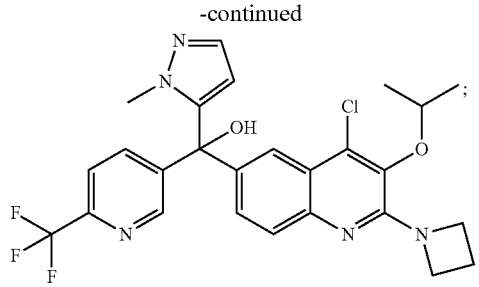
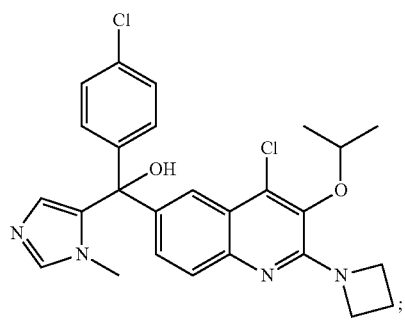
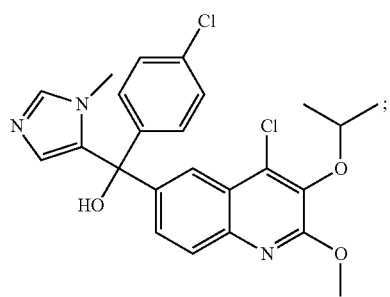
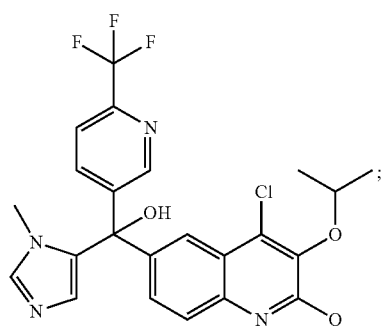
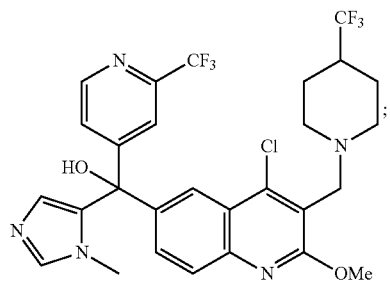
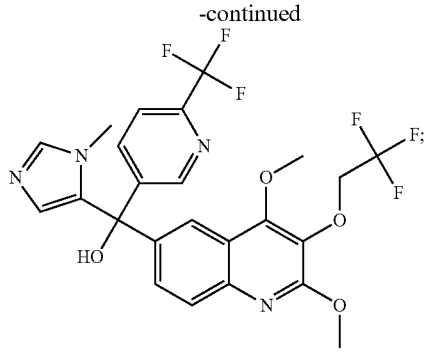
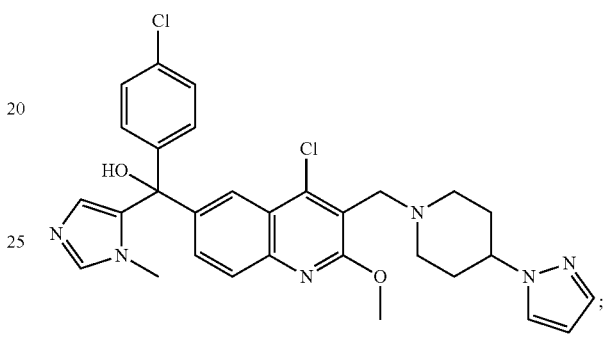
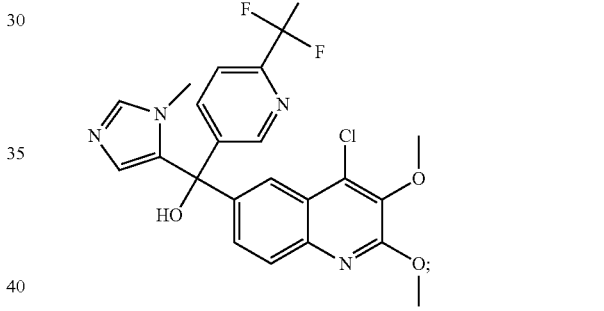
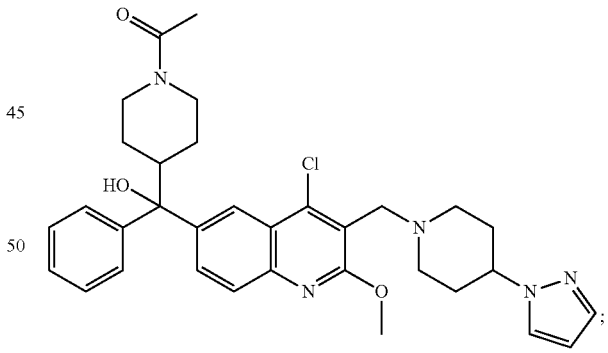
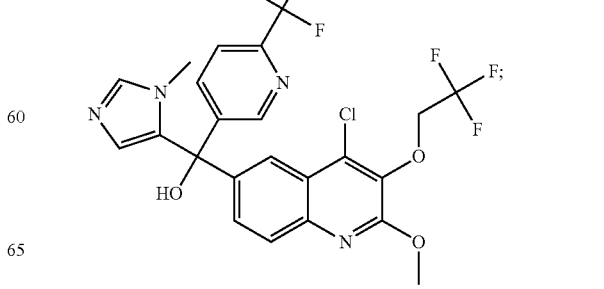

-continued
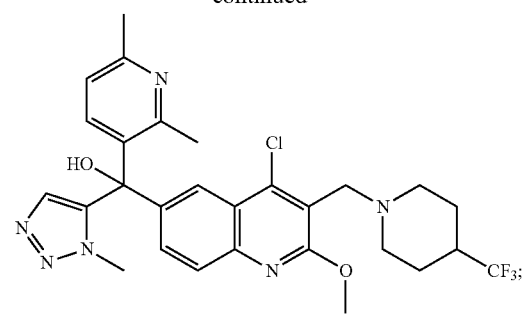
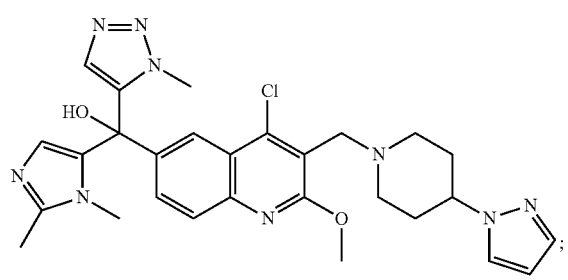
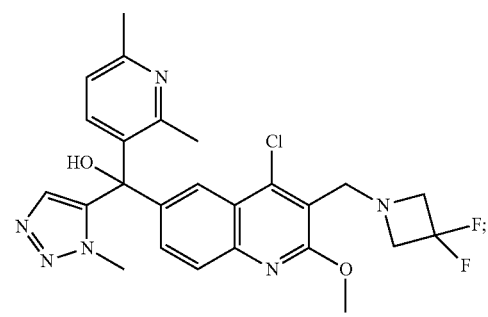
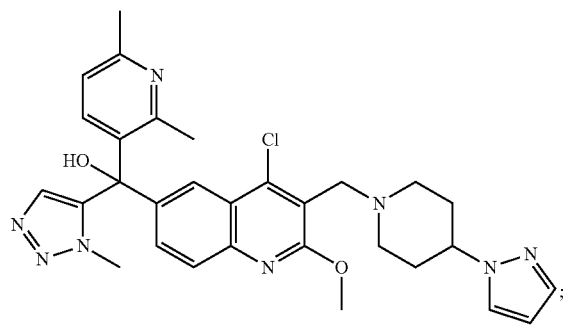
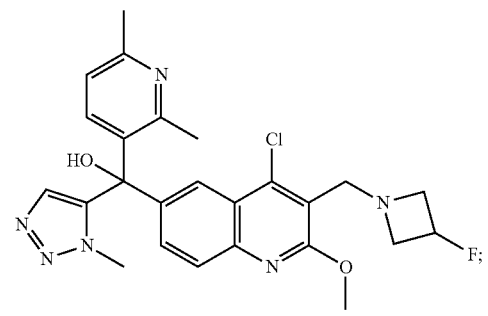
-continued
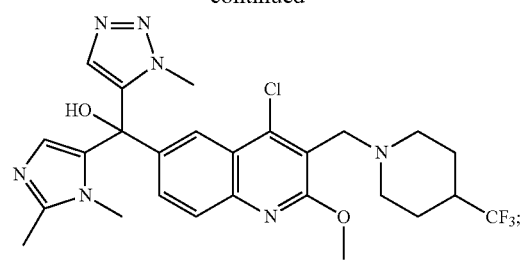
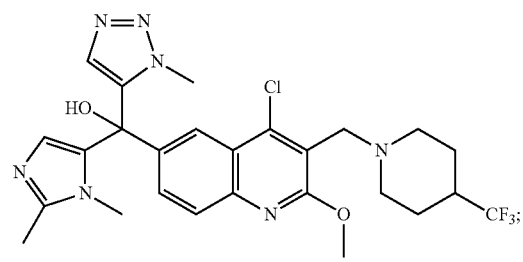
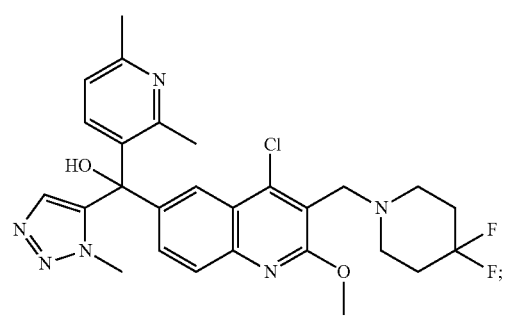
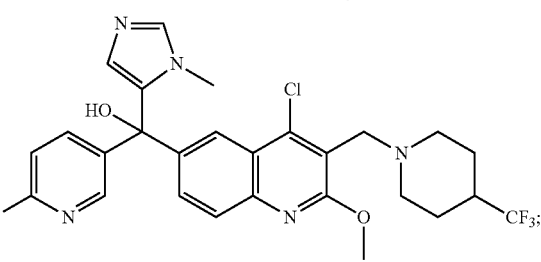
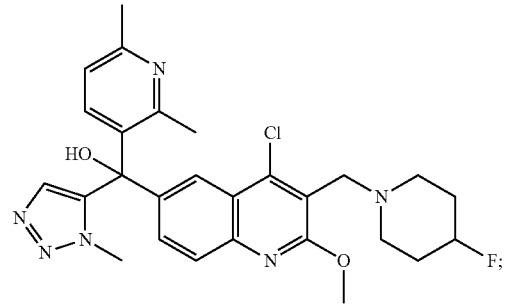
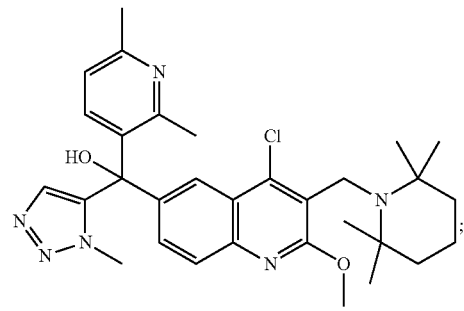

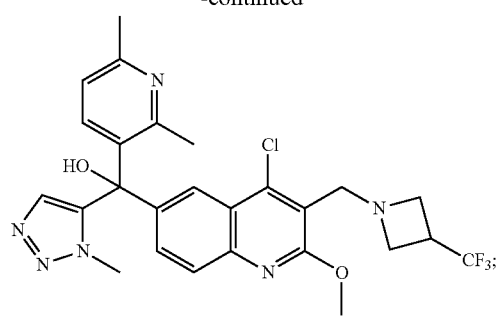
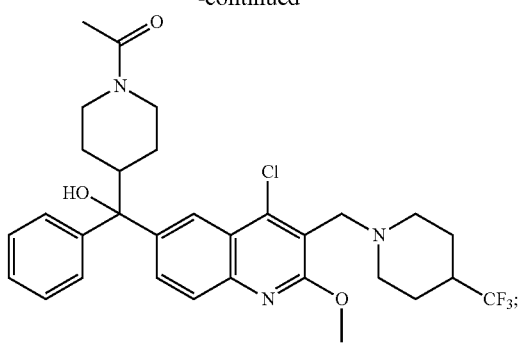
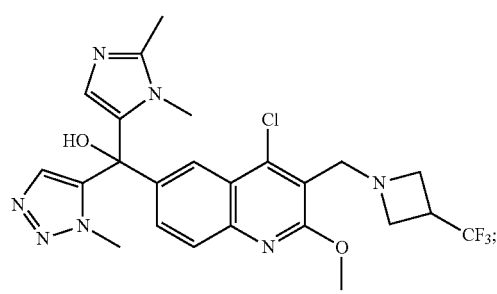
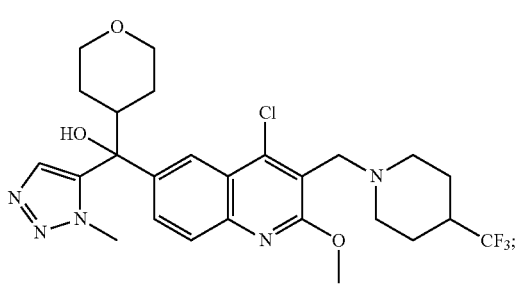
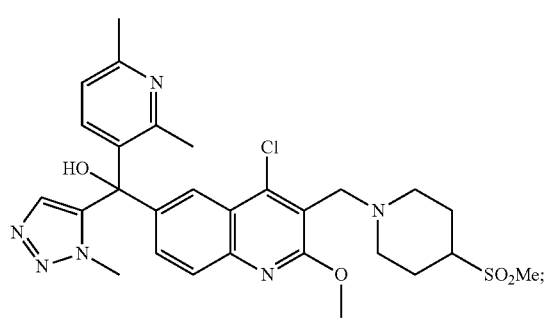
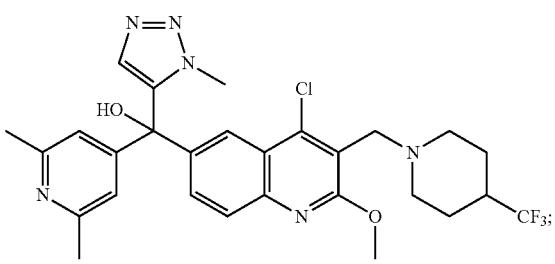
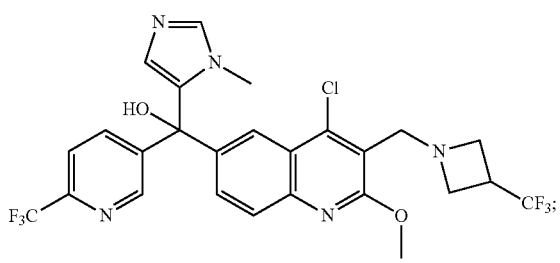
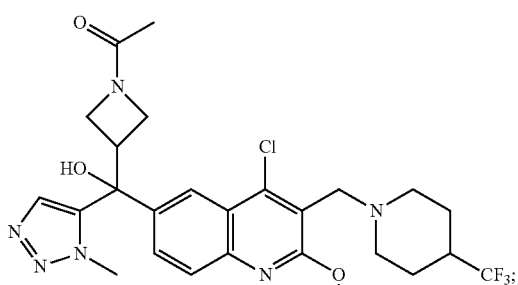
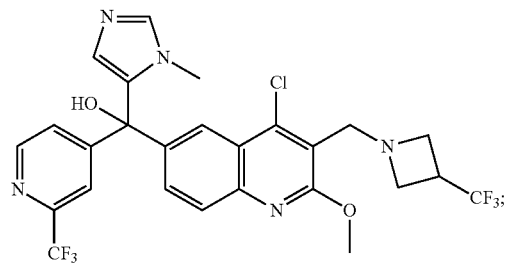
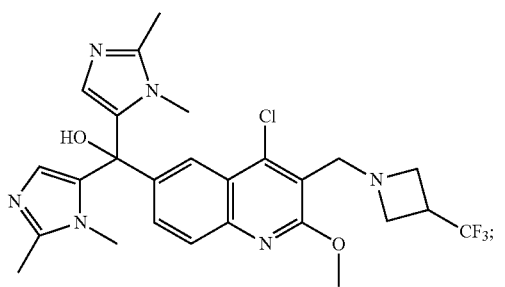

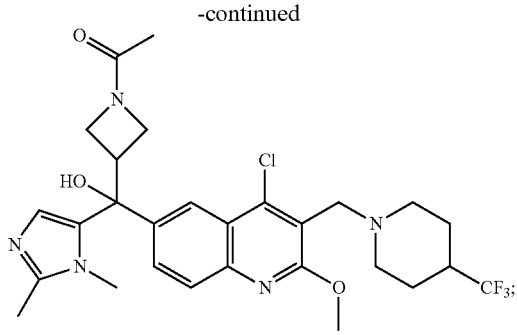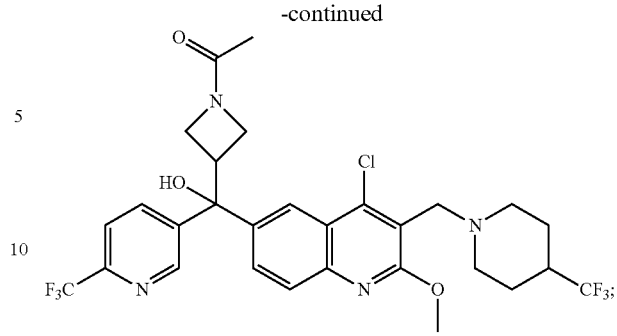

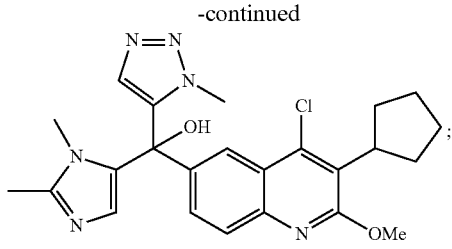
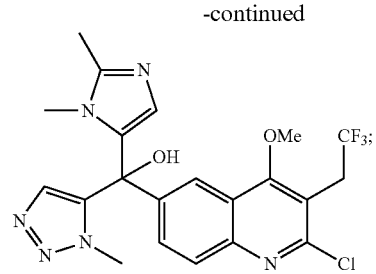
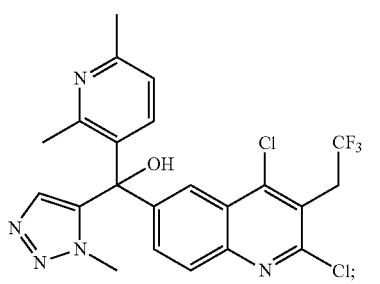
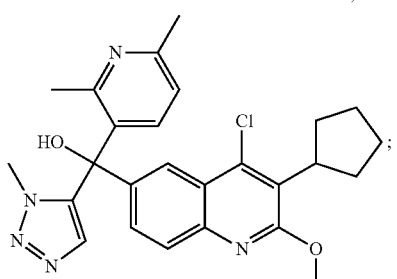
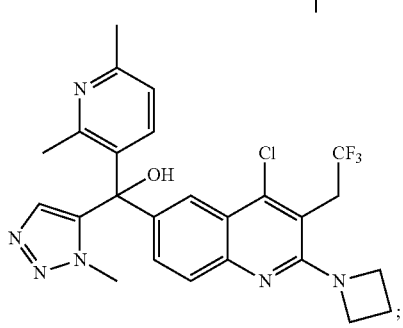
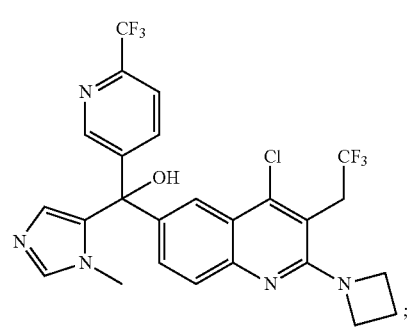
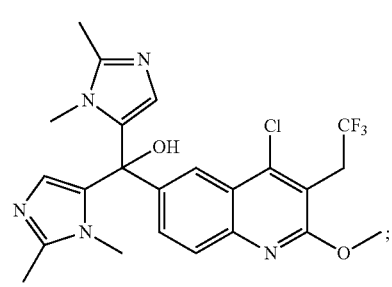
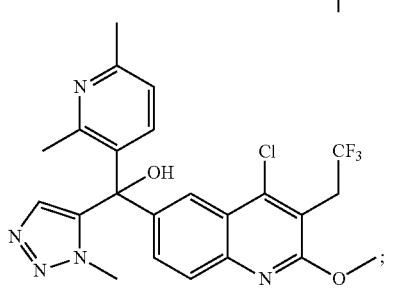
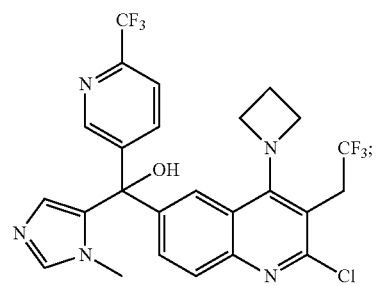

53
-continued
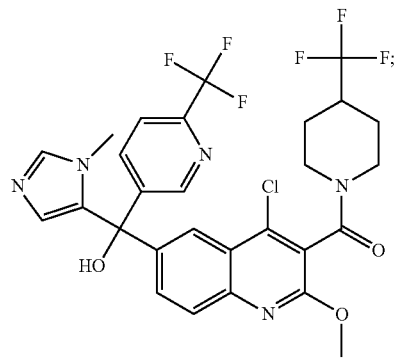
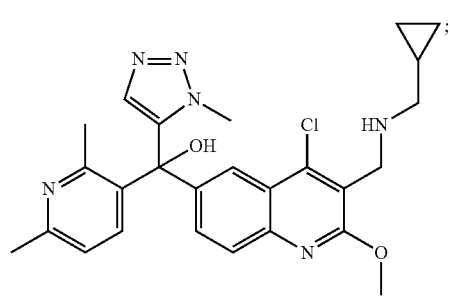
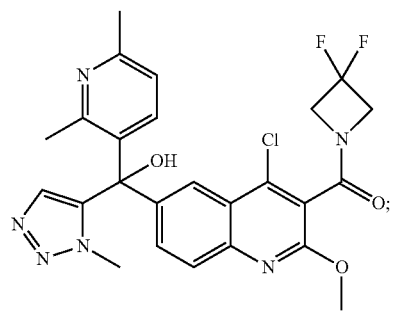
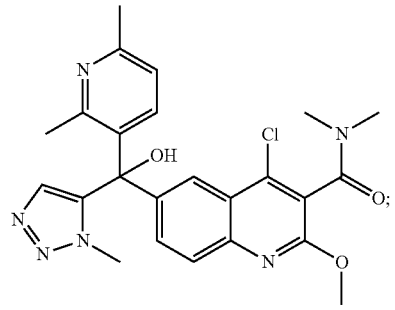
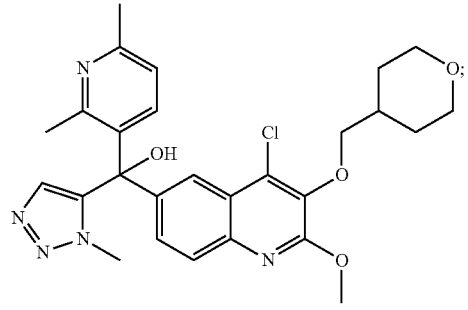
54
-continued
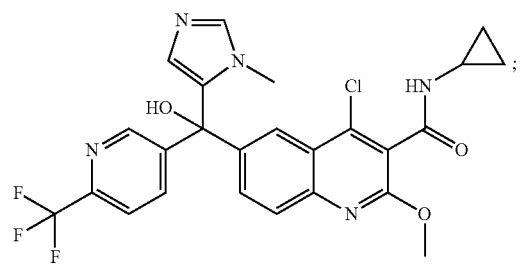
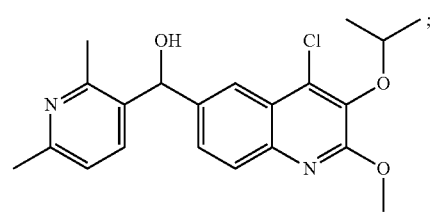
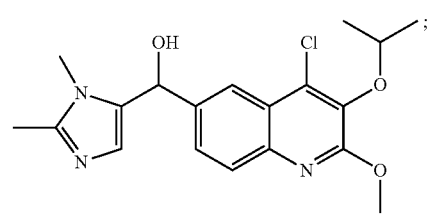
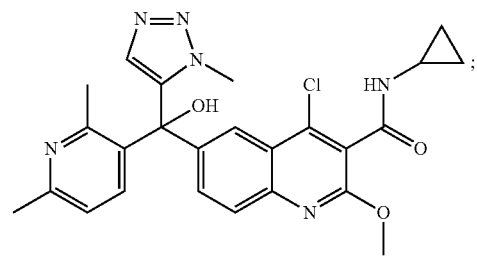
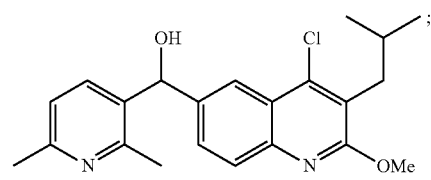
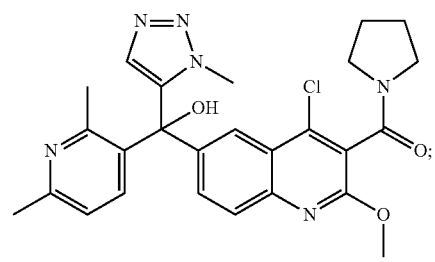
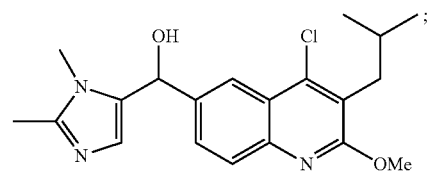

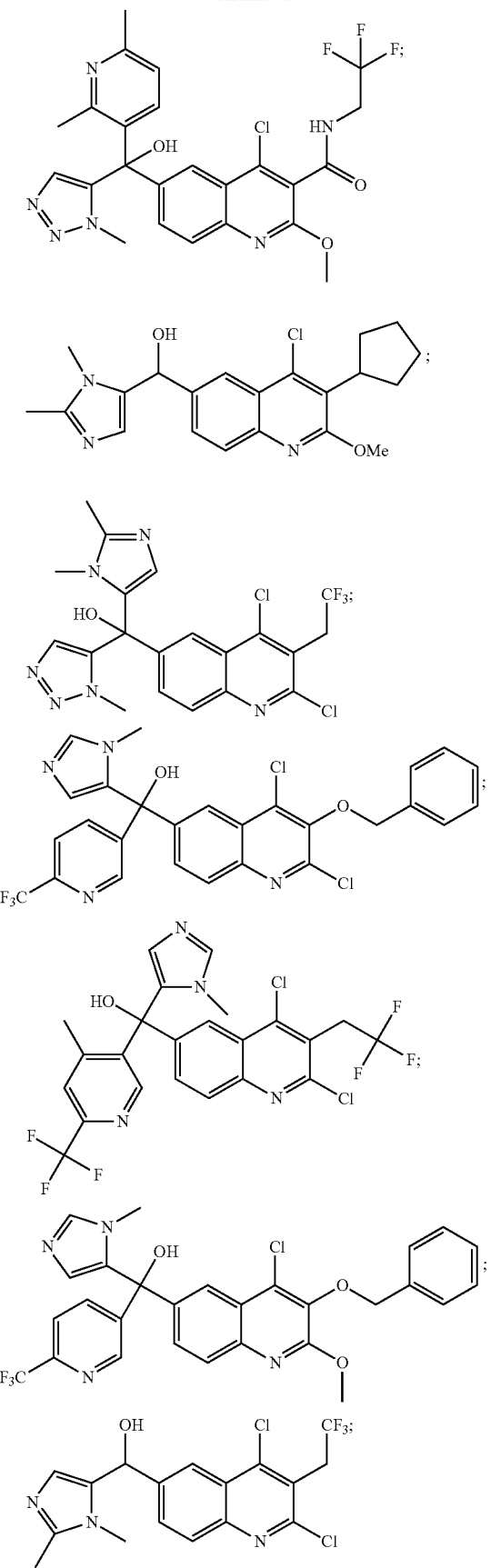
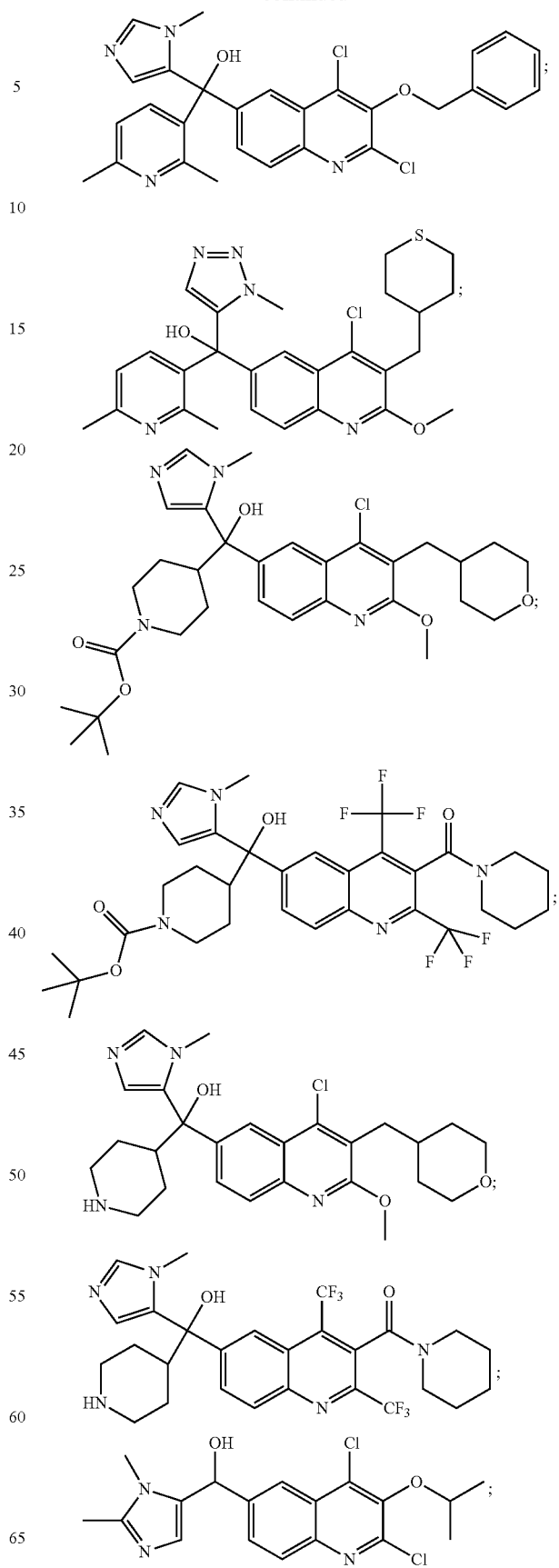

57
-continued
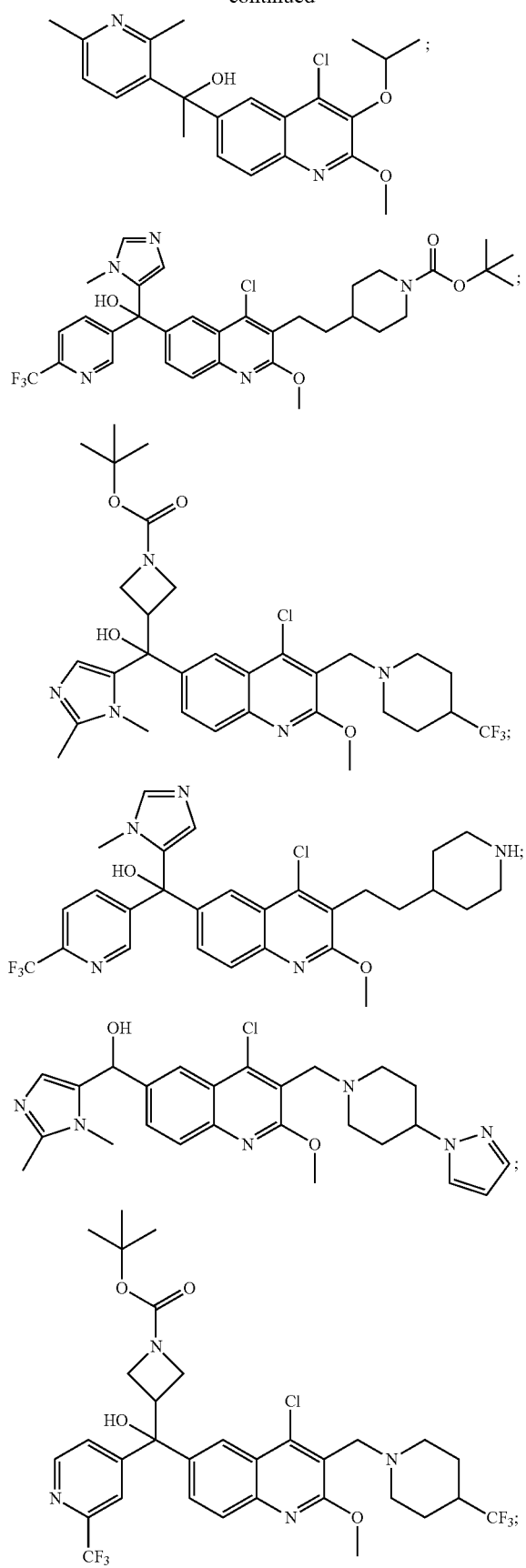
58
-continued
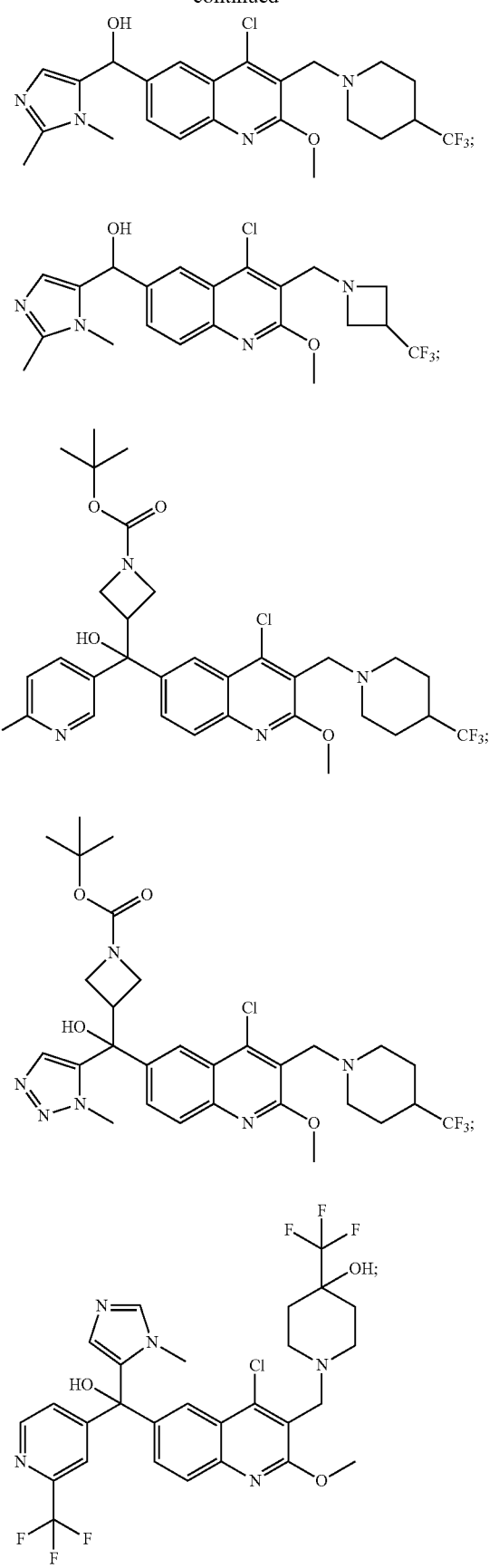

59
-continued
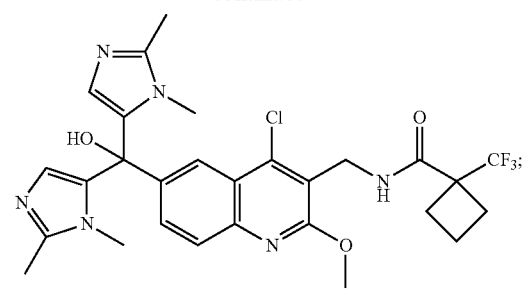
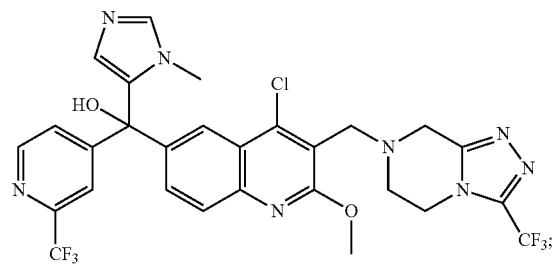
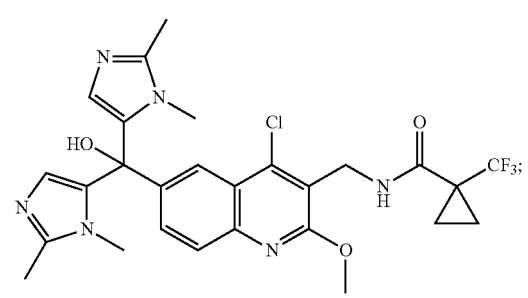
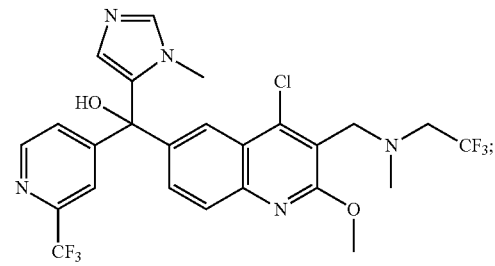
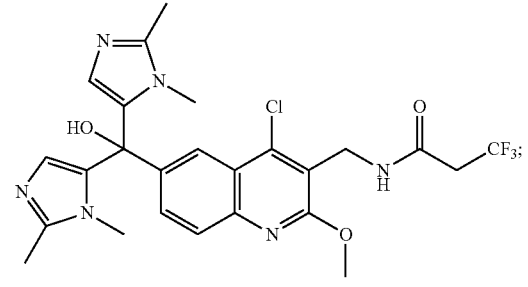
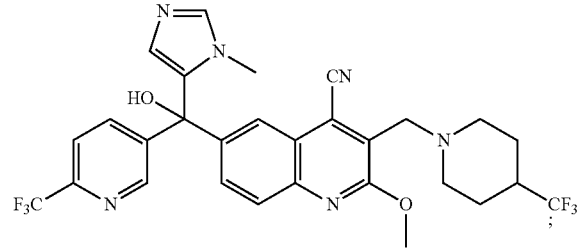
60
-continued
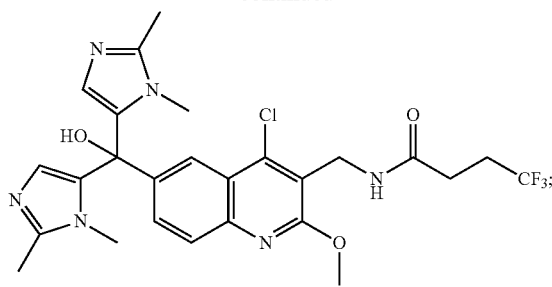
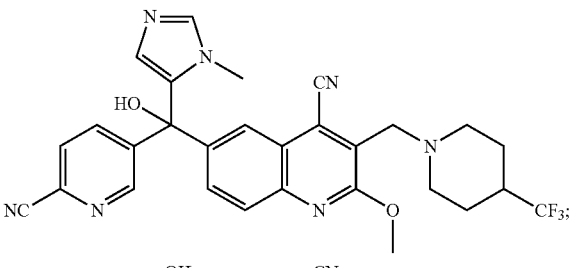
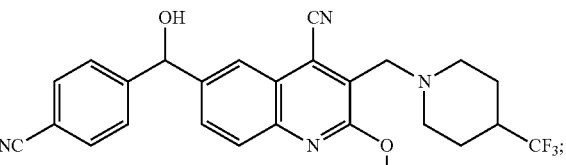
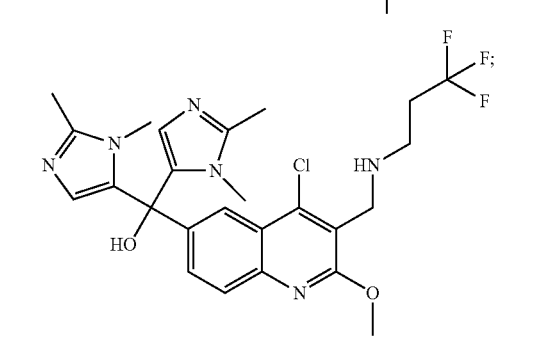
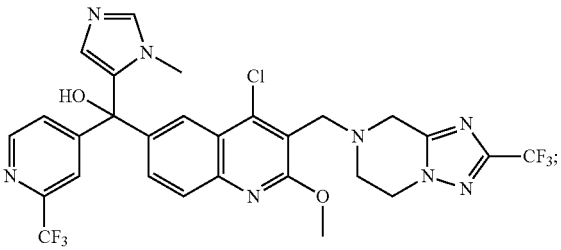
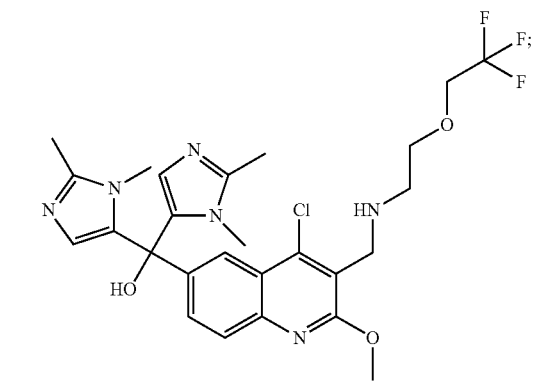

61
-continued
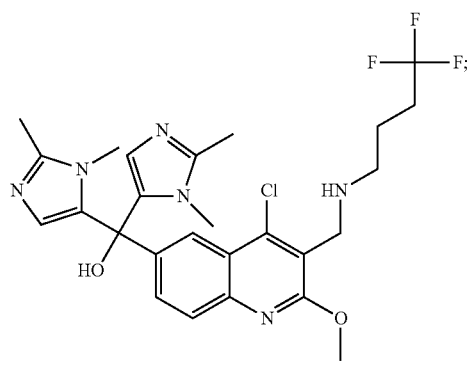
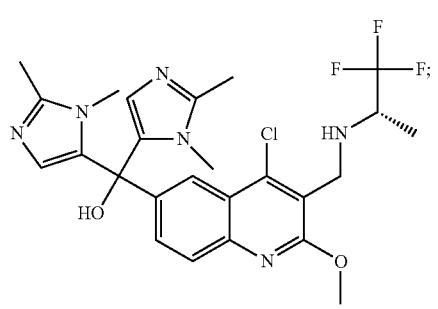
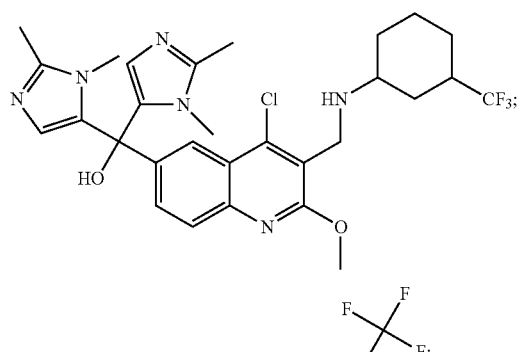
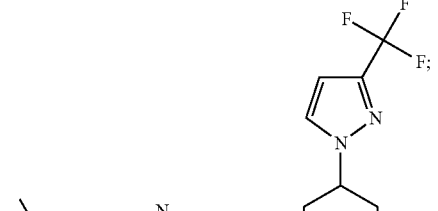
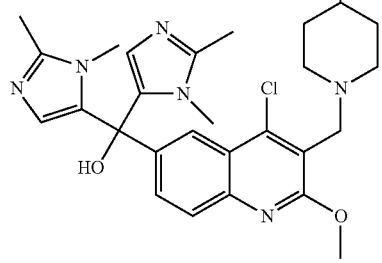
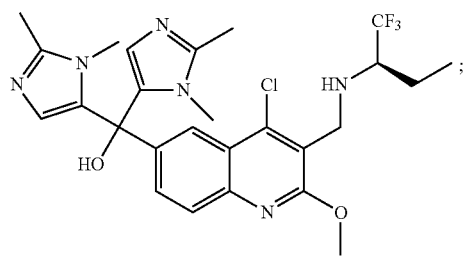
62
-continued
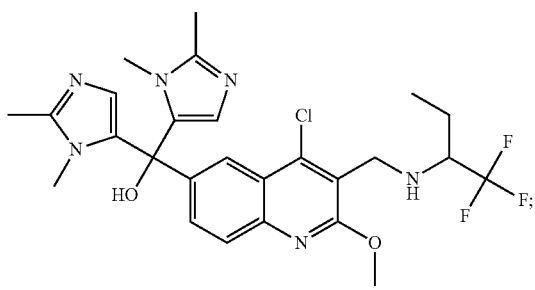
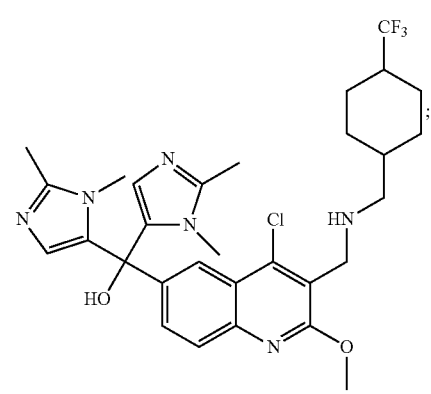
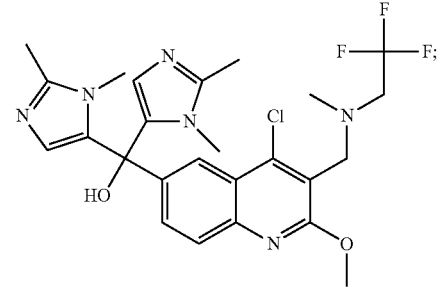
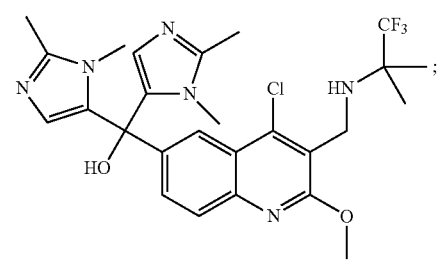
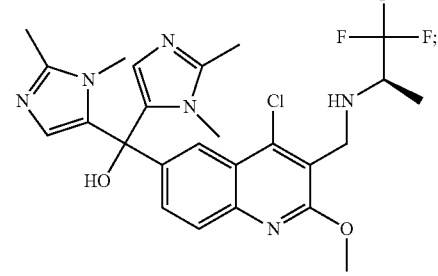

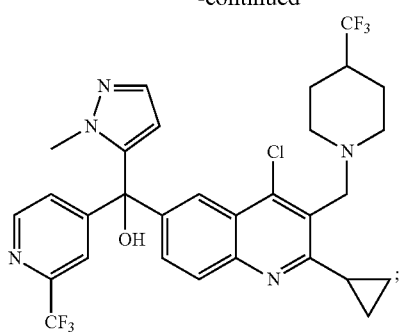
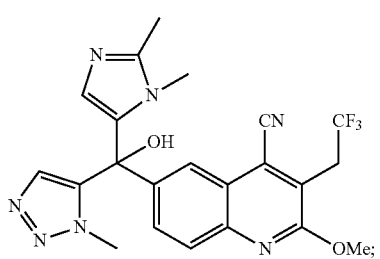
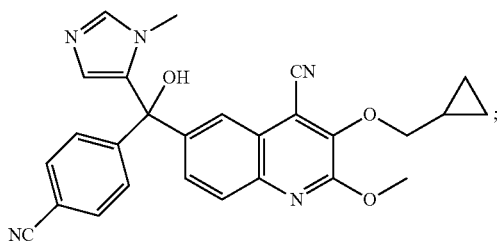
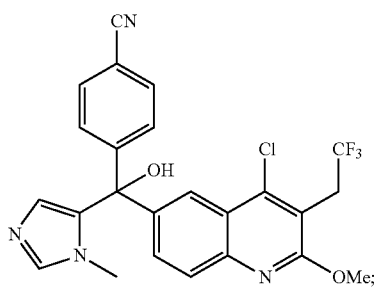
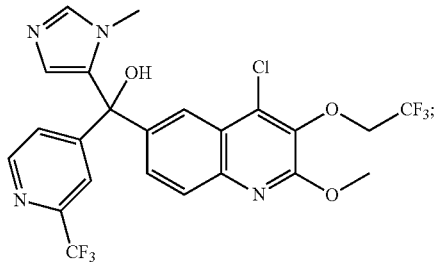
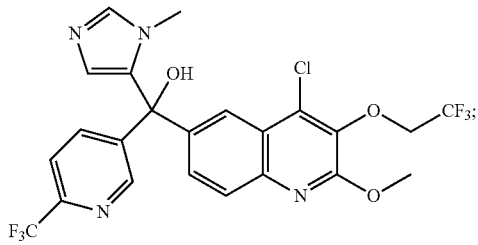
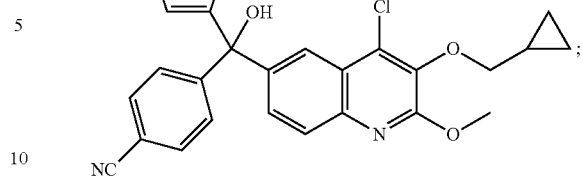
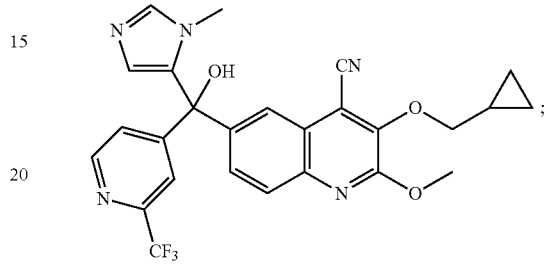
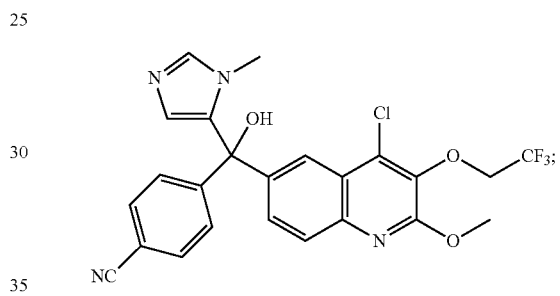
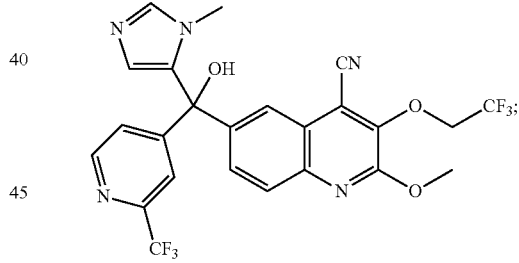
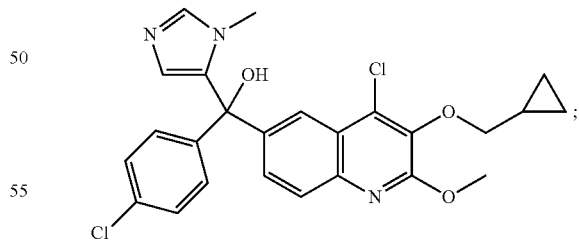
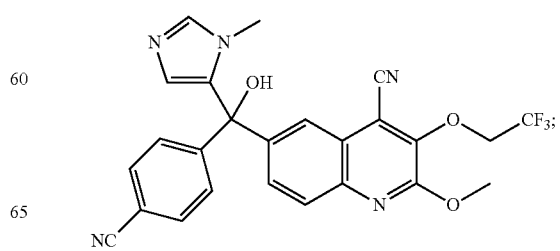

-continued
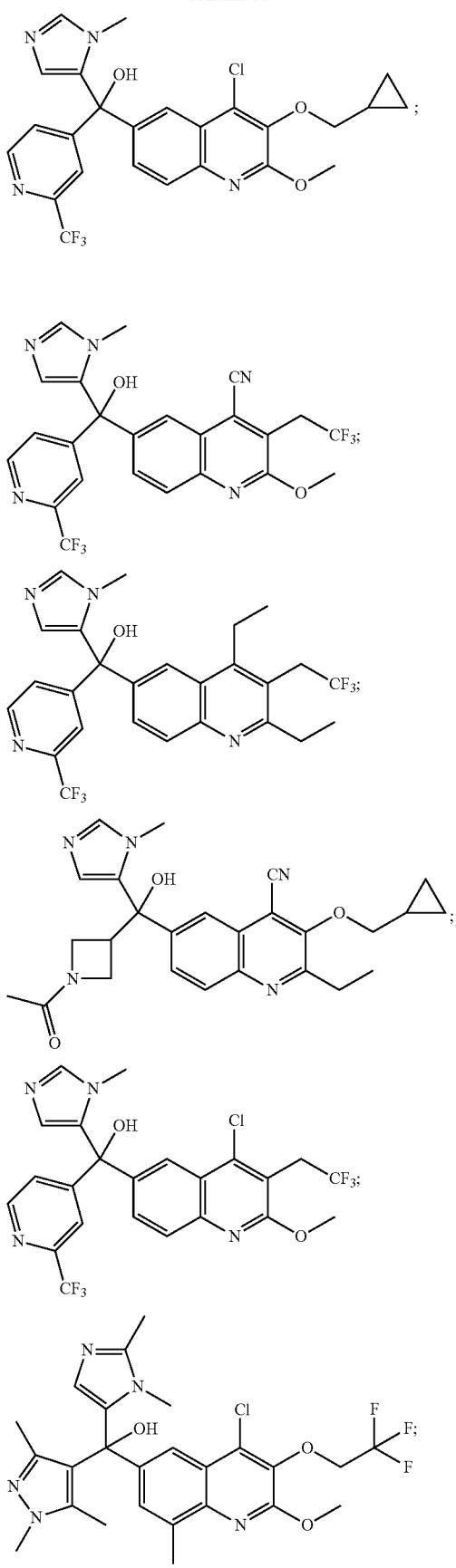
-continued
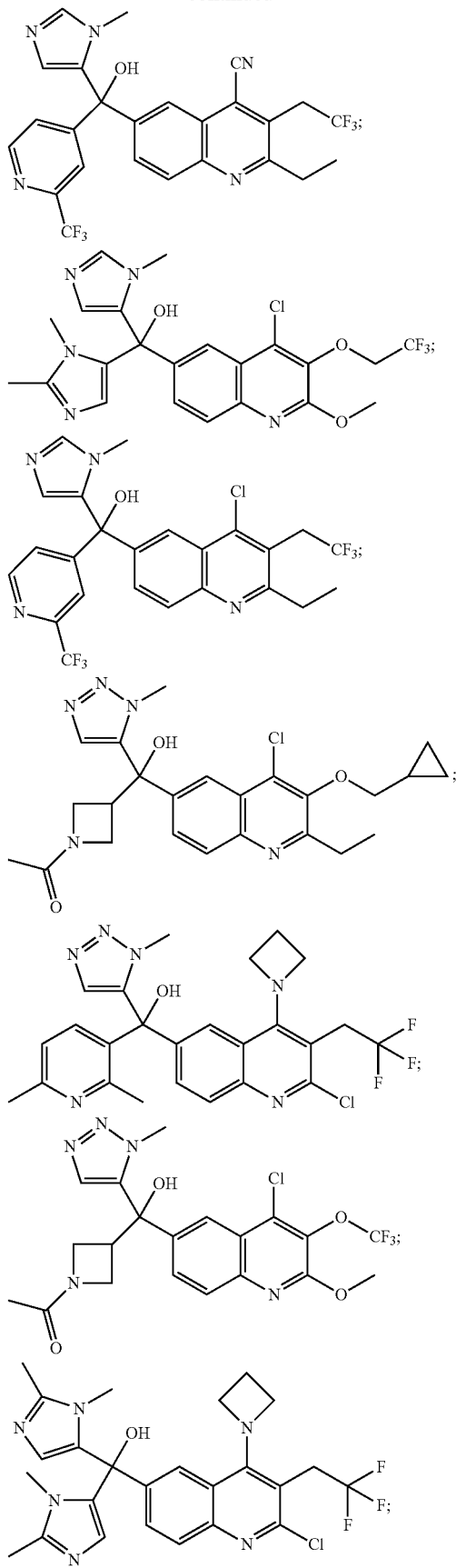

-continued

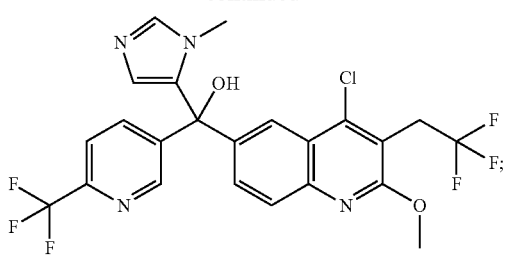

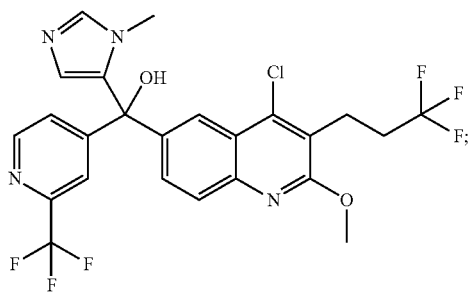

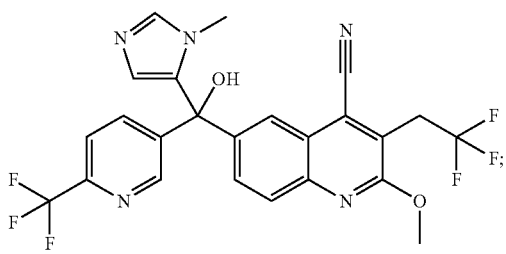

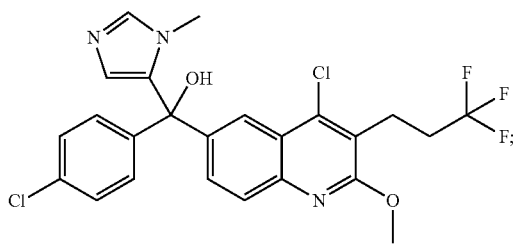

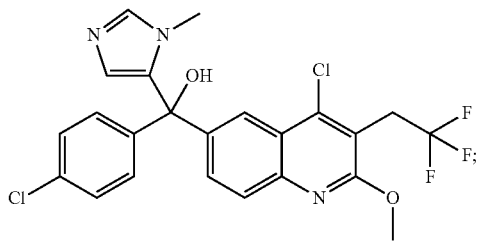

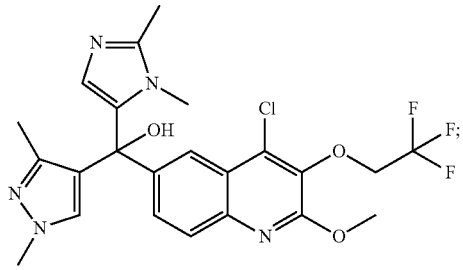

-continued

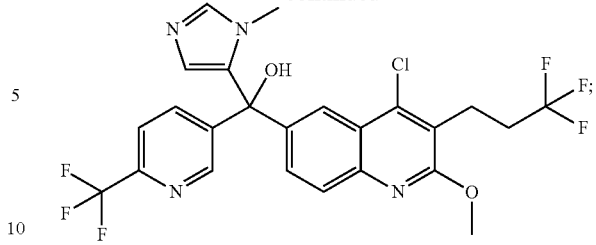

and pharmaceutically acceptable salts thereof.

Another embodiment of the invention comprises a compound of Formula I and a pharmaceutically acceptable carrier.

The present invention also provides a method for preventing, treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, systic fibrosis, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphylococcia, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodontitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel disease, wherein said inflammatory bowel disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The invention also relates to methods of modulating RORγt activity in a mammal by administration of an effective amount of at least one compound of Formula I.

Definitions

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be an animal, typically a mammal, typically a human, which has been the object of treatment, observation or experiment and is at risk of (or susceptible to) developing a syndrome, disorder or disease that is associated with abberant RORγt expression or RORγt overexpression, or a patient with an inflammatory condition that accompanies syndromes, disorders or diseases associated with abberant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-6)}$cycloalkyl, $C_{(5-8)}$cycloalkyl, decahydronaphthalenyl, and 2,3,4,5,6,7-hexahydro-1H-indenyl. Any cycloalkyl group may be optionally substituted with one $OCH_3$, one OH, or up to two fluorine atoms.

As used herein, the term "thiophenyl" is intended to describe the radical formed by removing a hydrogen atom from the molecule with the structure:

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well. Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate.

Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula I, shall comprise all isotopes and isotopic mixtures of said element, either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. Radiolabelled compounds of Formula I may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereo center, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Abbreviations

Herein and throughout the application, the following abbreviations may be used.
Å angstrom
Ac acetyl
ACN acetonitrile
Ac$_2$O acetic anhydride
AIBN 2,2'-azobis(2-methylpropionitrile)
Boc tert-butyloxy carbonyl
BHT butylated hydroxytoluene
Bn benzyl
br broad
Bu butyl
n-BuLi n-butyl lithium
d doublet
dba dibenzylideneacetone
CDI 1,1'-carbonyldiimidazole
DCC dicyclohexylcarbodiimide
DCE 1,2-dichloroethane
DCM dichloromethane
Dess-Martin periodinane 1,1,1-tris(acetyloxy)-1,1-dihydro-1,2-benziodoxol-3-(1H)-one
DIAD diisopropyl azodicarboxylate
DIPEA diisopropylethyl amine
DMA dimethylacetamide
DMF N,N-dimethylformamide
DMSO dimethyl sulfoxide
DPPA diphenyl phosphoryl azide
dppf (diphenylphosphino)ferrocene Eaton's Reagent 7.7 wt % phosphorus pentoxide solution in methanesulfonic acid
EDCI N-(3-dimethylaminopropyl)-N'-ethylcarbodiimide hydrochloride
ESI electrospray ionization
Et ethyl
Et$_2$O diethyl ether
EtOAc ethyl acetate
EtOH ethyl alcohol
FCC flash column chromatography
Hantzch ester diethyl 1,4-dihydro-2,6-dimethyl-3,5-pyridinedicarboxylate
HATU O-(7-azabenzotriazol-1-yl)-N,N,N',N'-tetramethyluronium hexafluorophosphate
Hept heptet
HOBt 1-hydroxybenzotriazole
HPLC high pressure liquid chromatography
Hunig's base N,N-diisopropylethylamine
Hz hertz
i-PrOH isopropyl alcohol
KHMDS potassium bis(trimethylsilyl) amide
LCMS liquid chromatography-mass spectrometry
LDA lithium diisopropylamide
m multiplet
M molar (moles/liter)
mCPBA meta-chloroperoxybenzoic acid
Me methyl
Meldrum's acid 2,2-dimethyl-1,3-dioxane-4,6-dione
MeOH methanol
MHz megahertz
min minutes
mL milliliters
MTBE methyl tertiary butyl ether
m/z mass to charge ratio
NBS N-bromosuccinimide
nm nanometers
NaOiPr sodium isopropoxide
NMR nuclear magnetic resonance
Ph phenyl
PPA poly phosphoric acid
ppm parts per million
Pr propyl
q quartet
RP-HPLC reverse phase high pressure liquid chromatography
s singlet
SFC supercritical fluid chromatography
t triplet
TBAF tetrabutyl ammonium fluoride
TEA triethylamine
TEMPO (2,2,6,6-tetramethylpiperidin-1-yl)oxidanyl
TFA trifluoroacetic acid
THF tetrahydrofuran
TLC thin layer chromatography
UV ultra-violet
X-Phos 2-dicyclohexylphosphino-2',4',6'-triisopropylbiphenyl General Schemes:

Compounds of Formula I in the present invention can be synthesized in accordance with the general synthetic methods known to those who are skilled in the art. The following reaction schemes are only meant to represent examples of the invention and are in no way meant to be a limit of the invention.

Scheme 1 describes the preparation of 6-bromo or 6-iodoquinolines of the Formula IV by various methods. As illustrated in path 1, hydroxyquinolin-2(1H)-ones II can be prepared by condensation of readily available 6-bromo or 6-iodoanilines with Meldrum's acid and then subsequently heated in the presence of Eaton's reagent or PPA as described by W. T. Gao, et al. (*Synthetic Communications* 2010, 40, 732). Condensation with substituted aldehydes in the presence of a Hantzsch ester, such as diethyl 2,6-dimethyl-1,4-dihydropyridine-3,5-dicarboxylate, in solvents like ethanol or pyridine can afford substituted 6-halo-4-hydroxyquinolin-2(1H)-ones III wherein $R^6$ is $C_{(1-4)}$alkylQ and Q is defined above. Subsequent heating of quinolines III in the presence of phosphorus oxychloride at temperatures between 80-120° C. with or without a solvent, such as acetonitrile, can provide the 6-bromo or 6-iodoquinolines IV wherein $R^5$ and $R^7$ are Cl. Displacement of the 2-Cl of 2,4-dichloroquinoline IV with sodium alkoxides can be accomplished in an alcoholic solvent such as methanol, ethanol or isopropanol or at elevated temperatures in a non-polar solvent such as toluene (Alan Osborne et. al. *J Chem. Soc. Perkin Trans.* 1 (1993) 181-184 and *J. Chem. Research* (S), 2002, 4) to provide substituted quinolines IV wherein $R^6$ is $C_{(1-4)}$alkylQ and $R^5$ and $R^7$ are either Cl or Oalkyl or $R^5$ and $R^7$ are both Oalkyl.

Alternatively, as shown in path 2, the 6-haloanilines can be condensed with substituted malonic acids V in phosphorus oxychloride at temperatures between 80-120° C. affording 6-haloquinolines IV wherein $R^6$ is C(1-4)alkylQ, cycloalkyls (eg. cyclopropyl, cyclobutyl, cyclopentyl or cyclohexyl) or saturated heterocycles (eg. tetrahydropyranyl, oxetan-3-yl or tetrahydrofuranyl or 4H-thiopyran-4-yl) and both $R^5$ and $R^7$ are Cl. The malonic acids V can be obtained commercially or prepared by addition of ketones to Meldrum's acid and Hantzsch ester, such as diethyl 2,6-dimethyl-1,4-dihydropyridine-3,5-dicarboxylate under conditions described by Ramachary, Dhevalapally. B. et al (*European Journal of Organic Chemistry* 2008 (6) 975-993). Displacement of the chlorines at positions 2 and/or 4 with an Oalkyl can be accomplished as described above to provide 6-haloquinolines of Formula IV wherein $R^5$ and $R^7$ are either Cl or Oalkyl or $R^5$ and $R^7$ are both Oalkyl.

In path 3, methyl 2-aminobenzoates VI can undergo acylation with acid chlorides VII, obtained from commercial sources or from the corresponding substituted carboxylic acids by treatment with thionyl chloride or oxalyl chloride using known procedures, to form the amide intermediate VIII. The amide can then be further cyclized by treatment with a base such as sodium ethoxide, or by lithium (LiHMDS) or potassium bis(trimethylsilyl)amide (KHMDS) in a solvent such as tetrahydrofuran. Conversion of the resulting hydroxyquinolin-2(1H)-ones III to 2,4-dichloroquinolines can be carried out in refluxing phosphorus oxychloride then subsequently treated with NaOalkyl as described earlier to provide 6-haloquinolines of Formula IV wherein $R^6$ is OQ, or $C_{(1-4)}$alkylQ and $R^5$ and $R^7$ are either Cl or Oalkyl or $R^5$ and $R^7$ are both Oalkyl.

Path 4 illustrates an alternative route to incorporate an oxygen linked substituent at the quinoline C-3 position. The intermediate amides IX can be prepared by the addition of bromoacetyl bromide to the haloaniline VI in the presence of an amine base such as triethylamine or Hunig's base in a chlorinated solvent. The bromine can then be displaced with substituted hydroxyl nucleophiles under basic conditions to provide compounds of Formula VIII wherein $R^6$ is OQ. Cyclization with a base such as potassium bis(trimethylsilyl) amide followed by sequential steps of chloride addition at the quinoline 2 and 4-position followed by chloride displacement with sodium alkoxide as previously described may afford the 6-haloquinolines of Formula IV wherein $R^6$ is OQ and $R^5$ and $R^7$ are either Cl or Oalkyl or $R^5$ and $R^7$ are both Oalkyl.

The chlorines at the 2 and 4-positions of 6-haloquinolines of Formula IV can also be displaced with substituted amines as shown in path 5. Therefore, nucleophilic displacement of the 2-Cl and/or the 4-Cl atom(s) with primary or secondary alkyl amine reagents can be accomplished by heating the 2,4-dichloroquinoline IV with excess amine reagent at temperatures between 80 and 100° C. in an appropriate solvent like DMF to provide the haloquinolines IV wherein $R^5$ or $R^7$ are either Cl or $NA^3A^4$ or both $R^5$ or $R^7$ are $NA^3A^4$.

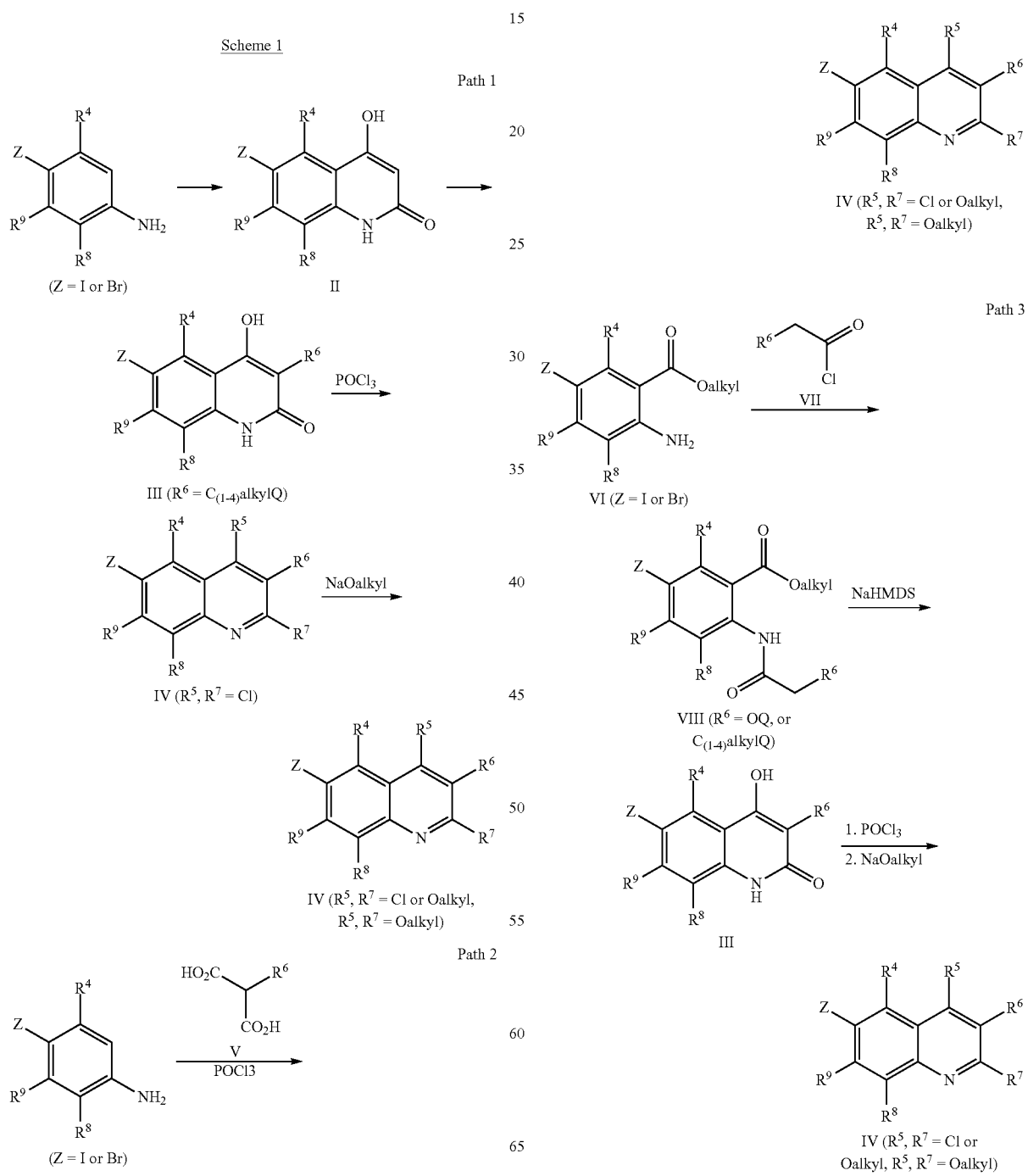

-continued

Path 4

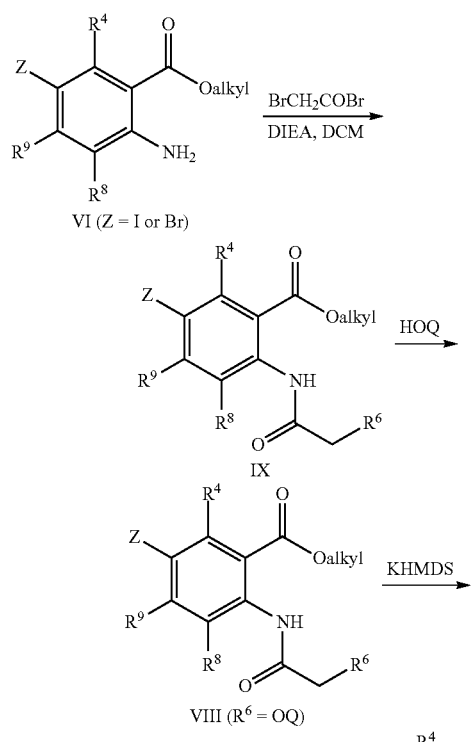

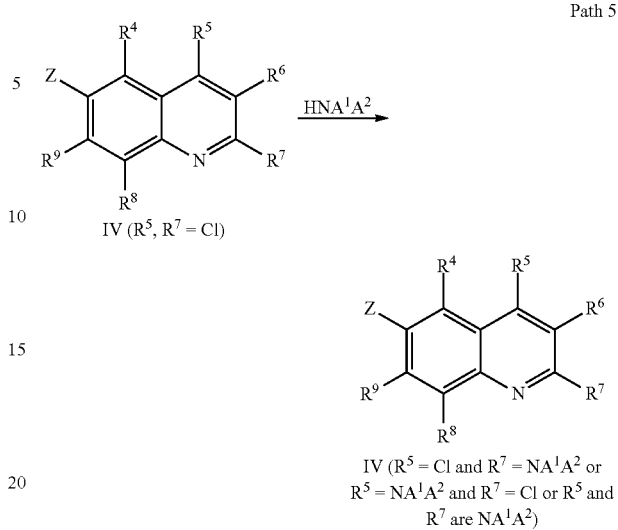

The synthesis of 6-haloquinolines containing a trialkylsilyl group at the C3-position of the quinoline is described in Scheme 2. Hydroxyquinolin-2(1H)-ones II can be transformed into 2,4-dichloroquinolines X wherein $R^5$ and $R^7$ are Cl (path 1) using phosphorous oxychloride.

Treatment with NaOalkyl as previously described to displace the chlorine at the quinoline 2-position followed by deprotonation with a strong base, such as lithium diisopropylamide to afford a 3-lithio quinoline intermediate that can be trapped with a formylating reagent such as dimethylformamide, can provide the intermediate aldehyde that can be subsequently reduced with a reducing reagent, such as sodium borohydride, to furnish the 6-haloquinolines XI. Protection of the primary alcohol functional group with trialkylsilyl chloride reagents furnishes the protected 6-haloquinolines XII. Path 2 describes an alternative sequence starting with 2,4-dichloroquinoline X. Formylation of quinoline X followed by reduction then treatment with trialkylsilyl chloride as previously described can provide the 2,4-dichloroquinoline XII wherein $R^5$ and $R^7$ are Cl. Final displacement of the 2-Cl group with NaOalkyl as described above can provide haloquinolines XII wherein $R^5$ is Cl and $R^7$ is Oalkyl.

Scheme 2

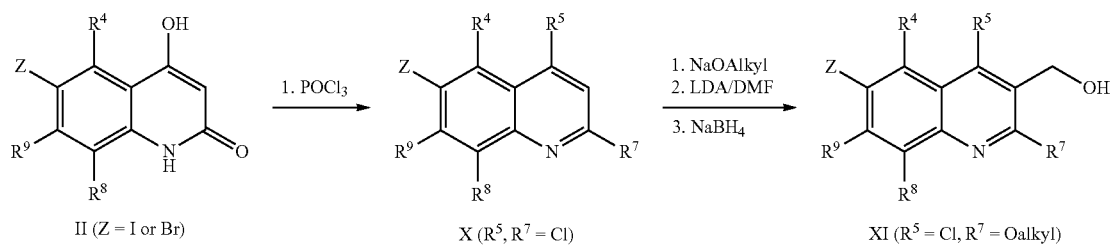

Path 2

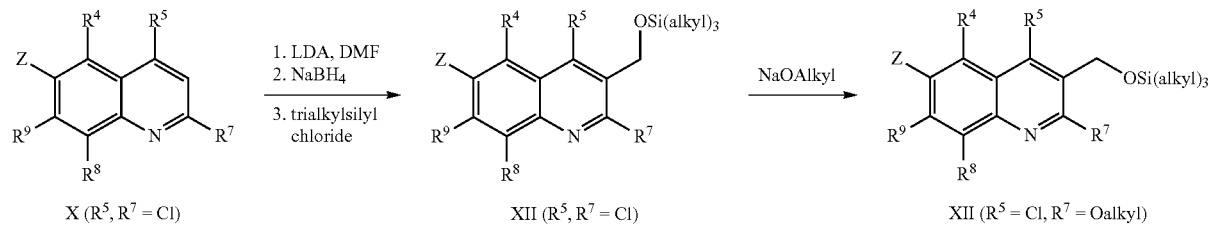

X ($R^5, R^7$ = Cl) → XII ($R^5, R^7$ = Cl) → XII ($R^5$ = Cl, $R^7$ = Oalkyl)

1. LDA, DMF
2. NaBH$_4$
3. trialkylsilyl chloride

NaOAlkyl

Scheme 3 describes the synthesis of 6-haloquinolines IV containing a methylamino functional group at the C3-position of the quinoline core. As shown in path 1, installing an aldehyde at the 3-position of 2,4-dichloroquinolines X, as previously described, followed by reduction can provide an intermediate 3-hydroxymethylquinoline that can be further chlorinated with thionyl chloride in a solvent such as dichloromethane to provide the corresponding 6-haloquinoline of Formula XIII wherein $R^6$ is CH$_2$Cl. Displacement with mono or disubstituted amine reagents provides the quinolines of Formula IV wherein $R^6$ is CH$_2$NA$^3$A$^4$. Alternatively, the 3-methylquinolines of Formula IV can be transformed into the bromomethyl quinolines XIV by treatment with N-bromosuccinimide and a radical initiator such as azobisisobutyronitrile (AIBN) or 1,1'-azobis(cyclohexanecarbonitrile) (ABCN) in a solvent such as carbon tetrachloride or benzene (path 2). Displacement of the bromine atom with mono or disubstituted amine reagents in the presence of a base such as N,N-diisopropylethylamine in a solvent such as dichloromethane can also provide 6-haloquinolines IV wherein $R^6$ is CH$_2$NA$^3$A$^4$.

Scheme 3

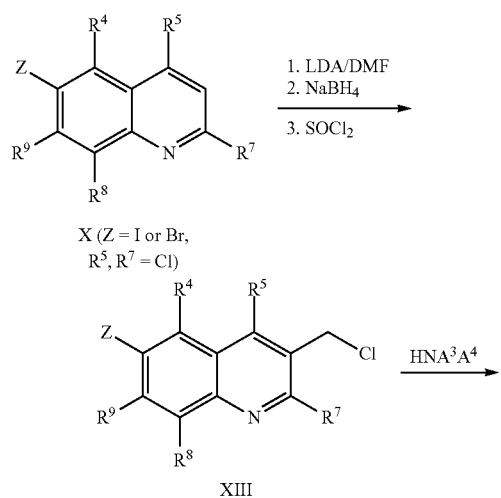

Path 1

X (Z = I or Br, $R^5, R^7$ = Cl)

1. LDA/DMF
2. NaBH$_4$
3. SOCl$_2$

XIII

HNA$^3$A$^4$

-continued

IV ($R^6$ = CH$_2$NA$^3$A$^4$, $R^5, R^7$ = Cl)

Path 2

NBS

IV ($R^6$ = CH$_3$)

XIV

HNA$^3$A$^4$

IV ($R^6$ = CH$_2$NA$^3$A$^4$)

Scheme 4 outlines routes (paths 1 and 2) to intermediate quinolones XVI containing an ester at the quinoline 3-position. The 4-hydroxyquinolones XVI can be synthesized by condensing haloanilines VI (Z=Br or I) with dialkylmalonates XV in the presence of a base such as a sodium alkoxide in a suitable solvent such as an alcohol (path 1). Alternatively, the 4-hydroxyquinolones XVI can be prepared in two steps from haloaniline VI by first coupling with a 3-chloro-3-oxopropanoate XVII in the presence of a base such as sodium bicarbonate to provide amides XVIII followed by cyclization with a base such as a sodium alkoxide in a solvent such as tetrahydrofuran (path 2).

As shown in path 3, the quinolone esters XVI can be chlorinated with phosphorus oxychloride at temperatures between 80-120° C. with or without a solvent, such as acetonitrile to provide the 6-haloquinolines of Formula XIX wherein $R^5$ and $R^7$ are Cl. The 2-Cl substituent can be further displaced with sodium alkoxides as described above to provide the 6-haloquinolines XX wherein $R^5$ is Cl and $R^7$ is Oalkyl.

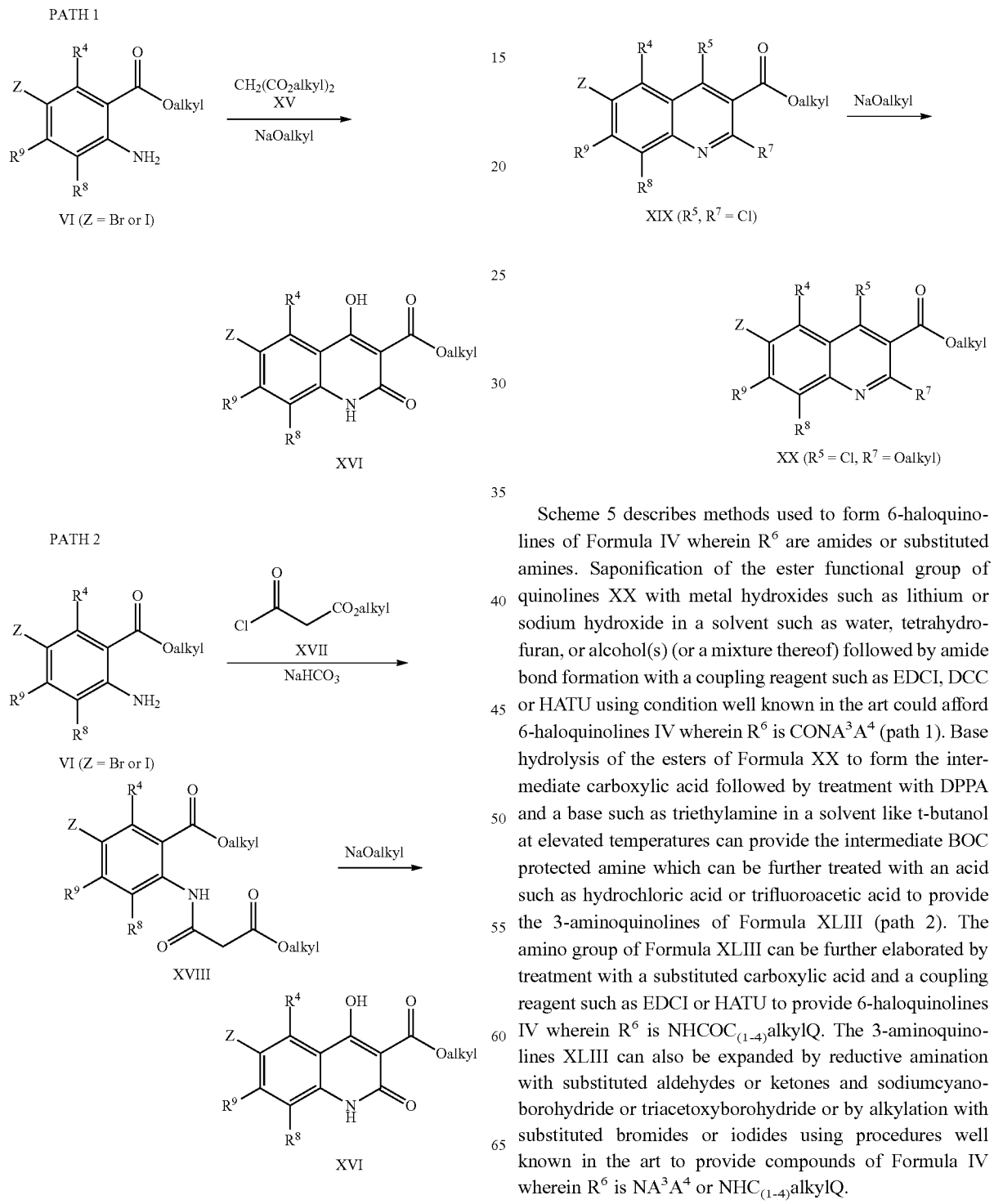

Scheme 5 describes methods used to form 6-haloquinolines of Formula IV wherein $R^6$ are amides or substituted amines. Saponification of the ester functional group of quinolines XX with metal hydroxides such as lithium or sodium hydroxide in a solvent such as water, tetrahydrofuran, or alcohol(s) (or a mixture thereof) followed by amide bond formation with a coupling reagent such as EDCI, DCC or HATU using condition well known in the art could afford 6-haloquinolines IV wherein $R^6$ is $CONA^3A^4$ (path 1). Base hydrolysis of the esters of Formula XX to form the intermediate carboxylic acid followed by treatment with DPPA and a base such as triethylamine in a solvent like t-butanol at elevated temperatures can provide the intermediate BOC protected amine which can be further treated with an acid such as hydrochloric acid or trifluoroacetic acid to provide the 3-aminoquinolines of Formula XLIII (path 2). The amino group of Formula XLIII can be further elaborated by treatment with a substituted carboxylic acid and a coupling reagent such as EDCI or HATU to provide 6-haloquinolines IV wherein $R^6$ is $NHCOC_{(1-4)}$alkylQ. The 3-aminoquinolines XLIII can also be expanded by reductive amination with substituted aldehydes or ketones and sodiumcyanoborohydride or triacetoxyborohydride or by alkylation with substituted bromides or iodides using procedures well known in the art to provide compounds of Formula IV wherein $R^6$ is $NA^3A^4$ or $NHC_{(1-4)}$alkylQ.

Scheme 5

Step 1

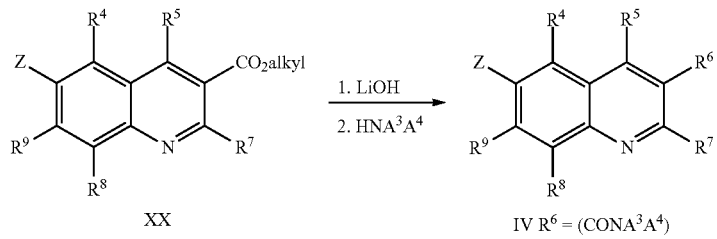

Step 2

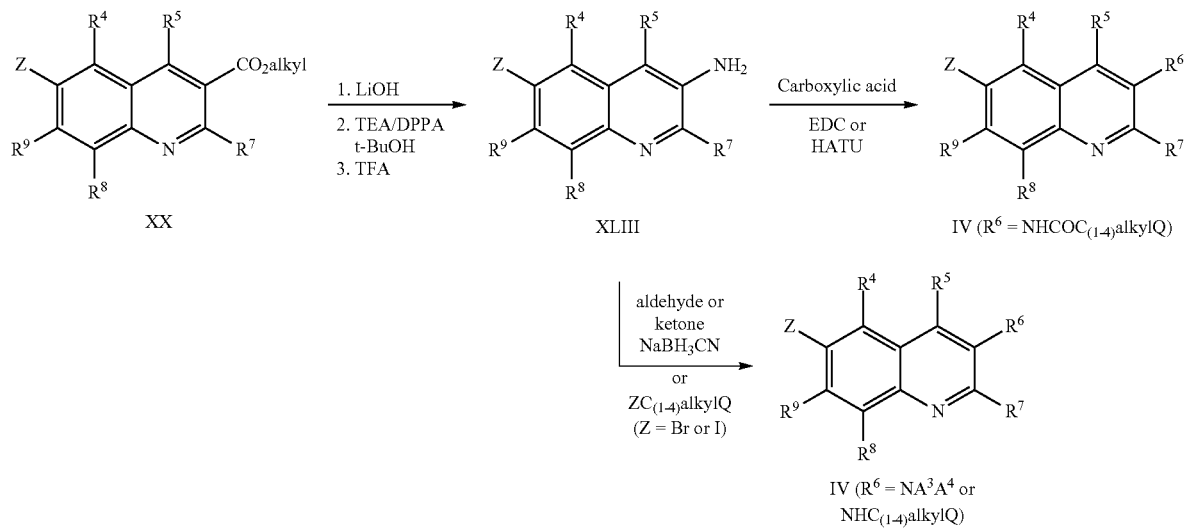

Scheme 6 exemplifies methods used to convert the halogen at C-6 position of the quinoline to an ester. The starting 6-haloquinolines IV can be treated with n-butyl lithium at temperatures ranging from −50 to −78° C., quenched with carbon dioxide then subsequently treated with methyl iodide as described in U.S. Pat. No. 4,710,507 A1, 1987 to provide the methyl ester XXI.

Scheme 6

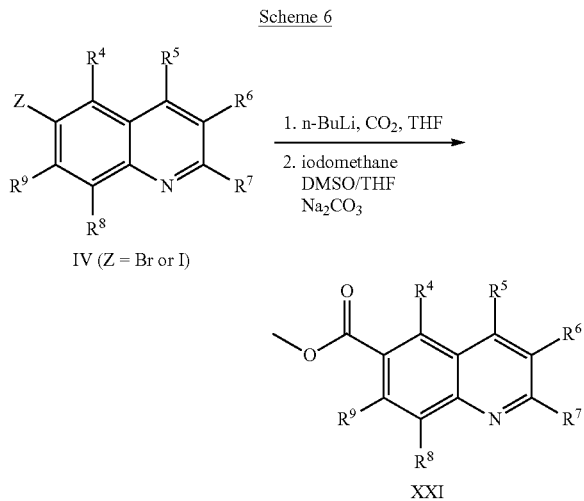

Scheme 7 outlines synthetic routes (path 1 to 5) to aryl ketones of Formula XXVI. In path 1, Weinreb amides XXIII can be prepared from carboxylic acids XXII and N,O-dimethylhydroxylamine hydrochloride in the presence of a base such as triethylamine or Hunig's base and a coupling reagent such as EDCI. The amides XXIII can be further treated with Grignard reagents such as $R^2MgX$ (X is Br or Cl) XXIV that can be obtained commercially or preformed by treatment of $R^2Z$ XXV (Z=Br or I) with organometallic reagents such as i-PrMgCl or EtMgCl in THF or dichloromethane to afford the ketones XXVI, wherein $R^1$ and $R^2$ are as defined above. As shown in path 2, aldehydes XXVII can also be treated with Grignard reagents to afford the intermediate alcohols XXVIII. Subsequent oxidation with Dess-Martin periodinane or $MnO_2$ in a suitable solvent such as 1,4-dioxane or tetrahydrofuran at elevated temperatures can provide ketones XXVI. Path 3, which employs palladium catalyzed cross-coupling of arylboronic acids XXIX with acid chlorides XXX using $K_3PO_4$ as a base and $(Ph_3P)_2PdCl_2$ as a catalyst in a high boiling non-polar solvent such as toluene, can also be used to generate ketones XXVI. In path 4, aryl ketones XXVI, wherein $R^2$ is triazolyl, can be prepared by treatment of 1-methyl-1H-1,2,3-triazole, made according to PCT Int. Appl. 2008098104, with n-butyl-lithium followed by reaction with aldehydes XXVII to yield the secondary alcohols XXVIII, which can undergo oxidation with Dess-Martin periodinane or $MnO_2$. Path 5 exemplifies the preparation of symmetrical ketones XXVI, wherein $R^1$ and $R^2$ are the same. As illustrated, an aryl or heteroaryl group containing an acidic proton XXXI (Y=$R^1$ or $R^2$) can be deprotonated in the presence of a strong base such as n-butyllithium in a preferred solvent such as tetrahydrofuran at temperatures between 0 and −78° C. then added in excess to ethyl methoxy(methyl)carbamate to provide aryl ketones XXVI wherein $R^1$ and $R^2$ are the same. Aryl or heteroaryl bromide XXXII can also be lithiated through a lithium/halogen exchange with n-butyllithium before adding in excess to ethyl methoxy(methyl)carbamate as previously described to provide symmetrical ketones XXVI.

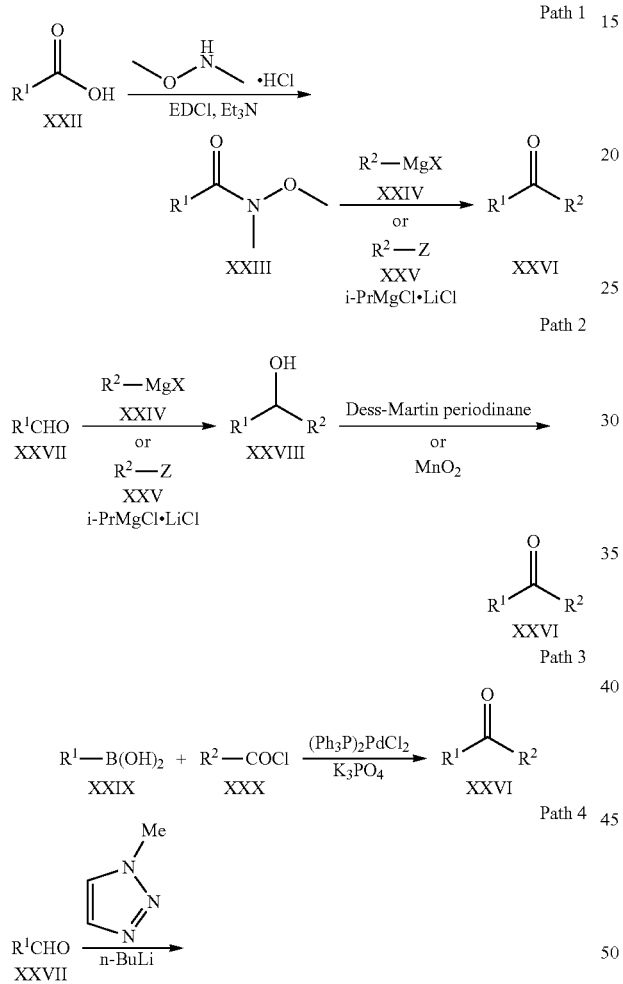

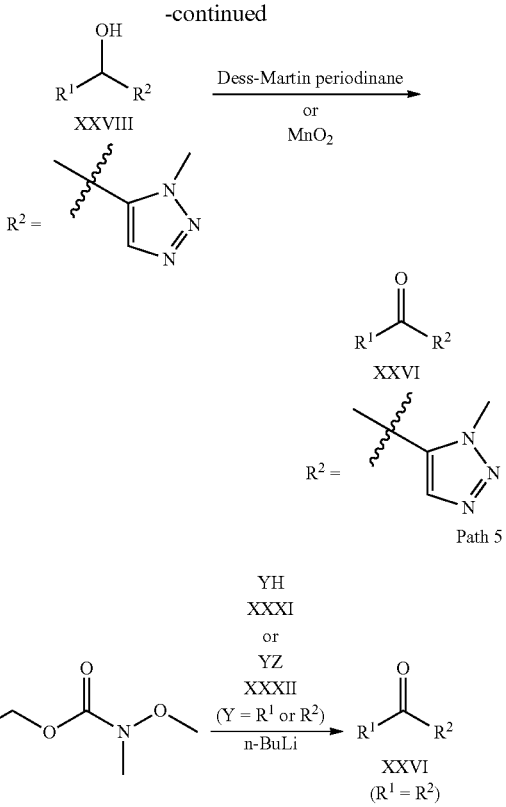

Scheme 8 illustrates routes for the synthesis of ketoquinolines XXXIII and XXXV. As shown in path 1, treatment of 6-bromo or 6-iodoquinolines IV with n-BuLi followed by addition of aldehydes XXVII, at temperatures between 0 and −78° C., provides secondary alcohol quinolines of Formula I ($R^2$ is H and $R^3$ is OH). Oxidation to ketoquinoline XXXIII can be achieved with Dess-Martin periodinane in a solvent such as dichloromethane or with $MnO_2$ in a solvent such as 1,4-dioxane or tetrahydrofuran at elevated temperatures. Alternatively, 6-bromo or 6-iodoquinolines IV can be treated with n-BuLi at −78° C. then quenched with DMF to afford quinoline carboxaldehydes XXXIV (path 2). Ketoquinolines XXXV, wherein Y is $R^1$ or $R^2$, can then be obtained in a two-step process by addition of the aldehydes XXXIV to a reaction mixture of aryl halides XXXII (Y=$R^1$ or $R^2$ and Z=Br or I) and i-PrMgCl.LiCl (or n-BuLi) followed by oxidation with $MnO_2$ (path 2). Reduction of the ketoquinolines XXXV with sodium borohydride can offer an additional method to secondary alcohols of Formula I wherein $R^2$ is H and $R^3$ is OH.

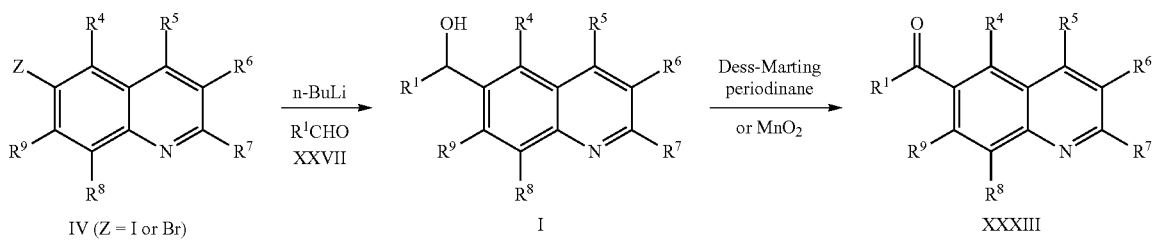

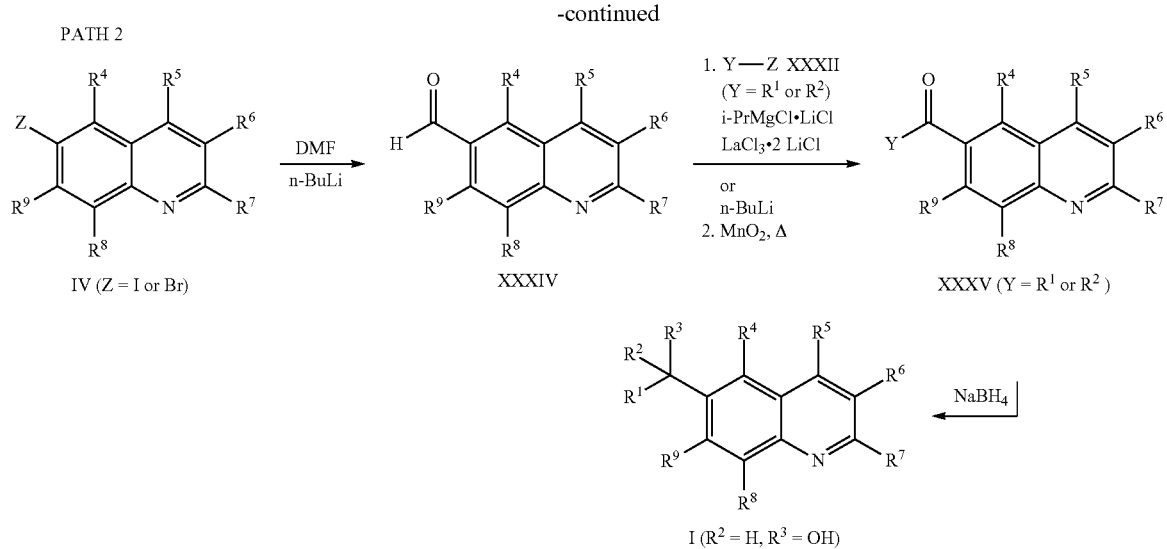

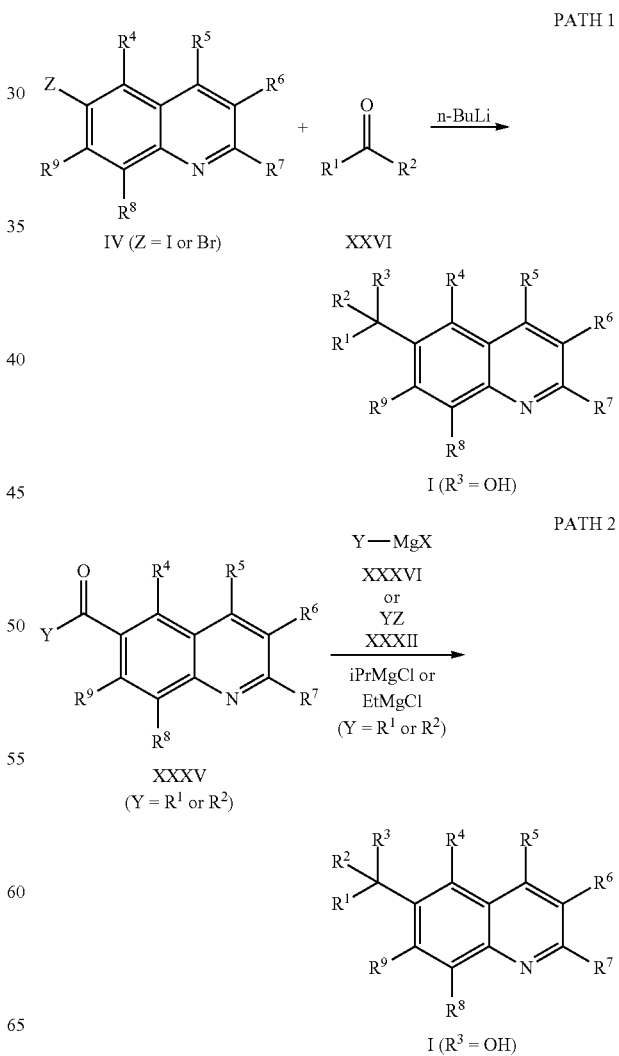

Scheme 9 exemplifies synthetic methods that could be used to prepare compounds of Formula I (paths 1-4). As illustrated in path 1, 6-bromo or 6-iodoquinolines IV in an appropriate solvent such as THF can be either premixed with the ketones XXVI at −78° C. followed by addition of n-BuLi or can be pretreated with n-BuLi at −78° C. prior to the addition of the ketones XXVI to afford the tertiary alcohols of Formula I, wherein $R^3$ is OH.

Path 2 illustrates the formation of tertiary alcohols of Formula I by treatment of the ketoquinolines XXXV (Y is $R^1$ or $R^2$) with Grignard reagents XXXVI that are either commercially available or can be prepared by a halogen-metal exchange of aryl halides XXXII with ethyl or isopropyl magnesium chloride as previously described. Similarly, as shown in path 3, an organometallic reagent, such as n-BuLi can be added to an aryl halide XXXII at temperatures between −78° C. and ambient temperature in a preferred solvent such as tetrahydrofuran followed by the addition of the ketoquinolines XXXV to afford the tertiary alcohols of Formula I wherein $R^3$ is OH and $R^1$ and $R^2$ are as defined above. Path 4 describes a method that can be used to incorporate an $R^2$ alkyl group by treating ketoquinolines XXXIII with an alkyl lithium at a temperature between −78 and −40° C. once solubilized in an appropriate solvent such as tetrahydropyran to provide quinolines of Formula I wherein $R^2$ is alkyl and $R^3$ is OH.

The ketoquinolines XXXIII can also be treated with a protected alkynyl lithium such as TMS-lithiumacetylide at temperatures between 0° C. and ambient temperature in a solvent such as THF followed by deprotection with a base such as KOH in a polar alcohol solvent such as methanol or ethanol to provide compounds of Formula I where in $R^2$ is acetylene and $R^3$ is OH (path 5).

PATH 3

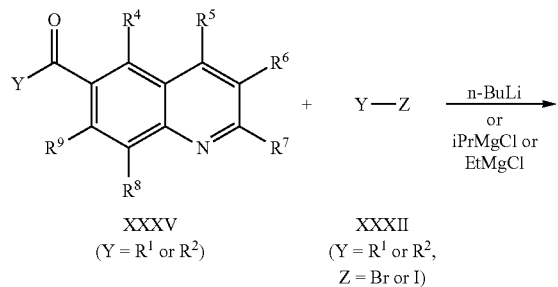

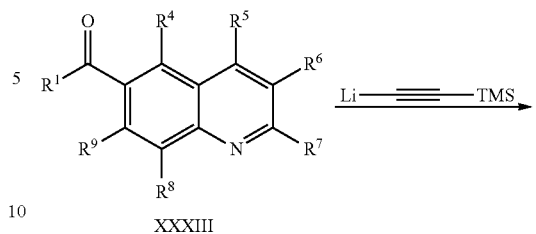

PATH 4

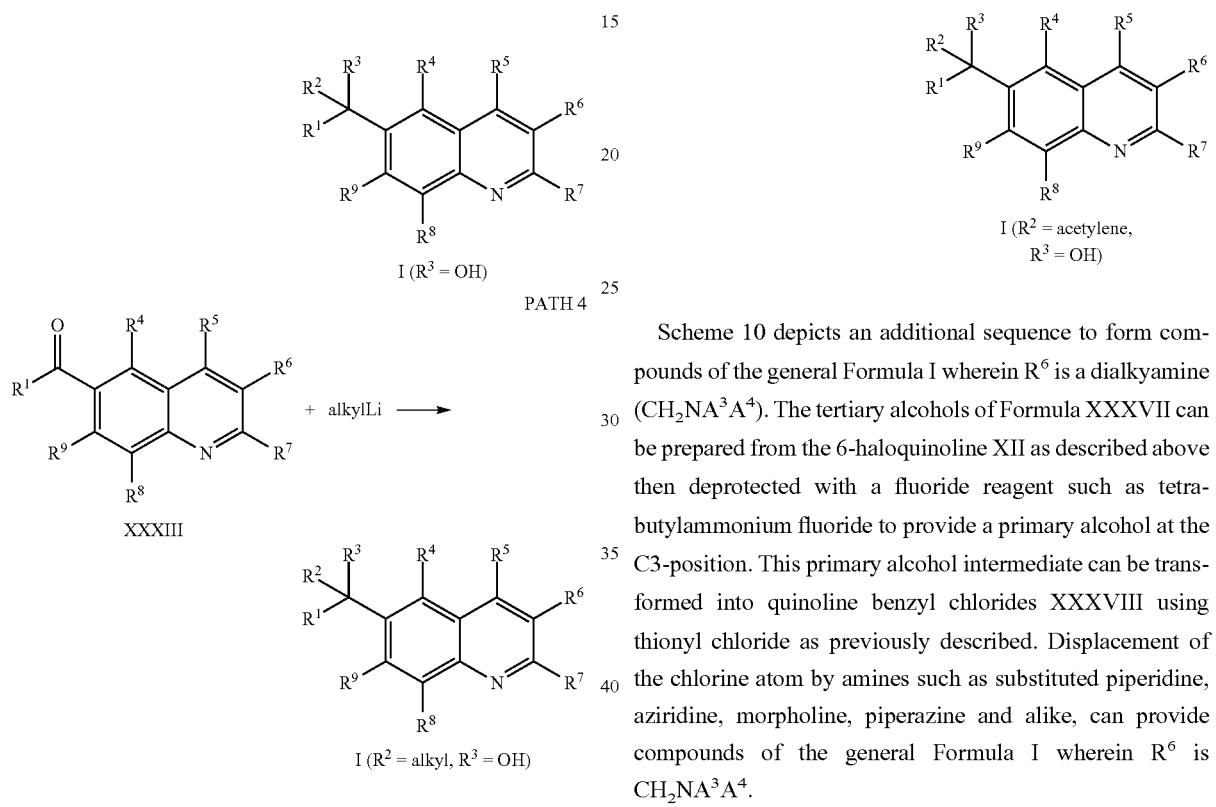

Scheme 10 depicts an additional sequence to form compounds of the general Formula I wherein $R^6$ is a dialkyamine ($CH_2NA^3A^4$). The tertiary alcohols of Formula XXXVII can be prepared from the 6-haloquinoline XII as described above then deprotected with a fluoride reagent such as tetrabutylammonium fluoride to provide a primary alcohol at the C3-position. This primary alcohol intermediate can be transformed into quinoline benzyl chlorides XXXVIII using thionyl chloride as previously described. Displacement of the chlorine atom by amines such as substituted piperidine, aziridine, morpholine, piperazine and alike, can provide compounds of the general Formula I wherein $R^6$ is $CH_2NA^3A^4$.

Scheme 10

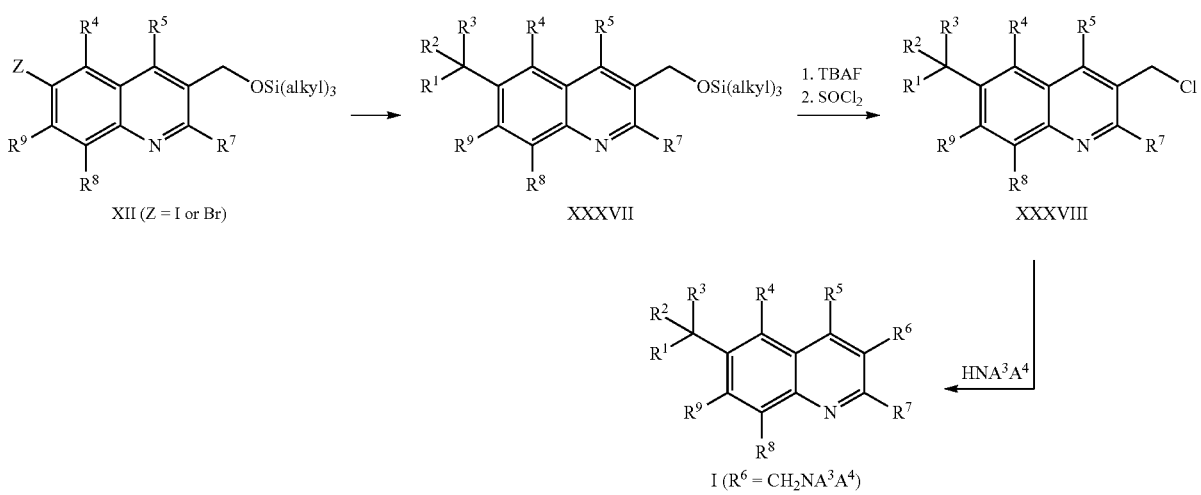

Scheme 11 illustrates methods used to synthesize compounds of Formula I wherein either the chlorine at $R^7$ or $R^5$ or at both $R^5$ and $R^7$ positions are replaced with nitrogen, oxygen, sulfur or alkyl groups. In path 1 and 4, nucleophilic displacement of 2,4-dichloroquinolines I ($R^5$ and $R^7$ are Cl) with NaO(alkyl) or NaS(alkyl), such as NaOMe, NaSMe, NaOEt, or NaOiPr, in an appropriate solvent, such as MeOH, EtOH, i-PrOH or DMF at elevated temperatures or with substituted hydroxy reagents such as 2-methoxyethanol in the presence of a base like sodium hydride in a non-polar solvent such as toluene provides compounds of Formula I wherein $R^5$ is Cl and $R^7$ is O(alkyl), O(CH$_2$)$_2$OCH$_3$ or S(alkyl) and compounds of Formula I wherein $R^5$ and $R^7$ are O(alkyl) or S(alkyl). Likewise, nucleophilic displacement of 2,4-dichloroquinolines I ($R^5$ and $R^7$ are Cl) with primary or secondary alkyl amines, heterocyclic amines, or N,O-dimethylhydroxylamine in polar solvents such as MeOH, EtOH, or Et$_2$NCHO, or DMF provides quinolines of Formula I (path 2) wherein $R^5$ and $R^7$ are either Cl or NA$^1$A$^2$, wherein A$^1$ and A$^2$ are as defined above. Introduction of cyclic amides can be accomplished using Buchwald palladium catalyzed coupling conditions to provide compounds of Formula I, wherein $R^7$ are rings such as azetidin-2-ones or pyrrolidin-2-ones. Replacement of chlorine at positions 2 and 4 of quinolines I ($R^5$ and $R^7$ are Cl) with alkyl groups can be carried out using Zn(alkyl)$_2$ in the presence of K$_2$CO$_3$ and a palladium catalyst, such as PdCl$_2$(dppf), to afford 2-alkyl and 2,4-dialkylquinolines of Formula I (path 3). Displacement of chlorine at the 2-position of 2,4-dichloroquinolines I with methylsulfone can be accomplished with methanesulfinic acid in a solvent such as DMF under elevated temperature between 90 and 110° C. (path 5).

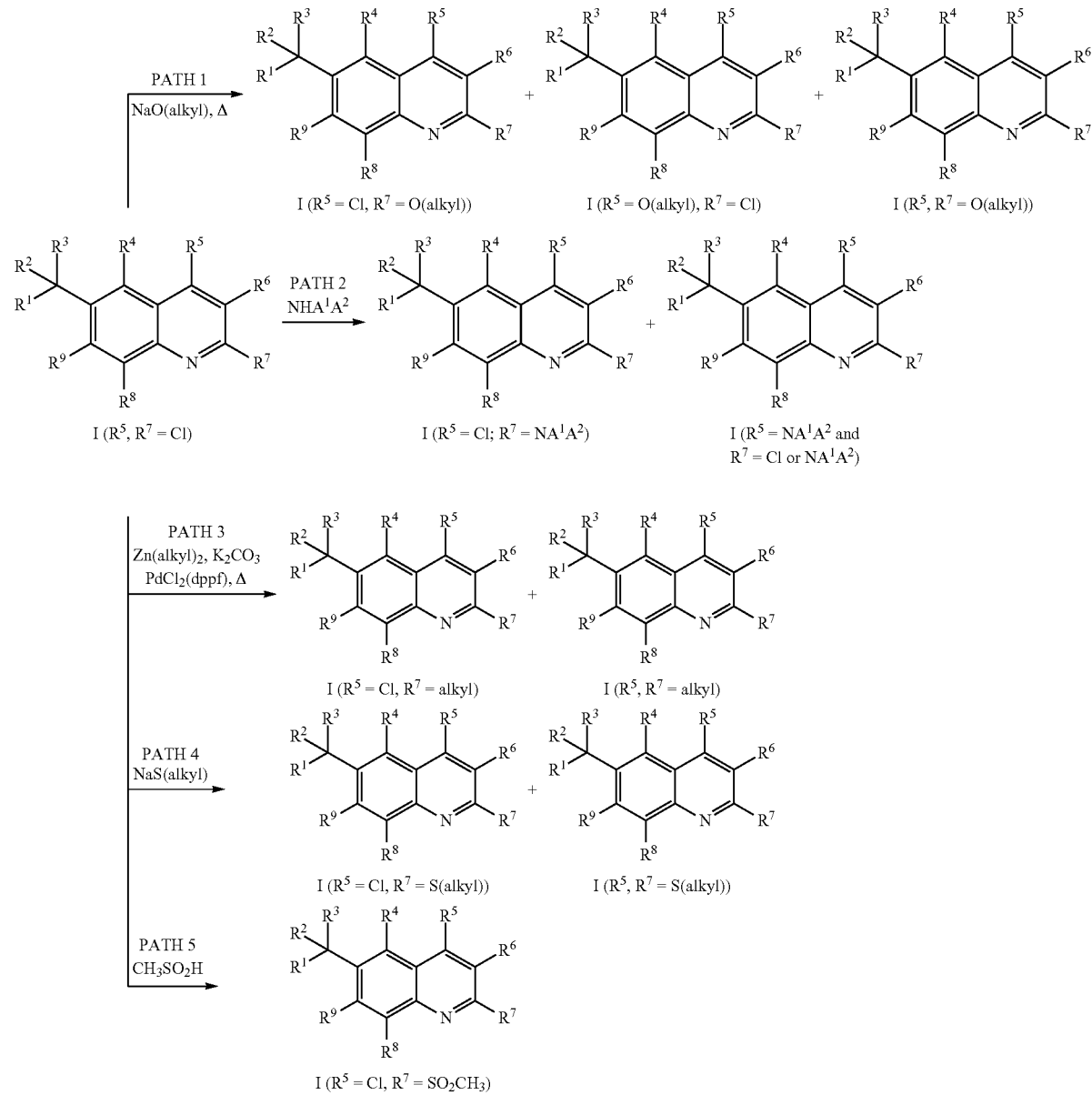

Compounds of Formula I, wherein $R^1$ and $R^2$ are the same, can also be prepared as described in Scheme 12. The intermediate quinoline methyl ester XXI can be treated with excess YLi, or YMgBr, in the presence or absence or lanthanum chloride, to afford the symmetrical compounds of Formula I.

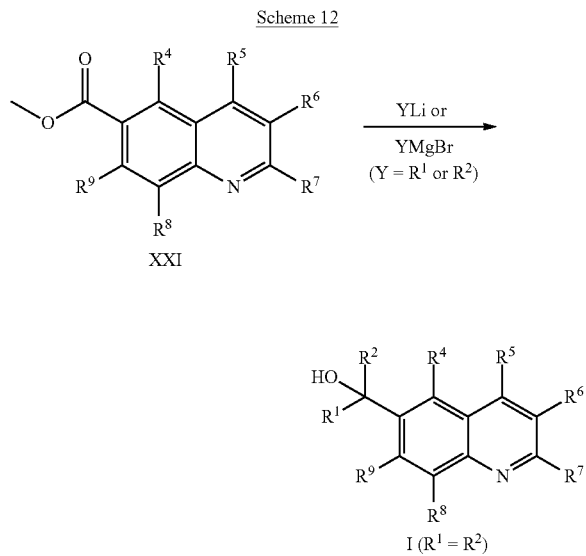

Scheme 13 describes a path to the introduction of trifluoromethyl groups at the quinoline 2 and 4-positions. The starting aniline XXXIX, prepared as described in Tetrahedron Letters (1986) 27, 1423-1424 and JMC (2009) 52, 7289-7300, can be converted to the quinoline esters of Formula XX ($R^5$ and $R^7$ are $CF_3$) by heating with alkyl 4,4,4-trifluoro-3-oxobutanoate and a base like piperidine in an alcoholic solvent like ethanol as described in WO2010/112826. The quinoline esters of Formula XX could then be further elaborated as described above to provide quinolines of Formula I wherein $R^6$ is $CO_2$alkyl and $R^5$ and $R^7$ are $CF_3$.

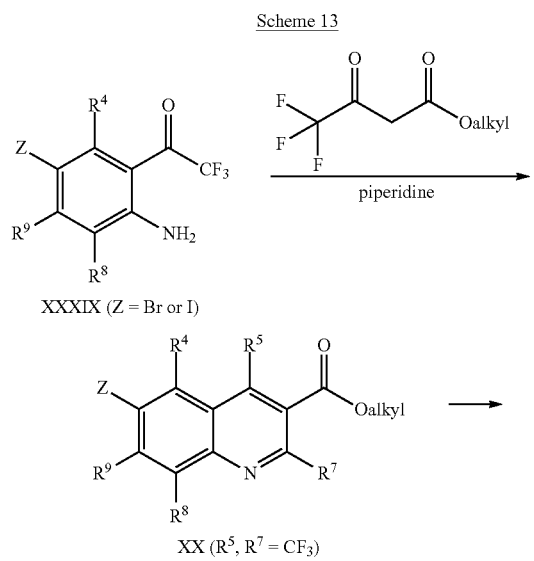

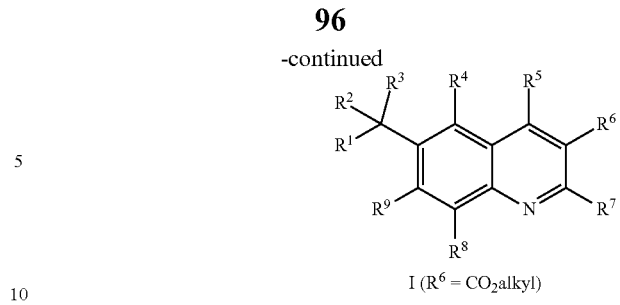

Scheme 14 outlines synthetic methods used to elaborate the quinoline 3-position of compounds of Formula I. Palladium-catalyzed hydrogenation of compounds of Formula I wherein $R^6$ is benzyloxy can provide intermediate quinolin-3-ols XL. As shown in path 1, the quinoline-3-ol XL can be substituted by a displacement reaction (Mitsunobu reaction) in the presence of a dialkylazodicarboxylate, such as diisopropylazodicarboxylate, and a triaryl phosphine, such as triphenylphosphine to provide compounds of Formula I wherein $R^6$ is OQ. Alternatively, the quinolin-3-ol XL can be converted into the corresponding triflate XLI with trifluoromethanesulfonic acid in the presence of a base, such as pyridine, in a solvent such as dichloromethane (path 2). Palladium-catalyzed cross coupling of the triflate XLI with organoboron reagents of the formula $R^6B(OR)_2$ in the presence of a base, such as potassium carbonate, in a solvent mixture such as 1,4-dioxane/water can provide compounds of Formula I wherein $R^6$ is a substituted or unsubstituted carbo or heterocyclic ring containing a double bond (eg. 1-methyl-1,2,3,6-tetrahydropyridin-4-yl, 2,2,6,6-tetramethyl-3,6-dihydro-2H-pyran-4-yl, 1-((trifluoromethyl)sulfonyl)-1,2,3,6-tetrahydropyridin-4-yl, 4,4-difluorocyclohex-1-en-1-yl, cyclopenten-1yl, etc. and alike). The double bond can be reduced by palladium catalyzed hydrogenation to provide compounds of Formula I wherein $R^6$ is a substituted or unsubstituted saturated carbo or heterocyclic ring.

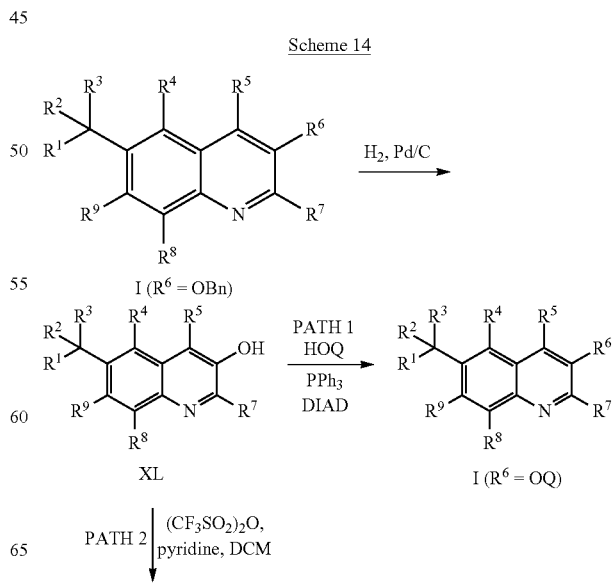

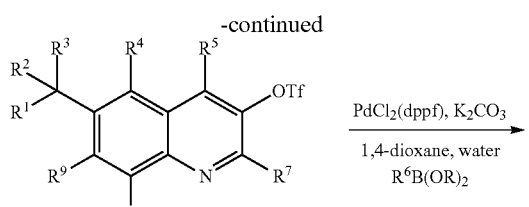

Scheme 16 describes additional methods that can be used to prepare compounds of Formula I wherein $R^6$ is 4-methyltetrahydro-2H-thiopyran 1,1-dioxide by treating quinolines of Formula XLII with 3-chlorobenzoyl peroxide in the presence of phosphorus tribromide in a solvent mixture such as dichloromethane and dimethylformamide.

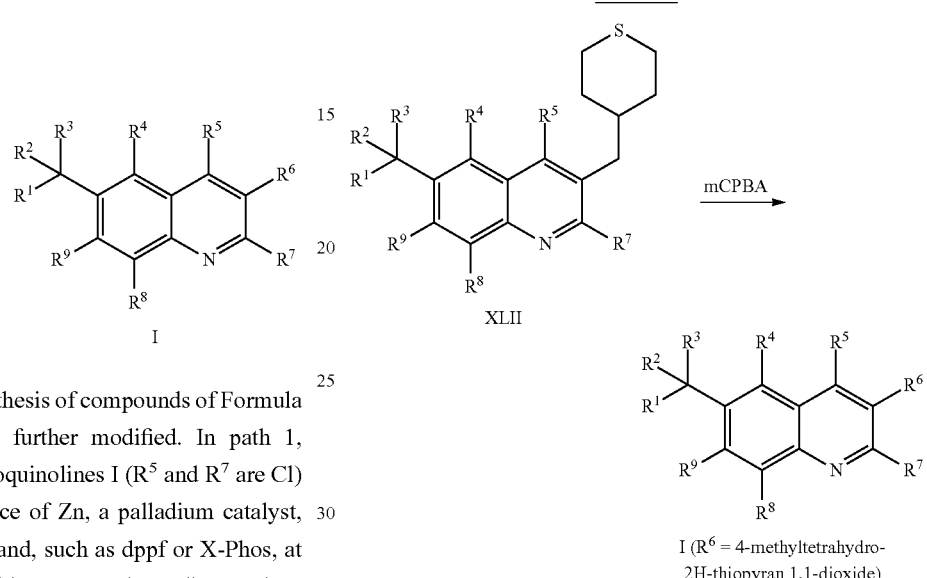

Scheme 15 details the synthesis of compounds of Formula I, wherein $R^5$ and $R^7$ are further modified. In path 1, cyanation of the 2,4-dichloroquinolines I ($R^5$ and $R^7$ are Cl) with $Zn(CN)_2$ in the presence of Zn, a palladium catalyst, such as $Pd_2(dba)_3$, and a ligand, such as dppf or X-Phos, at high temperatures can provide 2-CN and 2,4-diCN quinolines of Formula I.

The 2,4-dichloroquinolines I can also undergo a Suzuki palladium catalyzed cross-coupling reaction with alkyl or aryl boronic acids or esters with a palladium catalyst, such as $PdCl_2(dppf)$, yielding compounds of Formula I wherein $R^7$ is alkyl, aryl or heteroaryl (path 2).

As illustrated in Scheme 17, compounds of Formula I wherein only $R^5$ is a chlorine can be further substituted by treatment with alkylboronic acids or esters under Suzuki reaction conditions (path 1), with sodium alkoxides (path 2), or with zinc cyanide (path 3) using conditions previously described to provide compounds of Formula I wherein $R^5$ is alkyl, O(alkyl) or CN and $R^7$ is as defined above.

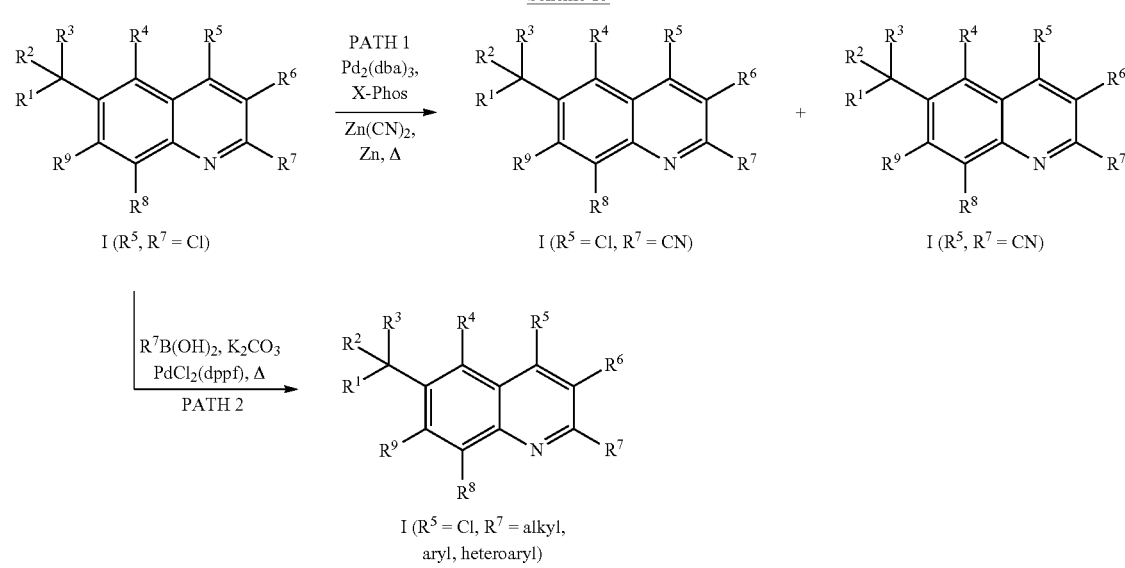

Scheme 17

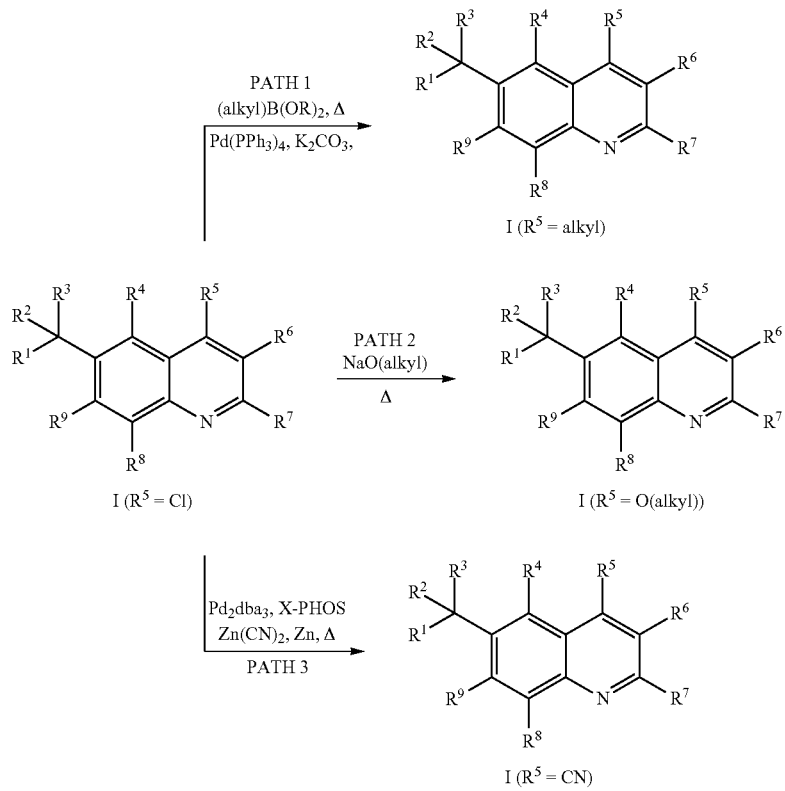

As shown in Scheme 18, tertiary alcohols of Formula I can be treated with base, such as NaH, and alkylated with MeI in DMF to provide compounds of Formula I wherein $R^3$ is OMe.

Scheme 18

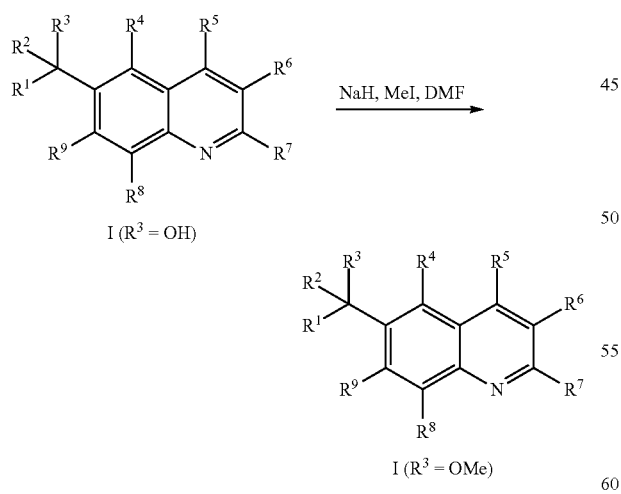

Synthetic routes to compounds of Formula I, wherein $R^3$ is $NH_2$, are illustrated in Scheme 19. Ketimines XLIII may be prepared by Ti(OEt)$_4$ mediated condensation of ketones XXVI with 2-methylpropane-2-sulfinamide in refluxing THF. Addition of n-BuLi to the reaction mixture of ketimines XLIII and 6-bromo or 6-iodoquinolines IV at −78° C. followed by cleavage of the tert-butanesulfinyl group with HCl in MeOH liberates tertiary amines of Formula I.

Alternatively, compounds of Formula I, wherein $R^3$ is OH can be treated with sodium hydride followed by addition of acetic anhydride or acetyl chloride and stirred at room temperature over a 24 to 72 hour period to provide the intermediate acetate wherein $R^3$ is OAc. The acetate can then be combined with a solution of ammonia in methanol and heated at temperatures between 60 and 85° C. to provide compounds of Formula I, wherein $R^3$ is $NH_2$.

Scheme 19

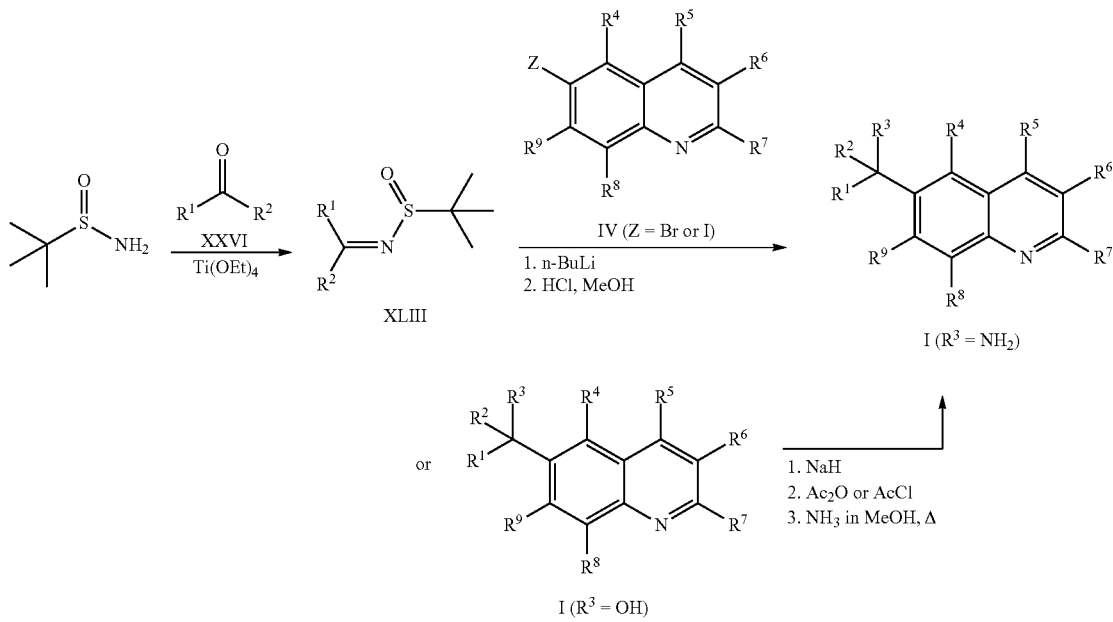

As shown in Scheme 20, the quinolines of Formula I wherein $R^7$ is CN can be hydrolyzed as described in US20080188521 by treatment with sodium carbonate and hydrogen peroxide to provide compounds of Formula I wherein $R^7$ is $CONH_2$ (path 1) or can be treated with a strong acid like HCl to convert CN to a carboxylic acid XLIV (path 2). Once formed, the acid can be further coupled to substituted amines using appropriate coupling reagents such as EDCI or HATU in the presence of a base like triethylamine or Hunig's base to provide compounds of Formula I wherein $R^7$ is $CONA^1A^2$.

Synthesis of compounds of Formula I, wherein $R^7$ is an aminoalkylaminomethylene or an aminoalkoxymethylene can be prepared from 2-methylquinolines as shown in Scheme 21. Bromination of 2-methylquinolines of Formula I can be accomplished with N-bromosuccinimide in acetic acid at elevated temperatures as described in WO2010151740, to provide the methylbromide intermediate XLV. Nucleophilic displacement of the bromide under basic conditions using procedures known in the art could afford compounds of Formula I wherein $R^7$ is $-CH_2NHC_{(2-3)}alkylNA^1A^2$ or $-CH_2N(CH_3)C_{(2-3)}alkylNA^1A^2$ (path 1) or $CH_2OC_{(2-3)}alkylNA^1A^2$ (path 2) and $A^1$ and $A^2$ are as defined above.

Scheme 20

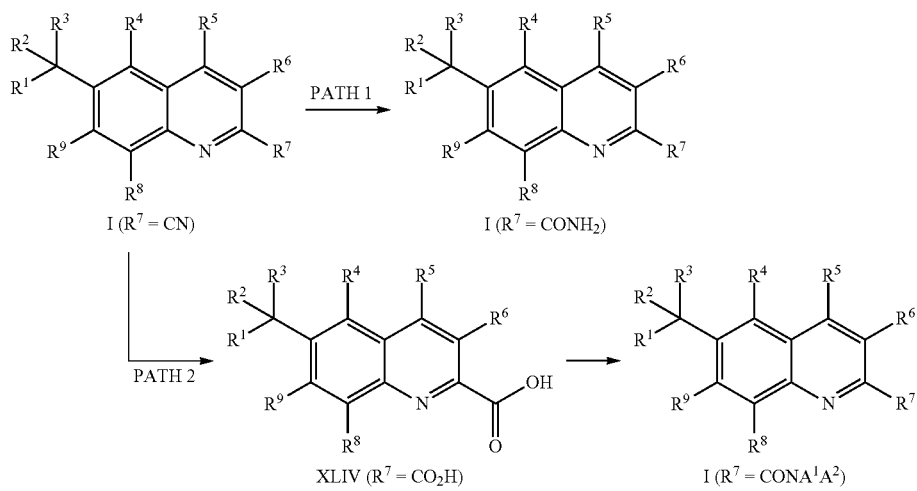

Scheme 21

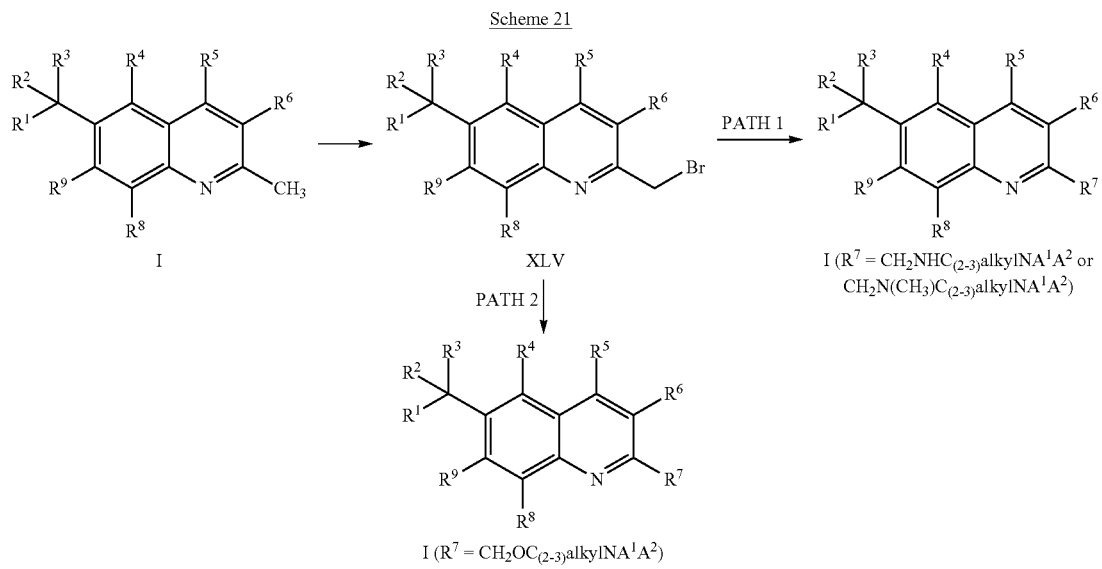

Compounds of Formula I wherein $R^1$, $R^2$ or $R^6$ are or contain a pyridyl can be treated with m-chloroperbenzoic acid in a chlorinated solvent at ambient temperature to 40° C. to form the pyridyl-N-oxides of Formula I.

Precursors to compounds of formula IV, wherein $R^8$ is H or $CH_3$, can be prepared from methyl-2-nitrobenzoates XLVI by first hydrogenation of the nitro group in the presence of Raney nickel in a solvent such as methanol followed by bromination with N-bromosuccinimide in dichloromethane to provide methyl-2-aminobenzoates VI (Scheme 22). Methyl-2-aminobenzoates VI can be transformed into compounds of formula IV as detailed above.

Scheme 22

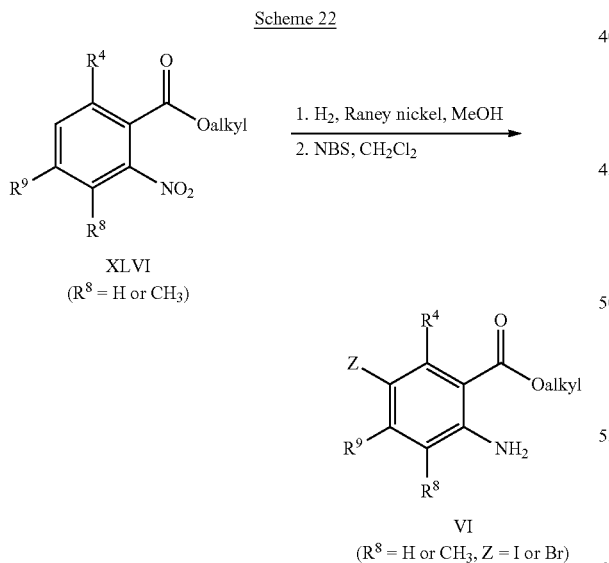

Compounds of formula I, wherein $R^6$ is —$OCH_2CF_3$ can be prepared as shown in Scheme 23. Treatment of compounds of formula XL with 2,2,2-trifluoroethyl trifluoromethanesulfonate in the presence of a base such as cesium carbonate in a solvent such as tetrahydrofuran affords compounds of formula I ($R^6$ is —$OCH_2CF_3$).

Scheme 23

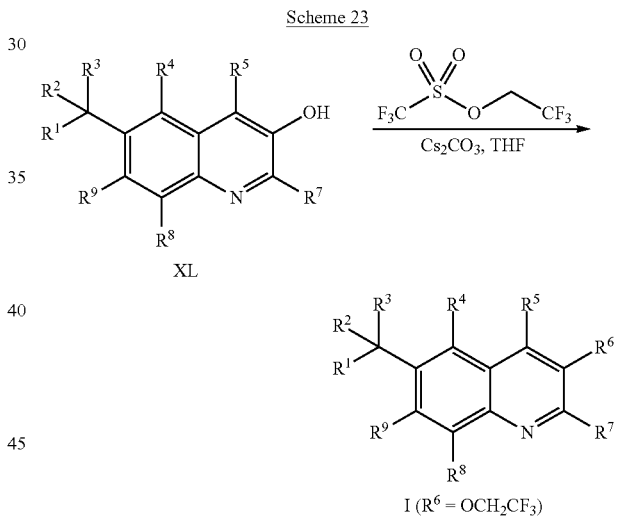

Compounds of formula XXI, wherein $R^6$ is —$CH_2Br$ or —$CH_2OTBS$ can be prepared as shown in Scheme 24. Starting with condensation of 4-amino benzoates with malonic acids V ($R^6$=$CH_3$) in the presence of phosphorus oxychloride followed by treatment with NaOalkyl as described above affords compounds of formula XXI ($R^6$=$CH_3$). Benzylic halogenation with a bromination reagent such as N-bromosuccinimide in the presence of a radical initiator such as azobisisobutyronitrile in a solvent such as carbon tetrachloride provides compounds of formula XXI ($R^6$=$CH_2Br$). Conversion of the benzylic bromide into the benzylic alcohol can be achieved with a reagent such as silver sulfate in a solvent mixture such as water/dioxane and, following protection of the alcohol functional group with tert-butylchlorodimethylsilane (TBSCl) in the presence of imidazole in a solvent such as dimethylformamide, furnishes the compound of formula XXI ($R^6$=$CH_2OTBS$).

Scheme 24

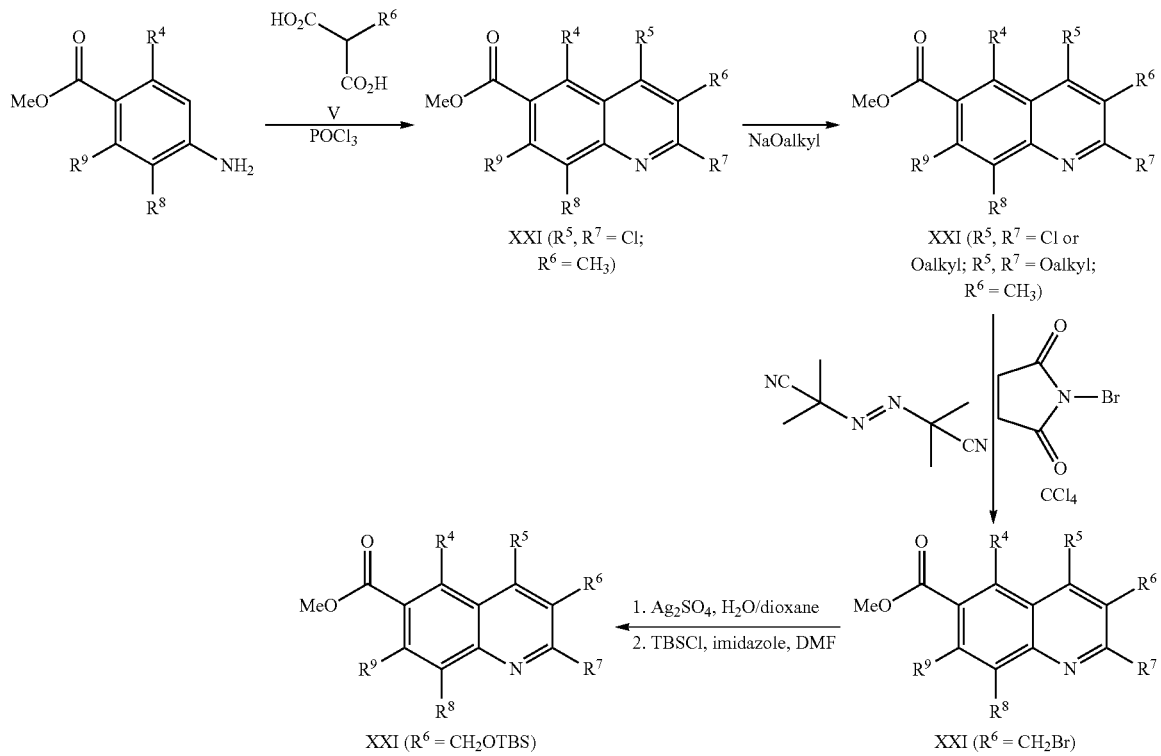

Compounds of formula I, wherein $R^1$ and $R^2$ are the same and $R^6$ is —$CH_2NA^3A^4$, can also be prepared as described in Scheme 25. Treatment of compounds of the formula XXI [$R^6$=$CH_2OSi(alkyl)_3$] with excess YLi or YMgBr affords compounds of formula XXXVII. Treatment with trifluoroacetic acid in a solvent such as dichloromethane followed by chlorination with a reagent such as thionyl chloride in a solvent such as tetrahydrofuran affords compounds of formula XXXVIII. Displacement of the chlorine atom by amines in the presence of a base such as triethylamine with or without the addition of potassium iodide can provide compounds of the general formula I, wherein $R^6$ is —$CH_2NA^3A^4$.

Scheme 25

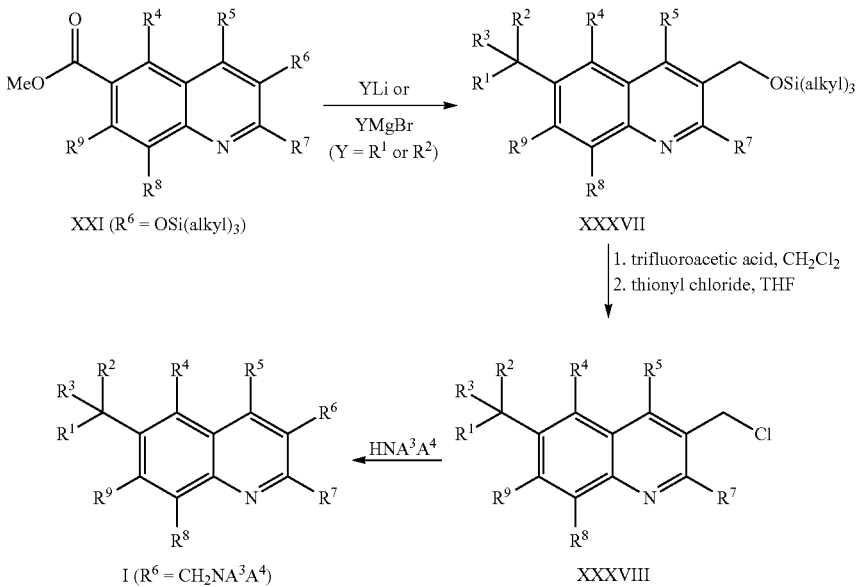

Compounds of formula I, wherein $R^1$ and $R^2$ are the same and $R^6$ is —$CH_2NA^3A^4$, can also be prepared as described in Scheme 26. Displacement of the bromine atom in XXI ($R^6$=$CH_2Br$) with diallylamine affords XLVII. Addition of excess YLi or YMgBr affords compounds of formula XLVIII. Removal of the allyl groups with tetrakis(triphenylphosphine)palladium (0) and 1,3-dimethylpyrimidine-2,4,6 (1H,3H,5H)-trione followed by amide bond formation using standard coupling conditions provided compounds of the formula I ($R^6$=$CH_2NA^3A^4$)

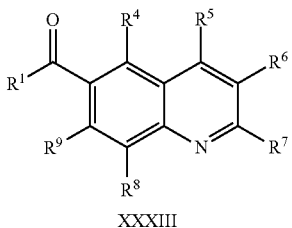

XXXIII

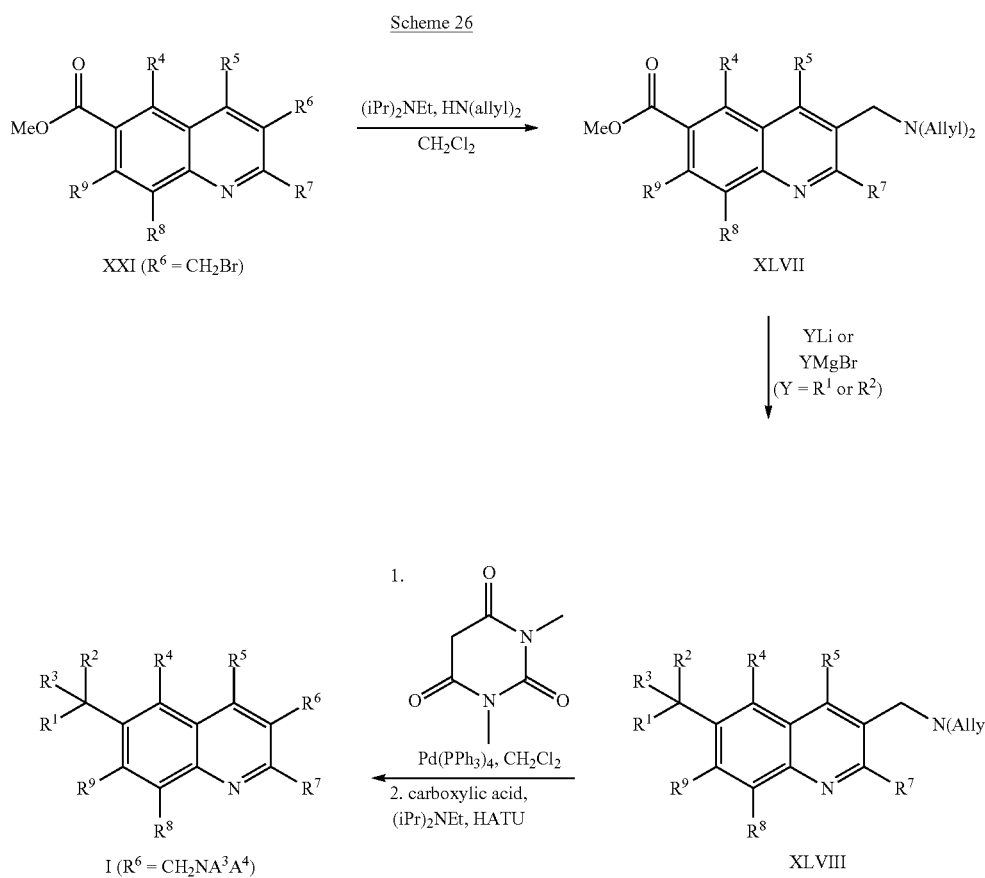

Compounds of the general formula XXXIII can be formed by coupling of the organolithium or organomagnesium intermediate derived from compounds of the formula IV with amides of the general structure XXIII (Scheme 27).

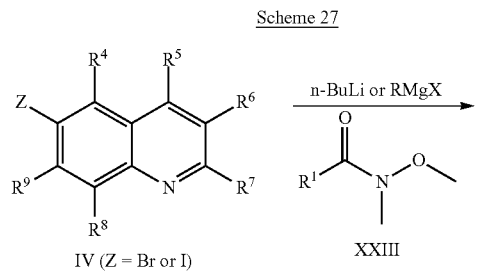

Compounds of the general formula I, wherein $R^2$ is N-acyl- or sulfonyl-azetidinyl or N-acyl- or sulfonyl-piperidinyl can be prepared as detailed in Scheme 28. N-Boc protected compounds of the general formula I ($R^2$=N-Boc-azetidin-3-yl or N-Boc-piperidin-4-yl) are treated with an acid such as trifluoroacetic acid in a solvent such as dichloromethane to remove the Boc protecting group. Acylation or sulfonylation with reagents such as acetic anhydride/acid chlorides or sulfonyl chlorides, respectively, in the presence of a base such as triethylamine, affords compounds of the formula I ($R^2$ is N-acyl- or sulfonyl-azetidinyl or N-acyl- or sulfonyl-piperidinyl).

Scheme 28

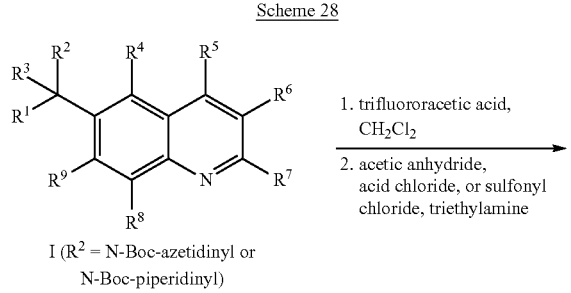

I (R² = N-Boc-azetidinyl or N-Boc-piperidinyl)

1. trifluororacetic acid, CH₂Cl₂
2. acetic anhydride, acid chloride, or sulfonyl chloride, triethylamine chlorination with phosphorus oxychloride as described previously affords compounds of the general formula XIX ($R^5$=Cl, Z=Br). Reduction of the ester functional group with a reagent such as DIBAL-H provides compounds of the general formula XIX. Transformation of the alcohol functional group into the corresponding alkyl chloride with a reagent such as methane sulfonylchloride in the presence of a base such as diisopropylethyl amine furnishes compounds of the general formula XIII. Compounds of the general formula I can be synthesized by displacement of the alkyl chloride by amines and formation of the tertiary alcohol as described previously.

Scheme 29

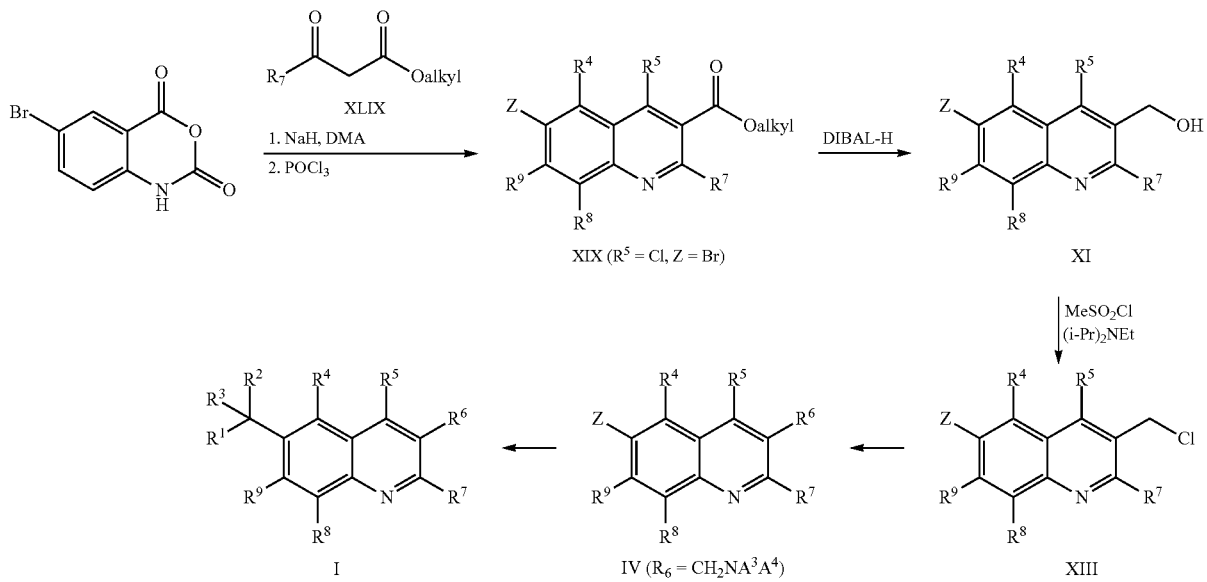

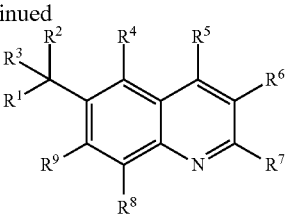

I (R² = N-acyl- or sulfonyl-azetidinyl or N-acyl- or sulfonyl-piperidinyl)

Compounds of the general formula I, wherein $R^7$ is alkyl or cycloalkyl can be prepared as detailed in Scheme 29. Coupling of 6-bromo-1H-benzo[d][1,3]oxazine-2,3-dione (5-bromoisatoic anhydride) with 3-alkyl/cycloalkyl-3-oxo-propanoates (XLIX, pre-treated with a base such as sodium hydride) in a solvent such as dimethylacetamide followed by

EXAMPLES

Compounds of the present invention can be prepared by methods known to those who are skilled in the art. The following examples are only meant to represent examples of the invention and are in no way meant to be a limit of the invention.

Intermediate 1: Step a

6-Bromo-2,4-dichloroquinoline

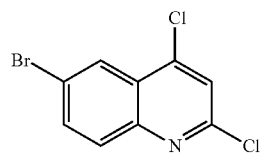 [SMILES: Clc1cc(Cl)c2cc(Br)ccc2n1]

Into a 250-mL round-bottom flask was placed a solution of 4-bromoaniline (10.0 g, 58.13 mmol, 100%) and propanedioic acid (6.4 g, 61.50 mmol) in POCl₃ (30 mL). The resulting solution was stirred for 12 hours at 100° C. The reaction was then quenched by the addition of 200 mL of water/ice. The resulting solution was extracted with 3×100 mL of ethyl acetate. The combined organic layer was dried over anhydrous sodium sulfate, filtered and concentrated under vacuum. The residue was purified by chromatography over a silica gel column with ethyl acetate/petroleum ether (1:50-1:10) to afford the title compound as a white solid.

Intermediate 1: Step b

6-Bromo-2,4-dichloroquinoline-3-carbaldehyde

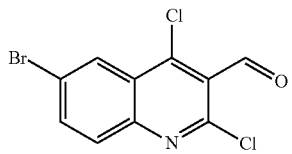

Into a 100-mL round-bottom flask was placed a solution of bis(propan-2-yl)amine (1.44 g, 14.23 mmol, 100%) in 20 mL THF, and then n-BuLi (5.24 mL, 13.1 mmol, 2.5 M in hexanes) at −78° C. After 30 minutes, 6-bromo-2,4-dichloroquinoline (3.3 g, 11.92 mmol, Intermediate 1: step a) was added. The resulting solution was stirred for 1 hour at −78° C. A solution of N,N-dimethylformamide (1.04 g, 14.23 mmol) in tetrahydrofuran (30 mL) was then added. The resulting solution was stirred for an additional 5 hours at −78° C. The reaction was then quenched by the addition of 10 mL of water. The resulting solution was extracted with 3×50 mL of ethyl acetate. The combined organic layers were dried over anhydrous sodium sulfate, filtered and concentrated under vacuum. The residue was purified by chromatography over a silica gel column with dichloromethane/petroleum ether (100:1) to afford the title compound as a yellow solid.

Intermediate 1: Step c (6-Bromo-2,4-dichloroquinolin-3-yl)methanol

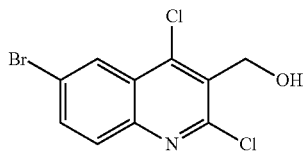

Into a 100-mL round-bottom flask was placed a solution of 6-bromo-2,4-dichloroquinoline-3-carbaldehyde (1.5 g, 4.92 mmol, Intermediate 1: step b) in tetrahydrofuran (20 mL). NaBH$_3$CN (930 mg, 14.80 mmol) was then added and the resulting solution was stirred for 12 hours at 25° C. The resulting mixture was concentrated under vacuum. The residue was purified by chromatography over a silica gel column and eluted with ethyl acetate/petroleum ether (1:4) to afford the title compound as a white solid.

Intermediate 1: Step d

6-Bromo-2,4-dichloro-3-(chloromethyl)quinoline

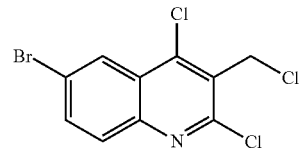 [SMILES: ClCc1c(Cl)nc2ccc(Br)cc2c1Cl]

Into a 250-mL round-bottom flask, was placed a solution of (6-bromo-2,4-dichloroquinolin-3-yl) methanol (650 mg, 2.12 mmol, Intermediate 1: step c) and thionyl chloride (2.5 g, 21.2 mmol) in dichloromethane (100 mL). The resulting solution was stirred for 12 hours at 25° C. The resulting mixture was concentrated under vacuum. The residue was purified by chromatography over a silica gel column and eluted with ethyl acetate/petroleum ether (1:10) to afford the title compound as a white solid.

Intermediate 1: Step e 4-((6-Bromo-2,4-dichloroquinolin-3-yl)methyl)morpholine

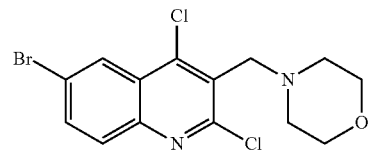 [SMILES: Clc1nc2ccc(Br)cc2c(Cl)c1CN1CCOCC1]

Into a 100-mL round-bottom flask purged and maintained with an inert atmosphere of nitrogen, was placed a solution of morpholine (88.4 mg, 1.01 mmol), sodium hydride (44.3 mg, 1.11 mmol, 60%) and 6-bromo-2,4-dichloro-3-(chloromethyl)quinoline (300 mg, 0.92 mmol, Intermediate 1: step d) in N,N-dimethylformamide (10 mL). The resulting mixture was stirred for 2 hours at room temperature. The reaction was then quenched by the addition of 30 mL of water. The resulting solution was extracted with 3×20 mL of ethyl acetate. The combined organic layer was dried (Na$_2$SO$_4$), filtered and concentrated under vacuum. The residue was purified by chromatography over a silica gel column with ethyl acetate/petroleum ether (1:4) to afford the title compound as a white solid.

Intermediate 2: Step a 1-(5-Bromo-2-fluorophenyl)-2,2,2-trifluoroethanone

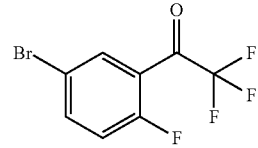 [SMILES: O=C(c1cc(Br)ccc1F)C(F)(F)F]

A solution of diisopropylamine (22.1 mL, 157 mmol) in 140 mL THF was stirred under argon at −68° C. while n-BuLi (57.9 mL, 2.59 M in hexane, 150 mmol) was added in a fine stream in 2 portions over 6 minutes. The resulting pale yellow homogeneous solution was removed from the acetone/dry ice bath and stirred at ambient conditions for 9 minutes, and was then cooled back down to −68° C. and a solution of 1-bromo-4-fluorobenzene (15.6 mL, 143 mmol) in THF (30 mL) was added rapidly dropwise over 5 minutes. The reaction was then stirred in the cold bath for another 6 minutes, and the pale yellow reaction was then treated rapidly dropwise with a solution of ethyl trifluoroacetate (18.7 mL, 157 mmol) in THF (30 mL) over ~8 minutes (internal temp rose to −47° C.). The pale yellow reaction was then stirred overnight as the acetone/dry ice bath expired (15 hours). The resulting yellow homogeneous solution was washed with 5 M aqueous NH$_4$Cl (2×50 mL), and the organic layer was dried (Na$_2$SO$_4$), filtered, and concentrated to provide the crude title compound as a clear dark yellow oil.

Intermediate 2: Step b 1-(2-Amino-5-bromophenyl)-2,2,2-trifluoroethanone

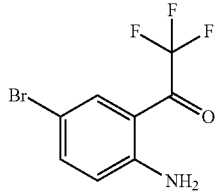

A solution of 1-(5-bromo-2-fluorophenyl)-2,2,2-trifluoroethanone (6.67 g, 24.6 mmol, Intermediate 2: step a) in DMSO (6.2 mL) was treated with NaN$_3$ (1.76 g, 27.0 mmol) and stirred under air (lightly capped) at 95° C. for 1 hour. The brownish-red opaque reaction was then cooled to room temperature on an ice bath, diluted with EtOAc (49 mL), treated with SnCl$_2$.dihydrate (6.66 g, 29.5 mmol) in several portions over ~30 seconds followed by water (1.33 mL, 73.8 mmol), and the mixture was stirred at room temperature for 30 minutes. The reddish solution with heavy off-white particulates was then treated with anhydrous Na$_2$SO$_4$ (~6 g; ~40 mmol; ~400 mmol water capacity) and stirred vigorously for a few minutes. The mixture was then filtered over a bed of Celite®, and the cloudy orange filtrate was dry load flash chromatographed (~60 g silica gel) with a heptane to 50% DCM/heptane gradient to provide the title compound as an orange oil that crystallized upon standing.

Intermediate 2: Step c

Ethyl 6-bromo-2,4-bis(trifluoromethyl)quinoline-3-carboxylate

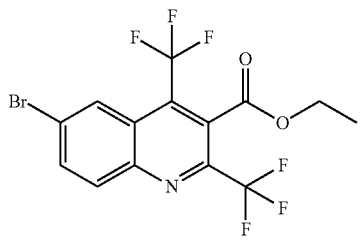 [SMILES: CCOC(=O)c1c(C(F)(F)F)nc2ccc(Br)cc2c1C(F)(F)F]

A mixture of 1-(2-amino-5-bromophenyl)-2,2,2-trifluoroethanone (0.416 g, 1.55 mmol, Intermediate 2: step b), ethyl 4,4,4-trifluoro-3-oxobutanoate (0.286 g, 1.55 mmol), piperidine (0.153 mL, 1.55 mmol), and EtOH (0.5 mL) was heated in a microwave reactor at 130° C. for 30 minutes (Biotage® Initiator). The homogeneous amber solution was concentrated and the residue flash chromatographed (2%-50% DCM in heptane) to provide the title compound as a clear yellow oil.

Intermediate 3: Step a tert-Butyl 4-((4-fluorophenyl)(hydroxy)methyl)piperidine-1-carboxylate

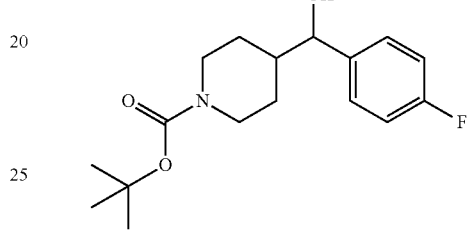

A solution of tert-butyl 4-formylpiperidine-1-carboxylate (10.4 g, 48.7 mmol) in THF (70 mL) was stirred at ~−70° C. under argon while 4-fluorophenylmagnesium bromide (1.10 M in THF, 45.6 mL, 50.1 mmol) was added dropwise over 9 minutes. The reaction was then immediately removed from the cold bath and allowed to warm to room temperature with stirring. The yellow homogeneous reaction was allowed to sit at room temperature for 2 days, and was then quenched with 5 M aqueous NH$_4$Cl (20 mL) and partitioned with MTBE (25 mL). The aqueous layer was extracted with MTBE (25 mL), and the combined organic layers were dried (Na$_2$SO$_4$), filtered, and concentrated. The residue was flash chromatographed (0-100% EtOAc in heptane) to provide the title compound as a clear colorless thick oil.

Intermediate 3: Step b tert-Butyl 4-((4-fluoro-3-(2,2,2-trifluoroacetyl)phenyl)(hydroxy)methyl)piperidine-1-carboxylate A translucent solution of tert-butyl 4-((4-fluorophenyl)(hydroxy)methyl)piperidine-1-carboxylate (3.24 g, 10.5 mmol, Intermediate 3: step a), N,N,N',N',N"-pentamethyldiethylenetriamine (4.59 mL, 22.0 mmol), and KOtBu (1.02 M in THF, 21.6 mL, 22.0 mmol) was stirred at −70° C. (internal temperature) while sec-BuLi (1.42 M in cyclohexane, 15.5 mL, 22.0 mmol) was added dropwise over 9 minutes. After stirring for an additional 20 minutes, 2,2,2-trifluoro-N-methoxy-N-methylacetamide (2.66 mL, 22.0 mmol) was added dropwise over 5 minutes and stirred for an additional 10 minutes. The reaction was then quenched with 5 M aqueous NH$_4$Cl (20 mL) and extracted with MTBE (1×20 mL, 1×30 mL). The combined organic layers were washed with 1 M aqueous NaH$_2$PO$_4$ (2×25 mL), dried (Na$_2$SO$_4$), filtered, and concentrated to provide the title compound as a clear yellow oil.

Intermediate 3: Step c tert-Butyl 4-(4-fluoro-3-(2,2,2-trifluoroacetyl)benzoyl)piperidine-1-carboxylate

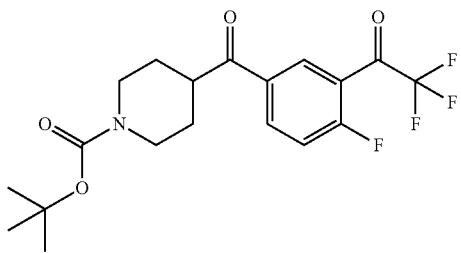 [SMILES: CC(C)(C)OC(=O)N1CCC(C(=O)c2ccc(F)c(C(=O)C(F)(F)F)c2)CC1]

A solution of tert-butyl 4-((4-fluoro-3-(2,2,2-trifluoroacetyl)phenyl)(hydroxy)methyl)piperidine-1-carboxylate (4.45 g, 11.0 mmol, Intermediate 3: step b) and TEMPO (51.5 mg, 0.329 mmol) in DCM (22 mL) was treated with a solution of KBr (131 mg, 1.10 mmol) in 1 M aqueous NaHCO$_3$ (3.84 mL, 3.84 mmol) while stirring in an ice bath. NaOCl (0.89 M in water, 6.15 w/w % Clorox® bleach, 13.6 mL, 12.1 mmol) was then added dropwise over 4 minutes (internal temperature stayed below 14° C.). After 30 minutes stirring in the ice bath, the aqueous layer was extracted with CHCl$_3$ (2×20 mL). The combined organic layers were washed with 5 M aqueous NaCl (40 mL), dried (Na$_2$SO$_4$), and concentrated to provide the crude title compound as a clear dark yellow thick oil that was used without further purification.

Intermediate 3: Step d tert-Butyl 4-(4-amino-3-(2,2,2-trifluoroacetyl)benzoyl)piperidine-1-carboxylate

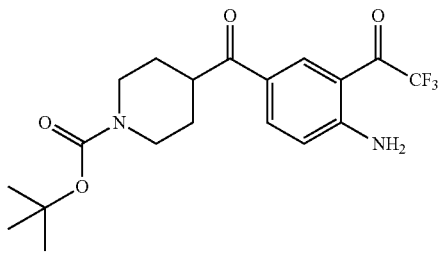 [SMILES: CC(C)(C)OC(=O)N1CCC(C(=O)c2ccc(N)c(C(=O)C(F)(F)F)c2)CC1]

A solution of tert-butyl 4-(4-fluoro-3-(2,2,2-trifluoroacetyl)benzoyl)piperidine-1-carboxylate (3.67 g, 9.10 mmol, Intermediate 3: step c) in DMSO (2.25 mL) was bubbled with ammonia for 1 minute in a 200 mL capacity round bottomed pressure flask, and was then sealed and stirred at 100° C. for 2 hours. The reaction was then cooled to room temperature and partitioned with MTBE (20 mL) and 1 M aqueous NaHCO$_3$ (20 mL), and the aqueous layer was extracted with MTBE (20 mL). The combined organic layers were dried (Na$_2$SO$_4$), filtered, and concentrated to dryness. The residue was dry load flash chromatographed (0-50% acetone in heptane) to provide the title compound as a thick orange oil.

Intermediate 3: Step e (Z)-4,4,4-Trifluoro-3-hydroxy-1-(piperidin-1-yl)but-2-en-1-one

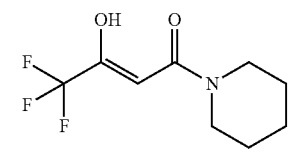 [SMILES: O=C(/C=C(\O)C(F)(F)F)N1CCCCC1]

A solution of ethyl 4,4,4-trifluoro-3-oxobutanoate (20 g, 108 mmol) in m-xylene (20 mL) was treated with piperidine (9.66 mL, 97.8 mmol) in one portion at room temperature. The reaction immediately became hot, and this was refluxed under air (heating mantle 170° C.) for 30 minutes. The reaction was cooled to room temperature and vacuum distilled through a short path Vigreaux microdistillation apparatus and vacuum re-distilled through a ~5" Vigreaux column to provide the title compound as a clear very pale yellow oil.

Intermediate 3: Step f tert-Butyl 4-(3-(piperidine-1-carbonyl)-2,4-bis(trifluoromethyl)quinoline-6-carbonyl)piperidine-1-carboxylate

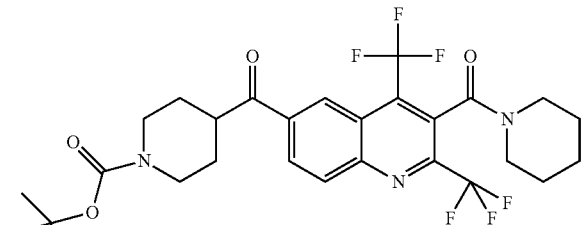

A solution of tert-butyl 4-(4-amino-3-(2,2,2-trifluoroacetyl)benzoyl)piperidine-1-carboxylate (0.964 g, 2.36 mmol, Intermediate 3: step d) and (Z)-4,4,4-trifluoro-3-hydroxy-1-(piperidin-1-yl)but-2-en-1-one (0.665 g, 2.98 mmol, Intermediate 3: step e) in DMF (2.4 mL) was treated with tributylamine (0.618 mL, 2.60 mmol) and stirred at 130° C. for 3 hours. The reaction was cooled to room temperature and partitioned with diethyl ether (8 mL) and 1 M aqueous NaH$_2$PO$_4$ (8 mL). The organic layer was washed with 1 M aqueous NaH$_2$PO$_4$ (8 mL), dried (Na$_2$SO$_4$), filtered, and concentrated. The residue was flash chromatographed (0-50% acetone in heptane over 20 column volumes) to provide the title compound as a clear light amber thick oil.

Intermediate 4: Step a

4-Hydroxy-6-iodoquinolin-2(1H)-one

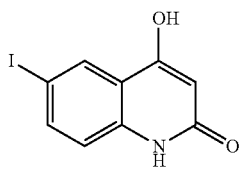 [SMILES: O=c1cc(O)c2cc(I)ccc2[nH]1]

A mixture of 4-iodoaniline (13.1 g, 59.7 mmol) and Meldrum's acid (8.61 g, 59.7 mmol) was stirred at 85° C. for 1 hour, and a stream of nitrogen gas was then blown onto the reaction for 15 minutes to remove acetone. The resulting dark semi-solid was then removed from the heating block and Eaton's Reagent (7.4 w/w % P2O5, 88.1 mL, 68.7 mmol) was added in one portion. The reaction was stirred for 3 hours at 75° C., and the reaction was then stirred in an ice bath while water (180 mL) was slowly poured in as a constant stream. The reaction was stirred in the ice bath for ~15 minutes and then filtered. The brown filter cake was washed with water (2×25 mL) and air dried at 110° C. to provide the title compound as a light brown powder.

Intermediate 4: Step b 2,4-Dichloro-6-iodo-3-((tetrahydro-2H-pyran-4-yl)methyl)quinoline

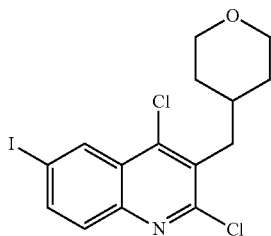 [SMILES: Clc1nc2ccc(I)cc2c(Cl)c1CC1CCOCC1]

A mixture of 4-hydroxy-6-iodoquinolin-2(1H)-one (7.20 g, 25.1 mmol, Intermediate 4: step a), tetrahydro-2H-pyran-4-carbaldehyde (3.20 g, 28.0 mmol), and diethyl 2,6-dimethyl-1,4-dihydropyridine-3,5-dicarboxylate (7.06 g, 27.9 mmol) in pyridine (50 mL) was stirred under argon at 130° C. for 30 minutes. The reaction was concentrated, and the residue was treated with POCl₃ (23.5 mL, 252 mmol) and stirred at 90° C. for 1 hour. The reaction was cooled to room temperature, diluted with DCM (75 mL), and stirred in an ice bath while ice water (50 mL) was poured in one portion. The dark solution was stirred in the ice bath for a few minutes and then at room temperature for 30 minutes. The aqueous layer was partitioned between water (100 mL) and DCM (40 mL), and the organic layers were combined and washed with water (2×100 mL), dried (Na₂SO₄), filtered, and concentrated. The residue was purified by FCC (DCM isocratic elution) twice to afford the title compound as a thick dark yellow oil.

Intermediate 4: Step c

4-Chloro-6-iodo-2-methoxy-3-((tetrahydro-2H-pyran-4-yl)methyl)quinoline

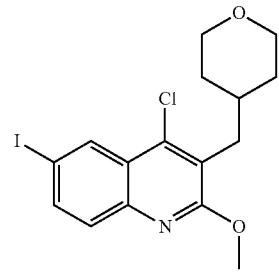 [SMILES: COc1nc2ccc(I)cc2c(Cl)c1CC1CCOCC1]

A mixture of 2,4-dichloro-6-iodo-3-((tetrahydro-2H-pyran-4-yl)methyl)quinoline (3.59 g, 8.51 mmol, Intermediate 4: step b), sodium methoxide (4.61 g, 85.3 mmol), and toluene (85 mL) was stirred at 100° C. under argon for 22 hours. The reaction was cooled to room temperature, filtered, and the filter cake was washed with DCM (50 mL). The combined filtrates were concentrated to provide the title compound as a light yellow solid.

Intermediate 5 tert-Butyl 4-(4-chloro-2-methoxy-3-((tetrahydro-2H-pyran-4-yl)methyl)quinoline-6-carbonyl)piperidine-1-carboxylate

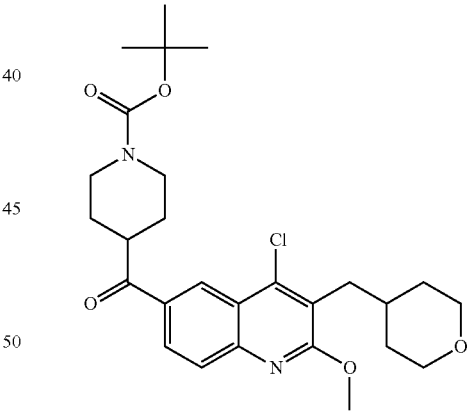

A solution of 4-chloro-6-iodo-2-methoxy-3-((tetrahydro-2H-pyran-4-yl)methyl)quinoline (692 mg, 1.66 mmol, Intermediate 4: step c) in THF (5.6 mL) was stirred at ~−70° C. under argon while n-BuLi (1.63 M in hexane, 0.97 mL, 1.58 mmol) was added dropwise over 2.5 minutes. After stirring an additional 1 minute, a solution of tert-butyl 4-(methoxy(methyl)carbamoyl)piperidine-1-carboxylate (538 mg, 1.98 mmol) in THF (1 mL) was added dropwise over 45 seconds. The reaction was stirred in the cold bath for 1 hour, removed from the cold bath and stirred at ambient conditions for 20 minutes, and was then quenched with 5 M aqueous NH₄Cl (0.5 mL). The organic layer was dried (Na₂SO₄), filtered, and concentrated, and the residue was flash chromatographed (0-50% EtOAc in heptane over 18 column volumes) to provide the title compound as an off-white crystalline solid.

Intermediate 6: Step a

Methyl 5-iodo-2-(2-(tetrahydro-2H-pyran-4-yl)acetamido)benzoate

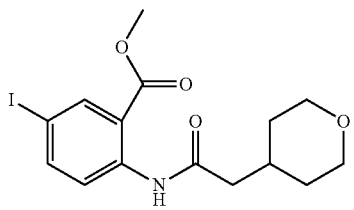 [SMILES: COC(=O)c1cc(I)ccc1NC(=O)CC1CCOCC1]

A solution of methyl 2-amino-5-iodobenzoate (7.02 g, 25.3 mmol) and 2-(tetrahydro-2H-pyran-4-yl)acetic acid (3.76 g, 26.1 mmol) in pyridine (25 mL) was stirred at ~−40° C. under argon while POCl$_3$ (2.58 g, 27.8 mmol) was added dropwise over 3 minutes. The cold bath was immediately removed and the reaction was allowed to stir for 1 hour. The reaction was then diluted with water (75 mL) and extracted with DCM (75 mL). The combined orange organic layers were washed with 6 M aqueous HCl (50 mL), 1 M aqueous HCl (50 mL), and 2 M aqueous K$_3$PO$_4$ (50 mL), dried (Na$_2$SO$_4$), filtered, and concentrated to provide the title compound as an orange solid.

Intermediate 6: Step b

4-Hydroxy-6-iodo-3-(tetrahydro-2H-pyran-4-yl)quinolin-2(1H)-one

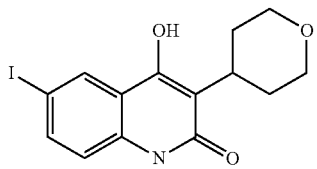 [SMILES: O=c1[nH]c2ccc(I)cc2c(O)c1C1CCOCC1]

A solution of methyl 5-iodo-2-(2-(tetrahydro-2H-pyran-4-yl)acetamido)benzoate (7.21 g, 17.9 mmol, Intermediate 6: step a) in THF (179 mL) was stirred on a dry ice/acetone bath under argon while sodium bis(trimethylsilyl)amide (1.01 M in THF, 37.2 mL, 37.6 mmol) was added dropwise over 6 minutes. The reaction was stirred for 20 minutes, and then removed from the cold bath and stirred at ambient conditions for 100 minutes. LCMS showed the reaction had stalled with only a few % conversion, so the reaction was chilled to ~−70° C. again and treated with additional sodium bis(trimethylsilyl)amide (1.01 M in THF, 16.8 mL, 17.0 mmol) dropwise over 4 minutes, and stirred for 15 minutes before removing the cold bath and allowing the reaction to stir under ambient conditions overnight. LCMS after 15 hours showed a ~2:1:1 ratio of methyl 5-iodo-2-(2-(tetrahydro-2H-pyran-4-yl)acetamido)benzoate/5-iodo-2-(2-(tetrahydro-2H-pyran-4-yl)acetamido)benzoic acid/title compound. Therefore, the reaction was chilled in a dry ice/acetone bath again while potassium bis(trimethylsilyl)amide (0.52 M in toluene, 15.5 mL, 8.05 mmol) was added dropwise over 3 minutes, the cold bath was immediately removed, and the reaction was allowed to stir under ambient conditions for 3 hours. LCMS showed ~no further conversion to title compound, so the reaction was quenched with 6 M aqueous HCl (21 mL, 126 mmol) and the organic layer was dried (Na$_2$SO$_4$), filtered, and concentrated to provide the impure title compound that was used without further purification.

Intermediate 6: Step c 2,4-Dichloro-6-iodo-3-(tetrahydro-2H-pyran-4-yl)quinoline

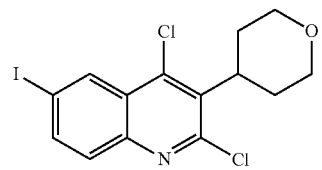 [SMILES: Clc1nc2ccc(I)cc2c(Cl)c1C1CCOCC1]

A mixture of very impure 4-hydroxy-6-iodo-3-(tetrahydro-2H-pyran-4-yl)quinolin-2(1H)-one (7.74 g crude, "20.9 mmol", Intermediate 6: step b) and POCl$_3$ (19.4 mL, 208 mmol) was stirred at 90° C. for 2.5 hours. The reaction was then cooled to room temperature, dissolved in DCM (100 mL), stirred in an ice bath for ~10 minutes, and then treated with ice water (100 mL) in one portion. This was stirred in the ice bath for ~45 minutes, and the resulting slurry was filtered over a bed of Celite®. The clear dark organic layer filtrate was dried (Na$_2$SO$_4$), filtered, and concentrated, and the residue was dry load flash chromatographed (0-30% EtOAc in heptanes over 13 column volumes) to afford the title compound as a yellow solid.

Intermediate 6: Step d

4-Chloro-6-iodo-2-methoxy-3-(tetrahydro-2H-pyran-4-yl)quinoline

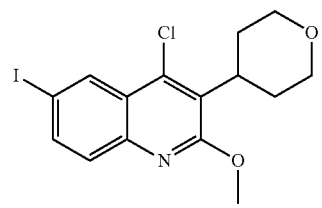 [SMILES: COc1nc2ccc(I)cc2c(Cl)c1C1CCOCC1]

A mixture of 2,4-dichloro-6-iodo-3-(tetrahydro-2H-pyran-4-yl)quinoline (0.734 g, 1.80 mmol, Intermediate 6: step c), sodium methoxide (0.972 g, 18.0 mmol), and toluene (18 mL) was stirred at 120° C. under argon for 20 hours. The reaction was cooled to room temperature, filtered, and the filter cake was washed with toluene (2×3 mL). The combined filtrates were concentrated to provide the title compound as a yellow solid.

Intermediate 7

1-(4-Benzoylpiperidin-1-yl)ethanone

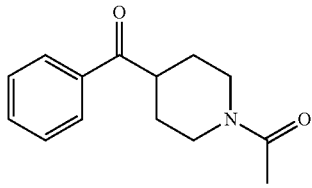 [SMILES: CC(=O)N1CCC(C(=O)c2ccccc2)CC1]

A mixture of phenyl(piperidin-4-yl)methanone hydrochloride (743 mg, 3.29 mmol) in dichloromethane (13.2 mL) and triethylamine (1.10 mL, 7.90 mmol) in an ice bath under argon was treated with Ac$_2$O (0.373 mL, 3.95 mmol) dropwise over 1 minute, and the resulting translucent mixture was immediately removed from the ice bath and stirred at room temperature overnight. The reaction was then extracted with 1 M aqueous HCl (8 mL) followed by 1 M aqueous NaOH (8 mL). The organic layer was dried (Na$_2$SO$_4$), filtered, and concentrated to provide the title compound as a translucent beige oil that crystallized upon standing.

Intermediate 8

6-Bromo-3-methoxy-2-phenylquinoline

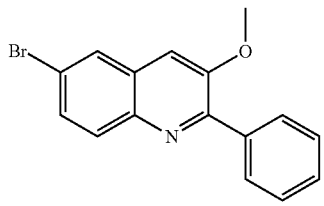 [SMILES: COc1cc2cc(Br)ccc2nc1-c1ccccc1]

A mixture of KOH pellets (0.775 g, ~15 w/w % water, ~11.8 mmol), 2-amino-5-bromobenzaldehyde (2.31 g, 11.6 mmol), and absolute EtOH (36 mL) was treated with 2-methoxy-1-phenylethanone (1.67 mL, 12.1 mmol), and the dark solution with undissolved KOH was stirred at 95° C. for 15 minutes. The dark homogeneous reaction was allowed to cool to room temperature, and within 1 hour crystallization seemed complete. The reaction was then shaken with water (36 mL) and filtered, and the orange-red filter cake was washed with water (36 mL). The filter cake was air-dried at 110° C. to provide the title compound as orange-tan fine crystals.

Intermediate 9: Step a

6-Bromo-2,4-dichloro-3-methylquinoline

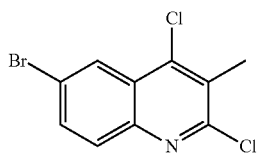

A mixture of 4-bromoaniline (77 g, 450 mmol) and 2-methylmalonic acid (53 g, 450 mmol) in phosphorus oxychloride (500 mL) was stirred at 100° C. for 5 hours. Initially, the mixture was a white slurry, which then turned into a homogeneous red solution. The reaction mixture was cooled to room temperature and stirred overnight. Most of the phosphorus oxychloride was removed by rotary evaporation. The thick red residue was slowly poured into ice (1 L). A yellow solid crashed out and was collected by filtration. The collected solids were placed into a 500 mL flask cooled in an ice-water bath. Concentrated aqueous ammonia solution was added until the pH was between 8-9 (by litmus paper test). The resulting suspension was stirred at room temperature for 20 minutes and filtered. The solids were rinsed with water (500 mL) and then collected. The collected solids were dried and then suspended in acetonitrile (500 mL). The suspension was sonicated for 15 minutes at room temperature. The solids were collected by filtration, rinsed with acetonitrile (200 mL), and dried to afford the title compound.

Intermediate 9: Step b

6-Bromo-4-chloro-2-methoxy-3-methylquinoline

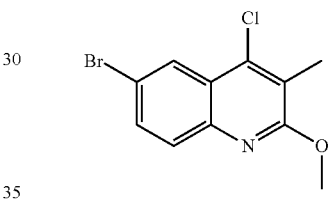

Sodium methoxide (151 g, 2.80 mol) was added to a solution of 6-bromo-2,4-dichloro-3-methylquinoline (67.8 g, 233 mmol, Intermediate 9: step a) in toluene (750 mL) with stirring. The mixture was stirred at 100° C. for 2 hours and then cooled to room temperature. Dichloromethane (500 mL) was added and then the mixture was filtered. The filter cake was washed with dichloromethane (200 mL). The filtrate was concentrated to provide a crude solid which was recrystallized from acetonitrile to provide the title compound as a white solid.

Intermediate 10: Step a

6-(Trifluoromethyl)nicotinoyl chloride

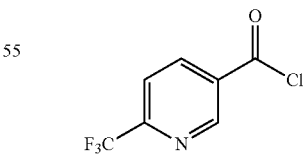

To a 1 L 3-neck flask equipped with an overhead stirrer, Claisen adaptor, nitrogen bubbler, 60 mL addition funnel, and thermocouple was added 6-(trifluoromethyl)nicotinic acid (45 g, 235.5 mmol), dichloromethane (540 mL) and DMF (0.910 mL, 11.77 mmol) via syringe. To this solution was added oxalyl chloride (24.51 mL, 282.56 mmol) and the reaction was allowed to stir at ambient temperature overnight. The reaction was then filtered and the clear filtrate was condensed in vacuo to afford the title compound as a brownish semisolid.

Intermediate 10: Step b

N-Methoxy-N-methyl-6-(trifluoromethyl)nicotinamide

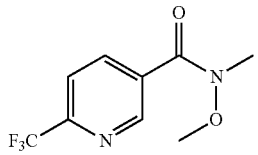

To a 1 L 3-neck flask equipped with an overhead stirrer, Claisen adaptor, nitrogen bubbler, 125 mL addition funnel, and thermocouple was added 6-(trifluoromethyl)nicotinoyl chloride (49.3 g, 235.2 mmol, Intermediate 10: step a), dichloromethane (493 mL), and N,O-dimethylhydroxylamine hydrochloride (25.63 g, 258.8 mmol). After the mixture was cooled to 7° C., diisopropylethylamine (90.263 mL, 517.6 mmol) was added such that the addition temperature did not exceed 16° C. After the addition, the reaction was allowed to warm to room temperature. The reaction was then transferred to a separatory funnel and the organic layer was washed with saturated aqueous NaHCO₃ (2×100 mL) followed by water (100 mL) and then dried over sodium sulfate, then filtered. Solvent removal afforded the title compound as a brownish oil.

Intermediate 10: Step c (1-Methyl-1H-imidazol-5-yl)(6-(trifluoromethyl)pyridin-3-yl)methanone

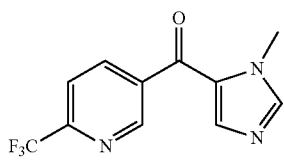

To a 3 L 4-neck flask equipped with an overhead stirrer, nitrogen bubbler, and thermocouple was added 5-bromo-1-methyl-1H-imidazole (47.96 g, 297.9 mmol), followed by THF (537 mL). To this room temperature solution was added isopropylmagnesium chloride/lithium chloride complex [1.3 M in THF] (246.8 mL, 320.8 mmol) (addition temperature maintained between 16.6 and 25° C.) to afford a milky suspension and the reaction was stirred for 60 minutes and then cooled to 5.3° C. in an ice bath. To this mixture was added a solution of N-methoxy-N-methyl-6-(trifluoromethyl)nicotinamide (53.66 g, 229.14 mmol, Intermediate 10: step b) in THF (268.3 mL) (addition temperature between 5.3 and 5.6° C.) to afford an orange mixture. After addition, the reaction was warmed to room temperature over 2 hours. After stirring at room temperature for 18 hours, THF (200 mL) was added and the reaction was stirred for 2 hours. The reaction was then cooled to 4° C. with an ice bath and carefully quenched with 2 N aqueous HCl to pH=7, quenching temperature reached 12° C. The mixture was diluted with ethyl acetate (500 mL), phase split and the organic layer was washed with brine (2×200 mL), dried over sodium sulfate, filtered, and the solvent was removed. Hot ether was added and the suspension was then filtered to afford the title compound as a solid.

Intermediate 11: Step a (2,6-Dimethylpyridin-3-yl)(1-methyl-1H-1,2,3-triazol-5-yl)methanol

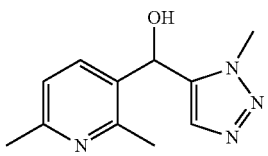 [SMILES: Cc1ccc(C(O)c2cnnn2C)c(C)n1]

A solution of n-butyllithium in hexanes (2.5 M, 22.5 mL, 56.3 mmol) was added dropwise by syringe to a stirring solution of 1-methyl-1H-1,2,3-triazole (5.00 g, 60.2 mmol, prepared according to PCT Int. Appl., 2008098104) in dry tetrahydrofuran (400 mL) at −55° C. The resulting off-white slurry was stirred at −45° C. for 20 minutes, whereupon a solution of 2,6-dimethyl-pyridine-3-carbaldehyde (8.33 g, 61.7 mmol) in dry tetrahydrofuran (10 mL) was added dropwise by syringe. After 5 minutes, the cooling bath was removed and the reaction mixture was allowed to slowly warm. After 45 minutes, saturated aqueous ammonium chloride solution (10 mL) and ethyl acetate (100 mL) were added. The mixture was concentrated by rotary evaporation. The residue was dissolved in ethyl acetate (300 mL). The organic solution was washed with saturated aqueous sodium chloride solution (100 mL, containing excess solid sodium chloride). The aqueous layer was extracted with ethyl acetate (2×100 mL). The organic layers were combined and the combined solution was concentrated. Ether (100 mL) was added to the residue and the mixture was sonicated for 20 minutes during which time a white solid crashed out. The solids were collected by filtration. Ether (100 mL) was added to the collected solids and the mixture sonicated a second time. After 20 minutes, the mixture was filtered and the solids were collected to provide the title compound as a fine powder.

Intermediate 11: Step b (2,6-Dimethylpyridin-3-yl)(1-methyl-1H-1,2,3-triazol-5-yl)methanone

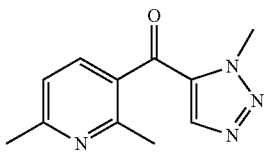 [SMILES: Cc1ccc(C(=O)c2cnnn2C)c(C)n1]

A mixture containing (2,6-dimethylpyridin-3-yl)(1-methyl-1H-1,2,3-triazol-5-yl)methanol (9.8 g, 44.9 mmol, Intermediate 11: step a) and manganese dioxide (18.8 g, 184 mmol) in dry 1,4-dioxane (225 mL) was heated to 100° C. with stirring. After 1 hour, the mixture was cooled to 40° C. The cooled mixture was filtered through a 2 cm pad of Celite® rinsing with tetrahydrofuran (100 mL). The filtrate was concentrated in vacuo to provide the title compound as an off-white solid.

Intermediate 12: Step a (2,4-Dimethylthiazol-5-yl)(1-methyl-1H-1,2,3-triazol-5-yl)methanol

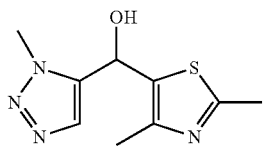

1-Methyl-1H-1,2,3-triazole was prepared according to the literature reference WO2008/98104. To a 2 L flask containing 1-methyl-1H-1,2,3-triazole (9 g, 108.3 mmol) was added THF (1500 mL) and the solution was cooled to −40° C. To this colorless homogeneous solution was added n-butyllithium (2.5 M in hexanes, 45 mL, 112.5 mmol) dropwise which immediately afforded a dark brown viscous mixture. The mixture was kept between −10 to −20° C. for 60 minutes, then a THF solution of 2,4-dimethylthiazole-5-carbaldehyde (17.2 g, 121.8 mmol in 200 mL THF) was introduced via cannula. Once the aldehyde was added the reaction was allowed to warm to room temperature. After 3 hours, the reaction was quenched by pouring it into a saturated solution of aqueous NH$_4$Cl. The aqueous portion was extracted with EtOAc in portions, 7×400 mL. The combined organics were washed with brine, dried over MgSO$_4$, filtered and concentrated to dryness to give a brown oil. Chromatography on silica gel (10% acetone-DCM increasing to 50% acetone and increasing to 10% MeOH-DCM) provided the title compound as an amber solid.

Intermediate 12: Step b (2,4-Dimethylthiazol-5-yl)(1-methyl-1H-1,2,3-triazol-5-yl)methanone

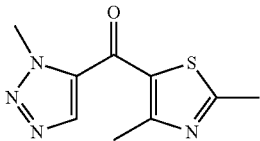

To a 500 mL flask containing (2,4-dimethylthiazol-5-yl)(1-methyl-1H-1,2,3-triazol-5-yl)methanol (10.5 g, 46.8 mmol, Intermediate 12: step a) was added 1,4-dioxane (400 mL) and the contents were warmed to form a homogeneous solution. Activated MnO$_2$ (18 g, 207 mmol) was added and the dark brownish mixture was heated to reflux in an aluminum heating mantle under an atmosphere of N$_2$. After 1.5 hours, the contents were filtered while still hot through Celite® and rinsed with warm THF. The resulting light orange solution was concentrated and passed through a silica gel column (25% acetone-DCM) to provide the title compound as a light orange solid.

Intermediate 13: Step a 3-(Cyclopropylmethyl)-4-hydroxy-6-iodoquinolin-2(1H)-one

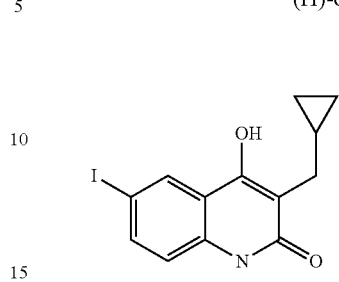

A mixture containing 4-hydroxy-6-iodoquinolin-2(1H)-one (2.0 g, 7.0 mmol, Intermediate 4: step a), cyclopropylcarboxaldehyde (0.52 mL, 7.0 mmol), and diethyl 1,4-dihydro-2,6-dimethyl-3,5-pyridinedicarboxylate (1.9 g, 7.0 mmol) in pyridine (23 mL) was heated to 80° C. After 2 hours, the flask was allowed to cool to 23° C. Diethyl ether (30 mL) was added and then the mixture was concentrated, resulting in a solid residue. The solid was suspended in diethyl ether (50 mL) and then sonicated for 5 minutes. The solids were collected by filtration through paper, rinsing with diethyl ether. The washed solids were dried under high vacuum at 50° C. to afford the title compound as a tan solid.

Intermediate 13: Step b 2,4-Dichloro-3-(cyclopropylmethyl)-6-iodoquinoline

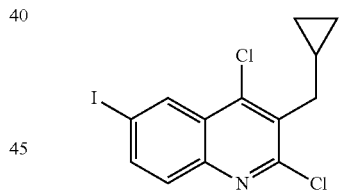

A mixture containing 3-(cyclopropylmethyl)-4-hydroxy-6-iodoquinolin-2(H)-one (1.47 g, 4.00 mmol, Intermediate 13: step a) and phosphorus oxychloride (3.0 mL, 32 mmol) in acetonitrile (20 mL) was heated to 100° C. After 3 hours, the flask was allowed to cool to 23° C. and the mixture was concentrated. The residue was dissolved in dichloromethane (100 mL). Ice (50 mL) and water (50 mL) were added sequentially with stirring. Saturated aqueous ammonia solution was added dropwise until the pH was 10 by litmus paper test. The biphasic mixture was stirred for 15 minutes. The layers were separated. The aqueous layer was extracted with dichloromethane (50 mL). The organic layers were combined and the combined solution was dried with sodium sulfate. The dried solution was filtered. Celite® (4 g) was added to the filtrate and the solvent was removed by rotary evaporation to afford a free-flowing powder. The powder was loaded onto a column of silica gel for purification. Elution with hexanes initially, grading to 5% ethyl acetate-hexanes provided the title compound as an off-white solid.

Intermediate 13: Step c

4-Chloro-3-(cyclopropylmethyl)-6-iodo-2-methoxy-quinoline

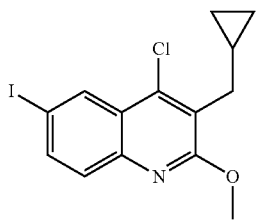 [SMILES: COc1nc2ccc(I)cc2c(Cl)c1CC1CC1]

Sodium methoxide (1.7 g, 31 mmol) was added to a solution of 2,4-dichloro-3-(cyclopropylmethyl)-6-iodoquinoline (1.19 g, 3.15 mmol, Intermediate 13: step b) in toluene (31 mL) with stirring. The mixture was heated to 110° C. After 18 hours, the flask was allowed to cool to 23° C. Dichloromethane (50 mL) was added. The mixture was filtered through Celite®, rinsing with dichloromethane. Celite® (5 g) was added to the filtrate and the solvent was removed by rotary evaporation to afford a free-flowing powder. The powder was loaded onto a column of silica gel for purification. Elution with hexanes initially, grading to 5% ethyl acetate-hexanes provided the title compound as a solid.

Intermediate 14: Step a (1-Methyl-1H-imidazol-5-yl)(2-(trifluoromethyl)pyridin-4-yl)methanol

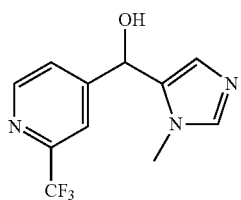 [SMILES: Cn1cncc1C(O)c1ccnc(C(F)(F)F)c1]

A solution of isopropylmagnesium chloride/lithium chloride complex (1.3 M in THF, 10.6 mL, 13.8 mmol) was added dropwise by syringe to a solution of 4-bromo-2-(trifluoromethyl)pyridine (3.12 g, 13.8 mmol) in dry THF (50 mL) at 0° C. After 30 minutes, a solution of 1-methyl-1H-imidazole-5-carbaldehyde (1.38 g, 12.5 mmol) in THF (28.5 mL) was added to the Grignard solution by syringe at 0° C. The reaction mixture was warmed to room temperature over 2 hours after which it was quenched with saturated aqueous ammonium chloride solution. The mixture was partitioned between water and ethyl acetate. The separated aqueous phase was further extracted with ethyl acetate and washed with saturated aqueous NaCl solution. The organic phase was dried (MgSO$_4$), filtered, and concentrated. The crude product was purified by flash column chromatography (silica gel, 0-10% MeOH-DCM) to provide the title compound.

Intermediate 14: Step b (1-Methyl-1H-imidazol-5-yl)(2-(trifluoromethyl)pyridin-4-yl)methanone

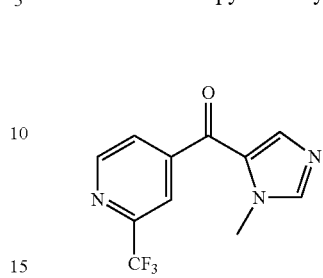

A heterogeneous mixture of (1-methyl-1H-imidazol-5-yl)(2-(trifluoromethyl)pyridin-4-yl)methanol (0.300 g, 1.16 mmol, Intermediate 14: step a) and manganese dioxide (0.506 g, 5.83 mmol) in 1,4-dioxane (12 mL) was stirred at 100° C. for 1 hour. The reaction mixture was then cooled to room temperature, filtered through Celite®, washed with EtOAc, and concentrated. The organic phase was dried (MgSO$_4$), filtered, and concentrated. The crude product was purified by flash column chromatography (silica gel, 0-100% EtOAc-DCM) to provide the title compound as a white solid.

Intermediate 15

6-Bromo-3-(bromomethyl)-4-chloro-2-methoxyquinoline

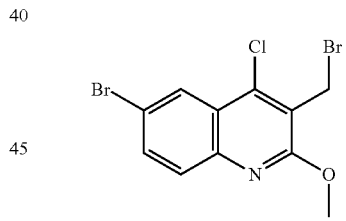

A round-bottomed flask was charged with 6-bromo-4-chloro-2-methoxy-3-methylquinoline (2.86 g, 9.98 mmol, Intermediate 9: step b), N-bromosuccinimide (2.84 g, 15.9 mmol), 1,1'-azobis (cyanocyclohexanecarbonitrile) (0.97 g, 3.9 mmol) and the head space was purged with nitrogen for 5 minutes. Deoxygenated CCl$_4$ (50 mL, deoxygenation was carried out by purging the solvent with argon for 30 minutes) was added to the mixture and heated to 90° C. for 6 hours. The reaction mixture was cooled to room temperature, and silica gel (15 g), DCM and EtOAc were added and the solvents were removed to provide a free-flowing powder. The powder was loaded onto a silica gel column. Elution with hexanes initially, grading to 10% ethyl acetate-hexanes provided the title compound as a white solid.

Intermediate 16

1-((6-Bromo-4-chloro-2-methoxyquinolin-3-yl)methyl)-4-(trifluoromethyl)piperidin-4-ol

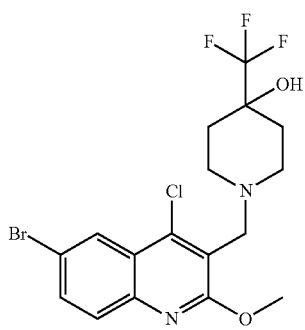 [SMILES: COc1nc2ccc(Br)cc2c(Cl)c1CN1CCC(O)(C(F)(F)F)CC1]

To a mixture containing 6-bromo-3-(bromomethyl)-4-chloro-2-methoxyquinoline (1.0 g, 2.7 mmol, Intermediate 15) and 4-(trifluoromethyl)piperidin-4-ol (0.70 g, 4.1 mmol) in dichloromethane (14 mL) was added N,N-diisopropylethylamine (1.5 mL, 8.7 mmol). After 18 hours, dichloromethane (100 mL) was added and the solution was washed with saturated aqueous sodium bicarbonate solution (50 mL). The washed organic solution was dried with sodium sulfate and the dried solution was filtered. Celite® (8 g) was added to the filtrate and the mixture was concentrated to afford a free flowing powder. The powder was loaded onto a silica gel column. Elution with hexanes initially, grading to 20% ethyl acetate-hexanes provided the title compound as a white solid.

Intermediate 17: Step a

6-Bromo-4-chloro-2-methoxy-3-((4-(2,2,2-trifluoroethyl)piperazin-1-yl)methyl)quinoline

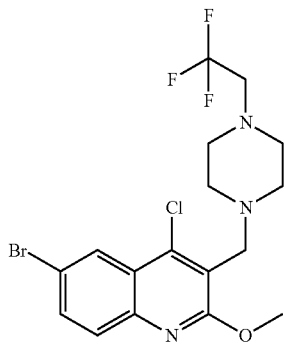 [SMILES: COc1nc2ccc(Br)cc2c(Cl)c1CN1CCN(CC(F)(F)F)CC1]

To a mixture containing 6-bromo-3-(bromomethyl)-4-chloro-2-methoxyquinoline (0.75 g, 2.1 mmol, Intermediate 15) and 1-(2,2,2-trifluoroethyl)piperazine (0.63 g, 3.1 mmol) in dichloromethane (10 mL) was added N,N-diisopropylethylamine (1.1 mL, 6.4 mmol). After 18 hours, the reaction mixture was concentrated. The residue was dissolved with ethyl acetate (30 mL). The solution was washed sequentially with saturated aqueous sodium bicarbonate solution (10 mL) and saturated aqueous sodium chloride solution (10 mL). The washed organic solution was dried with sodium sulfate and the dried solution was filtered. Celite® (6 g) was added to the filtrate and the mixture was concentrated to afford a free flowing powder. The powder was loaded onto a silica gel column. Elution with hexanes initially, grading to 20% ethyl acetate-hexanes provided the title compound as an off-white solid.

Intermediate 17: Step b (4-Chloro-2-methoxy-3-((4-(2,2,2-trifluoroethyl)piperazin-1-yl)methyl)quinolin-6-yl)(1-methyl-1H-1,2,3-triazol-5-yl)methanone

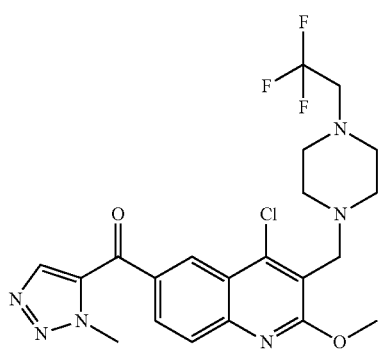 [SMILES: COc1nc2ccc(C(=O)c3cnnn3C)cc2c(Cl)c1CN1CCN(CC(F)(F)F)CC1]

A solution of n-butyllithium in hexanes (2.5 M, 0.270 mL, 0.680 mmol) was added dropwise by syringe to a dry ice-acetone cooled (−78° C.), stirring solution of 6-bromo-4-chloro-2-methoxy-3-((4-(2,2,2-trifluoroethyl)piperazin-1-yl)methyl)quinoline (300 mg, 0.663 mmol, Intermediate 17: step a) in tetrahydrofuran (5 mL). After 1 minute, a solution of N-methoxy-N,1-dimethyl-1H-1,2,3-triazole-5-carboxamide (170 mg, 0.999 mmol, Intermediate 72) in dry tetrahydrofuran (2 mL) was added dropwise by syringe. After 5 minutes, the flask was removed from the cooling bath. After 5 minutes, the flask was placed into an ice-water bath. After 15 minutes, water (5 mL) and ethyl acetate (25 mL) were added in sequence. The biphasic mixture was partitioned between half-saturated aqueous sodium chloride solution (25 mL) and ethyl acetate (25 mL). The layers were separated. The organic layer was dried with sodium sulfate and the dried solution was filtered. Celite® (5 g) was added to the filtrate and the mixture was concentrated in vacuo to afford a free-flowing powder. The powder was loaded onto a silica gel column for flash-column chromatography. Elution with 100% dichloromethane initially, grading to 5% methanol-dichloromethane provided the title compound as a white solid.

Intermediate 18: Step a 2-(tert-Butyl)malonic acid

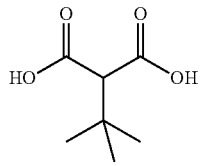

A mixture of diethyl 2-(tert-butyl)malonate (4.3 g, 20 mmol) and NaOH (3 M aqueous, 20 mL, 60 mmol) in THF (50 mL) was stirred at 30° C. for 2 days. The mixture was cooled to room temperature and concentrated to dryness. Ice was added to the residue and the aqueous was acidified by the addition of 3 N aqueous HCl. The aqueous was extracted with EtOAc three times and the organics combined and washed with water. The organics were dried (Na$_2$SO$_4$), filtered and concentrated to dryness to afford the title compound as a white solid.

Intermediate 18: Step b

6-Bromo-3-(tert-butyl)-2,4-dichloroquinoline

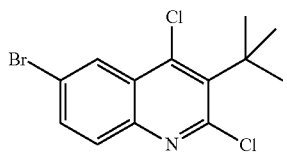 [SMILES: CC(C)(C)c1c(Cl)nc2ccc(Br)cc2c1Cl]

A mixture of 4-bromoaniline (3.1 g, 18 mmol) and 2-(tert-butyl)malonic acid (2.89 g, 18 mmol, Intermediate 18: step a) in phosphorus oxychloride (20 mL) was stirred at reflux for 3 hours then cooled to 80° C. and stirred overnight. The mixture was cooled to room temperature and most of the phosphorous oxychloride was removed by rotary evaporation. The residue was poured into ice-water and the pH adjusted to ~pH 9-10 by the addition of saturated aqueous NH$_4$OH. The aqueous was extracted with DCM twice, the organics combined and washed with water. Then the organics were dried (Na$_2$SO$_4$), filtered and concentrated to dryness. The residue was purified by FCC (10-50% DCM/heptane) to provide the title compound as a white solid.

Intermediate 19: Step a

2-Cyclohexylmalonic acid

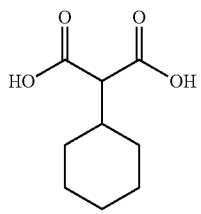

A mixture of dimethyl 2-cyclohexylmalonate (5 g, 23.3 mmol) and NaOH (3 M aqueous, 23.3 mL, 70 mmol) in THF (50 mL) was stirred at 30° C. for 2 days. The mixture was cooled to room temperature and concentrated to dryness. Ice was added to the residue and the aqueous was acidified by the addition of 3 N aqueous HCl. The aqueous was extracted with EtOAc three times and the organics combined and washed with water. The organics were dried (Na$_2$SO$_4$), filtered and concentrated to dryness to afford the title compound as a white solid.

Intermediate 19: Step b

6-Bromo-2,4-dichloro-3-cyclohexylquinoline

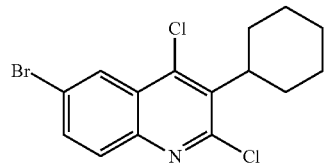 [SMILES: Clc1nc2ccc(Br)cc2c(Cl)c1C1CCCCC1]

A mixture of 4-bromoaniline (3.44 g, 20 mmol) and 2-cyclohexylmalonic acid (3.72 g, 20 mmol, Intermediate 19: step a) in phosphorus oxychloride (20 mL) was stirred at reflux for 3 hours then cooled to 80° C. and stirred overnight. The mixture was cooled to room temperature and most of the phosphorous oxychloride was removed by rotary evaporation. The residue was poured into ice-water and the pH adjusted to ~pH 9-10 by the addition of saturated aqueous NH$_4$OH. The aqueous was extracted with DCM twice, the organics combined and washed with water. Then the organics were dried (Na$_2$SO$_4$), filtered and concentrated to dryness. The residue was purified by FCC (20-50% DCM/heptane) to provide the title compound as a white solid.

Intermediate 20: Step a

Isopropyl 2-isopropoxyacetate

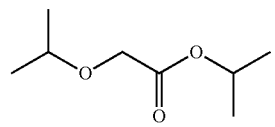

To a solution of isopropanol (403 mL, 5.3 mol) was added sodium metal (4.67 g, 203 mmol) portionwise. The mixture was heated to reflux for 2 hours, then ethyl bromoacetate (20 mL, 177 mmol) was added dropwise over 1 hour. The resulting mixture was stirred at reflux for 2.5 hours, then cooled to room temperature and stirred overnight. The mixture was concentrated to dryness and the residue then dissolved in water (250 mL) and extracted with EtOAc (3×125 mL). The organics were combined, washed with cold water (2×150 mL), dried (Na$_2$SO$_4$), filtered and concentrated to dryness to provide the title compound as a light yellow oil.

Intermediate 20: Step b

6-Bromo-4-hydroxy-3-isopropoxyquinolin-2(1H)-one

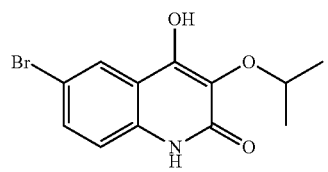 [SMILES: CC(C)Oc1c(O)c2cc(Br)ccc2[nH]c1=O]

To a solution of methyl 2-amino-5-bromobenzoate (3.74 g, 15.6 mmol) and isopropyl 2-isopropoxyacetate (3 g, 18.7 mmol, Intermediate 20: step a) in THF (109 mL) was added KHMDS (1 M in THF, 46.8 mL, 46.8 mmol) in one portion. The resulting solution was stirred at room temperature for 50 minutes, during which it turned orange. Additional KHMDS (1 M in THF, 15.6 mL, 15.6 mmol) was then added and the solution stirred at room temperature for 1 hour. MeOH (60 mL) was added to the reaction mixture and the solution stirred for 10 minutes. The solution was concentrated to dryness and then the resulting residue was dissolved in water and acidified with 1 N aqueous HCl to ~pH 3, where a precipitate appeared. The precipitate was filtered off, washed with water and air dried to afford a sticky orange solid. The crude product was purified by FCC (0.5-5% MeOH/DCM) to provide the title compound as a yellow solid.

Intermediate 20: Step c

6-Bromo-2,4-dichloro-3-isopropoxyquinoline

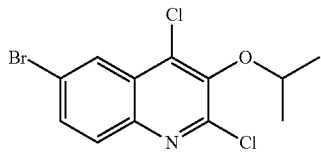 [SMILES: CC(C)Oc1c(Cl)nc2ccc(Br)cc2c1Cl]

A mixture of 6-bromo-4-hydroxy-3-isopropoxyquinolin-2(1H)-one (3.43 g, 11.5 mmol, Intermediate 20: step b) in POCl$_3$ (12.8 mL, 138 mmol) was heated to 105° C. for 25 minutes, then the reaction was allowed to cool to room temperature. The solution was diluted with DCM and poured into a mixture of 6 N aqueous KOH (45 mL) and ice and then stirred for 30 minutes. The pH of the mixture was then adjusted to ~pH 10 by adding more 6 N aqueous KOH. The mixture was poured into a separatory funnel and the layers were separated. The aqueous was further extracted with DCM (140 mL), then the organics were combined, dried (Na$_2$SO$_4$), filtered and concentrated to dryness to afford the crude product as a brown solid. The crude material was purified by filtering through a pad of silica with 1% EtOAc/hexanes, then concentrating the filtrate to dryness to provide the title compound as a cream-colored solid.

Intermediate 21: Step a

6-Bromo-3-ethoxy-4-hydroxyquinolin-2(1H)-one

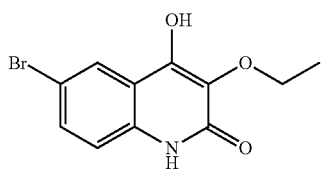 [SMILES: CCOc1c(O)c2cc(Br)ccc2[nH]c1=O]

To a solution of methyl 2-amino-5-bromobenzoate (5 g, 20.9 mmol) and ethyl ethoxyacetate (3.46 mL, 25 mmol) in THF (146 mL) was added KHMDS (1 M in THF, 62.6 mL, 62.6 mmol) in one portion. The resulting solution was stirred at room temperature for 50 minutes. KHMDS (1 M in THF, 20.8 mL, 20.8 mmol) was then added and the solution stirred at room temperature for 30 minutes. MeOH (100 mL) was added to the reaction mixture and the solution stirred for 10 minutes. The solution was concentrated to dryness and then the resulting residue was dissolved in water and acidified with 1 N aqueous HCl to ~pH 3, where a precipitate appeared. The precipitate was filtered off, washed with water and air dried to afford the crude product as a sticky red-orange solid. The crude product was purified by FCC (0.5-5% MeOH/DCM) to provide the title compound as a pink solid.

Intermediate 21: Step b

6-Bromo-2,4-dichloro-3-ethoxyquinoline

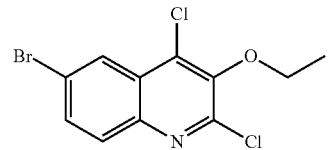 [SMILES: CCOc1c(Cl)nc2ccc(Br)cc2c1Cl]

A mixture of 6-bromo-3-ethoxy-4-hydroxyquinolin-2(1H)-one (1.45 g, 5.1 mmol, Intermediate 21: step a) in POCl$_3$ (5.7 mL, 61.3 mmol) was heated to 105° C. for 5 hours, then the reaction was allowed to cool to room temperature. The solution was diluted with DCM and poured into a mixture of 6 N aqueous KOH (31 mL) and ice and then stirred for 30 minutes (pH>10). The mixture was poured into a separatory funnel and the layers were separated. The aqueous was further extracted with DCM (100 mL), then the organics were combined, dried (Na$_2$SO$_4$), filtered and concentrated to dryness to afford a brown solid. The crude material was purified by filtering through a pad of silica with 1% EtOAc/hexanes, then concentrating the filtrate to dryness to provide the title compound as a tan solid.

Intermediate 22: Step a

4-Chloro-N-methoxy-N-methylbenzamide

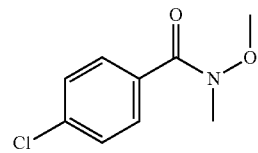

Pyridine (27.6 mL, 343 mmol) was added to N,O-dimethylhydroxylamine hydrochloride (16.7 g, 172 mmol) in DCM (400 mL). 4-Chlorobenzoyl chloride (20 mL, 156 mmol) was then added and the mixture was stirred at room temperature for 3 days. Solids were removed by vacuum filtration, washing with DCM. The filtrate was washed with 1 N aqueous HCl followed by water. The organic phase was dried (Na$_2$SO$_4$), filtered, and concentrated, affording the crude title compound as a colorless liquid which was used without purification in the next step.

Intermediate 22: Step b (4-Chlorophenyl)(1-methyl-1H-imidazol-5-yl)methanone

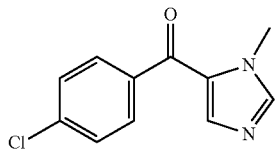

Ethyl magnesium bromide (3.0 M in diethyl ether, 21.5 mL, 64.4 mmol) was added via syringe over a few minutes to a clear colorless solution of 5-bromo-1-methyl-1H-imidazole (10.4 g, 64.4 mmol) in THF (100 mL) under a nitrogen atmosphere in an ice bath. A white precipitate formed during the addition. The mixture was removed from the ice bath and was stirred for 20 minutes, then was again cooled in an ice bath before addition of 4-chloro-N-methoxy-N-methylbenzamide (10.7 g, 53.6 mmol, Intermediate 22: step a). The resulting white suspension was stirred overnight at room temperature. The reaction was quenched by addition of saturated aqueous NH$_4$Cl and diluted with water. The mixture was partially concentrated to remove THF and was diluted with DCM. The mixture was acidified to pH 1 with 1 N aqueous HCl, then neutralized with saturated aqueous NaHCO$_3$. The phases were separated and the aqueous phase was further extracted with DCM. The organic extracts were washed with water, then were dried (Na$_2$SO$_4$), filtered, and concentrated, affording a white solid. The crude product was triturated with a mixture of EtOAc:heptanes (1:1, 150 mL). The precipitated solid was collected by vacuum filtration, washing with heptanes, to afford the title compound.

Intermediate 23: Step a

Methyl 5-bromo-2-(2-bromoacetamido)benzoate

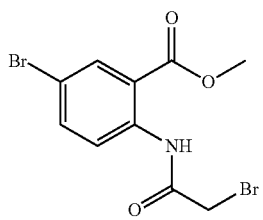 [SMILES: COC(=O)c1cc(Br)ccc1NC(=O)CBr]

To a solution of methyl 2-amino-5-bromobenzoate (7 g, 29.2 mmol) in DCM (88 mL) was added diisopropylethylamine (5 mL, 29.2 mmol) and the resulting solution was cooled to −78° C. Then, bromoacetyl bromide (2.6 mL, 29.2 mmol) was added dropwise over 5 minutes and the mixture stirred at −78° C. for 1 hour. The cooling bath was removed and the reaction was allowed to warm to room temperature and then stir at room temperature for 1 hour. The mixture was cooled to −78° C., bromoacetyl bromide (1.3 mL, 14.6 mmol) was added and then the reaction was stirred at room temperature for 1 hour. The mixture was cooled to −78° C., bromoacetyl bromide (0.26 mL, 2.92 mmol) was added and then the reaction was stirred at room temperature for 2 hours. The reaction mixture was poured into a separatory funnel and washed with saturated aqueous NaHCO$_3$ (75 mL), water (75 mL), and brine (75 mL). The organic layer was dried (Na$_2$SO$_4$), filtered and concentrated to dryness to afford a green-brown solid. The crude material was purified by FCC (1-100% EtOAc/hexanes) to provide the title compound as a cream-colored solid.

Intermediate 23: Step b

Methyl 5-bromo-2-(2-(2,2,2-trifluoroethoxy)acetamido)benzoate

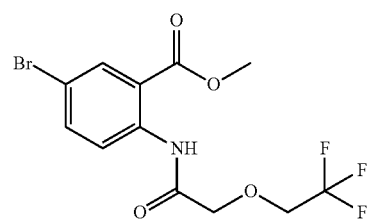 [SMILES: COC(=O)c1cc(Br)ccc1NC(=O)COCC(F)(F)F]

To a solution of 2,2,2-trifluoroethanol (1.9 mL, 25.6 mmol) in THF (43 mL) was added KHMDS (1 M in THF, 25.6 mL, 25.6 mmol) in one portion and the resulting mixture was stirred at room temperature for 10 minutes. Then, methyl 5-bromo-2-(2-bromoacetamido)benzoate (3 g, 8.55 mmol, Intermediate 23: step a) was added and the reaction stirred at room temperature for 1.25 hours. The mixture was then concentrated to dryness. The residue was dissolved in DCM (75 mL), washed with water (75 mL) followed by brine (75 mL), dried (Na$_2$SO$_4$), filtered and concentrated to dryness to provide the title compound as a yellow solid.

Intermediate 23: Step c

6-Bromo-4-hydroxy-3-(2,2,2-trifluoroethoxy)quinolin-2(1H)-one

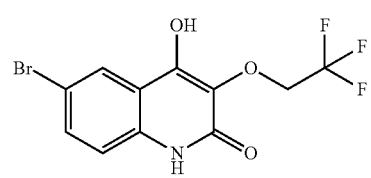 [SMILES: O=c1[nH]c2ccc(Br)cc2c(O)c1OCC(F)(F)F]

To a solution of methyl 5-bromo-2-(2-(2,2,2-trifluoroethoxy)acetamido)benzoate (2.06 g, 5.57 mmol, Intermediate 23: step b) in THF (28 mL) was added KHMDS (1 M in THF, 5.6 mL, 5.57 mmol) and the resulting solution was stirred at room temperature for 35 minutes. KHMDS (1 M in THF, 5.6 mL, 5.57 mmol) was added and the mixture stirred at room temperature for 1.5 hours. KHMDS (1 M in THF, 5.6 mL, 5.57 mmol) was added and the mixture stirred at room temperature for an additional hour. MeOH (50 mL) was then added and the reaction stirred at room temperature for 10 minutes, after which it was concentrated to dryness. The residue was dissolved in water and the pH was adjusted to ~pH 3 by the addition of aqueous 1 N HCl. The mixture was then concentrated to dryness to afford a yellow solid.

The crude material was purified by FCC (1-30% EtOAc/DCM) to provide the title compound as a peach solid.

Intermediate 23: Step d

6-Bromo-2,4-dichloro-3-(2,2,2-trifluoroethoxy)quinoline

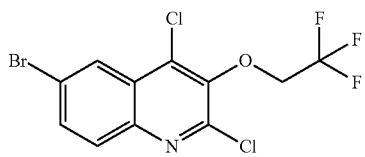 [SMILES: FC(F)(F)COc1c(Cl)nc2ccc(Br)cc2c1Cl]

A mixture of 6-bromo-4-hydroxy-3-(2,2,2-trifluoroethoxy)quinolin-2(1H)-one (807 mg, 2.03 mmol, Intermediate 23: step c) in POCl₃ (2.3 mL, 24.4 mmol) was heated to 105° C. for 2 hours, then the reaction was allowed to cool to room temperature. The solution was diluted with DCM and poured into a mixture of 6 N aqueous KOH and ice and then stirred for 30 minutes. The pH of the mixture was then adjusted to ~pH 10 by adding more 6 N aqueous KOH. The mixture was poured into a separatory funnel and the layers were separated. The aqueous was further extracted with DCM (75 mL), then the organics were combined, dried (Na₂SO₄), filtered and concentrated to dryness to afford a brown solid. The crude material was purified by filtering through a pad of silica with 1% EtOAc/hexanes, then concentrating the filtrate to dryness to provide the title compound as a tan solid.

Intermediate 24: Step a

6-Bromo-3-(cyclopropylmethoxy)-4-hydroxyquinolin-2(1H)-one

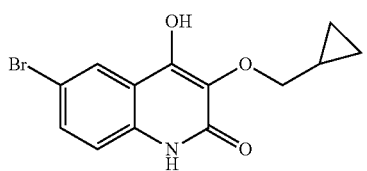 [SMILES: O=c1[nH]c2ccc(Br)cc2c(O)c1OCC1CC1]

To a solution of cyclopropanemethanol (2.08 mL, 25.6 mmol) in THF (43 mL) was added KHMDS (1 M in THF, 25.6 mL, 25.6 mmol) in one portion and the resulting mixture was stirred at room temperature for 10 minutes. Then, methyl 5-bromo-2-(2-bromoacetamido)benzoate (3 g, 8.55 mmol, Intermediate 23: step a) was added and the reaction stirred at room temperature for 1 hour. KHMDS (1 M in THF, 8.5 mL, 8.5 mmol) was added and the mixture stirred at room temperature for an additional 45 minutes. KHMDS (1 M in THF, 8.5 mL, 8.5 mmol) was added and the mixture stirred at room temperature for an additional 2 hours. MeOH (80 mL) was then added and the reaction stirred at room temperature for 10 minutes, after which it was concentrated to dryness. The residue was dissolved in water and the pH was adjusted to ~pH 3 by the addition of aqueous 1 N HCl. The slurry was then concentrated to dryness to afford a sticky brown solid. The crude material was purified by FCC (0.5-5% MeOH/DCM) to provide the title compound as a cream-colored solid.

Intermediate 24: Step b

6-Bromo-2,4-dichloro-3-(cyclopropylmethoxy)quinoline

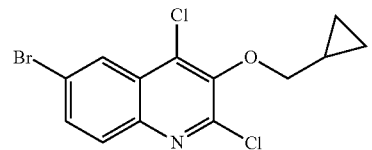 [SMILES: Clc1nc2ccc(Br)cc2c(Cl)c1OCC1CC1]

To a mixture of 6-bromo-3-(cyclopropylmethoxy)-4-hydroxyquinolin-2(1H)-one (673 mg, 2.17 mmol, Intermediate 24: step a) in POCl₃ (2.4 mL, 26 mmol) was added diisopropylethylamine (860 μL, 4.99 mmol) dropwise and the resulting solution was heated to 90° C. for 2 hours. The reaction was allowed to cool to room temperature, then the solution was diluted with DCM and poured into a mixture of 6 N aqueous KOH and ice and stirred for 30 minutes. The pH of the mixture was then adjusted to ~pH 10 by adding more 6 N aqueous KOH. The mixture was poured into a separatory funnel and the layers were separated. The aqueous was further extracted with DCM (35 mL), then the organics were combined, dried (Na₂SO₄), filtered and concentrated to dryness to afford a brown solid. The crude material was purified by filtering through a pad of silica with 1% EtOAc/hexanes, then concentrating the filtrate to dryness to provide the title compound as a tan solid.

Intermediate 25

(2,4-Dichloro-3-isopropoxyquinolin-6-yl)(1,2-dimethyl-1H-imidazol-5-yl)methanone

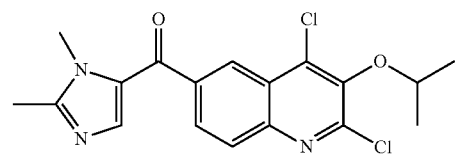 [SMILES: Cc1ncc(C(=O)c2ccc3nc(Cl)c(OC(C)C)c(Cl)c3c2)n1C]

To a solution of (2,4-dichloro-3-isopropoxyquinolin-6-yl)(1,2-dimethyl-1H-imidazol-5-yl)methanol (115 mg, 0.3 mmol, Example 172) in 1,4-dioxane (4.1 mL) was added manganese dioxide (117 mg, 1.35 mmol). The resulting mixture was stirred at 100° C. for 1.25 hours. The reaction mixture was then filtered through Celite® while still hot, rinsing with warm THF followed by EtOAc. The filtrate was concentrated to dryness to provide the title compound as a white solid.

Intermediate 26

6-Bromo-4-chloro-3-isopropoxy-2-methoxyquinoline

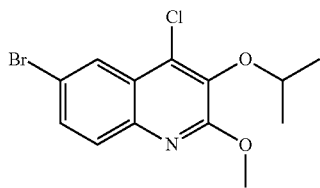 [SMILES: COc1nc2ccc(Br)cc2c(Cl)c1OC(C)C]

To a mixture of 6-bromo-2,4-dichloro-3-isopropoxyquinoline (1 g, 2.98 mmol, Intermediate 20: step c) in toluene (30 mL) was added NaOMe (1.61 g, 29.8 mmol) and the resulting mixture heated to 100° C. for 22 hours. The mixture was then cooled to room temperature, diluted with DCM and filtered through a pad of Celite®, rinsing the filter cake with DCM. The filtrate was concentrated to dryness to afford the title compound as a white solid.

Intermediate 27

(4-Chloro-3-isopropoxy-2-methoxyquinolin-6-yl)(1,2-dimethyl-1H-imidazol-5-yl)methanone

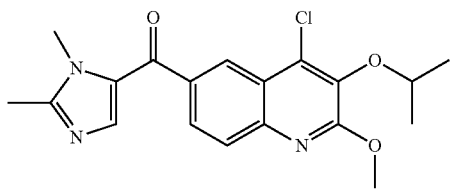 [SMILES: COc1nc2ccc(C(=O)c3cnc(C)n3C)cc2c(Cl)c1OC(C)C]

The title compound was prepared using (4-chloro-3-isopropoxy-2-methoxyquinolin-6-yl)(1,2-dimethyl-1H-imidazol-5-yl)methanol (Example 156) in place of (2,4-dichloro-3-isopropoxyquinolin-6-yl)(1,2-dimethyl-1H-imidazol-5-yl)methanol using the procedure described for Intermediate 25.

Intermediate 28

(4-Chloro-3-isopropoxy-2-methoxyquinolin-6-yl)(2,6-dimethylpyridin-3-yl)methanone

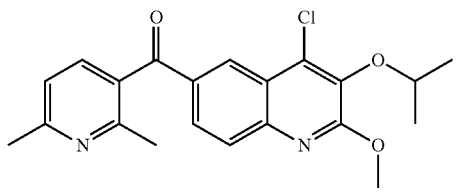 [SMILES: COc1nc2ccc(C(=O)c3ccc(C)nc3C)cc2c(Cl)c1OC(C)C]

To a solution of (4-chloro-3-isopropoxy-2-methoxyquinolin-6-yl)(2,6-dimethylpyridin-3-yl)methanol (181 mg, 0.36 mmol, Example 155) in 1,4-dioxane (4.9 mL) was added manganese dioxide (140 mg, 1.61 mmol). The resulting mixture was stirred at 100° C. for 19 hours. Additional manganese dioxide (140 mg, 1.61 mmol) was added and the reaction stirred at 100° C. for 3 hours. Additional manganese dioxide (140 mg, 1.61 mmol) was added and the reaction stirred at 100° C. for 1.5 hours. The reaction mixture was then filtered through Celite® while still hot, rinsing with warm THF followed by EtOAc. The filtrate was concentrated to dryness and then resubjected to the reaction conditions. To a solution of crude material in 1,4-dioxane (4.9 mL) was added manganese dioxide (140 mg, 1.61 mmol). The resulting mixture was stirred at 100° C. for 3 hours. Additional manganese dioxide (140 mg, 1.61 mmol) was added and the reaction stirred at 100° C. for 16 hours. The reaction mixture was then filtered through Celite® while still hot, rinsing with warm THF followed by EtOAc. The filtrate was concentrated to dryness and purified by FCC (0.5-5% MeOH/DCM) to provide the title compound as a clear colorless oil.

Intermediate 29: Step a

Methyl 2-(2-(benzyloxy)acetamido)-5-bromobenzoate

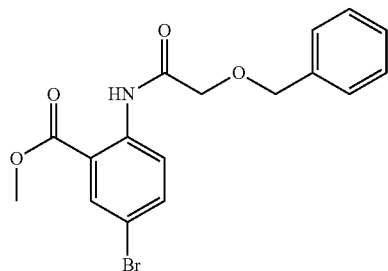 [SMILES: COC(=O)c1cc(Br)ccc1NC(=O)COCc1ccccc1]

To a solution of methyl-2-amino-5-bromobenzoate (15 g, 62.6 mmol) in DCM (241 mL) at 0° C. was added benzyloxyacetyl chloride (12.5 mL, 75.1 mmol) followed by Et$_3$N (20 mL, 144 mmol) dropwise. The resulting white suspension was stirred at room temperature for 3 hours. The mixture was then washed with saturated aqueous NH$_4$Cl (200 mL) followed by water (200 mL). The organics were dried (Na$_2$SO$_4$), filtered and concentrated to dryness. The crude solid was triturated with MeOH (90 mL) and dried under vacuum to afford the title compound as a white solid.

Intermediate 29: Step b

3-(Benzyloxy)-6-bromo-4-hydroxyquinolin-2(1H)-one

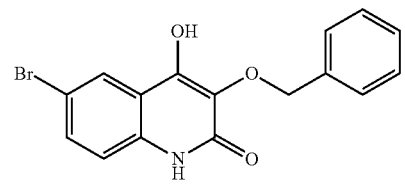 [SMILES: O=c1[nH]c2ccc(Br)cc2c(O)c1OCc1ccccc1]

To a solution of methyl 2-(2-(benzyloxy)acetamido)-5-bromobenzoate (15 g, 39.7 mmol, Intermediate 29: step a) in THF (198 mL) was added KHMDS (1 M in THF, 119 mL, 119 mmol). The resulting solution was stirred at room temperature for 40 minutes and then additional KHMDS Intermediate 29: Step c 3-(Benzyloxy)-6-bromo-2,4-dichloroquinoline

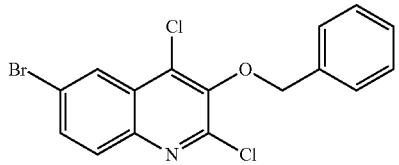 [SMILES: Clc1nc2ccc(Br)cc2c(Cl)c1OCc1ccccc1]

To a suspension of 3-(benzyloxy)-6-bromo-4-hydroxyquinolin-2(1H)-one (12.4 g, 35.8 mmol, Intermediate 29: step b) in acetonitrile (119 mL) was added POCl₃ (10 mL, 107.5 mmol) followed by 2,6-lutidine (6.26 mL, 53.7 mmol) dropwise. The suspension was heated to 100° C. for 4 hours, then the reaction was allowed to cool to room temperature. The solids were filtered, rinsed with MeOH and dried under vacuum to afford the title compound as a tan solid.

Intermediate 29: Step d 3-(Benzyloxy)-6-bromo-4-chloro-2-methoxyquinoline

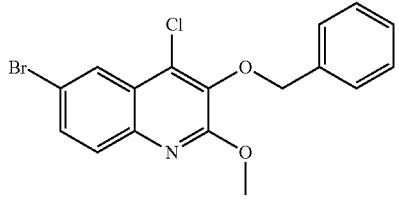 [SMILES: COc1nc2ccc(Br)cc2c(Cl)c1OCc1ccccc1]

To a mixture of 3-(benzyloxy)-6-bromo-2,4-dichloroquinoline (7 g, 18.3 mmol, Intermediate 29: step c) in toluene (183 mL) was added NaOMe (9.87 g, 182.7 mmol) and the resulting mixture heated to 60° C. for 16.5 hours. Additional NaOMe (1.97 g, 36.5 mmol) was added and the mixture stirred for 30 minutes at 60° C. The mixture was then cooled to room temperature, diluted with DCM and stirred for 15 minutes. The mixture was filtered through a pad of Celite®, rinsing the filter cake with DCM followed by THF. The filtrate was concentrated to dryness to afford the title compound as a cream-colored solid.

(19.8 mL, 19.8 mmol) was added and stirring continued at room temperature for 2 hours. The mixture was quenched with water (225 mL) and the layers were separated. The aqueous layer was acidified with 1 N aqueous HCl to pH 2-3. Some of the title compound precipitated out of solution and was collected by filtration. The aqueous was then extracted with EtOAc (3×200 mL). The organics were combined with the solid collected previously and sonicated. The solution was dried (Na₂SO₄), filtered and concentrated to dryness to provide the title compound as a yellow solid.

Intermediate 30

4-Chloro-6-(hydroxy(1-methyl-1H-imidazol-5-yl)(6-(trifluoromethyl)pyridin-3-yl)methyl)-2-methoxyquinolin-3-ol

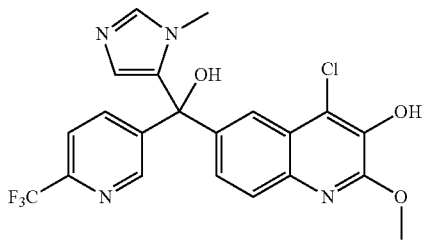 [SMILES: COc1nc2ccc(C(O)(c3ccc(C(F)(F)F)nc3)c3cncn3C)cc2c(Cl)c1O]

To a solution of (3-(benzyloxy)-4-chloro-2-methoxyquinolin-6-yl)(1-methyl-1H-imidazol-5-yl)(6-(trifluoromethyl)pyridin-3-yl)methanol (2.56 g, 4.61 mmol, Example 168) in MeOH (97 mL) was added 10% Pd/C (246 mg, 0.23 mmol). The reaction vessel was evacuated and then placed under an atmosphere of hydrogen for 1.5 hours. The mixture was then flushed with N₂ and filtered through a pad of Celite®. The filtrate was concentrated to dryness, then DCM was added and the solution concentrated to dryness. The resulting solid was dried in the oven. The solid was then purified by FCC (15% MeOH/DCM) to provide the title compound.

Intermediate 31

4-Chloro-6-((2,6-dimethylpyridin-3-yl)(hydroxy)(1-methyl-1H-1,2,3-triazol-5-yl)methyl)-2-methoxyquinolin-3-ol

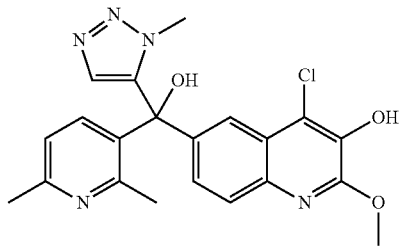

To a solution of (3-(benzyloxy)-4-chloro-2-methoxyquinolin-6-yl)(2,6-dimethylpyridin-3-yl)(1-methyl-1H-1,2,3-triazol-5-yl)methanol (2.28 g, 4.42 mmol, Example 169) in MeOH (88 mL) was added 10% Pd/C (235 mg, 0.22 mmol). The reaction vessel was evacuated and then placed under an atmosphere of hydrogen for 2.5 hours. The mixture was then flushed with N₂ and filtered through a pad of Celite®. The Celite® was rinsed with MeOH followed by THF and the filtrate was concentrated to dryness. The residue was purified by FCC (0-5% MeOH/DCM) to provide the title compound as a white solid.

Intermediate 32

Methyl 3-(benzyloxy)-4-chloro-2-methoxyquinoline-6-carboxylate

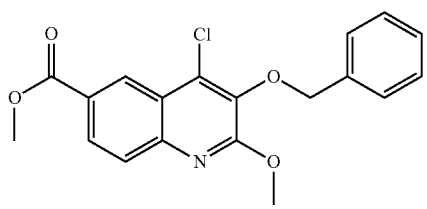 [SMILES: COC(=O)c1ccc2nc(OC)c(OCc3ccccc3)c(Cl)c2c1]

n-BuLi (1.23 M in hexanes, 5.37 mL, 6.6 mmol) was added dropwise to a stirred solution of 3-(benzyloxy)-6-bromo-4-chloro-2-methoxyquinoline (2.5 g, 6.6 mmol, Intermediate 29: step d) in THF (11.5 mL) under nitrogen at −78° C. After an additional minute, a pellet of dry ice was added to the dark solution, and the flask was quickly resealed, evacuated and flushed with nitrogen. After 5 minutes, the resulting yellow solution was removed from the cold bath and stirred under ambient conditions for 15 minutes. The reaction was then transferred to an ice bath and quenched with iodomethane (410 µL, 6.6 mmol) and DMSO (6.6 mL). The reaction was stirred at 0° C. for 5 minutes, and was then rotovapped to remove the THF. The mixture was treated with Na₂CO₃ (700 mg, 6.6 mmol) and iodomethane (820 µL, 13.2 mmol) and stirred at 40° C. for 30 minutes. The mixture was then diluted with DCM (65 mL), washed with water (2×75 mL), dried (Na₂SO₄), filtered, and concentrated to dryness to provide a yellow solid. The crude material was purified by FCC (1-10% EtOAc/hexanes) to provide the title compound as a white solid.

Intermediate 33

6-(Bis(1,2-dimethyl-1H-imidazol-5-yl)(hydroxy)methyl)-4-chloro-2-methoxyquinolin-3-ol

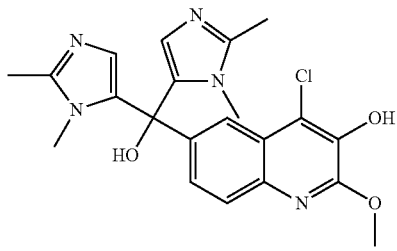

To a solution of [3-(benzyloxy)-4-chloro-2-methoxyquinolin-6-yl][bis(1,2-dimethyl-1H-imidazol-5-yl)]methanol (3.04 g, 5.87 mmol, Example 75) in MeOH (117 mL) was added 10% Pd/C (313 mg, 0.29 mmol). The reaction vessel was evacuated and then placed under an atmosphere of hydrogen for 2.5 hours. The mixture was then flushed with N₂ and filtered through a pad of Celite®. The Celite® was rinsed with MeOH and the filtrate was concentrated to dryness. The residue was purified by FCC (0-15% MeOH/DCM) to give a white amorphous solid. The solid was azeotroped with toluene (4×) and dried under vacuum at 45° C. to afford the title compound as a peach solid (containing a small amount of MeOH).

Intermediate 34: Step a

Ethyl 6-bromo-4-hydroxy-2-oxo-1,2-dihydroquinoline-3-carboxylate

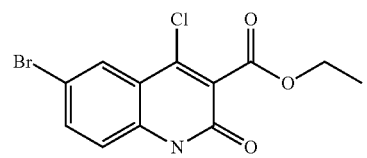 [SMILES: CCOC(=O)c1c(Cl)c2cc(Br)ccc2[nH]c1=O]

To a solution of methyl 2-amino-5-bromobenzoate (5 g, 20.9 mmol) and diethyl malonate (3.2 mL, 20.9 mmol) in EtOH (24.5 mL) was added NaOEt (21% solution in EtOH, 8.2 mL, 21.9 mmol) dropwise over 2 minutes. The resulting mixture was stirred at room temperature for 30 minutes. The EtOH was then removed under vacuum. The mixture was heated to 140° C. for 16 hours then allowed to cool to room temperature. The solid obtained was washed with diethyl ether then dissolved in water (50 mL) and the insoluble material was filtered off. The filtrate was acidified to ~pH 2-3 by the addition of 1 N aqueous HCl. A precipitate formed during acidification which was collected by filtration. The solid was washed with water and dried under vacuum to provide the title compound as a cream-colored solid.

Intermediate 34: Step b

Ethyl 6-bromo-2,4-dichloroquinoline-3-carboxylate

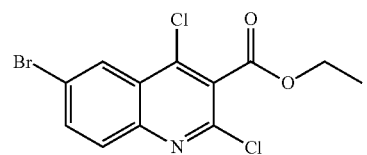 [SMILES: CCOC(=O)c1c(Cl)nc2ccc(Br)cc2c1Cl]

A solution of ethyl 6-bromo-4-hydroxy-2-oxo-1,2-dihydroquinoline-3-carboxylate (2.42 g, 7.75 mmol, Intermediate 34: step a) in POCl₃ (7.2 mL, 77.5 mmol) was heated to 110° C. for 1 hour. The reaction was cooled to room temperature and concentrated to dryness. The residue was then dissolved in DCM (35 mL) and poured into ice-water. The resulting mixture was basified to ~pH 10-11 by the addition of 1 N aqueous NaOH then extracted with EtOAc (2×75 mL). The organics were combined and washed with water (50 mL) followed by brine (50 mL). The organics were dried (Na₂SO₄), filtered and concentrated to dryness to afford a yellow solid.

Intermediate 34: Step c

Ethyl 6-bromo-4-chloro-2-methoxyquinoline-3-carboxylate

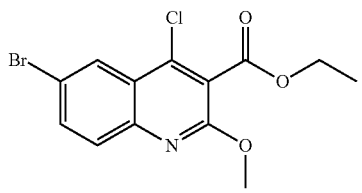 [SMILES: CCOC(=O)c1c(OC)nc2ccc(Br)cc2c1Cl]

To a mixture of ethyl 6-bromo-2,4-dichloroquinoline-3-carboxylate (1.07 g, 3.07 mmol, Intermediate 34: step b) in toluene (31 mL) was added NaOMe (346 mg, 6.28 mmol) and the resulting mixture stirred at room temperature for 1.75 hours. The mixture was heated to 40° C. and stirred for 2.5 hours. The mixture was then heated to 60° C. and stirred for 1 hour. The reaction was allowed to cool to room temperature. The mixture was diluted with DCM, stirred for 15 minutes, and filtered through a pad of Celite®, rinsing the filter cake with DCM followed by THF. The filtrate was concentrated to dryness to afford a light yellow solid. The crude material was purified by FCC (0-10% EtOAc/hexanes) to provide the title compound as a white solid.

Intermediate 34: Step d

6-Bromo-4-chloro-2-methoxyquinoline-3-carboxylic acid

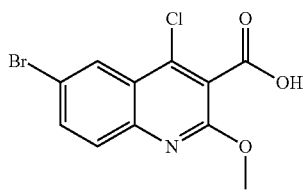 [SMILES: COc1nc2ccc(Br)cc2c(Cl)c1C(=O)O]

To a solution of ethyl 6-bromo-4-chloro-2-methoxyquinoline-3-carboxylate (598 mg, 1.74 mmol, Intermediate 34: step c) in THF (14.5 mL), iPrOH (5.8 mL) and water (5.8 mL) was added LiOH (364 mg, 8.68 mmol) and the reaction stirred at room temperature for 1 hour. The reaction was then heated to 45° C. for 1.75 hours and then 65° C. for 46 hours. The mixture was cooled to room temperature and the pH adjusted to ~pH 2-3 by the addition of 1 N aqueous HCl. The organics were removed under vacuum and then the aqueous was extracted with EtOAc (3×10 mL). The organics were combined, dried (Na₂SO₄), filtered and concentrated to dryness to afford the title compound as a yellow solid.

Intermediate 34: Step e (6-Bromo-4-chloro-2-methoxyquinolin-3-yl)(pyrrolidin-1-yl)methanone

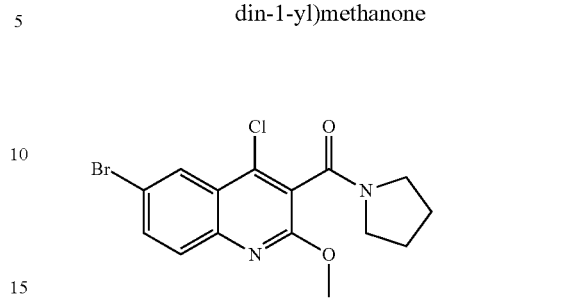

A mixture of 6-bromo-4-chloro-2-methoxyquinoline-3-carboxylic acid (945 mg, 2.84 mmol, Intermediate 34: step d), EDCI (832 mg, 4.25 mmol) and HOBt (581 mg, 4.25 mmol) in DMF (28.4 mL) was stirred at room temperature for 15 minutes. Then, pyrrolidine (1.16 mL, 13.9 mmol) was added and the reaction mixture stirred at room temperature for 1.5 hours. The mixture was concentrated to dryness and the residue partitioned between DCM (50 mL) and saturated aqueous NaHCO₃ (50 mL). The layers were separated and the aqueous further extracted with DCM (50 mL). The organics were combined, dried (Na₂SO₄), filtered and concentrated to dryness to afford a light brown solid. The crude material was purified by FCC (0-50% EtOAc/hexanes) to provide the title compound as a white solid.

Intermediate 35: Step a

Methyl 5-iodo-2-(3-methoxy-3-oxopropanamido)benzoate

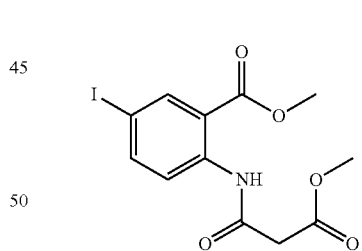

To a solution of methyl 5-iodoanthranilate (1.5 g, 5.3 mmol) and sodium bicarbonate (892 mg, 10.6 mmol) in DCM (29.5 mL) at 0° C. was added methyl 3-chloro-3-oxopropionate (587 µL, 5.3 mmol) dropwise over 2 minutes. The cream-colored mixture was stirred at 0° C. for 19 hours. The reaction mixture was then diluted with DCM (25 mL), water (25 mL) was added and the biphasic mixture stirred vigorously for 15 minutes. The layers were separated and the aqueous extracted with DCM (25 mL). The organics were combined, dried (Na₂SO₄), filtered and concentrated to dryness to afford a cream-colored solid. The crude material was purified by FCC (0-50% EtOAc/hexanes) to provide the title compound as a cream-colored solid.

Intermediate 35: Step b

Methyl 4-hydroxy-6-iodo-2-oxo-1,2-dihydroquinoline-3-carboxylate

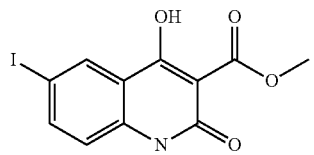 [SMILES: COC(=O)c1c(O)c2cc(I)ccc2[nH]c1=O]

To a solution of methyl 5-iodo-2-(3-methoxy-3-oxopropanamido)benzoate (1.88 g, 4.98 mmol, Intermediate 35: step a) in THF (29.3 mL) was added NaOMe (25% solution in MeOH, 11.4 mL, 49.8 mmol) dropwise over 5 minutes. The resulting thick cream-colored suspension was stirred at room temperature for 1.5 hours. The mixture was then acidified to ~pH 2-3 by the addition of 1 N aqueous HCl. During the acidification the mixture became a clear solution then solids crashed out at ~pH 3. The suspension was stirred at room temperature for 15 minutes then filtered, washing the solids with water. The solids were dried under vacuum to provide the title compound as a white solid.

Intermediate 35: Step c

Methyl 2,4-dichloro-6-iodoquinoline-3-carboxylate

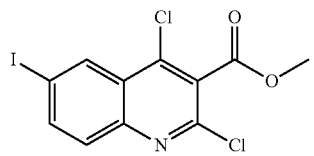 [SMILES: COC(=O)c1c(Cl)nc2ccc(I)cc2c1Cl]

A solution of methyl 4-hydroxy-6-iodo-2-oxo-1,2-dihydroquinoline-3-carboxylate (7.31 g, 21.2 mmol, Intermediate 35: step b) in $POCl_3$ (19.7 mL, 211.8 mmol) was heated to 110° C. for 1 hour. The reaction was cooled to room temperature and concentrated to dryness. The residue was then dissolved in DCM (100 mL) and poured into ice-water. The resulting mixture was basified to ~pH 10-11 by the addition of 6 N aqueous NaOH then extracted with DCM (2×100 mL). The organics were combined and washed with water (100 mL) followed by brine (100 mL). The organics were dried ($Na_2SO_4$), filtered and concentrated to dryness to afford a brown solid. The crude material was purified by FCC (0-10% EtOAc/hexanes) to provide the title compound as a light yellow solid.

Intermediate 35: Step d

Methyl 4-chloro-6-iodo-2-methoxyquinoline-3-carboxylate

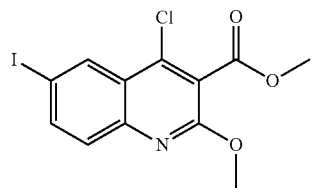 [SMILES: COC(=O)c1c(OC)nc2ccc(I)cc2c1Cl]

To a mixture of methyl 2,4-dichloro-6-iodoquinoline-3-carboxylate (250 mg, 0.65 mmol, Intermediate 35: step c) in toluene (6.5 mL) was added NaOMe (74 mg, 1.34 mmol) and the resulting mixture stirred at room temperature for 16 hours. The mixture was diluted with DCM, stirred for 15 minutes, and filtered through a pad of Celite®, rinsing the filter cake with DCM followed by THF. The filtrate was concentrated to dryness to afford a light yellow oil. The crude material was purified by FCC (0-10% EtOAc/hexanes) to provide the title compound as a clear colorless oil.

Intermediate 35: Step e

4-Chloro-6-iodo-2-methoxyquinoline-3-carboxylic acid

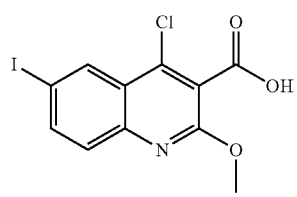 [SMILES: COc1nc2ccc(I)cc2c(Cl)c1C(=O)O]

To a solution of methyl 4-chloro-6-iodo-2-methoxyquinoline-3-carboxylate (153 mg, 0.41 mmol, Intermediate 35: step d) in THF (3.4 mL), iPrOH (1.35 mL) and water (1.35 mL) was added LiOH (85 mg, 2.03 mmol) and the reaction stirred at room temperature for 70 minutes. The reaction was then heated to 45° C. for 1 hour and then 65° C. for 20 hours. The mixture was cooled to room temperature and the pH adjusted to ~pH 2-3 by the addition of 1 N aqueous HCl. The organics were removed under vacuum and then the aqueous was extracted with EtOAc (3×10 mL). The organics were combined, dried ($Na_2SO_4$), filtered and concentrated to dryness to afford the title compound as a yellow solid.

Intermediate 35: Step f (4-Chloro-6-iodo-2-methoxyquinolin-3-yl)(4-(trifluoromethyl)piperidin-1-yl)methanone

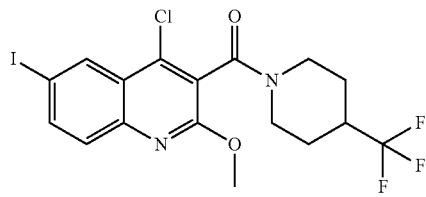 [SMILES: COc1nc2ccc(I)cc2c(Cl)c1C(=O)N1CCC(C(F)(F)F)CC1]

To a mixture of 4-chloro-6-iodo-2-methoxyquinoline-3-carboxylic acid (148 mg, 0.39 mmol, Intermediate 35: step e), HOBt (79.2 mg, 0.58 mmol) and triethylamine (107 µL, 0.77 mmol) in DMF (3.9 mL) was added 4-(trifluoromethyl) piperidine-HCl (367 mg, 1.9 mmol). The resulting mixture was stirred at room temperature for 15 minutes, then EDCI (114 mg, 0.58 mmol) was added and the mixture stirred at room temperature for an additional 23 hours. The reaction was concentrated to dryness and the residue partitioned between DCM (15 mL) and saturated aqueous NaHCO$_3$ (15 mL). The layers were separated and the aqueous extracted with DCM (15 mL). The organics were combined, dried (Na$_2$SO$_4$), filtered and concentrated to dryness to afford an orange solid. The crude material was purified by FCC (0-50% EtOAc/hexanes) to provide the title compound as a white solid.

Intermediate 36

4-Chloro-6-(hydroxy(1-methyl-1H-imidazol-5-yl)(6-(trifluoromethyl)pyridin-3-yl)methyl)-2-methoxyquinoline-3-carboxylic acid

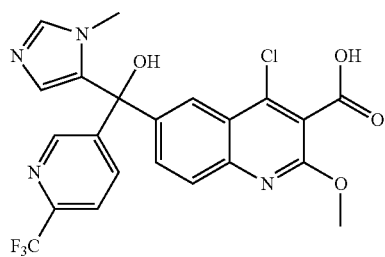 [SMILES: COc1nc2ccc(C(O)(c3ccc(C(F)(F)F)nc3)c3cncn3C)cc2c(Cl)c1C(=O)O]

To a solution of 4-chloro-6-iodo-2-methoxyquinoline-3-carboxylic acid (100 mg, 0.28 mmol, Intermediate 35: step e) and (1-methyl-1H-imidazol-5-yl)(6-(trifluoromethyl) pyridin-3-yl)methanone (88 mg, 0.34 mmol, Intermediate 10: step c) in THF (6.6 mL) at −78° C. was added n-BuLi (1.85 M in hexanes, 320 µL, 0.59 mmol) dropwise. The resulting orange solution was stirred at −78° C. for 15 minutes, then warmed to 0° C. and stirred for an additional 30 minutes. Saturated aqueous NH$_4$Cl (7 mL), water (20 mL) and EtOAc (20 mL) were added and the layers separated. The aqueous layer was acidified to ~pH 2 by addition of 1 N aqueous HCl, then extracted with EtOAc (20 mL). The EtOAc was back-extracted with water (15 mL). The aqueous layers were combined and basified to ~pH 5 by addition of 1 N aqueous NaOH and saturated with NaCl. The aqueous was then extracted with 2-methyl-THF (4×25 mL). The organics were combined, dried (Na$_2$SO$_4$), filtered and concentrated to dryness to afford the title compound as a white amorphous solid.

Intermediate 37

4-Chloro-6-((2,6-dimethylpyridin-3-yl)(hydroxy)(1-methyl-1H-1,2,3-triazol-5-yl)methyl)-2-methoxyquinoline-3-carboxylic acid

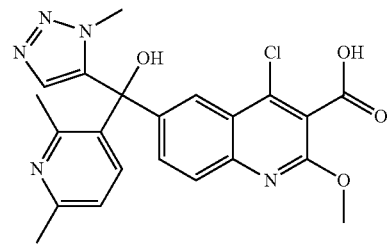 [SMILES: COc1nc2ccc(C(O)(c3ccc(C)nc3C)c3cnnn3C)cc2c(Cl)c1C(=O)O]

To a solution of 4-chloro-6-iodo-2-methoxyquinoline-3-carboxylic acid (300 mg, 0.83 mmol, Intermediate 35: step e) and (2,6-dimethylpyridin-3-yl)(1-methyl-1H-1,2,3-triazol-5-yl)methanone (223 mg, 1.03 mmol, Intermediate 11: step b) in THF (9.8 mL) at −78° C. was added n-BuLi (1.85 M in hexanes, 959 µL, 1.77 mmol) dropwise. The resulting yellow solution was stirred at −78° C. for 5 minutes, then warmed to 0° C. and stirred for an additional 30 minutes. Saturated aqueous NH$_4$Cl (20 mL), water (40 mL) and EtOAc (40 mL) were added and the layers separated. The aqueous layer was acidified to ~pH 2 by addition of 1 N aqueous HCl, then extracted with EtOAc (40 mL). The aqueous layer was then basified to ~pH 5 by addition of 1 N aqueous NaOH and saturated with NaCl. The aqueous was then extracted with 2-methyl-THF (4×40 mL). The organics were combined, dried (Na$_2$SO$_4$), filtered and concentrated to dryness to afford the title compound as a light yellow solid.

Intermediate 38: Step a 3-((4-Bromophenyl)amino)-3-oxopropanoic acid

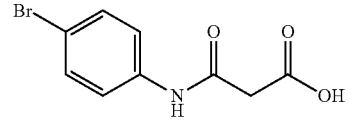 [SMILES: O=C(O)CC(=O)Nc1ccc(Br)cc1]

A mixture of 4-bromoaniline (241.6 g, 1.41 mol) and 2,2-dimethyl-1,3-dioxane-4,6-dione (203.4 g, 1.41 mol) in a round bottom flask was heated to 80° C. The solids start to melt around 70° C. After 1 hour, the melted solids resolidified. The mixture was cooled to room temperature, and then ethyl acetate (200 mL) was added. The resulting mixture was heated to 70° C. for 1 hour then cooled to room temperature. Ethyl acetate was removed by evaporation, and the residue was suspended in diethyl ether (300 mL), sonicated and filtered. The filter cake was washed with minimal amounts of diethyl ether and dried under high vacuum to afford the title compound as a white solid.

Intermediate 38: Step b

6-Bromo-4-hydroxyquinolin-2(1H)-one

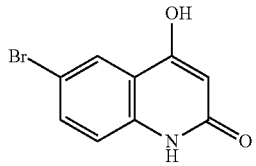

Procedure A:

A mixture of 3-((4-bromophenyl)amino)-3-oxopropanoic acid (Intermediate 38: step a, 50.0 g, 194 mmol) and Eaton's reagent (100 mL) was stirred at 70° C. for 20 hours, cooled to room temperature, and poured into an ice/water mixture (200 mL). The resulting slurry was sonicated for 30 minutes and filtered. The collected solid was dried under high vacuum, then suspended in ethanol (100 mL) and sonicated. The solid was collected by filtration and dried under high vacuum to afford the title compound as a yellow solid.

Procedure B:

According to the general method described in Synthetic Communications 2010, 40, 732, a mixture of 4-bromoaniline (30.0 g, 174 mmol) and 2,2-dimethyl-1,3-dioxan-4,6-dione (25.1 g, 174 mmol) was heated to 80° C. for 1.5 hours and cooled to ambient temperature to receive 3-((4-bromophenyl)amino)-3-oxopropanoic acid. The acetone byproduct was removed under vacuum to provide the intermediate product as a dry solid. Eaton's reagent (100 mL) was added to the solid, then heated to 70° C. overnight and cooled to room temperature. The mixture was poured into water and the brown precipitate was filtered and rinsed with water. The brown precipitate was triturated with ethanol, then filtered to provide the title compound as a light brown solid.

Intermediate 38: Step c

Tert-Butyl 4-(2-(6-bromo-2,4-dihydroxyquinolin-3-yl)ethyl)piperidine-1-carboxylate

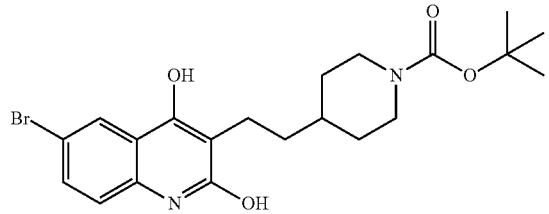 [SMILES: CC(C)(C)OC(=O)N1CCC(CCc2c(O)nc3ccc(Br)cc3c2O)CC1]

To a solution of 6-bromo-4-hydroxyquinolin-2(1H)-one (1.05 g, 4.37 mmol, Intermediate 38: step b) and tert-butyl 4-(2-oxoethyl)piperidine-1-carboxylate (0.99 g, 4.37 mmol) in pyridine (7.9 mL) was added diethyl 1,4-dihydro-2,6-dimethyl-3,5-pyridinecarboxylate (1.11 g, 4.37 mmol) and the resulting suspension heated to 100° C. for 5 hours. The mixture was cooled to room temperature and diluted with Et$_2$O. The ether was decanted and the residue then concentrated to dryness to afford a solid. Diethyl ether was added and the resulting suspension filtered. The solids were dried to provide the title compound.

Intermediate 38: Step d

6-Bromo-2,4-dichloro-3-(2-(piperidin-4-yl)ethyl)quinoline

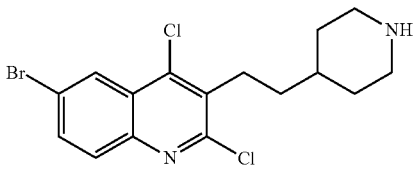 [SMILES: Clc1nc2ccc(Br)cc2c(Cl)c1CCC1CCNCC1]

To a suspension of tert-butyl 4-(2-(6-bromo-2,4-dihydroxyquinolin-3-yl)ethyl)piperidine-1-carboxylate (1.36 g, 3.01 mmol, Intermediate 38: step c) in acetonitrile (10 mL) was added POCl$_3$ (0.84 mL, 9.04 mmol) and the mixture heated to 100° C. overnight. The resulting suspension was filtered and MeOH was then added to the solids and the suspension stirred at room temperature for 1 hour. The suspension was filtered and the filtrate concentrated to dryness to afford a solid. The solids were suspended in DCM and the mixture cooled to 0° C. The pH was neutralized by the addition of concentrated aqueous NH$_4$OH dropwise. The mixture was then diluted with water and extracted with DCM. The organics were combined, dried (MgSO$_4$), filtered and concentrated to dryness to provide the title compound.

Intermediate 38: Step e tert-Butyl 4-(2-(6-bromo-2,4-dichloroquinolin-3-yl)ethyl)piperidine-1-carboxylate

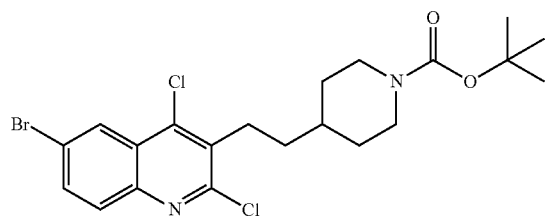 [SMILES: CC(C)(C)OC(=O)N1CCC(CCc2c(Cl)nc3ccc(Br)cc3c2Cl)CC1]

To a solution of 6-bromo-2,4-dichloro-3-(2-(piperidin-4-yl)ethyl)quinoline (490 mg, 1.26 mmol, Intermediate 38: step d) in DCM (4.2 mL) was added 4-(dimethylamino)pyridine (31 mg, 0.25 mmol) and Et$_3$N (350 μL, 2.52 mmol) followed by di-tert-butyl dicarbonate (331 mg, 1.51 mmol). The resulting mixture was stirred at room temperature for 6 hours. The solution was diluted with DCM and washed with saturated aqueous NaHCO$_3$ followed by water. The organics were dried (MgSO$_4$), filtered and concentrated to dryness to provide the title compound which was used without further purification.

Intermediate 38: Step f tert-Butyl 4-(2-(6-bromo-4-chloro-2-methoxyquinolin-3-yl)ethyl)piperidine-1-carboxylate

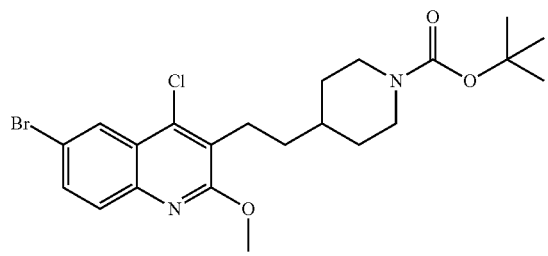 [SMILES: COc1nc2ccc(Br)cc2c(Cl)c1CCC1CCN(C(=O)OC(C)(C)C)CC1]

To a solution of tert-butyl 4-(2-(6-bromo-2,4-dichloroquinolin-3-yl)ethyl)piperidine-1-carboxylate (616 mg, 1.26 mmol, Intermediate 38: step e) in toluene (4 mL) was added NaOMe (341 mg, 6.31 mmol) and the resulting suspension stirred at 110° C. overnight. The mixture was allowed to cool to room temperature and then diluted with EtOAc and washed with water. The organics were dried (MgSO$_4$), filtered and concentrated to dryness. The residue was purified by FCC (0-10% EtOAc/heptane) to provide the title compound.

Intermediate 39

4-Chloro-6-(hydroxy(1-methyl-1H-imidazol-5-yl)(6-(trifluoromethyl)pyridin-3-yl)methyl)-2-methoxyquinolin-3-yl trifluoromethanesulfonate

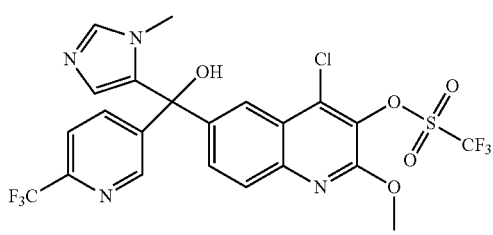 [SMILES: COc1nc2ccc(C(O)(c3ccc(C(F)(F)F)nc3)c3cncn3C)cc2c(Cl)c1OS(=O)(=O)C(F)(F)F]

To a suspension of 4-chloro-6-(hydroxy(1-methyl-1H-imidazol-5-yl)(6-(trifluoromethyl)pyridin-3-yl)methyl)-2-methoxyquinolin-3-ol (750 mg, 1.61 mmol, Intermediate 30) in CH$_2$Cl$_2$ (15 mL) was added pyridine (390 µL, 4.84 mmol) and the reaction became a solution. The solution was cooled to 0° C. and trifluoromethanesulfonic anhydride (683 mg, 2.42 mmol) was added dropwise. The reaction was stirred at 0° C. for 1 hour, then the ice bath was removed and stirring continued for an additional hour. Trifluoromethanesulfonic anhydride (683 mg, 2.42 mmol) was then added and the mixture stirred at room temperature for 1 hour. The solution was poured into a mixture of 1 N aqueous HCl (20 mL) and ice and then the aqueous was extracted with CH$_2$Cl$_2$. The organics were washed with water followed by saturated aqueous NaHCO$_3$ and brine. The aqueous layers were combined and back-extracted with EtOAc. The EtOAc layers were combined and washed with water followed by saturated aqueous NaHCO$_3$ and brine. The CH$_2$Cl$_2$ and EtOAc layers were combined, dried (MgSO$_4$), filtered and concentrated to dryness. The crude material was purified by FCC (0-5% MeOH/CH$_2$Cl$_2$) to provide the title compound.

Intermediate 40

6-Bromo-4-chloro-2-methoxy-3-((4-(trifluoromethyl)piperidin-1-yl)methyl)quinoline

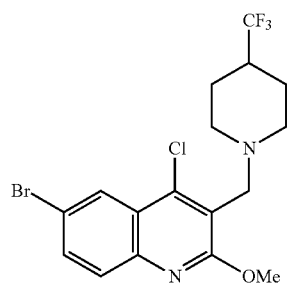 [SMILES: COc1nc2ccc(Br)cc2c(Cl)c1CN1CCC(C(F)(F)F)CC1]

Diisopropylethylamine (0.850 mL, 4.93 mmol) was added to a stirring solution of 6-bromo-3-(bromomethyl)-4-chloro-2-methoxyquinoline (0.900 g, 2.46 mmol, Intermediate 15) and 4-(trifluoromethyl)piperidine hydrochloride (0.490 g, 2.60 mmol) in DCM (25 mL). The resulting mixture was stirred for 3 hours at room temperature. DCM was added and the organic layer was washed with a saturated aqueous solution of NaHCO$_3$, and a saturated aqueous NaCl solution. The organic phase was dried (MgSO$_4$), filtered, and concentrated to dryness. The crude product was purified by flash column chromatography (silica gel, 0-10% EtOAc-hexanes) to provide the title compound as a white solid.

Intermediate 41

3-((4-(1H-Pyrazol-1-yl)piperidin-1-yl)methyl)-6-bromo-4-chloro-2-methoxyquinoline

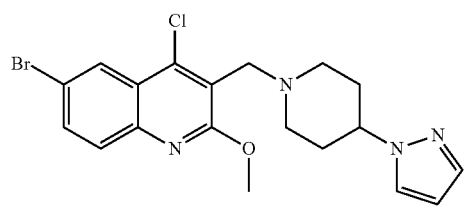 [SMILES: COc1nc2ccc(Br)cc2c(Cl)c1CN1CCC(n2cccn2)CC1]

The title compound was prepared analogously to the method in Intermediate 40 using 4-(1H-pyrazol-1-yl)piperidine in place of 4-(trifluoromethyl)piperidine hydrochloride.

Intermediate 42

(3-((4-(1H-Pyrazol-1-yl)piperidin-1-yl)methyl)-4-chloro-2-methoxyquinolin-6-yl)(1,2-dimethyl-1H-imidazol-5-yl)methanone

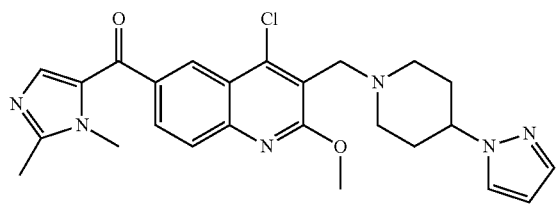 [SMILES: COc1nc2ccc(C(=O)c3cnc(C)n3C)cc2c(Cl)c1CN1CCC(n2cccn2)CC1]

A heterogeneous mixture of (3-((4-(1H-pyrazol-1-yl)piperidin-1-yl)methyl)-4-chloro-2-methoxyquinolin-6-yl)(1,2-dimethyl-1H-imidazol-5-yl)methanol (0.24 g, 0.49 mmol, Example 175) and manganese dioxide (0.217 g, 2.49 mmol) in 1,4-dioxane (5 mL) was stirred at 100° C. for 1 hour. The reaction mixture was then cooled to room temperature, filtered through Celite®, washed with THF, and EtOAc and concentrated to provide the title compound.

Intermediate 43

(4-Chloro-2-methoxy-3-((4-(trifluoromethyl)piperidin-1-yl)methyl)quinolin-6-yl)(1,2-dimethyl-1H-imidazol-5-yl)methanone

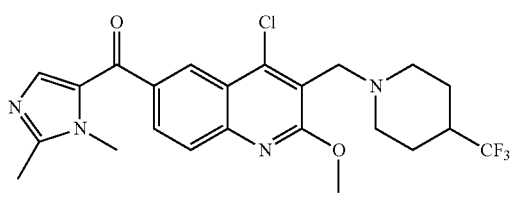 [SMILES: COc1nc2ccc(C(=O)c3cnc(C)n3C)cc2c(Cl)c1CN1CCC(C(F)(F)F)CC1]

The title compound was prepared analogously to the method in Intermediate 42 using (4-chloro-2-methoxy-3-((4-(trifluoromethyl)piperidin-1-yl)methyl)quinolin-6-yl)(1,2-dimethyl-1H-imidazol-5-yl)methanol (Example 176) in place of (3-((4-(1H-pyrazol-1-yl)piperidin-1-yl)methyl)-4-chloro-2-methoxyquinolin-6-yl)(1,2-dimethyl-1H-imidazol-5-yl)methanol.

Intermediate 44

6-Bromo-4-chloro-3-((4,4-difluoropiperidin-1-yl)methyl)-2-methoxyquinoline

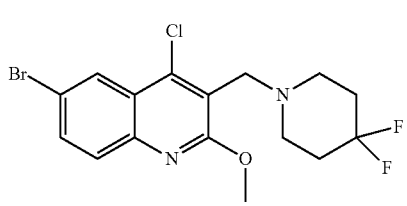 [SMILES: COc1nc2ccc(Br)cc2c(Cl)c1CN1CCC(F)(F)CC1]

The title compound was prepared analogously to the method in Intermediate 40 using 4,4-difluoropiperidine hydrochloride in place of 4-(trifluoromethyl)piperidine hydrochloride.

Intermediate 45

6-Bromo-4-chloro-3-((4-fluoropiperidin-1-yl)methyl)-2-methoxyquinoline

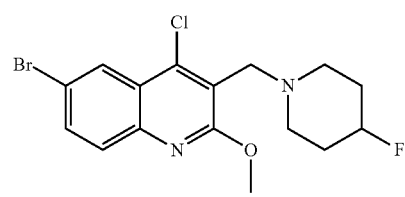 [SMILES: COc1nc2ccc(Br)cc2c(Cl)c1CN1CCC(F)CC1]

The title compound was prepared analogously to the method in Intermediate 40 using 4-fluoropiperidine hydrochloride in place of 4-(trifluoromethyl)piperidine hydrochloride.

Intermediate 46

6-Bromo-4-chloro-3-((3,3-difluoroazetidin-1-yl)methyl)-2-methoxyquinoline

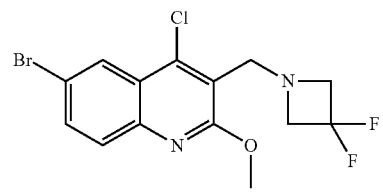 [SMILES: COc1nc2ccc(Br)cc2c(Cl)c1CN1CC(F)(F)C1]

The title compound was prepared analogously to the method in Intermediate 40 using 3,3-difluoroazetidine hydrochloride in place of 4-(trifluoromethyl)piperidine hydrochloride.

Intermediate 47

6-Bromo-4-chloro-3-((3-fluoroazetidin-1-yl)methyl)-2-methoxyquinoline

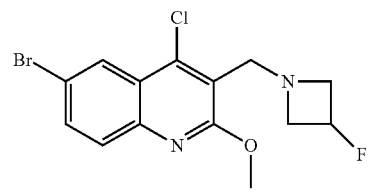 [SMILES: COc1nc2ccc(Br)cc2c(Cl)c1CN1CC(F)C1]

The title compound was prepared analogously to the method in Intermediate 40 using 3-fluoroazetidine hydrochloride in place of 4-(trifluoromethyl)piperidine hydrochloride.

Intermediate 48

6-Bromo-4-chloro-2-methoxy-3-((2,2,6,6-tetramethylpiperidin-1-yl)methyl)quinoline

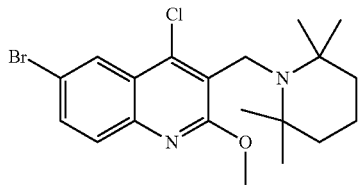 [SMILES: COc1nc2ccc(Br)cc2c(Cl)c1CN1C(C)(C)CCCC1(C)C]

The title compound was prepared analogously to the method in Intermediate 40 using 2,2,6,6-tetramethylpiperidine in place of 4-(trifluoromethyl)piperidine hydrochloride.

Intermediate 49

6-Bromo-4-chloro-2-methoxy-3-((3-(trifluoromethyl)azetidin-1-yl)methyl)quinoline

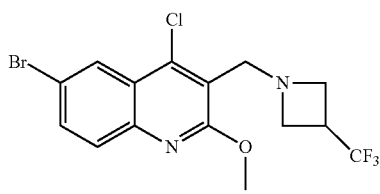 [SMILES: COc1nc2ccc(Br)cc2c(Cl)c1CN1CC(C(F)(F)F)C1]

The title compound was prepared analogously to the method in Intermediate 40 using 3-(trifluoromethyl)azetidine hydrochloride in place of 4-(trifluoromethyl)piperidine hydrochloride.

Intermediate 50: Step a

6-Bromo-2,4-dichloroquinoline

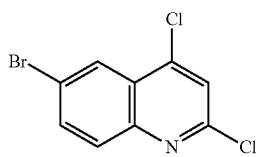

DIPEA (62 mL, 360 mmol) was carefully added (fuming observed) to a mixture of 6-bromo-4-hydroxyquinolin-2 (1H)-one (43.0 g, 180 mmol, Intermediate 38: step b) and phosphorus oxychloride (250 mL). The mixture was stirred at 90° C. for 5 hours, cooled to room temperature, and slowly poured into ice water (200 mL). The resulting mixture was stirred at 0° C. for 1 hour, basified to pH=8 with saturated NaOH aqueous solution at 0° C. The precipitated solid was collected by filtration and further purified by flash column chromatography (silica gel, petroleum ether:ethyl acetate=5:1) to afford the title compound as a yellow solid.

Intermediate 50: Step b

6-Bromo-4-chloro-2-methoxyquinoline

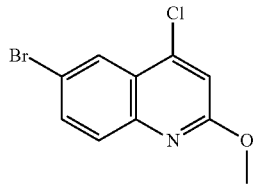

Sodium methoxide (50.1 g, 928 mmol) was added to a solution of 6-bromo-2,4-dichloroquinoline (32 g, 116 mmol, Intermediate 50: step a) in toluene (200 mL). The mixture was stirred at 120° C. for 2 hours then poured into water (200 mL). The resulting mixture was extracted with ethyl acetate (3×200 mL). The combined organic phase was dried over $Na_2SO_4$ and concentrated. The residue was rinsed with minimal amounts of ethyl acetate and filtered to afford the title compound as a yellow solid.

Intermediate 50: Step c

6-Bromo-4-chloro-2-methoxyquinoline-3-carbaldehyde

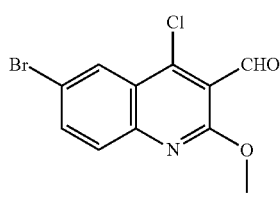 [SMILES: COc1nc2ccc(Br)cc2c(Cl)c1C=O]

A 1 L, three-necked, round-bottomed flask equipped with a nitrogen inlet, magnetic stirrer, and rubber septum was charged with tetrahydrofuran (60 mL) and diisopropylamine (58.5 mL, 416 mmol). The reaction mixture was cooled to −78° C. and n-BuLi (2.5 M in hexane, 160 mL, 400 mmol,) was added. The solution was stirred at −78° C. for 10 minutes, warmed to 0° C. and stirred for an additional 30 minutes. This freshly prepared LDA solution was added to a solution of 6-bromo-4-chloro-2-methoxyquinoline (36.0 g, 130 mmol, Intermediate 50: step b) in dry THF (1.6 L) under a nitrogen atmosphere at −78° C. over 30 minutes. The resulting brown reaction mixture was stirred at −78° C. for 2 hours, and then dry DMF (16 mL, 200 mmol) was added. The reaction mixture was stirred at −78° C. for another 3 hours, quenched with saturated $NH_4Cl$ aqueous solution (400 mL) and extracted with EtOAc (3×300 mL). The combined organic phase was washed with brine (500 mL), dried over $Na_2SO_4$, filtered and concentrated to afford the title compound as a yellow solid, which was directly used without any further purification.

Intermediate 50: Step d (6-Bromo-4-chloro-2-methoxyquinolin-3-yl)methanol

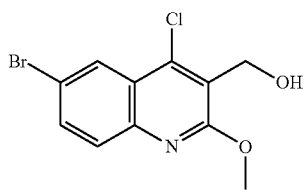

NaBH$_4$ (6.08 g, 160 mmol) was added slowly to a solution of 6-bromo-4-chloro-2-methoxyquinoline-3-carbaldehyde (24 g, 80 mmol, Intermediate 50: step c) in methanol (100 mL) at 0° C. The mixture was warmed up to room temperature, stirred for 0.5 hour, and quenched with water (100 mL). The resulting mixture was extracted with ethyl acetate (3×100 mL). The combined organic phase was washed with brine (300 mL), dried over Na$_2$SO$_4$, concentrated and purified by flash column chromatography (silica gel, petroleum ether:ethyl acetate=5:1) to afford the title compound as a white solid.

Intermediate 50: Step e

6-Bromo-4-chloro-2-methoxy-3-(((triisopropylsilyl)oxy)methyl)quinoline

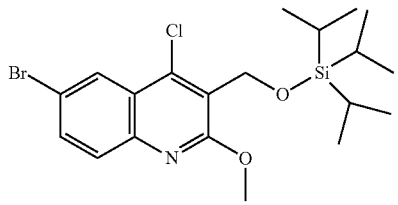 [SMILES: COc1nc2ccc(Br)cc2c(Cl)c1CO[Si](C(C)C)(C(C)C)C(C)C]

Chlorotriisopropylsilane (0.57 g, 2.98 mmol) was added to a mixture of (6-bromo-4-chloro-2-methoxyquinolin-3-yl)methanol (0.600 g, 1.98 mmol, Intermediate 50: step d) and imidazole (0.405 g, 5.95 mmol) in DMF (5 mL). The mixture was stirred for 15 minutes at room temperature and then heated to 70° C. for 1 hour. The mixture was cooled to room temperature, water was added and the aqueous layer was extracted with EtOAc, washed with brine, dried (MgSO$_4$) and concentrated to dryness to afford the title compound.

Intermediate 50: Step f (4-Chloro-2-methoxy-3-(((triisopropylsilyl)oxy)methyl)quinolin-6-yl)(2,6-dimethylpyridin-3-yl)(1-methyl-1H-1,2,3-triazol-5-yl)methanol

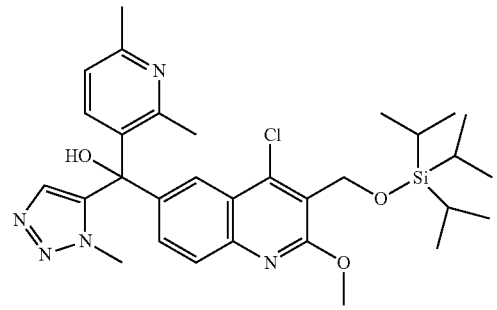 [SMILES: COc1nc2ccc(C(O)(c3ccc(C)nc3C)c3cnnn3C)cc2c(Cl)c1CO[Si](C(C)C)(C(C)C)C(C)C]

A solution of n-butyllithium (2.5 M in hexanes, 0.6 mL, 1.51 mmol) was added dropwise by syringe to a solution of 6-bromo-4-chloro-2-methoxy-3-(((triisopropylsilyl)oxy)methyl)quinoline (0.800 g, 1.66 mmol, Intermediate 50: step e) in dry THF (22 mL) at −78° C. After 2 minutes, a solution of (2,6-dimethylpyridin-3-yl)(1-methyl-1H-1,2,3-triazol-5-yl)methanone (0.32 g, 1.51 mmol, Intermediate 11: step b) in dry THF (6 mL) was added dropwise by syringe. An additional 2 mL of THF was used to complete the quantitative addition. After 10 minutes, the flask was removed from the dry-ice bath and placed into an ice-water bath. After 2 hours, the reaction was quenched with saturated aqueous ammonium chloride solution and the mixture was partitioned between water and EtOAc. The layers were separated and the aqueous phase was further extracted with EtOAc and washed with saturated aqueous NaCl solution. The organic phase was dried (MgSO$_4$), filtered, and concentrated to dryness. The crude product was purified by flash column chromatography (silica gel, 0-60% EtOAc/hexanes) to provide the title compound.

Intermediate 50: Step g (4-Chloro-3-(hydroxymethyl)-2-methoxyquinolin-6-yl)(2,6-dimethylpyridin-3-yl)(1-methyl-1H-1,2,3-triazol-5-yl)methanol

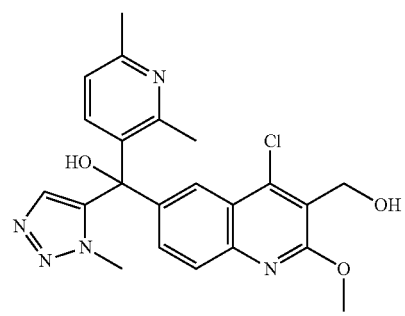 [SMILES: COc1nc2ccc(C(O)(c3ccc(C)nc3C)c3cnnn3C)cc2c(Cl)c1CO]

TBAF (0.42 mL, 0.42 mmol, 1 M in THF) was added to a solution of (4-chloro-2-methoxy-3-(((triisopropylsilyl)oxy)methyl)quinolin-6-yl)(2,6-dimethylpyridin-3-yl)(1-methyl-1H-1,2,3-triazol-5-yl)methanol (0.25 g, 0.42 mmol, Intermediate 50: step f) in THF (17 mL). After stirring at room temperature for 3 hours, the mixture was diluted with EtOAc, washed with aqueous saturated NaCl solution, dried (MgSO₄), filtered and concentrated. The crude product was purified by flash column chromatography (silica gel, 0-100% EtOAc/DCM) to provide the title compound.

Intermediate 51: Step a (1-Methyl-1H-1,2,3-triazol-5-yl)(2-(trifluoromethyl) pyridin-4-yl)methanol

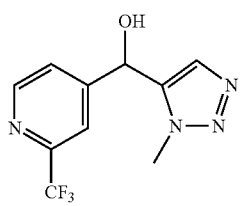

A solution of n-BuLi (0.73 mL, 1.8 mmol, 2.5 M solution in hexane) was added slowly to a solution of 1-methyl-1H-1,2,3-triazole (0.83 g, 10 mmol) in THF (12 mL) at −50° C. After addition, stirring was continued for an additional 30 minutes and 2-(trifluoromethyl)isonicotinaldehyde (0.350 g, 2.0 mmol,) dissolved in THF (4 mL) was slowly added. An additional 2 mL of THF was used to complete the quantitative addition. The mixture was stirred at −50° C. for 5 minutes then warmed to room temperature and stirred overnight. The solution was quenched with saturated aqueous NH₄Cl solution. H₂O was added and layers were separated. The aqueous layer was extracted with EtOAc and the combined organic extracts washed with brine, dried over MgSO₄, filtered, and evaporated in vacuo. The crude product was purified using flash column chromatography (0 to 50% EtOAc/DCM) to provide the title compound.

Intermediate 51: Step b (1-Methyl-1H-1,2,3-triazol-5-yl)(2-(trifluoromethyl) pyridin-4-yl)methanone

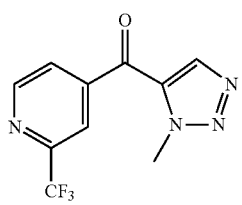 [SMILES: Cn1nncc1C(=O)c1ccnc(C(F)(F)F)c1]

The title compound was prepared analogously to the method in Intermediate 14: step b using (1-methyl-1H-1,2,3-triazol-5-yl)(2-(trifluoromethyl)pyridin-4-yl)methanol (Intermediate 51: step a) in place of (1-methyl-1H-imidazol-5-yl)(2-(trifluoromethyl)pyridin-4-yl)methanol.

Intermediate 52

(4-Chloro-2-methoxy-3-((3-(trifluoromethyl)azetidin-1-yl)methyl)quinolin-6-yl)(1,2-dimethyl-1H-imidazol-5-yl)methanone

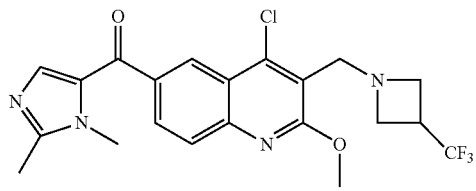 [SMILES: COc1nc2ccc(C(=O)c3cnc(C)n3C)cc2c(Cl)c1CN1CC(C(F)(F)F)C1]

The title compound was prepared analogously to the method in Intermediate 42 using (4-chloro-2-methoxy-3-((3-(trifluoromethyl)azetidin-1-yl)methyl)quinolin-6-yl)(1,2-dimethyl-1H-imidazol-5-yl)methanol (Example 177) in place of (3-((4-(1H-pyrazol-1-yl)piperidin-1-yl)methyl)-4-chloro-2-methoxyquinolin-6-yl)(1,2-dimethyl-1H-imidazol-5-yl)methanol.

Intermediate 53: Step a

N-Methoxy-N-methyltetrahydro-2H-pyran-4-carboxamide

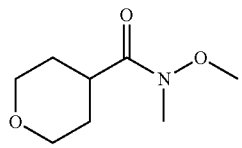

To a solution of tetrahydro-2H-pyran-4-carboxylic acid (5.2 g, 39.9 mmol) in DCM (8.3 mL), CDI (7.12 g, 43.9 mmol) was added and the mixture was stirred for 45 minutes after which N,O-dimethylhydroxylamine hydrochloride (4.29 g, 43.9 mmol) was added and the mixture was stirred for 48 hours. The reaction mixture was quenched with 0.3 M aqueous solution of NaOH and partitioned between water and DCM. The aqueous layer was extracted with DCM, washed with aqueous saturated solution of NaCl, dried (MgSO₄) and concentrated. The crude product was used without any further purification.

Intermediate 53: Step b (1-Methyl-1H-1,2,3-triazol-5-yl)(tetrahydro-2H-pyran-4-yl)methanone

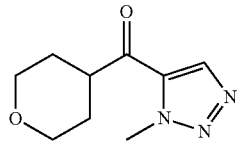

The title compound was prepared analogously to the method in Intermediate 64: step b using N-methoxy-N- methyltetrahydro-2H-pyran-4-carboxamide (Intermediate 53: step a) in place of N-methoxy-N,2,6-trimethylisonicotinamide.

Intermediate 54: Step a

6-Bromo-3-((tetrahydro-2H-thiopyran-4-yl)methyl)quinoline-2,4-diol

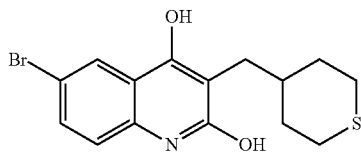 [SMILES: Oc1nc2ccc(Br)cc2c(O)c1CC1CCSCC1]

The title compound was prepared using tetrahydro-2H-thiopyran-4-carbaldehyde in place of 4,4-difluorocyclohexanecarbaldehyde using the procedure described for Intermediate 56: step a, with the exception that the reaction was carried out at 80° C. for 3.5 hours.

Intermediate 54: Step b

6-Bromo-2,4-dichloro-3-((tetrahydro-2H-thiopyran-4-yl)methyl)quinoline

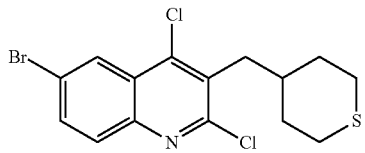

A heterogeneous mixture of 6-bromo-3-((tetrahydro-2H-thiopyran-4-yl)methyl)quinoline-2,4-diol (3.72 g, 10.5 mmol, Intermediate 54: step a), phosphoryl trichloride (5.5 mL, 59 mmol), and CH$_3$CN (25 mL) was stirred at 100° C. for 2.5 hours, during which time it became a clear solution. After cooling down to room temperature, the mixture was concentrated in vacuo. To the residue water was added slowly. The precipitated solid was filtered, washed with water, and dried under air overnight. The solid was dissolved in DCM and purified by FCC (silica gel, 20%-80% DCM in heptanes) to provide the title compound as a yellow solid.

Intermediate 54: Step c

6-Bromo-4-chloro-2-methoxy-3-((tetrahydro-2H-thiopyran-4-yl)methyl)quinoline

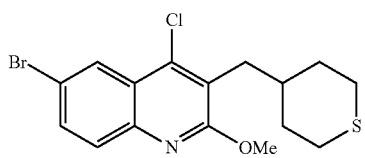 [SMILES: COc1nc2ccc(Br)cc2c(Cl)c1CC1CCSCC1]

The title compound was prepared using 6-bromo-2,4-dichloro-3-((tetrahydro-2H-thiopyran-4-yl)methyl)quinoline (Intermediate 54: step b) in place of 6-bromo-2,4-dichloro-3-((4,4-difluorocyclohexyl)methyl)quinoline (Intermediate 56: step b) using the procedure described for Intermediate 56: step c.

Intermediate 55: Step a tert-Butyl 3-(hydroxy(1-methyl-1H-1,2,3-triazol-5-yl)methyl)azetidine-1-carboxylate

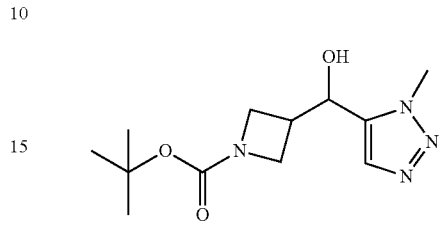

A 2.5 M solution of n-butyllithium in hexanes (9.60 mL, 24.0 mmol) was added dropwise to a stirring solution of 1-methyl-1H-1,2,3-triazole (2.00 g, 24.0 mmol, prepared according to PCT Int. Appl., 2008098104) in dry THF (100 mL) at −50° C. The reaction became heterogeneous and yellow during addition. After 15 minutes, a solution of tert-butyl 3-formylazetidine-1-carboxylate (4.45 g, 24.0 mmol) in dry THF (10 mL) was added dropwise by syringe. The reaction mixture became homogeneous and was allowed to slowly warm to 0° C. Water (10 mL) and ethyl acetate (100) mL were added. The biphasic mixture was warmed to 23° C. The mixture was partitioned between half-saturated aqueous sodium chloride solution (100 mL) and ethyl acetate (300 mL). The layers were separated. The organic layer was dried with sodium sulfate and the dried solution was filtered. Celite® (14 g) was added to the filtrate and the solvents were removed by rotary evaporation to provide a free-flowing powder. The powder was loaded onto a silica gel column. Elution with ethyl acetate initially, grading to 5% methanol-ethyl acetate provided the title compound as a white foam.

Intermediate 55: Step b tert-Butyl 3-(1-methyl-1H-1,2,3-triazole-5-carbonyl)azetidine-1-carboxylate

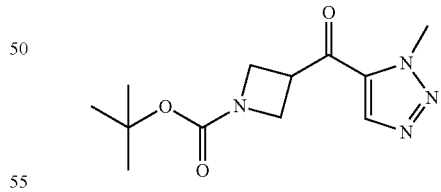

Dess-Martin periodinane (10.9 g, 25.7 mmol) was added in one portion to a stirring solution of tert-butyl 3-(hydroxy(1-methyl-1H-1,2,3-triazol-5-yl)methyl)azetidine-1-carboxylate (4.60 g, 17.1 mmol, Intermediate 55: step a) in dry dichloromethane (86 mL). The resulting mixture was stirred at 23° C. After 18 hours, a mixture containing equal parts water, saturated aqueous sodium thiosulfate solution, and saturated aqueous sodium bicarbonate solution was added (200 mL). Dichloromethane (100 mL) was added. The resulting biphasic mixture was stirred for 15 minutes. The layers were separated. The organic layer was dried with sodium sulfate and the dried solution was concentrated. The residue was purified by flash-column chromatography on silica gel eluting with dichloromethane initially, grading to 5% methanol-dichloromethane to provide the title compound as a clear, colorless oil.

Intermediate 56: Step a

6-Bromo-3-((4,4-difluorocyclohexyl)methyl)quinoline-2,4-diol

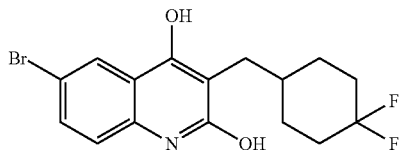 [SMILES: Oc1nc2ccc(Br)cc2c(O)c1CC1CCC(F)(F)CC1]

A mixture of 4,4-difluorocyclohexanecarbaldehyde (1.01 g, 6.84 mmol), 6-bromo-4-hydroxyquinolin-2(1H)-one (1.65 g, 6.85 mmol, Intermediate 38: step b), diethyl 2,6-dimethyl-1,4-dihydropyridine-3,5-dicarboxylate (1.82 g, 7.20 mmol), and pyridine (30 mL) was stirred at 80° C. overnight. After removal of most pyridine in vacuo, a solid precipitated. Pyridine (12 mL) and $Et_2O$ (20 mL) were added and the mixture was stirred for 15 minutes. The white solid was collected by filtration, washed with $Et_2O$, and dried to provide the title compound as a white solid.

Intermediate 56: Step b

6-Bromo-2,4-dichloro-3-((4,4-difluorocyclohexyl)methyl)quinoline

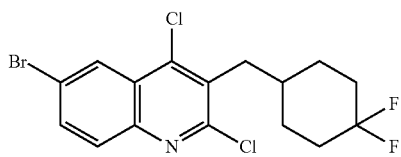 [SMILES: FC1(F)CCC(Cc2c(Cl)nc3ccc(Br)cc3c2Cl)CC1]

A heterogeneous mixture of 6-bromo-3-((4,4-difluorocyclohexyl)methyl)quinoline-2,4-diol (2.98 g, 8.01 mmol, Intermediate 56: step a), phosphoryl trichloride (5.0 mL, 54 mmol), and $CH_3CN$ (20 mL) was stirred at 100° C. for 2.5 hours, during which time it became a clear solution. After cooling down to room temperature, a white solid precipitated. A small amount of water was added resulting in the dissolution of the solid. After concentration in vacuo, water was added to the residue slowly. The precipitated off-white solid was filtered, washed with water, and dried under air overnight. The solid was dissolved in DCM and purified by FCC (silica gel, 100% DCM) to afford the title compound as a white solid.

Intermediate 56: Step c

6-Bromo-4-chloro-3-((4,4-difluorocyclohexyl)methyl)-2-methoxyquinoline

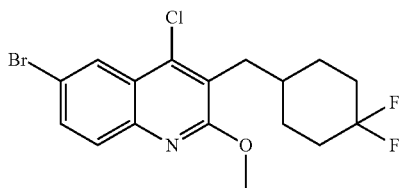 [SMILES: COc1nc2ccc(Br)cc2c(Cl)c1CC1CCC(F)(F)CC1]

A heterogeneous mixture of 6-bromo-2,4-dichloro-3-((4,4-difluorocyclohexyl)methyl)quinoline (1.31 g, 3.20 mmol, Intermediate 56: step b) and NaOMe (1.64 g, 30.4 mmol) in toluene (27 mL) was heated at 105° C. for 15 hours. The solvent was evaporated, and the residue was purified by flash column chromatography (silica gel, 40-80% DCM in heptanes) to provide the title compound.

Intermediate 57: Step a tert-Butyl 3-((1,2-dimethyl-1H-imidazol-5-yl)(hydroxy)methyl)azetidine-1-carboxylate

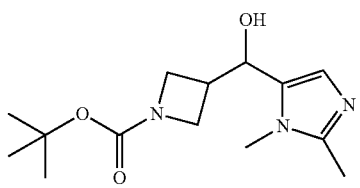 [SMILES: Cc1ncc(C(O)C2CN(C(=O)OC(C)(C)C)C2)n1C]

A solution of n-BuLi (2.0 mL, 5 mmol, 2.5 M solution in hexane) was slowly added to a solution of 5-bromo-1,2-dimethyl-1H-imidazole (0.88 g, 5.1 mmol) in THF (35 mL) at −78° C. After addition, stirring was continued for an additional 30 minutes and tert-butyl 3-formylazetidine-1-carboxylate (0.94 g, 5.1 mmol) dissolved in THF (12 mL) was slowly added. An additional 4 mL of THF was used to complete the quantitative addition. The mixture was stirred at −78° C. for 5 minutes then warmed to room temperature and stirred for 1 hour. The solution was quenched with aqueous saturated $NH_4Cl$ solution and layers were separated. The aqueous layer was extracted with EtOAc and the combined organic extracts washed with brine, dried over $MgSO_4$, filtered and evaporated in vacuo. The crude product was purified by triturating with DCM to provide the title compound.

Intermediate 57: Step b tert-Butyl 3-(1,2-dimethyl-1H-imidazole-5-carbonyl)azetidine-1-carboxylate

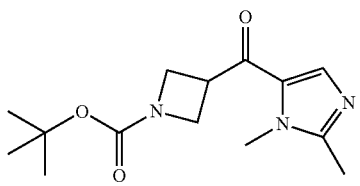 [SMILES: Cc1ncc(C(=O)C2CN(C(=O)OC(C)(C)C)C2)n1C]

A heterogeneous mixture of tert-butyl 3-((1,2-dimethyl-1H-imidazol-5-yl)(hydroxy)methyl)azetidine-1-carboxylate (0.39 g, 1.4 mmol, Intermediate 57: step a) and manganese dioxide (0.843 g, 9.70 mmol) in 1,4-dioxane (28 mL) was stirred at 100° C. for 16 hours. The reaction mixture was then cooled to room temperature, filtered through Celite®, washed with THF, DCM, and EtOAc and concentrated to provide the title compound.

Intermediate 58: Step a tert-Butyl 3-(hydroxy(2-(trifluoromethyl)pyridin-4-yl)methyl)azetidine-1-carboxylate

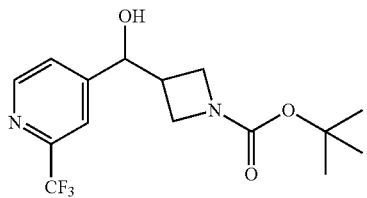 [SMILES: CC(C)(C)OC(=O)N1CC(C(O)c2ccnc(C(F)(F)F)c2)C1]

The title compound was prepared analogously to the method in Intermediate 14: step a using tert-butyl-3-formylazetidine-1-carboxylate in place of 1-methyl-1H-imidazole-5-carbaldehyde.

Intermediate 58: Step b tert-Butyl 3-(2-(trifluoromethyl)isonicotinoyl)azetidine-1-carboxylate

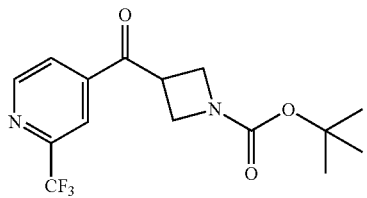 [SMILES: CC(C)(C)OC(=O)N1CC(C(=O)c2ccnc(C(F)(F)F)c2)C1]

Dess-Martin periodinane reagent (3.32 g, 7.82 mmol) was added to a solution of tert-butyl 3-(hydroxy(2-(trifluoromethyl)pyridin-4-yl)methyl)azetidine-1-carboxylate (0.520 g, 1.56 mmol, Intermediate 58: step a) in DCM (15.6 mL) at room temperature and the mixture was stirred for 15 hours. The reaction mixture was diluted with 30 mL of DCM and treated with 20 mL of a saturated aqueous solution of NaHCO$_3$ containing 4 g of Na$_2$S$_2$O$_3$. After 10 minutes of stirring, the mixture was transferred to a separatory funnel and the layers were separated. The aqueous layer was extracted with DCM, and washed with saturated aqueous NaCl solution. The organic phase was dried (MgSO$_4$), filtered, and concentrated. The crude product was purified by flash column chromatography (silica gel, 0-40% EtOAc-DCM) to provide the title compound.

Intermediate 59: Step a

6-Bromo-2-chloro-4-methoxy-3-(2,2,2-trifluoroethyl)quinoline

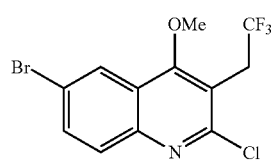 [SMILES: COc1c(CC(F)(F)F)c(Cl)nc2ccc(Br)cc12]

To a flask containing 6-bromo-2,4-dichloro-3-(2,2,2-trifluoroethyl)quinoline (2.0 g, 5.57 mmol, Intermediate 69: step d) was added MeOH (125 mL) and the suspension needed to be sonicated and warmed to become homogeneous. Then, solid NaOMe (635 mg, 11.4 mmol, 97% purity) was added at room temperature. The mixture was heated to 45° C. for 5 hours, and then at room temperature for 18 hours. The solvent was removed under reduced pressure to yield a white solid. The solid was partitioned between water and CHCl$_3$ (40 mL), and the aqueous further extracted with CHCl$_3$ (4×40 mL). The combined organics were washed with brine, dried over MgSO$_4$, filtered and concentrated to dryness. The residue was chromatographed on silica gel (90% hexanes-CHCl$_3$ increasing to 30% hexanes) to afford the title compound as a white solid.

Intermediate 59: Step b (2-Chloro-4-methoxy-3-(2,2,2-trifluoroethyl)quinolin-6-yl)(1,2-dimethyl-1H-imidazol-5-yl)methanol

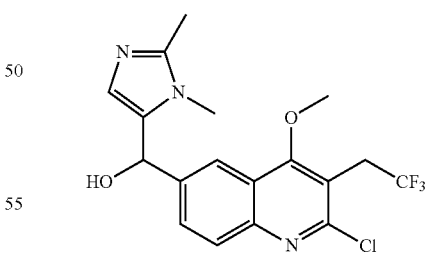

To a flask containing 6-bromo-2-chloro-4-methoxy-3-(2,2,2-trifluoroethyl)quinoline (505 mg, 1.42 mmol, Intermediate 59: step a) was added THF (15 mL) and the solution was cooled to −78° C. Then, n-BuLi (2.5 M in hexanes, 0.68 mmol, 1.7 mmol) was introduced. After 2 minutes, 1,2-dimethyl-1H-imidazole-5-carbaldehyde (208 mg, 1.68 mmol, in 2 mL THF) was introduced. The reaction temperature was allowed to rise gradually to −30° C. over 20 minutes and then quenched with aqueous NH$_4$Cl solution.

The aqueous portion was extracted with EtOAc (3×35 mL) and the combined organics were washed with brine, dried over MgSO$_4$, filtered and concentrated. The residue was chromatographed on silica gel (1% MeOH-DCM increasing to 10% MeOH) to afford the title compound.

Intermediate 59: Step c (2-Chloro-4-methoxy-3-(2,2,2-trifluoroethyl)quinolin-6-yl)(1,2-dimethyl-1H-imidazol-5-yl)methanone

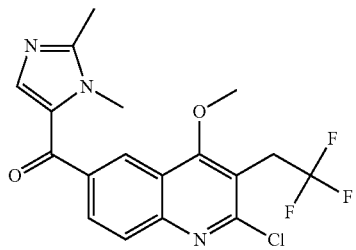 [SMILES: COc1c(CC(F)(F)F)c(Cl)nc2ccc(C(=O)c3cnc(C)n3C)cc12]

To a flask containing (2-chloro-4-methoxy-3-(2,2,2-trifluoroethyl)quinolin-6-yl)(1,2-dimethyl-1H-imidazol-5-yl)methanol (350 mg, 0.88 mmol, Intermediate 59: step b) was added THF (25 mL) providing a homogeneous solution. Then, manganese dioxide (300 mg, 3.45 mmol) was added and the reaction mixture was heated to reflux for 1 hour at which time the reaction was complete by TLC. Filter through Celite®, rinse with THF and concentrate to afford the title compound which was pure by NMR and used without further purification.

Intermediate 60: Step a (1,2-Dimethyl-1H-imidazol-5-yl)(2-(trifluoromethyl)pyridin-4-yl)methanol

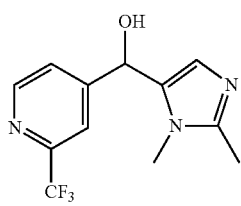 [SMILES: Cc1ncc(C(O)c2ccnc(C(F)(F)F)c2)n1C]

The title compound was prepared analogously to the method in Intermediate 14: step a using 1,2-dimethyl-1H-imidazole-5-carbaldehyde in place of 1-methyl-1H-imidazole-5-carbaldehyde.

Intermediate 60: Step b (1,2-Dimethyl-1H-imidazol-5-yl)(2-(trifluoromethyl)pyridin-4-yl)methanone

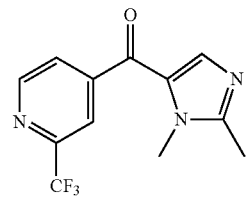 [SMILES: Cc1ncc(C(=O)c2ccnc(C(F)(F)F)c2)n1C]

The title compound was prepared analogously to the method in Intermediate 57: step b using (1,2-dimethyl-1H-imidazol-5-yl)(2-(trifluoromethyl)pyridin-4-yl)methanol (Intermediate 60: step a) in place of tert-butyl 3-((1,2-dimethyl-1H-imidazol-5-yl)(hydroxy)methyl)azetidine-1-carboxylate.

Intermediate 61: Step a (Tetrahydro-2H-pyran-4-yl)(2-(trifluoromethyl)pyridin-4-yl)methanol

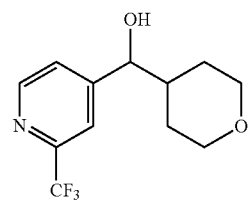 [SMILES: OC(c1ccnc(C(F)(F)F)c1)C1CCOCC1]

The title compound was prepared analogously to the method in Intermediate 14: step a using tetrahydro-2H-pyran-4-carbaldehyde in place of 1-methyl-1H-imidazole-5-carbaldehyde.

Intermediate 61: Step b (Tetrahydro-2H-pyran-4-yl)(2-(trifluoromethyl)pyridin-4-yl)methanone

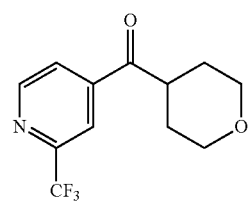 [SMILES: O=C(c1ccnc(C(F)(F)F)c1)C1CCOCC1]

The title compound was prepared analogously to the method in Intermediate 58: step b using (tetrahydro-2H-pyran-4-yl)(2-(trifluoromethyl)pyridin-4-yl)methanol (Intermediate 61: step a) in place of tert-butyl 3-(hydroxy(2-(trifluoromethyl)pyridin-4-yl)methyl)azetidine-1-carboxylate.

Intermediate 62

(1,2-Dimethyl-1H-imidazol-5-yl)(tetrahydro-2H-pyran-4-yl)methanone

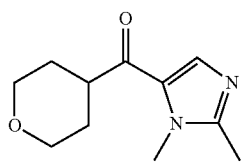

A solution of n-BuLi (4.0 mL, 10 mmol, 2.5 M solution in hexane) was slowly added to a solution of 5-bromo-1,2-dimethyl-1H-imidazole (1.77 g, 10.2 mmol) in THF (70 mL) at −78° C. After addition, stirring was continued for an additional 30 minutes and N-methoxy-N-methyltetrahydro-2H-pyran-4-carboxamide (1.76 g, 10.1 mmol, Intermediate 53: step a) dissolved in THF (25 mL) was slowly added. An additional 6 mL of THF was used to complete the quantitative addition. The mixture was stirred at −78° C. for 5 minutes then warmed to room temperature and stirred for 1 hour. The solution was quenched with water and layers were separated. The aqueous layer was extracted with DCM and the combined organic extracts washed with brine, dried over MgSO₄, filtered and evaporated in vacuo. The crude product was purified using flash column chromatography (0 to 6% MeOH/DCM) to provide the title compound.

Intermediate 63: Step a tert-Butyl 3-(hydroxy(6-(trifluoromethyl)pyridin-3-yl)methyl)azetidine-1-carboxylate

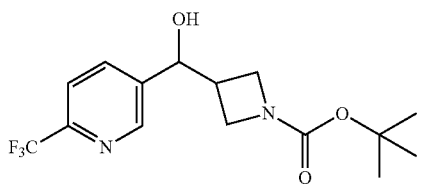 [SMILES: CC(C)(C)OC(=O)N1CC(C(O)c2ccc(C(F)(F)F)nc2)C1]

A solution of isopropylmagnesium chloride (2.0 M in THF, 1.5 mL, 3.0 mmol) was added dropwise by syringe to a solution of 5-bromo-2-(trifluoromethyl)pyridine (0.68 g, 3.0 mmol) in dry THF (12 mL) at 0° C. After 30 minutes, a solution of tert-butyl 3-formylazetidine-1-carboxylate (0.505 g, 2.73 mmol) in THF was added to the Grignard solution by syringe at 0° C. The reaction mixture was warmed to room temperature over 1 hour after which it was quenched with saturated aqueous ammonium chloride solution. The mixture was partitioned between water and ethyl acetate. The separated aqueous phase was further extracted with ethyl acetate and washed with saturated aqueous NaCl solution. The organic phase was dried (MgSO₄), filtered, and concentrated. The crude product was purified by flash column chromatography (silica gel, 0-40% EtOAc-DCM) to provide the title compound.

Intermediate 63: Step b tert-Butyl 3-(6-(trifluoromethyl)nicotinoyl)azetidine-1-carboxylate

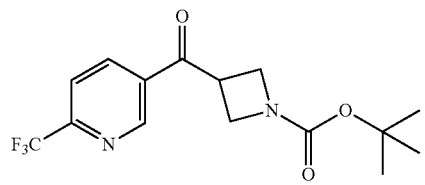 [SMILES: CC(C)(C)OC(=O)N1CC(C(=O)c2ccc(C(F)(F)F)nc2)C1]

The title compound was prepared analogously to the method in Intermediate 57: step b using tert-butyl 3-(hydroxy(6-(trifluoromethyl)pyridin-3-yl)methyl)azetidine-1-carboxylate (Intermediate 63: step a) in place of tert-butyl 3-((1,2-dimethyl-1H-imidazol-5-yl)(hydroxy)methyl)azetidine-1-carboxylate.

Intermediate 64: Step a

N-Methoxy-N,2,6-trimethylisonicotinamide

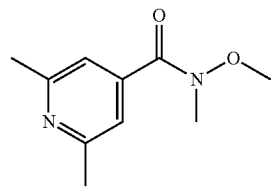

To a solution of 2,6-dimethylisonicotinic acid (1.00 g, 6.61 mmol) in DCM (8.3 mL), CDI (1.18 g, 7.27 mmol) was added and the mixture was stirred for 45 minutes after which N,O-dimethylhydroxylamine hydrochloride (0.71 g, 7.3 mmol) was added and the mixture was stirred for 20 hours. The reaction mixture was quenched with 0.3 M aqueous solution of NaOH and partitioned between water and DCM. The aqueous layer was extracted with DCM, washed with aqueous saturated solution of NaCl, dried (MgSO₄) and concentrated. The crude product was purified by flash column chromatography (silica gel, 0-100% EtOAc-DCM) to provide the title compound.

Intermediate 64: Step b (2,6-Dimethylpyridin-4-yl)(1-methyl-1H-1,2,3-triazol-5-yl)methanone

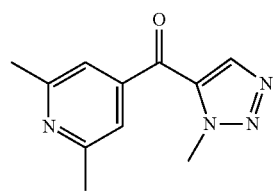 [SMILES: Cc1cc(C(=O)c2cnnn2C)cc(C)n1]

A solution of n-BuLi (3.8 mL, 9.5 mmol, 2.5 M solution in hexane) was added slowly to a solution of 1-methyl-1H-

1,2,3-triazole (0.83 g, 10 mmol) in THF (48 mL) at −50° C. After addition, stirring was continued for an additional 30 minutes and N-methoxy-N,2,6-trimethylisonicotinamide (0.97 g, 5.0 mmol, Intermediate 64: step a) dissolved in THF (12 mL) was slowly added. An additional 2 mL of THF was used to complete the quantitative addition. The mixture was stirred at −50° C. for 5 minutes then warmed to room temperature and stirred overnight. The solution was quenched with saturated aqueous NH$_4$Cl. H$_2$O was added and layers were separated. The aqueous layer was extracted with EtOAc and the combined organic extracts washed with brine, dried over MgSO$_4$, filtered and evaporated in vacuo. The crude product was purified using flash column chromatography (0 to 100% EtOAc/DCM) to provide the title compound.

Intermediate 65

(4-Chloro-3-isobutyl-2-methoxyquinolin-6-yl)(1,2-dimethyl-1H-imidazol-5-yl)methanone

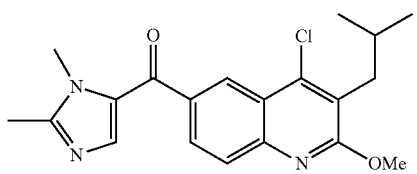 [SMILES: COc1nc2ccc(C(=O)c3cnc(C)n3C)cc2c(Cl)c1CC(C)C]

To a flask containing (4-chloro-3-isobutyl-2-methoxyquinolin-6-yl)(1,2-dimethyl-1H-imidazol-5-yl)methanol (570 mg, 1.52 mmol, Example 158) was added 1,4-dioxane (20 mL) followed by activated MnO$_2$ (500 mg, 5.75 mmol) and the mixture was heated to 95° C. After 2 hours, the contents were filtered while still hot through Celite® and rinsed with THF and concentrated to dryness to provide the title compound as a white amorphous solid which was used without purification.

Intermediate 66: Step a

2-Isobutylmalonic acid

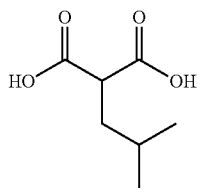

The mixture of diethyl 2-isobutylmalonate (10.0 g, 46.23 mmol) and NaOH (9.2 g, 231.15 mmol) in EtOH (50 mL) and water (20 mL) was stirred at room temperature overnight. The reaction mixture was poured into water (150 mL), and then a 2 N aqueous HCl solution (25 mL) was added to the mixture. The mixture was stirred at room temperature for 30 minutes and then extracted with EtOAc. The organic layer was dried (Na$_2$SO$_4$), filtered and concentrated in vacuo to provide the title compound as a white solid.

Intermediate 66: Step b

6-Bromo-2,4-dichloro-3-isobutylquinoline

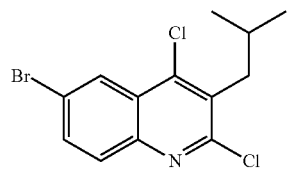 [SMILES: CC(C)Cc1c(Cl)nc2ccc(Br)cc2c1Cl]

To a mixture of 2-isobutylmalonic acid (6.41 g, 40.01 mmol, Intermediate 66: step a) and 4-bromoaniline (6.88 g, 40.01 mmol) was added POCl$_3$ (150 mL) at 0° C. The mixture was stirred at 90° C. overnight. The mixture was cooled to room temperature, concentrated in vacuo, and the residue was purified by flash chromatography to provide the title compound as a white solid.

Intermediate 66: Step c

6-Bromo-4-chloro-3-isobutyl-2-methoxyquinoline

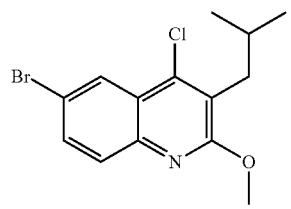 [SMILES: COc1nc2ccc(Br)cc2c(Cl)c1CC(C)C]

To a flask containing 6-bromo-2,4-dichloro-3-isobutylquinoline (5 g, 15.0 mmol, Intermediate 66: step b) was added toluene (100 mL) followed by solid NaOMe (9 g, 166.6 mmol) at room temperature. The white suspension was stirred at 110° C. for 48 hours. The reaction mixture was filtered through Celite® while still warm and the filter cake was rinsed with toluene (125 mL). The effluent was concentrated and the crude material was chromatographed on silica gel (90% hexane-DCM increasing to 50% DCM) to provide the title compound initially as a colorless viscous gum. The product was dissolved in Et$_2$O and hexane and concentrated to dryness to afford a white solid.

Intermediate 66: Step d (4-Chloro-3-isobutyl-2-methoxyquinolin-6-yl)(2,6-dimethylpyridin-3-yl)methanone

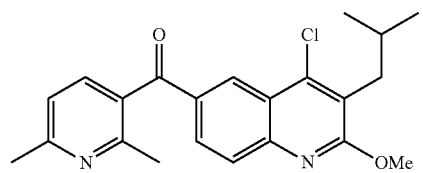 [SMILES: COc1nc2ccc(C(=O)c3ccc(C)nc3C)cc2c(Cl)c1CC(C)C]

To a flask containing (4-chloro-3-isobutyl-2-methoxyquinolin-6-yl)(2,6-dimethylpyridin-3-yl)methanol (925 mg, 2.4 mmol, Example 157) was added 1,4-dioxane (75 mL) followed by activated manganese dioxide (800 mg, 9.2 mmol) and the mixture was heated to reflux. After 1 hour, the contents were filtered while still hot through Celite® and the filter cake was rinsed with THF. The filtrate was concentrated and chromatographed on silica gel (100% DCM increasing to 3% MeOH-DCM) to provide the title compound as an off white solid.

Intermediate 67: Step a

6-Bromo-2,4-dichloro-3-isopropylquinoline

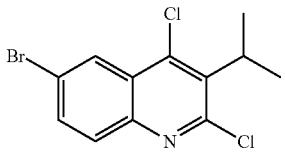 [SMILES: CC(C)c1c(Cl)nc2ccc(Br)cc2c1Cl]

A flask fitted with a reflux condenser was charged with POCl₃ at room temperature and then 2-isopropylmalonic acid (10 g, 68.4 mmol) was added followed by 4-bromoaniline (12 g, 69.7 mmol). The heterogeneous mixture was heated in an aluminum mantle to 100° C. which resulted in a light brown homogenous solution after approximately 10 minutes. The reaction mixture was stirred at reflux for 4 hours and then at room temperature for 16 hours. After 20 hours, the excess POCl₃ was removed under reduced pressure. The resulting crude material was then poured onto ice chips (~500 g) in a 1 L flask pre-cooled to 0° C. DCM (~200 mL) was added and the mixture was stirred at 0° C. as a solution of 6 M aqueous KOH was added carefully to bring the contents to pH=10. The neutralization process was kept at 0° C. throughout. The organic phase was separated and the aqueous portion was washed with DCM (3×250 mL). The combined organics were washed with brine, dried over Na₂SO₄, filtered and concentrated. The crude material was first passed through a silica gel plug (100% DCM) and the effluent was concentrated. Trituration of the resulting material with CH₃CN provided the title compound as a white solid.

Intermediate 67: Step b

6-Bromo-4-chloro-3-isopropyl-2-methoxyquinoline

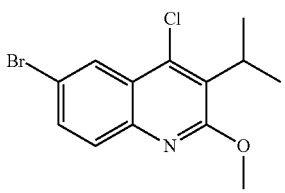 [SMILES: COc1nc2ccc(Br)cc2c(Cl)c1C(C)C]

To a flask containing 6-bromo-2,4-dichloro-3-isopropylquinoline (12 g, 37.6 mmol, Intermediate 67: step a) was added toluene (300 mL) and to this homogeneous solution at room temperature was added solid NaOMe (18 g, 333.2 mmol). The resulting suspension was stirred at reflux (118° C.) in an aluminum mantle for 8 hours, then at 85° C. for 18 hours. The reaction mixture was then filtered through Celite® while still warm and the filter cake was rinsed with toluene (300 mL). The filtrate was concentrated to dryness to afford the title compound as a white solid.

Intermediate 68: Step a

6-Bromo-2,4-dichloro-3-cyclopentylquinoline

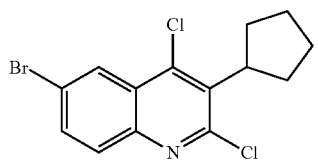 [SMILES: Clc1nc2ccc(Br)cc2c(Cl)c1C1CCCC1]

A flask fitted with a reflux condenser and a Drierite® drying tube, was charged with POCl₃ (150 mL) at room temperature. 2-Cyclopentylmalonic acid (10 g, 58.1 mmol) was added followed by 4-bromoaniline (10.3 g, 59.8 mmol). Once the thick heterogeneous mixture was heated to reflux a homogeneous light yellow solution resulted. The reaction mixture was stirred at reflux for 4 hours. The excess POCl₃ was removed under reduced pressure. The resulting crude material was then poured onto ice chips (~500 g) in a 1 L flask pre-cooled to 0° C. DCM was added (~200 mL) and the solution was stirred at 0° C. as 10 M aqueous KOH (~300 mL) was added carefully to pH=9. The neutralization process was kept at 0° C. throughout. The organic phase was separated and the aqueous portion was washed with DCM (3×250 mL). The combined organics were washed with brine, dried over MgSO₄ filtered and concentrated. The crude material was passed through a short column of silica gel (20% toluene-DCM) and the effluent was concentrated. The material was recrystallized from MeOH overnight. The resulting solid was collected by filtration and dried to afford the title compound as an off white solid.

Intermediate 68: Step b

6-Bromo-4-chloro-3-cyclopentyl-2-methoxyquinoline

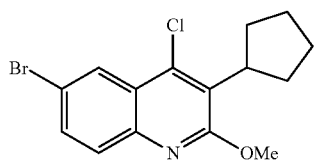 [SMILES: COc1nc2ccc(Br)cc2c(Cl)c1C1CCCC1]

To a flask containing 6-bromo-2,4-dichloro-3-cyclopentylquinoline (5 g, 14.5 mmol, Intermediate 68: step a) was added toluene (300 mL) followed by solid NaOMe (6.93 g, 128.3 mmol) at room temperature. The suspension was stirred at reflux for 5 hours and then at 95° C. for 16 hours. The reaction mixture was filtered through Celite® while still warm and the filter cake was rinsed with toluene (300 mL). The filtrate was concentrated to give an off white solid. Chromatography on silica gel (90% hexane-DCM increasing to 70% DCM) provided the title compound as a white solid.

Intermediate 68: Step c (4-Chloro-3-cyclopentyl-2-methoxyquinolin-6-yl)(1,2-dimethyl-1H-imidazol-5-yl)methanone

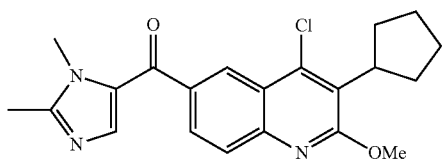 [SMILES: COc1nc2ccc(C(=O)c3cnc(C)n3C)cc2c(Cl)c1C1CCCC1]

To a flask containing (4-chloro-3-cyclopentyl-2-methoxyquinolin-6-yl)(1,2-dimethyl-1H-imidazol-5-yl)methanol (500 mg, 1.3 mmol, Example 159) was added THF (25 mL) followed by activated $MnO_2$ (500 mg, 4.44 mmol) and the mixture was heated to reflux. After 60 minutes, the contents were filtered while still hot through Celite® and rinsed with additional THF and concentrated to afford the title compound.

Intermediate 69: Step a 4,4,4-Trifluorobutanoyl chloride

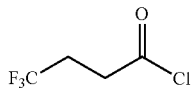

4,4,4-Trifluorobutyric acid (20.0 g, 137 mmol), dichloromethane (275 mL), and oxalyl chloride (12.4 mL, 145 mmol) were added to a round bottom flask and cooled to 0° C. in an ice water bath. DMF (1.06 mL, 13.7 mmol) was then added and the contents stirred at 0° C. for 15 minutes. The ice bath was then removed and the contents were allowed to warm to room temperature. Gas evolution was noticed immediately after addition of DMF (significant, but not violent) and continued at a moderate pace after the ice bath was removed and the reaction warmed to room temperature and ceased after one and a half hours of stirring. The solution of the title compound was used as is in a subsequent reaction.

Intermediate 69: Step b

Methyl 5-bromo-2-(4,4,4-trifluorobutanamido)benzoate

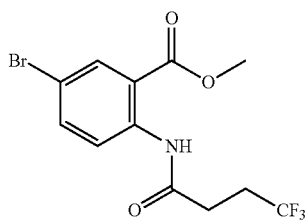 [SMILES: COC(=O)c1cc(Br)ccc1NC(=O)CCC(F)(F)F]

Methyl 2-amino-5-bromobenzoate (26.0 g, 113 mmol), triethylamine (18.9 mL, 136 mmol), and dichloromethane (400 mL) were combined in a round bottom flask. The contents were cooled to 0° C. in an ice water bath, then a solution of 4,4,4-trifluorobutanoyl chloride in dichloromethane (137 mmol, Intermediate 69: step a) was cannulated into the reaction vessel over approximately 15 minutes. The reaction solution was stirred at 0° C. for one hour, then the ice bath was removed and the contents allowed to warm to room temperature gradually, then stirred at room temperature overnight. Reaction contents were quenched with the addition of saturated, aqueous $NH_4Cl$ solution then transferred to a separatory funnel with EtOAc dilution. The organic phase was separated and the aqueous layer was extracted twice with additional EtOAc. The combined organic phases were dried over $MgSO_4$, filtered and rotovapped to dryness to afford the title compound.

Intermediate 69: Step c

6-Bromo-4-hydroxy-3-(2,2,2-trifluoroethyl)quinolin-2(1H)-one

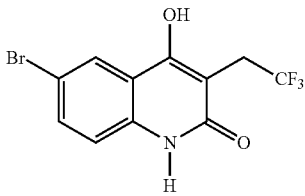 [SMILES: O=c1[nH]c2ccc(Br)cc2c(O)c1CC(F)(F)F]

Methyl 5-bromo-2-(4,4,4-trifluorobutanamido)benzoate (20.04 g, 56.59 mmol, Intermediate 69: step b) and THF (350 mL) were combined in a round bottom flask. Potassium hexamethyldisilazane (KHMDS, 0.5 M in toluene, 340 mL, 170 mmol) was then added over 15 minutes. The contents were stirred for approximately 6 hours yielding a tan heterogeneous mixture. To the reaction mixture was added deionized water (approx. 50 mL) then 1 M aqueous NaOH solution (approximately 100 mL) and the reaction contents were stirred until homogeneous. The solution was then transferred to a separatory funnel and the aqueous phase was separated. The organic phase was extracted with a 0.5 M aqueous NaOH solution and the basic, aqueous layers were combined in a large Erlenmeyer flask. Upon acidification of the combined aqueous layers (to approx. pH 4) with 6 M aqueous HCl solution, a tan precipitate was formed which was collected by cooling the heterogeneous aqueous mixture to 0° C. in an ice-water bath, collecting the precipitate on a Buchner funnel with deionized water rinsing. The precipitate was air-dried then further dried under reduced pressure to provide the title compound.

Intermediate 69: Step d

6-Bromo-2,4-dichloro-3-(2,2,2-trifluoroethyl)quinoline

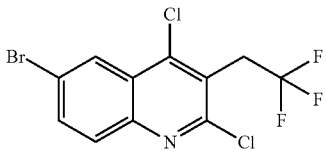 [SMILES: FC(F)(F)Cc1c(Cl)nc2ccc(Br)cc2c1Cl]

6-Bromo-4-hydroxy-3-(2,2,2-trifluoroethyl)quinolin-2 (1H)-one (15.5 g, 48.1 mmol, Intermediate 69: step c) and POCl$_3$ (135 mL, 1.44 mol) were combined in a round bottom flask and heated to 100° C. for three hours. The reaction was then cooled and excess phosphorous oxychloride was removed by reduced pressure distillation. The dark crude was taken up into chloroform, cooled to 0° C. in an ice water bath, then any residual phosphorous oxychloride was quenched with dionized water and saturated aqueous NH$_4$Cl solution. The solution was then transferred to a separatory funnel where the organic layer was separated and the aqueous layer was extracted once with chloroform. The combined organic phases were dried over MgSO$_4$, filtered and solvent removed by reduced pressure distillation. The crude product was purified by flash column chromatography (silica gel, 0-20% hexane/ethyl acetate) to afford the title compound.

Intermediate 69: Step e

6-Bromo-4-chloro-2-methoxy-3-(2,2,2-trifluoroethyl)quinoline

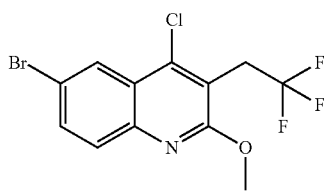 [SMILES: COc1nc2ccc(Br)cc2c(Cl)c1CC(F)(F)F]

6-Bromo-2,4-dichloro-3-(2,2,2-trifluoroethyl)quinoline (4.93 g, 13.7 mmol, Intermediate 69, step d), toluene (700 mL), MeOH (70 mL) and NaOMe (2.23 g, 41.2 mmol) were combined under nitrogen and heated to 65° C. and maintained at that temperature for 2 days. The reaction contents were then cooled to room temperature and transferred to a separatory funnel with EtOAc and saturated, aqueous ammonium chloride solution. The organic phase was separated then the aqueous was extracted twice with EtOAc. The combined organics were dried over MgSO$_4$, filtered and concentrated under reduced pressure. The crude product was purified by flash column chromatography (silica gel, 0-10% DCM/hexanes) to provide the title compound.

Intermediate 70

(2,4-Dichloro-3-(2,2,2-trifluoroethyl)quinolin-6-yl) (1,2-dimethyl-1H-imidazol-5-yl)methanone

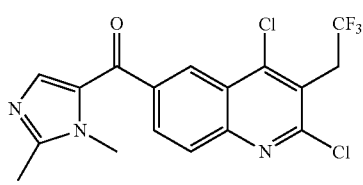 [SMILES: Cc1ncc(C(=O)c2ccc3nc(Cl)c(CC(F)(F)F)c(Cl)c3c2)n1C]

To a flask containing (2,4-dichloro-3-(2,2,2-trifluoroethyl)quinolin-6-yl)(1,2-dimethyl-1H-imidazol-5-yl)methanol (505 mg, 1.25 mmol, Example 162) was added 1,4-dioxane (30 mL) followed by manganese dioxide (475 mg, 5.5 mmol) and the mixture was heated to reflux. After 1 hour, the contents were filtered through Celite® and rinsed with THF, and the effluent was concentrated. The crude material was chromatographed on silica gel (1% MeOH-DCM increasing to 5% MeOH) to provide the title compound as a tan solid.

Intermediate 71

Methyl 2,4-dichloro-3-(2,2,2-trifluoroethyl)quinoline-6-carboxylate

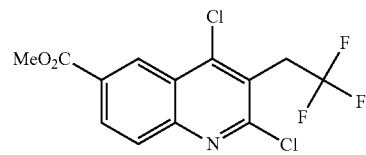 [SMILES: COC(=O)c1ccc2nc(Cl)c(CC(F)(F)F)c(Cl)c2c1]

6-Bromo-2,4-dichloro-3-(2,2,2-trifluoroethyl)quinoline (1.00 g, 2.79 mmol, Intermediate 69: step d) and THF (15 mL) were combined in a round bottom flask under an N$_2$ atmosphere and cooled to −78° C. in a dry ice acetone bath. n-BuLi (1.6 M in hexanes, 1.74 mL, 2.79 mmol) was then added dropwise via syringe over approximately 2 minutes and allowed to stir at that temperature for an additional 2 minutes. Several pieces of dry ice were then added to the reaction vessel and the contents were stirred for 5 minutes in the dry ice acetone bath, then the bath was removed and contents allowed to gradually warm to room temperature over approximately 2 hours. The mixture was then re-cooled to 0° C. in an ice water bath followed by addition of methyl iodide (0.52 mL, 8.4 mmol) and sodium carbonate (295 mg, 2.79 mmol) then the ice the bath was removed and the contents were warmed to 40° C. for one hour. DMSO (3 mL) was added and the mixture stirred overnight at 40° C. The mixture was then cooled to room temperature, diluted with water and ethyl acetate then transferred to a separatory funnel. The aqueous layer was separated and the organic layer was washed three times with deionized water. The organic phase was dried over MgSO$_4$, filtered and concentrated under reduced pressure. The crude product was purified by flash column chromatography (silica gel, 0-25% hexane/ethyl acetate) to afford the title compound.

Intermediate 72

N-Methoxy-N,1-dimethyl-1H-1,2,3-triazole-5-carboxamide

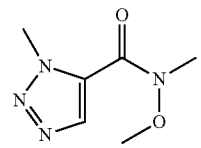

A solution of 1-methyl-1H-1,2,3-triazole (12.9 g, 155 mmol) in THF (260 mL) was cooled to −45° C. Maintaining a temperature of <−35° C., n-BuLi (62.1 mL, 2.5 M in hexanes, 155 mmol) was added over 10 minutes. The reaction mixture was stirred for 30 minutes with cooling to −45° C. and then treated with a sub-surface stream of CO$_{2(g)}$ for a period of 2 hours. After flushing the −35° C. slurry with N$_{2(g)}$ for 5 minutes, thionyl chloride (11.8 mL, 163 mmol) was added. The mixture was allowed to warm to room temperature with stirring over 1.25 hours. Addition of N,O-dimethylhydroxylamine hydrochloride (18.14 g, 186 mmol) and N,N-diisopropylethylamine (68.3 mL, 396 mmol) was followed by stirring for 15 hours. Aqueous sodium carbonate (500 mL, 10 wt %) was then added, and the layers were mixed and separated. The aqueous layer was washed with dichloromethane (250 mL and then 125 mL), and the combined organic layers were dried over MgSO$_4$, filtered, and concentrated. The concentrate was taken up in ethyl acetate (225 mL), treated with MgSO$_4$, and filtered through a pad of silica gel (115 g). The silica gel pad was washed with additional ethyl acetate (800 mL). The eluent was concentrated to dryness to provide the title compound as a yellow solid.

Intermediate 73: Step a

Methyl 2,4-dichloro-3-methylquinoline-6-carboxylate

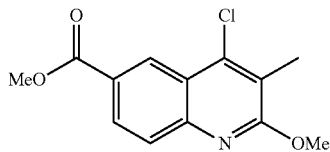 [SMILES: COC(=O)c1ccc2nc(OC)c(C)c(Cl)c2c1]

A mixture of methyl 4-aminobenzoate (1.0 g, 6.6 mmol) and 2-methylmalonic acid (860 mg, 7.28 mmol) in POCl$_3$ (10 mL) was stirred at 100° C. for 5 hours. The reaction mixture was initially a white slurry and then turned into a homogeneous red solution. The reaction mixture was cooled to room temperature and stirred overnight. Most of the POCl$_3$ was removed by evaporation under vacuum. The thick red syrup residue was slowly poured into ice/water (50 mL). A yellow solid that precipitated from the mixture was collected by filtration. The filter cake was placed in 100 mL flask cooled in an ice-water bath. Aqueous ammonia solution (about 20 mL) was added until pH~8-9. The resulting suspension was stirred at room temperature for 20 minutes and then filtered by suction, rinsed with water (50 mL) and dried. The solid was suspended in CH$_3$CN (10 mL), sonicated for 15 minutes at room temperature, filtered, rinsed with CH$_3$CN (10 mL) and then dried to provide the title compound as a white solid.

Intermediate 73: Step b

Methyl 4-chloro-2-methoxy-3-methylquinoline-6-carboxylate

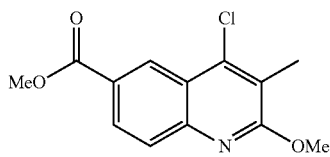 [SMILES: COC(=O)c1ccc2nc(OC)c(C)c(Cl)c2c1]

Sodium methoxide (1.38 g, 25.6 mmol) was added to a stirred solution of methyl 2,4-dichloro-3-methylquinoline-6-carboxylate (860 mg, 3.2 mmol, Intermediate 73: step a) in toluene (20 mL). The mixture was stirred at 80° C. for 4 hours, cooled to room temperature and diluted with water (50 mL). The mixture was extracted with ethyl acetate (3×20 mL). The organic layers were combined and washed with brine (50 mL), dried over Na$_2$SO$_4$ and concentrated to give the title compound as a white solid.

Intermediate 73: Step c

Methyl 3-(bromomethyl)-4-chloro-2-methoxyquinoline-6-carboxylate

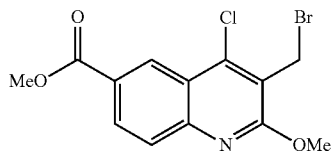 [SMILES: COC(=O)c1ccc2nc(OC)c(CBr)c(Cl)c2c1]

To a stirred solution of methyl 4-chloro-2-methoxy-3-methylquinoline-6-carboxylate (300 mg, 1.13 mmol, Intermediate 73: step b) in CCl$_4$ (20 mL), NBS (201 mg, 1.13 mmol) and AIBN (18.5 mg, 0.113 mmol) were added sequentially. The reaction mixture was stirred at 80° C. overnight, cooled to room temperature and diluted with DCM (20 mL), and then washed with water (20 mL) and brine (20 mL), dried over Na$_2$SO$_4$ and concentrated to dryness. The residue was purified by silica gel column chromatography (eluting with petroleum ether/ethyl acetate=20:1) to provide the title compound as a white solid.

Intermediate 74: Step a

Methyl 4-chloro-3-((diallylamino)methyl)-2-methoxyquinoline-6-carboxylate

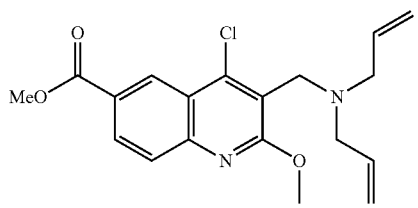 [SMILES: C=CCN(CC=C)Cc1c(OC)nc2ccc(C(=O)OC)cc2c1Cl]

The title compound was prepared analogously to the method described for Intermediate 40 using diallyl amine in place of 4-(trifluoromethyl)piperidine hydrochloride and methyl 3-(bromomethyl)-4-chloro-2-methoxyquinoline-6-carboxylate (Intermediate 73: step c) in place of 6-bromo-3-(bromomethyl)-4-chloro-2-methoxyquinoline.

Intermediate 74: Step b (4-Chloro-3-((diallylamino)methyl)-2-methoxyquinolin-6-yl)bis(1,2-dimethyl-1H-imidazol-5-yl)methanol

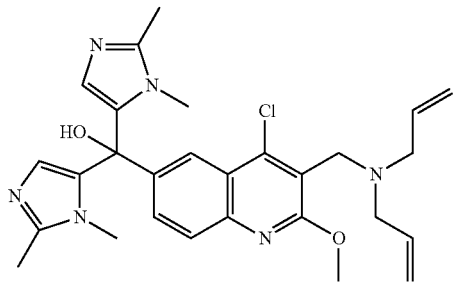 [SMILES: C=CCN(CC=C)Cc1c(OC)nc2ccc(C(O)(c3cnc(C)n3C)c3cnc(C)n3C)cc2c1Cl]

THF (50 mL) was added to 5-bromo-1,2-dimethyl-1H-imidazole (1.37 g, 7.87 mmol), and the mixture was stirred at room temperature for 10 minutes (a clear solution). The mixture was immersed in a dry-ice bath at −78° C. for 3 minutes and then n-BuLi (3 mL, 7.5 mmol, 2.5 M in THF) was added dropwise slowly. After 20 minutes of stirring, a clear solution of methyl 4-chloro-3-((diallylamino)methyl)-2-methoxyquinoline-6-carboxylate (Intermediate 74: step a, 1.2 g, 3.3 mmol) in THF (25 mL+7 mL to quantitate transfer) was added and the mixture stirred for 2 hours, allowing the reaction to warm up slowly to room temperature. The reaction mixture was quenched with saturated aqueous ammonium chloride solution, and the aqueous layer was extracted with ethyl acetate, washed with brine, dried (MgSO$_4$) and concentrated to dryness. The crude product was purified by FCC (0 to 15% MeOH in DCM) to provide the title compound.

Intermediate 75

6-Bromo-4-chloro-2-methoxy-3-((2-(trifluoromethyl)-5,6-dihydro-[1,2,4]triazolo[1,5-a]pyrazin-7(8H)-yl)methyl)quinoline

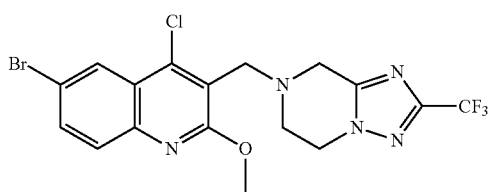 [SMILES: COc1nc2ccc(Br)cc2c(Cl)c1CN1CCn2nc(C(F)(F)F)nc2C1]

The title compound was prepared analogously to the method described for Intermediate 40 using 2-(trifluoromethyl)-5,6,7,8-tetrahydro-[1,2,4]triazolo[1,5-a]pyrazine in place of 4-(trifluoromethyl)piperidine hydrochloride.

Intermediate 76

6-Bromo-4-chloro-2-methoxy-3-((3-(trifluoromethyl)-5,6-dihydro-[1,2,4]triazolo[4,3-a]pyrazin-7(8H)-yl)methyl)quinoline

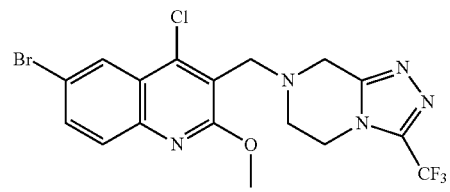 [SMILES: COc1nc2ccc(Br)cc2c(Cl)c1CN1CCn2c(nnc2C(F)(F)F)C1]

The title compound was prepared analogously to the method described for Intermediate 40 using 3-(trifluoromethyl)-5,6,7,8-tetrahydro-[1,2,4]triazolo[4,3-a]pyrazine in place of 4-(trifluoromethyl)piperidine hydrochloride.

Intermediate 77

N-((6-Bromo-4-chloro-2-methoxyquinolin-3-yl)methyl)-2,2,2-trifluoro-N-methylethanamine

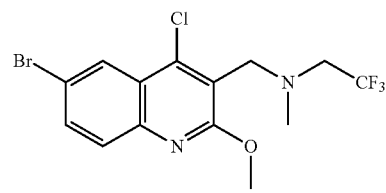 [SMILES: COc1nc2ccc(Br)cc2c(Cl)c1CN(C)CC(F)(F)F]

The title compound was prepared analogously to the method described for Intermediate 40 using 2,2,2-trifluoro-N-methylethanamine in place of 4-(trifluoromethyl)piperidine hydrochloride.

Intermediate 78: Step a

4-Cyano-N-methoxy-N-methylbenzamide

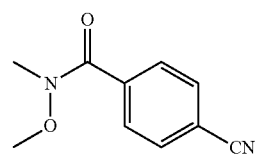

A mixture of 4-cyanobenzoic acid (164.3 g, 1.094 mol) and N,O-dimethylhydroxylamine hydrochloride (106.8 g, 1.094 mol) in 2-methyltetrahydrofuran (1.61 L) was treated with propylphosphonic anhydride (977 mL, 50% in ethyl acetate, 1.642 mol) and then cooled to 15° C. Diisopropylethylamine (377 mL, 2.189 mol) was added and an exotherm to 40° C. was observed. The reaction mixture was stirred at 45° C. for 45 minutes and then cooled to room temperature. Aqueous sodium carbonate (323 g in 3 L total volume) was then added and an exotherm to 32° C. and some off-gassing were observed. Solids were removed by filtration, and the layers were separated. The aqueous layer was washed with ethyl acetate (1 L). The combined organic layers were dried over magnesium sulfate, filtered, and concentrated under reduced pressure to a dark tan solid. The residue was taken up in MTBE (650 mL) at 55° C. and then cooled with stirring. The resulting suspension was cooled to 0° C., and the solids were isolated through filtration and washed with cold 3/1 heptane/MTBE (400 mL), affording the title compound.

Intermediate 78: Step b 4-(4-Chloro-2-methoxy-3-((4-(trifluoromethyl)piperidin-1-yl)methyl)quinoline-6-carbonyl)benzonitrile

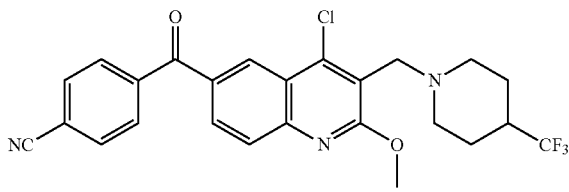 [SMILES: COc1nc2ccc(C(=O)c3ccc(C#N)cc3)cc2c(Cl)c1CN1CCC(C(F)(F)F)CC1]

A solution of n-butyllithium (2.5 M in hexanes, 0.8 mL, 2.0 mmol) was added dropwise by syringe to a solution of 6-bromo-4-chloro-2-methoxy-3-((4-(trifluoromethyl)piperidin-1-yl)methyl)quinoline (0.964 g, 2.20 mmol, Intermediate 40) in dry deoxygenated THF (14 mL) at −78° C. After 2 minutes, a solution of 4-cyano-N-methoxy-N-methylbenzamide (0.13 g, 0.50 mmol, Intermediate 78: step a) in dry THF (4 mL) was added dropwise by syringe. An additional 2 mL of THF was used to complete the quantitative addition. After 2 hours of stirring at −78° C., the reaction was quenched with saturated aqueous ammonium chloride solution and the mixture was partitioned between water and EtOAc. The layers were separated and the aqueous phase was further extracted with EtOAc and washed with saturated aqueous NaCl solution. The organic phase was dried (MgSO₄), filtered, and concentrated to dryness. The crude product was purified by flash column chromatography to provide the title compound.

Intermediate 79: Step a

Methyl 4-chloro-3-(hydroxymethyl)-2-methoxyquinoline-6-carboxylate

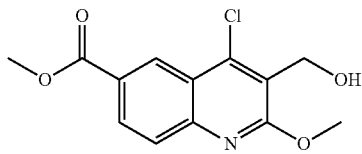

To a solution of methyl 3-(bromomethyl)-4-chloro-2-methoxyquinoline-6-carboxylate (16 g, 46.6 mmol, Intermediate 73: step c) in 1,4-dioxane/H₂O (100 mL/100 mL) in a 500 mL round bottomed flask was added Ag₂SO₄ (14.4 g, 46.6 mmol). The reaction mixture was stirred at 110° C. for 3 hours, cooled to room temperature and diluted with brine (150 mL). The resulting mixture was stirred for 10 minutes and then extracted with ethyl acetate (5×150 mL). The combined organic phase was washed with H₂O (3×50 mL) and brine (100 mL), dried over Na₂SO₄ and concentrated to dryness to provide the title compound as a white solid.

Intermediate 79: Step b

Methyl 3-(((tert-butyldimethylsilyl)oxy)methyl)-4-chloro-2-methoxyquinoline-6-carboxylate

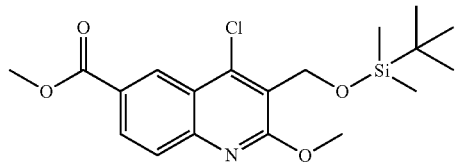 [SMILES: COC(=O)c1ccc2nc(OC)c(CO[Si](C)(C)C(C)(C)C)c(Cl)c2c1]

To a solution of tert-butylchlorodimethylsilane (15 g, 100 mmol) in DMF (120 mL) in a 500 mL round bottomed flask was added imidazole (14 g, 200 mmol). The mixture was stirred at 25° C. for 30 minutes and then a solution of methyl 4-chloro-3-(hydroxymethyl)-2-methoxyquinoline-6-carboxylate (28 g, 100 mmol, Intermediate 79: step a) in DMF (80 mL) was added dropwise. After the reaction mixture was stirred at room temperature for 12 hours, it was poured into H₂O (200 mL) and then extracted with ethyl acetate (5×200 mL). The organic layers were combined and washed with H₂O (50 mL×3) and brine (100 mL), dried over Na₂SO₄ and concentrated to dryness to provide the title compound as a white solid.

Intermediate 79: Step c (3-(((Tert-butyldimethylsilyl)oxy)methyl)-4-chloro-2-methoxyquinolin-6-yl)bis(1,2-dimethyl-1H-imidazol-5-yl)methanol

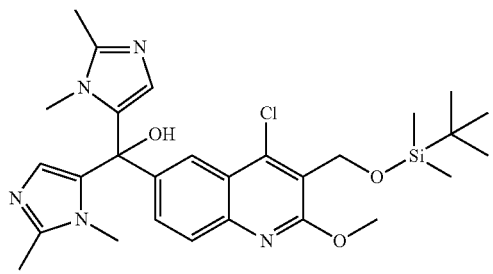 [SMILES: COc1nc2ccc(C(O)(c3cnc(C)n3C)c3cnc(C)n3C)cc2c(Cl)c1CO[Si](C)(C)C(C)(C)C]

n-BuLi (12 mL, 26 mmol) was added dropwise over 10 minutes to a solution 5-bromo-1,2-dimethyl-1H-imidazole (5.22 g, 30 mmol) in anhydrous THF (50 mL) in a 250 mL three-necked round bottomed flask at −70° C. under N₂. After the mixture was stirred at −70° C. under N₂ for 30 minutes, a solution of methyl 3-((tert-butyldimethylsilyloxy)methyl)-4-chloro-2-methoxyquinoline-6-carboxylate (3.95 g, 10 mmol, Intermediate 79: step b) in THF (20 mL) was added dropwise and stirring was continued for 2 hours at −60° C. under N₂. The reaction was quenched by adding NH₄Cl aqueous solution (1 N, 20 mL) and then extracted with ethyl acetate (2×150 mL). The organic layers were combined and washed with H₂O (3×50 mL) and brine (100 mL), dried over Na₂SO₄ and concentrated to dryness to provide the title compound as a yellow solid.

Intermediate 79: Step d (4-Chloro-3-(hydroxymethyl)-2-methoxyquinolin-6-yl)bis(1,2-dimethyl-1H-imidazol-5-yl)methanol

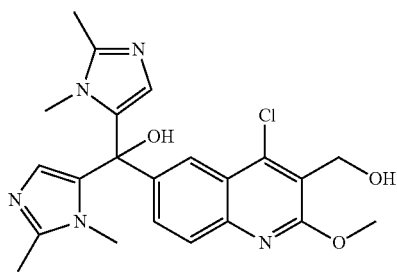 [SMILES: COc1nc2ccc(C(O)(c3cnc(C)n3C)c3cnc(C)n3C)cc2c(Cl)c1CO]

To a solution of (3-(((tert-butyldimethylsilyl)oxy)methyl)-4-chloro-2-methoxyquinolin-6-yl)bis(1,2-dimethyl-1H-imidazol-5-yl)methanol (5.56 g, 1 mmol, Intermediate 79: step c) in methylene chloride (10 mL) in a 100 mL round bottomed flask was added trifluoroacetic acid (20 mL). The reaction mixture was stirred at 25° C. for 12 hours, concentrated to dryness and purified by FCC (silica gel, DCM/MeOH=100/1 to 5/1) to provide the title compound as a white solid.

Intermediate 79: Step e (4-Chloro-3-(chloromethyl)-2-methoxyquinolin-6-yl)bis(1,2-dimethyl-1H-imidazol-5-yl)methanol

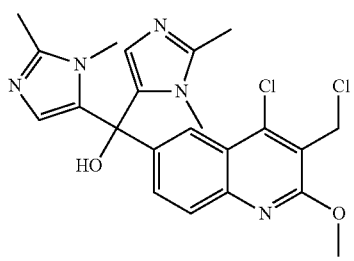 [SMILES: COc1nc2ccc(C(O)(c3cnc(C)n3C)c3cnc(C)n3C)cc2c(Cl)c1CCl]

(4-Chloro-3-(hydroxymethyl)-2-methoxyquinolin-6-yl)bis(1,2-dimethyl-1H-imidazol-5-yl)methanol (1.586 g, 3.69 mmol, Intermediate 79: step d) was dissolved in tetrahydrofuran (18 mL). Thionyl chloride (2.6 mL, 35.8 mmol) was added and the mixture was stirred at ambient temperature for 1.5 hours. The suspension was concentrated to dryness and used without purification.

Intermediate 80: Step a

Ethyl 6-bromo-2-cyclopropyl-4-hydroxyquinoline-3-carboxylate

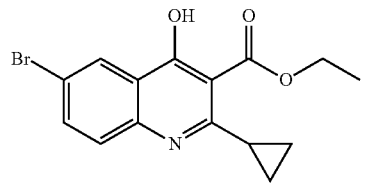 [SMILES: CCOC(=O)c1c(C2CC2)nc2ccc(Br)cc2c1O]

To a 200 mL round bottom flask fitted with an air condenser was added ethyl 3-cyclopropyl-3-oxopropanoate (1.6 g, 10.2 mmol) and DMA (42 mL). Sodium hydride (413 mg, 10.3 mmol) was then added portion wise over 10 minutes. To this mixture was added a solution of 6-bromo-1H-benzo[d][1,3]oxazine-2,3-dione (3 g, 12.4 mmol) in DMA (18 mL). The reaction was then stirred at 120° C. for 2 hours. The reaction was cooled to room temperature followed by removal of most of the solvent under reduced pressure. Then, 200 mL of water was added and the resulting precipitate collected by filtration. The precipitate was washed with water (100 mL). A second crop of precipitate was collected from the filtrate the next day and washed with water (100 mL) to provide the title compound. The crude precipitate was used in the next step without further purification.

Intermediate 80: Step b

Ethyl 6-bromo-4-chloro-2-cyclopropylquinoline-3-carboxylate

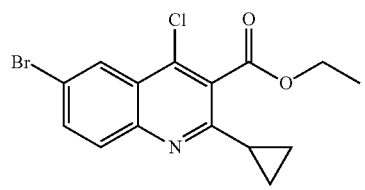 [SMILES: CCOC(=O)c1c(C2CC2)nc2ccc(Br)cc2c1Cl]

In a 100 mL round bottom flask was added ethyl 6-bromo-2-cyclopropyl-4-hydroxyquinoline-3-carboxylate (2.0 g, 5.9 mL, Intermediate 80: step a) and acetonitrile (15 mL). To this solution was added POCl$_3$ (1.7 mL, 18.3 mmol) and the resulting mixture was stirred at 65° C. for 2 hours. The reaction was cooled to room temperature, added dropwise to a mixture of ice (100 mL) and aqueous ammonia (28-30%, 100 mL). The product was then extracted with ethyl acetate (2×100 mL). The combined organic layers were dried (sodium sulfate) and concentrated in vacuo. The crude residue was purified by silica gel chromatography (20% ethyl acetate/hexanes, 120 g column) to afford the title compound.

Intermediate 80: Step c (6-Bromo-4-chloro-2-cyclopropylquinolin-3-yl)methanol

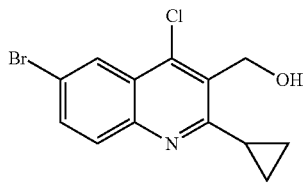 [SMILES: OCc1c(C2CC2)nc2ccc(Br)cc2c1Cl]

In a 100 mL round bottom flask under nitrogen was added ethyl 6-bromo-4-chloro-2-cyclopropylquinoline-3-carboxylate (1.35 g, 3.8 mmol, Intermediate 80: step b), and dichloromethane (15 mL). The solution was cooled to 10° C., and then a 1.0 M solution of DIBAL in DCM (11.4 mL) was added dropwise. The reaction was stirred at 10° C. for 1 hour, and then poured into a 20% solution of aqueous potassium sodium tartrate (150 mL). The mixture was stirred vigorously for 18 hours then filtered through a pad of Celite®. The filtrate was extracted twice with DCM and the combined extracts were washed sequentially with water and brine. The solvent was removed under reduced pressure, residue taken up into ether, filtered and dried to provide the title compound. The crude material was used in the next step without further purification.

Intermediate 80: Step d

6-Bromo-4-chloro-3(chloromethyl)-2-cyclopropylquinoline

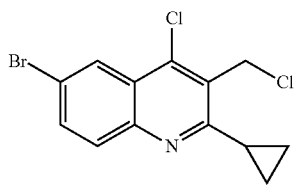 [SMILES: ClCc1c(C2CC2)nc2ccc(Br)cc2c1Cl]

To a 200 mL round bottom flask under nitrogen was added (6-bromo-4-chloro-2-cyclopropylquinolin-3-yl)methanol (1.2 g, 3.8 mmol, Intermediate 80: step c) and toluene (25 mL). The flask was cooled to 0° C. then methanesulfonyl chloride (0.63 mL, 8.1 mmol) and N,N-diisopropylethylamine (1.3 mL, 8.1 mmol) were added dropwise. The reaction was allowed to stir at 0° C. for 30 minutes then the ice bath was removed. The reaction was checked after stirring for 1 hour at room temperature by LC/MS which showed about 50% conversion to the desired chloride product with the remainder being sulfonate intermediate. Then, 1 eq. of solid LiCl (161 mg, 3.80 mmol) was added to the reaction mixture and it was allowed to stir overnight. The reaction was then partitioned between saturated aqueous NaHCO$_3$ (150 mL) and ethyl acetate (150 mL). The aqueous layer was extracted once more with ethyl acetate (100 mL), and then the organic layers were combined and washed with brine. The organic layer was dried (sodium sulfate) and the solvent removed under reduced pressure to provide the title compound. The crude material was used in the next step without additional purification.

Intermediate 80: Step e

6-Bromo-4-chloro-2-cyclopropyl-3-((4-trifluoromethyl)piperidin-1-yl)methyl)quinoline

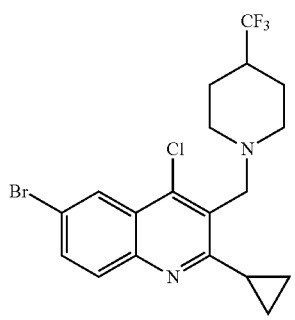 [SMILES: FC(F)(F)C1CCN(Cc2c(C3CC3)nc3ccc(Br)cc3c2Cl)CC1]

To a 200 mL round bottom flask was added 6-bromo-4-chloro-3(chloromethyl)-2-cyclopropylquinoline (1.1 g, 3.3 mmol, Intermediate 80: step d), 4-(trifluoromethyl)piperidine hydrochloride (630 mg, 3.3 mmol), N,N-diisopropylethyl amine (1.7 mL, 9.9 mmol) and DCM (32 mL). The reaction was then stirred at room temperature for 4 hours. LC/MS showed about 60% conversion to product so an additional 0.25 eq. of amine and base were added (157 mg, 0.830 mmol) and the reaction allowed to stir overnight at room temperature. The reaction was poured into saturated aqueous sodium bicarbonate (150 mL) and extracted with DCM (2×100 mL). The combined organic layers were dried (sodium sulfate) and concentrated in vacuo. The crude product was purified by silica gel chromatography eluting with (25% ethyl acetate/hexanes) to afford the title compound.

Intermediate 81

4-(4-Chloro-2-methoxy-3-(2,2,2-trifluoroethyl)quinoline-6-carbonyl)benzonitrile

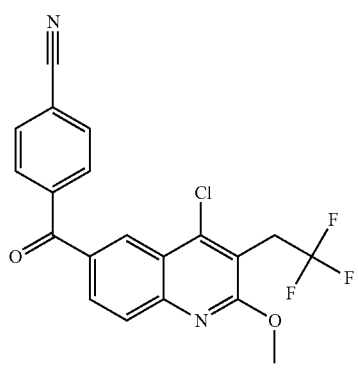 [SMILES: COc1nc2ccc(C(=O)c3ccc(C#N)cc3)cc2c(Cl)c1CC(F)(F)F]

To a 25 mL 2-necked flask containing 6-bromo-4-chloro-2-methoxy-3-(2,2,2-trifluoroethyl)quinoline (200 mg, 0.560 mmol, Intermediate 69: step e) was added THF (12 mL) and the solution was cooled to −78° C. Then, n-BuLi (2.5 M in hexanes, 0.25 mL, 0.63 mmol) was added drop wise which resulted in a dark brown mixture. After 2 minutes, 4-cyano-N-methoxy-N-methylbenzamide (155 mg, 0.79 mmol in 2 mL THF, Intermediate 78: step a) was introduced and the solution became a dark green color. After 10 minutes, the reaction mixture was placed in an ice-water bath and the solution changed to a light yellow color. The mixture was stirred at 0° C. for 20 minutes, then at room temperature for 15 minutes at which time the mixture was quenched with saturated aqueous NH₄Cl solution. The aqueous portion was extracted with EtOAc (3×40 mL) and the combined organics were washed with brine, dried over MgSO₄, filtered and concentrated to give an amber gum. Chromatography on silica gel (50% hexanes-DCM increasing to 10% hexanes-DCM) afforded the title compound as a white solid.

Intermediate 82

4-Chloro-6-(hydroxy(1-methyl-1H-imidazol-5-yl)(2-(trifluoromethyl)pyridin-4-yl)methyl)-2-methoxyquinolin-3-ol

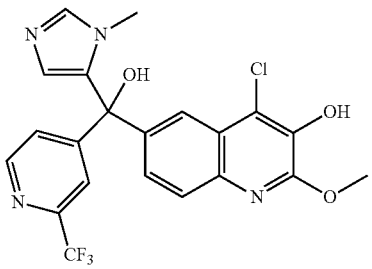 [SMILES: COc1nc2ccc(C(O)(c3ccnc(C(F)(F)F)c3)c3cncn3C)cc2c(Cl)c1O]

The title compound was prepared using (3-(benzyloxy)-4-chloro-2-methoxyquinolin-6-yl)(1-methyl-1H-imidazol-5-yl)(2-(trifluoromethyl)pyridin-4-yl)methanol (Example 228) in place of (3-(benzyloxy)-4-chloro-2-methoxyquinolin-6-yl)(2,6-dimethylpyridin-3-yl)(1-methyl-1H-1,2,3-triazol-5-yl)methanol using the procedure described for Intermediate 31.

Intermediate 83: Step a 4-(3-(Benzyloxy)-4-chloro-2-methoxyquinoline-6-carbonyl)benzonitrile

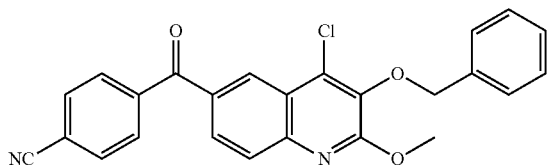 [SMILES: COc1nc2ccc(C(=O)c3ccc(C#N)cc3)cc2c(Cl)c1OCc1ccccc1]

A solution of n-butyllithium in hexanes (1.6 M, 0.91 mL, 1.46 mmol) was added dropwise by syringe to a dry ice-acetone cooled (−78° C.), stirring solution of 3-(benzyloxy)-6-bromo-4-chloro-2-methoxyquinoline (500 mg, 1.32 mmol, Intermediate 29: step d) in tetrahydrofuran (18 mL). After 5 minutes, a solution of 4-cyano-N-methoxy-N-methylbenzamide (351 mg, 1.85 mmol, Intermediate 78: step a) in dry tetrahydrofuran (8 mL) was added dropwise by syringe. The flask was rinsed with THF (2 mL), which was also added to the reaction. After 15 minutes, the flask was removed from the dry-ice-acetone bath and placed into an ice-water bath for 30 minutes. Then, the ice-water bath was removed and the mixture was allowed to stir at room temperature for 15 minutes. Then, saturated NH₄Cl solution was added followed by water (35 mL) and EtOAc (35 mL) and the layers separated. The aqueous was further extracted with EtOAc (2×30 mL). The organic layers were combined, dried (Na₂SO₄), filtered and concentrated to dryness. The residue was purified by FCC (MeOH/CH₂Cl₂) to provide the title compound as a cream-colored amorphous solid.

Intermediate 83: Step b 4-((4-Chloro-3-hydroxy-2-methoxyquinolin-6-yl)(hydroxy)(1-methyl-1H-imidazol-5-yl)methyl)benzonitrile

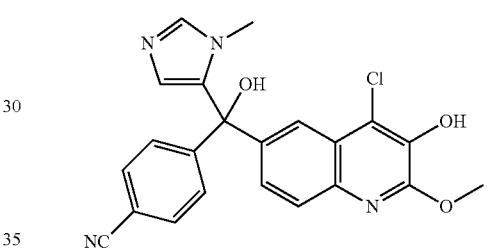

The title compound was prepared using 4-((3-(benzyloxy)-4-chloro-2-methoxyquinolin-6-yl)(hydroxy)(1-methyl-1H-imidazol-5-yl)methyl)benzonitrile (Example 229) in place of (3-(benzyloxy)-4-chloro-2-methoxyquinolin-6-yl)(2,6-dimethylpyridin-3-yl)(1-methyl-1H-1,2,3-triazol-5-yl)methanol using the procedure described for Intermediate 31.

Intermediate 84

4-Chloro-6-((4-chlorophenyl)(hydroxy)(1-methyl-1H-imidazol-5-yl)methyl)-2-methoxyquinolin-3-ol

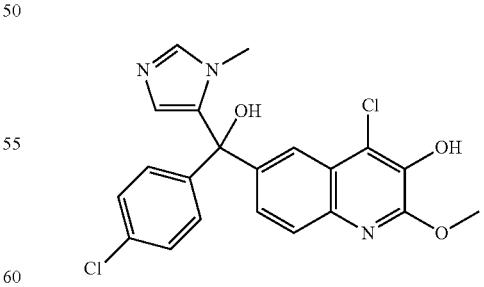

The title compound was prepared using (3-(benzyloxy)-4-chloro-2-methoxyquinolin-6-yl)(4-chlorophenyl)(1-methyl-1H-imidazol-5-yl)methanol (Example 230) in place of (3-(benzyloxy)-4-chloro-2-methoxyquinolin-6-yl)(2,6-dimethylpyridin-3-yl)(1-methyl-1H-1,2,3-triazol-5-yl)methanol using the procedure described for Intermediate 31.

Intermediate 85 tert-Butyl 3-((4-chloro-2-ethyl-3-hydroxyquinolin-6-yl)(hydroxy)(1-methyl-1H-1,2,3-triazol-5-yl)methyl)azetidine-1-carboxylate

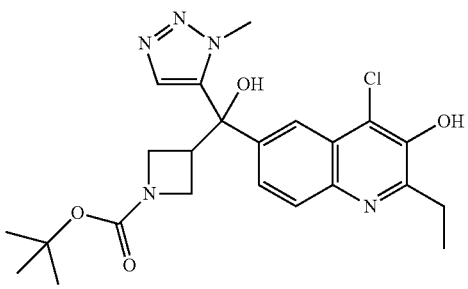 [SMILES: CCc1nc2ccc(C(O)(c3cnnn3C)C3CN(C(=O)OC(C)(C)C)C3)cc2c(Cl)c1O]

To an oven-dried round-bottom flask was added tert-butyl 3-((3-(benzyloxy)-2,4-dichloroquinolin-6-yl)(hydroxy)(1-methyl-1H-1,2,3-triazol-5-yl)methyl)azetidine-1-carboxylate (1.2 g, 2.09 mmol, Example 232), PdCl$_2$(dppf) (153 mg, 0.21 mmol) and THF (21 mL). The mixture was sparged with nitrogen for 20 minutes then Et$_2$Zn (15 wt % in toluene, 2.26 mL, 2.51 mmol) was added. The resulting mixture was stirred at 65° C. for 50 minutes and additional Et$_2$Zn (15 wt % in toluene, 2.26 mL, 2.51 mmol) was added and stirring was continued at 65° C. for 50 minutes. The starting material still remained when monitored by LCMS, therefore additional Et$_2$Zn (15 wt % in toluene, 2.26 mL, 2.51 mmol) was added and stirring was continued at 65° C. for 60 minutes. The mixture was allowed to cool to room temperature and saturated aqueous NH$_4$Cl (50 mL) was added slowly to quench the reaction. The aqueous layer was then extracted with EtOAc (3×40 mL). The organic layers were combined, dried (Na$_2$SO$_4$), filtered and concentrated to dryness. The residue was purified by reverse-phase HPLC (acetonitrile/water+NH$_4$OH) to provide the title compound as a light yellow amorphous solid.

Intermediate 86: Step a

6-Iodo-3-(3,3,3-trifluoropropyl)quinoline-2,4-diol

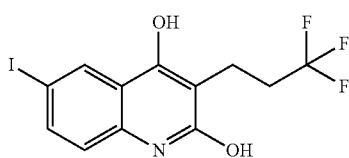 [SMILES: Oc1nc2ccc(I)cc2c(O)c1CCC(F)(F)F]

6-Iodoquinoline-2,4-diol (8.0 g, 28 mmol), 3,3,3-trifluoropropanal (7.1 g, 6 mmol) and diethyl 1,4-dihydro-2,6-dimethy-3,5 pyridinedicarboxylate (7.06 g, 27.9 mmol) were combined in the reaction vessel under N$_2$ followed by the addition of pyridine (186 mL, 27.9 mmol). The contents were then heated to 60° C. and maintained at that temperature for 2 days. The reaction was cooled to room temperature and the solvent was removed under reduced pressure. The contents were taken up into EtOAc then extracted with 10% aqueous HCl then a saturated, aqueous sodium chloride solution. The organic phase was then separated, dried over magnesium sulfate, filtered and concentrated under reduced pressure to afford the title compound.

Intermediate 86: Step b 2,4-Dichloro-6-iodo-3-(3,3,3-trifluoropropyl)quinoline

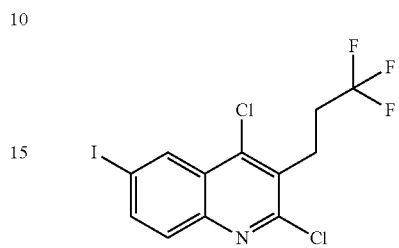

6-Iodo-3-(3,3,3-trifluoropropyl)quinoline-2,4-diol (5.0 g, 13 mmol, Intermediate 86: step a), acetonitrile (100 mL) and phosphorous oxychloride (3.7 mL, 39 mmol) were combined in a reaction vessel under N$_2$ and heated to 80° C. for two hours. Additional phosphorous oxychloride (3.7 mL, 39 mmol) was then added and the contents were re-heated to 80° C. for 4 hours, then the contents were allowed to gradually cool to room temperature and stir overnight. Additional phosphorous oxychloride (3.7 mL, 39 mmol) was then added and the contents were re-heated to 80° C. for approximately 6 hours. The contents were cooled to room temperature, then solvent and excess phosphorous oxychloride were removed under reduced pressure. The crude material was then taken up into chloroform and any remaining phosphorous oxychloride was quenched by the addition of saturated, aqueous ammonium chloride, deionized water and methanol. The contents were transferred to a separatory funnel with chloroform and the organic phase was separated and the aqueous was extracted twice with chloroform. The combined organic layers were dried over magnesium sulfate, filtered and concentrated under reduced pressure. The crude product was purified by flash column chromatography (silica gel, 0-10% hexanes/ethyl acetate) to provide the title compound.

Intermediate 86: Step c

4-Chloro-6-iodo-2-methoxy-3-(3,3,3-trifluoropropyl)quinoline

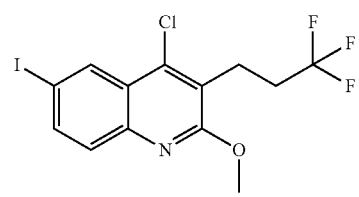 [SMILES: COc1nc2ccc(I)cc2c(Cl)c1CCC(F)(F)F]

To a reaction vessel under nitrogen was added 2,4-dichloro-6-iodo-3-(3,3,3-trifluoropropyl)quinoline (5.01 g, 11.9 mmol, Intermediate 86: step b), toluene (600 mL) and MeOH (60 mL, 11.9 mmol) followed by NaOMe (1.93 g, 35.8 mmol). The contents were then heated to 65° C. and stirred at that temperature overnight, then cooled to room temperature. The reaction contents were then transferred to a separatory funnel with EtOAc and NH₄Cl (saturated, aqueous solution). The organic phase was separated then the aqueous was extracted twice with EtOAc. The combined organics were dried over MgSO₄, filtered and concentrated under reduced pressure. The crude product was purified by flash column chromatography (silica gel, 0-50% hexanes/DCM) to afford the title compound.

Intermediate 87: Step a (3-(Benzyloxy)-4-chloro-2-methoxyquinolin-6-yl)(1,3,5-trimethyl-1H-pyrazol-4-yl)methanol

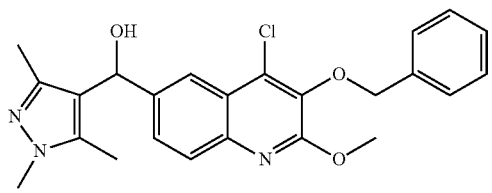 [SMILES: COc1nc2ccc(C(O)c3c(C)nn(C)c3C)cc2c(Cl)c1OCc1ccccc1]

n-BuLi (2.1 mL, 2.5 M in hexanes, 5.2 mmol) was added drop-wise to a −50° C. solution consisting of 3-(benzyloxy)-6-bromo-4-chloro-2-methoxyquinoline (2.0 g, 5.3 mmol, Intermediate 29: step d) and THF (50 mL). The resultant reaction mixture was stirred at −50° C. for 20 minutes and then treated with a solution of 1,3,5-trimethyl-1H-pyrazole-4-carbaldehyde (730 mg, 5.28 mmol) and THF (15 mL) at −50° C. The resulting mixture was stirred at room temperature for 20 minutes before quenching with saturated aqueous NH₄Cl (20 mL) and extracting with dichloromethane: methanol (5:1, 50 mL×10). The combined organic extracts were dried over Na₂SO₄, filtered and concentrated to dryness under reduced pressure to give the crude product, which was purified by FCC (silica gel, eluent: petroleum ether: ethyl acetate=5:1 to 1:1) to afford the title compound.

Intermediate 87: Step b (3-(Benzyloxy)-4-chloro-2-methoxyquinolin-6-yl)(1,3,5-trimethyl-1H-pyrazol-4-yl)methanone

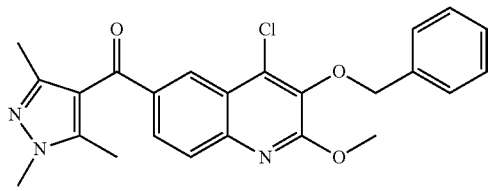 [SMILES: COc1nc2ccc(C(=O)c3c(C)nn(C)c3C)cc2c(Cl)c1OCc1ccccc1]

(3-(Benzyloxy)-4-chloro-2-methoxyquinolin-6-yl)(1,3,5-trimethyl-1H-pyrazol-4-yl)methanol (1.5 g, 3.4 mmol, Intermediate 87: step a), MnO₂ (3.0 g, 34 mmol) and dichloromethane (50 mL) were added to a 100 mL round-bottomed flask. The reaction mixture was stirred at room temperature for 16 hours. The suspension was filtered through a pad of Celite® and the pad was washed with dichloromethane (100 mL). The filtrate was concentrated to dryness under reduced pressure to give the crude product, which was purified by FCC (silica gel, eluent: petroleum ether:ethyl acetate=5:1 to 1:1) to afford the title compound.

Intermediate 88

4-Chloro-6-((1,2-dimethyl-1H-imidazol-5-yl)(hydroxy)(1,3,5-trimethyl-1H-pyrazol-4-yl)methyl)-2-methoxyquinolin-3-ol

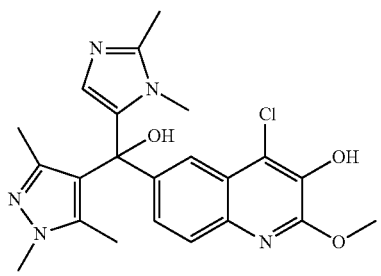 [SMILES: COc1nc2ccc(C(O)(c3c(C)nn(C)c3C)c3cnc(C)n3C)cc2c(Cl)c1O]

(3-(Benzyloxy)-4-chloro-2-methoxyquinolin-6-yl)(1,2-dimethyl-1H-imidazol-5-yl)(1,3,5-trimethyl-1H-pyrazol-4-yl)methanol (410 mg, 0.771 mmol, Example 246), methanol (20 mL) and wet Pd/C (40 mg, 10 wt. %) were added to a 250 mL round-bottomed flask. The resultant reaction mixture was stirred under H₂ (1 atm, balloon) at room temperature for 0.5 hours. The suspension was filtered through a pad of Celite® and the pad was washed with methanol (50 mL). The filtrate was concentrated to dryness under reduced pressure to afford the title compound.

Intermediate 89: Step a

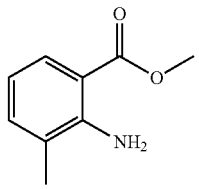

Methyl 2-amino-3-methylbenzoate Methyl 3-methyl-2-nitrobenzoate (45.0 g, 230 mmol), methanol (1 L) and Raney Ni (5 g) were added to a 2 L round-bottomed flask. The resultant reaction mixture was stirred under H₂ (1 atm, balloon) at room temperature for 16 hours. The suspension was filtered through a pad of Celite® and the pad was washed with methanol (500 mL). The filtrate was concentrated to dryness under reduced pressure to afford the title compound.

Intermediate 89: Step b

Methyl 2-amino-5-bromo-3-methylbenzoate

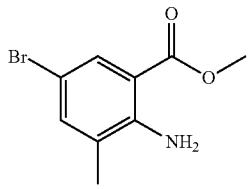

N-Bromosuccinimide (38.5 g, 216 mmol) was added to a mixture consisting of methyl 2-amino-3-methylbenzoate (32.4 g, 196 mmol, Intermediate 89: step a) and dichloromethane (300 mL). The resultant reaction mixture was stirred at room temperature for 16 hours before it was poured into water (200 mL) and the aqueous phase was extracted with dichloromethane (200 mL×3). The combined organic extracts were dried over Na$_2$SO$_4$, filtered and concentrated to dryness under reduced pressure to afford the title compound.

Intermediate 89: Step c

Methyl 2-(2-(benzyloxy)acetamido)-5-bromo-3-methylbenzoate

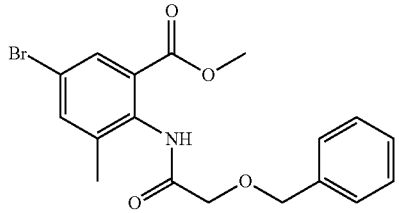 [SMILES: COC(=O)c1cc(Br)cc(C)c1NC(=O)COCc1ccccc1]

Et$_3$N (25.5 mL, 183 mmol) was added dropwise to a 0° C. (ice/water bath) solution consisting of methyl 2-amino-5-bromo-3-methylbenzoate (15 g, 61 mmol, Intermediate 89: step b), 2-(benzyloxy)acetyl chloride (15 mL, 95 mmol) and dichloromethane (200 mL). The resulting mixture was stirred at room temperature for 16 hours before pouring it into saturated aqueous NH$_4$Cl (200 mL). The aqueous phase was extracted with dichloromethane (200 mL×2). The combined organic extracts were dried over Na$_2$SO$_4$, filtered and concentrated to dryness under reduced pressure to give the crude product, which was purified by FCC (eluent: petroleum ether:ethyl acetate=5:1) to afford the title compound.

Intermediate 89: Step d 3-(Benzyloxy)-6-bromo-4-hydroxy-8-methylquinolin-2(1H)-one

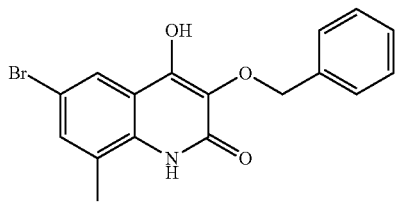 [SMILES: Cc1cc(Br)cc2c(O)c(OCc3ccccc3)c(=O)[nH]c12]

KHMDS (176 mL, 1 M in THF, 176 mmol) was added dropwise to a 50° C. solution consisting of methyl 2-(2-(benzyloxy)acetamido)-5-bromo-3-methylbenzoate (23 g, 59 mmol, Intermediate 89: step c) and toluene (350 mL). The resultant reaction mixture was stirred at 50° C. for 0.5 hours before it was cooled to room temperature, poured into aqueous 1 N HCl (300 mL) and the aqueous phase was extracted with ethyl acetate (500 mL×3). The combined organic extracts were dried over Na$_2$SO$_4$, filtered and concentrated to dryness under reduced pressure to afford the title compound.

Intermediate 89: Step e 3-(Benzyloxy)-6-Bromo-2,4-Dichloro-8-Methylquinoline

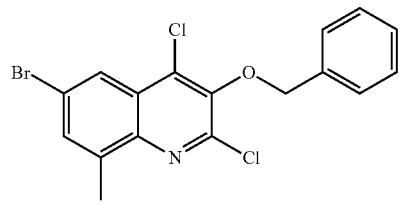 [SMILES: Cc1cc(Br)cc2c(Cl)c(OCc3ccccc3)c(Cl)nc12]

POCl$_3$ (25.5 g, 166 mmol) and 2,6-lutidine (9.7 mL, 83 mmol) was added dropwise to a solution consisting of 3-(benzyloxy)-6-bromo-4-hydroxy-8-methylquinolin-2(1H)-one (20.0 g, 55.5 mmol, Intermediate 89: step d) and ACN (350 mL). The resultant mixture was stirred at 100° C. for 8 hours before it was cooled to room temperature, poured into water (300 mL), and the aqueous phase was extracted with dichloromethane (600 mL×2). The combined organic extracts were dried over Na$_2$SO$_4$, filtered and concentrated to dryness under reduced pressure to give the crude title product, which was purified by FCC (eluent: petroleum ether:ethyl acetate=20:1) to afford the title compound.

Intermediate 89: Step f 3-(Benzyloxy)-6-bromo-4-chloro-2-methoxy-8-methylquinoline

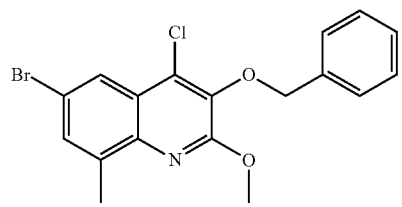 [SMILES: COc1nc2c(C)cc(Br)cc2c(Cl)c1OCc1ccccc1]

3-(Benzyloxy)-6-bromo-2,4-dichloro-8-methylquinoline (4.0 g, 10 mmol, Intermediate 89: step e), sodium methoxide (5.40 g, 100 mmol) and toluene (100 mL) were added to a 250 mL round-bottomed flask. The reaction mixture was stirred at 70° C. for 16 hours. After cooling to room temperature, the mixture was diluted with dichloromethane (150 mL), filtered through a pad of Celite® and the pad was washed with THF (30 mL×3). The filtrate was concentrated to dryness under reduced pressure to give the crude title product, which was purified by FCC (silica gel, eluent: petroleum ether:ethyl acetate=5:1 to 1:1) to afford the title compound.

Intermediate 89: Step g (3-(Benzyloxy)-4-chloro-2-methoxy-8-methylquinolin-6-yl)((1,3,5-trimethyl-1H-pyrazol-4-yl)methanol

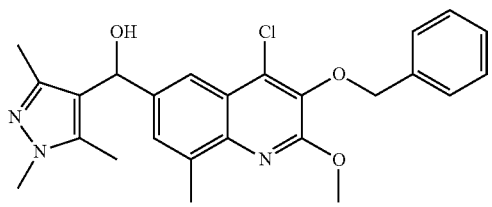 [SMILES: COc1nc2c(C)cc(C(O)c3c(C)nn(C)c3C)cc2c(Cl)c1OCc1ccccc1]

n-BuLi (1.02 mL, 2.5 M in hexane, 2.55 mmol) was added drop-wise to a −70° C. solution consisting of 3-(benzyloxy)-6-bromo-4-chloro-2-methoxy-8-methylquinoline (1.0 g, 2.5 mmol, Intermediate 89: step f) and THF (50 mL). The resultant reaction mixture was stirred at −70° C. for 20 minutes and then treated with a solution of 1,3,5-trimethyl-1H-pyrazole-4-carbaldehyde (352 mg, 2.55 mmol) and THF (15 mL) at −70° C. The resulting mixture was stirred at room temperature for 20 minutes before quenching with saturated aqueous NH₄Cl (20 mL) and extracting with dichloromethane:methanol (5:1, 50 mL×10). The combined organic extracts were dried over Na₂SO₄, filtered and concentrated to dryness under reduced pressure to give the crude product, which was purified by FCC (silica gel, eluent: petroleum ether:ethyl acetate=5:1 to 1:1) to afford the title compound.

Intermediate 89: Step h (3-(Benzyloxy)-4-chloro-2-methoxy-8-methylquinolin-6-yl)((1,3,5-trimethyl-1H-pyrazol-4-yl)methanone

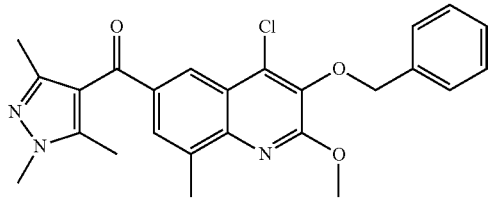 [SMILES: COc1nc2c(C)cc(C(=O)c3c(C)nn(C)c3C)cc2c(Cl)c1OCc1ccccc1]

(3-(Benzyloxy)-4-chloro-2-methoxy-8-methylquinolin-6-yl)(1,3,5-trimethyl-1H-pyrazol-4-yl)methanol (2.0 g, 4.4 mmol, Intermediate 89: step g), MnO₂ (3.8 g, 44 mmol) and dichloromethane (100 mL) were added to a 250 mL round-bottomed flask. The reaction mixture was stirred at room temperature for 16 hours. The suspension was filtered through a pad of Celite® and the pad was washed with dichloromethane (100 mL). The filtrate was concentrated to dryness under reduced pressure to afford the title compound.

Intermediate 90

4-Chloro-6-((1,2-dimethyl-1H-imidazol-5-yl)(hydroxy)(1,3,5-trimethyl-1H-pyrazol-4-yl)methyl)-2-methoxy-8-methylquinolin-3-ol

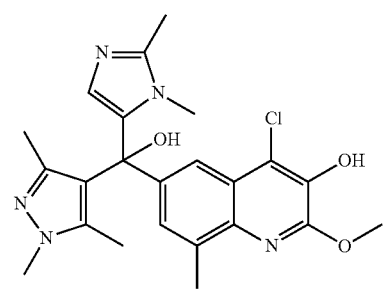 [SMILES: COc1nc2c(C)cc(C(O)(c3c(C)nn(C)c3C)c3cnc(C)n3C)cc2c(Cl)c1O]

(3-(Benzyloxy)-4-chloro-2-methoxy-8-methylquinolin-6-yl)(1,2-dimethyl-1H-imidazol-5-yl)(1,3,5-trimethyl-1H-pyrazol-4-yl)methanol (600 mg, 1.10 mmol, Example 247), MeOH (50 mL) and wet Pd/C (60 mg, 10 wt. %) were added to a 100 mL round-bottomed flask. The resultant reaction mixture was stirred under H₂ (1 atm, balloon) at room temperature for 0.5 hours. The suspension was filtered through a pad of Celite® and the pad was washed with methanol (50 mL). The filtrate was concentrated to dryness under reduced pressure to afford the title product.

Example 1a: (4-Chloro-3-((4,4-difluorocyclohexyl)methyl)-2-methoxyquinolin-6-yl)(2,6-dimethylpyridin-3-yl)(1-methyl-1H-1,2,3-triazol-5-yl)methanol

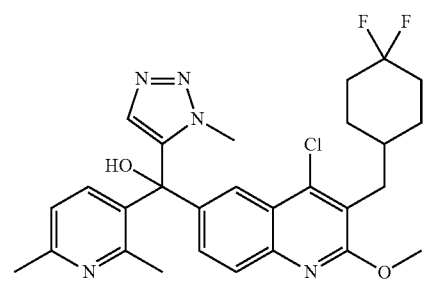

A solution of 6-bromo-4-chloro-3-((4,4-difluorocyclohexyl)methyl)-2-methoxyquinoline (1.27 g, 3.14 mmol, Intermediate 56: step c) in THF (40 mL) was purged with N₂ for 10 minutes and cooled to −78° C. To the solution was added n-BuLi (1.6 M in hexanes, 2.1 mL, 3.4 mmol) dropwise. After stirring for 10 minutes at −78° C., a solution of (2,6-dimethylpyridin-3-yl)(1-methyl-1H-1,2,3-triazol-5-yl)methanone (645 mg, 2.98 mmol, Intermediate 11: step b) in THF (5 mL) was added followed by 5 mL of THF all by cannula. The cooling bath was removed, and the reaction mixture was stirred at −78° C. to room temperature for 1 hour. Saturated NH₄Cl (aqueous) was added and the organic layer was separated. The aqueous layer was extracted with dichloromethane. The combined organic phases were dried (Na₂SO₄), filtered, and concentrated to afford an oil. Some solid precipitated after standing at room temperature for several hours. A small amount of DCM was added, the white solid was filtered, washed with Et₂O, and dried under vacuum overnight to provide the title compound. The filtrate was concentrated and purified by flash column chromatography (silica gel, 30-100% EtOAc/heptane) to give more of the racemic product. $^1$H NMR (400 MHz, CDCl$_3$) δ ppm 8.06 (d, J=2.02 Hz, 1H), 7.81 (d, J=8.59 Hz, 1H), 7.36 (dd, J=2.02, 8.59 Hz, 1H), 6.94 (d, J=9.09 Hz, 3H), 4.10 (s, 3H), 3.94 (s, 3H), 2.89 (d, J=7.07 Hz, 2H), 2.55 (s, 3H), 2.38 (s, 3H), 2.02-2.13 (m, 2H), 1.78-1.90 (m, 1H), 1.68-1.77 (m, 3H), 1.57-1.68 (m, 1H), 1.46-1.60 (m, 2H); MS m/e 542.1 [M+H]$^+$.

Example 1a was purified by chiral HPLC (Chiralcel OD, MeOH) to give 2 enantiomers. Example 1b: (first enantiomer to elute off chiral column)$^1$H NMR (400 MHz, DMSO-d$_6$) δ ppm 8.09 (d, J=2.02 Hz, 1H), 7.83 (d, J=8.59 Hz, 1H), 7.42 (dd, J=2.27, 8.84 Hz, 1H), 7.39 (s, 1H), 7.06 (d, J=8.08 Hz, 1H), 6.93 (d, J=8.08 Hz, 1H), 6.90 (s, 1H), 4.04 (s, 3H), 3.84 (s, 3H), 2.85 (d, J=7.07 Hz, 2H), 2.43 (s, 3H), 2.22 (s, 3H), 1.91-2.05 (m, 2H), 1.61-1.91 (m, 5H), 1.30-1.43 (m, 2H); MS m/e 542.3 [M+H]$^+$ and Example 1c: (second enantiomer to elute off chiral column, further purified by flash column chromatography (silica gel, 50-60% Et$_2$O-DCM)). $^1$H NMR (400 MHz, DMSO-d$_6$) δ ppm 8.09 (s, 1H), 7.83 (d, J=8.59 Hz, 1H), 7.42 (d, J=9.09 Hz, 1H), 7.39 (s, 1H), 7.06 (d, J=8.08 Hz, 1H), 6.93 (d, J=8.08 Hz, 1H), 6.89 (s, 1H), 4.04 (s, 3H), 3.84 (s, 3H), 2.85 (d, J=7.07 Hz, 2H), 2.43 (s, 3H), 2.22 (s, 3H), 1.91-2.05 (m, 2H), 1.60-1.91 (m, 5H), 1.28-1.45 (m, 2H); MS m/e 542.3 [M+H]$^+$.

Example 2a: 4-((4-Chloro-6-((2,6-dimethylpyridin-3-yl)(hydroxy)(1-methyl-1H-1,2,3-triazol-5-yl)methyl)-2-methoxyquinolin-3-yl)methyl)tetrahydro-2H-thiopyran 1,1-dioxide

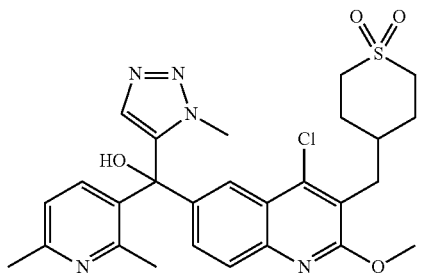 [SMILES: COc1nc2ccc(C(O)(c3ccc(C)nc3C)c3cnnn3C)cc2c(Cl)c1CC1CCS(=O)(=O)CC1]

A mixture of (4-chloro-2-methoxy-3-((tetrahydro-2H-thiopyran-4-yl)methyl)quinolin-6-yl)(2,6-dimethylpyridin-3-yl)(1-methyl-1H-1,2,3-triazol-5-yl)methanol (726 mg, 1.39 mmol, Example 163), 3-chloroperbenzoic acid (~77%, 1.24 g, 5.54 mmol) and DCM (70 mL) was stirred at room temperature for 1 hour. LCMS showed the major peak as MS m/e 572 [M+H]$^+$.

To the mixture was added tribromophosphine (1.0 M in DCM, 5.0 mL, 5.0 mmol) dropwise, and a white suspension formed at the end of the addition. DMF (10 mL) was then added and the suspension dissolved. After stirring for 1 h, 1 M K$_2$CO$_3$ (aqueous) was added, the organic layer was separated and the aqueous layer was extracted with DCM. The combined organic phases were washed with 1 M K$_2$CO$_3$ (aqueous), and the aqueous layer was back extracted with DCM. The organic phases were combined, dried (Na$_2$SO$_4$), filtered, and concentrated. The residue was purified by flash column chromatography (silica gel, 30-100% EtOAc in heptanes, 10% MeOH in DCM) to provide the title compound. MS m/e 556.0 [M+H]$^+$.

Example 2a was purified by chiral HPLC (Chiralcel OD, MeOH) to give 2 enantiomers. The enantiomers were then further purified on plug silica gel columns (0-4% MeOH-DCM). Example 2b: (first enantiomer to elute off chiral column)$^1$H NMR (400 MHz, DMSO-d$_6$) δ ppm 8.10 (s, 1H), 7.83 (d, J=8.80 Hz, 1H), 7.37-7.48 (m, 2H), 7.06 (d, J=7.83 Hz, 1H), 6.92 (d, J=8.07 Hz, 1H), 6.89 (s, 1H), 4.05 (s, 3H), 3.84 (s, 3H), 3.04-3.15 (m, 2H), 2.94-3.04 (m, 2H), 2.87 (d, J=7.09 Hz, 2H), 2.43 (s, 3H), 2.22 (s, 3H), 1.99-2.14 (m, 1H), 1.86-1.98 (m, 2H), 1.72-1.86 (m, 2H); MS m/e 556.2 [M+H]$^+$ and Example 2c: (second enantiomer to elute off chiral column)$^1$H NMR (400 MHz, DMSO-d$_6$) δ ppm 8.10 (s, 1H), 7.84 (d, J=8.56 Hz, 1H), 7.38-7.47 (m, 2H), 7.06 (d, J=8.07 Hz, 1H), 6.92 (d, J=8.07 Hz, 1H), 6.89 (s, 1H), 4.05 (s, 3H), 3.84 (s, 3H), 3.04-3.15 (m, 2H), 2.94-3.04 (m, 2H), 2.87 (d, J=7.09 Hz, 2H), 2.43 (s, 3H), 2.22 (s, 3H), 2.00-2.14 (m, 1H), 1.86-1.98 (m, 2H), 1.72-1.85 (m, 2H); MS m/e 556.2 [M+H]$^+$.

Example 3: (4-Chlorophenyl)(2,4-dichloro-3-(morpholinomethyl)quinolin-6-yl)(1-methyl-1H-imidazol-5-yl)methanol.TFA

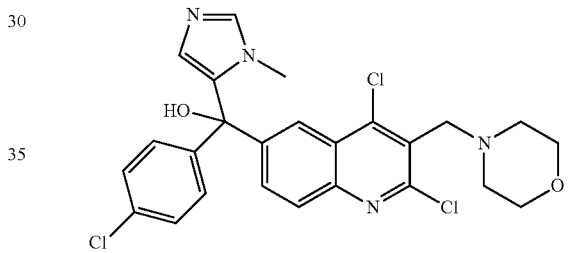

Into a 100-mL round-bottom flask purged and maintained with an inert atmosphere of nitrogen, was placed a solution of 6-bromo-2,4-dichloro-3-(morpholin-4-ylmethyl)quinoline (180 mg, 0.48 mmol, 100%, Intermediate 1: step e) in tetrahydrofuran (10 mL). Then n-BuLi (0.23 mL, 0.58 mmol, 2.5 M in hexanes) was added at −78° C. The resulting mixture was stirred for 10 minutes at −78° C., and then 5-[(4-chlorophenyl)carbonyl]-1-methyl-1H-imidazole (116 mg, 0.53 mmol, Intermediate 22: step b) was added to this solution. The resulting mixture was allowed to react, with stirring, for an additional 8 hours at room temperature. The reaction was then quenched by the addition of 10 mL of water. The resulting solution was extracted with 3×50 mL of ethyl acetate. The combined organic layer was dried over anhydrous sodium sulfate, filtered and concentrated under vacuum. The crude product was purified by Prep-HPLC with the following conditions (1#-Waters 2767-1): Column, SunFire Prep C18, 5 μm, 19×150 mm; mobile phase, water in 0.05% TFA and CH$_3$CN (46% CH$_3$CN up to 90% in 10 minutes, up to 100% in 2 minutes, down to 46% in 2 minutes) to afford the title compound trifluoroacetic acid salt as a white solid. $^1$H NMR (300 MHz, CD$_3$OD) δ ppm 9.50 (s, 1H), 8.86 (s, 1H), 8.60-8.57 (d, J=8.7 Hz, 1H), 8.48-8.44 (m, 1H), 7.98-7.91 (m, 4H), 7.46 (s, 1H), 5.37 (s, 3H), 4.64 (m, 4H), 4.40 (s, 2H), 4.19-3.98 (m, 4H); MS (ES, m/z) 517 [M+H]$^+$.

Example 4a: 1-(4-((4-Chloro-2-methoxy-3-((tetrahydro-2H-pyran-4-yl)methyl)quinolin-6-yl)(hydroxy)(phenyl)methyl)piperidin-1-yl)ethanone

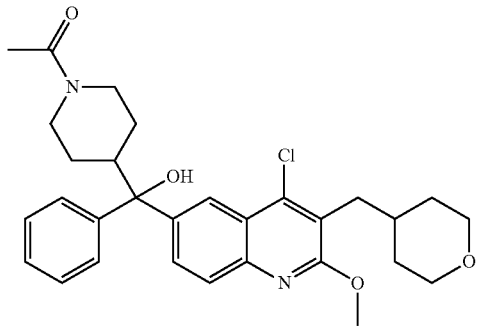 [SMILES: COc1nc2ccc(C(O)(c3ccccc3)C3CCN(C(C)=O)CC3)cc2c(Cl)c1CC1CCOCC1]

A solution of 4-chloro-6-iodo-2-methoxy-3-((tetrahydro-2H-pyran-4-yl)methyl)quinoline (161.8 mg, 0.387 mmol, Intermediate 4: step c) in THF (1.9 mL) was stirred on an ice bath under argon while iPrMgCl (2.01 M in THF, 0.212 mL, 0.426 mmol) was added dropwise over 1 minute, and was stirred for another 7 minutes before transferring the reaction to a dry ice/$CH_3CN$ bath. In a separate vial, $LaCl_3 \cdot 2LiCl$ (0.5 M in THF, 0.775 mL, 0.387 mmol) was added under argon to a solution of 1-(4-benzoylpiperidin-1-yl)ethanone (81.2 mg, 0.351 mmol, Intermediate 7) in THF (1.9 mL), and this was added dropwise over 1 minute to the ~−50° C. Grignard solution which had been stirring in the dry ice/$CH_3CN$ bath for 8 minutes. After stirring for 1 additional minute in the dry ice/$CH_3CN$ bath, the reaction was transferred to an ice bath and stirred at 0° C. for 20 minutes, and was then quenched in one portion with 5 M aqueous $NH_4Cl$ (0.128 mL), dried ($Na_2SO_4$), filtered through Celite®, and concentrated. The residue was dry load flash chromatographed (EtOAc isocratic elution) to afford the title compound contaminated with starting material 1-(4-benzoylpiperidin-1-yl)ethanone. This was further purified by C18 HPLC (20% to 100% $CH_3CN$ gradient with 0.1% TFA throughout). The product fractions were combined, neutralized with 2 M aqueous $K_2CO_3$, and concentrated to remove the organic solvent. The aqueous layer was then extracted with DCM, and the organic layer was dried ($Na_2SO_4$), filtered, and concentrated to dryness to provide the title compound as a white foam. $^1$H NMR (400 MHz, $CDCl_3$) δ ppm 8.26 (d, J=9.09 Hz, 1H), 7.71-7.78 (m, 1H), 7.59-7.69 (m, 1H), 7.52 (t, J=6.82 Hz, 2H), 7.29-7.38 (m, 2H), 7.18-7.25 (m, 1H), 4.62-4.76 (m, 1H), 4.05 (s, 3H), 3.93 (d, J=11.12 Hz, 2H), 3.83 (t, J=15.41 Hz, 1H), 3.25-3.38 (m, 2H), 3.09 (qd, J=2.53, 13.31 Hz, 1H), 2.89 (d, J=7.07 Hz, 2H), 2.76 (t, J=11.87 Hz, 1H), 2.51-2.66 (m, 1H), 2.05 (s, ~1.5H), 2.04 (s, ~1.5H), 1.87-2.02 (m, 1H), 1.62-1.74 (m, 1H), 1.28-1.57 (m, 7H); MS m/e 523.2 [M+H]$^+$.

Example 4a was purified by chiral HPLC (Chiralcel OD, 100% $CH_3CN$) to give 2 enantiomers. Example 4b: (first enantiomer to elute off chiral column)$^1$H NMR (400 MHz, $CDCl_3$) δ ppm 8.26 (d, J=7.58 Hz, 1H), 7.70-7.78 (m, 1H), 7.60-7.70 (m, 1H), 7.53 (t, J=6.82 Hz, 2H), 7.29-7.38 (m, 2H), 7.17-7.26 (m, 1H), 4.68 (t, J=13.39 Hz, 1H), 4.05 (s, 3H), 3.93 (d, J=11.12 Hz, 2H), 3.82 (t, J=14.15 Hz, 1H), 3.25-3.38 (m, 2H), 3.00-3.16 (m, 1H), 2.88 (d, J=7.07 Hz, 2H), 2.76 (t, J=11.62 Hz, 1H), 2.50-2.63 (m, 1H), 2.04 (s, ~1.5H), 2.03 (s, ~1.5H), 1.95 (dt, J=7.71, 14.91 Hz, 1H), 1.66 (t, J=15.66 Hz, 1H), 1.29-1.59 (m, 7H); MS m/e 523.2 [M+H]$^+$; and Example 4c: (second enantiomer to elute off chiral column)$^1$H NMR (400 MHz, $CDCl_3$) δ ppm 8.27 (d, J=7.58 Hz, 1H), 7.70-7.78 (m, 1H), 7.60-7.70 (m, 1H), 7.53 (t, J=6.82 Hz, 2H), 7.29-7.37 (m, 2H), 7.17-7.26 (m, 1H), 4.67 (t, J=13.39 Hz, 1H), 4.05 (s, 3H), 3.93 (d, J=10.61 Hz, 2H), 3.82 (t, J=14.40 Hz, 1H), 3.25-3.38 (m, 2H), 3.01-3.16 (m, 1H), 2.88 (d, J=7.07 Hz, 2H), 2.70-2.81 (m, 1H), 2.50-2.65 (m, 1H), 2.04 (s, ~1.5H), 2.04 (s, ~1.5H), 1.86-1.99 (m, 1H), 1.56-1.73 (m, 1H), 1.29-1.55 (m, 7H); MS m/e 523.2 [M+H]$^+$.

Example 5a: 1-(4-((4-Chloro-2-methoxy-3-((tetrahydro-2H-pyran-4-yl)methyl)quinolin-6-yl)(hydroxy)(1-methyl-1H-imidazol-5-yl)methyl)piperidin-1-yl)ethanone

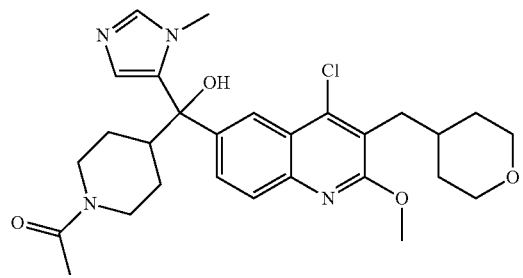 [SMILES: COc1nc2ccc(C(O)(c3cncn3C)C3CCN(C(C)=O)CC3)cc2c(Cl)c1CC1CCOCC1]

A solution of (4-chloro-2-methoxy-3-((tetrahydro-2H-pyran-4-yl)methyl)quinolin-6-yl)(1-methyl-1H-imidazol-5-yl)(piperidin-4-yl)methanol (232 mg, 0.479 mmol, Example 171) in TEA (0.0733 mL, 0.527 mmol) and DCM (9.6 mL) was stirred at ~0° C. under argon while acetic anhydride was added dropwise over 1 minute. The reaction was stirred at 0° C. for 30 minutes and was then washed with 1 M aqueous $NaH_2PO_4$ (1×8 mL), water (2×8 mL), and 2 M aqueous $K_2CO_3$ (1×3 mL). The organic layer was dried ($Na_2SO_4$), filtered, and concentrated to provide the title compound as a white foam. $^1$H NMR (400 MHz, $CDCl_3$) δ ppm 8.14 (s, ~0.5H), 8.06 (s, ~0.5H), 7.74 (dd, J=4.04, 8.59 Hz, 1H), 7.38 (t, J=9.85 Hz, 1H), 7.29 (s, 1H), 7.17 (s, 1H), 4.75 (d, J=13.64 Hz, ~0.5H), 4.57 (d, J=13.1 Hz, ~0.5H), 4.08 (s, 3H), 3.89-3.98 (m, ~2.5H), 3.66-3.77 (m, ~0.5H), 3.28-3.39 (m, 2H), 3.25 (s, ~1.5H), 3.23 (s, ~1.5H), 3.11-3.21 (m, ~0.5H), 2.96 (m, ~0.5H), 2.85-2.93 (m, 2H), 2.56-2.68 (m, ~0.5H), 2.37-2.52 (m, ~1.5H), 2.23-2.36 (m, 1H), 2.03 (s, ~1.5H), 1.98 (s, ~1.5H), 1.93-2.00 (m, 1H), 1.10-1.60 (m, 7H); MS m/e 527.2 [M+H]$^+$.

Example 5a was purified by chiral HPLC (Chiralcel OD, 20% EtOH in heptane, then 100% EtOH) to give 2 enantiomers. Example 5b: (first enantiomer to elute off chiral column)$^1$H NMR (400 MHz, $CDCl_3$) δ ppm 8.13 (s, ~0.5H), 8.06 (s, ~0.5H), 7.75 (dd, J=4.04, 9.09 Hz, 1H), 7.38 (dd, J=8.59, 14.15 Hz, 1H), 7.29 (d, J=4.04 Hz, 1H), 7.19 (s, 1H), 4.75 (d, J=13.1H, ~0.5 Hz), 4.58 (d, J=13.2 Hz, ~0.5H), 4.08 (s, 3H), 3.89-3.98 (m, ~2.5H), 3.69-3.75 (m, ~0.5H), 3.27-3.38 (m, 2H), 3.24 (s, ~1.5H), 3.23 (s, ~1.5H), 3.12-3.20 (m, ~0.5H), 2.93-3.10 (m, ~0.5H), 2.85-2.93 (m, 2H), 2.56-2.67 (m, ~0.5H), 2.38-2.52 (m, ~1.5H), 2.21-2.37 (m, 1H), 2.03 (s, ~1.5H), 2.01 (s, ~1.5H), 1.93-2.00 (m, 1H), 1.14-1.58 (m, 7H); MS m/e 527.2 [M+H]$^+$; and Example 5c: (second enantiomer to elute off chiral column)$^1$H NMR (400 MHz, $CDCl_3$) δ ppm 8.13 (s, ~0.5H), 8.07 (s, ~0.5H), 7.75 (dd, J=4.04, 8.59 Hz, 1H), 7.33-7.44 (m, 1H), 7.28 (d, J=4.55 Hz, 1H), 7.18 (s, 1H), 4.76 (d, J=12.8H, 0.5H), 4.57

(d, J=13.0 Hz, ~0.5H), 4.08 (s, 3H), 3.86-4.01 (m, ~2.5H), 3.68-3.78 (m, ~0.5H), 3.27-3.38 (m, 2H), 3.24 (s, ~1.5H), 3.23 (s, ~1.5H), 3.10-3.21 (m, ~0.5H), 2.93-3.02 (m, ~0.5H), 2.90 (d, J=7.07 Hz, 2H), 2.56-2.67 (m, ~0.5H), 2.38-2.52 (m, ~1.5H), 2.21-2.36 (m, 1H), 2.02 (s, ~1.5H), 2.01 (s, ~1.5H), 1.92-2.01 (m, 1H), 1.14-1.58 (m, 7H); MS m/e 527.2 [M+H]$^+$.

Example 6a: (4-Chloro-2-methoxy-3-((tetrahydro-2H-pyran-4-yl)methyl)quinolin-6-yl)(1-methyl-1H-imidazol-5-yl)(1-(methylsulfonyl)piperidin-4-yl)methanol

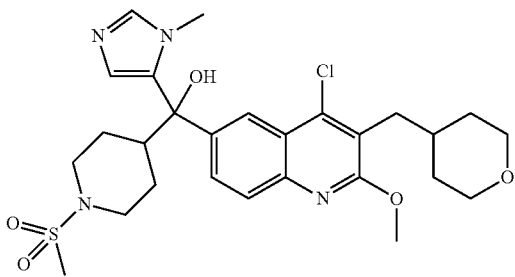 [SMILES: COc1nc2ccc(C(O)(c3cncn3C)C3CCN(S(C)(=O)=O)CC3)cc2c(Cl)c1CC1CCOCC1]

A solution of (4-chloro-2-methoxy-3-((tetrahydro-2H-pyran-4-yl)methyl)quinolin-6-yl)(1-methyl-1H-imidazol-5-yl)(piperidin-4-yl)methanol (106 mg, 0.219 mmol, Example 171) in TEA (0.0334 mL, 0.24 mmol) and DCM (0.88 mL) was stirred at 0° C. under argon while CH$_3$SO$_2$Cl (0.0178 mL, 0.229 mmol) was added dropwise over ~1 minute. The solution was stirred at ~0° C. while allowing the ice bath to expire overnight. The reaction was concentrated and partitioned with 9:1 EtOAc/MeOH (8 mL) and water (8 mL), and the organic layer was washed with water (1×8 mL), 1 M aqueous NaH$_2$PO$_4$ (1×8 mL), and 2 M aqueous K$_2$CO$_3$ (1×3 mL), dried (Na$_2$SO$_4$), filtered, and concentrated to provide the title compound as a white foam. The combined aqueous layers were made basic with 5 M aqueous K$_2$CO$_3$ and extracted with 9:1 EtOAc/MeOH (3×30 mL). The combined organic layers were dried (Na$_2$SO$_4$), filtered, and concentrated to provide additional title compound. $^1$H NMR (400 MHz, CDCl$_3$) δ ppm 8.08 (s, 1H), 7.75 (d, J=8.59 Hz, 1H), 7.37 (d, J=8.3 Hz, 1H), 7.34 (s, 1H), 7.19 (s, 1H), 4.08 (s, 3H), 3.93 (d, J=2.53 Hz, 3H), 3.71-3.79 (m, 1H), 3.28-3.38 (m, 2H), 3.24 (s, 3H), 2.90 (d, J=7.07 Hz, 2H), 2.73-2.82 (m, 4H), 2.54-2.63 (m, 1H), 2.29-2.42 (m, 2H), 1.91-2.04 (m, 1H), 1.19-1.60 (m, 7H); MS m/e 563.3 [M+H]$^+$.

Example 6a was purified by chiral HPLC (Chiralcel OD, 50% EtOH in heptane) to give 2 enantiomers. Example 6b: (first enantiomer to elute off chiral column)$^1$H NMR (400 MHz, CDCl$_3$) δ ppm 8.09 (s, 1H), 7.75 (d, J=8.59 Hz, 1H), 7.37 (d, J=9.09 Hz, 1H), 7.33 (s, 1H), 7.18 (s, 1H), 4.08 (s, 3H), 3.89-3.99 (m, 3H), 3.75 (d, J=11.12 Hz, 1H), 3.29-3.39 (m, 2H), 3.24 (s, 3H), 2.90 (d, J=7.07 Hz, 2H), 2.72-2.82 (m, 4H), 2.58 (td, J=3.03, 11.87 Hz, 1H), 2.28-2.43 (m, 2H), 1.92-2.04 (m, 1H), 1.20-1.60 (m, 7H); MS m/e 563.3 [M+H]$^+$; and Example 6c: (second enantiomer to elute off chiral column)$^1$H NMR (400 MHz, CDCl$_3$) δ ppm 8.09 (s, 1H), 7.75 (d, J=9.09 Hz, 1H), 7.38 (d, J=7.07 Hz, 1H), 7.32 (s, 1H), 7.17 (s, 1H), 4.08 (s, 3H), 3.94 (d, J=11.12 Hz, 3H), 3.70-3.80 (m, 1H), 3.28-3.37 (m, 2H), 3.24 (s, 3H), 2.87-2.94 (m, 2H), 2.72-2.82 (m, 4H), 2.58 (td, J=3.03, 11.87 Hz, 1H), 2.28-2.42 (m, 2H), 1.91-2.05 (m, 1H), 1.17-1.59 (m, 7H); MS m/e 563.3 [M+H]$^+$.

Example 7a: 1-(4-((4-Chloro-2-methoxy-3-(tetrahydro-2H-pyran-4-yl)quinolin-6-yl)(hydroxy)(phenyl)methyl)piperidin-1-yl)ethanone

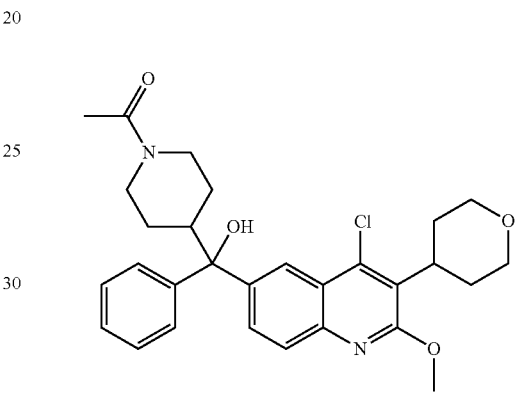

The title compound was prepared as described for Example 4a using 4-chloro-6-iodo-2-methoxy-3-(tetrahydro-2H-pyran-4-yl)quinoline (Intermediate 6: step d) in place of 4-chloro-6-iodo-2-methoxy-3-((tetrahydro-2H-pyran-4-yl)methyl)quinoline (Intermediate 4: step c), except 1.0 equivalent of each reagent was used. $^1$H NMR (400 MHz, CDCl$_3$) δ ppm 8.29 (dd, J=2.02, 8.59 Hz, 1H), 7.69-7.77 (m, 1H), 7.58-7.68 (m, 1H), 7.52 (t, J=6.82 Hz, 2H), 7.29-7.38 (m, 2H), 7.18-7.24 (m, 1H), 4.62-4.76 (m, 1H), 4.01-4.15 (m, 5H), 3.69-3.85 (m, 2H), 3.57 (t, J=11.12 Hz, 2H), 3.01-3.17 (m, 1H), 2.70-2.83 (m, 1H), 2.49-2.66 (m, 3H), 2.06 (s, ~1.5H), 2.05 (s, ~1.5H), 1.61-1.76 (m, 1H), 1.43-1.52 (m, 3H), 1.28-1.43 (m, 2H); MS m/e 509.1 [M+H]$^+$.

Example 7a was purified by chiral HPLC (Chiralpak AS, 95% CH$_3$CN, 5% EtOH) to give 2 enantiomers. Example 7b: (first enantiomer to elute off chiral column)$^1$H NMR (400 MHz, CDCl$_3$) δ ppm 8.30 (d, J=7.07 Hz, 1H), 7.69-7.76 (m, 1H), 7.58-7.69 (m, 1H), 7.52 (t, J=7.07 Hz, 2H), 7.28-7.37 (m, 2H), 7.18-7.25 (m, 1H), 4.68 (t, J=14.40 Hz, 1H), 4.03-4.14 (m, 5H), 3.69-3.89 (m, 2H), 3.57 (t, J=11.12 Hz, 2H), 3.01-3.16 (m, 1H), 2.70-2.82 (m, 1H), 2.50-2.65 (m, 3H), 2.03 (s, 3H), 1.61-1.76 (m, 1H), 1.46 (d, J=11.62 Hz, 3H), 1.30-1.42 (m, 2H); MS m/e 509.2 [M+H]$^+$; and Example 7c: (second enantiomer to elute off chiral column) $^1$H NMR (400 MHz, CDCl$_3$) δ ppm 8.29 (d, J=7.07 Hz, 1H), 7.70-7.75 (m, 1H), 7.60-7.67 (m, 1H), 7.52 (t, J=7.07 Hz, 2H), 7.30-7.36 (m, 2H), 7.18-7.25 (m, 1H), 4.69 (t, J=14.40 Hz, 1H), 4.05-4.12 (m, 5H), 3.65-3.88 (m, 2H), 3.57 (t, J=11.12 Hz, 2H), 3.03-3.15 (m, 1H), 2.76 (t, J=11.87 Hz, 1H), 2.52-2.64 (m, 3H), 2.05 (s, ~1.5H), 2.05 (s, ~1.5H), 1.64-1.73 (m, 1H), 1.53-1.64 (m, 3H), 1.23-1.50 (m, 2H); MS m/e 509.2 [M+H]$^+$.

Example 8: Ethyl 6-(hydroxydi(pyridin-3-yl)methyl)-2,4-bis(trifluoromethyl)quinoline-3-carboxylate.TFA

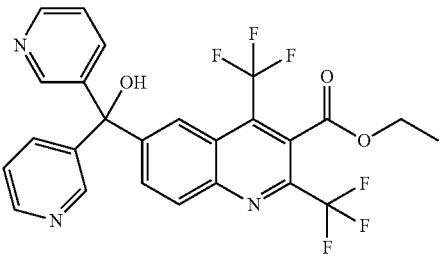 [SMILES: CCOC(=O)c1c(C(F)(F)F)nc2ccc(C(O)(c3cccnc3)c3cccnc3)cc2c1C(F)(F)F]

An opaque yellow slurry of ethyl 6-bromo-2,4-bis(trifluoromethyl)quinoline-3-carboxylate (0.318 g, 0.764 mmol, Intermediate 2: step c) and di(pyridin-3-yl)methanone (0.155 g, 0.841 mmol) in THF (6 mL) at −70° C. (internal temperature) was stirred under argon while n-BuLi (0.577 mL, 1.59 M in hexane, 0.917 mmol) was added dropwise. The reaction was stirred at −70° C. for 30 minutes, and was then removed from the cold bath and allowed to warm to 0° C. over 11 minutes. The homogeneous dark brown solution was then quenched with 1 M HCl (aq) (1 mL) and partitioned with 1 M aqueous NaHCO$_3$ (3 mL). The aqueous layer was extracted with EtOAc (1×4 mL), and the combined organic layers were dried (Na$_2$SO$_4$), filtered, and concentrated to dryness. The residue was flash chromatographed (0-100% EtOAc in heptane) and further purified by C18 HPLC (20-100% CH$_3$CN in water with 0.1% TFA throughout) to provide, after lyophilization, the title compound as a pale yellow gum. $^1$H NMR (400 MHz, CD$_3$OD) δ ppm 8.83 (d, J=2.02 Hz, 2H), 8.76 (dd, J=1.01, 5.22 Hz, 2H), 8.40 (d, J=9.09 Hz, 1H), 8.34-8.37 (m, 1H), 8.27-8.31 (m, 2H), 8.07 (dd, J=2.02, 9.09 Hz, 1H), 7.84 (dd, J=5.56, 8.08 Hz, 2H), 4.48 (q, J=7.41 Hz, 2H), 1.40 (t, J=7.33 Hz, 3H); MS m/e 522.2 [M+H]$^+$.

Example 9: 1-(4-(Hydroxy(1-methyl-1H-imidazol-5-yl)(3-(piperidine-1-carbonyl)-2,4-bis(trifluoromethyl)quinolin-6-yl)methyl)piperidin-1-yl)ethanone

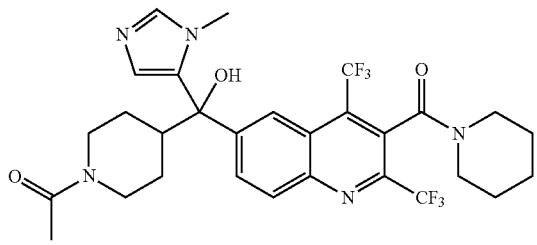 [SMILES: CC(=O)N1CCC(C(O)(c2ccc3nc(C(F)(F)F)c(C(=O)N4CCCCC4)c(C(F)(F)F)c3c2)c2cncn2C)CC1]

A ~1:1 mixture of (6-(hydroxy(1-methyl-1H-imidazol-5-yl)(piperidin-4-yl)methyl)-2,4-bis(trifluoromethyl)quinolin-3-yl)(piperidin-1-yl)methanone and (2-(1-methyl-1H-imidazol-5-yl)-3-(piperidine-1-carbonyl)-2,4-bis(trifluoromethyl)-1,2-dihydroquinolin-6-yl)(piperidin-4-yl)methanone (94.1 mg total, 0.165 mmol total, Example 165) in DCM (1 mL) and TEA (0.0299 mL, 0.215 mmol) was treated with acetic anhydride dropwise at room temperature, and was stirred for 45 minutes. The reaction was then concentrated, partitioned with EtOAc (3 mL) and 1 M aqueous NaHCO$_3$ (3 mL), and the aqueous layer was extracted with EtOAc (1×3 mL). The combined organic layers were dried (Na$_2$SO$_4$), filtered, and concentrated to provide a ~1:1 mixture of the title compound and 1-(4-(2-(1-methyl-1H-imidazol-5-yl)-3-(piperidine-1-carbonyl)-2,4-bis(trifluoromethyl)-1,2-dihydroquinoline-6-carbonyl)piperidin-1-yl)ethanone. This mixture was dissolved in MeOH (2.8 mL) and treated with NaBH$_4$ (19.6 mg, 0.519 mmol) with stirring for 7 minutes at room temperature to reduce the (2-(1-methyl-1H-imidazol-5-yl)-3-(piperidine-1-carbonyl)-2,4-bis(trifluoromethyl)-1,2-dihydroquinolin-6-yl)(piperidin-4-yl)methanone side product to allow for easier isolation of pure title compound via chromatography. The reaction was quenched with HOAc (0.2 mL) followed by 1 M aqueous NaHCO$_3$ (3 mL), and extracted with CHCl$_3$ (3×3 mL). The combined organic layers were dried (Na$_2$SO$_4$), filtered, and concentrated. The residue was flash chromatographed (0-10% MeOH in DCM) and further purified with C18 HPLC (20% CH$_3$CN to 100% CH$_3$CN gradient, with 0.1% TFA throughout) to provide, after lyophilization, the TFA salt of the title compound. This was partitioned between DCM (3×2 mL) and 2 M aqueous K$_2$CO$_3$, and the combined organic layers were dried (Na$_2$SO$_4$), filtered, and concentrated to provide the title compound (4 diastereomers with atropisomerism) as a white solid. $^1$H NMR (400 MHz, CDCl$_3$) δ ppm 8.40-8.51 (m, "0.82H"), 8.28-8.18 (m, "1.18H"), 7.79-7.84 (m, "0.15H"), 7.62-7.73 (m, "0.59H"), 7.54-7.59 (m, "0.26H"), 7.41-7.47 (m, 1H), 7.20 (s, 1H), 4.51-4.71 (m, 1H), 3.81-3.97 (m, "1.44H"), 3.65-3.76 (m, "1.66H"), 3.35 (s, "0.70H"), 3.29 (s, "1.10H"), 3.27 (s, "0.49H"), 3.26 (s, "0.71H"), 3.12-3.23 (m, "2.42H"), 2.90-3.03 (m, "0.58H"), 2.58-2.68 (m, "0.63H"), 2.37-2.57 (m, "2.14H"), 2.28-2.37 (m, "0.63H"), 2.16-2.27 (m, "0.61H"), 2.03 (s, "0.71H"), 2.01 (s, "0.52H"), 1.96 (s, "0.74H"), 1.96 (s, "1.03H"), 1.70 (br. s, 4H), 1.08-1.48 (m, 4H); MS m/e 612.3 [M+H]$^+$.

Example 10: (2,4-Dimethylthiazol-5-yl)(3-methoxy-2-phenylquinolin-6-yl)(1-methyl-1H-1,2,3-triazol-5-yl)methanol

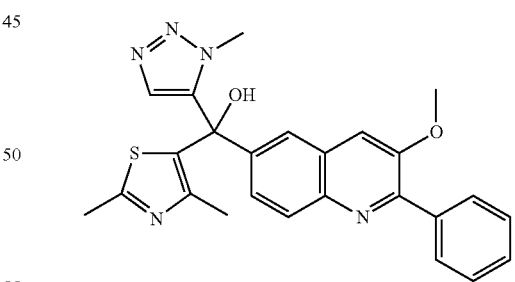

A yellow solution of 6-bromo-3-methoxy-2-phenylquinoline (61 mg, 0.194 mmol, Intermediate 8) in THF (2.2 mL) was stirred under argon ~−70° C. while n-BuLi (1.60 M in hexane, 0.121 mL, 0.194 mmol) was added dropwise over 30 seconds. The resulting dark solution was stirred in the cold bath for another 1.5 minutes, and was then treated with a solution of (2,4-dimethylthiazol-5-yl)(1-methyl-1H-1,2,3-triazol-5-yl)methanone (43.8 mg, 0.197 mmol, Intermediate 12: step b) in THF (0.8 mL) over 1 minute. After an additional 3 minutes, the reaction was removed from the cold bath and stirred under ambient conditions for 1 minute, and was then transferred to an ice bath and stirred at 0° C. for 45 minutes. The yellow homogeneous reaction was then quenched with 5 M aqueous NH$_4$Cl (0.060 mL), dried (Na$_2$SO$_4$), filtered, and concentrated. The residue was purified by FCC(EtOAc) to provide the title compound. $^1$H NMR (400 MHz, CDCl$_3$) δ ppm 8.16 (d, J=8.59 Hz, 1H), 7.96 (dd, J=1.66, 7.96 Hz, 2H), 7.54-7.61 (m, 2H), 7.46-7.54 (m, 3H), 7.44 (s, 1H), 7.30 (s, 1H), 3.97 (s, 3H), 3.95 (s, 3H), 3.29 (s, 1H), 2.61 (s, 3H), 2.18 (s, 3H); MS m/e 458.1 [M+H]$^+$.

Example 11a: 1-(4-((4-Chloro-2-methoxy-3-methylquinolin-6-yl)(hydroxy)(phenyl)methyl)piperidin-1-yl)ethanone

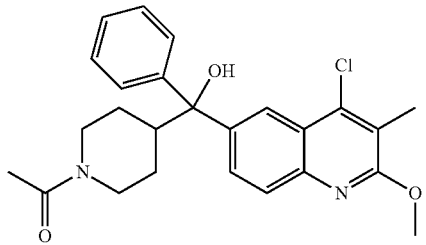 [SMILES: COc1nc2ccc(C(O)(c3ccccc3)C3CCN(C(C)=O)CC3)cc2c(Cl)c1C]

A solution of n-butyllithium in hexanes (1.6 M, 2.0 mL, 3.2 mmol) was added dropwise to a stirring solution of 6-bromo-4-chloro-2-methoxy-3-methylquinoline (1.0 g, 3.5 mmol, Intermediate 9: step b) in tetrahydrofuran (15 mL) at −78° C. After 5 minutes, a solution of 1-(4-benzoylpiperidin-1-yl)ethanone (814 mg, 3.5 mmol, Intermediate 7) in tetrahydrofuran (5 mL) was added dropwise. After 5 minutes, the flask was placed into an ice-water bath. After 90 minutes, water (10 mL) and ethyl acetate (100 mL) were added. The biphasic mixture was stirred at 23° C. for 5 minutes. Half-saturated aqueous sodium chloride solution was added and the layers were separated. The organic layer was dried with sodium sulfate and the dried solution was filtered. Silica gel (5 g) was added to the filtrate and the mixture was concentrated by rotary evaporation to afford a free-flowing powder. The powder was loaded onto a silica gel column for flash-column chromatography purification. Elution with 100% hexanes initially, grading to 100% ethyl acetate provided the title compound as a white solid. $^1$H NMR (500 MHz, CDCl$_3$) δ ppm 8.27-8.21 (m, 1H), 7.77-7.70 (m, 1H), 7.66-7.58 (m, 1H), 7.55-7.48 (m, 2H), 7.37-7.28 (m, 2H), 7.26-7.18 (m, 1H), 4.74-4.63 (m, 1H), 4.06 (s, 3H), 3.87-3.76 (m, 1H), 3.15-3.01 (m, 1H), 2.79-2.70 (m, 1H), 2.64-2.51 (m, 1H), 2.42 (s, 3H), 2.29 (d, J=1.9 Hz, 1H), 2.05 (s, 3H), 1.72-1.57 (m, 1H), 1.56-1.28 (m, 3H); MS (ESI): mass calcd. for C$_{25}$H$_{27}$ClN$_2$O$_3$, 438.2; m/z found, 439.0 [M+H]$^+$. 1-(4-((4-Chloro-2-methoxy-3-methylquinolin-6-yl)(hydroxy)(phenyl)methyl)piperidin-1-yl)ethanone was purified by chiral SFC (Chiralpak AD-H, 5 μm, 250×20 mm, mobile phase: 60% CO$_2$, 40% mixture of methanol-isopropanol 50/50 v/v) to provide two enantiomers. The first eluting enantiomer was Example 11b: $^1$H NMR (400 MHz, CDCl$_3$, * denotes rotameric peaks) δ ppm 8.26-8.22 (m, 1H), 7.77-7.71 (m, 1H), 7.66-7.58 (m, 1H), 7.55-7.48 (m, 2H), 7.37-7.29 (m, 2H), 7.25-7.18 (m, 1H), 4.77-4.62 (m, 1H), 4.06 (s, 3H), 3.82 (t, J=14.1 Hz, 1H), 3.17-3.00 (m, 1H), 2.82-2.67 (m, 1H), 2.64-2.52 (m, 1H), 2.42 (s, 3H), 2.21 (s, 1H), 2.05* (s, 3H), 2.04* (s, 3H), 1.71-1.30 (m, 4H); MS (ESI): mass calcd. for C$_{25}$H$_{27}$ClN$_2$O$_3$, 438.2; m/z found, 439.0 [M+H]$^+$ and the second eluting enantiomer was Example 11c: $^1$H NMR (400 MHz, CDCl$_3$, * denotes rotameric peaks) δ 8.26-8.22 (m, 1H), 7.74 (dd, J=8.8, 6.1 Hz, 1H), 7.66-7.59 (m, 1H), 7.55-7.48 (m, 2H), 7.37-7.30 (m, 2H), 7.25-7.18 (m, 1H), 4.75-4.62 (m, 1H), 4.06 (s, 3H), 3.89-3.77 (m, 1H), 3.16-3.01 (m, 1H), 2.81-2.69 (m, 1H), 2.64-2.51 (m, 1H), 2.42 (s, 3H), 2.20 (s, 1H), 2.05* (s, 3H), 2.04* (s, 3H), 1.72-1.29 (m, 4H); MS (ESI): mass calcd. for C$_{25}$H$_{27}$ClN$_2$O$_3$, 438.2; m/z found, 439.0 [M+H]$^+$.

Example 12a: (4-Chloro-2-methoxy-3-methylquinolin-6-yl)(2,6-dimethylpyridin-3-yl)(1-methyl-1H-1,2,3-triazol-5-yl)methanol

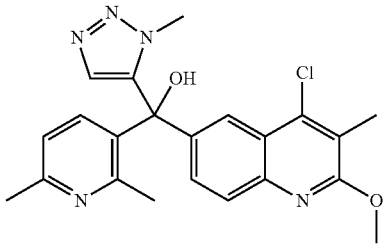

A solution of n-butyllithium in hexanes (2.5 M, 0.28 mL, 0.70 mmol) was added dropwise to a stirring solution of 6-bromo-4-chloro-2-methoxy-3-methylquinoline (200 mg, 0.70 mmol, Intermediate 9: step b) in tetrahydrofuran (6 mL) at −78° C. After 2 minutes, a solution of (2,6-dimethylpyridin-3-yl)(1-methyl-1H-1,2,3-triazol-5-yl)methanone (166 mg, 0.768 mmol, Intermediate 11: step b) in tetrahydrofuran (2 mL) was added dropwise. After 3 minutes, the flask was removed from the cooling bath and allowed to warm to 23° C. After 20 minutes, water (5 mL) and ethyl acetate (50 mL) were added. The biphasic mixture was poured into saturated aqueous sodium chloride solution (30 mL). The layers were separated. The organic layer was dried with sodium sulfate and the dried solution was filtered. Silica gel (3 g) was added to the filtrate and the mixture was concentrated by rotary evaporation to afford a free-flowing powder. The powder was loaded onto a silica gel column for flash column chromatography purification. Elution with dichloromethane initially, grading to 5% methanol-dichloromethane provided the title compound as a white solid. $^1$H NMR (400 MHz, CDCl$_3$) δ ppm 8.04 (d, J=2.2 Hz, 1H), 7.80 (d, J=8.8 Hz, 1H), 7.36-7.28 (m, 1H), 7.00-6.90 (m, 3H), 4.11 (s, 3H), 3.94 (s, 3H), 3.62 (s, 1H), 2.55 (s, 3H), 2.43 (s, 3H), 2.38 (s, 3H); MS (ESI): mass calcd. for C$_{22}$H$_{22}$ClN$_5$O$_2$, 423.1; m/z found, 423.9 [M+H]$^+$. (4-Chloro-2-methoxy-3-methylquinolin-6-yl)(2,6-dimethylpyridin-3-yl)(1-methyl-1H-1,2,3-triazol-5-yl)methanol was purified by chiral SFC (Chiralpak AD-H, 5 μm, 250×20 mm, mobile phase: 80% CO$_2$, 20% methanol containing 0.03% isopropylamine) to provide two enantiomers. The first eluting enantiomer was Example 12b: $^1$H NMR (500 MHz, CDCl$_3$) δ ppm 8.04 (d, J=2.2 Hz, 1H), 7.80 (d, J=8.7 Hz, 1H), 7.31 (dd, J=8.7, 2.2 Hz, 1H), 6.99-6.92 (m, 3H), 4.11 (s, 3H), 3.94 (s, 3H), 3.61 (br s, 1H), 2.55 (s, 3H), 2.43 (s, 3H), 2.38 (s, 3H); MS (ESI): mass calcd. for C$_{22}$H$_{22}$ClN$_5$O$_2$, 423.1; m/z found, 424.4 [M+H]$^+$ and the second eluting enantiomer was Example 12c: $^1$H NMR (500 MHz, CDCl$_3$) δ ppm 8.03 (d, J=2.2 Hz, 1H), 7.81 (d, J=8.7 Hz, 1H), 7.35-7.30 (m, 1H), 6.99-6.92 (m, 3H), 4.11 (s, 3H), 3.94 (s, 3H), 3.37 (br s, 1H), 2.56 (s, 3H), 2.44

(s, 3H), 2.39 (s, 3H); MS (ESI): mass calcd. for $C_{22}H_{22}ClN_5O_2$, 423.1; m/z found, 424.4 $[M+H]^+$.

Example 13a: (4-Chloro-2-methoxy-3-methylquinolin-6-yl)(2,4-dimethylthiazol-5-yl)(1-methyl-1H-1,2,3-triazol-5-yl)methanol

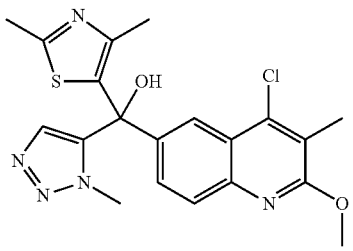

A solution of n-butyllithium in hexanes (2.5 M, 0.47 mL, 1.2 mmol) was added dropwise to a stirring solution of 6-bromo-4-chloro-2-methoxy-3-methylquinoline (300 mg, 1.0 mmol, Intermediate 9: step b) in tetrahydrofuran (8 mL) at −78° C. After 2 minutes, a solution of (2,4-dimethylthiazol-5-yl)(1-methyl-1H-1,2,3-triazol-5-yl)methanone (233 mg, 1.05 mmol, Intermediate 12: step b) in tetrahydrofuran (1.5 mL) was added dropwise. After 5 minutes, the flask was placed into an ice-water bath. After 60 minutes, water (5 mL) was added and the mixture was allowed to warm to 23° C. The mixture was partitioned between half-saturated aqueous sodium chloride solution (25 mL) and ethyl acetate (50 mL). The layers were separated. The organic layer was dried with sodium sulfate and the dried solution was filtered. Silica gel (3 g) was added to the filtrate and the mixture was concentrated by rotary evaporation to afford a free-flowing powder. The powder was loaded onto a silica gel column for flash column chromatography purification. Elution with 40% ethyl acetate-hexanes initially, grading to 90% ethyl acetate-hexanes provided the title compound as a white solid. $^1H$ NMR (500 MHz, CDCl$_3$) δ ppm 8.12-8.07 (m, 1H), 7.86-7.81 (m, 1H), 7.51-7.45 (m, 1H), 7.25-7.22 (m, 1H), 4.11 (s, 3H), 3.92 (s, 3H), 3.50 (s, 1H), 2.59 (s, 3H), 2.44 (s, 3H), 2.15 (s, 3H); MS (ESI): mass calcd. for $C_{20}H_{20}ClN_5O_2S$, 429.1; m/z found, 430.1 $[M+H]^+$.

(4-Chloro-2-methoxy-3-methylquinolin-6-yl)(2,4-dimethylthiazol-5-yl)(1-methyl-1H-1,2,3-triazol-5-yl)methanol was purified by chiral SFC (Chiralpak AD, 5 m, 250×30 mm, mobile phase: 75% CO$_2$, 25% mixture containing methanol-isopropanol 50/50 v/v containing 0.03% isopropylamine) to provide two enantiomers. The first eluting enantiomer was Example 13b: $^1H$ NMR (400 MHz, CDCl$_3$) δ ppm 8.10 (d, J=2.3 Hz, 1H), 7.83 (d, J=8.7 Hz, 1H), 7.51-7.44 (m, 1H), 7.22 (s, 1H), 4.11 (s, 3H), 3.93 (s, 3H), 3.71 (s, 1H), 2.59 (s, 3H), 2.43 (s, 3H), 2.15 (s, 3H); MS (ESI): mass calcd. for $C_{20}H_{20}ClN_5O_2S$, 429.1; m/z found, 430.0 $[M+H]^+$ and the second eluting enantiomer was Example 13c: $^1H$ NMR (400 MHz, CDCl$_3$) δ ppm 8.10 (d, J=2.2 Hz, 1H), 7.84 (d, J=8.7 Hz, 1H), 7.48 (dd, J=8.8, 2.2 Hz, 1H), 7.24 (s, 1H), 4.11 (s, 3H), 3.92 (s, 3H), 3.47 (s, 1H), 2.59 (s, 3H), 2.44 (s, 3H), 2.16 (s, 3H); MS (ESI): mass calcd. for $C_{20}H_{20}ClN_5O_2S$, 429.1; m/z found, 430.0 $[M+H]^+$.

Example 14a: (4-Chloro-3-(cyclopropylmethyl)-2-methoxyquinolin-6-yl)(2,6-dimethylpyridin-3-yl)(1-methyl-1H-1,2,3-triazol-5-yl)methanol

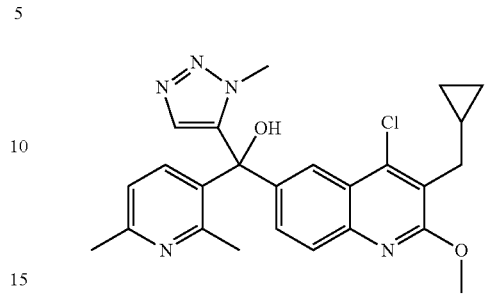

A solution of n-butyllithium (2.5 M in hexanes, 0.32 mL, 0.80 mmol) was added dropwise by syringe to a stirring solution of 4-chloro-3-(cyclopropylmethyl)-6-iodo-2-methoxyquinoline (300 mg, 0.80 mmol, Intermediate 13: step c) in dry THF (6 mL) at −78° C. After 1 minute, a solution of (2,6-dimethylpyridin-3-yl)(1-methyl-1H-1,2,3-triazol-5-yl)methanone (174 mg, 0.803 mmol, Intermediate 11: step b) in dry THF (2 mL) was added dropwise by syringe. After 2 minutes, the flask was removed from the cooling bath and allowed to warm. After 2 minutes, the flask was placed into an ice-water bath. After 10 minutes, water (5 mL) was added. The biphasic mixture was partitioned between half-saturated aqueous sodium chloride solution (25 mL) and ethyl acetate (50 mL). The layers were separated. The organic layer was dried with sodium sulfate and the dried solution was filtered. Celite® (5 g) was added to the filtrate and the solvents were removed by rotary evaporation to provide a free-flowing powder. The powder was loaded onto a silica gel column. Elution with dichloromethane initially, grading to 5% methanol-dichloromethane provided the title compound as a white solid. $^1H$ NMR (600 MHz, CDCl$_3$) δ ppm 8.06 (d, J=2.2 Hz, 1H), 7.81 (d, J=8.7 Hz, 1H), 7.35-7.32 (m, 1H), 6.98-6.92 (m, 3H), 4.11 (s, 3H), 3.94 (s, 3H), 3.67 (s, 1H), 2.86 (d, J=6.9 Hz, 2H), 2.55 (s, 3H), 2.39 (s, 3H), 1.15-1.07 (m, 1H), 0.46-0.39 (m, 2H), 0.37-0.32 (m, 2H); MS (ESI): mass calcd. for $C_{25}H_{26}ClN_5O_2$, 463.2; m/z found, 464.1 $[M+H]^+$. (4-Chloro-3-(cyclopropylmethyl)-2-methoxyquinolin-6-yl)(2,6-dimethylpyridin-3-yl)(1-methyl-1H-1,2,3-triazol-5-yl)methanol was purified by chiral SFC (Chiralpak AD-H, 5 μm, 250×20 mm, mobile phase: 80% CO$_2$, 20% mixture containing methanol-isopropanol 50/50 v/v containing 0.03% isopropylamine) to provide two enantiomers. The first eluting enantiomer was Example 14b: $^1H$ NMR (400 MHz, CDCl$_3$) δ ppm 8.05 (d, J=2.2 Hz, 1H), 7.82 (d, J=8.7 Hz, 1H), 7.36-7.32 (m, 1H), 6.99 (s, 1H), 6.99-6.93 (m, 2H), 4.11 (s, 3H), 3.95 (s, 3H), 3.28 (s, 1H), 2.87 (d, J=6.9 Hz, 2H), 2.56 (s, 3H), 2.40 (s, 3H), 1.17-1.06 (m, 1H), 0.47-0.40 (m, 2H), 0.38-0.31 (m, 2H); MS (ESI): mass calcd. for $C_{25}H_{26}ClN_5O_2$, 463.2; m/z found, 464.1 $[M+H]^+$ and the second eluting enantiomer was Example 14c: $^1H$ NMR (500 MHz, CDCl$_3$) δ ppm 8.06-8.04 (m, 1H), 7.84-7.81 (m, 1H), 7.34 (dd, J=8.7, 2.2 Hz, 1H), 6.99 (s, 1H), 6.98-6.93 (m, 2H), 4.11 (s, 3H), 3.94 (s, 3H), 3.31 (s, 1H), 2.87 (d, J=6.9 Hz, 2H), 2.56 (s, 3H), 2.40 (s, 3H), 1.17-1.06 (m, 1H), 0.47-0.41 (m, 2H), 0.37-0.31 (m, 2H); MS (ESI): mass calcd. for $C_{25}H_{26}ClN_5O_2$, 463.2; m/z found, 464.1 $[M+H]^+$.

Example 15a: 1-(4-((4-Chloro-3-(cyclopropylmethyl)-2-methoxyquinolin-6-yl)(hydroxy)(phenyl)methyl)piperidin-1-yl)ethanone

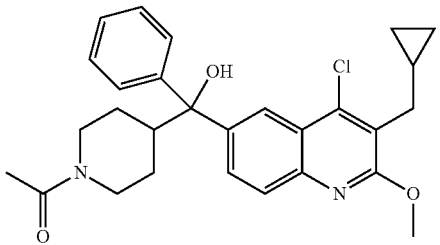 [SMILES: COc1nc2ccc(C(O)(c3ccccc3)C3CCN(C(C)=O)CC3)cc2c(Cl)c1CC1CC1]

A solution of n-butyllithium (2.5 M in hexanes, 0.21 mL, 0.54 mmol) was added dropwise by syringe to a stirring solution of 4-chloro-3-(cyclopropylmethyl)-6-iodo-2-methoxyquinoline (200 mg, 0.54 mmol, Intermediate 13: step c) in dry tetrahydrofuran (4 mL) at −78° C. After 1 minute, a solution of 1-(4-benzoylpiperidin-1-yl)ethanone (124 mg, 0.54 mmol, Intermediate 7) in dry tetrahydrofuran (1 mL) was added dropwise by syringe. After 2 minutes, the flask was removed from the cooling bath and allowed to warm. After 2 minutes, the flask was placed into an ice-water bath. After 10 minutes, water (5 mL) and ethyl acetate (50 mL) were added. The biphasic mixture was poured into half-saturated aqueous sodium chloride solution (25 mL). The layers were separated. The organic layer was dried with sodium sulfate and the dried solution was filtered. Celite® (5 g) was added to the filtrate and the solvents were removed by rotary evaporation to provide a free-flowing powder. The powder was loaded onto a silica gel column. Elution with hexanes initially, grading to 90% ethyl acetate-hexanes provided the title compound as a white solid. MS (ESI): mass calcd. for $C_{28}H_{31}ClN_2O_3$, 478.2; m/z found, 479.1 [M+H]$^+$.

1-(4-((4-Chloro-3-(cyclopropylmethyl)-2-methoxyquinolin-6-yl)(hydroxy)(phenyl)methyl)piperidin-1-yl)ethanone was purified by chiral SFC (Chiralpak AD-H, 5 μm, 250×20 mm, mobile phase: 65% CO$_2$, 35% mixture containing methanol-isopropanol 50/50 v/v containing 0.03% isopropylamine) to provide two enantiomers. The first eluting enantiomer was Example 15b: $^1$H NMR (400 MHz, CDCl$_3$) δ ppm 8.29-8.24 (m, 1H), 7.78-7.72 (m, 1H), 7.68-7.59 (m, 1H), 7.56-7.49 (m, 2H), 7.38-7.30 (m, 2H), 7.25-7.18 (m, 1H), 4.77-4.64 (m, 1H), 4.06 (s, 3H), 3.90-3.76 (m, 1H), 3.17-3.01 (m, 1H), 2.86 (d, J=6.8 Hz, 2H), 2.83-2.71 (m, 1H), 2.66-2.51 (m, 1H), 2.21 (s, 1H), 2.05 (s, 3H), 1.74-1.23 (m, 4H), 1.18-1.04 (m, 1H), 0.48-0.28 (m, 4H); MS (ESI): mass calcd. for $C_{28}H_{31}ClN_2O_3$, 478.2; m/z found, 479.1 [M+H]$^+$ and the second eluting enantiomer was Example 15c: $^1$H NMR (400 MHz, CDCl$_3$) δ ppm 8.26 (dd, J=6.4, 2.1 Hz, 1H), 7.78-7.72 (m, 1H), 7.67-7.60 (m, 1H), 7.56-7.49 (m, 2H), 7.37-7.30 (m, 2H), 7.25-7.19 (m, 1H), 4.76-4.64 (m, 1H), 4.06 (s, 3H), 3.89-3.76 (m, 1H), 3.15-3.02 (m, 1H), 2.86 (d, J=6.8 Hz, 2H), 2.82-2.72 (m, 1H), 2.65-2.52 (m, 1H), 2.23 (s, 1H), 2.05 (s, 3H), 1.74-1.29 (m, 4H), 1.17-1.05 (m, 1H), 0.45-0.29 (m, 4H); MS (ESI): mass calcd. for $C_{28}H_{31}ClN_2O_3$, 478.2; m/z found, 479.1 [M+H]$^+$.

Example 16: 1-((4-Chloro-6-(hydroxy(1-methyl-1H-imidazol-5-yl)(2-(trifluoromethyl)pyridin-4-yl)methyl)-2-methoxyquinolin-3-yl)methyl)-4-(trifluoromethyl)piperidin-4-ol

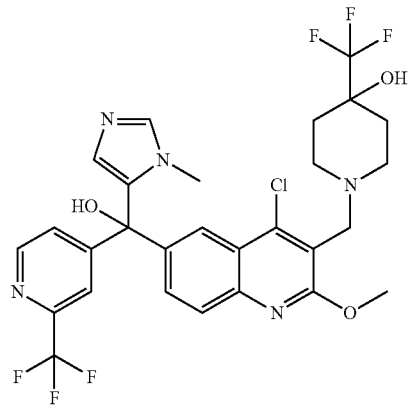 [SMILES: COc1nc2ccc(C(O)(c3ccnc(C(F)(F)F)c3)c3cncn3C)cc2c(Cl)c1CN1CCC(O)(C(F)(F)F)CC1]

A solution of methyllithium in ether (1.6 M, 0.300 mL, 0.480 mmol) was added dropwise to a dry ice-acetone cooled, stirring solution of 1-((6-bromo-4-chloro-2-methoxyquinolin-3-yl)methyl)-4-(trifluoromethyl)piperidin-4-ol (200 mg, 0.441 mmol, Intermediate 16) in dry tetrahydrofuran (4 mL). After 1 minute, a solution of n-butyllithium (2.5 M, 0.180 mL, 0.450 mmol) was added dropwise by syringe. After 1 minute, a solution of (1-methyl-1H-imidazol-5-yl)(2-(trifluoromethyl)pyridin-4-yl)methanone (148 mg, 0.580 mmol, Intermediate 14: step b) in dry tetrahydrofuran (1 mL) was added dropwise by syringe. After 5 minutes, the flask was removed from the cooling bath. After 5 minutes, the flask was placed into an ice-water bath. After 15 minutes, water (20 mL) and ethyl acetate (50 mL) were added sequentially. The layers were separated. The organic layer was dried with sodium sulfate and the dried solution was filtered. Celite® (7 g) was added to the filtrate and the mixture was concentrated in vacuo. The dry solid was loaded onto a silica gel column for flash column chromatography. Elution with dichloromethane initially, grading to 10% methanol-dichloromethane provided the title compound as an off-white solid. $^1$H NMR (400 MHz, CDCl$_3$) δ ppm 8.68 (d, J=5.1 Hz, 1H), 8.15 (d, J=2.1 Hz, 1H), 7.88 (d, J=1.6 Hz, 1H), 7.82 (d, J=8.8 Hz, 1H), 7.57-7.52 (m, 1H), 7.51-7.47 (m, 1H), 7.36 (s, 1H), 6.37 (s, 1H), 4.70 (s, 1H), 4.09 (s, 3H), 3.85 (s, 2H), 3.36 (s, 3H), 2.88-2.79 (m, 2H), 2.60-2.50 (m, 2H), 1.97 (s, 1H), 1.93-1.82 (m, 2H), 1.65 (d, J=13.3 Hz, 2H); MS (ESI): mass calcd. for $C_{28}H_{26}ClF_6N_5O_3$, 629.2; m/z found, 630.0 [M+H]$^+$.

Example 17a: (4-Chloro-2-methoxy-3-((4-(2,2,2-trifluoroethyl)piperazin-1-yl)methyl)quinolin-6-yl)(1,2-dimethyl-1H-imidazol-5-yl)(1-methyl-1H-1,2,3-triazol-5-yl)methanol

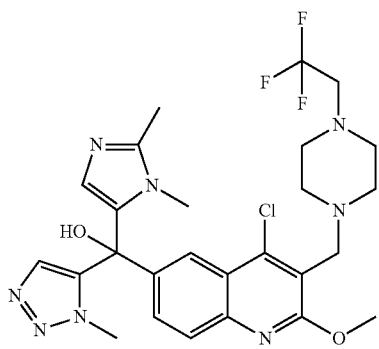 [SMILES: COc1nc2ccc(C(O)(c3cnnn3C)c3cnc(C)n3C)cc2c(Cl)c1CN1CCN(CC(F)(F)F)CC1]

A 2.5 M solution of n-butyllithium in hexanes (0.260 mL, 0.650 mmol) was added dropwise to a dry ice-acetone cooled solution of 5-bromo-1,2-dimethyl-1H-imidazole (120 mg, 0.686 mmol) in tetrahydrofuran (2 mL). After 30 seconds, a solution of (4-chloro-2-methoxy-3-((4-(2,2,2-trifluoroethyl)piperazin-1-yl)methyl)quinolin-6-yl)(1-methyl-1H-1,2,3-triazol-5-yl)methanone (157 mg, 0.325 mmol, Intermediate 17: step b) in tetrahydrofuran (1 mL) was added dropwise by syringe. After 2 minutes, the flask was removed from the cooling bath. After 3 minutes, the flask was placed into an ice-water bath. After 45 minutes, water (20 mL) and ethyl acetate (50 mL) were added sequentially. The layers were separated. The organic layer was dried with sodium sulfate and the dried solution was filtered. Celite® (7 g) was added to the filtrate and the mixture was concentrated in vacuo. The dry solid was loaded onto a silica gel column for flash-column chromatography. Elution with dichloromethane initially, grading to 10% methanol-dichloromethane provided impure title compound. Further purification by RP-HPLC eluting with 5% acetonitrile-water containing 0.2% TFA and partitioning of the combined fractions between dichloromethane-saturated aqueous sodium bicarbonate solution provided the title compound as a white solid. $^1$H NMR (500 MHz, CDCl$_3$) δ ppm 8.20 (d, J=2.2 Hz, 1H), 7.72 (d, J=8.7 Hz, 1H), 7.41-7.34 (m, 1H), 7.12 (s, 1H), 6.05 (s, 1H), 5.89 (s, 1H), 4.09 (s, 3H), 3.91 (s, 3H), 3.88-3.80 (m, 2H), 3.37 (s, 3H), 2.99-2.87 (m, 2H), 2.65 (s, 8H), 2.24 (s, 3H); MS (ESI): mass calcd. for $C_{26}H_{30}ClF_3N_8O_2$, 578.2; m/z found, 579.1 [M+H]$^+$. (4-Chloro-2-methoxy-3-((4-(2,2,2-trifluoroethyl)piperazin-1-yl)methyl)quinolin-6-yl)(1,2-dimethyl-1H-imidazol-5-yl)(1-methyl-1H-1,2,3-triazol-5-yl)methanol was purified by chiral SFC (Chiralpak AD-H, 5 μm, 250 mm×30 mm, mobile phase: 85% CO$_2$, 15% isopropanol containing 0.2% isopropylamine) to provide two enantiomers. The first eluting enantiomer was Example 17b: $^1$H NMR (500 MHz, CDCl$^3$) δ ppm 8.17 (d, J=2.1 Hz, 1H), 7.75 (d, J=8.7 Hz, 1H), 7.40-7.35 (m, 1H), 7.18 (s, 1H), 6.13 (s, 1H), 4.54 (s, 1H), 4.09 (s, 3H), 3.92 (s, 3H), 3.85 (s, 2H), 3.40 (s, 3H), 2.98-2.89 (m, 2H), 2.70-2.62 (m, 8H), 2.33 (s, 3H); MS (ESI): mass calcd. for $C_{26}H_{30}ClF_3N_8O_2$, 578.2; m/z found, 579.1 [M+H]$^+$ and the second eluting enantiomer was Example 17c: $^1$H NMR (500 MHz, CDCl$_3$) δ ppm 8.16 (d, J=2.2 Hz, 1H), 7.77 (d, J=8.7 Hz, 1H), 7.41-7.36 (m, 1H), 7.20 (s, 1H), 6.16 (s, 1H), 4.16-4.06 (m, 4H), 3.93 (s, 3H), 3.86 (s, 2H), 3.41 (s, 3H), 2.98-2.88 (m, 2H), 2.71-2.61 (m, 8H), 2.35 (s, 3H); MS (ESI): mass calcd. for $C_{26}H_{30}ClF_3N_8O_2$, 578.2; m/z found, 579.1 [M+H]$^+$.

Example 18: (4-Chloro-2-methoxy-3-methylquinolin-6-yl)(1-methyl-1H-imidazol-5-yl)(6-(trifluoromethyl)pyridin-3-yl)methanol

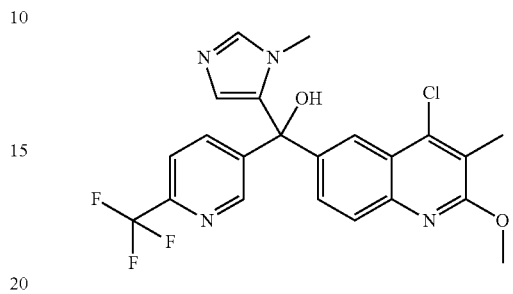

A solution of n-butyllithium in hexanes (1.6 M, 0.65 mL, 1.0 mmol) was added dropwise to a stirring suspension of 6-bromo-4-chloro-2-methoxy-3-methylquinoline (0.3 g, 1.0 mmol, Intermediate 9: step b) in tetrahydrofuran (5 mL) at −78° C. After 3 minutes, a solution of (1-methyl-1H-imidazol-5-yl)(6-(trifluoromethyl)pyridin-3-yl)methanone (294 mg, 1.15 mmol, Intermediate 10: step c) in tetrahydrofuran (5 mL) was added dropwise. After 10 minutes, the flask was placed in an ice-water bath. After 20 minutes, water (5 mL) and ethyl acetate (25 mL) were added sequentially. The biphasic mixture was partitioned between saturated aqueous sodium chloride solution (50 mL) and ethyl acetate (50 mL). The layers were separated. The organic layer was dried with sodium sulfate and the dried solution was filtered. Silica gel (5 g) was added to the filtrate and the mixture was concentrated by rotary evaporation to afford a free-flowing powder. The powder was loaded onto a silica gel column for flash column chromatography purification. Elution with dichloromethane initially, grading to 5% methanol-dichloromethane provided the title compound as an off-white solid. $^1$H NMR (500 MHz, CDCl$_3$) δ ppm 8.81 (d, J=2.2 Hz, 1H), 8.10 (d, J=2.2 Hz, 1H), 7.89 (d, J=10.1 Hz, 1H), 7.80 (dd, J=8.6, 0.6 Hz, 1H), 7.65 (dd, J=8.2, 0.8 Hz, 1H), 7.48 (dd, J=8.8, 2.2 Hz, 1H), 7.37-7.32 (m, 1H), 6.36 (d, J=1.1 Hz, 1H), 4.70 (br s, 1H), 4.09 (s, 3H), 3.37 (s, 3H), 2.43 (s, 3H); MS (ESI): mass calcd. for $C_{22}H_{18}ClF_3N_4O_2$, 462.1; m/z found, 463.0 [M+H]$^+$.

Example 19: (3-Chlorophenyl)[2,4-dichloro-3-(1-methylethyl)quinolin-6-yl]pyridin-3-ylmethanol.TFA

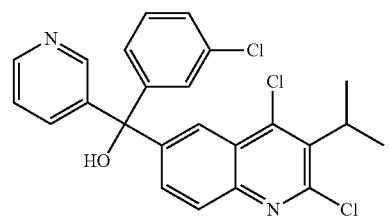 [SMILES: CC(C)c1c(Cl)nc2ccc(C(O)(c3cccnc3)c3cccc(Cl)c3)cc2c1Cl]

To a solution of 6-bromo-2,4-dichloro-3-isopropylquinoline (640 mg, 2.01 mmol, Intermediate 67: step a) and (3-chlorophenyl)(pyridin-3-yl)methanone (481 mg, 2.21 mmol) in THF (20 mL) at −78° C. was added n-BuLi (1.6 M in hexanes, 1.63 mL, 2.61 mmol). The resulting solution was stirred at −78° C. for 10 minutes, then allowed to warm to room temperature. The mixture was quenched with saturated aqueous NH$_4$Cl and extracted with DCM. The organics were combined, dried, filtered and concentrated to dryness. The residue was purified by FCC (0-80% EtOAc/heptane) followed by HPLC to provide the title compound as a white solid. $^1$H NMR (400 MHz, CDCl$_3$) δ ppm 1.50 (d, J=7.6 Hz, 6H), 3.93-4.16 (m, 1H), 7.11 (d, J=7.6 Hz, 1H), 7.23-7.30 (m, 1H), 7.30-7.40 (m, 2H), 7.59 (dd, J=8.6, 2.0 Hz, 1H), 7.85 (dd, J=8.6, 5.6 Hz, 1H), 7.98 (d, J=8.6 Hz, 1H), 8.14 (d, J=2.0 Hz, 1H), 8.27 (d, J=8.1 Hz, 1H), 8.81 (d, J=4.5 Hz, 1H), 9.11 (s, 1H). MS (ESI): mass calcd. for C$_{24}$H$_{19}$Cl$_3$N$_2$O, 456.1; m/z found, 456.8 [M+H]$^+$.

Example 20: [4-Chloro-3-(1-methylethyl)-2-pyrimidin-5-ylquinolin-6-yl](3-chlorophenyl)pyridin-3-ylmethanol

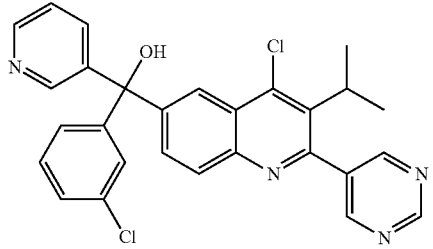 [SMILES: CC(C)c1c(-c2cncnc2)nc2ccc(C(O)(c3cccnc3)c3cccc(Cl)c3)cc2c1Cl]

A mixture of (3-chlorophenyl)[2,4-dichloro-3-(1-methylethyl)quinolin-6-yl]pyridin-3-ylmethanol (80 mg, 0.15 mmol, Example 19), pyrimidin-5-ylboronic acid (23 mg, 0.18 mmol), PdCl$_2$(dppf) (11 mg, 0.015 mmol) and K$_2$CO$_3$ (43 mg, 0.31 mmol) in 1,4-dioxane (10 mL) and water (2 mL) was heated to 70° C. for 3 hours. The mixture was cooled to room temperature, diluted with EtOAc and washed with water. The organics were dried (Na$_2$SO$_4$), filtered and concentrated to dryness. The residue was purified by FCC (0-6% MeOH/EtOAc) to provide the title compound as a white solid. $^1$H NMR (400 MHz, CDCl$_3$) δ ppm 1.45 (d, J=7.1 Hz, 6H), 3.40 (dt, J=14.3, 7.3 Hz, 1H), 3.72 (s, 1H), 7.19 (d, J=7.6 Hz, 1H), 7.28-7.39 (m, 4H), 7.64-7.74 (m, 2H), 8.04 (d, J=9.1 Hz, 1H), 8.32 (d, J=2.0 Hz, 1H), 8.57 (br. s., 2H), 8.87 (s, 2H), 9.32 (s, 1H). MS (ESI): mass calcd. for C$_{28}$H$_{22}$Cl$_2$N$_4$O, 500.1; m/z found, 500.9 [M+H]$^+$.

Example 21: (3-Chlorophenyl)(2,4-dichloro-3-methylquinolin-6-yl)pyridin-3-ylmethanol.TFA

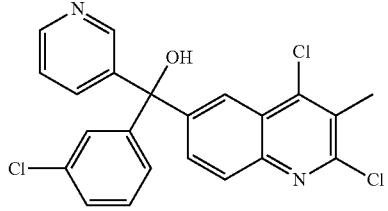 [SMILES: Cc1c(Cl)nc2ccc(C(O)(c3cccnc3)c3cccc(Cl)c3)cc2c1Cl]

The title compound was prepared using 6-bromo-2,4-dichloro-3-methylquinoline (Intermediate 9: step a) in place of 6-bromo-2,4-dichloro-3-isopropylquinoline using the procedure described for Example 19. $^1$H NMR (400 MHz, CDCl$_3$) δ ppm 2.65 (s, 3H), 7.11 (d, J=7.6 Hz, 1H), 7.27 (br. s., 1H), 7.29-7.38 (m, 2H), 7.57 (dd, J=8.6, 2.0 Hz, 1H), 7.82 (dd, J=8.1, 5.6 Hz, 1H), 7.96 (d, J=9.1 Hz, 1H), 8.06 (d, J=2.0 Hz, 1H), 8.23 (d, J=8.1 Hz, 1H), 8.76 (d, J=5.1 Hz, 1H), 9.09 (br. s., 1H). MS (ESI): mass calcd. for C$_{22}$H$_{15}$Cl$_3$N$_2$O, 428.0; m/z found, 428.9 [M+H]$^+$.

Example 22: (4-Chloro-3-methyl-2-pyrimidin-5-ylquinolin-6-yl)(3-chlorophenyl)pyridin-3-ylmethanol

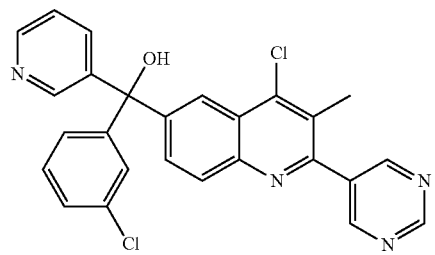 [SMILES: Cc1c(-c2cncnc2)nc2ccc(C(O)(c3cccnc3)c3cccc(Cl)c3)cc2c1Cl]

A mixture of (3-chlorophenyl)(2,4-dichloro-3-methylquinolin-6-yl)pyridin-3-ylmethanol (80 mg, 0.16 mmol, Example 21), pyrimidin-5-ylboronic acid (24 mg, 0.19 mmol), PdCl$_2$(dppf) (12 mg, 0.016 mmol) and K$_2$CO$_3$ (44 mg, 0.32 mmol) in 1,4-dioxane (10 mL) and water (2 mL) was heated to 70° C. for 3 hours. The mixture was cooled to room temperature, diluted with EtOAc and washed with water. The organics were dried (Na$_2$SO$_4$), filtered and concentrated to dryness. The residue was purified by FCC (0-6% MeOH/EtOAc) to provide the title compound as a white solid. $^1$H NMR (400 MHz, CDCl$_3$) δ ppm 2.58 (s, 3H), 3.49 (s, 1H), 7.19 (d, J=7.1 Hz, 1H), 7.28-7.40 (m, 4H), 7.64-7.75 (m, 2H), 8.08 (d, J=8.6 Hz, 1H), 8.24 (d, J=2.0 Hz, 1H), 8.59 (br. s., 2H), 8.99 (s, 2H), 9.32 (s, 1H). MS (ESI): mass calcd. for C$_{26}$H$_{18}$Cl$_2$N$_4$O, 472.1; m/z found, 472.8 [M+H]$^+$.

Example 23: [4-Chloro-3-(1-methylethyl)-2-thiophen-3-ylquinolin-6-yl](3-chlorophenyl)pyridin-3-ylmethanol

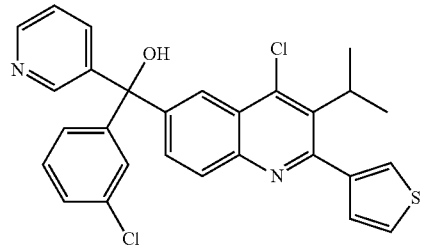 [SMILES: CC(C)c1c(-c2ccsc2)nc2ccc(C(O)(c3cccnc3)c3cccc(Cl)c3)cc2c1Cl]

The title compound was prepared using thiophen-3-ylboronic acid in place of pyrimidin-5-ylboronic acid using the procedure described for Example 20. $^1$H NMR (400 MHz, CDCl$_3$) δ ppm 1.45 (d, J=7.1 Hz, 6H), 3.64 (quin, J=7.2 Hz, 1H), 7.10 (d, J=7.6 Hz, 1H), 7.28 (d, J=4.0 Hz, 2H), 7.31-7.40 (m, 3H), 7.53 (dd, J=5.1, 3.0 Hz, 1H), 7.69-7.77 (m, 2H), 7.80 (dd, J=8.1, 5.6 Hz, 1H), 8.23 (d, J=8.1 Hz, 1H), 8.27 (d, J=9.1 Hz, 1H), 8.32 (d, J=2.0 Hz, 1H), 8.76 (d, J=4.0 Hz, 1H), 8.95 (s, 1H). MS (ESI): mass calcd. for C$_{28}$H$_{22}$Cl$_2$N$_2$OS, 504.1; m/z found, 504.9 [M+H]$^+$.

Example 24: [4-Chloro-3-methyl-2-(1-methyl-1H-indazol-5-yl)quinolin-6-yl](3-chlorophenyl)pyridin-3-ylmethanol

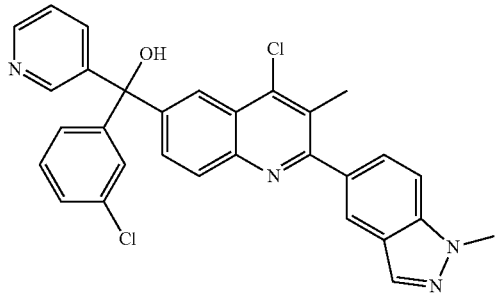 [SMILES: Cc1c(-c2ccc3c(cnn3C)c2)nc2ccc(C(O)(c3cccnc3)c3cccc(Cl)c3)cc2c1Cl]

The title compound was prepared using (1-methyl-1H-indazol-5-yl)boronic acid in place of pyrimidin-5-ylboronic acid using the procedure described for Example 22. $^1$H NMR (400 MHz, CDCl$_3$) δ ppm 2.54 (s, 3H), 3.56 (s, 1H), 4.14 (s, 3H), 7.19 (d, J=7.3 Hz, 1H), 7.27-7.34 (m, 3H), 7.39 (s, 1H), 7.51 (d, J=8.6 Hz, 1H), 7.60 (d, J=8.8 Hz, 2H), 7.70 (d, J=8.1 Hz, 1H), 7.92 (s, 1H), 8.04-8.10 (m, 2H), 8.19 (d, J=1.7 Hz, 1H), 8.55 (d, J=3.9 Hz, 1H), 8.59 (br. s., 1H). MS (ESI): mass calcd. for C$_{30}$H$_{22}$Cl$_2$N$_4$O, 524.1; m/z found, 524.8 [M+H]$^+$.

Example 25: [4-Chloro-3-methyl-2-(1-methyl-1H-indazol-6-yl)quinolin-6-yl](3-chlorophenyl)pyridin-3-ylmethanol

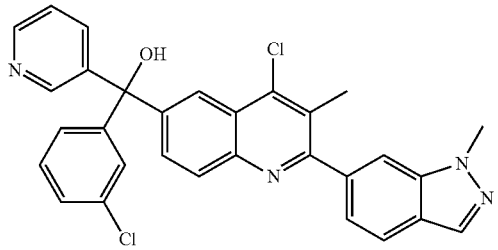 [SMILES: Cc1c(-c2ccc3cnn(C)c3c2)nc2ccc(C(O)(c3cccnc3)c3cccc(Cl)c3)cc2c1Cl]

The title compound was prepared using (1-methyl-1H-indazol-6-yl)boronic acid in place of pyrimidin-5-ylboronic acid using the procedure described for Example 22. $^1$H NMR (400 MHz, CDCl$_3$) δ ppm 2.53 (s, 3H), 3.55 (s, 1H), 4.12 (s, 3H), 7.20 (d, J=7.1 Hz, 1H), 7.27-7.36 (m, 4H), 7.39 (s, 1H), 7.59-7.64 (m, 2H), 7.70 (d, J=8.1 Hz, 1H), 7.83 (d, J=7.6 Hz, 1H), 8.04 (s, 1H), 8.10 (d, J=8.6 Hz, 1H), 8.22 (d, J=2.0 Hz, 1H), 8.58 (d, J=9.1 Hz, 2H). MS (ESI): mass calcd. for C$_{30}$H$_{22}$Cl$_2$N$_4$O, 524.1; m/z found, 524.8 [M+H]$^+$.

Example 26: (3-tert-Butyl-2,4-dichloroquinolin-6-yl)(3-chlorophenyl)pyridin-3-ylmethanol.TFA

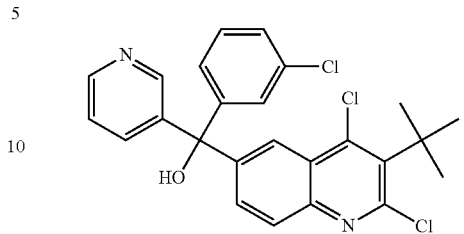

To a solution of 6-bromo-3-(tert-butyl)-2,4-dichloroquinoline (666 mg, 2 mmol, Intermediate 18: step b) and (3-chlorophenyl)(pyridin-3-yl)methanone (479 mg, 2.2 mmol) in THF (20 mL) at −78° C. was added n-BuLi (1.6 M in hexanes, 1.63 mL, 2.6 mmol). The resulting solution was stirred at −78° C. for 10 minutes, then allowed to warm to room temperature. The mixture was quenched with saturated aqueous NH$_4$Cl, the layers separated, and the aqueous further extracted with DCM. The organics were combined, dried, filtered and concentrated to dryness. The residue was purified by FCC (0-80% EtOAc/heptane) followed by HPLC to provide the title compound as a white solid. $^1$H NMR (400 MHz, CDCl$_3$) δ ppm 1.78 (s, 9H), 7.11 (d, J=7.6 Hz, 1H), 7.28 (s, 1H), 7.32-7.41 (m, 2H), 7.57 (dd, J=8.8, 2.3 Hz, 1H), 7.84 (dd, J=8.1, 5.6 Hz, 1H), 7.95 (d, J=8.6 Hz, 1H), 8.23 (d, J=2.0 Hz, 1H), 8.27 (d, J=8.1 Hz, 1H), 8.82 (d, J=4.5 Hz, 1H), 9.07 (s, 1H). MS (ESI): mass calcd. for C$_{25}$H$_{21}$Cl$_3$N$_2$O, 470.1; m/z found, 471.8 [M+H]$^+$.

Example 27: {3-tert-Butyl-4-chloro-2-[(E)-2-phenylethenyl]quinolin-6-yl}(3-chlorophenyl)pyridin-3-ylmethanol.TFA

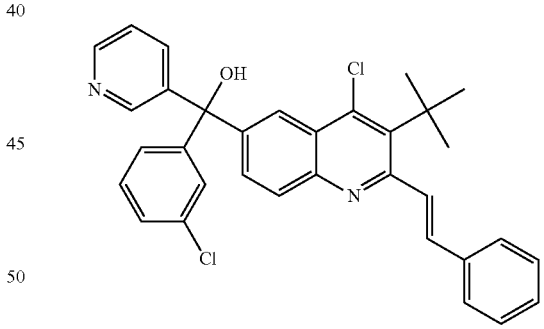

A mixture of (3-tert-butyl-2,4-dichloroquinolin-6-yl)(3-chlorophenyl)pyridin-3-ylmethanol (80 mg, 0.14 mmol, Example 26), (E)-styrylboronic acid (25 mg, 0.17 mmol), PdCl$_2$(dppf) (11 mg, 0.014 mmol) and K$_2$CO$_3$ (39 mg, 0.28 mmol) in 1,4-dioxane (10 mL) and water (2 mL) was heated to 70° C. for 3 hours. The mixture was cooled to room temperature, diluted with EtOAc and washed with water. The organics were dried (Na$_2$SO$_4$), filtered and concentrated to dryness. The residue was purified by FCC (0-100% EtOAc/Heptane) followed by reverse-phase HPLC (acetonitrile/water+TFA) to provide the title compound as a yellow solid. $^1$H NMR (400 MHz, CDCl$_3$) δ ppm 1.69-1.81 (m, 9H), 7.04-7.16 (m, 2H), 7.27-7.37 (m, 3H), 7.39-7.44 (m, 2H), 7.49 (s, 2H), 7.53-7.61 (m, 2H), 7.74-7.86 (m, 2H), 8.25 (d, J=8.6 Hz, 1H), 8.28-8.43 (m, 2H), 8.71 (d, J=4.5 Hz, 1H), 8.93 (s, 1H). MS (ESI): mass calcd. for $C_{33}H_{28}Cl_2N_2O$, 538.2; m/z found, 539.2 [M+H]$^+$.

Example 28: (3-tert-Butyl-2,4-difuran-2-ylquinolin-6-yl)(3-chlorophenyl)pyridin-3-ylmethanol.TFA

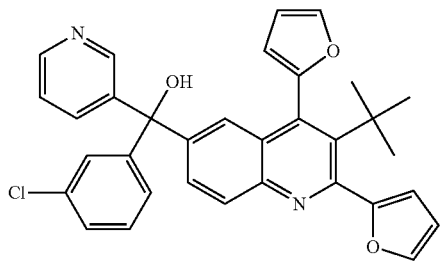 [SMILES: CC(C)(C)c1c(-c2ccco2)nc2ccc(C(O)(c3cccnc3)c3cccc(Cl)c3)cc2c1-c1ccco1]

The title compound was prepared using furan-2-ylboronic acid in place of (E)-styrylboronic acid using the procedure described for Example 27. $^1$H NMR (400 MHz, CDCl$_3$) δ ppm 1.04-1.21 (m, 9H), 6.40 (d, J=2.9 Hz, 1H), 6.48 (br. s., 1H), 6.55-6.69 (m, 1H), 6.85-7.01 (m, 2H), 7.07 (br. s., 1H), 7.29 (br. s., 3H), 7.49 (s, 1H), 7.55-7.77 (m, 3H), 8.17 (d, J=8.6 Hz, 2H), 8.80 (br. s., 2H). MS (ESI): mass calcd. for $C_{33}H_{27}ClN_2O_3$, 534.2; m/z found, 535.2 [M+H]$^+$.

Example 29: (3-Chlorophenyl)(2,4-dichloro-3-cyclohexylquinolin-6-yl)pyridin-3-ylmethanol.TFA

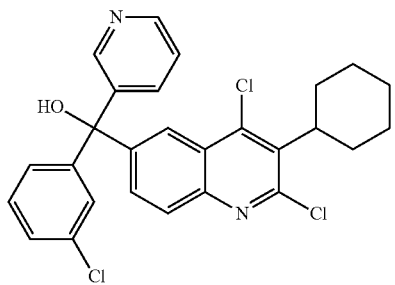 [SMILES: OC(c1cccnc1)(c1cccc(Cl)c1)c1ccc2nc(Cl)c(C3CCCCC3)c(Cl)c2c1]

To a solution of 6-bromo-2,4-dichloro-3-cyclohexylquinoline (710 mg, 1.98 mmol, Intermediate 19: step b) and (3-chlorophenyl)(pyridin-3-yl)methanone (474 mg, 2.18 mmol) in THF (31 mL) at −78° C. was added n-BuLi (1.6 M in hexanes, 1.61 mL, 2.57 mmol). The resulting solution was stirred at −78° C. for 10 minutes, then allowed to warm to room temperature. The mixture was quenched with saturated aqueous NH$_4$Cl, the layers separated, and the aqueous further extracted with DCM. The organics were combined, dried, filtered and concentrated to dryness. The residue was purified by FCC (0-80% EtOAc/heptane) followed by reverse-phase HPLC (acetonitrile/water+TFA) to provide the title compound as a white solid. $^1$H NMR (400 MHz, CDCl$_3$) δ ppm 1.28-1.52 (m, 3H), 1.58-1.83 (m, 3H), 1.93 (s, 1H), 1.90 (s, 1H), 2.26-2.53 (m, 2H), 3.67 (br. s., 1H), 7.11 (d, J=7.6 Hz, 1H), 7.28 (s, 1H), 7.32-7.42 (m, 2H), 7.57 (dd, J=8.8, 2.3 Hz, 1H), 7.77 (dd, J=8.1, 5.6 Hz, 1H), 7.99 (d, J=8.6 Hz, 1H), 8.12-8.25 (m, 2H), 8.80 (d, J=4.0 Hz, 1H), 8.94 (d, J=2.0 Hz, 1H). MS (ESI): mass calcd. for $C_{27}H_{23}Cl_3N_2O$, 496.1; m/z found, 496.8 [M+H]$^+$.

Example 30: (4-Chloro-3-cyclohexyl-2-pyrimidin-5-ylquinolin-6-yl)(3-chlorophenyl)pyridin-3-ylmethanol

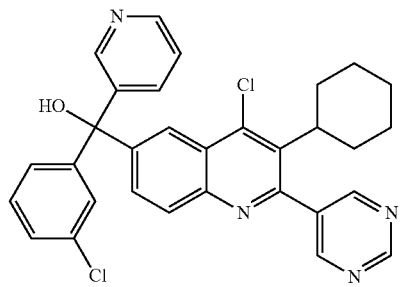 [SMILES: OC(c1cccnc1)(c1cccc(Cl)c1)c1ccc2nc(-c3cncnc3)c(C3CCCCC3)c(Cl)c2c1]

A mixture of (3-chlorophenyl)(2,4-dichloro-3-cyclohexylquinolin-6-yl)pyridin-3-ylmethanol (85 mg, 0.14 mmol, Example 29), pyrimidin-5-ylboronic acid (20 mg, 0.16 mmol), PdCl$_2$(dppf) (10 mg, 0.014 mmol) and K$_2$CO$_3$ (38 mg, 0.27 mmol) in 1,4-dioxane (10 mL) and water (2 mL) was heated to 70° C. for 3 hours. The mixture was cooled to room temperature, diluted with EtOAc and washed with water. The organics were dried (Na$_2$SO$_4$), filtered and concentrated to dryness. The residue was purified by FCC (0-10% MeOH/EtOAc) to provide the title compound as a white solid. $^1$H NMR (400 MHz, CDCl$_3$) δ ppm 1.08-1.31 (m, 3H), 1.68 (br. s., 2H), 1.66 (br. s., 1H), 1.82 (br. s., 1H), 1.79 (br. s., 1H), 2.32 (br. s., 2H), 2.98 (br. s., 1H), 7.19 (d, J=7.1 Hz, 1H), 7.28-7.35 (m, 3H), 7.37 (s, 1H), 7.62-7.74 (m, 2H), 8.03 (d, J=8.6 Hz, 1H), 8.33 (d, J=2.0 Hz, 1H), 8.51-8.63 (m, 2H), 8.86 (s, 2H), 9.28-9.38 (m, 1H). MS (ESI): mass calcd. for $C_{31}H_{26}Cl_2N_4O$, 540.1; m/z found, 540.9 [M+H]$^+$.

Example 31: [2-Azetidin-1-yl-3-(benzyloxy)-4-chloroquinolin-6-yl](1-methyl-1H-imidazol-5-yl)[6-(trifluoromethyl)pyridin-3-yl]methanol.TFA

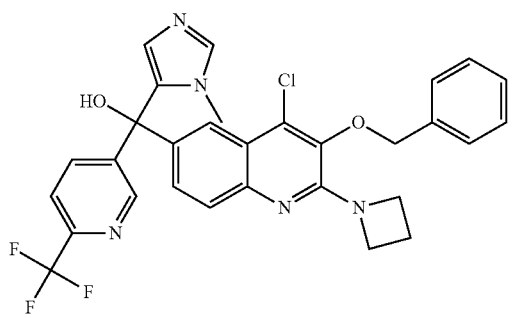 [SMILES: Cn1cncc1C(O)(c1ccc(C(F)(F)F)nc1)c1ccc2nc(N3CCC3)c(OCc3ccccc3)c(Cl)c2c1]

To a sealed tube was added (3-(benzyloxy)-2,4-dichloroquinolin-6-yl)(1-methyl-1H-imidazol-5-yl)(6-(trifluoromethyl)pyridin-3-yl)methanol (200 mg, 0.36 mmol, Example 167), azetidine (20.4 mg, 0.36 mmol) and dimethylformamide (1 mL). The reaction vessel was sealed and heated to 60° C. for 2 hours. One drop of azetidine was then added and the vessel sealed and stirred at 60° C. for 2 hours. Additional azetidine (one drop) was added and the mixture stirred for another 2 hours at 60° C. The reaction was cooled to room temperature, diluted with EtOAc and washed with water five times. The organics were dried (MgSO$_4$), filtered and concentrated to dryness. The crude material was purified by reverse-phase HPLC (acetonitrile/water+0.1% TFA) to provide the title compound as a white solid. ¹H NMR (400 MHz, CD₃OD) δ ppm 9.02 (s, 1H), 8.80-8.77 (m, 1H), 8.17 (d, J=2.0 Hz, 1H), 8.11-8.07 (m, 1H), 7.90 (d, J=8.3 Hz, 1H), 7.87-7.83 (m, 1H), 7.70-7.66 (m, 1H), 7.56-7.52 (m, 2H), 7.45-7.39 (m, 3H), 7.08 (s, 1H), 5.18 (s, 2H), 4.56 (t, J=7.8 Hz, 4H), 3.69 (s, 3H), 2.55-2.46 (m, 2H). MS (ESI): mass calcd. for $C_{30}H_{25}ClF_3N_5O_2$, 579.2; m/z found, 580.2 $[M+H]^+$.

Example 32: {3-[2-(1-Acetylpiperidin-4-yl)ethyl]-4-chloro-2-methoxyquinolin-6-yl}(1-methyl-1H-imidazol-5-yl)[6-(trifluoromethyl)pyridin-3-yl]methanol

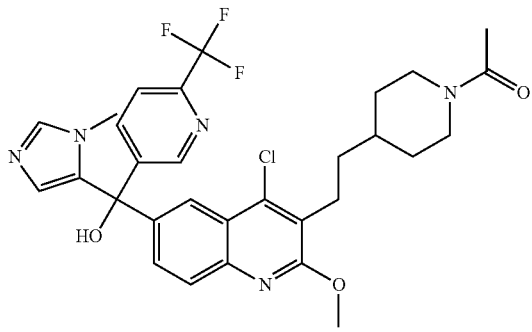 [SMILES: COc1nc2ccc(C(O)(c3ccc(C(F)(F)F)nc3)c3cncn3C)cc2c(Cl)c1CCC1CCN(C(C)=O)CC1]

To a solution of (4-chloro-2-methoxy-3-(2-(piperidin-4-yl)ethyl)quinolin-6-yl)(1-methyl-1H-imidazol-5-yl)(6-(trifluoromethyl)pyridin-3-yl)methanol (50 mg, 0.089 mmol, Example 174) in DCM (1.7 mL) was added Et₃N (14 μL, 0.098 mmol) and the solution cooled to 0° C. Then, acetic anhydride (9 μL, 0.094 mmol) was added dropwise and the mixture stirred at 0° C. for 30 minutes. The solution was diluted with DCM and washed with saturated aqueous NaHCO₃. The organics were dried (MgSO₄), filtered and concentrated to dryness, and the residue was purified by reverse-phase HPLC (acetonitrile/water+0.1% TFA). The acidic fractions were neutralized by diluting with EtOAc and washing with saturated aqueous NaHCO₃. The organics were concentrated to dryness, dissolved in 1/1 acetonitrile/water and lyophilized to provide the title compound as a white solid. ¹H NMR (500 MHz, DMSO-d₆) δ ppm 8.78-8.75 (m, 1H), 8.09 (d, J=2.1 Hz, 1H), 7.95-7.90 (m, 2H), 7.83 (d, J=8.8 Hz, 1H), 7.74 (s, 1H), 7.56 (dd, J=8.6, 2.1 Hz, 1H), 7.43 (s, 1H), 6.22 (s, 1H), 4.40-4.33 (m, 1H), 4.04 (s, 3H), 3.84-3.78 (m, 1H), 3.34 (s, 3H), 3.04-2.97 (m, 1H), 2.92-2.86 (m, 2H), 1.99 (s, 3H), 1.82-1.74 (m, 2H), 1.58-1.51 (m, 1H), 1.50-1.44 (m, 1H), 1.27-0.92 (m, 3H). MS (ESI): mass calcd. for $C_{30}H_{31}ClF_3N_5O_3$, 601.2; m/z found, 602.2 $[M+H]^+$.

Example 33: [4-Chloro-2-methoxy-3-(1-methyl-1,2,3,6-tetrahydropyridin-4-yl)quinolin-6-yl](1-methyl-1H-imidazol-5-yl)[6-(trifluoromethyl)pyridin-3-yl]methanol.TFA

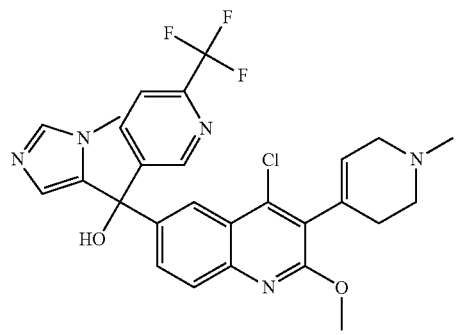 [SMILES: COc1nc2ccc(C(O)(c3ccc(C(F)(F)F)nc3)c3cncn3C)cc2c(Cl)c1C1=CCN(C)CC1]

A mixture of 4-chloro-6-(hydroxy(1-methyl-1H-imidazol-5-yl)(6-(trifluoromethyl)pyridin-3-yl)methyl)-2-methoxyquinolin-3-yl trifluoromethanesulfonate (40 mg, 0.067 mmol, Intermediate 39), 1-methyl-4-(4,4,5,5-tetramethyl-1,3,2-dioxaborolan-2-yl)-1,2,3,6-tetrahydropyridine (23 mg, 0.1 mmol), PdCl₂(dppf) (5 mg, 0.007 mmol) and K₂CO₃ (9 mg, 0.067 mmol) was sparged with nitrogen three times. To this mixture was added 1,4-dioxane (1.1 mL) and water (0.17 mL) and the suspension purged with nitrogen. The resulting solution was heated to 85° C. for 18 hours. The reaction was allowed to cool to room temperature and concentrated to dryness. The residue was dissolved in DMSO, filtered and purified by reverse-phase HPLC (acetonitrile/water+0.1% TFA) to provide the title compound. ¹H NMR (400 MHz, CD₃OD) δ ppm 8.96 (s, 1H), 8.79 (d, J=2.2 Hz, 1H), 8.23 (d, J=2.4 Hz, 1H), 8.11-8.06 (m, 1H), 7.95 (d, J=8.8 Hz, 1H), 7.89 (d, J=8.3 Hz, 1H), 7.74-7.69 (m, 1H), 7.05-7.01 (m, 1H), 5.84-5.78 (m, 1H), 4.19-4.09 (m, 1H), 4.08 (s, 3H), 3.96-3.79 (m, 1H), 3.75-3.63 (m, 4H), 3.55-3.40 (m, 1H), 3.05 (s, 3H), 2.90-2.74 (m, 1H), 2.64-2.51 (m, 1H). MS (ESI): mass calcd. for $C_{27}H_{25}ClF_3N_5O_2$, 543.2; m/z found, 544.2 $[M+H]^+$.

Example 34a: [4-Chloro-2-methoxy-3-(tetrahydrofuran-2-ylmethoxy)quinolin-6-yl][bis(1,2-dimethyl-1H-imidazol-5-yl)]methanol

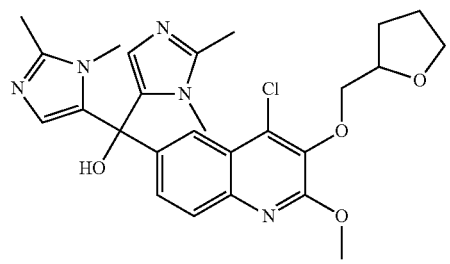 [SMILES: COc1nc2ccc(C(O)(c3cnc(C)n3C)c3cnc(C)n3C)cc2c(Cl)c1OCC1CCCO1]

A mixture of 6-(bis(1,2-dimethyl-1H-imidazol-5-yl)(hydroxy)methyl)-4-chloro-2-methoxyquinolin-3-ol (150 mg, 0.35 mmol, Intermediate 33), tetrahydrofurfuryl alcohol (103 μL, 1.05 mmol) and PPh₃ (276 mg, 1.05 mmol) in THF (0.7 mL) was sonicated to mix the reagents. While sonicating, DIAD (218 μL, 1.05 mmol) was added dropwise and the mixture was sonicated for 15 minutes. The reaction was concentrated to dryness and purified by FCC (1-10% MeOH/DCM) followed by reverse-phase HPLC (acetonitrile/water+NH$_4$OH) to afford the title compound as a white solid. $^1$H NMR (400 MHz, CDCl$_3$) δ ppm 8.15-8.12 (m, 1H), 7.67 (d, J=8.7 Hz, 1H), 7.35-7.30 (m, 1H), 6.18 (s, 2H), 4.84 (s, 1H), 4.37-4.30 (m, 1H), 4.25-4.20 (m, 1H), 4.14-4.11 (m, 4H), 3.99-3.93 (m, 1H), 3.88-3.81 (m, 1H), 3.42-3.39 (m, 6H), 2.31 (s, 6H), 2.16-2.09 (m, 1H), 2.02-1.91 (m, 3H). MS (ESI): mass calcd. for C$_{26}$H$_{30}$ClN$_5$O$_4$, 511.2; m/z found, 512.3 [M+H]$^+$. [4-Chloro-2-methoxy-3-(tetrahydrofuran-2-ylmethoxy)quinolin-6-yl][bis(1,2-dimethyl-1H-imidazol-5-yl)]methanol was purified by chiral SFC (Stationary phase: CHIRALPAK AD-H 5 µM 250×20 mm, Mobile phase: 75% CO$_2$, 25% EtOH (0.3% iPrNH$_2$)) to give 2 enantiomers. The first eluting enantiomer was Example 34b: $^1$H NMR (600 MHz, CDCl$_3$) δ ppm 8.11-8.09 (m, 1H), 7.74 (d, J=8.7 Hz, 1H), 7.39-7.35 (m, 1H), 6.29-6.25 (m, 2H), 4.35-4.31 (m, 1H), 4.22-4.18 (m, 1H), 4.13 (s, 3H), 4.12-4.09 (m, 1H), 3.98-3.94 (m, 1H), 3.86-3.82 (m, 1H), 3.44 (d, J=1.9 Hz, 6H), 3.43-3.40 (m, 1H), 2.36 (s, 6H), 2.15-2.08 (m, 1H), 2.03-1.98 (m, 1H), 1.96-1.91 (m, 2H). MS (ESI): mass calcd. for C$_{26}$H$_{30}$ClN$_5$O$_4$, 511.2; m/z found, 512.1 [M+H]$^+$ and the second eluting enantiomer was Example 34c: $^1$H NMR (600 MHz, CDCl$_3$) δ ppm 8.13-8.10 (m, 1H), 7.73 (d, J=8.5 Hz, 1H), 7.37-7.35 (m, 1H), 6.27-6.23 (m, 2H), 4.35-4.30 (m, 1H), 4.22-4.19 (m, 1H), 4.13 (s, 3H), 4.12-4.09 (m, 1H), 3.98-3.94 (m, 1H), 3.86-3.82 (m, 1H), 3.64 (s, 1H), 3.43 (d, J=2.2 Hz, 6H), 2.35 (s, 6H), 2.15-2.08 (m, 1H), 2.03-1.98 (m, 1H), 1.97-1.91 (m, 2H). MS (ESI): mass calcd. for C$_{26}$H$_{30}$ClN$_5$O$_4$, 511.2; m/z found, 512.1 [M+H]$^+$.

Example 35: (4-Chloro-2,3-dimethoxyquinolin-6-yl)[bis(1,2-dimethyl-1H-imidazol-5-yl)]methanol

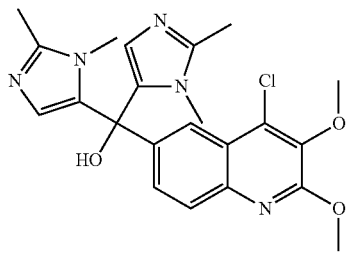 [SMILES: COc1nc2ccc(C(O)(c3cnc(C)n3C)c3cnc(C)n3C)cc2c(Cl)c1OC]

A mixture of 6-(bis(1,2-dimethyl-1H-imidazol-5-yl)(hydroxy)methyl)-4-chloro-2-methoxyquinolin-3-ol (175 mg, 0.41 mmol, Intermediate 33), 2,2-difluorocyclopropylmethanol (57 µL, 0.67 mmol) and PPh$_3$ (161 mg, 0.61 mmol) in THF (0.8 mL) was sonicated to mix the reagents. While sonicating, DIAD (127 µL, 0.61 mmol) was added dropwise and the mixture was sonicated for 15 minutes. Additional 2,2-difluorocyclopropylmethanol (52 µL, 0.61 mmol), PPh$_3$ (161 mg, 0.61 mmol) and DIAD (127 µL, 0.61 mmol) were added and sonication continued for 15 minutes. HPLC indicated two major products, the desired cyclopropyl product as well as the methyl ether by-product. The reaction was concentrated to dryness and purified by FCC (1-10% MeOH/DCM) followed by reverse-phase HPLC (acetonitrile/water+NH$_4$OH) to afford the title compound. $^1$H NMR (400 MHz, CDCl$_3$) δ ppm 8.09 (d, J=2.2 Hz, 1H), 7.76 (d, J=8.7 Hz, 1H), 7.40 (dd, J=8.6, 2.2 Hz, 1H), 6.28 (s, 2H), 4.15 (s, 3H), 3.99 (s, 3H), 3.44 (s, 6H), 2.36 (s, 6H). MS (ESI): mass calcd. for C$_{22}$H$_{24}$ClN$_5$O$_3$, 441.2; m/z found, 442.0 [M+H]$^+$.

Example 36a: {4-Chloro-2-methoxy-3-[(3-methyloxetan-3-yl)methoxy]quinolin-6-yl}(2,6-dimethylpyridin-3-yl)(1-methyl-1H-1,2,3-triazol-5-yl)methanol

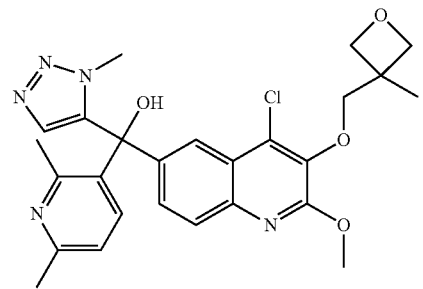 [SMILES: COc1nc2ccc(C(O)(c3ccc(C)nc3C)c3cnnn3C)cc2c(Cl)c1OCC1(C)COC1]

A mixture of 4-chloro-6-((2,6-dimethylpyridin-3-yl)(hydroxy)(1-methyl-1H-1,2,3-triazol-5-yl)methyl)-2-methoxyquinolin-3-ol (200 mg, 0.47 mmol, Intermediate 31), 3-methyl-3-oxetanemethanol (71 µL, 0.7 mmol) and PPh$_3$ (185 mg, 0.7 mmol) in THF (0.94 mL) was sonicated to mix the reagents. While sonicating, DIAD (146 µL, 0.7 mmol) was added dropwise and the mixture was sonicated for 15 minutes. The reaction was concentrated to dryness and purified by FCC (1-10% MeOH/DCM) to afford the title compound as a cloudy white oil. $^1$H NMR (500 MHz, CDCl$_3$) δ ppm 8.00 (d, J=2.2 Hz, 1H), 7.83 (d, J=8.7 Hz, 1H), 7.34-7.31 (m, 1H), 6.99 (s, 1H), 6.95 (s, 2H), 4.74 (d, J=6.0 Hz, 2H), 4.50 (d, J=6.0 Hz, 2H), 4.20 (s, 2H), 4.15 (s, 3H), 3.95 (s, 3H), 3.30 (s, 1H), 2.56 (s, 3H), 2.40 (s, 3H), 1.53-1.52 (m, 3H). MS (ESI): mass calcd. for C$_{26}$H$_{28}$ClN$_5$O$_4$, 509.2; m/z found, 510.5 [M+H]$^+$. {4-Chloro-2-methoxy-3-[(3-methyloxetan-3-yl)methoxy]quinolin-6-yl}(2,6-dimethylpyridin-3-yl)(1-methyl-1H-1,2,3-triazol-5-yl)methanol was purified by chiral SFC (Stationary phase: CHIRALPAK AD 5 µM 250×30 mm, Mobile phase: 80% CO$_2$, 20% MeOH/iPrOH 50/50 v/v+(0.3% iPrNH$_2$)) to give 2 enantiomers. The first eluting enantiomer was Example 36b: $^1$H NMR (400 MHz, CD$_3$OD) δ ppm 8.07-8.05 (m, 1H), 7.86 (d, J=8.6 Hz, 1H), 7.50-7.45 (m, 1H), 7.12-7.06 (m, 2H), 6.97 (s, 1H), 4.82-4.79 (m, 2H), 4.61 (s, 1H), 4.50-4.45 (m, 2H), 4.19 (s, 2H), 4.15 (s, 3H), 3.95 (s, 3H), 2.52 (s, 3H), 2.35 (s, 3H), 1.50 (s, 3H). MS (ESI): mass calcd. for C$_{26}$H$_{28}$ClN$_5$O$_4$, 509.2; m/z found, 510.1 [M+H]$^+$ and the second eluting enantiomer was Example 36c: $^1$H NMR (400 MHz, CD$_3$OD) δ ppm 8.07-8.05 (m, 1H), 7.86 (d, J=8.8 Hz, 1H), 7.49-7.45 (m, 1H), 7.12-7.06 (m, 2H), 6.97-6.96 (m, 1H), 4.81-4.79 (m, 2H), 4.61 (s, 1H), 4.49-4.46 (m, 2H), 4.19 (s, 2H), 4.15 (s, 3H), 3.95 (s, 3H), 2.51 (s, 3H), 2.35 (s, 3H), 1.50 (s, 3H). MS (ESI): mass calcd. for C$_{26}$H$_{28}$ClN$_5$O$_4$, 509.2; m/z found, 510.1 [M+H]$^+$.

Example 37a: [4-Chloro-2-methoxy-3-(2-morpholin-4-ylethoxy)quinolin-6-yl](2,6-dimethylpyridin-3-yl)(1-methyl-1H-1,2,3-triazol-5-yl)methanol

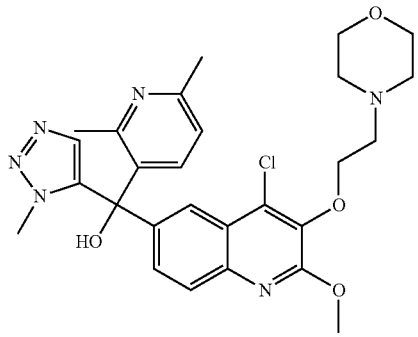 [SMILES: COc1nc2ccc(C(O)(c3ccc(C)nc3C)c3cnnn3C)cc2c(Cl)c1OCCN1CCOCC1]

A mixture of 4-chloro-6-((2,6-dimethylpyridin-3-yl)(hydroxy)(1-methyl-1H-1,2,3-triazol-5-yl)methyl)-2-methoxyquinolin-3-ol (200 mg, 0.47 mmol, Intermediate 31), 4-(2-hydroxyethyl)-morpholine (87 μL, 0.7 mmol) and PPh$_3$ (185 mg, 0.7 mmol) in THF (1.88 mL) was cooled to 0° C. Then DIAD (146 μL, 0.7 mmol) was added dropwise and the mixture was warmed to room temperature and stirred for 30 minutes. The reaction was concentrated to dryness and purified by FCC (1-10% MeOH/DCM) to afford the title compound as a clear colorless oil. $^1$H NMR (400 MHz, CDCl$_3$) δ ppm 8.01 (d, J=2.2 Hz, 1H), 7.79 (d, J=8.7 Hz, 1H), 7.34-7.30 (m, 1H), 6.97-6.91 (m, 2H), 6.89 (s, 1H), 4.55 (s, 1H), 4.27-4.24 (m, 2H), 4.13 (s, 3H), 3.92 (s, 3H), 3.72-3.69 (m, 2H), 3.69-3.65 (m, 4H), 3.62-3.58 (m, 1H), 2.86-2.83 (m, 2H), 2.53 (s, 3H), 2.51-2.49 (m, 1H), 2.35 (s, 3H). MS (ESI): mass calcd. for C$_{27}$H$_{31}$ClN$_6$O$_4$, 538.2; m/z found, 539.1 [M+H]$^+$. [4-Chloro-2-methoxy-3-(2-morpholin-4-ylethoxy)quinolin-6-yl](2,6-dimethylpyridin-3-yl)(1-methyl-1H-1,2,3-triazol-5-yl)methanol was purified by chiral SFC (Stationary phase: CHIRALPAK AD-H 5 μM 250×20 mm, Mobile phase: 75% CO$_2$, 25% MeOH/iPrOH 50/50 v/v+(0.3% iPrNH$_2$)) to give 2 enantiomers. The second eluting enantiomer was Example 37c: $^1$H NMR (400 MHz, CDCl$_3$) δ ppm 7.98 (d, J=2.2 Hz, 1H), 7.82 (d, J=8.8 Hz, 1H), 7.35-7.31 (m, 1H), 6.98 (s, 1H), 6.95 (s, 2H), 4.27 (t, J=5.5 Hz, 2H), 4.13 (s, 3H), 3.94 (s, 3H), 3.71-3.67 (m, 4H), 3.24 (s, 1H), 2.87-2.83 (m, 2H), 2.61-2.56 (m, 4H), 2.56 (s, 3H), 2.40 (s, 3H). MS (ESI): mass calcd. for C$_{27}$H$_{31}$ClN$_6$O$_4$, 538.2; m/z found, 539.1 [M+H]$^+$.

Example 38a: [2-Azetidin-1-yl-4-chloro-3-(1-methylethoxy)quinolin-6-yl](2,6-dimethylpyridin-3-yl)(1-methyl-1H-1,2,3-triazol-5-yl)methanol.TFA

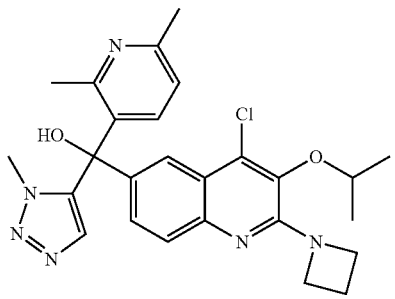 [SMILES: Cc1ccc(C(O)(c2ccc3nc(N4CCC4)c(OC(C)C)c(Cl)c3c2)c2cnnn2C)c(C)n1]

To a sealed tube was added [2,4-dichloro-3-(1-methylethoxy)quinolin-6-yl](2,6-dimethylpyridin-3-yl)(1-methyl-1H-1,2,3-triazol-5-yl)methanol.TFA (182 mg, 0.31 mmol, Example 42), azetidine (107 μL, 1.55 mmol) and dimethylformamide (1.6 mL). The reaction vessel was sealed and heated in a 100° C. oil bath. After overnight heating, the vessel was cooled and the contents concentrated to dryness. The residue was dissolved in EtOAc (25 mL) and washed with saturated aqueous ammonium chloride (2×20 mL). The organics were dried (Na$_2$SO$_4$), filtered and concentrated to dryness to afford a cream-colored foam. The crude material was purified by reverse-phase HPLC (acetonitrile/water+ 0.05% TFA) to provide the title compound as a clear colorless oil. $^1$H NMR (500 MHz, CDCl$_3$) δ ppm 8.04 (d, J=8.8 Hz, 1H), 7.91 (d, J=2.1 Hz, 1H), 7.49-7.46 (m, 1H), 7.44-7.41 (m, 1H), 7.36 (d, J=8.3 Hz, 1H), 6.99 (s, 1H), 4.94-4.89 (m, 1H), 4.78-4.73 (m, 4H), 3.95 (s, 3H), 3.41-3.39 (m, 1H), 2.78 (s, 3H), 2.67 (s, 3H), 2.62-2.55 (m, 2H), 1.43-1.40 (m, 6H). MS (ESI): mass calcd. for C$_{26}$H$_{29}$ClN$_6$O$_2$, 492.2; m/z found, 493.0 [M+H]$^+$. [2-Azetidin-1-yl-4-chloro-3-(1-methylethoxy)quinolin-6-yl](2,6-dimethylpyridin-3-yl)(1-methyl-1H-1,2,3-triazol-5-yl)methanol was purified by chiral SFC (Stationary phase: CHIRALPAK AD-H 5 μM 250×20 mm, Mobile phase: 70% CO$_2$, 30% MeOH/iPrOH 50/50 v/v+(0.3% iPrNH$_2$)) followed by FCC (0.4% NH$_4$OH, 96% DCM, 4% MeOH) to give 2 enantiomers. The first eluting enantiomer was Example 38b: $^1$H NMR (500 MHz, CDCl$_3$) δ ppm 7.85 (d, J=2.2 Hz, 1H), 7.67 (d, J=8.8 Hz, 1H), 7.23-7.19 (m, 1H), 7.01-6.97 (m, 2H), 6.95-6.91 (m, 1H), 4.69-4.63 (m, 1H), 4.32-4.28 (m, 4H), 3.92 (s, 3H), 3.48 (s, 1H), 2.55 (s, 3H), 2.42-2.34 (m, 5H), 1.34 (d, J=6.1 Hz, 6H). MS (ESI): mass calcd. for C$_{26}$H$_{29}$ClN$_6$O$_2$, 492.2; m/z found, 493.2 [M+H]$^+$ and the second eluting enantiomer was Example 38c: $^1$H NMR (500 MHz, CDCl$_3$) δ ppm 7.85 (d, J=2.2 Hz, 1H), 7.67 (d, J=8.8 Hz, 1H), 7.21 (dd, J=8.8, 2.2 Hz, 1H), 7.00-6.97 (m, 2H), 6.95-6.91 (m, 1H), 4.69-4.63 (m, 1H), 4.32-4.27 (m, 4H), 3.92 (s, 3H), 3.57 (s, 1H), 2.54 (s, 3H), 2.41-2.34 (m, 5H), 1.34 (d, J=6.1 Hz, 6H). MS (ESI): mass calcd. for C$_{26}$H$_{29}$ClN$_6$O$_2$, 492.2; m/z found, 493.2 [M+H]$^+$.

Example 39: [2,4-Dichloro-3-(2,2,2-trifluoroethoxy)quinolin-6-yl](1-methyl-1H-imidazol-5-yl)[6-(trifluoromethyl)pyridin-3-yl]methanol

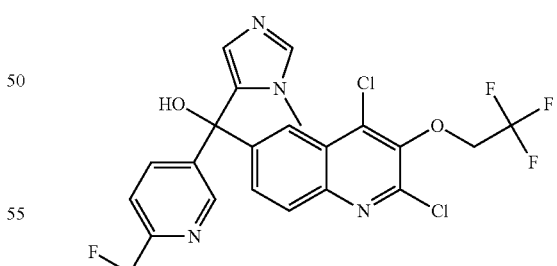

To a solution of 6-bromo-2,4-dichloro-3-(2,2,2-trifluoroethoxy)quinoline (288 mg, 0.77 mmol, Intermediate 23: step d) and (1-methyl-1H-imidazol-5-yl)(6-(trifluoromethyl)pyridin-3-yl)methanone (196 mg, 0.77 mmol, Intermediate 10: step c) in THF (18.3 mL) at −40° C. was added n-BuLi (1.23 M in hexanes, 624 μL, 0.77 mmol) dropwise. The resulting dark yellow solution was stirred at −40° C. for 30 minutes. n-BuLi (1.23 M in hexanes, 624 μL, 0.77 mmol) was added and the mixture stirred at −40° C. for 30 minutes, then warmed to 0° C. and stirred for an additional 30 minutes. Saturated aqueous NH$_4$Cl (7 mL), water (15 mL) and EtOAc (20 mL) were added and the layers separated. The aqueous layer was further extracted with EtOAc (20 mL). The organics were combined, dried (Na$_2$SO$_4$), filtered and concentrated to dryness to afford a yellow oil. The crude material was purified by FCC (0.5-7.5% MeOH/DCM) followed by reverse-phase HPLC (acetonitrile/water+0.05% TFA) to provide the title compound as a light yellow oil. $^1$H NMR (500 MHz, CDCl$_3$) δ ppm 8.87-8.85 (m, 1H), 8.33-8.30 (m, 1H), 8.24-8.22 (m, 1H), 8.08 (d, J=8.8 Hz, 1H), 7.93-7.90 (m, 1H), 7.72 (d, J=8.2 Hz, 1H), 7.71-7.67 (m, 1H), 6.73-6.71 (m, 1H), 4.58-4.51 (m, 2H), 3.63 (s, 3H). MS (ESI): mass calcd. for C$_{22}$H$_{14}$Cl$_2$F$_6$N$_4$O$_2$, 550.0; m/z found, 552.9 [M+H]$^+$.

Example 40: [2,4-Dichloro-3-(cyclopropylmethoxy)quinolin-6-yl](1-methyl-1H-imidazol-5-yl)[6-(trifluoromethyl)pyridin-3-yl]methanol.TFA

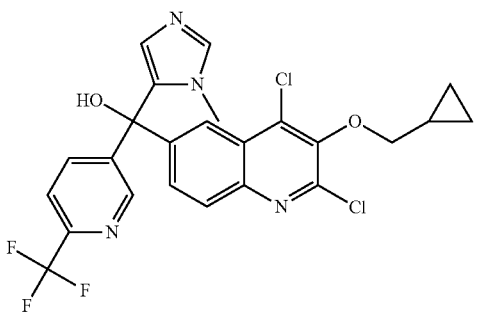 [SMILES: Cn1cncc1C(O)(c1ccc(C(F)(F)F)nc1)c1ccc2nc(Cl)c(OCC3CC3)c(Cl)c2c1]

To a solution of 6-bromo-2,4-dichloro-3-(cyclopropylmethoxy)quinoline (263 mg, 0.76 mmol, Intermediate 24: step b) and (1-methyl-1H-imidazol-5-yl)(6-(trifluoromethyl)pyridin-3-yl)methanone (193 mg, 0.76 mmol, Intermediate 10: step c) in THF (18 mL) at −40° C. was added n-BuLi (1.23 M in hexanes, 616 μL, 0.76 mmol) dropwise. The resulting orange solution was stirred at −40° C. for 30 minutes. n-BuLi (1.23 M in hexanes, 542 μL, 0.67 mmol) was added and the mixture stirred at −40° C. for 2 hours, then warmed to 0° C. and stirred for an additional 30 minutes. Saturated aqueous NH$_4$Cl (7 mL), water (15 mL) and EtOAc (20 mL) were added and the layers separated. The aqueous layer was further extracted with EtOAc (20 mL). The organics were combined, dried (Na$_2$SO$_4$), filtered and concentrated to dryness to afford a yellow foam. The crude material was purified by FCC (0.5-7.5% MeOH/DCM) followed by reverse-phase HPLC (acetonitrile/water+0.05% TFA) to provide the title compound as a clear colorless oil. $^1$H NMR (500 MHz, CDCl$_3$) δ ppm 8.80-8.77 (m, 1H), 8.70 (s, 1H), 8.19-8.17 (m, 1H), 8.01 (d, J=8.8 Hz, 1H), 7.97-7.94 (m, 1H), 7.71 (d, J=8.3 Hz, 1H), 7.64-7.60 (m, 1H), 6.79 (s, 1H), 4.01 (d, J=7.3 Hz, 2H), 3.61 (s, 3H), 1.43-1.36 (m, 1H), 0.68-0.63 (m, 2H), 0.40-0.34 (m, 2H). MS (ESI): mass calcd. for C$_{24}$H$_{19}$Cl$_2$F$_3$N$_4$O$_2$, 522.1; m/z found, 523.0 [M+H]$^+$.

Example 41: [2,4-Dichloro-3-(1-methylethoxy)quinolin-6-yl](1,2-dimethyl-1H-imidazol-5-yl)(1-methyl-1H-1,2,3-triazol-5-yl)methanol.TFA

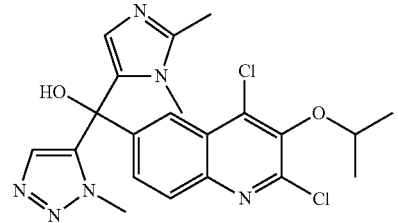 [SMILES: Cc1ncc(C(O)(c2ccc3nc(Cl)c(OC(C)C)c(Cl)c3c2)c2cnnn2C)n1C]

n-BuLi (1.23 M in hexanes, 447 μL, 0.55 mmol) was added dropwise to a stirred slurry of 1-methyl-1,2,3-triazole (46 mg, 0.55 mmol) in THF (1 mL) at −40° C. under nitrogen. After stirring for 30 minutes at −40° C., the mixture was treated dropwise with a solution of (2,4-dichloro-3-isopropoxyquinolin-6-yl)(1,2-dimethyl-1H-imidazol-5-yl)methanone (104 mg, 0.27 mmol, Intermediate 25) in THF (1 mL). The reaction was allowed to warm to room temperature over 1 hour. The reaction was then quenched with saturated aqueous NH$_4$Cl. The mixture was poured into a separatory funnel and extracted with DCM (2×25 mL). The organics were combined, washed with brine, dried (Na$_2$SO$_4$), filtered and concentrated to dryness to afford an orange-brown foam. The crude material was purified by FCC (1-7.5% MeOH/DCM) followed by reverse-phase HPLC (acetonitrile/water+0.05% TFA) to provide the title compound as a clear colorless oil. $^1$H NMR (500 MHz, CDCl$_3$) δ ppm 8.23-8.20 (m, 1H), 7.98 (d, J=8.8 Hz, 1H), 7.52-7.48 (m, 1H), 7.24 (s, 1H), 6.40 (s, 1H), 4.80-4.73 (m, 1H), 3.92 (s, 3H), 3.63 (s, 3H), 2.58 (s, 3H), 1.44-1.41 (m, 6H). MS (ESI): mass calcd. for C$_{21}$H$_{22}$Cl$_2$N$_6$O$_2$, 460.1; m/z found, 461.1 [M+H]$^+$.

Example 42: [2,4-Dichloro-3-(1-methylethoxy)quinolin-6-yl](2,6-dimethylpyridin-3-yl)(1-methyl-1H-1,2,3-triazol-5-yl)methanol.TFA

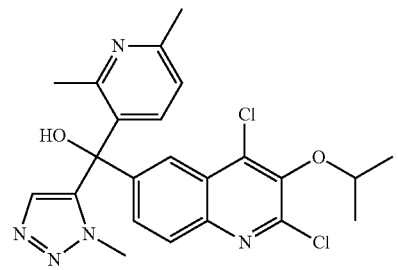 [SMILES: Cc1ccc(C(O)(c2ccc3nc(Cl)c(OC(C)C)c(Cl)c3c2)c2cnnn2C)c(C)n1]

To a solution of 6-bromo-2,4-dichloro-3-isopropoxyquinoline (150 mg, 0.45 mmol, Intermediate 20: step c) and (2,6-dimethylpyridin-3-yl)(1-methyl-1H-1,2,3-triazol-5-yl)methanone (97 mg, 0.45 mmol, Intermediate 11: step b) in THF (10.7 mL) at −40° C. was added n-BuLi (1.23 M in hexanes, 364 μL, 0.45 mmol) dropwise. The resulting red-orange solution was stirred at −40° C. for 30 minutes. Additional n-BuLi (1.23 M in hexanes, 91 μL, 0.11 mmol) and (2,6-dimethylpyridin-3-yl)(1-methyl-1H-1,2,3-triazol-5-yl)methanone (22 mg, 0.1 mmol, Intermediate 11: step b) were added and the mixture stirred at −40° C. for 30 minutes, then warmed to 0° C. and stirred for an additional 30 minutes. Saturated aqueous NH₄Cl (4 mL), water (25 mL) and EtOAc (35 mL) were added and the layers separated. The aqueous layer was further extracted with EtOAc (35 mL). The organics were combined, dried (Na₂SO₄), filtered and concentrated to dryness to afford a yellow oil. The crude material was purified by reverse-phase HPLC (acetonitrile/water+0.05% TFA) to provide the title compound as a clear colorless oil. $^1$H NMR (500 MHz, CDCl₃) δ ppm 8.10-8.08 (m, 1H), 8.07 (d, J=8.8 Hz, 1H), 7.55 (d, J=8.3 Hz, 1H), 7.47-7.44 (m, 1H), 7.37 (d, J=8.4 Hz, 1H), 7.09 (s, 1H), 4.83-4.77 (m, 1H), 3.97 (s, 3H), 2.77 (s, 3H), 2.66 (s, 3H), 1.47-1.44 (m, 6H). MS (ESI): mass calcd. for C₂₃H₂₃Cl₂N₅O₂, 471.1; m/z found, 472.0 [M+H]⁺.

Example 43: [2,4-Dichloro-3-(1-methylethoxy)quinolin-6-yl](2,4-dimethyl-1,3-thiazol-5-yl)(1-methyl-1H-1,2,3-triazol-5-yl)methanol.TFA

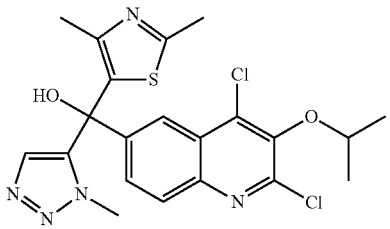 [SMILES: Cc1nc(C)c(C(O)(c2ccc3nc(Cl)c(OC(C)C)c(Cl)c3c2)c2cnnn2C)s1]

To a solution of 6-bromo-2,4-dichloro-3-isopropoxyquinoline (250 mg, 0.75 mmol, Intermediate 20: step c) and (2,4-dimethylthiazol-5-yl)(1-methyl-1H-1,2,3-triazol-5-yl)methanone (166 mg, 0.75 mmol, Intermediate 12: step b) in THF (17.8 mL) at −40° C. was added n-BuLi (1.23 M in hexanes, 607 μL, 0.75 mmol) dropwise. The resulting red-orange solution was stirred at −40° C. for 30 minutes. Additional n-BuLi (1.23 M in hexanes, 152 μL, 0.19 mmol) and (2,4-dimethylthiazol-5-yl)(1-methyl-1H-1,2,3-triazol-5-yl)methanone (41.5 mg, 0.19 mmol, Intermediate 12: step b) were added and the mixture stirred at −40° C. for 30 minutes, then warmed to 0° C. and stirred for an additional 30 minutes. Saturated aqueous NH₄Cl (7 mL), water (25 mL) and EtOAc (35 mL) were added and the layers separated. The aqueous layer was further extracted with EtOAc (35 mL). The organics were combined, dried (Na₂SO₄), filtered and concentrated to dryness to afford a yellow foam. The crude material was purified by FCC (0.5-7.5% MeOH/DCM) followed by reverse-phase HPLC (acetonitrile/water+0.05% TFA) to provide the title compound as a clear colorless oil. $^1$H NMR (500 MHz, CDCl₃) δ ppm 8.19 (d, J=2.1 Hz, 1H), 8.03 (d, J=8.8 Hz, 1H), 7.63 (dd, J=8.9, 2.2 Hz, 1H), 7.27-7.25 (m, 1H), 4.83-4.75 (m, 1H), 3.92 (s, 3H), 2.70 (s, 3H), 2.20 (s, 3H), 1.45 (d, J=6.2 Hz, 6H). MS (ESI): mass calcd. for C₂₁H₂₁Cl₂N₅O₂S, 477.1; m/z found, 478.0 [M+H]⁺.

Example 44: (1-Acetylpiperidin-4-yl)[2,4-dichloro-3-(1-methylethoxy)quinolin-6-yl]phenylmethanol.TFA

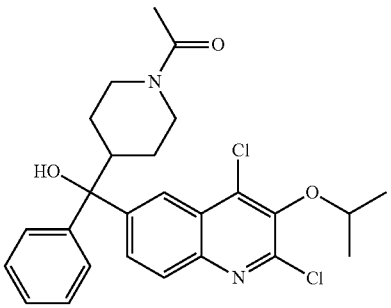 [SMILES: CC(=O)N1CCC(C(O)(c2ccccc2)c2ccc3nc(Cl)c(OC(C)C)c(Cl)c3c2)CC1]

n-BuLi (1.23 M in hexanes, 364 μL, 0.45 mmol) was added dropwise to a stirred solution of 6-bromo-2,4-dichloro-3-isopropoxyquinoline (150 mg, 0.45 mmol, Intermediate 20: step c) in THF (8 mL) at −40° C. under nitrogen. After stirring for 5 minutes at −40° C., the mixture was treated dropwise with a solution of 1-(4-benzoylpiperidin-1-yl)ethanone (104 mg, 0.45 mmol, Intermediate 7) in THF (3 mL). The flask was rinsed with THF (3 mL), which was then added to the reaction. The resulting brown solution was stirred at −40° C. for 15 minutes, then warmed to 0° C. and stirred for an additional 30 minutes. Saturated aqueous NH₄Cl (5 mL), water (20 mL) and EtOAc (25 mL) were added and the layers separated. The aqueous layer was further extracted with EtOAc (25 mL). The organics were combined, dried (Na₂SO₄), filtered and concentrated to dryness to afford a yellow oil. The crude material was purified by reverse-phase HPLC (acetonitrile/water+0.05% TFA) to provide the title compound as a clear colorless oil. $^1$H NMR (500 MHz, CDCl₃) δ ppm 8.36-8.31 (m, 1H), 7.93-7.88 (m, 1H), 7.74-7.66 (m, 1H), 7.56-7.51 (m, 2H), 7.38-7.32 (m, 2H), 7.25-7.22 (m, 1H), 4.79-4.73 (m, 1H), 4.71-4.63 (m, 1H), 3.89-3.79 (m, 1H), 3.30-3.20 (m, 1H), 3.17-3.05 (m, 2H), 2.83-2.75 (m, 1H), 2.68-2.56 (m, 1H), 2.09-2.06 (m, 3H), 1.78-1.70 (m, 1H), 1.52-1.47 (m, 1H), 1.44 (d, J=6.2 Hz, 6H). MS (ESI): mass calcd. for C₂₆H₂₈Cl₂N₂O₃, 486.1; m/z found, 487.0 [M+H]⁺.

Example 45: (4-Chlorophenyl)[2,4-dichloro-3-(2,2,2-trifluoroethoxy)quinolin-6-yl](1-methyl-1H-imidazol-5-yl)methanol

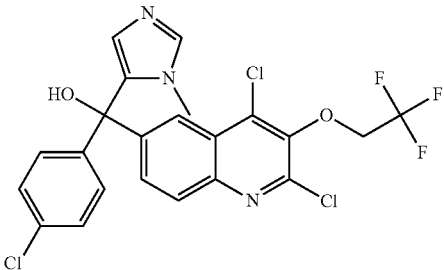 [SMILES: Cn1cncc1C(O)(c1ccc(Cl)cc1)c1ccc2nc(Cl)c(OCC(F)(F)F)c(Cl)c2c1]

To a suspension of 6-bromo-2,4-dichloro-3-(2,2,2-trifluoroethoxy)quinoline (250 mg, 0.67 mmol, Intermediate 23: step d) and (4-chlorophenyl)(1-methyl-1H-imidazol-5-yl)

methanone (147 mg, 0.67 mmol, Intermediate 22: step b) in THF (16 mL) at −40° C. was added n-BuLi (1.23 M in hexanes, 542 µL, 0.67 mmol) dropwise. The resulting dark yellow-brown solution was stirred at −40° C. for 30 minutes. n-BuLi (1.23 M in hexanes, 542 µL, 0.67 mmol) was added and the mixture stirred at −40° C. for 30 minutes, then warmed to 0° C. and stirred for an additional 30 minutes. Saturated aqueous NH₄Cl (6 mL), water (25 mL) and EtOAc (35 mL) were added and the layers separated. The aqueous layer was further extracted with EtOAc (35 mL). The organics were combined, dried (Na₂SO₄), filtered and concentrated to dryness to give a light orange foam. The crude material was purified by FCC (0.5-7.5% MeOH/DCM) followed by reverse-phase HPLC (acetonitrile/water+TFA) to afford the title compound as a clear colorless oil. ¹H NMR (400 MHz, CDCl₃) δ ppm 8.67-8.64 (m, 1H), 8.17 (d, J=2.1 Hz, 1H), 8.07 (d, J=8.8 Hz, 1H), 7.64 (dd, J=8.9, 2.1 Hz, 1H), 7.44-7.39 (m, 2H), 7.29-7.26 (m, 2H), 6.77-6.74 (m, 1H), 4.58-4.50 (m, 2H), 3.67 (s, 3H). MS (ESI): mass calcd. for $C_{22}H_{15}Cl_3F_3N_3O_2$, 515.0; m/z found, 516.8 [M+H]⁺.

Example 46: (2,4-Dichloro-3-ethoxyquinolin-6-yl)(1-methyl-1H-imidazol-5-yl)[6-(trifluoromethyl)pyridin-3-yl]methanol.TFA

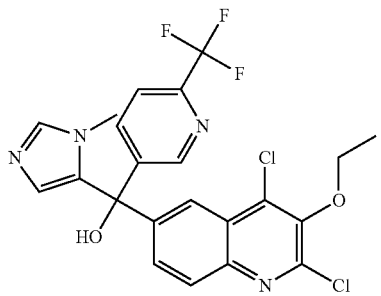 [SMILES: CCOc1c(Cl)nc2ccc(C(O)(c3ccc(C(F)(F)F)nc3)c3cncn3C)cc2c1Cl]

To a solution of 6-bromo-2,4-dichloro-3-ethoxyquinoline (100 mg, 0.31 mmol, Intermediate 21: step b) and (1-methyl-1H-imidazol-5-yl)(6-(trifluoromethyl)pyridin-3-yl)methanone (80 mg, 0.31 mmol, Intermediate 10: step c) in THF (7.4 mL) at −40° C. was added n-BuLi (1.23 M in hexanes, 253 µL, 0.31 mmol) dropwise. The resulting dark yellow solution was stirred at −40° C. for 30 minutes. n-BuLi (1.23 M in hexanes, 253 µL, 0.31 mmol) was added and the mixture stirred at −40° C. for 30 minutes, then warmed to 0° C. and stirred for an additional 30 minutes. Saturated aqueous NH₄Cl (1.5 mL), water (10 mL) and EtOAc (20 mL) were added and the layers separated. The aqueous layer was further extracted with EtOAc (20 mL). The organics were combined, dried (Na₂SO₄), filtered and concentrated to dryness to afford a yellow foam. The crude material was purified by FCC (0.5-7.5% MeOH/DCM) followed by reverse-phase HPLC (acetonitrile/water+0.05% TFA) to provide the title compound as a clear colorless oil. ¹H NMR (500 MHz, CDCl₃) δ ppm 8.90-8.87 (s, 1H), 8.59-8.55 (m, 1H), 8.23-8.20 (m, 1H), 8.06-8.02 (d, J=8.8 Hz, 1H), 7.97-7.93 (m, 1H), 7.73-7.69 (d, J=8.3 Hz, 1H), 7.66-7.63 (m, 1H), 6.85-6.82 (s, 1H), 4.27-4.22 (m, 2H), 3.66-3.63 (s, 3H), 1.56-1.53 (m, 3H). MS (ESI): mass calcd. for $C_{22}H_{17}Cl_2F_3N_4O_2$, 496.1; m/z found, 498.0 [M+H]⁺.

Example 47: (4-Chlorophenyl)(2,4-dichloro-3-ethoxyquinolin-6-yl)(1-methyl-1H-imidazol-5-yl)methanol.TFA

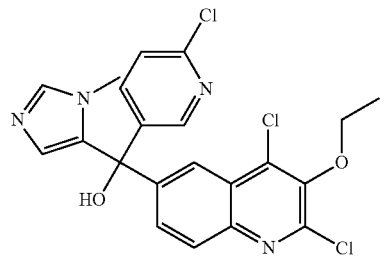 [SMILES: CCOc1c(Cl)nc2ccc(C(O)(c3ccc(Cl)nc3)c3cncn3C)cc2c1Cl]

To a suspension of 6-bromo-2,4-dichloro-3-ethoxyquinoline (250 mg, 0.78 mmol, Intermediate 21: step b) and (4-chlorophenyl)(1-methyl-1H-imidazol-5-yl)methanone (172 mg, 0.78 mmol, Intermediate 22: step b) in THF (18.5 mL) at −40° C. was added n-BuLi (1.23 M in hexanes, 633 µL, 0.78 mmol) dropwise. The resulting dark yellow solution was stirred at −40° C. for 30 minutes, then warmed to 0° C. and stirred for an additional 30 minutes. Saturated aqueous NH₄Cl (9 mL), water (50 mL) and EtOAc (100 mL) were added and the layers separated. The aqueous layer was further extracted with EtOAc (100 mL). The organics were combined, dried (Na₂SO₄), filtered and concentrated to dryness to afford a yellow oil. The crude material was purified by FCC (5-100% EtOAc/hexanes) followed by reverse-phase HPLC (acetonitrile/water+0.05% TFA) to provide the title compound as a clear colorless oil. ¹H NMR (500 MHz, CDCl₃) δ ppm 8.57-8.53 (s, 1H), 8.12-8.10 (m, 1H), 8.05-8.00 (m, 2H), 7.61-7.58 (m, 1H), 7.42-7.38 (m, 2H), 7.30-7.27 (d, J=8.7 Hz, 2H), 6.70-6.68 (s, 1H), 4.28-4.22 (m, 2H), 3.66-3.64 (s, 3H), 1.57-1.53 (m, 3H). MS (ESI): mass calcd. for $C_{22}H_{18}Cl_3N_3O_2$, 461.0; m/z found, 462.0 [M+H]⁺.

Example 48: [2,4-Dichloro-3-(1-methylethoxy)quinolin-6-yl](1-methyl-1H-imidazol-5-yl)[6-(trifluoromethyl)pyridin-3-yl]methanol.TFA

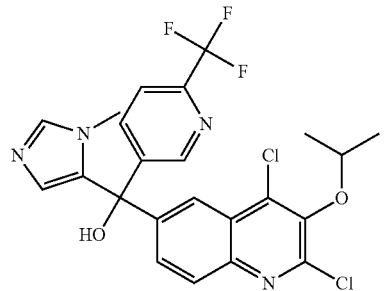 [SMILES: CC(C)Oc1c(Cl)nc2ccc(C(O)(c3ccc(C(F)(F)F)nc3)c3cncn3C)cc2c1Cl]

To a solution of 6-bromo-2,4-dichloro-3-isopropoxyquinoline (300 mg, 0.9 mmol, Intermediate 20: step c) and (1-methyl-1H-imidazol-5-yl)(6-(trifluoromethyl)pyridin-3-yl)methanone (229 mg, 0.9 mmol, Intermediate 10: step c) in THF (21 mL) at −40° C. was added n-BuLi (1.23 M in hexanes, 728 µL, 0.9 mmol) dropwise. The resulting orange solution was stirred at −40° C. for 30 minutes. n-BuLi (1.23 M in hexanes, 728 µL, 0.9 mmol) was added and the mixture stirred at −40° C. for 30 minutes, then warmed to 0° C. and stirred for an additional 30 minutes. Saturated aqueous NH$_4$Cl (7 mL), water (25 mL) and EtOAc (35 mL) were added and the layers separated. The aqueous layer was further extracted with EtOAc (35 mL). The organics were combined, dried (Na$_2$SO$_4$), filtered and concentrated to dryness to afford a yellow foam. The crude material was purified by FCC (0.5-7.5% MeOH/DCM) followed by reverse-phase HPLC (acetonitrile/water+0.05% TFA) to provide the title compound as a clear colorless oil. $^1$H NMR (500 MHz, CDCl$_3$) δ ppm 8.91-8.87 (m, 1H), 8.58-8.53 (m, 1H), 8.23-8.19 (m, 1H), 8.06-8.02 (d, J=8.8 Hz, 1H), 7.98-7.93 (m, 1H), 7.73-7.70 (d, J=8.3 Hz, 1H), 7.66-7.61 (m, 1H), 6.84-6.81 (s, 1H), 4.82-4.75 (m, 1H), 3.67-3.63 (s, 3H), 1.46-1.43 (m, 6H). MS (ESI): mass calcd. for C$_{23}$H$_{19}$Cl$_2$F$_3$N$_4$O$_2$, 510.1; m/z found, 512.1 [M+H]$^+$.

Example 49a: (4-Chlorophenyl)[2,4-dichloro-3-(1-methylethoxy)quinolin-6-yl](1-methyl-1H-imidazol-5-yl)methanol.TFA

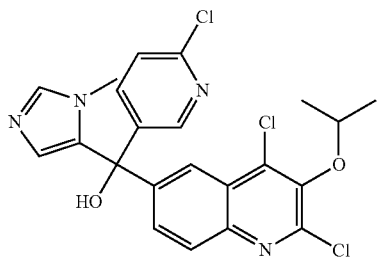 [SMILES: CC(C)Oc1c(Cl)nc2ccc(C(O)(c3ccc(Cl)nc3)c3cncn3C)cc2c1Cl]

To a solution of 6-bromo-2,4-dichloro-3-isopropoxyquinoline (75 mg, 0.22 mmol, Intermediate 20: step c) and (4-chlorophenyl)(1-methyl-1H-imidazol-5-yl)methanone (49.4 mg, 0.22 mmol, Intermediate 22: step b) in THF (5.3 mL) at −40° C. was added n-BuLi (1.23 M in hexanes, 182 μL, 0.22 mmol) dropwise. The resulting dark yellow solution was stirred at −40° C. for 30 minutes. n-BuLi (1.23 M in hexanes, 182 μL, 0.22 mmol) was added and the mixture stirred at −40° C. for 30 minutes, then warmed to 0° C. and stirred for an additional 30 minutes. Saturated aqueous NH$_4$Cl (1 mL), water (10 mL) and EtOAc (15 mL) were added and the layers separated. The aqueous layer was further extracted with EtOAc (10 mL). The organics were combined, dried (Na$_2$SO$_4$), filtered and concentrated to dryness to afford a light yellow oil. The crude material was purified by FCC (0.5-7.5% MeOH/DCM) followed by reverse-phase HPLC (acetonitrile/water+0.05% TFA) to provide the title compound as a clear colorless oil. $^1$H NMR (500 MHz, CDCl$_3$) δ ppm 8.49-8.43 (m, 1H), 8.13-8.10 (m, 1H), 8.01-7.97 (d, J=8.8 Hz, 1H), 7.63-7.59 (m, 1H), 7.39-7.35 (m, 2H), 7.33-7.29 (m, 2H), 6.62-6.58 (s, 1H), 4.80-4.75 (m, 1H), 3.64-3.60 (s, 3H), 1.46-1.43 (m, 6H). MS (ESI): mass calcd. for C$_{23}$H$_{20}$Cl$_3$N$_3$O$_2$, 475.1; m/z found, 477.0 [M+H]$^+$. (4-Chlorophenyl)[2,4-dichloro-3-(1-methylethoxy)quinolin-6-yl](1-methyl-1H-imidazol-5-yl)methanol was purified by achiral SFC (Stationary phase: CHIRALPAK OD-H column, Mobile phase: 90% CO$_2$, 10% MeOH+0.2% iPrNH$_2$) followed by chiral SFC (Stationary phase: CHIRALPAK OJ-H column, Mobile phase: 87% CO$_2$, 13% iPrOH+0.2% iPrNH$_2$) to give 2 enantiomers. The first eluting enantiomer was Example 49b: $^1$H NMR (500 MHz, CDCl$_3$) δ ppm 8.17-8.15 (m, 1H), 7.96 (d, J=8.8 Hz, 1H), 7.64-7.60 (m, 1H), 7.51-7.48 (m, 1H), 7.36-7.30 (m, 4H), 6.51-6.47 (m, 1H), 4.79-4.74 (m, 1H), 3.42 (s, 3H), 3.01-2.97 (m, 1H), 1.44 (d, J=6.2 Hz, 6H). MS (ESI): mass calcd. for C$_{23}$H$_{20}$Cl$_3$N$_3$O$_2$, 475.1; m/z found, 477.0 [M+H]$^+$ and the second eluting enantiomer was Example 49c: $^1$H NMR (500 MHz, CDCl$_3$) δ ppm 8.17-8.15 (m, 1H), 7.96 (d, J=8.8 Hz, 1H), 7.63-7.59 (m, 1H), 7.54-7.49 (m, 1H), 7.36-7.30 (m, 4H), 6.53-6.47 (m, 1H), 4.80-4.74 (m, 1H), 3.42 (s, 3H), 3.05-3.01 (m, 1H), 1.44 (d, J=6.2 Hz, 6H). MS (ESI): mass calcd. for C$_{23}$H$_{20}$Cl$_3$N$_3$O$_2$, 475.1; m/z found, 477.0 [M+H]$^+$.

Example 50a: 1-({4-Chloro-6-[(2,6-dimethylpyridin-3-yl)(hydroxy)(1-methyl-1H-1,2,3-triazol-5-yl)methyl]-2-methoxyquinolin-3-yl}oxy)-2-methylpropan-2-ol

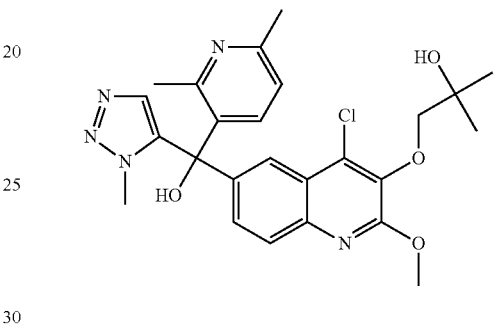

Step A. (3-(2-(benzyloxy)-2-methylpropoxy)-4-chloro-2-methoxyquinolin-6-yl)(2,6-dimethylpyridin-3-yl)(1-methyl-1H-1,2,3-triazol-5-yl)methanol. A mixture of 4-chloro-6-((2,6-dimethylpyridin-3-yl)(hydroxy)(1-methyl-1H-1,2,3-triazol-5-yl)methyl)-2-methoxyquinolin-3-ol (335 mg, 0.79 mmol, Intermediate 31), 2-benzyloxy-2-methylpropan-1-ol (214 μL, 1.18 mmol) and PPh$_3$ (310 mg, 1.18 mmol) in THF (1.57 mL) was sonicated to mix the reagents. While sonicating, DIAD (245 μL, 1.18 mmol) was added dropwise and the mixture was sonicated for 15 minutes. Additional 2-benzyloxy-2-methylpropan-1-ol (214 μL, 1.18 mmol), PPh$_3$ (310 mg, 1.18 mmol) and DIAD (245 μL, 1.18 mmol) were added and sonication continued for 45 minutes. Additional 2-benzyloxy-2-methylpropan-1-ol (214 μL, 1.18 mmol), PPh$_3$ (310 mg, 1.18 mmol) and DIAD (245 μL, 1.18 mmol) were added and sonication continued for 1 hour. Additional 2-benzyloxy-2-methylpropan-1-ol (214 μL, 1.18 mmol), PPh$_3$ (310 mg, 1.18 mmol) and DIAD (245 μL, 1.18 mmol) were added and sonication continued for 30 minutes. Additional 2-benzyloxy-2-methylpropan-1-ol (214 μL, 1.18 mmol), PPh$_3$ (310 mg, 1.18 mmol) and DIAD (245 μL, 1.18 mmol) were added and sonication continued for 1 hour. The reaction was concentrated to dryness and purified twice by FCC (1-10% MeOH/DCM) to afford the title compound as a yellow oil. MS (ESI): mass calcd. for C$_{32}$H$_{34}$ClN$_5$O$_4$, 587.2; m/z found 588.2 [M+H]$^+$.

Step B. To a solution of (3-(2-(benzyloxy)-2-methylpropoxy)-4-chloro-2-methoxyquinolin-6-yl)(2,6-dimethylpyridin-3-yl)(1-methyl-1H-1,2,3-triazol-5-yl)methanol (216 mg, 0.37 mmol, step A) in MeOH (88 mL) was added 10% Pd/C (235 mg, 0.22 mmol). The reaction vessel was evacuated and then placed under an atmosphere of hydrogen for 21.5 hours. The mixture was then flushed with N$_2$ and filtered through a pad of Celite®. The Celite® was rinsed with MeOH and the filtrate was concentrated to dryness. The residue was then resubjected to the reaction conditions, utilizing the H-cube. The solution was run through the H-cube at 1 mL/minute and 40° C. for 3 hours. The solution was concentrated to dryness and the residue was purified by FCC (1-40% acetonitrile/DCM) followed by reverse-phase HPLC (acetonitrile/water+NH$_4$OH) to provide the title compound as a cream-colored solid. $^1$H NMR (500 MHz, CDCl$_3$) δ ppm 8.00 (d, J=2.2 Hz, 1H), 7.82 (d, J=8.7 Hz, 1H), 7.34-7.31 (m, 1H), 6.97 (s, 1H), 6.95 (s, 2H), 4.15 (s, 3H), 4.00 (s, 2H), 3.94 (s, 3H), 3.32 (s, 1H), 2.97 (s, 1H), 2.56 (s, 3H), 2.40 (s, 3H), 1.37 (s, 6H). MS (ESI): mass calcd. for C$_{25}$H$_{28}$ClN$_5$O$_4$, 497.2; m/z found, 498.1 [M+H]$^+$. 1-({4-Chloro-6-[(2,6-dimethylpyridin-3-yl)(hydroxy)(1-methyl-1H-1,2,3-triazol-5-yl)methyl]-2-methoxyquinolin-3-yl}oxy)-2-methylpropan-2-ol was purified by chiral SFC (Stationary phase: CHIRALCEL OD-H 5 μM 250×20 mm, Mobile phase: 65% CO$_2$, 35% iPrOH (0.3% iPrNH$_2$)) to give 2 enantiomers. The first eluting enantiomer was Example 50b: $^1$H NMR (600 MHz, CDCl$_3$) δ ppm 8.02-8.00 (m, 1H), 7.82-7.80 (m, 1H), 7.36-7.33 (m, 1H), 6.96 (s, 2H), 6.95 (s, 1H), 4.14 (s, 3H), 3.95 (s, 3H), 3.68 (d, J=6.8 Hz, 2H), 3.56 (s, 1H), 3.26-3.23 (m, 1H), 2.56 (s, 3H), 2.40 (s, 3H), 1.41 (d, J=3.5 Hz, 6H). MS (ESI): mass calcd. for C$_{25}$H$_{28}$ClN$_5$O$_4$, 497.2; m/z found, 498.1 [M+H]$^+$ and the second eluting enantiomer was Example 50c: $^1$H NMR (600 MHz, CDCl$_3$) δ ppm 8.02-8.00 (m, 1H), 7.83-7.81 (m, 1H), 7.36-7.33 (m, 1H), 6.97 (s, 1H), 6.96 (s, 2H), 4.14 (s, 3H), 3.95 (s, 3H), 3.68 (d, J=6.7 Hz, 2H), 3.41 (s, 1H), 3.24-3.21 (m, 1H), 2.56 (s, 3H), 2.40 (s, 3H), 1.41 (d, J=3.9 Hz, 6H). MS (ESI): mass calcd. for C$_{25}$H$_{28}$ClN$_5$O$_4$, 497.2; m/z found, 498.1 [M+H]$^+$.

Example 51a: (4-Chloro-2-methoxy-3-{[1-methylpiperidin-3-yl]oxy}quinolin-6-yl)[bis(1,2-dimethyl-1H-imidazol-5-yl)]methanol

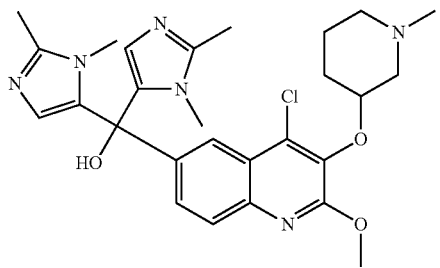 [SMILES: COc1nc2ccc(C(O)(c3cnc(C)n3C)c3cnc(C)n3C)cc2c(Cl)c1OC1CCCN(C)C1]

The title compound was prepared using 3-hydroxy-1-methyl-piperidine in place of tetrahydrofurfuryl alcohol using the procedure described for Example 34a. MS (ESI): mass calcd. for C$_{27}$H$_{33}$ClN$_6$O$_3$, 524.2; m/z found, 525.3 [M+H]$^+$. (4-Chloro-2-methoxy-3-{[1-methylpiperidin-3-yl]oxy}quinolin-6-yl)[bis(1,2-dimethyl-1H-imidazol-5-yl)]methanol was purified by achiral SFC (Stationary phase: CYANO 6 μM 150×21.2 mm, Mobile phase: 85% CO$_2$, 15% MeOH (0.3% iPrNH$_2$)) followed by chiral SFC (Stationary phase: CHIRALPAK AD-H 5 μM 250×20 mm, Mobile phase: 80% CO$_2$, 20% EtOH (0.3% iPrNH$_2$)) to give 2 enantiomers. The first eluting enantiomer was Example 51b: $^1$H NMR (500 MHz, CDCl$_3$) δ ppm 8.10-8.07 (m, 1H), 7.76 (d, J=8.7 Hz, 1H), 7.41-7.37 (m, 1H), 6.29 (d, J=7.4 Hz, 2H), 4.48-4.41 (m, 1H), 4.12 (s, 3H), 3.46-3.44 (m, 6H), 3.15-3.09 (m, 1H), 3.08-2.99 (m, 1H), 2.71-2.62 (m, 1H), 2.37 (s, 6H), 2.36-2.29 (m, 3H), 2.17-2.00 (m, 1H), 1.95-1.86 (m, 1H), 1.64-1.59 (m, 2H). MS (ESI): mass calcd. for C$_{27}$H$_{33}$ClN$_6$O$_3$, 524.2; m/z found, 525.2 [M+H]$^+$ and the second eluting enantiomer was Example 51c: $^1$H NMR (400 MHz, CDCl$_3$) δ ppm 8.17-8.14 (m, 1H), 7.66 (d, J=8.6 Hz, 1H), 7.36-7.29 (m, 1H), 6.20-6.10 (m, 2H), 5.61 (s, 1H), 4.48-4.38 (m, 1H), 4.11 (s, 3H), 3.39 (d, J=6.2 Hz, 6H), 3.09-3.01 (m, 1H), 2.68-2.61 (m, 1H), 2.33 (s, 3H), 2.29-2.26 (m, 6H), 2.13-2.04 (m, 2H), 1.94-1.85 (m, 2H), 1.65-1.55 (m, 2H). MS (ESI): mass calcd. for C$_{27}$H$_{33}$ClN$_6$O$_3$, 524.2; m/z found, 525.2 [M+H]$^+$.

Example 52: {4-Chloro-2-methoxy-3-[(1-methyl-pyrrolidin-2-yl)methoxy]quinolin-6-yl}[bis(1,2-dimethyl-1H-imidazol-5-yl)]methanol

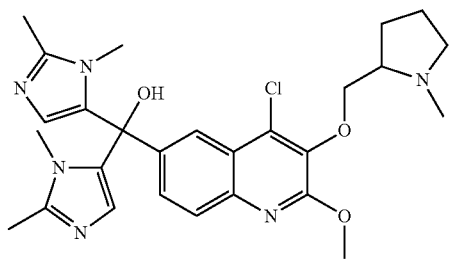 [SMILES: COc1nc2ccc(C(O)(c3cnc(C)n3C)c3cnc(C)n3C)cc2c(Cl)c1OCC1CCCN1C]

The title compound was prepared using 3-hydroxy-1-methyl-piperidine in place of tetrahydrofurfuryl alcohol using the procedure described for Example 34a. Purification was accomplished using achiral SFC (Stationary phase: CYANO 6 μM 150×21.2 mm, Mobile phase: 85% CO$_2$, 15% MeOH (0.3% iPrNH$_2$)). $^1$H NMR (500 MHz, CDCl$_3$) δ ppm 8.10-8.07 (m, 1H), 7.76 (d, J=8.7 Hz, 1H), 7.40-7.37 (m, 1H), 6.29 (d, J=3.7 Hz, 2H), 4.13 (s, 3H), 4.10-4.05 (m, 1H), 3.45-3.44 (m, 6H), 3.16-3.10 (m, 1H), 3.09-3.05 (m, 1H), 2.71-2.62 (m, 1H), 2.52 (s, 3H), 2.37 (s, 6H), 2.33-2.26 (m, 1H), 2.11-2.03 (m, 1H), 1.99-1.90 (m, 1H), 1.90-1.83 (m, 1H), 1.82-1.74 (m, 1H). MS (ESI): mass calcd. for C$_{27}$H$_{33}$ClN$_6$O$_3$, 524.2; m/z found, 525.2 [M+H]$^+$.

Example 53a: [4-Chloro-2-methoxy-3-(tetrahydrofuran-3-ylmethoxy)quinolin-6-yl][bis(1,2-dimethyl-1H-imidazol-5-yl)]methanol

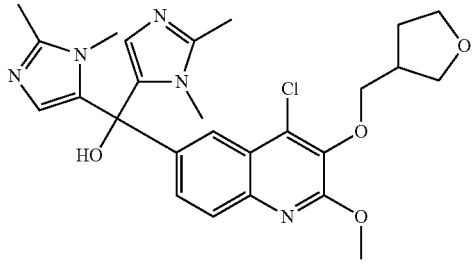 [SMILES: COc1nc2ccc(C(O)(c3cnc(C)n3C)c3cnc(C)n3C)cc2c(Cl)c1OCC1CCOC1]

The title compound was prepared using tetrahydro-3-furan-methanol in place of tetrahydrofurfuryl alcohol using the procedure described for Example 34a. $^1$H NMR (400 MHz, CDCl$_3$) δ ppm 8.14-8.12 (m, 1H), 7.68 (d, J=8.7 Hz, 1H), 7.37-7.32 (m, 1H), 6.19 (s, 2H), 4.74-4.50 (m, 1H), 4.14-4.11 (m, 4H), 4.07-4.04 (m, 1H), 4.02-3.96 (m, 1H), 3.93-3.86 (m, 2H), 3.83-3.76 (m, 1H), 3.41 (s, 6H), 2.87-2.77 (m, 1H), 2.32 (s, 6H), 2.19-2.09 (m, 1H), 1.87-1.78 (m, 1H). MS (ESI): mass calcd. for C$_{26}$H$_{30}$ClN$_5$O$_4$, 511.2; m/z found, 512.3 [M+H]⁺. [4-Chloro-2-methoxy-3-(tetrahydrofuran-3-ylmethoxy)quinolin-6-yl][bis(1,2-dimethyl-1H-imidazol-5-yl)]methanol was purified by chiral SFC (Stationary phase: CHIRALPAK AD-H 5 µM 250×20 mm, Mobile phase: 75% CO$_2$, 25% EtOH (0.3% iPrNH$_2$)) to give 2 enantiomers. The first eluting enantiomer was Example 53b: ¹H NMR (500 MHz, CDCl$_3$) δ ppm 8.11 (s, 1H), 7.73 (d, J=8.6 Hz, 1H), 7.39-7.35 (m, 1H), 6.25 (s, 2H), 4.14-4.11 (m, 4H), 4.05-4.02 (m, 1H), 4.00-3.96 (m, 1H), 3.93-3.86 (m, 2H), 3.82-3.78 (m, 1H), 3.73-3.64 (m, 1H), 3.43 (s, 6H), 2.86-2.79 (m, 1H), 2.35 (s, 6H), 2.18-2.10 (m, 1H), 1.85-1.79 (m, 1H). MS (ESI): mass calcd. for C$_{26}$H$_{30}$ClN$_5$O$_4$, 511.2; m/z found, 512.1 [M+H]⁺ and the second eluting enantiomer was Example 53c: ¹H NMR (500 MHz, CDCl$_3$) δ ppm 8.10 (s, 1H), 7.73 (d, J=8.6 Hz, 1H), 7.37 (d, J=8.7 Hz, 1H), 6.25 (s, 2H), 4.15-4.12 (m, 4H), 4.06-4.01 (m, 1H), 4.00-3.96 (m, 1H), 3.94-3.86 (m, 2H), 3.82-3.77 (m, 1H), 3.75-3.68 (m, 1H), 3.43 (s, 6H), 2.85-2.79 (m, 1H), 2.35 (s, 6H), 2.17-2.10 (m, 1H), 1.85-1.78 (m, 1H). MS (ESI): mass calcd. for C$_{26}$H$_{30}$ClN$_5$O$_4$, 511.2; m/z found, 512.1 [M+H]⁺.

Example 54: 1-({6-[Bis(1,2-dimethyl-1H-imidazol-5-yl)(hydroxy)methyl]-4-chloro-2-methoxyquinolin-3-yl}oxy)-2-methylpropan-2-ol

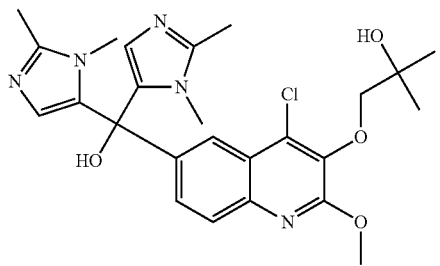 [SMILES: COc1nc2ccc(C(O)(c3cnc(C)n3C)c3cnc(C)n3C)cc2c(Cl)c1OCC(C)(C)O]

The title compound was prepared using 2-methyl-1,2-propanediol in place of tetrahydrofurfuryl alcohol using the procedure described for Example 34a. ¹H NMR (400 MHz, CDCl$_3$) δ ppm 8.11 (d, J=2.1 Hz, 1H), 7.74 (d, J=8.7 Hz, 1H), 7.41 (dd, J=8.7, 2.1 Hz, 1H), 6.25 (s, 2H), 4.13 (s, 3H), 3.68 (s, 2H), 3.44 (s, 6H), 2.35 (s, 6H), 1.42-1.41 (m, 6H). MS (ESI): mass calcd. for C$_{25}$H$_{30}$ClN$_5$O$_4$, 499.2; m/z found, 500.1 [M+H]⁺.

Example 55a: [4-Chloro-2-methoxy-3-(oxetan-2-ylmethoxy)quinolin-6-yl][bis(1,2-dimethyl-1H-imidazol-5-yl)]methanol

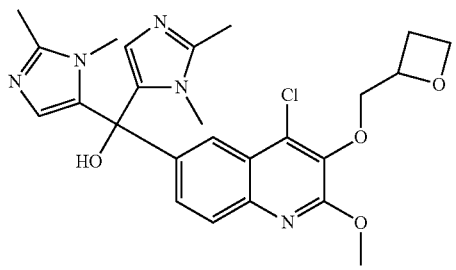 [SMILES: COc1nc2ccc(C(O)(c3cnc(C)n3C)c3cnc(C)n3C)cc2c(Cl)c1OCC1CCO1]

The title compound was prepared using 2-hydroxymethyloxetane in place of tetrahydrofurfuryl alcohol using the procedure described for Example 34a. ¹H NMR (400 MHz, CDCl$_3$) δ ppm 8.17-8.14 (m, 1H), 7.66 (d, J=8.6 Hz, 1H), 7.35-7.30 (m, 1H), 6.15 (s, 2H), 5.47 (s, 1H), 5.19-5.12 (m, 1H), 4.76-4.66 (m, 2H), 4.41-4.30 (m, 2H), 4.14 (s, 3H), 3.40 (s, 6H), 2.89-2.78 (m, 2H), 2.28 (s, 6H). MS (ESI): mass calcd. for C$_{25}$H$_{28}$ClN$_5$O$_4$, 497.2; m/z found, 498.1 [M+H]⁺. [4-Chloro-2-methoxy-3-(oxetan-2-ylmethoxy)quinolin-6-yl][bis(1,2-dimethyl-1H-imidazol-5-yl)]methanol was purified by chiral SFC (Stationary phase: CHIRALPAK AD-H 5 µM 250×20 mm, Mobile phase: 70% CO$_2$, 30% EtOH (0.3% iPrNH$_2$)) to give 2 enantiomers. The first eluting enantiomer was Example 55b: ¹H NMR (400 MHz, CDCl$_3$) δ ppm 8.12-8.09 (m, 1H), 7.75 (d, J=8.7 Hz, 1H), 7.40-7.36 (m, 1H), 6.27 (s, 2H), 5.18-5.12 (m, 1H), 4.75-4.66 (m, 2H), 4.39-4.28 (m, 2H), 4.14 (s, 3H), 3.44 (s, 6H), 3.41-3.37 (m, 1H), 2.87-2.79 (m, 2H), 2.36 (s, 6H). MS (ESI): mass calcd. for C$_{25}$H$_{28}$ClN$_5$O$_4$, 497.2; m/z found, 498.1 [M+H]⁺ and the second eluting enantiomer was Example 55c: ¹H NMR (400 MHz, CDCl$_3$) δ ppm 8.12-8.10 (m, 1H), 7.75 (d, J=8.7 Hz, 1H), 7.41-7.36 (m, 1H), 6.27 (s, 2H), 5.19-5.12 (m, 1H), 4.75-4.66 (m, 2H), 4.39-4.29 (m, 2H), 4.14 (s, 3H), 3.44 (s, 6H), 2.86-2.77 (m, 2H), 2.36 (s, 6H). MS (ESI): mass calcd. for C$_{25}$H$_{28}$ClN$_5$O$_4$, 497.2; m/z found, 498.1 [M+H]⁺.

Example 56a: {4-Chloro-3-[(2,2-difluorocyclopropyl)methoxy]-2-methoxyquinolin-6-yl}[bis(1,2-dimethyl-1H-imidazol-5-yl)]methanol

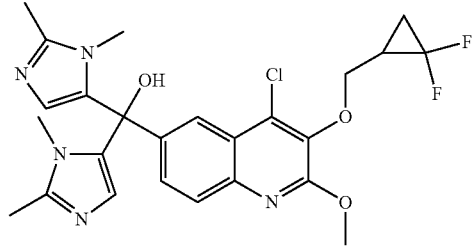 [SMILES: COc1nc2ccc(C(O)(c3cnc(C)n3C)c3cnc(C)n3C)cc2c(Cl)c1OCC1CC1(F)F]

The title compound was prepared using 2,2-difluorocyclopropylmethanol in place of tetrahydrofurfuryl alcohol using the procedure described for Example 34a. ¹H NMR (400 MHz, CDCl$_3$) δ ppm 8.18-8.15 (m, 1H), 7.65 (d, J=8.7 Hz, 1H), 7.37-7.32 (m, 1H), 6.18-6.11 (m, 2H), 5.66 (s, 1H), 4.32-4.17 (m, 2H), 4.13 (s, 3H), 3.39 (s, 6H), 2.29-2.26 (m, 6H), 2.21-2.14 (m, 1H), 1.65-1.55 (m, 1H), 1.39-1.30 (m, 1H). MS (ESI): mass calcd. for C$_{25}$H$_{26}$ClF$_2$N$_5$O$_3$, 517.2; m/z found, 518.1 [M+H]⁺. {4-Chloro-3-[(2,2-difluorocyclopropyl)methoxy]-2-methoxyquinolin-6-yl}[bis(1,2-dimethyl-1H-imidazol-5-yl)]methanol was purified by chiral SFC (Stationary phase: CHIRALPAK AD-H 5 µM 250×20 mm, Mobile phase: 80% CO$_2$, 20% EtOH (0.3% iPrNH$_2$)) to give 2 enantiomers. The first eluting enantiomer was Example 56b: ¹H NMR (400 MHz, CDCl$_3$) δ ppm 8.13-8.09 (m, 1H), 7.75 (d, J=8.7 Hz, 1H), 7.42-7.38 (m, 1H), 6.27 (s, 2H), 4.31-4.17 (m, 2H), 4.14 (s, 3H), 3.55-3.47 (m, 1H), 3.44 (s, 6H), 2.36 (s, 6H), 2.21-2.11 (m, 1H), 1.37-1.28 (m, 2H). MS (ESI): mass calcd. for C$_{25}$H$_{26}$ClF$_2$N$_5$O$_3$, 517.2; m/z found, 518.1 [M+H]⁺ and the second eluting enantiomer was Example 56c: ¹H NMR (400 MHz, CDCl$_3$) δ ppm 8.13-8.09 (m, 1H), 7.75 (d, J=8.7 Hz, 1H), 7.42-7.37 (m, 1H), 6.26 (s, 2H), 4.30-4.18 (m, 2H), 4.14 (s, 3H), 3.73-3.56 (m, 1H), 3.44 (s, 6H), 2.36 (s, 6H), 2.21-2.12 (m, 1H), 1.36-1.29 (m, 2H). MS (ESI): mass calcd. for $C_{25}H_{26}ClF_2N_5O_3$, 517.2; m/z found, 518.1 $[M+H]^+$.

Example 57a: [4-Chloro-3-(1-cyclopropylethoxy)-2-methoxyquinolin-6-yl][bis(1,2-dimethyl-1H-imidazol-5-yl)]methanol

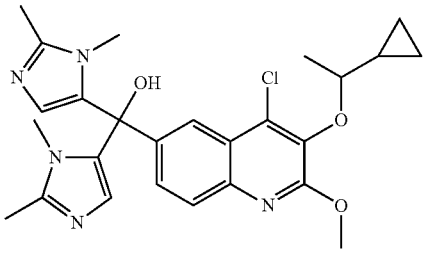 [SMILES: COc1nc2ccc(C(O)(c3cnc(C)n3C)c3cnc(C)n3C)cc2c(Cl)c1OC(C)C1CC1]

The title compound was prepared using alpha-methylcyclopropane methanol in place of tetrahydrofurfuryl alcohol using the procedure described for Example 34a. $^1$H NMR (400 MHz, CDCl$_3$) δ ppm 8.13-8.11 (m, 1H), 7.73 (d, J=8.7 Hz, 1H), 7.39-7.35 (m, 1H), 6.25 (s, 2H), 4.21 (s, 1H), 4.10 (s, 3H), 3.91-3.83 (m, 1H), 3.44-3.42 (m, 6H), 2.32 (s, 6H), 1.49-1.46 (m, 3H), 1.22-1.16 (m, 1H), 0.54-0.42 (m, 2H), 0.21-0.13 (m, 2H). MS (ESI): mass calcd. for $C_{26}H_{30}ClN_5O_3$, 495.2; m/z found, 496.2 $[M+H]^+$. [4-Chloro-3-(1-cyclopropylethoxy)-2-methoxyquinolin-6-yl][bis(1,2-dimethyl-1H-imidazol-5-yl)]methanol was purified by chiral SFC (Stationary phase: CHIRALPAK AD-H 5 μM 250×20 mm, Mobile phase: 70% CO$_2$, 30% EtOH (0.3% iPrNH$_2$)) to give 2 enantiomers. The first eluting enantiomer was Example 57b: $^1$H NMR (400 MHz, CDCl$_3$) δ ppm 8.09 (d, J=2.2 Hz, 1H), 7.77 (d, J=8.7 Hz, 1H), 7.40-7.36 (m, 1H), 6.31 (s, 2H), 4.11 (s, 3H), 3.94-3.84 (m, 1H), 3.47-3.44 (m, 6H), 3.00-2.97 (m, 1H), 2.37 (s, 6H), 1.47 (d, J=6.2 Hz, 3H), 0.55-0.41 (m, 2H), 0.22-0.12 (m, 2H). MS (ESI): mass calcd. for $C_{26}H_{30}ClN_5O_3$, 495.2; m/z found, 496.2 $[M+H]^+$ and the second eluting enantiomer was Example 57c: $^1$H NMR (400 MHz, CDCl$_3$) δ ppm 8.11-8.09 (m, 1H), 7.76 (d, J=8.6 Hz, 1H), 7.40-7.36 (m, 1H), 6.30 (s, 2H), 4.11 (s, 3H), 3.91-3.84 (m, 1H), 3.46-3.44 (m, 6H), 3.25-3.20 (m, 1H), 2.36 (s, 6H), 1.47 (d, J=6.2 Hz, 3H), 0.54-0.42 (m, 2H), 0.22-0.13 (m, 2H). MS (ESI): mass calcd. for $C_{26}H_{30}ClN_5O_3$, 495.2; m/z found, 496.2 $[M+H]^+$.

Example 58: {4-Chloro-3-[(1,3-dimethyl-1H-pyrazol-5-yl)methoxy]-2-methoxyquinolin-6-yl}[bis(1,2-dimethyl-1H-imidazol-5-yl)]methanol

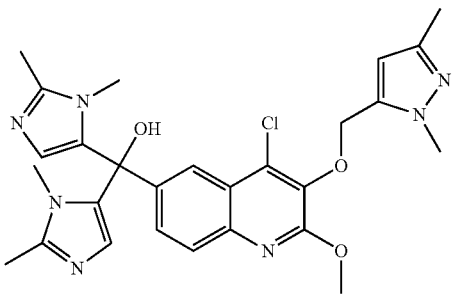 [SMILES: COc1nc2ccc(C(O)(c3cnc(C)n3C)c3cnc(C)n3C)cc2c(Cl)c1OCc1cc(C)nn1C]

The title compound was prepared using (1,3-dimethyl-1H-pyrazol-5-yl)methanol in place of tetrahydrofurfuryl alcohol using the procedure described for Example 34a. $^1$H NMR (400 MHz, CDCl$_3$) δ ppm 8.14-8.11 (m, 1H), 7.70 (d, J=8.7 Hz, 1H), 7.39-7.35 (m, 1H), 6.19 (s, 2H), 6.04 (s, 1H), 5.13 (s, 2H), 4.15 (s, 3H), 4.01 (s, 3H), 3.41 (s, 6H), 2.31 (s, 6H), 2.22 (s, 3H). MS (ESI): mass calcd. for $C_{27}H_{30}ClN_7O_3$, 535.2; m/z found, 536.1 $[M+H]^+$.

Example 59: [4-Chloro-2-methoxy-3-(tetrahydro-2H-pyran-4-yloxy)quinolin-6-yl][bis(1,2-dimethyl-1H-imidazol-5-yl)]methanol

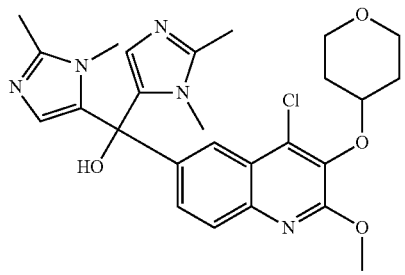 [SMILES: COc1nc2ccc(C(O)(c3cnc(C)n3C)c3cnc(C)n3C)cc2c(Cl)c1OC1CCOCC1]

The title compound was prepared using 4-hydroxytetrahydropyran in place of tetrahydrofurfuryl alcohol using the procedure described for Example 34a. Purification was accomplished by FCC (0-10% MeOH/DCM) followed by reverse-phase HPLC (acetonitrile/water+0.05% TFA) and achiral SFC (Stationary phase: CYANO 6 μM 150×21.2 mm, Mobile phase: 85% CO$_2$, 15% MeOH (0.3% iPrNH$_2$)). $^1$H NMR (500 MHz, CDCl$_3$) δ ppm 8.13-8.11 (m, 1H), 7.72 (d, J=8.7 Hz, 1H), 7.39-7.36 (m, 1H), 6.24 (s, 2H), 4.61-4.55 (m, 1H), 4.13 (s, 3H), 4.10-4.06 (m, 2H), 3.97-3.89 (m, 1H), 3.55-3.50 (m, 2H), 3.43 (s, 6H), 2.34 (s, 6H), 2.04-1.93 (m, 4H). MS (ESI): mass calcd. for $C_{26}H_{30}ClN_5O_4$, 511.2; m/z found, 512.1 $[M+H]^+$.

Example 60: [4-Chloro-2-methoxy-3-(oxetan-3-ylmethoxy)quinolin-6-yl][bis(1,2-dimethyl-1H-imidazol-5-yl)]methanol

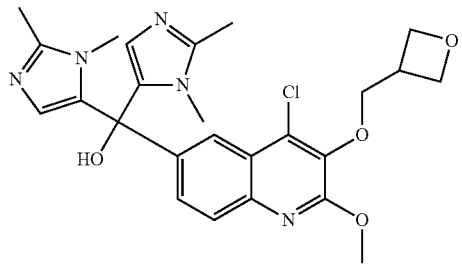 [SMILES: COc1nc2ccc(C(O)(c3cnc(C)n3C)c3cnc(C)n3C)cc2c(Cl)c1OCC1COC1]

The title compound was prepared using 3-oxetanemethanol in place of tetrahydrofurfuryl alcohol using the procedure described for Example 34a. $^1$H NMR (400 MHz, CDCl$_3$) δ ppm 8.15-8.12 (m, 1H), 7.69 (d, J=8.7 Hz, 1H), 7.38-7.33 (m, 1H), 6.19 (s, 2H), 4.94-4.89 (m, 2H), 4.72-4.69 (m, 1H), 4.69-4.65 (m, 2H), 4.40 (d, J=6.9 Hz, 2H), 4.14 (s, 3H), 3.54-3.45 (m, 1H), 3.42 (s, 6H), 2.32 (s, 6H). MS (ESI): mass calcd. for $C_{25}H_{28}ClN_5O_4$, 497.2; m/z found, 498.1 $[M+H]^+$.

Example 61: {4-Chloro-2-methoxy-3-[(1-methylcyclopropyl)methoxy]quinolin-6-yl}[bis(1,2-dimethyl-1H-imidazol-5-yl)]methanol

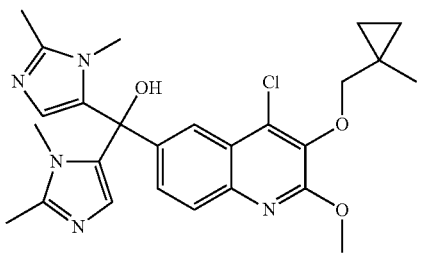

The title compound was prepared using 1-methylcyclopropanemethanol in place of tetrahydrofurfuryl alcohol using the procedure described for Example 34a. $^1$H NMR (400 MHz, CDCl$_3$) δ ppm 8.14-8.12 (m, 1H), 7.67 (d, J=8.7 Hz, 1H), 7.36-7.31 (m, 1H), 6.19 (s, 2H), 4.85 (s, 1H), 4.11 (s, 3H), 3.91 (s, 2H), 3.41 (s, 6H), 2.30 (s, 6H), 1.37 (s, 3H), 0.62-0.59 (m, 2H), 0.48-0.45 (m, 2H). MS (ESI): mass calcd. for C$_{26}$H$_{30}$ClN$_5$O$_3$, 495.2; m/z found, 496.2 [M+H]$^+$.

Example 62: {4-Chloro-3-[(3,5-dimethylisoxazol-4-yl)methoxy]-2-methoxyquinolin-6-yl}[bis(1,2-dimethyl-1H-imidazol-5-yl)]methanol

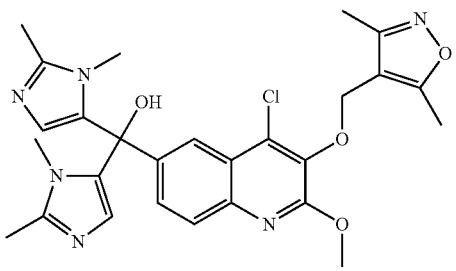 [SMILES: COc1nc2ccc(C(O)(c3cnc(C)n3C)c3cnc(C)n3C)cc2c(Cl)c1OCc1c(C)noc1C]

The title compound was prepared using (3,5-dimethyl-4-isoxazolyl) methanol in place of tetrahydrofurfuryl alcohol using the procedure described for Example 34a. $^1$H NMR (500 MHz, CDCl$_3$) δ ppm 8.13 (d, J=2.2 Hz, 1H), 7.69 (d, J=8.7 Hz, 1H), 7.38 (dd, J=8.8, 2.2 Hz, 1H), 6.15 (s, 2H), 5.34 (s, 1H), 4.95 (s, 2H), 4.16 (s, 3H), 3.41 (s, 6H), 2.40-2.38 (m, 6H), 2.29 (s, 6H). MS (ESI): mass calcd. for C$_{27}$H$_{29}$ClN$_6$O$_4$, 536.2; m/z found, 537.3 [M+H]$^+$.

Example 63: {4-Chloro-2-methoxy-3-[(3-methyloxetan-3-yl)methoxy]quinolin-6-yl}[bis(1,2-dimethyl-1H-imidazol-5-yl)]methanol

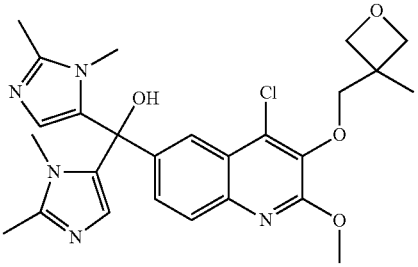

The title compound was prepared using 3-methyl-3-oxetanemethanol in place of tetrahydrofurfuryl alcohol using the procedure described for Example 34a. $^1$H NMR (400 MHz, CDCl$_3$) δ ppm 8.12 (d, J=2.2 Hz, 1H), 7.72 (d, J=8.7 Hz, 1H), 7.37 (dd, J=8.8, 2.2 Hz, 1H), 6.24 (s, 2H), 4.76 (d, J=5.9 Hz, 2H), 4.51 (d, J=6.0 Hz, 2H), 4.22 (s, 2H), 4.14 (s, 3H), 3.97 (s, 1H), 3.43 (s, 6H), 2.35 (s, 6H), 1.55-1.53 (m, 3H). MS (ESI): mass calcd. for C$_{26}$H$_{30}$ClN$_5$O$_4$, 511.2; m/z found, 512.3 [M+H]$^+$.

Example 64: [4-Chloro-3-(cyclopropylmethoxy)-2-methoxyquinolin-6-yl][bis(1,2-dimethyl-1H-imidazol-5-yl)]methanol

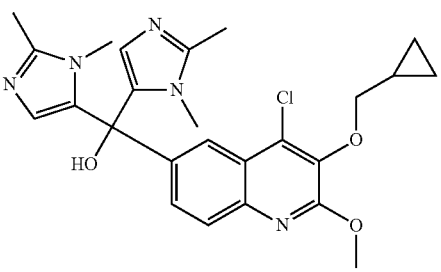 [SMILES: COc1nc2ccc(C(O)(c3cnc(C)n3C)c3cnc(C)n3C)cc2c(Cl)c1OCC1CC1]

The title compound was prepared using cyclopropanemethanol in place of 2,2-difluorocyclopropylmethanol using the procedure described for Example 35. $^1$H NMR (400 MHz, CDCl$_3$) δ ppm 8.09 (d, J=2.2 Hz, 1H), 7.76 (d, J=8.7 Hz, 1H), 7.39 (dd, J=8.7, 2.2 Hz, 1H), 6.29 (s, 2H), 4.13 (s, 3H), 4.00 (d, J=7.2 Hz, 2H), 3.44 (s, 6H), 3.21 (s, 1H), 2.36 (s, 6H), 1.39-1.31 (m, 1H), 0.65-0.60 (m, 2H), 0.38-0.32 (m, 2H). MS (ESI): mass calcd. for C$_{25}$H$_{28}$ClN$_5$O$_3$, 481.2; m/z found, 482.1 [M+H]$^+$.

Example 65a: {4-Chloro-2-methoxy-3-[(1-methylpiperidin-4-yl)oxy]quinolin-6-yl}(2,6-dimethylpyridin-3-yl)(1-methyl-1H-1,2,3-triazol-5-yl)methanol

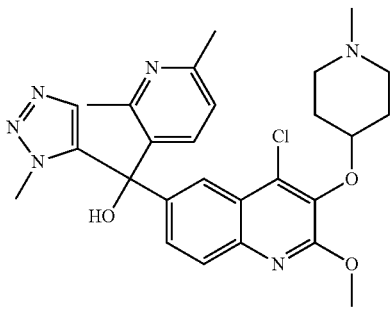 [SMILES: COc1nc2ccc(C(O)(c3ccc(C)nc3C)c3cnnn3C)cc2c(Cl)c1OC1CCN(C)CC1]

The title compound was prepared using 4-hydroxy-1-methylpiperidine in place of 3-methyl-3-oxetanemethanol using the procedure described for Example 36a. MS (ESI): mass calcd. for $C_{27}H_{31}ClN_6O_3$, 522.2; m/z found, 523.6 [M+H]$^+$. {4-Chloro-2-methoxy-3-[(1-methylpiperidin-4-yl)oxy]quinolin-6-yl}(2,6-dimethylpyridin-3-yl)(1-methyl-1H-1,2,3-triazol-5-yl)methanol was purified by chiral SFC (Stationary phase: CHIRALPAK AD 5 μM 250×30 mm, Mobile phase: 67% CO$_2$, 33% MeOH/iPrOH 50/50 v/v+(0.3% iPrNH$_2$)) to give 2 enantiomers. The second eluting enantiomer was Example 65b: $^1$H NMR (400 MHz, CDCl$_3$) δ ppm 7.99 (d, J=2.2 Hz, 1H), 7.81 (d, J=8.7 Hz, 1H), 7.31 (dd, J=8.8, 2.2 Hz, 1H), 6.99 (s, 1H), 6.98-6.93 (m, 2H), 4.47-4.40 (m, 1H), 4.13 (s, 3H), 3.94 (s, 3H), 3.31 (s, 1H), 2.84-2.76 (m, 2H), 2.56 (s, 3H), 2.40 (s, 3H), 2.30 (s, 3H), 2.25-2.16 (m, 2H), 2.01-1.95 (m, 4H). MS (ESI): mass calcd. for $C_{27}H_{31}ClN_6O_3$, 522.2; m/z found, 523.2 [M+H]$^+$.

Example 66a: [4-Chloro-2-methoxy-3-(pyrimidin-2-ylmethoxy)quinolin-6-yl](2,6-dimethylpyridin-3-yl)(1-methyl-1H-1,2,3-triazol-5-yl)methanol

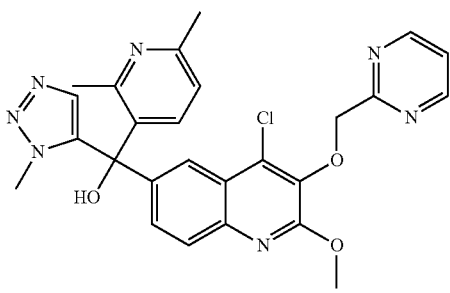 [SMILES: COc1nc2ccc(C(O)(c3ccc(C)nc3C)c3cnnn3C)cc2c(Cl)c1OCc1ncccn1]

The title compound was prepared using 2-pyrimidinemethanol in place of 3-methyl-3-oxetanemethanol using the procedure described for Example 36a. $^1$H NMR (500 MHz, CDCl$_3$) δ ppm 8.81 (d, J=4.9 Hz, 2H), 8.01-7.98 (m, 1H), 7.83 (d, J=8.7 Hz, 1H), 7.35-7.32 (m, 1H), 7.31-7.29 (m, 1H), 7.00 (s, 1H), 6.96-6.94 (m, 2H), 5.39 (s, 2H), 4.11 (s, 3H), 3.94 (s, 3H), 3.26 (s, 1H), 2.56 (s, 3H), 2.40 (s, 3H). MS (ESI): mass calcd. for $C_{26}H_{24}ClN_7O_3$, 517.2; m/z found, 518.5 [M+H]$^+$. [4-Chloro-2-methoxy-3-(pyrimidin-2-ylmethoxy)quinolin-6-yl](2,6-dimethylpyridin-3-yl)(1-methyl-1H-1,2,3-triazol-5-yl)methanol was purified by chiral SFC (Stationary phase: CHIRALPAK AD 5 μM 250×30 mm, Mobile phase: 70% CO$_2$, 30% MeOH/iPrOH 50/50 v/v+(0.3% iPrNH$_2$)) to give 2 enantiomers. The second eluting enantiomer was Example 66b: $^1$H NMR (400 MHz, CDCl$_3$) δ ppm 8.80 (d, J=4.9 Hz, 2H), 8.00-7.98 (m, 1H), 7.83 (d, J=8.7 Hz, 1H), 7.35-7.31 (m, 1H), 7.30-7.27 (m, 1H), 7.00 (s, 1H), 6.97-6.93 (m, 2H), 5.39 (s, 2H), 4.10 (s, 3H), 3.94 (s, 3H), 3.19 (s, 1H), 2.56 (s, 3H), 2.40 (s, 3H). MS (ESI): mass calcd. for $C_{26}H_{24}ClN_7O_3$, 517.2; m/z found, 518.1 [M+H]$^+$.

Example 67a: [4-Chloro-2-methoxy-3-(2-pyrrolidin-1-ylethoxy)quinolin-6-yl](2,6-dimethylpyridin-3-yl)(1-methyl-1H-1,2,3-triazol-5-yl)methanol

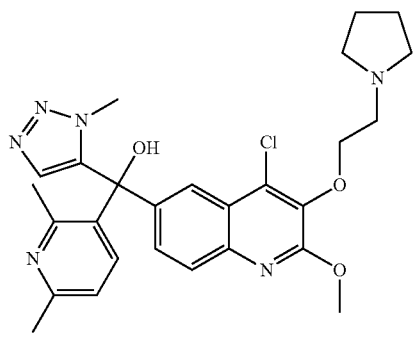 [SMILES: COc1nc2ccc(C(O)(c3ccc(C)nc3C)c3cnnn3C)cc2c(Cl)c1OCCN1CCCC1]

The title compound was prepared using 1-(2-hydroxyethyl)-pyrrolidine in place of 3-methyl-3-oxetanemethanol using the procedure described for Example 36a. MS (ESI): mass calcd. for $C_{27}H_{31}ClN_6O_3$, 522.2; m/z found, 523.6 [M+H]$^+$. [4-Chloro-2-methoxy-3-(2-pyrrolidin-1-ylethoxy)quinolin-6-yl](2,6-dimethylpyridin-3-yl)(1-methyl-1H-1,2,3-triazol-5-yl)methanol was purified by chiral SFC (Stationary phase: CHIRALPAK AD-H 5 μM 250×20 mm, Mobile phase: 70% CO$_2$, 30% MeOH/iPrOH 50/50 v/v+(0.3% iPrNH$_2$)) to give 2 enantiomers. The second eluting enantiomer was Example 67b: $^1$H NMR (400 MHz, CDCl$_3$) δ ppm 7.98-7.97 (m, 1H), 7.81 (d, J=8.7 Hz, 1H), 7.34-7.30 (m, 1H), 7.00 (s, 1H), 6.97-6.92 (m, 2H), 4.27-4.23 (m, 2H), 4.14 (s, 3H), 3.94 (s, 3H), 3.18 (s, 1H), 2.99-2.94 (m, 3H), 2.68-2.61 (m, 4H), 2.56 (s, 3H), 2.40 (s, 3H), 1.83-1.78 (m, 4H). MS (ESI): mass calcd. for $C_{27}H_{31}ClN_6O_3$, 522.2; m/z found, 523.0 [M+H]$^+$.

Example 68a: [4-Chloro-3-(cyclopropylmethoxy)-2-methoxyquinolin-6-yl](2,6-dimethylpyridin-3-yl)(1-methyl-1H-1,2,3-triazol-5-yl)methanol

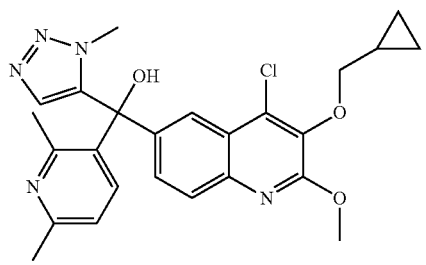 [SMILES: COc1nc2ccc(C(O)(c3ccc(C)nc3C)c3cnnn3C)cc2c(Cl)c1OCC1CC1]

The title compound was prepared using cyclopropanemethanol in place of 3-methyl-3-oxetanemethanol using the procedure described for Example 36a. $^1$H NMR (400 MHz, CDCl$_3$) δ ppm 8.02 (d, J=2.2 Hz, 1H), 7.77 (d, J=8.7 Hz, 1H), 7.32-7.28 (m, 1H), 6.97-6.91 (m, 2H), 6.86 (s, 1H), 4.64 (s, 1H), 4.13 (s, 3H), 3.98 (d, J=7.3 Hz, 2H), 3.91 (s, 3H), 2.51 (s, 3H), 2.34 (s, 3H), 1.38-1.28 (m, 1H), 0.65-0.59 (m, 2H), 0.36-0.31 (m, 2H). MS (ESI): mass calcd. for C$_{25}$H$_{26}$ClN$_5$O$_3$, 479.2; m/z found, 480.1 [M+H]$^+$. [4-Chloro-3-(cyclopropylmethoxy)-2-methoxyquinolin-6-yl](2,6-dimethylpyridin-3-yl)(1-methyl-1H-1,2,3-triazol-5-yl)methanol was purified by chiral SFC (Stationary phase: CHIRALPAK AD-H 5 μM 250×20 mm, Mobile phase: 75% CO$_2$, 25% MeOH/iPrOH 50/50 v/v+(0.3% iPrNH$_2$)) to give 2 enantiomers. The first eluting enantiomer was Example 68b: $^1$H NMR (400 MHz, CDCl$_3$) δ ppm 7.99-7.98 (m, 1H), 7.81 (d, J=8.7 Hz, 1H), 7.34-7.30 (m, 1H), 6.99 (s, 1H), 6.98-6.92 (m, 2H), 4.14 (s, 3H), 4.00 (d, J=7.3 Hz, 2H), 3.94 (s, 3H), 3.21 (s, 1H), 2.56 (s, 3H), 2.40 (s, 3H), 1.37-1.28 (m, 1H), 0.65-0.59 (m, 2H), 0.36-0.31 (m, 2H). MS (ESI): mass calcd. for C$_{25}$H$_{26}$ClN$_5$O$_3$, 479.2; m/z found, 480.1 [M+H]$^+$ and the second eluting enantiomer was Example 68c: $^1$H NMR (400 MHz, CDCl$_3$) δ ppm 8.00-7.97 (m, 1H), 7.82 (d, J=8.8 Hz, 1H), 7.34-7.30 (m, 1H), 7.00 (s, 1H), 6.99-6.92 (m, 2H), 4.16-4.13 (m, 3H), 4.00 (d, J=7.2 Hz, 2H), 3.96-3.93 (m, 3H), 3.16 (s, 1H), 2.56 (s, 3H), 2.40 (s, 3H), 1.37-1.29 (m, 1H), 0.65-0.59 (m, 2H), 0.36-0.31 (m, 2H). MS (ESI): mass calcd. for C$_{25}$H$_{26}$ClN$_5$O$_3$, 479.2; m/z found, 480.1 [M+H]$^+$.

Example 69a: [4-Chloro-2-methoxy-3-(tetrahydro-2H-pyran-4-yloxy)quinolin-6-yl](2,6-dimethylpyridin-3-yl)(1-methyl-1H-1,2,3-triazol-5-yl)methanol

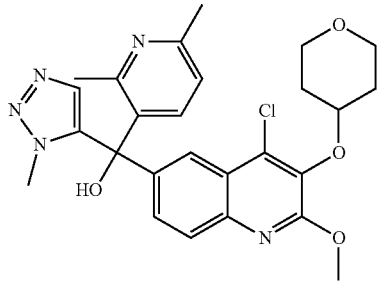 [SMILES: COc1nc2ccc(C(O)(c3ccc(C)nc3C)c3cnnn3C)cc2c(Cl)c1OC1CCOCC1]

The title compound was prepared using 4-hydroxytetrahydropyran in place of 3-methyl-3-oxetanemethanol using the procedure described for Example 36a. $^1$H NMR (400 MHz, CDCl$_3$) δ ppm 8.04 (d, J=2.2 Hz, 1H), 7.78 (d, J=8.7 Hz, 1H), 7.32-7.28 (m, 1H), 6.96-6.91 (m, 2H), 6.87 (s, 1H), 4.60 (s, 1H), 4.59-4.53 (m, 1H), 4.13 (s, 3H), 4.08-4.02 (m, 2H), 3.92 (s, 3H), 3.53-3.46 (m, 2H), 2.52 (s, 3H), 2.35 (s, 3H), 2.00-1.90 (m, 4H). MS (ESI): mass calcd. for C$_{26}$H$_{28}$ClN$_5$O$_4$, 509.2; m/z found, 510.1 [M+H]$^+$. [4-Chloro-2-methoxy-3-(tetrahydro-2H-pyran-4-yloxy)quinolin-6-yl](2,6-dimethylpyridin-3-yl)(1-methyl-1H-1,2,3-triazol-5-yl)methanol was purified by chiral SFC (Stationary phase: CHIRALPAK AD-H 5 μM 250×20 mm, Mobile phase: 75% CO$_2$, 25% MeOH/iPrOH 50/50 v/v+(0.3% iPrNH$_2$)) to give 2 enantiomers. The first eluting enantiomer was Example 69b: $^1$H NMR (400 MHz, CDCl$_3$) δ ppm 8.01-7.98 (m, 1H), 7.82 (d, J=8.7 Hz, 1H), 7.35-7.30 (m, 1H), 7.00-6.98 (m, 1H), 6.98-6.93 (m, 2H), 4.62-4.55 (m, 1H), 4.14 (s, 3H), 4.10-4.03 (m, 2H), 3.94 (s, 3H), 3.55-3.48 (m, 2H), 3.25 (s, 1H), 2.56 (s, 3H), 2.40 (s, 3H), 2.03-1.91 (m, 4H). MS (ESI): mass calcd. for C$_{26}$H$_{28}$ClN$_5$O$_4$, 509.2; m/z found, 510.1 [M+H]$^+$ and the second eluting enantiomer was Example 69c: $^1$H NMR (400 MHz, CDCl$_3$) δ ppm 8.00-7.98 (m, 1H), 7.82 (d, J=8.8 Hz, 1H), 7.34-7.31 (m, 1H), 6.99 (s, 1H), 6.96-6.94 (m, 2H), 4.61-4.55 (m, 1H), 4.14 (s, 3H), 4.09-4.04 (m, 2H), 3.94 (s, 3H), 3.55-3.48 (m, 2H), 3.16 (s, 1H), 2.56 (s, 3H), 2.40 (s, 3H), 2.01-1.90 (m, 4H). MS (ESI): mass calcd. for C$_{26}$H$_{28}$ClN$_5$O$_4$, 509.2; m/z found, 510.1 [M+H]$^+$.

Example 70a: {4-Chloro-2-methoxy-3-[2-(methylsulfonyl)ethoxy]quinolin-6-yl}(2,6-dimethylpyridin-3-yl)(1-methyl-1H-1,2,3-triazol-5-yl)methanol

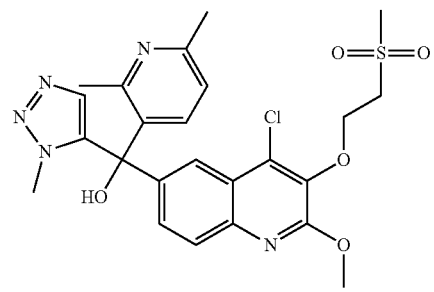 [SMILES: COc1nc2ccc(C(O)(c3ccc(C)nc3C)c3cnnn3C)cc2c(Cl)c1OCCS(C)(=O)=O]

A mixture of 4-chloro-6-((2,6-dimethylpyridin-3-yl)(hydroxy)(1-methyl-1H-1,2,3-triazol-5-yl)methyl)-2-methoxyquinolin-3-ol (200 mg, 0.47 mmol, Intermediate 31), 2-(methylsulfonyl)ethanol (68 μL, 0.7 mmol) and PPh$_3$ (185 mg, 0.7 mmol) in THF (1.88 mL) was cooled to 0° C. Then DIAD (146 μL, 0.7 mmol) was added dropwise and the mixture was warmed to room temperature and stirred for 30 minutes. Additional 2-(methylsulfonyl)ethanol (68 μL, 0.7 mmol), PPh$_3$ (185 mg, 0.7 mmol) and DIAD (146 μL, 0.7 mmol) were added and stirring continued at room temperature for 2.5 hours. The reaction was then placed into the sonicator, 2-(methylsulfonyl)ethanol (136 μL, 1.4 mmol), PPh$_3$ (370 mg, 1.4 mmol) and DIAD (292 μL, 1.4 mmol) were added and the mixture sonicated for 20 minutes. Additional 2-(methylsulfonyl)ethanol (136 μL, 1.4 mmol), PPh$_3$ (370 mg, 1.4 mmol) and DIAD (292 μL, 1.4 mmol) were added and sonication continued for 1 hour. Additional 2-(methylsulfonyl)ethanol (136 μL, 1.4 mmol), PPh$_3$ (370 mg, 1.4 mmol) and DIAD (292 μL, 1.4 mmol) were added and sonication continued for 1 hour. The reaction was concentrated to dryness and purified twice by FCC (1-10% MeOH/DCM) to afford the title compound as a light yellow amorphous solid. $^1$H NMR (500 MHz, CDCl$_3$) δ ppm 8.01 (d, J=2.2 Hz, 1H), 7.84 (d, J=8.8 Hz, 1H), 7.39-7.36 (m, 1H), 6.97-6.94 (m, 3H), 4.57-4.54 (m, 2H), 4.17 (s, 3H), 3.95 (s, 3H), 3.53-3.50 (m, 2H), 3.34 (s, 1H), 3.22-3.20 (m, 3H), 2.56 (s, 3H), 2.39 (s, 3H). MS (ESI): mass calcd. for C$_{24}$H$_{26}$ClN$_5$O$_5$S, 531.1; m/z found, 532.0 [M+H]$^+$. {4-Chloro-2-methoxy-3-[2-(methylsulfonyl)ethoxy]quinolin-6-yl}(2,6-dimethylpyridin-3-yl)(1-methyl-1H-1,2,3-triazol-5-yl)methanol was purified by chiral SFC (Stationary phase: CHIRALPAK AD-H 5 μM 250×20 mm, Mobile phase: 70% CO$_2$, 30% MeOH/iPrOH 50/50 v/v+(0.3% iPrNH$_2$)) followed by FCC (0.5% NH$_4$OH, 95% DCM, 5% MeOH) to give 2 enantiomers. The second eluting enantiomer was Example 70b: $^1$H NMR (400 MHz, CDCl$_3$) δ ppm 8.00 (d, J=2.2 Hz, 1H), 7.85 (d, J=8.8 Hz, 1H), 7.38 (dd, J=8.8, 2.3 Hz, 1H), 6.97 (s, 1H), 6.96-6.94 (m, 2H), 4.57-4.54 (m, 2H), 4.17 (s, 3H), 3.95 (s, 3H), 3.52 (t, J=5.3

Hz, 2H), 3.22-3.20 (m, 3H), 3.17 (s, 1H), 2.57 (s, 3H), 2.40 (s, 3H). MS (ESI): mass calcd. for $C_{24}H_{26}ClN_5O_5S$, 531.1; m/z found, 532.0 $[M+H]^+$.

Example 71a: {4-Chloro-3-[(3,5-dimethylisoxazol-4-yl)methoxy]-2-methoxyquinolin-6-yl}(2,6-dimethylpyridin-3-yl)(1-methyl-1H-1,2,3-triazol-5-yl)methanol

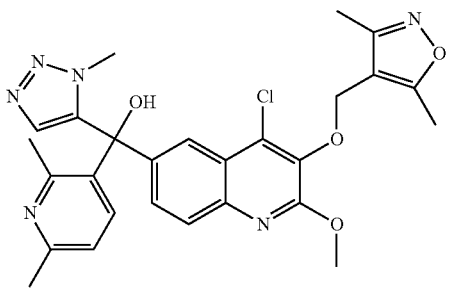 [SMILES: COc1nc2ccc(C(O)(c3ccc(C)nc3C)c3cnnn3C)cc2c(Cl)c1OCc1c(C)noc1C]

The title compound was prepared using (3,5-dimethyl-4-isoxazolyl) methanol in place of 3-methyl-3-oxetanemethanol using the procedure described for Example 36a. $^1$H NMR (500 MHz, CDCl$_3$) δ ppm 8.03 (d, J=2.2 Hz, 1H), 7.79 (d, J=8.7 Hz, 1H), 7.34 (dd, J=8.8, 2.2 Hz, 1H), 6.97-6.92 (m, 2H), 6.86 (s, 1H), 4.94 (s, 2H), 4.69 (s, 1H), 4.16 (s, 3H), 3.92 (s, 3H), 2.52 (s, 3H), 2.37-2.34 (m, 9H). MS (ESI): mass calcd. for $C_{27}H_{27}ClN_6O_4$, 534.2; m/z found, 535.2 $[M+H]^+$. {4-Chloro-3-[(3,5-dimethylisoxazol-4-yl)methoxy]-2-methoxyquinolin-6-yl}(2,6-dimethylpyridin-3-yl)(1-methyl-1H-1,2,3-triazol-5-yl)methanol was purified by chiral SFC (Stationary phase: CHIRALPAK AD-H 5 μM 250×20 mm, Mobile phase: 75% $CO_2$, 25% MeOH/iPrOH 50/50 v/v+(0.3% iPrNH$_2$)) to give 2 enantiomers. The first eluting enantiomer was Example 71b: $^1$H NMR (500 MHz, CDCl$_3$) δ ppm 7.99-7.98 (m, 1H), 7.82 (d, J=8.7 Hz, 1H), 7.37-7.32 (m, 1H), 6.96 (s, 1H), 6.95 (s, 2H), 4.96 (s, 2H), 4.17 (s, 3H), 3.94 (s, 3H), 3.48 (s, 1H), 2.56 (s, 3H), 2.39 (s, 3H), 2.39-2.37 (m, 6H). MS (ESI): mass calcd. for $C_{27}H_{27}ClN_6O_4$, 534.2; m/z found, 535.0 $[M+H]^+$ and the second eluting enantiomer was Example 71c: $^1$H NMR (400 MHz, CDCl$_3$) δ ppm 7.99 (d, J=2.2 Hz, 1H), 7.83 (d, J=8.8 Hz, 1H), 7.37-7.33 (m, 1H), 6.97 (s, 1H), 6.95 (s, 2H), 4.96 (s, 2H), 4.17 (s, 3H), 3.94 (s, 3H), 3.43 (s, 1H), 2.56 (s, 3H), 2.39 (s, 3H), 2.39-2.37 (m, 6H). MS (ESI): mass calcd. for $C_{27}H_{27}ClN_6O_4$, 534.2; m/z found, 535.0 $[M+H]^+$.

Example 72a: {4-Chloro-3-[(2,2-difluorocyclopropyl)methoxy]-2-methoxyquinolin-6-yl}(2,6-dimethylpyridin-3-yl)(1-methyl-1H-1,2,3-triazol-5-yl)methanol

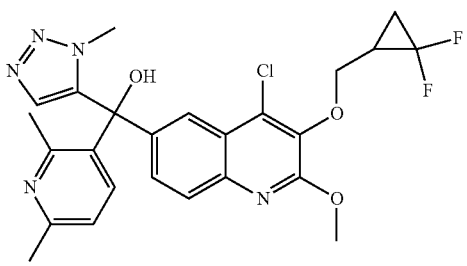 [SMILES: COc1nc2ccc(C(O)(c3ccc(C)nc3C)c3cnnn3C)cc2c(Cl)c1OCC1CC1(F)F]

The title compound was prepared using 2,2-difluorocyclopropylmethanol in place of 3-methyl-3-oxetanemethanol using the procedure described for Example 36a. $^1$H NMR (400 MHz, CDCl$_3$) δ ppm 8.00 (d, J=2.2 Hz, 1H), 7.82 (d, J=8.8 Hz, 1H), 7.36-7.32 (m, 1H), 6.98 (s, 1H), 6.95 (s, 2H), 4.30-4.18 (m, 2H), 4.15 (s, 3H), 3.94 (s, 3H), 3.30 (s, 1H), 2.56 (s, 3H), 2.40 (s, 3H), 2.21-2.10 (m, 1H), 1.64-1.57 (m, 1H), 1.35-1.26 (m, 1H). MS (ESI): mass calcd. for $C_{25}H_{24}ClF_2N_5O_3$, 515.2; m/z found, 516.2 $[M+H]^+$. {4-Chloro-3-[(2,2-difluorocyclopropyl)methoxy]-2-methoxyquinolin-6-yl}(2,6-dimethylpyridin-3-yl)(1-methyl-1H-1,2,3-triazol-5-yl)methanol was purified by chiral SFC (Stationary phase: CHIRALPAK AD-H 5 μM 250×20 mm, Mobile phase: 80% $CO_2$, 20% MeOH/iPrOH 50/50 v/v+(0.3% iPrNH$_2$)) to give 2 pairs of enantiomers. The first eluting enantiomer pair was Example 72b: $^1$H NMR (400 MHz, CDCl$_3$) δ ppm 8.00 (d, J=2.2 Hz, 1H), 7.82 (d, J=8.7 Hz, 1H), 7.33 (dd, J=8.7, 2.2 Hz, 1H), 6.96 (s, 1H), 6.95 (s, 2H), 4.29-4.19 (m, 2H), 4.15 (s, 3H), 3.94 (s, 3H), 3.41 (s, 1H), 2.56 (s, 3H), 2.39 (s, 3H), 2.20-2.10 (m, 1H), 1.65-1.59 (m, 1H), 1.35-1.27 (m, 1H). MS (ESI): mass calcd. for $C_{25}H_{24}ClF_2N_5O_3$, 515.2; m/z found, 516.0 $[M+H]^+$ and the second eluting enantiomer pair was Example 72c: $^1$H NMR (400 MHz, CDCl$_3$) δ ppm 8.00 (d, J=2.2 Hz, 1H), 7.83 (d, J=8.7 Hz, 1H), 7.36-7.32 (m, 1H), 6.99 (s, 1H), 6.95 (s, 2H), 4.29-4.18 (m, 2H), 4.15 (s, 3H), 3.95 (s, 3H), 3.23 (s, 1H), 2.56 (s, 3H), 2.40 (s, 3H), 2.20-2.09 (m, 1H), 1.63-1.58 (m, 1H), 1.35-1.27 (m, 1H). MS (ESI): mass calcd. for $C_{25}H_{24}ClF_2N_5O_3$, 515.2; m/z found, 516.0 $[M+H]^+$.

Example 73a: [4-Chloro-2-methoxy-3-(1,3-thiazol-2-ylmethoxy)quinolin-6-yl](2,6-dimethylpyridin-3-yl)(1-methyl-1H-1,2,3-triazol-5-yl)methanol

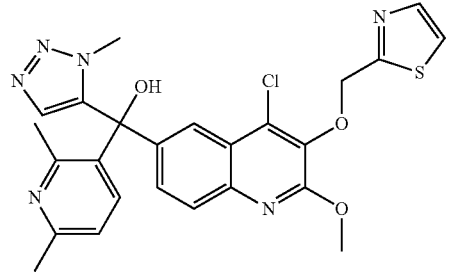 [SMILES: COc1nc2ccc(C(O)(c3ccc(C)nc3C)c3cnnn3C)cc2c(Cl)c1OCc1nccs1]

The title compound was prepared using 1,3-thiazol-2-ylmethanol in place of 3-methyl-3-oxetanemethanol using the procedure described for Example 36a. MS (ESI): mass calcd. for $C_{25}H_{23}ClN_6O_3S$, 522.1; m/z found, 523.0 $[M+H]^+$. [4-Chloro-2-methoxy-3-(1,3-thiazol-2-ylmethoxy)quinolin-6-yl](2,6-dimethylpyridin-3-yl)(1-methyl-1H-1,2,3-triazol-5-yl)methanol was purified by chiral SFC (Stationary phase: CHIRALPAK AD-H 5 μM 250×20 mm, Mobile phase: 70% $CO_2$, 30% MeOH/iPrOH 50/50 v/v+(0.3% iPrNH$_2$)) to give 2 enantiomers. The first eluting enantiomer was Example 73b: $^1$H NMR (400 MHz, CDCl$_3$) δ ppm 8.01 (d, J=2.2 Hz, 1H), 7.83 (d, J=8.7 Hz, 1H), 7.79 (d, J=3.2 Hz, 1H), 7.44 (d, J=3.2 Hz, 1H), 7.34 (dd, J=8.8, 2.2 Hz, 1H), 6.97 (s, 1H), 6.95 (s, 2H), 5.48 (s, 2H), 4.16 (s, 3H), 3.94 (s, 3H), 3.41 (s, 1H), 2.56 (s, 3H), 2.39 (s, 3H). MS (ESI): mass calcd. for $C_{25}H_{23}ClN_6O_3S$, 522.1; m/z found, 523.0 $[M+H]^+$ and the second eluting enantiomer was Example 73c: $^1$H NMR (400 MHz, CDCl$_3$) δ ppm 8.02 (d, J=2.2 Hz, 1H), 7.82 (d, J=8.7 Hz, 1H), 7.79 (d, J=3.3 Hz, 1H), 7.44 (d, J=3.3 Hz, 1H), 7.35-7.31 (m, 1H), 6.95 (s, 3H), 5.48 (s, 2H), 4.16 (s, 3H), 3.94 (s, 3H), 3.66 (s, 1H), 2.55 (s, 3H), 2.39 (s, 3H). MS (ESI): mass calcd. for $C_{25}H_{23}ClN_6O_3S$, 522.1; m/z found, 523.0 $[M+H]^+$.

Example 74a: {4-Chloro-3-[2-(dimethylamino)ethoxy]-2-methoxyquinolin-6-yl}(2,6-dimethylpyridin-3-yl)(1-methyl-1H-1,2,3-triazol-5-yl)methanol

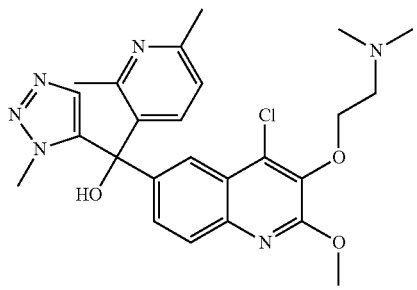 [SMILES: COc1nc2ccc(C(O)(c3ccc(C)nc3C)c3cnnn3C)cc2c(Cl)c1OCCN(C)C]

The title compound was prepared using N,N-dimethylethanolamine in place of 4-(2-hydroxyethyl)-morpholine using the procedure described for Example 37a. MS (ESI): mass calcd. for $C_{25}H_{29}ClN_6O_3$, 496.2; m/z found, 497.2 $[M+H]^+$. {4-Chloro-3-[2-(dimethylamino)ethoxy]-2-methoxyquinolin-6-yl}(2,6-dimethylpyridin-3-yl)(1-methyl-1H-1,2,3-triazol-5-yl)methanol was purified by chiral SFC (Stationary phase: CHIRALPAK AD-H 5 µM 250× 20 mm, Mobile phase: 75% $CO_2$, 25% MeOH/iPrOH 50/50 v/v+(0.3% iPrNH$_2$)) followed by FCC (0.5% NH$_4$OH, 95% DCM, 5% MeOH) to give 2 enantiomers. The second eluting enantiomer was Example 74b: $^1$H NMR (400 MHz, CDCl$_3$) δ ppm 8.00 (d, J=2.2 Hz, 1H), 7.81 (d, J=8.8 Hz, 1H), 7.34-7.30 (m, 1H), 6.98 (s, 1H), 6.96-6.94 (m, 2H), 4.23-4.18 (m, 2H), 4.14 (s, 3H), 3.94 (s, 3H), 3.38 (s, 1H), 2.82-2.77 (m, 2H), 2.56 (s, 3H), 2.40 (s, 3H), 2.38 (s, 6H). MS (ESI): mass calcd. for $C_{25}H_{29}ClN_6O_3$, 496.2; m/z found, 497.1 $[M+H]^+$.

Example 75: [3-(Benzyloxy)-4-chloro-2-methoxyquinolin-6-yl][bis(1,2-dimethyl-1H-imidazol-5-yl)]methanol

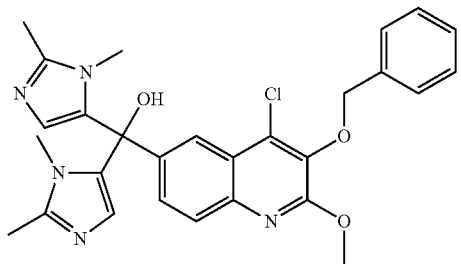 [SMILES: COc1nc2ccc(C(O)(c3cnc(C)n3C)c3cnc(C)n3C)cc2c(Cl)c1OCc1ccccc1]

n-BuLi (1.23 M in hexanes, 18.9 mL, 23.2 mmol) was added dropwise to a stirred slurry of 5-bromo-1,2-dimethyl-1H-imidazole (5.13 g, 27.8 mmol) in THF (40 mL) at −78° C. under nitrogen. After stirring for 20 minutes, the slurry was treated dropwise over 2 minutes with a solution of methyl 3-(benzyloxy)-4-chloro-2-methoxyquinoline-6-carboxylate (3.32 g, 9.28 mmol, Intermediate 32) in THF (20 mL). The flask was then rinsed with THF (10 mL), and that was added to the imidazole flask. The reaction was stirred in the dry ice/acetone bath for 10 minutes, then removed from the cold bath and stirred for 20 minutes, then stirred in an ice bath for 30 minutes. The reaction was then quenched with saturated aqueous NH$_4$Cl and concentrated to remove the THF. The aqueous residue was partitioned between water (300 mL) and DCM (250 mL). The layers were separated and the aqueous layer further extracted with DCM (250 mL). The organics were combined, dried (Na$_2$SO$_4$), filtered and concentrated to dryness to provide an orange oil. The crude material was purified by FCC (0-10% MeOH/DCM) to afford the title compound as a yellow solid. $^1$H NMR (500 MHz, CDCl$_3$) δ ppm 8.13 (s, 1H), 7.70 (d, J=8.7 Hz, 1H), 7.58-7.55 (m, 2H), 7.42-7.34 (m, 4H), 6.20 (s, 2H), 5.20 (s, 2H), 4.62 (s, 1H), 4.16 (s, 3H), 3.42 (s, 6H), 2.32 (s, 6H). MS (ESI): mass calcd. for $C_{28}H_{28}ClN_5O_3$, 517.2; m/z found, 518.1 $[M+H]^+$.

Example 76a: [4-Chloro-2-methoxy-3-(pyridin-3-ylmethoxy)quinolin-6-yl](1-methyl-1H-imidazol-5-yl)[6-(trifluoromethyl)pyridin-3-yl]methanol

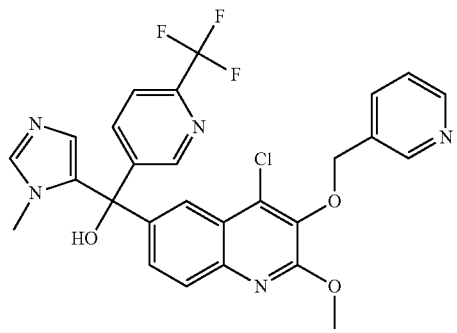 [SMILES: COc1nc2ccc(C(O)(c3ccc(C(F)(F)F)nc3)c3cncn3C)cc2c(Cl)c1OCc1cccnc1]

The title compound was prepared using 3-pyridinemethanol in place of 3-methyl-3-oxetanemethanol and 4-chloro-6-(hydroxy(1-methyl-1H-imidazol-5-yl)(6-(trifluoromethyl)pyridin-3-yl)methyl)-2-methoxyquinolin-3-ol (Intermediate 30) in place of 4-chloro-6-((2,6-dimethylpyridin-3-yl)(hydroxy)(1-methyl-1H-1,2,3-triazol-5-yl)methyl)-2-methoxyquinolin-3-ol using the procedure described for Example 36a. MS (ESI): mass calcd. for $C_{27}H_{21}ClF_3N_5O_3$, 555.1; m/z found, 556.0 $[M+H]^+$. [4-Chloro-2-methoxy-3-(pyridin-3-ylmethoxy)quinolin-6-yl](1-methyl-1H-imidazol-5-yl)[6-(trifluoromethyl)pyridin-3-yl]methanol was purified by chiral SFC (Stationary phase: CHIRALPAK AD-H 5 µM 250×20 mm, Mobile phase: 75% $CO_2$, 25% MeOH/iPrOH 50/50 v/v+(0.3% iPrNH$_2$)) to give 2 enantiomers. The first eluting enantiomer was Example 76b: $^1$H NMR (500 MHz, CDCl$_3$) δ ppm 8.83-8.81 (m, 1H), 8.73-8.71 (m, 1H), 8.61-8.59 (m, 1H), 8.06-8.04 (m, 1H), 7.93-7.90 (m, 2H), 7.85-7.82 (m, 1H), 7.70-7.67 (m, 1H), 7.53-7.49 (m, 2H), 7.36-7.33 (m, 1H), 6.52-6.51 (m, 1H), 5.20 (s, 2H), 4.16 (s, 3H), 3.42 (s, 3H), 3.29-3.27 (m, 1H). MS (ESI): mass calcd. for $C_{27}H_{21}ClF_3N_5O_3$, 555.1; m/z found, 556.5 $[M+H]^+$ and the second eluting enantiomer was Example 76c: $^1$H NMR (500 MHz, CDCl$_3$) δ ppm 8.83-8.81 (m, 1H), 8.73-8.71 (m, 1H), 8.61-8.59 (m, 1H), 8.06-8.04 (m, 1H), 7.93-7.89 (m, 2H), 7.85-7.81 (m, 1H), 7.71-7.67 (m, 1H), 7.54-7.49 (m, 2H), 7.36-7.33 (m, 1H), 6.53-6.51 (m, 1H), 5.20 (s, 2H), 4.16 (s, 3H), 3.42 (s, 3H), 3.26-3.24

(m, 1H). MS (ESI): mass calcd. for $C_{27}H_{21}ClF_3N_5O_3$, 555.1; m/z found, 556.5 $[M+H]^+$.

Example 77a: [2-Azetidin-1-yl-4-chloro-3-(1-methylethoxy)quinolin-6-yl](1,2-dimethyl-1H-imidazol-5-yl)(1-methyl-1H-1,2,3-triazol-5-yl)methanol

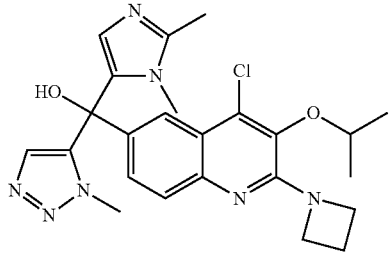 [SMILES: Cc1ncc(C(O)(c2ccc3nc(N4CCC4)c(OC(C)C)c(Cl)c3c2)c2cnnn2C)n1C]

The title compound was prepared using [2,4-dichloro-3-(1-methylethoxy)quinolin-6-yl](1,2-dimethyl-1H-imidazol-5-yl)(1-methyl-1H-1,2,3-triazol-5-yl)methanol.TFA (Example 41) in place of [2,4-dichloro-3-(1-methylethoxy)quinolin-6-yl](2,6-dimethylpyridin-3-yl)(1-methyl-1H-1,2,3-triazol-5-yl)methanol.TFA using the procedure described for Example 38a. MS (ESI): mass calcd. for $C_{24}H_{28}ClN_7O_2$, 481.2; m/z found, 482.1 $[M+H]^+$. [2-Azetidin-1-yl-4-chloro-3-(1-methylethoxy)quinolin-6-yl](1,2-dimethyl-1H-imidazol-5-yl)(1-methyl-1H-1,2,3-triazol-5-yl)methanol was purified by chiral SFC (Stationary phase: CHIRALPAK AD-H 5 μM 250×20 mm, Mobile phase: 60% $CO_2$, 40% iPrOH+(0.3% iPrNH$_2$)) followed by FCC (0.5% NH$_4$OH, 95% DCM, 5% MeOH) to give 2 enantiomers. The second eluting enantiomer was Example 77b: $^1$H NMR (500 MHz, CDCl$_3$) δ ppm 8.01-7.97 (m, 1H), 7.65 (d, J=8.7 Hz, 1H), 7.31-7.27 (m, 1H), 7.10 (s, 1H), 6.15 (s, 1H), 4.70-4.63 (m, 1H), 4.32-4.27 (m, 4H), 3.91 (s, 3H), 3.35 (s, 3H), 2.42-2.34 (m, 2H), 2.22 (s, 3H), 1.35 (d, J=6.1 Hz, 6H). MS (ESI): mass calcd. for $C_{24}H_{28}ClN_7O_2$, 481.2; m/z found, 482.1 $[M+H]^+$.

Example 78a: {4-Chloro-2-methoxy-3-[(3-methyloxetan-3-yl)methoxy]quinolin-6-yl}(1-methyl-1H-imidazol-5-yl)[6-(trifluoromethyl)pyridin-3-yl]methanol

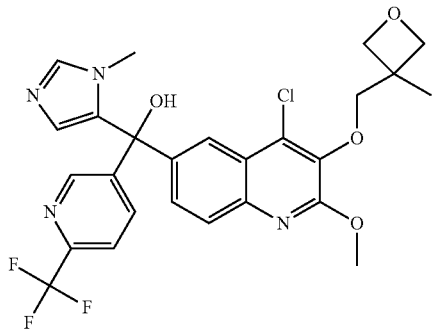 [SMILES: COc1nc2ccc(C(O)(c3ccc(C(F)(F)F)nc3)c3cncn3C)cc2c(Cl)c1OCC1(C)COC1]

The title compound was prepared using 4-chloro-6-(hydroxy(1-methyl-1H-imidazol-5-yl)(6-(trifluoromethyl)pyridin-3-yl)methyl)-2-methoxyquinolin-3-ol (Intermediate 30) in place of 4-chloro-6-((2,6-dimethylpyridin-3-yl)(hydroxy)(1-methyl-1H-1,2,3-triazol-5-yl)methyl)-2-methoxyquinolin-3-ol using the procedure described for Example 36a. MS (ESI): mass calcd. for $C_{26}H_{24}ClF_3N_4O_4$, 548.1; m/z found, 549.0 $[M+H]^+$. {4-Chloro-2-methoxy-3-[(3-methyloxetan-3-yl)methoxy]quinolin-6-yl}(1-methyl-1H-imidazol-5-yl)[6-(trifluoromethyl)pyridin-3-yl]methanol was purified by chiral SFC (Stationary phase: CHIRALCEL OJ-H 5 μM 250×20 mm, Mobile phase: 70% $CO_2$, 30% MeOH+(0.3% iPrNH$_2$)) to give 2 enantiomers. The first eluting enantiomer was Example 78b: $^1$H NMR (500 MHz, CDCl$_3$) δ ppm 8.83-8.79 (m, 1H), 8.08 (d, J=2.1 Hz, 1H), 7.93-7.89 (m, 1H), 7.82-7.79 (m, 1H), 7.68-7.65 (m, 1H), 7.48 (dd, J=8.7, 2.2 Hz, 1H), 7.37 (s, 1H), 6.39-6.36 (m, 1H), 4.75-4.72 (m, 2H), 4.71-4.64 (m, 1H), 4.51-4.48 (m, 2H), 4.17 (s, 2H), 4.13 (s, 3H), 3.37 (s, 3H), 1.54-1.51 (m, 3H). MS (ESI): mass calcd. for $C_{26}H_{24}ClF_3N_4O_4$, 548.1; m/z found, 549.2 $[M+H]^+$ and the second eluting enantiomer was Example 78c: $^1$H NMR (500 MHz, CDCl$_3$) δ ppm 8.82-8.79 (m, 1H), 8.08 (d, J=2.1 Hz, 1H), 7.93-7.88 (m, 1H), 7.80 (d, J=8.7 Hz, 1H), 7.68-7.64 (m, 1H), 7.50-7.46 (m, 1H), 7.35 (s, 1H), 6.38-6.34 (m, 1H), 4.94 (s, 1H), 4.75-4.71 (m, 2H), 4.50-4.47 (m, 2H), 4.17 (s, 2H), 4.13 (s, 3H), 3.37 (s, 3H), 1.53-1.50 (m, 3H). MS (ESI): mass calcd. for $C_{26}H_{24}ClF_3N_4O_4$, 548.1; m/z found, 549.2 $[M+H]^+$.

Example 79a: [4-Chloro-2-methoxy-3-(2-methoxyethoxy)quinolin-6-yl](1-methyl-1H-imidazol-5-yl)[6-(trifluoromethyl)pyridin-3-yl]methanol

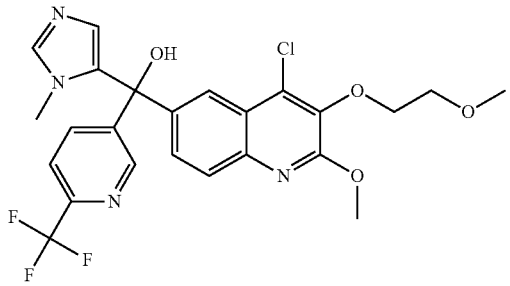 [SMILES: COCCOc1c(OC)nc2ccc(C(O)(c3ccc(C(F)(F)F)nc3)c3cncn3C)cc2c1Cl]

The title compound was prepared using 2-methoxyethanol in place of 4-(2-hydroxyethyl)-morpholine and 4-chloro-6-(hydroxy(1-methyl-1H-imidazol-5-yl)(6-(trifluoromethyl)pyridin-3-yl)methyl)-2-methoxyquinolin-3-ol (Intermediate 30) in place of 4-chloro-6-((2,6-dimethylpyridin-3-yl)(hydroxy)(1-methyl-1H-1,2,3-triazol-5-yl)methyl)-2-methoxyquinolin-3-ol using the procedure described for Example 37a. MS (ESI): mass calcd. for $C_{24}H_{22}ClF_3N_4O_4$, 522.1; m/z found, 523.0 $[M+H]^+$. [4-Chloro-2-methoxy-3-(2-methoxyethoxy)quinolin-6-yl](1-methyl-1H-imidazol-5-yl)[6-(trifluoromethyl)pyridin-3-yl]methanol was purified by chiral SFC (Stationary phase: CHIRALPAK AD-H 5 μM 250×20 mm, Mobile phase: 80% $CO_2$, 20% MeOH/iPrOH 50/50 v/v+(0.3% iPrNH$_2$)) to give 2 enantiomers. The first eluting enantiomer was Example 79b: $^1$H NMR (400 MHz, CDCl$_3$) δ ppm 8.84-8.80 (m, 1H), 8.06 (d, J=2.1 Hz, 1H), 7.93-7.89 (m, 1H), 7.81 (d, J=8.8 Hz, 1H), 7.67 (d, J=7.9 Hz, 1H), 7.51-7.45 (m, 2H), 6.47 (s, 1H), 4.30-4.27 (m, 2H), 4.13 (s, 3H), 3.80-3.76 (m, 2H), 3.45 (s, 3H), 3.40 (s, 3H). MS (ESI): mass calcd. for $C_{24}H_{22}ClF_3N_4O_4$, 522.1; m/z found, 523.0 $[M+H]^+$ and the second eluting enantiomer was Example 79c: $^1$H NMR (400 MHz, CDCl$_3$) δ ppm 8.83-8.80 (m, 1H), 8.06 (d, J=2.1 Hz, 1H), 7.94-7.89 (m, 1H), 7.80 (d, J=8.7 Hz, 1H), 7.67 (d, J=8.2 Hz, 1H), 7.50-7.46 (m, 1H), 7.43 (s, 1H), 6.44 (s, 1H), 4.31-4.26 (m, 2H), 4.13 (s, 3H), 3.80-3.75 (m, 2H), 3.45 (s, 3H), 3.39 (s, 3H). MS (ESI): mass calcd. for $C_{24}H_{22}ClF_3N_4O_4$, 522.1; m/z found, 523.0 [M+H]$^+$.

Example 80a: [4-Chloro-2-methoxy-3-(1-methylethoxy)quinolin-6-yl](1,2-dimethyl-1H-imidazol-5-yl)(1-methyl-1H-1,2,3-triazol-5-yl)methanol

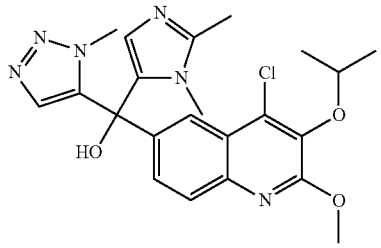 [SMILES: COc1nc2ccc(C(O)(c3cnnn3C)c3cnc(C)n3C)cc2c(Cl)c1OC(C)C]

n-BuLi (1.23 M in hexanes, 1.1 mL, 1.35 mmol) was added dropwise to a stirred slurry of 1-methyl-1,2,3-triazole (112 mg, 1.35 mmol) in THF (1 mL) at –40° C. under nitrogen. After stirring for another 30 minutes, the mixture was treated dropwise with a solution of (4-chloro-3-isopropoxy-2-methoxyquinolin-6-yl)(1,2-dimethyl-1H-imidazol-5-yl)methanone (252 mg, 0.67 mmol, Intermediate 27) in THF (5 mL). The reaction was allowed to warm to room temperature over 1 hour. The reaction was then quenched with saturated aqueous NH$_4$Cl. The mixture was poured into a separatory funnel and extracted with DCM (4×60 mL). The organics were combined, washed with brine, dried (Na$_2$SO$_4$), filtered and concentrated to dryness to afford a light yellow oil. The crude material was purified by FCC (1-7.5% MeOH/DCM) followed by reverse-phase HPLC (acetonitrile/water+NH$_4$OH) to provide the title compound as a white solid. $^1$H NMR (400 MHz, CDCl$_3$) δ ppm 8.08 (d, J=2.2 Hz, 1H), 7.78 (d, J=8.7 Hz, 1H), 7.33 (dd, J=8.6, 2.2 Hz, 1H), 7.18 (s, 1H), 6.18 (s, 1H), 4.74-4.67 (m, 1H), 4.32 (s, 1H), 4.13 (s, 3H), 3.94 (s, 3H), 3.39 (s, 3H), 2.32 (s, 3H), 1.39 (d, J=6.2 Hz, 6H). MS (ESI): mass calcd. for $C_{22}H_{25}ClN_6O_3$, 456.2; m/z found, 457.0 [M+H]$^+$. [4-Chloro-2-methoxy-3-(1-methylethoxy)quinolin-6-yl](1,2-dimethyl-1H-imidazol-5-yl)(1-methyl-1H-1,2,3-triazol-5-yl)methanol was purified by chiral SFC (Stationary phase: CHIRALPAK AD-H 5 µM 250×20 mm, Mobile phase: 70% CO$_2$, 30% MeOH/iPrOH 50/50 v/v+(0.3% iPrNH$_2$)) to give 2 enantiomers. The first eluting enantiomer was Example 80b: $^1$H NMR (400 MHz, CDCl$_3$) δ ppm 8.09 (d, J=2.2 Hz, 1H), 7.77 (d, J=8.7 Hz, 1H), 7.32 (dd, J=8.7, 2.2 Hz, 1H), 7.17 (s, 1H), 6.17 (s, 1H), 4.75-4.66 (m, 1H), 4.36 (s, 1H), 4.13 (s, 3H), 3.94 (s, 3H), 3.39 (s, 3H), 2.32 (s, 3H), 1.39 (d, J=6.2 Hz, 6H). MS (ESI): mass calcd. for $C_{22}H_{25}ClN_6O_3$, 456.2; m/z found, 457.2 [M+H]$^+$ and the second eluting enantiomer was Example 80c: $^1$H NMR (400 MHz, CDCl$_3$) δ ppm 8.06 (d, J=2.2 Hz, 1H), 7.80 (d, J=8.7 Hz, 1H), 7.35-7.32 (m, 1H), 7.21 (s, 1H), 6.24 (s, 1H), 4.74-4.67 (m, 1H), 4.13 (s, 3H), 3.95 (s, 3H), 3.52 (s, 1H), 3.42 (s, 3H), 2.37 (s, 3H), 1.39 (d, J=6.2 Hz, 6H). MS (ESI): mass calcd. for $C_{22}H_{25}ClN_6O_3$, 456.2; m/z found, 457.2 [M+H]$^+$.

Example 81a: [4-Chloro-2-methoxy-3-(1-methylethoxy)quinolin-6-yl](2,6-dimethylpyridin-3-yl)(1-methyl-1H-1,2,3-triazol-5-yl)methanol

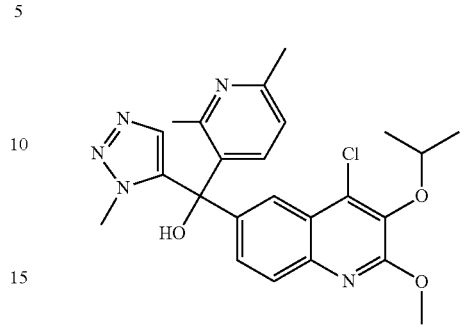

To a mixture of [2,4-dichloro-3-(1-methylethoxy)quinolin-6-yl](2,6-dimethylpyridin-3-yl)(1-methyl-1H-1,2,3-triazol-5-yl)methanol.TFA (182 mg, 0.31 mmol, Example 42) in toluene (3.1 mL) was added NaOMe (168 mg, 3.1 mmol) and the resulting mixture heated to 60° C. for 3 hours. The mixture was then cooled to room temperature, diluted with DCM and filtered through a pad of Celite®, rinsing the filter cake with DCM. The filtrate was concentrated to dryness and the residue purified by reverse-phase HPLC (acetonitrile/water+NH$_4$OH) to provide the title compound as a white solid. MS (ESI): mass calcd. for $C_{24}H_{26}ClN_5O_3$, 467.2; m/z found, 468.0 [M+H]$^+$. [4-Chloro-2-methoxy-3-(1-methylethoxy)quinolin-6-yl](2,6-dimethylpyridin-3-yl)(1-methyl-1H-1,2,3-triazol-5-yl)methanol was purified by chiral SFC (Stationary phase: CHIRALPAK AD-H 5 µM 250×20 mm, Mobile phase: 75% CO$_2$, 25% iPrOH+(0.3% iPrNH$_2$)) to give 2 enantiomers. The first eluting enantiomer was Example 81b: $^1$H NMR (500 MHz, CDCl$_3$) δ ppm 8.00-7.98 (m, 1H), 7.83-7.79 (m, 1H), 7.31 (d, J=8.7 Hz, 1H), 7.00-6.99 (m, 1H), 6.98-6.93 (m, 2H), 4.73-4.67 (m, 1H), 4.14-4.12 (m, 3H), 3.95-3.93 (m, 3H), 3.23 (s, 1H), 2.57-2.54 (m, 3H), 2.41-2.39 (m, 3H), 1.40-1.37 (m, 6H). MS (ESI): mass calcd. for $C_{24}H_{26}ClN_5O_3$, 467.2; m/z found, 468.1 [M+H]$^+$ and the second eluting enantiomer was Example 81c: $^1$H NMR (500 MHz, CDCl$_3$) δ ppm 8.00-7.98 (m, 1H), 7.83-7.80 (m, 1H), 7.32-7.29 (m, 1H), 7.00-6.99 (m, 1H), 6.98-6.93 (m, 2H), 4.73-4.67 (m, 1H), 4.14-4.13 (m, 3H), 3.95-3.93 (m, 3H), 3.25-3.23 (m, 1H), 2.57-2.55 (m, 3H), 2.41-2.39 (m, 3H), 1.40-1.37 (m, 6H). MS (ESI): mass calcd. for $C_{24}H_{26}ClN_5O_3$, 467.2; m/z found, 468.0 [M+H]$^+$.

Example 82a: [2-Azetidin-1-yl-4-chloro-3-(1-methylethoxy)quinolin-6-yl](2,4-dimethyl-1,3-thiazol-5-yl)(1-methyl-1H-1,2,3-triazol-5-yl)methanol.TFA

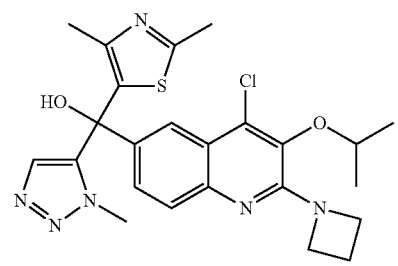 [SMILES: Cc1nc(C)c(C(O)(c2ccc3nc(N4CCC4)c(OC(C)C)c(Cl)c3c2)c2cnnn2C)s1]

To a sealed tube was added [2,4-dichloro-3-(1-methylethoxy)quinolin-6-yl](2,4-dimethyl-1,3-thiazol-5-yl)(1-methyl-1H-1,2,3-triazol-5-yl)methanol.TFA (185 mg, 0.31 mmol, Example 43), azetidine (107 μL, 1.56 mmol) and dimethylformamide (1.6 mL). The reaction vessel was sealed and heated in a 100° C. oil bath. After overnight heating, the vessel was cooled and the contents concentrated to dryness. The residue was dissolved in EtOAc (25 mL) and washed with saturated aqueous ammonium chloride (2×20 mL). The organics were dried ($Na_2SO_4$), filtered and concentrated to dryness to afford a light yellow oil. The crude material was purified by reverse-phase HPLC (acetonitrile/water+0.05% TFA) to provide the title compound as a clear colorless oil. $^1$H NMR (500 MHz, $CDCl_3$) δ ppm 8.05 (d, J=8.9 Hz, 1H), 7.86 (d, J=2.1 Hz, 1H), 7.75-7.72 (m, 1H), 7.13 (s, 1H), 4.93-4.86 (m, 1H), 4.78-4.73 (m, 4H), 3.94 (s, 3H), 2.65 (s, 3H), 2.61-2.55 (m, 2H), 2.09 (s, 3H), 1.42-1.39 (m, 6H). MS (ESI): mass calcd. for $C_{24}H_{27}ClN_6O_2S$, 498.2; m/z found, 499.0 [M+H]$^+$. [2-Azetidin-1-yl-4-chloro-3-(1-methylethoxy)quinolin-6-yl](2,4-dimethyl-1,3-thiazol-5-yl)(1-methyl-1H-1,2,3-triazol-5-yl)methanol was purified by chiral SFC (Stationary phase: Kromasil 5-Amycoat 5 μM 250×30 mm, Mobile phase: 85% $CO_2$, 15% EtOH+(0.2% $Et_3N$)) to give 2 enantiomers. The first eluting enantiomer was Example 82b: $^1$H NMR (500 MHz, $CDCl_3$) δ ppm 7.92-7.90 (m, 1H), 7.69 (d, J=8.8 Hz, 1H), 7.38-7.34 (m, 1H), 7.22 (s, 1H), 4.70-4.64 (m, 1H), 4.32-4.28 (m, 4H), 3.92 (s, 3H), 2.59 (s, 3H), 2.41-2.34 (m, 2H), 2.12 (s, 3H), 1.34 (d, J=6.1 Hz, 6H). MS (ESI): mass calcd. for $C_{24}H_{27}ClN_6O_2S$, 498.2; m/z found, 499.0 [M+H]$^+$ and the second eluting enantiomer was Example 82c: $^1$H NMR (500 MHz, $CDCl_3$) δ ppm 7.92-7.90 (m, 1H), 7.71-7.67 (m, 1H), 7.38-7.34 (m, 1H), 7.24-7.22 (m, 1H), 4.70-4.64 (m, 1H), 4.32-4.28 (m, 4H), 3.92 (s, 3H), 2.59 (s, 3H), 2.41-2.34 (m, 2H), 2.13 (s, 3H), 1.36-1.33 (m, 6H). MS (ESI): mass calcd. for $C_{24}H_{27}ClN_6O_2S$, 498.2; m/z found, 499.0 [M+H]$^+$.

Example 83: (4-Chloro-2-methoxy-3-{[4-(trifluoromethyl)piperidin-1-yl]carbonyl}quinolin-6-yl)(2,6-dimethylpyridin-3-yl)(1-methyl-1H-1,2,3-triazol-5-yl)methanol

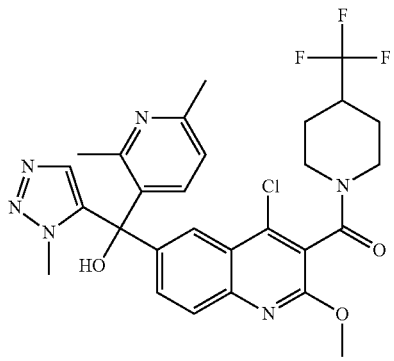 [SMILES: COc1nc2ccc(C(O)(c3ccc(C)nc3C)c3cnnn3C)cc2c(Cl)c1C(=O)N1CCC(C(F)(F)F)CC1]

n-BuLi (1.85 M in hexanes, 116 μL, 0.21 mmol) was added dropwise to a stirred solution of (4-chloro-6-iodo-2-methoxyquinolin-3-yl)(4-(trifluoromethyl)piperidin-1-yl)methanone (107 mg, 0.21 mmol, Intermediate 35: step f) in THF (3 mL) at −78° C. under nitrogen. After stirring for 5 minutes at −78° C., the mixture was treated dropwise with a solution of (2,6-dimethylpyridin-3-yl)(1-methyl-1H-1,2,3-triazol-5-yl)methanone (46 mg, 0.21 mmol, Intermediate 11: step b) in THF (2 mL). The flask was rinsed with THF (1 mL) and that THF was added to the reaction. The solution was stirred at −78° C. for 15 minutes, then warmed to 0° C. and stirred for an additional 30 minutes. Saturated aqueous $NH_4Cl$ (5 mL), water (20 mL) and EtOAc (20 mL) were added and the layers separated. The aqueous layer was further extracted with EtOAc (20 mL). The organics were combined, dried ($Na_2SO_4$), filtered and concentrated to dryness to afford a yellow oil. The crude material was purified by FCC (0.5-7.5% MeOH/DCM) to provide the title compound as a cream-colored amorphous solid. $^1$H NMR (500 MHz, $CDCl_3$) δ ppm 8.15-8.01 (m, 1H), 7.91-7.85 (m, 1H), 7.54-7.39 (m, 1H), 7.06-6.98 (m, 1H), 6.97-6.90 (m, 2H), 4.98-4.91 (m, 1H), 4.13-4.09 (m, 3H), 3.97-3.93 (m, 3H), 3.58-3.52 (m, 1H), 3.22-3.20 (m, 1H), 3.16-3.07 (m, 1H), 2.90-2.82 (m, 1H), 2.58-2.55 (m, 3H), 2.42-2.38 (m, 3H), 2.37-2.28 (m, 1H), 2.09-2.01 (m, 1H), 1.89-1.80 (m, 1H), 1.74-1.58 (m, 2H). MS (ESI): mass calcd. for $C_{28}H_{28}ClF_3N_6O_3$, 588.2; m/z found, 589.2 [M+H]$^+$.

Example 84a: (1-Acetylpiperidin-4-yl)[4-chloro-2-methoxy-3-(1-methylethoxy)quinolin-6-yl]phenylmethanol

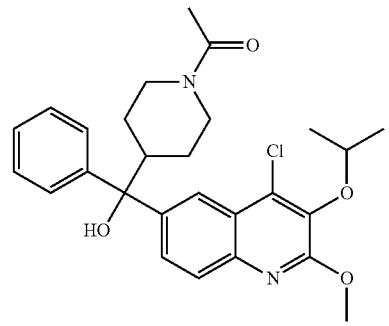 [SMILES: COc1nc2ccc(C(O)(c3ccccc3)C3CCN(C(C)=O)CC3)cc2c(Cl)c1OC(C)C]

To a mixture of (1-acetylpiperidin-4-yl)[2,4-dichloro-3-(1-methylethoxy)quinolin-6-yl]phenylmethanol.TFA (179 mg, 0.3 mmol, Example 44) in toluene (3 mL) was added NaOMe (161 mg, 2.98 mmol) and the resulting mixture heated to 60° C. for 17 hours. The mixture was then cooled to room temperature, diluted with DCM and filtered, rinsing the filter cake with DCM. The filtrate was concentrated to dryness to afford a white solid. The crude material was purified by reverse-phase HPLC (acetonitrile/water+$NH_4OH$) to provide the title compound as a white solid. $^1$H NMR (500 MHz, $CDCl_3$) δ ppm 8.21-8.18 (m, 1H), 7.76-7.71 (m, 1H), 7.63-7.57 (m, 1H), 7.54-7.50 (m, 2H), 7.36-7.30 (m, 2H), 7.24-7.21 (m, 1H), 4.74-4.68 (m, 1H), 4.68-4.64 (m, 1H), 4.09 (s, 3H), 3.88-3.79 (m, 1H), 3.14-3.04 (m, 1H), 2.80-2.72 (m, 1H), 2.63-2.53 (m, 1H), 2.20-2.18 (m, 1H), 2.06-2.04 (m, 3H), 1.70-1.57 (m, 1H), 1.51-1.41 (m, 1H), 1.38-1.36 (m, 6H), 1.35-1.24 (m, 1H). MS (ESI): mass calcd. for $C_{27}H_{31}ClN_2O_4$, 482.2; m/z found, 483.1 [M+H]$^+$. (1-Acetylpiperidin-4-yl)[4-chloro-2-methoxy-3-(1-methylethoxy)quinolin-6-yl]phenylmethanol was purified by chiral SFC (Stationary phase: CHIRALPAK AD-H 5 μM 250×20 mm, Mobile phase: 70% $CO_2$, 30% MeOH/iPrOH 50/50 v/v) to give 2 enantiomers. The first eluting enantiomer was Example 84b: $^1$H NMR (500 MHz, $CDCl_3$) δ ppm 8.20 (d, J=8.7 Hz, 1H), 7.75-7.71 (m, 1H), 7.63-7.57 (m, 1H), 7.55-7.50 (m, 2H), 7.36-7.30 (m, 2H), 7.24-7.20 (m, 1H), 4.74-4.68 (m, 1H), 4.68-4.63 (m, 1H), 4.10-4.08 (m, 3H), 3.87-3.78 (m, 1H), 3.13-3.04 (m, 1H), 2.80-2.72 (m, 1H), 2.63-2.53 (m, 1H), 2.21 (s, 1H), 2.07-2.04 (m, 3H), 1.73-1.56 (m, 2H), 1.51-1.41 (m, 1H), 1.37 (d, J=6.3 Hz, 6H), 1.34-1.29 (m, 1H). MS (ESI): mass calcd. for $C_{27}H_{31}ClN_2O_4$, 482.2; m/z found, 483.1 [M+H]$^+$ and the second eluting enantiomer was Example 84c: $^1$H NMR (500 MHz, CDCl$_3$) δ ppm 8.21-8.18 (m, 1H), 7.73 (t, J=8.6 Hz, 1H), 7.63-7.57 (m, 1H), 7.55-7.50 (m, 2H), 7.36-7.30 (m, 2H), 7.25-7.19 (m, 1H), 4.74-4.68 (m, 1H), 4.68-4.63 (m, 1H), 4.09 (s, 3H), 3.87-3.78 (m, 1H), 3.14-3.03 (m, 1H), 2.80-2.72 (m, 1H), 2.63-2.53 (m, 1H), 2.24-2.22 (m, 1H), 2.06-2.04 (m, 3H), 1.71-1.56 (m, 2H), 1.51-1.41 (m, 1H), 1.38-1.36 (m, 6H), 1.36-1.30 (m, 1H). MS (ESI): mass calcd. for $C_{27}H_{31}ClN_2O_4$, 482.2; m/z found, 483.1 [M+H]$^+$.

Example 85a: [4-Chloro-2-methoxy-3-(1-methylethoxy)quinolin-6-yl](2,4-dimethyl-1,3-thiazol-5-yl)(1-methyl-1H-1,2,3-triazol-5-yl)methanol

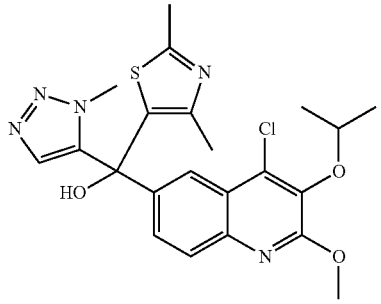 [SMILES: COc1nc2ccc(C(O)(c3sc(C)nc3C)c3cnnn3C)cc2c(Cl)c1OC(C)C]

To a mixture of [2,4-dichloro-3-(1-methylethoxy)quinolin-6-yl](2,4-dimethyl-1,3-thiazol-5-yl)(1-methyl-1H-1,2,3-triazol-5-yl)methanol.TFA (139 mg, 0.23 mmol, Example 43) in toluene (2.4 mL) was added NaOMe (127 mg, 2.4 mmol) and the resulting mixture heated to 60° C. for 5.5 hours. The mixture was then cooled to room temperature, diluted with DCM and filtered, rinsing the filter cake with DCM. The filtrate was concentrated to dryness to afford a white solid. The crude material was purified by basic HPLC to provide the title compound as a white solid. MS (ESI): mass calcd. for $C_{22}H_{24}ClN_5O_3S$, 473.1; m/z found, 474.0 [M+H]$^+$. [4-Chloro-2-methoxy-3-(1-methylethoxy)quinolin-6-yl](2,4-dimethyl-1,3-thiazol-5-yl)(1-methyl-1H-1,2,3-triazol-5-yl)methanol was purified by chiral SFC (Stationary phase: CHIRALPAK AD-H 5 μM 250×20 mm, Mobile phase: 80% CO$_2$, 20% MeOH) followed by achiral SFC (Stationary phase: CHIRALPAK IC 5 μM 250×20 mm, Mobile phase: 60% CO$_2$, 40% MeOH) to give 2 enantiomers. The first eluting enantiomer was Example 85b: $^1$H NMR (500 MHz, CDCl$_3$) δ ppm 8.08-8.06 (m, 1H), 7.82 (d, J=8.7 Hz, 1H), 7.46-7.43 (m, 1H), 7.23 (s, 1H), 4.73-4.66 (m, 1H), 4.13 (s, 3H), 3.92 (s, 3H), 3.65-3.63 (m, 1H), 2.59 (s, 3H), 2.15 (s, 3H), 1.38 (d, J=6.0 Hz, 6H). MS (ESI): mass calcd. for $C_{22}H_{24}ClN_5O_3S$, 473.1; m/z found, 474.0 [M+H]$^+$ and the second eluting enantiomer was Example 85c: $^1$H NMR (500 MHz, CDCl$_3$) δ ppm 8.07 (d, J=2.2 Hz, 1H), 7.82 (d, J=8.7 Hz, 1H), 7.46-7.43 (m, 1H), 7.23 (s, 1H), 4.73-4.67 (m, 1H), 4.13 (s, 3H), 3.92 (s, 3H), 3.65 (s, 1H), 2.59 (s, 3H), 2.15 (s, 3H), 1.38 (d, J=6.2 Hz, 6H). MS (ESI): mass calcd. for $C_{22}H_{24}ClN_5O_3S$, 473.1; m/z found, 474.0 [M+H]$^+$.

Example 86a: [4-Chloro-2-methoxy-3-(2,2,2-trifluoroethoxy)quinolin-6-yl](4-chlorophenyl)(1-methyl-1H-imidazol-5-yl)methanol

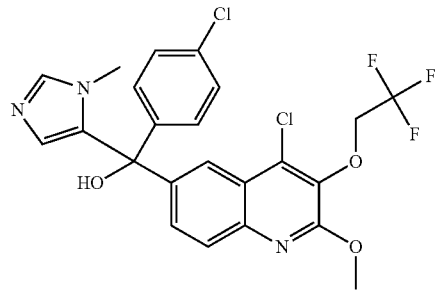 [SMILES: COc1nc2ccc(C(O)(c3ccc(Cl)cc3)c3cncn3C)cc2c(Cl)c1OCC(F)(F)F]

To a mixture of (4-chlorophenyl)[2,4-dichloro-3-(2,2,2-trifluoroethoxy)quinolin-6-yl](1-methyl-1H-imidazol-5-yl)methanol (133 mg, 0.26 mmol, Example 45) in toluene (2.6 mL) was added NaOMe (97 mg, 1.8 mmol) and the resulting mixture heated to 60° C. for 6 hours. The mixture was then cooled to room temperature, diluted with DCM and filtered, rinsing the filter cake with DCM. The filtrate was concentrated to dryness and the residue purified by reverse-phase HPLC (acetonitrile/water+NH$_4$OH) to provide the title compound as a white solid. MS (ESI): mass calcd. for $C_{23}H_{18}Cl_2F_3N_3O_3$, 511.1; m/z found, 512.9 [M+H]$^+$. [4-Chloro-2-methoxy-3-(2,2,2-trifluoroethoxy)quinolin-6-yl](4-chlorophenyl)(1-methyl-1H-imidazol-5-yl)methanol was purified by achiral SFC (Stationary phase: CHIRALPAK AD-H 5 μM 250×20 mm, Mobile phase: 80% CO$_2$, 20% MeOH) followed by chiral SFC (Stationary phase: CHIRALPAK AD-H 5 μM 250×20 mm, Mobile phase: 75% CO$_2$, 25% MeOH/iPrOH 50/50 v/v) to give 2 enantiomers. The first eluting enantiomer was Example 86b: $^1$H NMR (400 MHz, CDCl$_3$) δ ppm 8.08 (d, J=2.1 Hz, 1H), 7.77 (d, J=8.8 Hz, 1H), 7.53-7.48 (m, 1H), 7.35-7.28 (m, 5H), 6.37-6.34 (m, 1H), 4.51 (q, J=8.4 Hz, 2H), 4.15 (s, 3H), 4.13-4.05 (m, 1H), 3.37 (s, 3H). MS (ESI): mass calcd. for $C_{23}H_{18}Cl_2F_3N_3O_3$, 511.1; m/z found, 512.0 [M+H]$^+$ and the second eluting enantiomer was Example 86c: $^1$H NMR (400 MHz, CDCl$_3$) δ ppm 8.08 (d, J=2.1 Hz, 1H), 7.77 (d, J=8.8 Hz, 1H), 7.53-7.49 (m, 1H), 7.36-7.28 (m, 5H), 6.37-6.34 (m, 1H), 4.55-4.47 (m, 2H), 4.15 (s, 3H), 4.08 (s, 1H), 3.37 (s, 3H). MS (ESI): mass calcd. for $C_{23}H_{18}Cl_2F_3N_3O_3$, 511.1; m/z found, 512.0 [M+H]$^+$.

Example 87a: [2-Azetidin-1-yl-4-chloro-3-(cyclopropylmethoxy)quinolin-6-yl](1-methyl-1H-imidazol-5-yl)[6-(trifluoromethyl)pyridin-3-yl]methanol

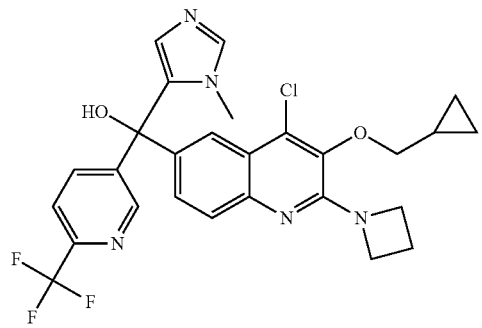 [SMILES: Cn1cncc1C(O)(c1ccc(C(F)(F)F)nc1)c1ccc2nc(N3CCC3)c(OCC3CC3)c(Cl)c2c1]

To a sealed tube was added [2,4-dichloro-3-(cyclopropylmethoxy)quinolin-6-yl](1-methyl-1H-imidazol-5-yl)[6-(trifluoromethyl)pyridin-3-yl]methanol.TFA (112 mg, 0.18 mmol, Example 40), azetidine (61 μL, 0.88 mmol) and dimethylformamide (0.92 mL). The reaction vessel was sealed and heated in a 100° C. oil bath. After overnight heating, the vessel was cooled and the contents concentrated to dryness. The residue was dissolved in EtOAc (15 mL) and washed with saturated aqueous ammonium chloride (2×15 mL). The organics were dried ($Na_2SO_4$), filtered and concentrated to dryness to afford a light yellow oil. The crude material was purified by reverse-phase HPLC (acetonitrile/water+0.05% TFA) to provide the title compound as a clear colorless oil. MS (ESI): mass calcd. for $C_{27}H_{25}ClF_3N_5O_2$, 543.2; m/z found, 544.0 [M+H]$^+$. [2-Azetidin-1-yl-4-chloro-3-(cyclopropylmethoxy)quinolin-6-yl](1-methyl-1H-imidazol-5-yl)[6-(trifluoromethyl)pyridin-3-yl]methanol was purified by chiral SFC (Stationary phase: CHIRALPAK AD-H 5 μM 250×21 mm, Mobile phase: 80% $CO_2$, 20% EtOH+0.2% $Et_3N$) to give 2 enantiomers. The first eluting enantiomer was Example 87b: $^1$H NMR (400 MHz, CDCl$_3$) δ ppm 8.81 (s, 1H), 7.93-7.85 (m, 2H), 7.68-7.61 (m, 2H), 7.41-7.34 (m, 1H), 7.34-7.28 (m, 1H), 6.39-6.28 (m, 1H), 4.35-4.30 (m, 4H), 3.82 (d, J=7.2 Hz, 2H), 3.36 (s, 3H), 2.43-2.35 (m, 2H), 1.35-1.30 (m, 1H), 0.68-0.62 (m, 2H), 0.38-0.32 (m, 2H). MS (ESI): mass calcd. for $C_{27}H_{25}ClF_3N_5O_2$, 543.2; m/z found, 544.0 [M+H]$^+$ and the second eluting enantiomer was Example 87c: $^1$H NMR (400 MHz, CDCl$_3$) δ ppm 8.81 (s, 1H), 7.92-7.85 (m, 2H), 7.68-7.62 (m, 2H), 7.40-7.34 (m, 1H), 7.34-7.29 (m, 1H), 6.39-6.28 (m, 1H), 4.35-4.29 (m, 4H), 3.82 (d, J=7.1 Hz, 2H), 3.36 (s, 3H), 2.43-2.34 (m, 2H), 1.34-1.29 (m, 1H), 0.67-0.61 (m, 2H), 0.37-0.32 (m, 2H). MS (ESI): mass calcd. for $C_{27}H_{25}ClF_3N_5O_2$, 543.2; m/z found, 544.0 [M+H]$^+$.

Example 88a: [4-Chloro-3-(cyclopropylmethoxy)-2-methoxyquinolin-6-yl](1-methyl-1H-imidazol-5-yl)[6-(trifluoromethyl)pyridin-3-yl]methanol

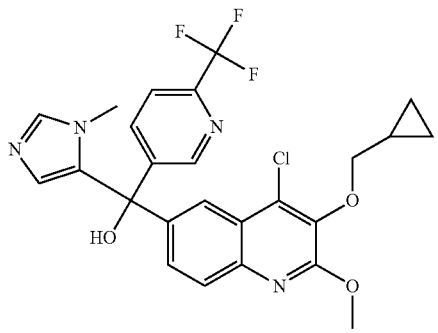 [SMILES: COc1nc2ccc(C(O)(c3ccc(C(F)(F)F)nc3)c3cncn3C)cc2c(Cl)c1OCC1CC1]

To a mixture of [2,4-dichloro-3-(cyclopropylmethoxy)quinolin-6-yl](1-methyl-1H-imidazol-5-yl)[6-(trifluoromethyl)pyridin-3-yl]methanol.TFA (112 mg, 0.21 mmol, Example 40) in toluene (2.1 mL) was added NaOMe (115 mg, 2.1 mmol) and the resulting mixture heated to 60° C. for 6 hours. The mixture was then cooled to room temperature, diluted with DCM and filtered, rinsing the filter cake with DCM. The filtrate was concentrated to dryness to afford a clear colorless oil. The crude material was purified by reverse-phase HPLC (acetonitrile/water+NH$_4$OH) to provide a white solid. MS (ESI): mass calcd. for $C_{25}H_{22}ClF_3N_4O_3$, 518.1; m/z found, 519.0 [M+H]$^+$. [4-Chloro-3-(cyclopropylmethoxy)-2-methoxyquinolin-6-yl](1-methyl-1H-imidazol-5-yl)[6-(trifluoromethyl)pyridin-3-yl]methanol was purified by chiral SFC (Stationary phase: CHIRALPAK AD-H 5 μM 250×20 mm, Mobile phase: 80% $CO_2$, 20% MeOH/iPrOH 50/50 v/v) to give 2 enantiomers. The first eluting enantiomer was Example 88b: $^1$H NMR (400 MHz, CDCl$_3$) δ ppm 8.85-8.82 (m, 1H), 8.06 (d, J=2.1 Hz, 1H), 7.91-7.86 (m, 1H), 7.81 (d, J=8.8 Hz, 1H), 7.68-7.64 (m, 1H), 7.52-7.48 (m, 1H), 7.48-7.46 (m, 1H), 6.41-6.37 (m, 1H), 4.12 (s, 3H), 3.98 (d, J=7.3 Hz, 2H), 3.42 (s, 3H), 3.41-3.39 (m, 1H), 1.37-1.28 (m, 1H), 0.64-0.59 (m, 2H), 0.36-0.31 (m, 2H). MS (ESI): mass calcd. for $C_{25}H_{22}ClF_3N_4O_3$, 518.1; m/z found, 519.0 [M+H]$^+$ and the second eluting enantiomer was Example 88c: $^1$H NMR (400 MHz, CDCl$_3$) δ ppm 8.85-8.82 (m, 1H), 8.07-8.04 (m, 1H), 7.90-7.85 (m, 1H), 7.82-7.79 (m, 1H), 7.69-7.64 (m, 1H), 7.52-7.47 (m, 2H), 6.39 (s, 1H), 4.14-4.11 (m, 3H), 4.00-3.96 (m, 2H), 3.44-3.41 (m, 3H), 3.41-3.38 (m, 1H), 1.37-1.28 (m, 1H), 0.65-0.58 (m, 2H), 0.36-0.30 (m, 2H). MS (ESI): mass calcd. for $C_{25}H_{22}ClF_3N_4O_3$, 518.1; m/z found, 519.0 [M+H]$^+$.

Example 89a: [2-Azetidin-1-yl-4-chloro-3-(2,2,2-trifluoroethoxy)quinolin-6-yl](1-methyl-1H-imidazol-5-yl)[6-(trifluoromethyl)pyridin-3-yl]methanol

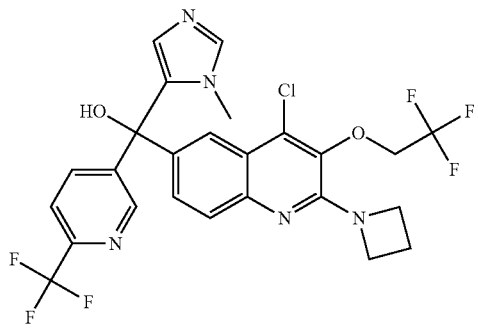 [SMILES: Cn1cncc1C(O)(c1ccc(C(F)(F)F)nc1)c1ccc2nc(N3CCC3)c(OCC(F)(F)F)c(Cl)c2c1]

To a sealed tube was added [2,4-dichloro-3-(2,2,2-trifluoroethoxy)quinolin-6-yl](1-methyl-1H-imidazol-5-yl)[6-(trifluoromethyl)pyridin-3-yl]methanol (86 mg, 0.13 mmol, Example 39), azetidine (54 μL, 0.78 mmol) and dimethylformamide (0.82 mL). The reaction vessel was sealed and heated in a 100° C. oil bath. After overnight heating, the vessel was cooled and the contents concentrated to dryness. The residue was dissolved in EtOAc (15 mL) and washed with saturated aqueous ammonium chloride (2×10 mL). The organics were dried ($Na_2SO_4$), filtered and concentrated to dryness to afford a light yellow oil. The crude material was purified by reverse-phase HPLC (acetonitrile/water+0.05% TFA) to provide the title compound as a clear colorless oil. MS (ESI): mass calcd. for $C_{25}H_{20}ClF_6N_5O_2$, 571.1; m/z found, 572.0 [M+H]$^+$. [2-Azetidin-1-yl-4-chloro-3-(2,2,2-trifluoroethoxy)quinolin-6-yl](1-methyl-1H-imidazol-5-yl)[6-(trifluoromethyl)pyridin-3-yl]methanol was purified by chiral SFC (Stationary phase: CHIRALPAK AD-H 5 μM 250×20 mm, Mobile phase: 70% $CO_2$, 30% EtOH) to give 2 enantiomers. The first eluting enantiomer was Example 89b: $^1$H NMR (400 MHz, CDCl$_3$) δ ppm 8.84-8.80 (m, 1H), 7.96-7.93 (m, 1H), 7.89-7.84 (m, 1H), 7.73-7.68 (m, 1H), 7.68-7.64 (m, 1H), 7.52-7.48 (m, 1H), 7.48-7.44 (m, 1H), 6.39 (s, 1H), 4.39-4.33 (m, 2H), 4.33-4.28 (m, 4H), 3.45-

3.42 (m, 3H), 3.42-3.40 (m, 1H), 2.47-2.41 (m, 2H). MS (ESI): mass calcd. for $C_{25}H_{20}ClF_6N_5O_2$, 571.1; m/z found, 572.0 [M+H]$^+$ and the second eluting enantiomer was Example 89c: $^1$H NMR (400 MHz, CDCl$_3$) δ ppm 8.84-8.80 (m, 1H), 7.95-7.92 (m, 1H), 7.89-7.84 (m, 1H), 7.71 (d, J=8.8 Hz, 1H), 7.68-7.64 (m, 1H), 7.50 (s, 1H), 7.48-7.43 (m, 1H), 6.39 (s, 1H), 4.39-4.33 (m, 2H), 4.33-4.28 (m, 4H), 3.42 (s, 3H), 3.42-3.39 (m, 1H), 2.47-2.41 (m, 2H). MS (ESI): mass calcd. for $C_{25}H_{20}ClF_6N_5O_2$, 571.1; m/z found, 572.0 [M+H]$^+$.

Example 90a: [2-Azetidin-1-yl-4-chloro-3-(2,2,2-trifluoroethoxy)quinolin-6-yl](4-chlorophenyl)(1-methyl-1H-imidazol-5-yl)methanol.TFA

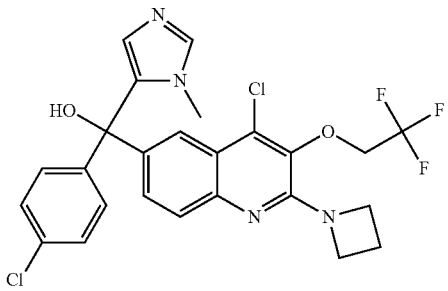 [SMILES: Cn1cncc1C(O)(c1ccc(Cl)cc1)c1ccc2nc(N3CCC3)c(OCC(F)(F)F)c(Cl)c2c1]

To a sealed tube was added (4-chlorophenyl)[2,4-dichloro-3-(2,2,2-trifluoroethoxy)quinolin-6-yl](1-methyl-1H-imidazol-5-yl)methanol (133 mg, 0.26 mmol, Example 45), azetidine (89 µL, 1.29 mmol) and dimethylformamide (1.35 mL). The reaction vessel was sealed and heated in a 100° C. oil bath. After overnight heating, the vessel was cooled and the contents concentrated to dryness. The residue was dissolved in EtOAc (15 mL) and washed with saturated aqueous ammonium chloride (2×10 mL). The organics were dried (Na$_2$SO$_4$), filtered and concentrated to dryness to afford a light yellow oil. The crude material was purified by reverse-phase HPLC (acetonitrile/water+0.05% TFA) to provide the title compound as a clear colorless oil. $^1$H NMR (500 MHz, CDCl$_3$) δ ppm 8.66 (s, 1H), 7.93-7.91 (m, 1H), 7.87-7.82 (m, 1H), 7.57-7.52 (m, 1H), 7.36-7.32 (m, 2H), 7.26-7.25 (m, 1H), 7.25-7.23 (m, 1H), 6.67-6.63 (m, 1H), 4.60-4.54 (m, 4H), 4.48-4.41 (m, 2H), 3.61-3.58 (m, 3H), 2.54-2.47 (m, 2H). MS (ESI): mass calcd. for $C_{25}H_{21}Cl_2F_3N_4O_2$, 536.1; m/z found, 537.0 [M+H]$^+$. [2-Azetidin-1-yl-4-chloro-3-(2,2,2-trifluoroethoxy)quinolin-6-yl](4-chlorophenyl)(1-methyl-1H-imidazol-5-yl)methanol was purified by chiral SFC (Stationary phase: CHIRALPAK AD-H 5 µM 250×21 mm, Mobile phase: 85% CO$_2$, 15% EtOH+0.2% Et$_3$N) to give 2 enantiomers. The first eluting enantiomer was Example 90b: $^1$H NMR (500 MHz, CDCl$_3$) δ ppm 7.94-7.90 (m, 1H), 7.68-7.64 (m, 1H), 7.45-7.40 (m, 1H), 7.39-7.34 (m, 1H), 7.33-7.28 (m, 4H), 6.44-6.32 (m, 1H), 4.36-4.31 (m, 2H), 4.31-4.27 (m, 4H), 3.38 (s, 3H), 2.44-2.37 (m, 2H). MS (ESI): mass calcd. for $C_{25}H_{21}Cl_2F_3N_4O_2$, 536.1; m/z found, 537.0 [M+H]$^+$ and the second eluting enantiomer was Example 90c: $^1$H NMR (500 MHz, CDCl$_3$) δ ppm 7.93-7.90 (m, 1H), 7.66 (d, J=8.7 Hz, 1H), 7.50-7.38 (m, 2H), 7.33-7.27 (m, 4H), 6.50-6.35 (m, 1H), 4.36-4.31 (m, 2H), 4.31-4.27 (m, 4H), 3.38 (s, 3H), 2.44-2.37 (m, 2H). MS (ESI): mass calcd. for $C_{25}H_{21}Cl_2F_3N_4O_2$, 536.1; m/z found, 537.0 [M+H]$^+$.

Example 91a: (4-Chloro-3-ethoxy-2-methoxyquinolin-6-yl)(1-methyl-1H-imidazol-5-yl)[6-(trifluoromethyl)pyridin-3-yl]methanol

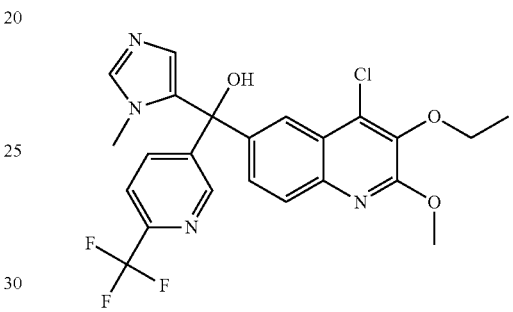

To a mixture of (2,4-dichloro-3-ethoxyquinolin-6-yl)(1-methyl-1H-imidazol-5-yl)[6-(trifluoromethyl)pyridin-3-yl]methanol.TFA (176 mg, 0.35 mmol, Example 46) in toluene (3.5 mL) was added NaOMe (191 mg, 3.5 mmol) and the resulting mixture heated to 60° C. for 2 hours. Then, the temperature was raised to 80° C. and stirring continued for 3 hours. The mixture was then cooled to room temperature, diluted with DCM and filtered, rinsing the filter cake with DCM. The filtrate was concentrated to dryness and the residue purified by reverse-phase HPLC (acetonitrile/water+NH$_4$OH) to afford the title compound as a tan solid. MS (ESI): mass calcd. for $C_{23}H_{20}ClF_3N_4O_3$, 492.1; m/z found, 493.0 [M+H]$^+$. (4-Chloro-3-ethoxy-2-methoxyquinolin-6-yl)(1-methyl-1H-imidazol-5-yl)[6-(trifluoromethyl)pyridin-3-yl]methanol was purified by chiral HPLC (Stationary phase: CHIRALPAK AD-H 5 µM Daicel column, Mobile phase: 85/12/3 heptane/ethanol/methanol (with 6 N ammonia)) followed by achiral SFC (Stationary phase: CHIRALPAK IC 5 µM 250×21 mm, Mobile phase: 90% CO$_2$, 10% EtOH+0.2% Et$_3$N) to give 2 enantiomers. The first eluting enantiomer was Example 91b: $^1$H NMR (400 MHz, CDCl$_3$) δ ppm 8.86-8.77 (m, 1H), 8.08 (s, 1H), 7.94-7.85 (m, 1H), 7.81-7.75 (m, 1H), 7.68-7.62 (m, 1H), 7.51-7.43 (m, 1H), 7.27-7.26 (m, 1H), 6.39-6.24 (m, 1H), 4.24-4.16 (m, 2H), 4.12 (s, 3H), 3.36 (s, 3H), 1.48-1.43 (m, 3H). MS (ESI): mass calcd. for $C_{23}H_{20}ClF_3N_4O_3$, 492.1; m/z found, 493.0 [M+H]$^+$ and the second eluting enantiomer was Example 91c: $^1$H NMR (600 MHz, CDCl$_3$) δ ppm 8.83-8.80 (m, 1H), 8.08 (d, J=2.2 Hz, 1H), 7.92-7.88 (m, 1H), 7.78 (d, J=8.7 Hz, 1H), 7.67-7.64 (m, 1H), 7.49-7.45 (m, 1H), 7.31-7.27 (m, 1H), 6.33-6.30 (m, 1H), 5.32 (s, 1H), 4.23-4.17 (m, 2H), 4.12 (s, 3H), 3.35 (s, 3H), 1.47-1.43 (m, 3H). MS (ESI): mass calcd. for $C_{23}H_{20}ClF_3N_4O_3$, 492.1; m/z found, 493.0 [M+H]$^+$.

Example 92a: (4-Chloro-3-ethoxy-2-methoxyquinolin-6-yl)(4-chlorophenyl)(1-methyl-1H-imidazol-5-yl)methanol

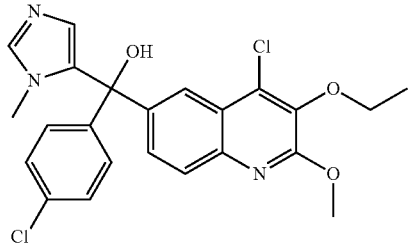 [SMILES: CCOc1c(OC)nc2ccc(C(O)(c3ccc(Cl)cc3)c3cncn3C)cc2c1Cl]

To a mixture of (4-chlorophenyl)(2,4-dichloro-3-ethoxyquinolin-6-yl)(1-methyl-1H-imidazol-5-yl)methanol.TFA (143 mg, 0.31 mmol, Example 47) in toluene (3.1 mL) was added NaOMe (167 mg, 3.1 mmol) and the resulting mixture heated to 60° C. for 6 hours. The reaction was then heated to 80° C. and stirred for 17.5 hours. The mixture was then cooled to room temperature, diluted with DCM and filtered, rinsing the filter cake with DCM. The filtrate was concentrated to dryness and purified by reverse-phase HPLC (acetonitrile/water+NH$_4$OH) to afford the title compound as a white solid. $^1$H NMR (500 MHz, CDCl$_3$) δ ppm 8.03-8.01 (m, 1H), 7.79-7.76 (d, J=8.7 Hz, 1H), 7.49-7.46 (m, 1H), 7.46-7.44 (m, 1H), 7.34-7.29 (m, 4H), 6.46-6.44 (m, 1H), 4.23-4.18 (m, 2H), 4.14-4.12 (s, 3H), 3.42-3.39 (s, 3H), 3.15-3.12 (s, 1H), 1.47-1.43 (m, 3H). MS (ESI): mass calcd. for C$_{23}$H$_{21}$Cl$_2$N$_3$O$_3$, 457.1; m/z found, 459.0 [M+H]$^+$. (4-Chloro-3-ethoxy-2-methoxyquinolin-6-yl)(4-chlorophenyl)(1-methyl-1H-imidazol-5-yl)methanol was purified by chiral HPLC (Stationary phase: CHIRALPAK AD-H 20 μM Daicel column, Mobile phase: 1/1 MeOH/EtOH) followed by silica plug (5% MeOH/DCM or 50% EtOAc/DCM) to give 2 enantiomers. The first eluting enantiomer was Example 92b: $^1$H NMR (400 MHz, CDCl$_3$) δ ppm 7.98 (d, J=2.1 Hz, 1H), 7.72 (d, J=8.8 Hz, 1H), 7.47-7.43 (m, 1H), 7.41 (s, 1H), 7.26-7.25 (m, 4H), 6.31 (s, 1H), 4.18-4.11 (m, 2H), 4.07 (s, 3H), 3.37 (s, 3H), 1.42-1.38 (m, 3H). MS (ESI): mass calcd. for C$_{23}$H$_{21}$Cl$_2$N$_3$O$_3$, 457.1; m/z found, 458.0 [M+H]$^+$ and the second eluting enantiomer was Example 92c: $^1$H NMR (400 MHz, CDCl$_3$) δ ppm 8.04 (d, J=2.1 Hz, 1H), 7.76 (d, J=8.7 Hz, 1H), 7.49-7.44 (m, 1H), 7.36 (s, 1H), 7.33-7.30 (m, 4H), 6.38 (s, 1H), 4.23-4.17 (m, 2H), 4.12 (s, 3H), 3.38 (s, 3H), 1.48-1.42 (m, 3H). MS (ESI): mass calcd. for C$_{23}$H$_{21}$Cl$_2$N$_3$O$_3$, 457.1; m/z found, 458.0 [M+H]$^+$.

Example 93a: [2-Azetidin-1-yl-4-chloro-3-(1-methylethoxy)quinolin-6-yl](1-methyl-1H-imidazol-5-yl)[6-(trifluoromethyl)pyridin-3-yl]methanol

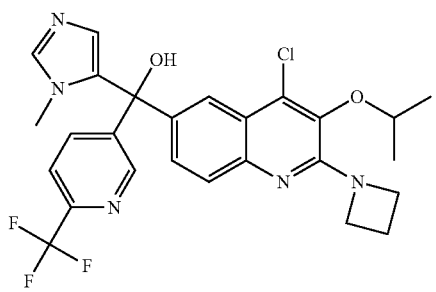 [SMILES: CC(C)Oc1c(N2CCC2)nc2ccc(C(O)(c3ccc(C(F)(F)F)nc3)c3cncn3C)cc2c1Cl]

To a sealed tube was added [2,4-dichloro-3-(1-methylethoxy)quinolin-6-yl](1-methyl-1H-imidazol-5-yl)[6-(trifluoromethyl)pyridin-3-yl]methanol.TFA (151 mg, 0.3 mmol, Example 48), azetidine (100 μL, 1.48 mmol) and dimethylformamide (1.55 mL). The reaction vessel was sealed and heated in a 100° C. oil bath. After overnight heating, the vessel was cooled to room temperature and the contents concentrated to dryness. The residue was dissolved in EtOAc (15 mL) and washed with saturated aqueous ammonium chloride (2×10 mL). The organics were dried (Na$_2$SO$_4$), filtered and concentrated to dryness to afford a light yellow foam. The crude material was purified by reverse-phase HPLC (acetonitrile/water+0.05% TFA) to provide the title compound as a clear colorless oil. MS (ESI): mass calcd. for C$_{26}$H$_{25}$ClF$_3$N$_5$O$_2$, 531.2; m/z found, 532.0 [M+H]$^+$. [2-Azetidin-1-yl-4-chloro-3-(1-methylethoxy)quinolin-6-yl](1-methyl-1H-imidazol-5-yl)[6-(trifluoromethyl)pyridin-3-yl]methanol was purified by chiral HPLC (Stationary phase: CHIRALPAK AD-H 5 μM Daicel column, Mobile phase: 75/22/3 heptane/ethanol/methanol (with 7 N ammonia)), followed by basic HPLC to give 2 enantiomers. The first eluting enantiomer was Example 93b: $^1$H NMR (400 MHz, CDCl$_3$) δ ppm 8.85-8.82 (m, 1H), 7.91 (d, J=2.2 Hz, 1H), 7.89-7.85 (m, 1H), 7.69 (d, J=8.8 Hz, 1H), 7.65 (d, J=8.2 Hz, 1H), 7.50-7.47 (m, 1H), 7.43-7.38 (m, 1H), 6.40-6.36 (m, 1H), 4.69-4.62 (m, 1H), 4.33-4.27 (m, 4H), 3.43 (s, 3H), 2.42-2.33 (m, 2H), 1.34 (d, J=6.2 Hz, 6H). MS (ESI): mass calcd. for C$_{26}$H$_{25}$ClF$_3$N$_5$O$_2$, 531.2; m/z found, 532.0 [M+H]$^+$ and the second eluting enantiomer was Example 93c: $^1$H NMR (400 MHz, CDCl$_3$) δ ppm 8.85-8.82 (m, 1H), 7.91 (d, J=2.2 Hz, 1H), 7.89-7.85 (m, 1H), 7.69 (d, J=8.8 Hz, 1H), 7.67-7.63 (m, 1H), 7.50-7.46 (m, 1H), 7.40 (dd, J=8.7, 2.2 Hz, 1H), 6.39-6.37 (m, 1H), 4.69-4.61 (m, 1H), 4.32-4.27 (m, 4H), 3.43 (s, 3H), 2.40-2.34 (m, 2H), 1.34 (d, J=6.1 Hz, 6H). MS (ESI): mass calcd. for C$_{26}$H$_{25}$ClF$_3$N$_5$O$_2$, 531.2; m/z found, 532.0 [M+H]$^+$.

Example 94a: [2-Azetidin-1-yl-4-chloro-3-(1-methylethoxy)quinolin-6-yl](4-chlorophenyl)(1-methyl-1H-imidazol-5-yl)methanol

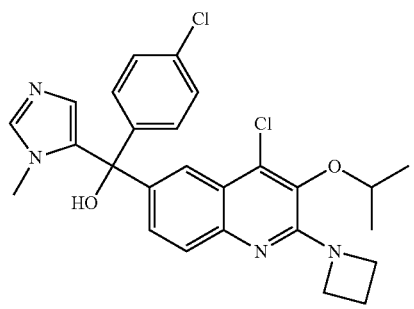 [SMILES: CC(C)Oc1c(N2CCC2)nc2ccc(C(O)(c3ccc(Cl)cc3)c3cncn3C)cc2c1Cl]

To a sealed tube was added (4-chlorophenyl)[2,4-dichloro-3-(1-methylethoxy)quinolin-6-yl](1-methyl-1H-imidazol-5-yl)methanol.TFA (110 mg, 0.23 mmol, Example 49a), azetidine (78 μL, 1.15 mmol) and dimethylformamide (1.2 mL). The reaction vessel was sealed and heated in a 100° C. oil bath. After overnight heating, the vessel was cooled to room temperature and the contents concentrated to dryness. The residue was dissolved in EtOAc (15 mL) and washed with saturated aqueous ammonium chloride (2×10 mL). The organics were dried (Na$_2$SO$_4$), filtered and concentrated to dryness to afford a light yellow oil. The crude material was purified by reverse-phase HPLC (acetonitrile/water+0.05% TFA) to provide the title compound as a clear colorless oil. MS (ESI): mass calcd. for $C_{26}H_{26}Cl_2N_4O_2$, 496.1; m/z found, 497.1 $[M+H]^+$. [2-Azetidin-1-yl-4-chloro-3-(1-methylethoxy)quinolin-6-yl](4-chlorophenyl)(1-methyl-1H-imidazol-5-yl)methanol was purified by HPLC (C-18 column, Mobile phase: 1/1 acetonitrile/water+2% ammonium bicarbonate) followed by chiral separation on a CHIRALPAK AD 20 µM Daicel column (Mobile phase: 1/1 EtOH/MeOH) to give 2 enantiomers. The first eluting enantiomer was Example 94b: $^1$H NMR (600 MHz, CDCl$_3$) δ ppm 7.90 (d, J=2.2 Hz, 1H), 7.65 (d, J=8.8 Hz, 1H), 7.38-7.35 (m, 2H), 7.32-7.30 (m, 4H), 6.39 (s, 1H), 4.67-4.61 (m, 1H), 4.29-4.25 (m, 4H), 3.74 (s, 1H), 3.38 (s, 3H), 2.39-2.33 (m, 2H), 1.33 (d, J=6.2 Hz, 6H). MS (ESI): mass calcd. for $C_{26}H_{26}Cl_2N_4O_2$, 496.1; m/z found, 497.1 $[M+H]^+$ and the second eluting enantiomer was Example 94c: $^1$H NMR (600 MHz, CDCl$_3$) δ ppm 7.90 (d, J=2.2 Hz, 1H), 7.65 (d, J=8.7 Hz, 1H), 7.40-7.34 (m, 2H), 7.32-7.29 (m, 4H), 6.40 (s, 1H), 4.67-4.61 (m, 1H), 4.30-4.25 (m, 4H), 3.69 (s, 1H), 3.38 (s, 3H), 2.40-2.33 (m, 2H), 1.33 (d, J=6.2 Hz, 6H). MS (ESI): mass calcd. for $C_{26}H_{26}Cl_2N_4O_2$, 496.1; m/z found, 497.1 $[M+H]^+$.

Example 95a: [4-Chloro-2-methoxy-3-(1-methylethoxy)quinolin-6-yl](1-methyl-1H-imidazol-5-yl)[6-(trifluoromethyl)pyridin-3-yl]methanol

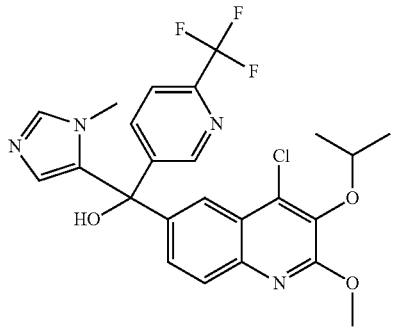 [SMILES: COc1nc2ccc(C(O)(c3ccc(C(F)(F)F)nc3)c3cncn3C)cc2c(Cl)c1OC(C)C]

To a mixture of [2,4-dichloro-3-(1-methylethoxy)quinolin-6-yl](1-methyl-1H-imidazol-5-yl)[6-(trifluoromethyl)pyridin-3-yl]methanol.TFA (125 mg, 0.2 mmol, Example 48) in toluene (2 mL) was added NaOMe (108 mg, 2 mmol) and the resulting mixture heated to 60° C. for 45 minutes. The mixture was then heated to 80° C. and stirred for an additional hour. The mixture was then cooled to room temperature, diluted with DCM and filtered, rinsing the filter cake with DCM. The filtrate was concentrated to dryness and the residue purified by reverse-phase HPLC (acetonitrile/water+0.05% TFA) to provide the title compound as a clear colorless oil. MS (ESI): mass calcd. for $C_{24}H_{22}ClF_3N_4O_3$, 506.1; m/z found, 507.0 $[M+H]^+$. [4-Chloro-2-methoxy-3-(1-methylethoxy)quinolin-6-yl](1-methyl-1H-imidazol-5-yl)[6-(trifluoromethyl)pyridin-3-yl]methanol was purified by achiral SFC (Stationary phase: Whelko-1 column, Mobile phase: 90% CO$_2$, 10% MeOH+ 0.2% iPrNH$_2$) followed by chiral SFC (Stationary phase: IC column, Mobile phase: 88% CO$_2$, 12% iPrOH+0.2% iPrNH$_2$) to give 2 enantiomers. The first eluting enantiomer was Example 95b: $^1$H NMR (500 MHz, CDCl$_3$) δ ppm 8.83-8.79 (m, 1H), 8.09-8.06 (m, 1H), 7.92-7.88 (m, 1H), 7.78 (d, J=8.6 Hz, 1H), 7.65 (d, J=8.2 Hz, 1H), 7.48-7.44 (m, 1H), 7.33-7.29 (m, 1H), 6.35-6.30 (m, 1H), 4.71-4.65 (m, 1H), 4.11 (s, 3H), 3.36 (s, 3H), 1.38-1.36 (m, 6H). MS (ESI): mass calcd. for $C_{24}H_{22}ClF_3N_4O_3$, 506.1; m/z found, 507.0 $[M+H]^+$ and the second eluting enantiomer was Example 95c: $^1$H NMR (500 MHz, CDCl$_3$) δ ppm 8.84-8.80 (m, 1H), 8.09-8.05 (m, 1H), 7.92-7.87 (m, 1H), 7.79 (d, J=8.8 Hz, 1H), 7.65 (d, J=8.2 Hz, 1H), 7.48-7.44 (m, 1H), 7.36-7.31 (m, 1H), 6.37-6.31 (m, 1H), 4.72-4.64 (m, 1H), 4.11 (s, 3H), 3.36 (s, 3H), 1.38-1.36 (m, 6H). MS (ESI): mass calcd. for $C_{24}H_{22}ClF_3N_4O_3$, 506.1; m/z found, 507.0 $[M+H]^+$.

Example 96: [2,4-Dimethoxy-3-(2,2,2-trifluoroethoxy)quinolin-6-yl](1-methyl-1H-imidazol-5-yl)[6-(trifluoromethyl)pyridin-3-yl]methanol

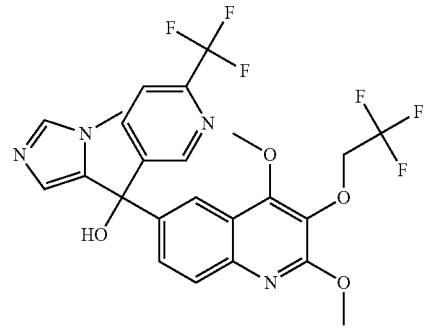 [SMILES: COc1nc2ccc(C(O)(c3ccc(C(F)(F)F)nc3)c3cncn3C)cc2c(OC)c1OCC(F)(F)F]

To a mixture of [2,4-dichloro-3-(2,2,2-trifluoroethoxy)quinolin-6-yl](1-methyl-1H-imidazol-5-yl)[6-(trifluoromethyl)pyridin-3-yl]methanol (86 mg, 0.16 mmol, Example 39) in toluene (1.6 mL) was added NaOMe (84 mg, 1.56 mmol) and the resulting mixture heated to 80° C. for 3.5 hours. The mixture was then cooled to room temperature, diluted with DCM and filtered, rinsing the filter cake with DCM. The filtrate was concentrated to dryness and the residue purified by reverse-phase HPLC (acetonitrile/water+ NH$_4$OH) to provide the title compound as a cream-colored solid. $^1$H NMR (500 MHz, CDCl$_3$) δ ppm 8.81-8.79 (m, 1H), 8.01-7.98 (m, 1H), 7.91-7.87 (m, 1H), 7.76-7.73 (m, 1H), 7.67-7.63 (m, 1H), 7.48-7.44 (m, 1H), 7.39-7.37 (m, 1H), 6.41-6.37 (m, 1H), 4.45-4.38 (m, 2H), 4.21 (s, 1H), 4.18 (s, 3H), 4.13 (s, 3H), 3.37 (s, 3H). MS (ESI): mass calcd. for $C_{24}H_{20}F_6N_4O_4$, 542.1; m/z found, 543.0 $[M+H]^+$.

Example 97: (4-Chloro-2,3-dimethoxyquinolin-6-yl)(1-methyl-1H-imidazol-5-yl)[6-(trifluoromethyl)pyridin-3-yl]methanol

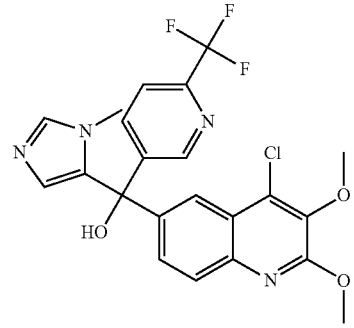 [SMILES: COc1nc2ccc(C(O)(c3ccc(C(F)(F)F)nc3)c3cncn3C)cc2c(Cl)c1OC]

To a mixture of [2,4-dichloro-3-(2,2,2-trifluoroethoxy)quinolin-6-yl](1-methyl-1H-imidazol-5-yl)[6-(trifluoromethyl)pyridin-3-yl]methanol (86 mg, 0.16 mmol, Example 39) in toluene (1.6 mL) was added NaOMe (84 mg, 1.56 mmol) and the resulting mixture heated to 80° C. for 3.5 hours. The mixture was then cooled to room temperature, diluted with DCM and filtered, rinsing the filter cake with DCM. The filtrate was concentrated to dryness and the residue purified by reverse-phase HPLC (acetonitrile/water+NH$_4$OH) to provide the title compound as a cream-colored solid. $^1$H NMR (500 MHz, CDCl$_3$) δ ppm 8.83-8.79 (m, 1H), 8.07 (d, J=2.1 Hz, 1H), 7.91-7.88 (m, 1H), 7.80 (d, J=8.7 Hz, 1H), 7.67-7.63 (m, 1H), 7.48 (dd, J=8.8, 2.2 Hz, 1H), 7.33-7.30 (m, 1H), 6.36-6.33 (m, 1H), 5.03 (s, 1H), 4.14 (s, 3H), 3.97 (s, 3H), 3.36 (s, 3H). MS (ESI): mass calcd. for C$_{22}$H$_{18}$ClF$_3$N$_4$O$_3$, 478.1; m/z found, 479.1 [M+H]$^+$.

Example 98a: [4-Chloro-2-methoxy-3-(2,2,2-trifluoroethoxy)quinolin-6-yl](1-methyl-1H-imidazol-5-yl)[6-(trifluoromethyl)pyridin-3-yl]methanol

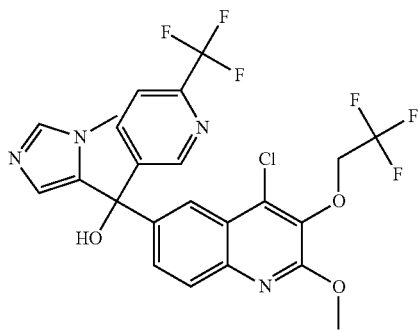 [SMILES: COc1nc2ccc(C(O)(c3ccc(C(F)(F)F)nc3)c3cncn3C)cc2c(Cl)c1OCC(F)(F)F]

To a mixture of [2,4-dichloro-3-(2,2,2-trifluoroethoxy)quinolin-6-yl](1-methyl-1H-imidazol-5-yl)[6-(trifluoromethyl)pyridin-3-yl]methanol (86 mg, 0.16 mmol, Example 39) in toluene (1.6 mL) was added NaOMe (84 mg, 1.56 mmol) and the resulting mixture heated to 80° C. for 3.5 hours. The mixture was then cooled to room temperature, diluted with DCM and filtered, rinsing the filter cake with DCM. The filtrate was concentrated to dryness and the residue purified by reverse-phase HPLC (acetonitrile/water+NH$_4$OH) to provide the title compound as a light yellow oil. $^1$H NMR (500 MHz, CDCl$_3$) δ ppm 8.82-8.80 (m, 1H), 8.11-8.09 (m, 1H), 7.93-7.89 (m, 1H), 7.84-7.80 (m, 1H), 7.69-7.65 (m, 1H), 7.52 (dd, J=8.8, 2.2 Hz, 1H), 7.43-7.41 (m, 1H), 6.44-6.42 (m, 1H), 4.52 (q, J=8.3 Hz, 2H), 4.16 (s, 3H), 4.05 (s, 1H), 3.39 (s, 3H). MS (ESI): mass calcd. for C$_{23}$H$_{17}$ClF$_6$N$_4$O$_3$, 546.1; m/z found, 547.1 [M+H]$^+$. [4-Chloro-2-methoxy-3-(2,2,2-trifluoroethoxy)-6-quinolyl]-(3-methylimidazol-4-yl)-[6-(trifluoromethyl)-3-pyridyl]methanol was purified by chiral SFC (Stationary phase: CHIRALCEL OJ-H 5 μM 250×20 mm, Mobile phase: 85% CO$_2$, 15% MeOH+0.3% iPrNH$_2$) to give 2 enantiomers. The first eluting enantiomer was Example 98b: $^1$H NMR (600 MHz, CDCl$_3$) δ 8.81 (d, J=2.2 Hz, 1H), 8.09 (d, J=2.2 Hz, 1H), 7.93-7.90 (m, 1H), 7.83 (d, J=8.8 Hz, 1H), 7.69-7.67 (m, 1H), 7.53-7.51 (m, 1H), 7.48 (s, 1H), 6.50-6.47 (m, 1H), 4.55-4.49 (m, 2H), 4.16 (s, 3H), 3.49 (s, 1H), 3.41 (s, 3H). MS (ESI): mass calcd. for C$_{23}$H$_{17}$ClF$_6$N$_4$O$_3$, 546.1; m/z found, 547.0 [M+H]$^+$ and the second eluting enantiomer was Example 98c: $^1$H NMR (600 MHz, CDCl$_3$) δ 8.83 (d, J=2.2 Hz, 1H), 8.11 (d, J=2.1 Hz, 1H), 7.95-7.91 (m, 1H), 7.83 (d, J=8.7 Hz, 1H), 7.71-7.68 (m, 1H), 7.52 (dd, J=8.8, 2.2 Hz, 1H), 7.50 (s, 1H), 6.50-6.47 (m, 1H), 4.53 (q, J=8.3 Hz, 2H), 4.16 (s, 3H), 3.61 (s, 1H), 3.41 (s, 3H). MS (ESI): mass calcd. for C$_{23}$H$_{17}$ClF$_6$N$_4$O$_3$, 546.1; m/z found, 547.0 [M+H]$^+$.

Example 99a: [4-Chloro-2-methoxy-3-(1-methylethoxy)quinolin-6-yl](4-chlorophenyl)(1-methyl-1H-imidazol-5-yl)methanol

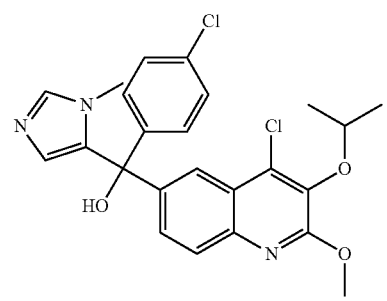 [SMILES: COc1nc2ccc(C(O)(c3ccc(Cl)cc3)c3cncn3C)cc2c(Cl)c1OC(C)C]

To a mixture of (4-chlorophenyl)[2,4-dichloro-3-(1-methylethoxy)quinolin-6-yl](1-methyl-1H-imidazol-5-yl)methanol.TFA (189 mg, 0.32 mmol, Example 49a) in toluene (3.2 mL) was added NaOMe (173 mg, 3.2 mmol) and the resulting mixture heated to 60° C. for 45 minutes. The mixture was then heated to 80° C. and stirred for an additional hour. The mixture was then cooled to room temperature, diluted with DCM and filtered, rinsing the filter cake with DCM. The filtrate was concentrated to dryness and the residue purified by reverse-phase HPLC (acetonitrile/water+0.05% TFA) to provide the title compound as a tan foam. MS (ESI): mass calcd. for C$_{24}$H$_{23}$Cl$_2$N$_3$O$_3$, 471.1; m/z found, 472.0 [M+H]$^+$. [4-Chloro-2-methoxy-3-(1-methylethoxy)quinolin-6-yl](4-chlorophenyl)(1-methyl-1H-imidazol-5-yl)methanol was purified by achiral SFC (Stationary phase: CHIRALPAK OD-H column, Mobile phase: 90% CO$_2$, 10% MeOH+0.2% iPrNH$_2$) followed by chiral SFC (Stationary phase: CHIRALPAK OJ-H column, Mobile phase: 87% CO$_2$, 13% iPrOH+0.2% iPrNH$_2$) to give 2 enantiomers. The first eluting enantiomer was Example 99b: $^1$H NMR (500 MHz, CDCl$_3$) δ ppm 8.04-8.01 (m, 1H), 7.77 (d, J=8.7 Hz, 1H), 7.48-7.44 (m, 2H), 7.35-7.29 (m, 4H), 6.48-6.43 (m, 1H), 4.70-4.64 (m, 1H), 4.12 (s, 3H), 3.41 (s, 3H), 3.16-3.09 (m, 1H), 1.37 (d, J=6.2 Hz, 6H). MS (ESI): mass calcd. for C$_{24}$H$_{23}$Cl$_2$N$_3$O$_3$, 471.1; m/z found, 473.1 [M+H]$^+$ and the second eluting enantiomer was Example 99c: $^1$H NMR (500 MHz, CDCl$_3$) δ ppm 8.03-8.01 (m, 1H), 7.79-7.75 (m, 1H), 7.48-7.44 (m, 2H), 7.34-7.29 (m, 4H), 6.47-6.44 (m, 1H), 4.71-4.64 (m, 1H), 4.12 (s, 3H), 3.41 (s, 3H), 3.18-3.11 (m, 1H), 1.37 (d, J=6.2 Hz, 6H). MS (ESI): mass calcd. for C$_{24}$H$_{23}$Cl$_2$N$_3$O$_3$, 471.1; m/z found, 473.1 [M+H]$^+$.

Example 100a: (4-Chloro-2-methoxy-3-((4-(trifluoromethyl)piperidin-1-yl)methyl)quinolin-6-yl)(1-methyl-1H-imidazol-5-yl)(2-(trifluoromethyl)pyridin-4-yl)methanol

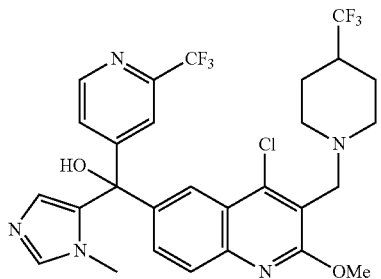 [SMILES: COc1nc2ccc(C(O)(c3ccnc(C(F)(F)F)c3)c3cncn3C)cc2c(Cl)c1CN1CCC(C(F)(F)F)CC1]

A solution of n-butyllithium (2.5 M in hexanes, 0.2 mL, 0.5 mmol) was added dropwise by syringe to a solution of 6-bromo-4-chloro-2-methoxy-3-((4-(trifluoromethyl)piperidin-1-yl)methyl)quinoline (0.24 g, 0.55 mmol, Intermediate 40) in dry deoxygenated THF (12 mL) at −78° C. After 2 minutes, a solution of (1-methyl-1H-imidazol-5-yl)(2-(trifluoromethyl)pyridin-4-yl)methanone (0.13 g, 0.50 mmol, Intermediate 14: step b) in dry THF (4 mL) was added dropwise by syringe. An additional 2 mL of THF was used to complete the quantitative addition. After 10 minutes, the flask was removed from the dry-ice bath and placed into an ice-water bath. After 1 hour, the reaction was quenched with saturated aqueous ammonium chloride solution and the mixture was partitioned between water and EtOAc. The layers were separated and the aqueous phase was further extracted with EtOAc and washed with saturated aqueous NaCl solution. The organic phase was dried ($MgSO_4$), filtered, and concentrated to dryness. The crude product was purified by flash column chromatography (silica gel, 0-7% MeOH-DCM) to provide the title compound. MS m/e 614.1 (M+H).

(4-Chloro-2-methoxy-3-((4-(trifluoromethyl)piperidin-1-yl)methyl)quinolin-6-yl)(1-methyl-1H-imidazol-5-yl)(2-(trifluoromethyl)pyridin-4-yl)methanol was purified by chiral SFC [ChiralPak IC column, 5 μm, 250 mm×20 mm, mobile phase: 70% carbon dioxide, 30% 2-propanol (containing 0.3% diisopropylamine)] to provide two pure enantiomers. The first eluting enantiomer was Example 100b: $^1$H NMR (500 MHz, $CDCl_3$) δ ppm 8.70 (d, J=5.2 Hz, 1H), 8.15 (d, J=2.1 Hz, 1H), 7.88 (dd, J=1.7, 0.9 Hz, 1H), 7.82 (d, J=8.8 Hz, 1H), 7.56 (dd, J=8.8, 2.2 Hz, 1H), 7.50 (dd, J=5.2, 1.7 Hz, 1H), 7.38 (s, 1H), 6.39 (s, 1H), 4.57 (s, 1H), 4.09 (s, 3H), 3.81 (s, 2H), 3.36 (s, 3H), 3.03 (d, J=10.9 Hz, 2H), 2.20 (t, J=11.6 Hz, 2H), 2.04-1.90 (m, 1H), 1.80-1.78 (m, 2H), 1.70-1.47 (m, 2H); MS m/e 614.1 (M+H) and the second eluting enantiomer was Example 100c: $^1$H NMR (500 MHz, $CDCl_3$) δ ppm 8.70 (d, J=5.1 Hz, 1H), 8.15 (d, J=2.1 Hz, 1H), 7.89 (dd, J=1.6, 0.8 Hz, 1H), 7.81 (d, J=8.7 Hz, 1H), 7.55 (dd, J=8.8, 2.2 Hz, 1H), 7.50 (dd, J=5.1, 1.7 Hz, 1H), 7.33 (s, 1H), 6.35 (s, 1H), 4.97 (s, 1H), 4.08 (s, 3H), 3.80 (s, 2H), 3.35 (s, 3H), 3.02 (d, J=9.9 Hz, 2H), 2.19 (t, J=11.9 Hz, 2H), 1.99-1.97 (m, 1H), 1.79-1.77 (m, 2H), 1.73-1.46 (m, 2H); MS m/e 614.1 (M+H).

Example 101a: (3-((4-(1H-Pyrazol-1-yl)piperidin-1-yl)methyl)-4-chloro-2-methoxyquinolin-6-yl)(4-chlorophenyl)(1-methyl-1H-imidazol-5-yl)methanol

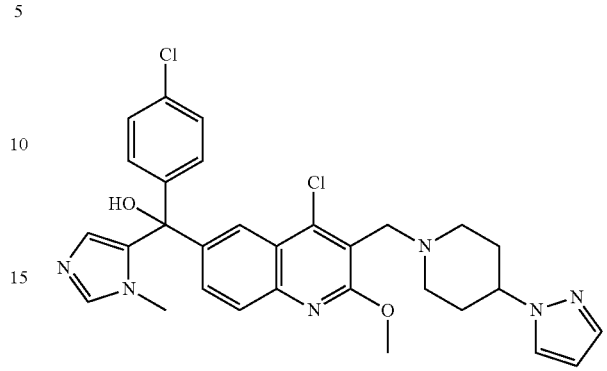

The title compound was prepared analogously to the method described in Example 100a using 3-((4-(1H-pyrazol-1-yl)piperidin-1-yl)methyl)-6-bromo-4-chloro-2-methoxyquinoline (Intermediate 41) and (4-chlorophenyl)(1-methyl-1H-imidazol-5-yl)methanone (Intermediate 22: step b). MS m/e 577.5 (M+H)+.

(3-((4-(1H-Pyrazol-1-yl)piperidin-1-yl)methyl)-4-chloro-2-methoxyquinolin-6-yl)(4-chlorophenyl)(1-methyl-1H-imidazol-5-yl)methanol was purified by chiral SFC (Chiralpak AD-H, 5 μm, 250×20 mm, mobile phase: 0.3% isopropyl amine, 60% $CO_2$, 40% mixture of methanol-isopropanol 50/50 v/v). The first eluting enantiomer was Example 101b: $^1$H NMR (500 MHz, $CDCl_3$) δ ppm 8.11 (d, J=2.1 Hz, 1H), 7.80 (d, J=8.7 Hz, 1H), 7.55 (dd, J=8.8, 2.2 Hz, 1H), 7.49-7.47 (m, 1H), 7.45 (s, 1H), 7.40 (d, J=2.3 Hz, 1H), 7.35-7.28 (m, 4H), 6.44 (d, J=1.2 Hz, 1H), 6.23 (t, J=2.1 Hz, 1H), 4.18-4.11 (m, 1H), 4.10 (s, 3H), 3.86 (s, 2H), 3.41 (s, 3H), 3.06 (d, J=11.5 Hz, 2H), 2.45-2.34 (m, 2H), 2.13-2.04 (m, 2H), 2.02-1.95 (m, 2H); MS m/e 577.5 (M+H)+ and the second eluting enantiomer was Example 101c: $^1$H NMR (500 MHz, $CDCl_3$) δ ppm 8.11 (d, J=2.2 Hz, 1H), 7.80 (d, J=8.7 Hz, 1H), 7.55 (dd, J=8.8, 2.2 Hz, 1H), 7.48 (d, J=1.7 Hz, 1H), 7.44 (s, 1H), 7.40 (d, J=2.3 Hz, 1H), 7.36-7.28 (m, 4H), 6.44 (d, J=1.2 Hz, 1H), 6.23 (t, J=2.1 Hz, 1H), 4.18-4.10 (m, 1H), 4.10 (s, 3H), 3.85 (s, 2H), 3.41 (s, 3H), 3.06 (d, J=11.7 Hz, 2H), 2.42-2.37 (m, 2H), 2.10-2.07 (m, 2H), 2.1-1.94 (m, 2H); MS m/e 577.5 (M+H)+.

Example 102a: 1-(4-((3-((4-(1H-Pyrazol-1-yl)piperidin-1-yl)methyl)-4-chloro-2-methoxyquinolin-6-yl)(hydroxy)(phenyl)methyl)piperidin-1-yl)ethanone

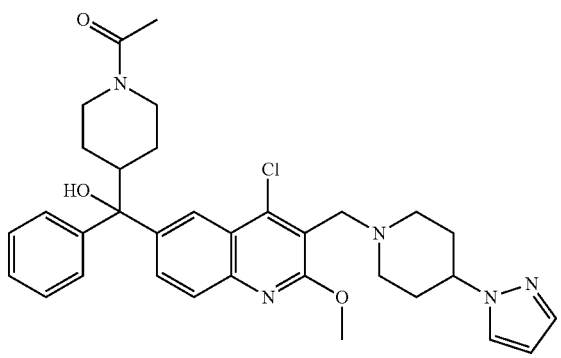 [SMILES: COc1nc2ccc(C(O)(c3ccccc3)C3CCN(C(C)=O)CC3)cc2c(Cl)c1CN1CCC(n2cccn2)CC1]

The title compound was prepared analogously to the method described in Example 100a using 3-((4-(1H-pyrazol-1-yl)piperidin-1-yl)methyl)-6-bromo-4-chloro-2-methoxyquinoline (Intermediate 41) and 1-(4-benzoylpiperidin-1-yl)ethanone (Intermediate 7). MS m/e 588.6 (M+H)$^+$. 1-(4-((3-((4-(1H-Pyrazol-1-yl)piperidin-1-yl)methyl)-4-chloro-2-methoxyquinolin-6-yl)(hydroxy)(phenyl)methyl)piperidin-1-yl)ethanone was purified by chiral SFC (Chiralpak AD-H, 5 μm, 250×20 mm, mobile phase: 0.3% isopropyl amine, 55% CO$_2$, 45% ethanol). The first eluting enantiomer was Example 102b: $^1$H NMR (500 MHz, CDCl$_3$) δ ppm 8.31-8.29 (m, 1H), 7.78-7.74 (m, 1H), 7.70-7.65 (m, 1H), 7.57-7.50 (m, 2H), 7.48 (s, 1H), 7.40 (d, J=2.4 Hz, 1H), 7.36-7.31 (m, 2H), 7.24-7.22 (m, 1H), 6.23-6.22 (m, 1H), 4.72-4.66 (m, 1H), 4.20-4.10 (m, 1H), 4.07 (s, 3H), 3.86-3.80 (m, 3H), 3.17-2.97 (m, 3H), 2.79-2.74 (m, 1H), 2.62-2.54 (m, 1H), 2.42-2.38 (m, 3H), 2.17-1.89 (m, 7H), 1.74-1.25 (m, 4H); MS m/e 588.6 (M+H)$^+$ and the second eluting enantiomer was Example 102c: $^1$H NMR (500 MHz, CDCl$_3$) δ ppm 8.30 (dd, J=8.3, 2.1 Hz, 1H), 7.79-7.73 (m, 1H), 7.70-7.65 (m, 1H), 7.54-7.51 (m, 2H), 7.49 (d, J=1.8 Hz, 1H), 7.40 (d, J=2.2 Hz, 1H), 7.36-7.31 (m, 2H), 7.25-7.19 (m, 1H), 6.25-6.23 (m, 1H), 4.73-4.66 (m, 1H), 4.16-4.14 (m, 1H), 4.07 (s, 3H), 3.90-3.78 (m, 3H), 3.17-3.00 (m, 3H), 2.82-2.71 (m, 1H), 2.66-2.50 (m, 1H), 2.44-2.36 (m, 2H), 2.31 (s, 1H), 2.15-1.90 (m, 7H), 1.56-1.27 (m, 4H); MS m/e 588.6 (M+H)$^+$.

Example 103a: (4-Chloro-2-methoxy-3-((4-(trifluoromethyl)piperidin-1-yl)methyl)quinolin-6-yl)(2,6-dimethylpyridin-3-yl)(1-methyl-1H-1,2,3-triazol-5-yl)methanol

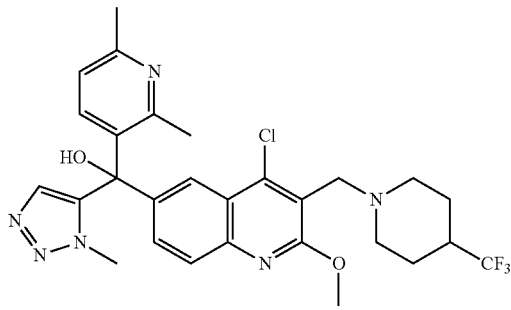 [SMILES: COc1nc2ccc(C(O)(c3ccc(C)nc3C)c3cnnn3C)cc2c(Cl)c1CN1CCC(C(F)(F)F)CC1]

The title compound was prepared analogously to the method described in Example 100a using (2,6-dimethylpyridin-3-yl)(1-methyl-1H-1,2,3-triazol-5-yl)methanone (Intermediate 11: step b). MS m/e 575.1 (M+H)$^+$. (4-Chloro-2-methoxy-3-((4-(trifluoromethyl)piperidin-1-yl)methyl)quinolin-6-yl)(2,6-dimethylpyridin-3-yl)(1-methyl-1H-1,2,3-triazol-5-yl)methanol was purified by chiral SFC (Chiralpak AD-H, 5 μm, 250×20 mm, mobile phase: 0.3% isopropyl amine, 80% CO$_2$, 20% mixture of methanol-isopropanol 50/50 v/v). The first eluting enantiomer was Example 103b: $^1$H NMR (500 MHz, CDCl$_3$) δ ppm 8.07 (s, 1H), 7.86-7.80 (m, 1H), 7.39 (d, J=9.1 Hz, 1H), 7.01-6.91 (m, 3H), 4.10 (s, 3H), 3.94 (s, 3H), 3.81 (s, 2H), 3.38 (s, 1H), 3.03 (d, J=11.4 Hz, 2H), 2.56 (s, 3H), 2.41 (s, 3H), 2.20 (t, J=11.8 Hz, 2H), 1.97 (s, 1H), 1.80-1.78 (m, 2H), 1.59-1.57 (m, 2H); MS m/e 577.5 (M+H)$^+$ and the second eluting enantiomer was Example 103c: $^1$H NMR (500 MHz, CDCl$_3$) δ ppm 8.08 (s, 1H), 7.85-7.79 (m, 1H), 7.39 (d, J=8.1 Hz, 1H), 6.99-6.91 (m, 3H), 4.10 (s, 3H), 3.94 (s, 3H), 3.81 (s, 2H), 3.46 (s, 1H), 3.03 (d, J=11.5 Hz, 2H), 2.56 (s, 3H), 2.39 (s, 3H), 2.20 (t, J=11.8 Hz, 3H), 1.99 (s, 1H), 1.80-1.78 (m, 2H), 1.61-1.57 (m, 2H); MS m/e 577.5 (M+H)$^+$.

Example 104a: (3-((4-(1H-Pyrazol-1-yl)piperidin-1-yl)methyl)-4-chloro-2-methoxyquinolin-6-yl)(1,2-dimethyl-1H-imidazol-5-yl)(1-methyl-1H-1,2,3-triazol-5-yl)methanol

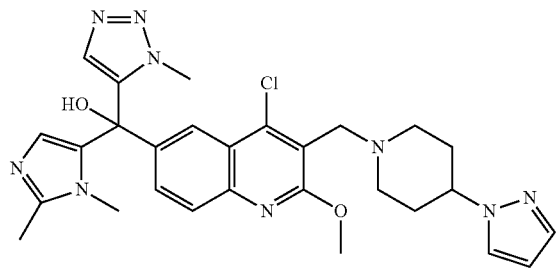 [SMILES: COc1nc2ccc(C(O)(c3cnnn3C)c3cnc(C)n3C)cc2c(Cl)c1CN1CCC(n2cccn2)CC1]

A solution of n-BuLi (0.3 mL, 0.75 mmol, 2.5 M solution in hexane) was added slowly to a solution of 1-methyl-1H-1,2,3-triazole (65.6 mg, 0.789 mmol) in THF (4 mL) at −45° C. After addition, stirring was continued for an additional 30 minutes at 40° C. and (3-((4-(1H-pyrazol-1-yl)piperidin-1-yl)methyl)-4-chloro-2-methoxyquinolin-6-yl)(1,2-dimethyl-1H-imidazol-5-yl)methanone (189 mg, 0.395 mmol, Intermediate 42) dissolved in THF (2 mL) was slowly added. An additional 1 mL of THF was used to complete the quantitative addition. The mixture was stirred at −40° C. for 5 minutes then warmed to room temperature and stirred for 1 hour. The solution was quenched with saturated aqueous NH$_4$Cl solution. H$_2$O was added and layers were separated. The aqueous layer was extracted with EtOAc and the combined organic extracts washed with brine, dried over MgSO$_4$, filtered, evaporated in vacuo. The crude product was purified using flash column chromatography (0 to 7% MeOH-DCM) to provide the title compound. MS m/e 562.6 (M+H)$^+$.

(3-((4-(1H-Pyrazol-1-yl)piperidin-1-yl)methyl)-4-chloro-2-methoxyquinolin-6-yl)(1,2-dimethyl-1H-imidazol-5-yl)(1-methyl-1H-1,2,3-triazol-5-yl)methanol was purified by chiral SFC (Chiralpak AD-H, 5 m, 250×20 mm, mobile phase: 0.3% isopropyl amine, 70% CO$_2$, 30% mixture of methanol-isopropanol 50/50 v/v). The first eluting enantiomer was Example 104b: $^1$H NMR (400 MHz, CDCl$_3$) δ ppm 8.20 (d, J=2.1 Hz, 1H), 7.75 (d, J=8.7 Hz, 1H), 7.49-7.44 (m, 1H), 7.42-7.34 (m, 2H), 7.18 (s, 1H), 6.23-6.21 (m, 1H), 6.13 (s, 1H), 4.88 (s, 1H), 4.19-4.15 (m, 1H), 4.11 (s, 3H), 3.92 (s, 3H), 3.85 (s, 2H), 3.40 (s, 3H), 3.08 (s, 2H), 2.44-2.38 (m, 2H), 2.33 (s, 3H), 2.15-1.89 (m, 4H); MS m/e 562.6 (M+H)$^+$ and the second eluting enantiomer was Example 104c: $^1$H NMR (400 MHz, CDCl$_3$) δ ppm 8.20 (d, J=2.2 Hz, 1H), 7.76 (d, J=8.5 Hz, 1H), 7.46 (dd, J=1.7, 0.7 Hz, 1H), 7.43-7.34 (m, 2H), 7.18 (s, 1H), 6.23-6.22 (m, 1H), 6.13 (s, 1H), 4.85 (s, 1H), 4.19-4.13 (m, 1H), 4.11 (s, 3H), 3.92 (s, 3H), 3.85 (s, 2H), 3.41 (s, 3H), 3.08 (s, 2H), 2.44-2.38 (m, 2H), 2.33 (s, 3H), 2.11-1.99 (m, 4H); MS m/e 562.6 (M+H)$^+$.

Example 105a: (3-((4-(1H-Pyrazol-1-yl)piperidin-1-yl)methyl)-4-chloro-2-methoxyquinolin-6-yl)(2,6-dimethylpyridin-3-yl)(1-methyl-1H-1,2,3-triazol-5-yl)methanol

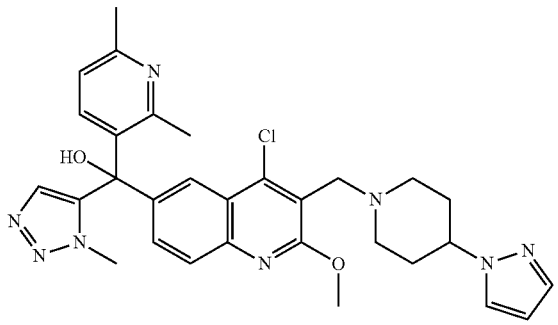 [SMILES: COc1nc2ccc(C(O)(c3ccc(C)nc3C)c3cnnn3C)cc2c(Cl)c1CN1CCC(n2cccn2)CC1]

The title compound was prepared analogously to the method described in Example 100a using 3-((4-(1H-pyrazol-1-yl)piperidin-1-yl)methyl)-6-bromo-4-chloro-2-methoxyquinoline (Intermediate 41) and (2,6-dimethylpyridin-3-yl)(1-methyl-1H-1,2,3-triazol-5-yl)methanone (Intermediate 11: step b). MS m/e 573.6 (M+H)+. (3-((4-(1H-Pyrazol-1-yl)piperidin-1-yl)methyl)-4-chloro-2-methoxyquinolin-6-yl)(2,6-dimethylpyridin-3-yl)(1-methyl-1H-1,2,3-triazol-5-yl)methanol was purified by chiral SFC (Chiralpak AD-H, 5 μm, 250×20 mm, mobile phase: 0.3% isopropyl amine, 75% $CO_2$, 25% mixture of methanol-isopropanol 50/50 v/v). The first eluting enantiomer was Example 105b: $^1$H NMR (400 MHz, CDCl$_3$) δ ppm 8.05 (s, 1H), 7.84 (d, J=8.8 Hz, 1H), 7.48-7.39 (m, 2H), 7.36 (s, 1H), 7.04-6.95 (m, 2H), 6.93-6.91 (m, 1H), 6.20 (s, 1H), 4.15-4.11 (m, 4H), 3.92 (s, 3H), 3.86 (s, 2H), 3.14-2.98 (m, 3H), 2.54 (s, 3H), 2.49-2.34 (m, 5H), 2.14-1.90 (m, 4H); MS m/e 573.6 (M+H)+ and the second eluting enantiomer was Example 105c: $^1$H NMR (400 MHz, CDCl$_3$) δ ppm 8.05 (s, 1H), 7.85-7.83 (m, 1H), 7.48-7.45 (m, 2H), 7.37 (s, 1H), 7.0-6.98 (m, 2H), 6.93-6.91 (m, 1H), 6.20 (s, 1H), 4.16-4.11 (m, 4H), 3.92 (s, 3H), 3.86 (s, 2H), 3.11-2.97 (m, 3H), 2.54 (s, 3H), 2.44-2.38 (d, J=2.9 Hz, 5H), 2.08-1.90 (m, 4H); MS m/e 573.6 (M+H)+.

Example 106a (4-Chloro-2-methoxy-3-((4-(trifluoromethyl)piperidin-1-yl)methyl)quinolin-6-yl)(1,2-dimethyl-1H-imidazol-5-yl)(1-methyl-1H-1,2,3-triazol-5-yl)methanol

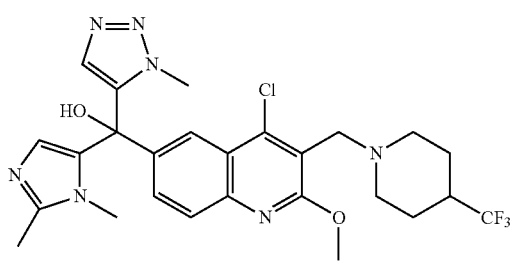 [SMILES: COc1nc2ccc(C(O)(c3cnnn3C)c3cnc(C)n3C)cc2c(Cl)c1CN1CCC(C(F)(F)F)CC1]

The title compound was prepared analogously to the method described in Example 104a using (4-chloro-2-methoxy-3-((4-(trifluoromethyl)piperidin-1-yl)methyl)quinolin-6-yl)(1,2-dimethyl-1H-imidazol-5-yl)methanone (Intermediate 43) in place of (3-((4-(1H-pyrazol-1-yl)piperidin-1-yl)methyl)-4-chloro-2-methoxyquinolin-6-yl)(1,2-dimethyl-1H-imidazol-5-yl)methanone. MS m/e 564.6 (M+H)+. (4-Chloro-2-methoxy-3-((4-(trifluoromethyl)piperidin-1-yl)methyl)quinolin-6-yl)(1,2-dimethyl-1H-imidazol-5-yl)(1-methyl-1H-1,2,3-triazol-5-yl)methanol was purified by chiral SFC (Chiralpak AD-H, 5 μm, 250×20 mm, mobile phase: 0.3% isopropyl amine, 80% $CO_2$, 20% mixture of methanol-isopropanol 50/50 v/v). The first eluting enantiomer was Example 106b: $^1$H NMR (400 MHz, CDCl$_3$) δ ppm 8.18 (d, J=2.2 Hz, 1H), 7.78-7.70 (m, 1H), 7.37 (dd, J=8.7, 2.2 Hz, 1H), 7.19 (s, 1H), 6.13 (s, 1H), 4.51 (s, 1H), 4.10 (s, 3H), 3.93 (s, 3H), 3.81 (s, 2H), 3.41 (s, 3H), 3.04 (s, 2H), 2.33 (s, 3H), 2.26-2.15 (m, 2H), 2.06-1.90 (m, 1H), 1.82-1.79 (m, 2H), 1.62-1.56 (m, 2H); MS m/e 564.6 (M+H)+ and the second eluting enantiomer was Example 106c: $^1$H NMR (400 MHz, CDCl$_3$) δ ppm 8.18 (d, J=2.2 Hz, 1H), 7.75 (d, J=8.7 Hz, 1H), 7.37 (dd, J=8.7, 2.2 Hz, 1H), 7.19 (s, 1H), 6.13 (s, 1H), 4.49 (s, 1H), 4.10 (s, 3H), 3.93 (s, 3H), 3.81 (s, 2H), 3.41 (s, 3H), 3.04 (s, 2H), 2.33 (s, 3H), 2.23-2.17 (m, 2H), 2.01-1.99 (m, 1H), 1.82-1.79 (m, 2H), 1.61-1.58 (m, 2H); MS m/e 564.6 (M+H)+.

Example 107a (4-Chloro-3-((4,4-difluoropiperidin-1-yl)methyl)-2-methoxyquinolin-6-yl)(2,6-dimethylpyridin-3-yl)(1-methyl-1H-1,2,3-triazol-5-yl)methanol

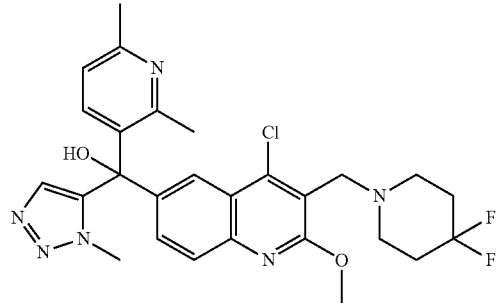 [SMILES: COc1nc2ccc(C(O)(c3ccc(C)nc3C)c3cnnn3C)cc2c(Cl)c1CN1CCC(F)(F)CC1]

The title compound was prepared analogously to the method described in Example 100a using 6-bromo-4-chloro-3-((4,4-difluoropiperidin-1-yl)methyl)-2-methoxyquinoline (Intermediate 44) and (2,6-dimethylpyridin-3-yl)(1-methyl-1H-1,2,3-triazol-5-yl)methanone (Intermediate 11: step b). MS m/e 543.6 (M+H)+.

(4-Chloro-3-((4,4-difluoropiperidin-1-yl)methyl)-2-methoxyquinolin-6-yl)(2,6-dimethylpyridin-3-yl)(1-methyl-1H-1,2,3-triazol-5-yl)methanol was purified by chiral SFC (Chiralpak AD, 5 μm, 250×30 mm, mobile phase: 0.3% isopropyl amine, 80% $CO_2$, 20% mixture of methanol-isopropanol 50/50 v/v). The first eluting enantiomer was Example 107b: $^1$H NMR (400 MHz, CDCl$_3$) δ ppm 8.08 (d, J=2.2 Hz, 1H), 7.83 (d, J=8.8 Hz, 1H), 7.40 (dd, J=8.7, 2.1 Hz, 1H), 7.02-6.90 (m, 3H), 4.11 (s, 3H), 3.94 (s, 3H), 3.87 (s, 2H), 3.40 (s, 1H), 2.72-2.69 (m, 4H), 2.56 (s, 3H), 2.40 (s, 3H), 2.00-1.91 (m, 4H); MS m/e 543.6 (M+H)+ and the second eluting enantiomer was Example 107c: $^1$H NMR (400 MHz, CDCl$_3$) δ ppm 8.10-8.06 (m, 1H), 7.83 (dd, J=8.7, 0.5 Hz, 1H), 7.39 (dd, J=8.8, 2.2 Hz, 1H), 7.02-6.90 (m, 3H), 4.11 (s, 3H), 3.94 (s, 3H), 3.86 (s, 2H), 2.72-2.69 (m, 4H), 2.56 (s, 3H), 2.39 (s, 3H), 2.01-1.91 (m, 4H); MS m/e 543.6 (M+H)⁺.

Example 108a (4-Chloro-3-((4-fluoropiperidin-1-yl)methyl)-2-methoxyquinolin-6-yl)(2,6-dimethylpyridin-3-yl)(1-methyl-1H-1,2,3-triazol-5-yl)methanol

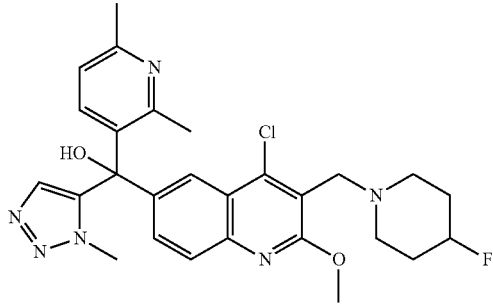 [SMILES: COc1nc2ccc(C(O)(c3ccc(C)nc3C)c3cnnn3C)cc2c(Cl)c1CN1CCC(F)CC1]

The title compound was prepared analogously to the method described in Example 100a using 6-bromo-4-chloro-3-((4-fluoropiperidin-1-yl)methyl)-2-methoxyquinoline (Intermediate 45) and (2,6-dimethylpyridin-3-yl)(1-methyl-1H-1,2,3-triazol-5-yl)methanone (Intermediate 11: step b). MS m/e 525.6 (M+H)⁺.

(4-Chloro-3-((4-fluoropiperidin-1-yl)methyl)-2-methoxyquinolin-6-yl)(2,6-dimethylpyridin-3-yl)(1-methyl-1H-1,2,3-triazol-5-yl)methanol was purified by chiral SFC (Chiralpak AD-H, 5 m, 250×20 mm, mobile phase: 0.3% isopropyl amine, 80% CO₂, 20% mixture of methanol-isopropanol 50/50 v/v). The first eluting enantiomer was Example 108b: ¹H NMR (400 MHz, CDCl₃) δ ppm 8.08 (d, J=2.2 Hz, 1H), 7.82 (d, J=8.7 Hz, 1H), 7.38 (dd, J=8.8, 2.2 Hz, 1H), 7.02-6.89 (m, 3H), 4.77-4.51 (m, 1H), 4.10 (s, 3H), 3.94 (s, 3H), 3.82 (s, 2H), 3.43 (s, 1H), 2.77-2.71 (m, 2H), 2.56-2.49 (m, 5H), 2.40 (s, 3H), 1.89-1.80 (m, 4H); MS m/e 525.6 (M+H)⁺ and the second eluting enantiomer was Example 108c: ¹H NMR (400 MHz, CDCl₃) δ ppm 8.08 (dd, J=2.3, 0.6 Hz, 1H), 7.82 (dd, J=8.8, 0.6 Hz, 1H), 7.38 (dd, J=8.8, 2.2 Hz, 1H), 7.03-6.88 (m, 3H), 4.76-4.51 (m, 1H), 4.10 (s, 3H), 3.94 (s, 3H), 3.82 (s, 2H), 3.58 (s, 1H), 2.75-2.71 (m, 2H), 2.55-2.51 (m, 5H), 2.39 (s, 3H), 1.89-1.80 (m, 4H); MS m/e 525.6 (M+H)⁺.

Example 109a (4-Chloro-3-((3,3-difluoroazetidin-1-yl)methyl)-2-methoxyquinolin-6-yl)(2,6-dimethylpyridin-3-yl)(1-methyl-1H-1,2,3-triazol-5-yl)methanol

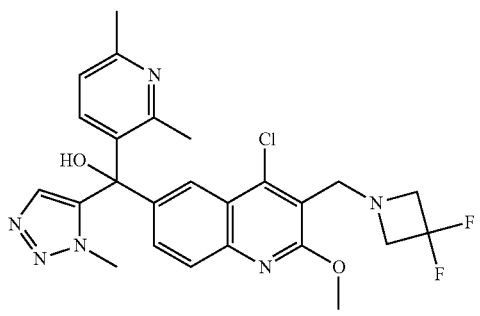 [SMILES: COc1nc2ccc(C(O)(c3ccc(C)nc3C)c3cnnn3C)cc2c(Cl)c1CN1CC(F)(F)C1]

The title compound was prepared analogously to the method described in Example 100a using 6-bromo-4-chloro-3-((3,3-difluoroazetidin-1-yl)methyl)-2-methoxyquinoline (Intermediate 46) and (2,6-dimethylpyridin-3-yl)(1-methyl-1H-1,2,3-triazol-5-yl)methanone (Intermediate 11: step b). MS m/e 515.2 (M+H)⁺.

(4-Chloro-3-((3,3-difluoroazetidin-1-yl)methyl)-2-methoxyquinolin-6-yl)(2,6-dimethylpyridin-3-yl)(1-methyl-1H-1,2,3-triazol-5-yl)methanol was purified by chiral SFC (Chiralpak AD, 5 μm, 250×30 mm, mobile phase: 0.3% isopropyl amine, 80% CO₂, 20% mixture of methanol-isopropanol 50/50 v/v). The first eluting enantiomer was Example 109b: ¹H NMR (400 MHz, CDCl₃) δ ppm 8.08 (dd, J=2.2, 0.6 Hz, 1H), 7.84 (dd, J=8.8, 0.6 Hz, 1H), 7.40 (dd, J=8.8, 2.2 Hz, 1H), 7.03-6.92 (m, 3H), 4.12 (s, 3H), 4.08 (s, 2H), 3.94 (s, 3H), 3.77 (t, J=12.0 Hz, 4H), 3.39 (s, 1H), 2.56 (s, 3H), 2.40 (s, 3H); MS m/e 515.2 (M+H)⁺ and the second eluting enantiomer was Example 109c: ¹H NMR (400 MHz, CDCl₃) δ ppm 8.13-8.02 (m, 1H), 7.92-7.76 (m, 1H), 7.40 (dd, J=8.8, 2.2 Hz, 1H), 7.06-6.89 (m, 3H), 4.12 (s, 3H), 4.08 (s, 2H), 3.94 (s, 3H), 3.77 (t, J=12.0 Hz, 4H), 3.38 (s, 1H), 2.56 (s, 3H), 2.40 (s, 3H); MS m/e 515.2 (M+H)⁺.

Example 110a (4-Chloro-3-((3-fluoroazetidin-1-yl)methyl)-2-methoxyquinolin-6-yl)(2,6-dimethylpyridin-3-yl)(1-methyl-1H-1,2,3-triazol-5-yl)methanol

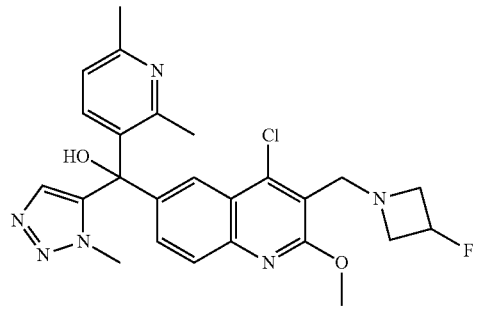 [SMILES: COc1nc2ccc(C(O)(c3ccc(C)nc3C)c3cnnn3C)cc2c(Cl)c1CN1CC(F)C1]

The title compound was prepared analogously to the method described in Example 100a using 6-bromo-4-chloro-3-((3-fluoroazetidin-1-yl)methyl)-2-methoxyquinoline (Intermediate 47) and (2,6-dimethylpyridin-3-yl)(1-methyl-1H-1,2,3-triazol-5-yl)methanone (Intermediate 11: step b). MS m/e 497.1 (M+H)⁺.

(4-Chloro-3-((3-fluoroazetidin-1-yl)methyl)-2-methoxyquinolin-6-yl)(2,6-dimethylpyridin-3-yl)(1-methyl-1H-1,2,3-triazol-5-yl)methanol was purified by chiral SFC (Chiralpak AD-H, 5 m, 250×20 mm, mobile phase: 0.3% isopropyl amine, 80% CO₂, 20% mixture of methanol-isopropanol 50/50 v/v). The first eluting enantiomer was Example 110b ¹H NMR (400 MHz, CDCl₃) δ ppm 8.07 (dd, J=2.2, 0.6 Hz, 1H), 7.83 (dd, J=8.7, 0.5 Hz, 1H), 7.39 (dd, J=8.8, 2.2 Hz, 1H), 7.03-6.91 (m, 3H), 5.23-4.95 (m, 1H), 4.12 (s, 3H), 4.01 (s, 2H), 3.94 (s, 3H), 3.78-3.71 (m, 2H), 3.46-3.31 (m, 3H), 2.56 (s, 3H), 2.39 (s, 3H); MS m/e 497.1 (M+H)⁺ and the second eluting enantiomer was Example 110c: ¹H NMR (400 MHz, CDCl₃) δ ppm 8.08 (dd, J=2.2, 0.6 Hz, 1H), 7.83 (dd, J=8.8, 0.6 Hz, 1H), 7.39 (dd, J=8.8, 2.2 Hz, 1H), 7.02-6.91 (m, 3H), 5.23-4.96 (m, 1H), 4.12 (s, 3H), 4.01 (s, 2H), 3.94 (s, 3H), 3.81-3.67 (m, 2H), 3.49-3.34 (m, 3H), 2.56 (s, 3H), 2.39 (s, 3H); MS m/e 497.1 (M+H)⁺.

Example 111

(4-Chloro-2-methoxy-3-((4-(trifluoromethyl)piperidin-1-yl)methyl)quinolin-6-yl)bis(1,2-dimethyl-1H-imidazol-5-yl)methanol

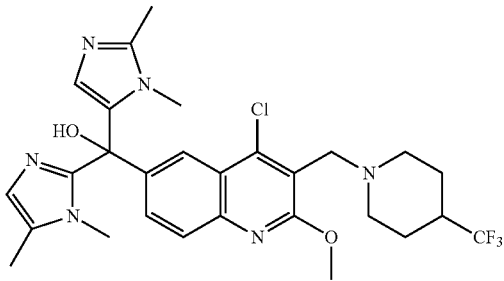 [SMILES: COc1nc2ccc(C(O)(c3cnc(C)n3C)c3ncc(C)n3C)cc2c(Cl)c1CN1CCC(C(F)(F)F)CC1]

A solution of n-BuLi (0.306 mL, 0.765 mmol, 2.5 M solution in hexane) was slowly added to a solution of 5-bromo-1,2-dimethyl-1H-imidazole (139 mg, 0.794 mmol) in THF (8 mL) at −78° C. After addition, stirring was continued for an additional 30 minutes and (4-chloro-2-methoxy-3-((4-(trifluoromethyl)piperidin-1-yl)methyl)quinolin-6-yl)(1,2-dimethyl-1H-imidazol-5-yl)methanone (Intermediate 43, 160 mg, 0.33 mmol) dissolved in THF (4 mL) was slowly added. An additional 1 mL of THF was used to complete the quantitative addition. The mixture was stirred at −78° C. for 5 minutes and the flask was removed from the dry-ice bath and placed into an ice-water bath. After 2 hours of stirring, the solution was quenched with aqueous saturated NH₄Cl solution. The aqueous layer was extracted with EtOAc and the combined organic extracts washed with brine, dried over MgSO₄, filtered, evaporated in vacuo. The crude product was purified using flash column chromatography (0 to 10% MeOH-DCM) to provide the title compound. ¹H NMR (500 MHz, CDCl₃) δ ppm 8.22 (s, 1H), 7.67 (d, J=8.7 Hz, 1H), 7.39 (dd, J=8.7, 2.2 Hz, 1H), 6.18 (s, 2H), 4.87 (s, 1H), 4.09 (s, 3H), 3.80 (s, 2H), 3.41 (s, 6H), 3.07-3.05 (m, 2H), 2.31 (s, 6H), 2.23-2.18 (m, 2H), 2.04-1.94 (m, 1H), 1.82-1.79 (m, 2H), 1.69-1.59 (m, 2H); MS m/e 577.2 (M+H)⁺.

Example 112a: (4-Chloro-2-methoxy-3-((4-(trifluoromethyl)piperidin-1-yl)methyl)quinolin-6-yl)(1-methyl-1H-imidazol-5-yl)(6-(trifluoromethyl)pyridin-3-yl)methanol

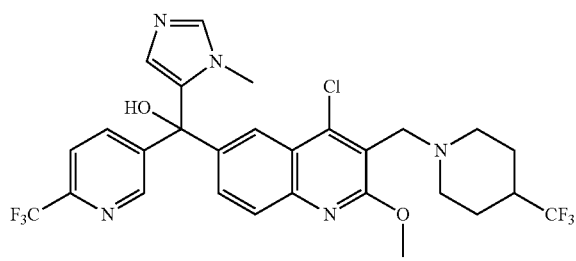

The title compound was prepared analogously to the method described in Example 100a using (1-methyl-1H-imidazol-5-yl)(6-(trifluoromethyl)pyridin-3-yl)methanone (Intermediate 10: step c). MS m/e 614.1 (M+H)⁺.

(4-Chloro-2-methoxy-3-((4-(trifluoromethyl)piperidin-1-yl)methyl)quinolin-6-yl)(1-methyl-1H-imidazol-5-yl)(6-(trifluoromethyl)pyridin-3-yl)methanol was purified by chiral SFC (Chiralpak AD-H, 5 μm, 250×20 mm, mobile phase: 0.3% isopropyl amine, 75% CO₂, 25% mixture of methanol-isopropanol 50/50 v/v). The first eluting enantiomer was Example 112b: ¹H NMR (600 MHz, CDCl₃) δ ppm 8.81 (d, J=2.2 Hz, 1H), 8.14 (d, J=2.1 Hz, 1H), 7.91 (dd, J=8.1, 2.2 Hz, 1H), 7.82 (dd, J=8.9, 0.6 Hz, 1H), 7.67 (dd, J=8.3, 0.8 Hz, 1H), 7.55 (dd, J=8.8, 2.2 Hz, 1H), 7.42 (s, 1H), 6.42 (d, J=1.2 Hz, 1H), 4.27 (s, 1H), 4.09 (s, 3H), 3.81 (s, 2H), 3.39 (s, 3H), 3.03 (d, J=11.0 Hz, 2H), 2.19 (t, J=11.8 Hz, 2H), 1.99-1.96 (m, 1H), 1.80-1.77 (m, 2H), 1.60-1.56 (m, 2H); MS m/e 614.1 (M+H)⁺ and the second eluting enantiomer was Example 112c: ¹H NMR (600 MHz, CDCl₃) δ ppm 8.81 (d, J=2.2 Hz, 1H), 8.14 (d, J=2.3 Hz, 1H), 7.91 (dd, J=8.2, 2.1 Hz, 1H), 7.84-7.79 (m, 1H), 7.67 (dd, J=8.3, 0.8 Hz, 1H), 7.55 (dd, J=8.8, 2.2 Hz, 1H), 7.43 (s, 1H), 6.42 (d, J=1.1 Hz, 1H), 4.09 (s, 3H), 3.81 (s, 2H), 3.39 (s, 3H), 3.03 (d, J=11.0 Hz, 2H), 2.19 (t, J=11.8 Hz, 2H), 2.04-1.90 (m, 1H), 1.80-1.78 (m, 2H), 1.64-1.57 (m, 2H); MS m/e 614.1 (M+H)⁺.

Example 113a (4-Chloro-2-methoxy-3-((2,2,6,6-tetramethylpiperidin-1-yl)methyl)quinolin-6-yl)(2,6-dimethylpyridin-3-yl)(1-methyl-1H-1,2,3-triazol-5-yl)methanol

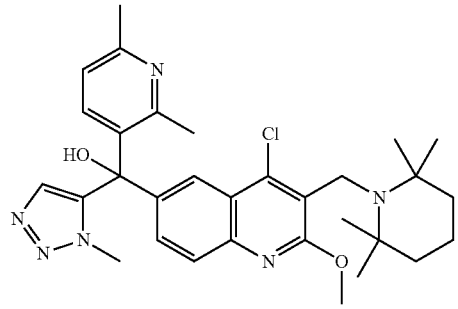 [SMILES: COc1nc2ccc(C(O)(c3ccc(C)nc3C)c3cnnn3C)cc2c(Cl)c1CN1C(C)(C)CCCC1(C)C]

The title compound was prepared analogously to the method described in Example 100a using 6-bromo-4-chloro-2-methoxy-3-((2,2,6,6-tetramethylpiperidin-1-yl)methyl)quinoline (Intermediate 48) and (2,6-dimethylpyridin-3-yl)(1-methyl-1H-1,2,3-triazol-5-yl)methanone (Intermediate 11: step b). MS m/e 563.3 (M+H)⁺.

(4-Chloro-2-methoxy-3-((2,2,6,6-tetramethylpiperidin-1-yl)methyl)quinolin-6-yl)(2,6-dimethylpyridin-3-yl)(1-methyl-1H-1,2,3-triazol-5-yl)methanol was purified by chiral SFC (Chiralpak AD-H, 5 m, 250×20 mm, mobile phase: 0.3% isopropyl amine, 80% CO₂, 20% mixture of methanol-isopropanol 50/50 v/v). The second eluting enantiomer was Example 113b: ¹H NMR (600 MHz, CDCl₃) δ ppm 8.09 (d, J=2.2 Hz, 1H), 7.78 (d, J=8.7 Hz, 1H), 7.36 (d, J=8.6 Hz, 1H), 7.03-6.97 (m, 2H), 6.97-6.92 (m, 1H), 4.13 (s, 2H), 4.09 (s, 3H), 4.05 (s, 1H), 3.94 (s, 3H), 2.56 (s, 3H), 2.39 (s, 3H), 1.59-1.52 (m, 2H), 1.49-1.47 (m, 4H), 1.07 (s, 12H); MS m/e 563.3 (M+H)⁺.

281

Example 114a: (4-Chloro-2-methoxy-3-((3-(trifluoromethyl)azetidin-1-yl)methyl)quinolin-6-yl)(2,6-dimethylpyridin-3-yl)(1-methyl-1H-1,2,3-triazol-5-yl)methanol

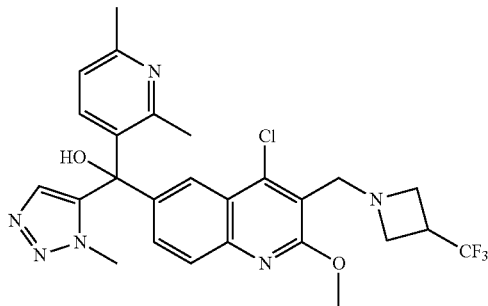 [SMILES: COc1nc2ccc(C(O)(c3ccc(C)nc3C)c3cnnn3C)cc2c(Cl)c1CN1CC(C(F)(F)F)C1]

The title compound was prepared analogously to the method described in Example 100a using 6-bromo-4-chloro-2-methoxy-3-((3-(trifluoromethyl)azetidin-1-yl)methyl)quinoline (Intermediate 49) and (2,6-dimethylpyridin-3-yl)(1-methyl-1H-1,2,3-triazol-5-yl)methanone (Intermediate 11: step b). MS m/e 547.2 (M+H)$^+$.

(4-Chloro-2-methoxy-3-((3-(trifluoromethyl)azetidin-1-yl)methyl)quinolin-6-yl)(2,6-dimethylpyridin-3-yl)(1-methyl-1H-1,2,3-triazol-5-yl)methanol was purified by chiral SFC (Chiralpak AD-H, 5 μm, 250×20 mm, mobile phase: 0.3% isopropyl amine, 80% CO$_2$, 20% mixture of methanol-isopropanol 50/50 v/v). The first eluting enantiomer was Example 114b: $^1$H NMR (600 MHz, CDCl$_3$) δ ppm 8.09 (d, J=2.2 Hz, 1H), 7.82 (d, J=8.7 Hz, 1H), 7.41 (dd, J=8.7, 2.2 Hz, 1H), 6.98-6.92 (m, 3H), 4.12 (s, 3H), 4.11 (s, 1H), 3.95 (s, 2H), 3.94 (s, 3H), 3.63-3.57 (m, 2H), 3.47 (t, J=7.7 Hz, 2H), 3.16 (dq, J=16.3, 8.2 Hz, 1H), 2.55 (s, 3H), 2.39 (s, 3H); MS m/e 547.2 (M+H)$^+$ and the second eluting enantiomer was Example 114c: $^1$H NMR (600 MHz, CDCl$_3$) δ ppm 8.08 (d, J=2.2 Hz, 1H), 7.83 (d, J=8.7 Hz, 1H), 7.41 (dd, J=8.7, 2.2 Hz, 1H), 7.00-6.93 (m, 3H), 4.12 (s, 3H), 3.99 (s, 2H), 3.93 (s, 3H), 3.66 (br s, 2H), 3.52-3.49 (m, 2H), 3.22-3.18 (m, 1H), 2.56 (s, 3H), 2.40 (s, 3H); MS m/e 547.2 (M+H)$^+$.

Example 115

(4-Chloro-2-methoxy-3-((4-(methylsulfonyl)piperidin-1-yl)methyl)quinolin-6-yl)(2,6-dimethylpyridin-3-yl)(1-methyl-1H-1,2,3-triazol-5-yl)methanol

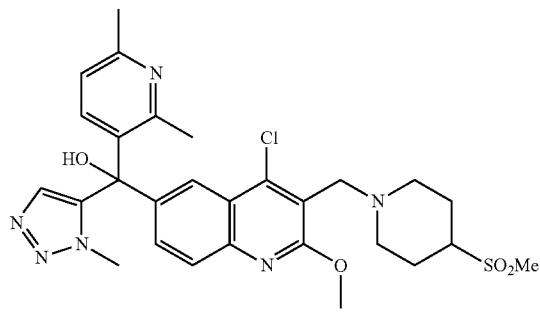 [SMILES: COc1nc2ccc(C(O)(c3ccc(C)nc3C)c3cnnn3C)cc2c(Cl)c1CN1CCC(S(C)(=O)=O)CC1]

282

SOCl$_2$ (0.098 mL, 1.36 mmol) was added to a solution of (4-chloro-3-(hydroxymethyl)-2-methoxyquinolin-6-yl)(2,6-dimethylpyridin-3-yl)(1-methyl-1H-1,2,3-triazol-5-yl)methanol (Intermediate 50: step g, 60 mg, 0.14 mmol) in DCM (2.7 mL) and the resulting mixture was stirred for 2 hours. The mixture was then concentrated on the rotary evaporator. 4-(methylsulfonyl)piperidine (22.2 mg, 0.136 mmol) and DIPEA (0.094 mL, 0.546 mmol) were then added sequentially to the crude mixture from above in DCE (2.7 mL) and the reaction mixture was stirred for 1 hour at room temperature and for 18 hours at 100° C. The reaction mixture was cooled to room temperature, diluted with EtOAc, washed with aqueous saturated NaHCO$_3$ solution followed by aqueous saturated NaCl solution, dried (MgSO$_4$), filtered and concentrated. The crude product was purified by reverse-phase HPLC (5-85% CH$_3$CN—H$_2$O, 0.05% TFA). The product was converted to the free base (neutralized with saturated aqueous NaHCO$_3$ and extracted with EtOAc) and the organic fractions were concentrated to afford the title compound. $^1$H NMR (500 MHz, CDCl$_3$) δ ppm 8.10 (d, J=2.2 Hz, 1H), 7.82 (d, J=8.7 Hz, 1H), 7.40 (dd, J=8.8, 2.2 Hz, 1H), 7.00-6.92 (m, 2H), 6.91 (s, 1H), 4.24 (s, 1H), 4.10 (s, 3H), 3.93 (s, 3H), 3.84 (s, 2H), 3.14-3.12 (m, 2H), 2.80-2.79 (m, 4H), 2.54 (s, 3H), 2.37 (s, 3H), 2.31-2.26 (m, 2H), 2.09 (d, J=12.2 Hz, 2H), 1.83-1.81 (m, 2H). MS m/e 585.1 (M+H).

Example 116a 1-(4-((4-Chloro-2-methoxy-3-((4-(trifluoromethyl)piperidin-1-yl)methyl)quinolin-6-yl)(hydroxy)(phenyl)methyl)piperidin-1-yl)ethanone

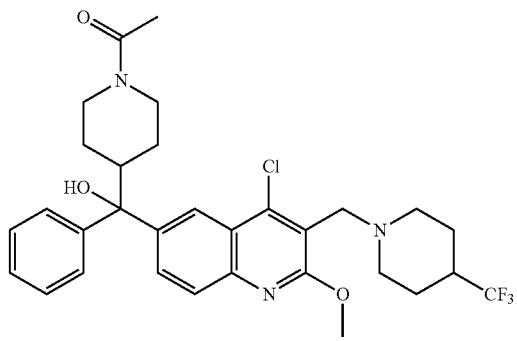 [SMILES: COc1nc2ccc(C(O)(c3ccccc3)C3CCN(C(C)=O)CC3)cc2c(Cl)c1CN1CCC(C(F)(F)F)CC1]

The title compound was prepared analogously to the method described in Example 100a using 1-(4-benzoylpiperidin-1-yl)ethanone (Intermediate 7). MS m/e 590.2 (M+H)$^+$. 1-(4-((4-Chloro-2-methoxy-3-((4-(trifluoromethyl)piperidin-1-yl)methyl)quinolin-6-yl)(hydroxy)(phenyl)methyl)piperidin-1-yl)ethanone was purified by chiral SFC (Chiralpak AD-H, 5 μm, 250×20 mm, mobile phase: 0.3% isopropyl amine, 70% CO$_2$, 30% mixture of methanol-isopropanol 50/50 v/v). The first eluting enantiomer was Example 116b: $^1$H NMR (600 MHz, CDCl$_3$, mixture of rotamers) δ ppm 8.30-8.28 (m, 1H), 7.77-7.74 (m, 1H), 7.69-7.65 (m, 1H), 7.53-7.50 (m, 2H), 7.35-7.31 (m, 2H), 7.25-7.19 (m, 1H), 4.72-4.67 (m, 1H), 4.05 (s, 3H), 3.86-3.81 (m, 3H), 3.14-3.06 (m, 1H), 3.04-3.02 (m, 2H), 2.78-2.74 (m, 1H), 2.63-2.53 (m, 2H), 2.22-2.13 (m, 3H), 2.05-2.04 (m, 3H), 1.98-1.95 (m, 1H), 1.79-1.77 (m, 2H), 1.71-1.64 (m, 1H), 1.61-1.54 (m, 2H), 1.48-1.23 (m, 3H); MS m/e 590.2 (M+H)$^+$ and the second eluting enantiomer was Example 116c: ¹H NMR (600 MHz, CDCl₃) δ ppm 8.30-8.28 (m, 1H), 7.79-7.73 (m, 1H), 7.69-7.65 (m, 1H), 7.56-7.48 (m, 2H), 7.35-7.31 (m, 2H), 7.25-7.18 (m, 1H), 4.72-4.66 (m, 1H), 4.05 (s, 3H), 3.86-3.81 (m, 3H), 3.18-2.95 (m, 3H), 2.78-2.74 (m, 1H), 2.66-2.49 (m, 1H), 2.28-2.12 (m, 3H), 2.05-2.04 (m, 3H) 1.98-1.89 (m, 1H), 1.82-1.72 (m, 2H), 1.71-1.64 (m, 1H), 1.59-1.54 (m, 2H), 1.51-1.28 (m, 3H); MS m/e 590.2 (M+H)⁺.

Example 117a: (4-Chloro-2-methoxy-3-((4-(trifluoromethyl)piperidin-1-yl)methyl)quinolin-6-yl)(2,6-dimethylpyridin-4-yl)(1-methyl-1H-1,2,3-triazol-5-yl)methanol

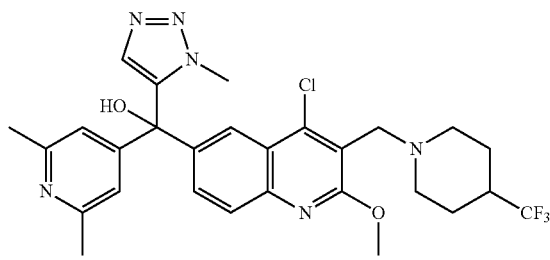 [SMILES: COc1nc2ccc(C(O)(c3cc(C)nc(C)c3)c3cnnn3C)cc2c(Cl)c1CN1CCC(C(F)(F)F)CC1]

The title compound was prepared analogously to the method described in Example 100a using (1-methyl-1H-1,2,3-triazol-5-yl)(2-(trifluoromethyl)pyridin-4-yl)methanone (Intermediate 64: step b). MS m/e 575.2 (M+H)⁺.

(4-Chloro-2-methoxy-3-((4-(trifluoromethyl)piperidin-1-yl)methyl)quinolin-6-yl)(2,6-dimethylpyridin-4-yl)(1-methyl-1H-1,2,3-triazol-5-yl)methanol was purified by chiral SFC (Chiralcel OD-H, 5 m, 250×20 mm, mobile phase: 0.3% isopropyl amine, 75% CO₂, 25% mixture of ethanol-isopropanol 50/50 v/v). The first eluting enantiomer was Example 117b: ¹H NMR (400 MHz, CDCl₃) δ ppm 8.07 (dd, J=2.3, 0.6 Hz, 1H), 7.84 (dd, J=8.8, 0.6 Hz, 1H), 7.48 (dd, J=8.8, 2.2 Hz, 1H), 7.14 (s, 1H), 6.90 (s, 2H), 4.10 (s, 3H), 3.87 (s, 3H), 3.81 (s, 2H), 3.29 (s, 1H), 3.03 (d, J=11.5 Hz, 2H), 2.52 (s, 6H), 2.22-2.17 (m, 2H), 2.05-1.88 (m, 1H), 1.80-1.77 (m, 2H), 1.6-1.54 (m, 2H); MS m/e 575.2 (M+H)⁺ and the second eluting enantiomer was Example 117c: ¹H NMR (400 MHz, CDCl₃) δ ppm 8.07 (d, J=2.2 Hz, 1H), 7.84 (d, J=8.8 Hz, 1H), 7.48 (dd, J=8.8, 2.2 Hz, 1H), 7.13 (s, 1H), 6.90 (s, 2H), 4.10 (s, 3H), 3.87 (s, 3H), 3.81 (s, 2H), 3.35 (s, 1H), 3.03 (d, J=11.6 Hz, 2H), 2.52 (s, 6H), 2.22-2.17 (m, 2H), 2.05-1.90 (m, 1H), 1.80-1.77 (m, 2H), 1.6-1.55 (m, 2H); MS m/e 575.2 (M+H)⁺.

Example 118: (4-Chloro-2-methoxy-3-((3-(trifluoromethyl)azetidin-1-yl)methyl)quinolin-6-yl)bis(1,2-dimethyl-1H-imidazol-5-yl)methanol

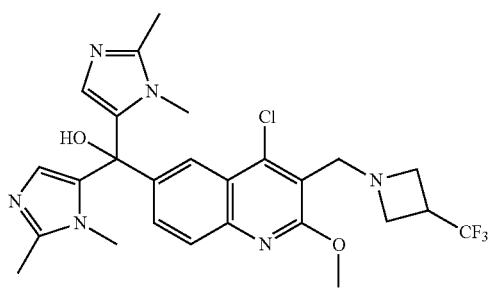 [SMILES: COc1nc2ccc(C(O)(c3cnc(C)n3C)c3cnc(C)n3C)cc2c(Cl)c1CN1CC(C(F)(F)F)C1]

A solution of n-BuLi (0.37 mL, 0.92 mmol, 2.5 M solution in hexane) was slowly added to a solution of 5-bromo-1,2-dimethyl-1H-imidazole (168 mg, 0.959 mmol) in THF (8 mL) at −78° C. After addition, stirring was continued for an additional 25 minutes and (4-chloro-2-methoxy-3-((3-(trifluoromethyl)azetidin-1-yl)methyl)quinolin-6-yl)(1,2-dimethyl-1H-imidazol-5-yl)methanone (Intermediate 52, 182 mg, 0.402 mmol) dissolved in THF (6 mL) was slowly added. An additional 2 mL of THF was used to complete the quantitative addition. The mixture was stirred at −78° C. for 5 minutes and the flask was removed from the dry-ice bath and placed into an ice-water bath. After 18 hours of stirring, the solution was quenched with aqueous saturated NH₄Cl solution. The aqueous layer was extracted with EtOAc and the combined organic extracts washed with brine, dried over MgSO₄, filtered, evaporated in vacuo. The crude product was purified by reverse-phase HPLC (5-85% CH₃CN—H₂O, 0.05% TFA). The product was converted to the free base (neutralized with saturated aqueous NaHCO₃ and extracted with DCM) and the organic fractions were concentrated to afford the title compound. ¹H NMR (500 MHz, CDCl₃) δ ppm 8.19 (d, J=2.1 Hz, 1H), 7.72 (d, J=8.7 Hz, 1H), 7.43 (dd, J=8.6, 2.1 Hz, 1H), 6.21 (s, 2H), 4.37 (s, 1H), 4.11 (s, 3H), 3.95 (s, 2H), 3.62-3.59 (m, 2H), 3.49-3.46 (m, 2H), 3.41 (s, 6H), 3.20-3.12 (m, 1H), 2.32 (s, 6H); MS m/e 549.2 (M+H)⁺.

Example 119a (4-Chloro-2-methoxy-3-((3-(trifluoromethyl)azetidin-1-yl)methyl)quinolin-6-yl)(1,2-dimethyl-1H-imidazol-5-yl)(1-methyl-1H-1,2,3-triazol-5-yl)methanol

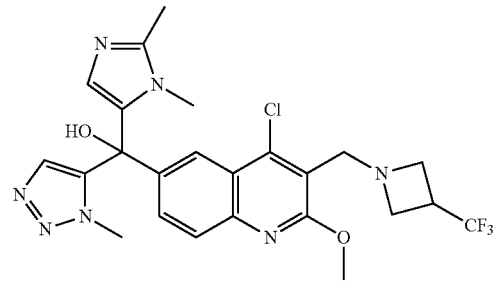 [SMILES: COc1nc2ccc(C(O)(c3cnnn3C)c3cnc(C)n3C)cc2c(Cl)c1CN1CC(C(F)(F)F)C1]

A solution of n-BuLi (0.37 mL, 0.92 mmol, 2.5 M solution in hexane) was added slowly to a solution of 1-methyl-1H-1,2,3-triazole (79.7 mg, 0.959 mmol) in THF (10 mL) at −50° C. After addition, stirring was continued for an additional 30 minutes at −50° C. and (4-chloro-2-methoxy-3-((3-(trifluoromethyl)azetidin-1-yl)methyl)quinolin-6-yl)(1,2-dimethyl-1H-imidazol-5-yl)methanone (Intermediate 52, 182 mg, 0.402 mmol) dissolved in THF (4 mL) was slowly added. An additional 2 mL of THF was used to complete the quantitative addition. The mixture was stirred at −50° C. for 10 minutes then warmed to room temperature and stirred for 18 hours. The solution was quenched with saturated aqueous NH₄Cl solution. H₂O was added and layers were separated. The aqueous layer was extracted with EtOAc and the combined organic extracts washed with brine, dried over MgSO₄, filtered, evaporated in vacuo. The crude product was purified using flash column chromatography (0 to 7% MeOH-DCM) to provide the title compound. MS m/e 536.1 (M+H)⁺.

(4-Chloro-2-methoxy-3-((3-(trifluoromethyl)azetidin-1-yl)methyl)quinolin-6-yl)(1,2-dimethyl-1H-imidazol-5-yl)(1-methyl-1H-1,2,3-triazol-5-yl)methanol was purified by chiral SFC (Chiralpak AD-H, 5 m, 250×20 mm, mobile phase: 0.3% isopropyl amine, 80% CO$_2$, 20% methanol). The first eluting enantiomer was Example 119b: $^1$H NMR (400 MHz, CDCl$_3$) δ ppm 8.19 (d, J=2.2 Hz, 1H), 7.75 (d, J=8.7 Hz, 1H), 7.39 (dd, J=8.7, 2.2 Hz, 1H), 7.13 (s, 1H), 6.09 (s, 1H), 5.46 (s, 1H), 4.12 (s, 3H), 3.94 (s, 2H), 3.91 (s, 3H), 3.66-3.56 (m, 2H), 3.49-3.45 (m, 2H), 3.38 (s, 3H), 3.23-3.08 (m, 1H), 2.28 (s, 3H); MS m/e 536.1 (M+H)$^+$ and the second eluting enantiomer was Example 119c: $^1$H NMR (400 MHz, CDCl$_3$) δ ppm 8.18 (d, J=2.1 Hz, 1H), 7.77 (d, J=8.7 Hz, 1H), 7.40 (dd, J=8.7, 2.2 Hz, 1H), 7.16 (s, 1H), 6.12 (s, 1H), 5.02 (s, 1H), 4.12 (s, 3H), 3.95 (s, 2H), 3.92 (s, 3H), 3.63-3.59 (m, 2H), 3.49-3.45 (m, 2H), 3.40 (s, 3H), 3.23-3.10 (m, 1H), 2.32 (s, 3H); MS m/e 536.1 (M+H)$^+$.

Example 120a: (4-Chloro-2-methoxy-3-((3-(trifluoromethyl)azetidin-1-yl)methyl)quinolin-6-yl)(1-methyl-1H-imidazol-5-yl)(6-(trifluoromethyl)pyridin-3-yl)methanol

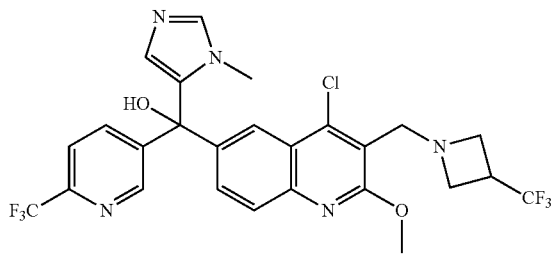 [SMILES: COc1nc2ccc(C(O)(c3ccc(C(F)(F)F)nc3)c3cncn3C)cc2c(Cl)c1CN1CC(C(F)(F)F)C1]

The title compound was prepared analogously to the method described in Example 100a using 6-bromo-4-chloro-2-methoxy-3-((3-(trifluoromethyl)azetidin-1-yl)methyl)quinoline (Intermediate 49) and (1-methyl-1H-imidazol-5-yl)(6-(trifluoromethyl)pyridin-3-yl)methanone (Intermediate 10: step c). MS m/e 586 (M+H)$^+$.

(4-Chloro-2-methoxy-3-((3-(trifluoromethyl)azetidin-1-yl)methyl)quinolin-6-yl)(1-methyl-1H-imidazol-5-yl)(6-(trifluoromethyl)pyridin-3-yl)methanol was purified by chiral SFC (Chiralpak AD-H, 5 µm, 250×20 mm, mobile phase: 0.3% isopropyl amine, 80% CO$_2$, 20% ethanol). The first eluting enantiomer was Example 120b: $^1$H NMR (600 MHz, CDCl$_3$) δ ppm 8.82 (d, J=2.3 Hz, 1H), 8.16 (d, J=2.2 Hz, 1H), 7.91 (dd, J=8.1, 2.2 Hz, 1H), 7.82 (d, J=8.8 Hz, 1H), 7.67 (dd, J=8.3, 0.8 Hz, 1H), 7.57 (dd, J=8.8, 2.2 Hz, 1H), 7.53 (s, 1H), 6.41 (s, 1H), 4.12 (s, 3H), 4.03 (s, 2H), 3.75-3.69 (m, 2H), 3.59-3.51 (m, 2H), 3.41 (s, 3H), 3.26-3.22 (m, 1H); MS m/e 586 (M+H)$^+$ and the second eluting enantiomer was Example 120c: $^1$H NMR (600 MHz, CDCl$_3$) δ ppm 8.82 (d, J=2.3 Hz, 1H), 8.16 (d, J=2.2 Hz, 1H), 7.91 (dd, J=8.3, 2.2 Hz, 1H), 7.82 (d, J=8.7 Hz, 1H), 7.67 (dd, J=8.4, 0.8 Hz, 1H), 7.57 (dd, J=8.8, 2.2 Hz, 1H), 7.51 (s, 1H), 6.40 (s, 1H), 4.12 (s, 3H), 4.03 (s, 2H), 3.75-3.69 (m, 2H), 3.55-3.52 (m, 2H), 3.41 (s, 3H), 3.26-3.22 (m, 1H); MS m/e 586 (M+H)$^+$.

Example 121a: (4-Chloro-2-methoxy-3-((3-(trifluoromethyl)azetidin-1-yl)methyl)quinolin-6-yl)(1-methyl-1H-imidazol-5-yl)(2-(trifluoromethyl)pyridin-4-yl)methanol

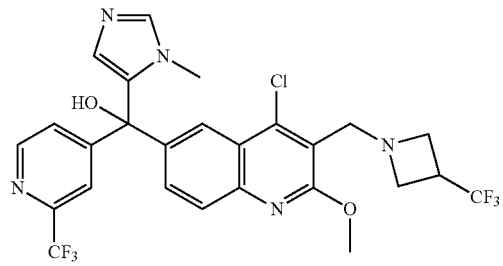

The title compound was prepared analogously to the method described in Example 100a, using 6-bromo-4-chloro-2-methoxy-3-((3-(trifluoromethyl)azetidin-1-yl)methyl)quinoline (Intermediate 49) and (1-methyl-1H-imidazol-5-yl)(2-(trifluoromethyl)pyridin-4-yl)methanone (Intermediate 14: step b). MS m/e 586 (M+H)$^+$.

(4-Chloro-2-methoxy-3-((3-(trifluoromethyl)azetidin-1-yl)methyl)quinolin-6-yl)(1-methyl-1H-imidazol-5-yl)(2-(trifluoromethyl)pyridin-4-yl)methanol was purified by chiral SFC (Chiralcel OJ-H, 5 µm, 250×20 mm, mobile phase: 0.3% isopropyl amine, 80% CO$_2$, 20% isopropanol). The first eluting enantiomer was Example 121b: $^1$H NMR (600 MHz, CDCl$_3$) δ ppm 8.72 (d, J=5.1 Hz, 1H), 8.15 (d, J=2.2 Hz, 1H), 7.88-7.86 (m, 1H), 7.83 (d, J=8.8 Hz, 1H), 7.57 (dd, J=8.8, 2.2 Hz, 1H), 7.50 (dd, J=5.1, 1.6 Hz, 1H), 7.47 (s, 1H), 6.42 (s, 1H), 4.12 (s, 3H), 4.04 (s, 2H), 3.76-3.69 (m, 2H), 3.59-3.52 (m, 2H), 3.39 (s, 3H), 3.27-3.24 (m, 1H); MS m/e 586 (M+H)$^+$ and the second eluting enantiomer was Example 121c: $^1$H NMR (600 MHz, CDCl$_3$) δ ppm 8.71 (d, J=5.1 Hz, 1H), 8.16 (d, J=2.2 Hz, 1H), 7.91-7.86 (m, 1H), 7.83 (d, J=8.7 Hz, 1H), 7.57 (dd, J=8.8, 2.2 Hz, 1H), 7.50 (d, J=5.1 Hz, 1H), 7.48 (s, 1H), 6.41 (s, 1H), 4.12 (s, 3H), 4.05 (s, 2H), 3.77-3.7 (m, 2H), 3.59-3.52 (m, 2H), 3.39 (s, 3H), 3.32-3.19 (m, 1H); MS m/e 586 (M+H)$^+$.

Example 122a: (4-Chloro-2-methoxy-3-((4-(trifluoromethyl)piperidin-1-yl)methyl)quinolin-6-yl)(1-methyl-1H-1,2,3-triazol-5-yl)(tetrahydro-2H-pyran-4-yl)methanol

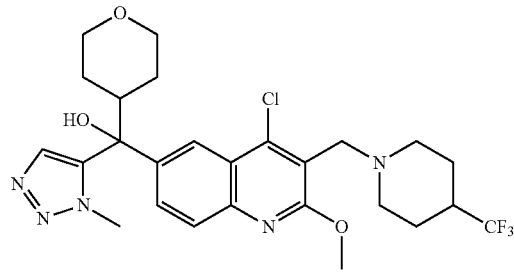 [SMILES: COc1nc2ccc(C(O)(c3cnnn3C)C3CCOCC3)cc2c(Cl)c1CN1CCC(C(F)(F)F)CC1]

The title compound was prepared analogously to the method described in Example 100a using (1-methyl-1H-1,2,3-triazol-5-yl)(tetrahydro-2H-pyran-4-yl)methanone (Intermediate 53: step b). MS m/e 554.1 (M+H)$^+$.

(4-Chloro-2-methoxy-3-((4-(trifluoromethyl)piperidin-1-yl)methyl)quinolin-6-yl)(1-methyl-1H-1,2,3-triazol-5-yl)(tetrahydro-2H-pyran-4-yl)methanol was purified by chiral SFC (Chiralpak AD-H, 5 m, 250×20 mm, mobile phase: 0.3% isopropyl amine, 83% $CO_2$, 17% methanol). The first eluting enantiomer was Example 122b: $^1$H NMR (400 MHz, CDCl$_3$) δ ppm 8.13 (d, J=2.1 Hz, 1H), 7.81-7.73 (m, 2H), 7.37 (dd, J=8.8, 2.1 Hz, 1H), 4.12-4.08 (m, 4H), 3.95-3.88 (m, 1H), 3.82 (s, 2H), 3.74 (s, 3H), 3.53 (td, J=11.6, 2.0 Hz, 1H), 3.34 (td, J=12.0, 2.2 Hz, 1H), 3.06-3.03 (m, 2H), 2.57 (s, 1H), 2.55-2.46 (m, 1H), 2.23-2.17 (m, 2H), 2.03-1.92 (m, 2H), 1.81-1.78 (m, 2H), 1.68-1.52 (m, 2H), 1.52-1.37 (m, 1H), 1.06-1.03 (m, 1H); MS m/e 554.1 (M+H)$^+$ and the second eluting enantiomer was Example 122c: $^1$H NMR (400 MHz, CDCl$_3$) δ ppm 8.13 (d, J=2.1 Hz, 1H), 7.81-7.74 (m, 2H), 7.37 (dd, J=8.7, 2.1 Hz, 1H), 4.12-4.08 (m, 4H), 3.94-3.92 (m, 1H), 3.82 (s, 2H), 3.74 (s, 3H), 3.53 (td, J=11.8, 2.1 Hz, 1H), 3.34 (td, J=11.9, 2.2 Hz, 1H), 3.06-3.04 (m, 2H), 2.57 (s, 1H), 2.56-2.48 (m, 1H), 2.28-2.12 (m, 2H), 2.0-1.97 (m, 2H), 1.81-1.78 (m, 2H), 1.69-1.52 (m, 2H), 1.51-1.37 (m, 1H), 1.06-1.03 (m, 1H); MS m/e 554.1 (M+H)$^+$.

Example 123a: 1-(3-((4-Chloro-2-methoxy-3-((4-(trifluoromethyl)piperidin-1-yl)methyl)quinolin-6-yl)(hydroxy)(1-methyl-1H-1,2,3-triazol-5-yl)methyl)azetidin-1-yl)ethanone

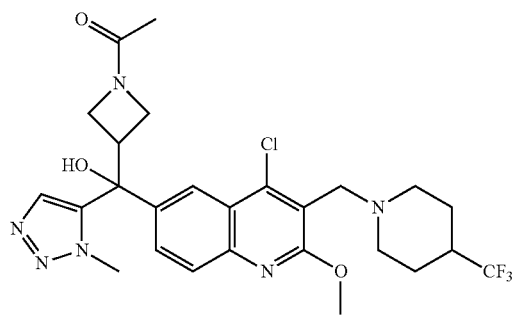 [SMILES: COc1nc2ccc(C(O)(c3cnnn3C)C3CN(C(C)=O)C3)cc2c(Cl)c1CN1CCC(C(F)(F)F)CC1]

TFA (0.441 mL, 5.75 mmol) was added to a solution of tert-butyl-3-((4-chloro-2-methoxy-3-((4-(trifluoromethyl)piperidin-1-yl)methyl)quinolin-6-yl)(hydroxy)(1-methyl-1H-1,2,3-triazol-5-yl)methyl)azetidine-1-carboxylate (Example 178, 360 mg, 0.576 mmol) in DCM (5.8 mL) and the mixture was heated to 40° C. After stirring for 4 hours, the mixture was cooled to room temperature, diluted with DCM, washed with aqueous saturated NaHCO$_3$ solution and aqueous saturated sodium chloride solution. The organic layer was dried over MgSO$_4$, filtered, and concentrated. TEA (0.37 mL, 2.6 mmol) and Ac$_2$O (0.20 mL, 2.1 mmol) were added sequentially to the crude mixture (280 mg, 0.53 mmol) above in DCM (10.7 mL). After stirring for 2 hours, the mixture was cooled to room temperature, diluted with DCM, washed with aqueous saturated NaHCO$_3$ solution and aqueous saturated sodium chloride solution. The organic layer was dried over MgSO$_4$, filtered, and concentrated. The crude product was purified using flash column chromatography (silica gel, 0 to 6% MeOH-DCM) to provide the title compound. MS m/e 567.2 (M+H)$^+$.

1-(3-((4-Chloro-2-methoxy-3-((4-(trifluoromethyl)piperidin-1-yl)methyl)quinolin-6-yl)(hydroxy)(1-methyl-1H-1,2,3-triazol-5-yl)methyl)azetidin-1-yl)ethanone was purified by chiral SFC (Chiralpak IC, 5 μm, 250×30 mm, mobile phase: 0.3% isopropyl amine, 55% $CO_2$, 45% ethanol). The first eluting enantiomer was Example 123b: $^1$H NMR (500 MHz, CDCl$_3$, mixture of rotamers) δ ppm 8.31 (d, J=2.1 Hz, 0.6H), 8.24 (d, J=2.1 Hz, 0.4H), 7.79-7.77 (m, 1H), 7.58-7.57 (m, 1H), 7.39-7.35 (m, 1H), 5.44 (s, 0.6H), 5.02 (s, 0.4H), 4.38-4.35 (m, 0.4H), 4.31-4.29 (m, 0.6H), 4.20-4.14 (m, 1H), 4.1-4.08 (m, 3.5H), 4.02-3.99 (m, 0.5H), 3.82-3.81 (m, 2H), 3.79-3.72 (m, 1H), 3.71-3.69 (m, 3H), 3.60-3.45 (m, 1H), 3.05-3.02 (m, 2H), 2.25-2.13 (m, 2H), 2.02-1.97 (m, 1H), 1.83 (s, 1.8H), 1.82-1.77 (m, 3.2H), 1.66-1.47 (m, 2H); MS m/e 567.2 (M+H)$^+$ and the second eluting enantiomer was Example 123c: $^1$H NMR (500 MHz, CDCl$_3$) δ ppm 8.31 (d, J=2.1 Hz, 0.6H), 8.24 (d, J=2.1 Hz, 0.4H), 7.79-7.77 (m, 1H), 7.58-7.57 (m, 1H), 7.39-7.35 (m, 1H), 5.33 (s, 0.6H), 4.92 (s, 0.4H), 4.38-4.35 (m, 0.4H), 4.30-4.27 (m, 0.6H), 4.24-4.12 (m, 1H), 4.11-4.08 (m, 3.5H), 4.02-3.99 (m, 0.5H), 3.82-3.81 (m, 2H), 3.79-3.73 (m, 1H), 3.71-3.69 (m, 3H), 3.56-3.41 (m, 1H), 3.09-2.96 (m, 2H), 2.25-2.13 (m, 2H), 2.02-1.96 (m, 1H), 1.83 (s, 1.8H), 1.82-1.77 (s, 3.2H), 1.66-1.50 (m, 2H); MS m/e 567.2 (M+H)$^+$.

Example 124a: 1-(3-((4-Chloro-2-methoxy-3-((4-(trifluoromethyl)piperidin-1-yl)methyl)quinolin-6-yl)(1,2-dimethyl-1H-imidazol-5-yl)(hydroxy)methyl)azetidin-1-yl)ethanone

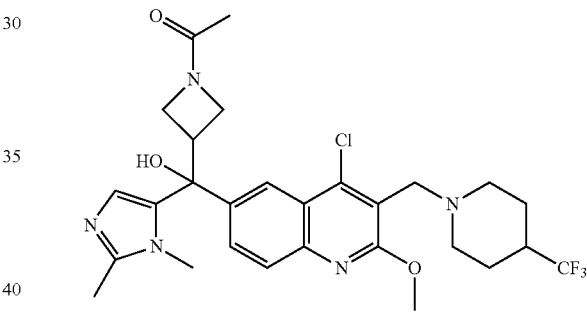

TFA (0.396 mL, 5.17 mmol) was added to a solution of tert-butyl-3-((4-chloro-2-methoxy-3-((4-(trifluoromethyl)piperidin-1-yl)methyl)quinolin-6-yl)(1,2-dimethyl-1H-imidazol-5-yl)(hydroxy)methyl)azetidine-1-carboxylate (Example 179, 330 mg, 0.517 mmol) in DCM (5.2 mL) and the mixture was heated to 40° C. After stirring for 4 hours, the mixture was cooled to room temperature, diluted with DCM, washed with aqueous saturated NaHCO$_3$ solution and aqueous saturated sodium chloride solution. The organic layer was dried over MgSO$_4$, filtered, and concentrated. TEA (0.19 mL, 1.4 mmol) and Ac$_2$O (0.10 mL, 1.2 mmol) were added sequentially to the crude mixture (150 mg, 0.279 mmol) above in DCM (5.6 mL). After stirring for 1 hour, the mixture was cooled to room temperature, diluted with DCM, washed with aqueous saturated NaHCO$_3$ solution and aqueous saturated sodium chloride solution. The organic layer was dried over MgSO$_4$, filtered, and concentrated. The crude product was purified using flash column chromatography (silica gel, 0 to 6% MeOH-DCM) to provide the title compound. MS m/e 580.2 (M+H)$^+$.

1-(3-((4-Chloro-2-methoxy-3-((4-(trifluoromethyl)piperidin-1-yl)methyl)quinolin-6-yl)(1,2-dimethyl-1H-imidazol-5-yl)(hydroxy)methyl)azetidin-1-yl)ethanone was purified by chiral SFC (Chiralpak AD-H, 5 μm, 250×30 mm, mobile phase: 0.3% isopropyl amine, 75% $CO_2$, 25% mixture of ethanol-isopropanol 50/50 v/v). The first eluting enantiomer was Example 124b: ¹H NMR (600 MHz, CDCl₃, mixture of rotamers) δ ppm 8.32-8.28 (m, 1H), 7.77-7.76 (m, 1H), 7.45-7.41 (m, 1H), 6.82-6.81 (m, 1H), 4.39-4.36 (m, 0.5H), 4.25-4.18 (m, 1H), 4.15-4.13 (m, 0.5H), 4.08 (s, 3H), 4.04-4.01 (m, 0.5H), 3.99-3.96 (m, 0.5H), 3.82 (s, 2H), 3.69-3.67 (m, 0.5H), 3.62-3.58 (m, 0.5H), 3.50-3.42 (m, 1H), 3.12 (s, 3H), 3.07-3.05 (m, 2H), 2.27-2.25 (m, 3H), 2.24-2.16 (m, 2H), 2.05-1.92 (m, 1H), 1.85-1.83 (m, 3H), 1.81-1.79 (m, 2H), 1.61-1.58 (m, 2H); MS m/e 580.2 (M+H)⁺ and the second eluting enantiomer was Example 124c: ¹H NMR (600 MHz, CDCl₃) δ ppm 8.32-8.28 (m, 1H), 7.77-7.76 (m, 1H), 7.45-7.41 (m, 1H), 6.83-6.79 (m, 1H), 4.38-4.35 (m, 0.5H), 4.25-4.17 (m, 1H), 4.15-4.13 (0.5H), 4.08 (s, 3H), 4.04-4.01 (m, 0.5H), 3.99-3.96 (m, 0.5H), 3.82 (s, 2H), 3.69-3.66 (m, 0.5H), 3.61-3.58 (m, 0.5H), 3.47-3.44 (m, 1H), 3.13-3.12 (m, 3H), 3.07-3.05 (m, 2H), 2.26-2.24 (m, 3H), 2.23-2.18 (m, 2H), 2.03-1.94 (m, 1H), 1.84-1.83 (m, 3H), 1.83-1.79 (m, 2H), 1.63-1.56 (m, 2H); MS m/e 580.2 (M+H)⁺.

Example 125a: 1-(3-((4-Chloro-2-methoxy-3-((4-(trifluoromethyl)piperidin-1-yl)methyl)quinolin-6-yl)(hydroxy)(2-(trifluoromethyl)pyridin-4-yl)methyl)azetidin-1-yl)ethanone

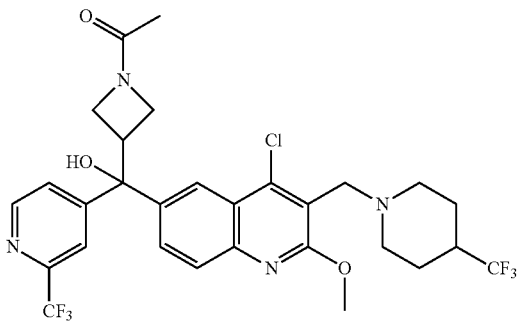 [SMILES: COc1nc2ccc(C(O)(c3ccnc(C(F)(F)F)c3)C3CN(C(C)=O)C3)cc2c(Cl)c1CN1CCC(C(F)(F)F)CC1]

The title compound was prepared analogously to the method described in Example 123a using tert-butyl-3-((4-chloro-2-methoxy-3-((4-(trifluoromethyl)piperidin-1-yl)methyl)quinolin-6-yl)(hydroxy)(2-(trifluoromethyl)pyridin-4-yl)methyl)azetidine-1-carboxylate (Example 180). MS m/e 631.1 (M+H)⁺.

1-(3-((4-Chloro-2-methoxy-3-((4-(trifluoromethyl)piperidin-1-yl)methyl)quinolin-6-yl)(hydroxy)(2-(trifluoromethyl)pyridin-4-yl)methyl)azetidin-1-yl)ethanone was purified by chiral SFC (Chiralpak AD, 5 μm, 250×30 mm, mobile phase: 80% CO₂, 20% methanol). The first eluting enantiomer was Example 125b: ¹H NMR (600 MHz, CDCl₃, mixture of rotamers) δ ppm 8.68-8.66 (m, 1H), 8.15 (d, J=2.2 Hz, 0.4H), 8.05 (d, J=2.1 Hz, 0.6H), 7.83-7.70 (m, 2H), 7.54-7.41 (m, 2H), 4.30-4.23 (m, 1H), 4.19-4.11 (m, 1H), 4.08-4.07 (m, 3H), 4.06-3.92 (m, 2H), 3.88-3.87 (m, 1H), 3.82-3.81 (m, 2H), 3.79-3.74 (m, 1H), 3.06-2.97 (m, 2H), 2.24-2.14 (m, 2H), 2.00-1.96 (m, 1H), 1.84 (s, 1.8H), 1.83-1.76 (m, 2H), 1.75 (s, 1.2H), 1.67-1.50 (m, 2H); MS m/e 631.1 (M+H)⁺ and the second eluting enantiomer was Example 125c: ¹H NMR (600 MHz, CDCl₃) δ ppm 8.68-8.66 (m, 1H), 8.16 (d, J=2.1 Hz, 0.4H), 8.05 (d, J=2.1 Hz, 0.6H), 7.81-7.78 (m, 1.6H), 7.73-7.72 (m, 0.4H), 7.53-7.42 (m, 2H), 4.30-4.22 (m, 1H), 4.18-4.11 (m, 1H), 4.08-4.07 (m, 3H), 4.06-3.92 (m, 3H), 3.82-3.81 (m, 2H), 3.79-3.74 (m, 1H), 3.06-2.96 (m, 2H), 2.22-2.16 (m, 2H), 2.01-1.96 (m, 1H), 1.84 (s, 1.8H), 1.80-1.76 (m, 2H), 1.74 (s, 1.2H), 1.65-1.49 (m, 2H); MS m/e 631.1 (M+H)⁺.

Example 126a: (4-Chloro-2-methoxy-3-((4-(trifluoromethyl)piperidin-1-yl)methyl)quinolin-6-yl)(1,2-dimethyl-1H-imidazol-5-yl)(2-(trifluoromethyl)pyridin-4-yl)methanol

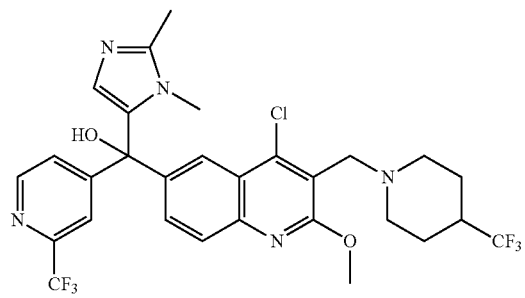 [SMILES: COc1nc2ccc(C(O)(c3ccnc(C(F)(F)F)c3)c3cnc(C)n3C)cc2c(Cl)c1CN1CCC(C(F)(F)F)CC1]

The title compound was prepared analogously to the method described in Example 100a using (1,2-dimethyl-1H-imidazol-5-yl)(2-(trifluoromethyl)pyridin-4-yl)methanone (Intermediate 60: step b). MS m/e 628 (M+H)⁺.

(4-Chloro-2-methoxy-3-((4-(trifluoromethyl)piperidin-1-yl)methyl)quinolin-6-yl)(1,2-dimethyl-1H-imidazol-5-yl)(2-(trifluoromethyl)pyridin-4-yl)methanol was purified by chiral SFC (Chiralcel OD-H, 5 m, 250×20 mm, mobile phase: 0.3% isopropyl amine, 75% CO₂, 25% methanol). The first eluting enantiomer was Example 126b: ¹H NMR (600 MHz, CDCl₃) δ ppm 8.69 (d, J=5.2 Hz, 1H), 8.16 (d, J=2.1 Hz, 1H), 7.90-7.88 (m, 1H), 7.82-7.76 (m, 1H), 7.56 (dd, J=8.8, 2.2 Hz, 1H), 7.50 (dd, J=5.1, 1.7 Hz, 1H), 6.21 (s, 1H), 4.08 (s, 3H), 3.79 (s, 2H), 3.24 (s, 3H), 3.05-2.95 (m, 2H), 2.25 (s, 3H), 2.20-2.18 (m, 2H), 2.00-1.95 (m, 1H), 1.79-1.77 (m, 2H), 1.62-1.53 (m, 2H); MS m/e 628 (M+H)⁺ and the second eluting enantiomer was Example 126c: ¹H NMR (600 MHz, CDCl₃) δ ppm 8.68 (d, J=5.1 Hz, 1H), 8.17 (d, J=2.1 Hz, 1H), 7.90-7.89 (m, 1H), 7.79 (d, J=8.7 Hz, 1H), 7.56 (dd, J=8.7, 2.2 Hz, 1H), 7.50 (dd, J=5.1, 1.7 Hz, 1H), 6.19 (s, 1H), 4.08 (s, 3H), 3.79 (s, 2H), 3.24 (s, 3H), 3.03-2.99 (m, 2H), 2.24 (s, 3H), 2.20-2.16 (m, 2H), 2.00-1.95 (m, 1H), 1.81-1.75 (m, 2H), 1.64-1.52 (m, 2H); MS m/e 628 (M+H)⁺.

Example 127a: (4-Chloro-2-methoxy-3-((4-(trifluoromethyl)piperidin-1-yl)methyl)quinolin-6-yl)(1-methyl-1H-1,2,3-triazol-5-yl)(1-(methylsulfonyl)azetidin-3-yl)methanol

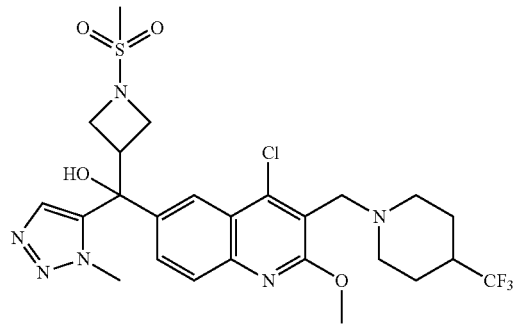 [SMILES: COc1nc2ccc(C(O)(c3cnnn3C)C3CN(S(C)(=O)=O)C3)cc2c(Cl)c1CN1CCC(C(F)(F)F)CC1]

TFA (0.39 mL, 5.1 mmol) was added to a solution of tert-butyl-3-((4-chloro-2-methoxy-3-((4-(trifluoromethyl)piperidin-1-yl)methyl)quinolin-6-yl)(hydroxy)(1-methyl-1H-1,2,3-triazol-5-yl)methyl)azetidine-1-carboxylate (Example 178, 320 mg, 0.512 mmol) in DCM (5.2 mL) and the mixture was heated to 40° C. After stirring for 4 hours, the mixture was cooled to room temperature, diluted with DCM, washed with aqueous saturated NaHCO₃ solution and aqueous saturated sodium chloride solution. The organic layer was dried over MgSO₄, filtered, and concentrated. TEA (0.19 mL, 1.4 mmol) and methylsulfonyl chloride (0.05 mL, 0.68 mmol) were added sequentially to the crude mixture (240 mg, 0.46 mmol) above in DCM (9.1 mL). After stirring for 4 hours, the mixture was diluted with DCM, washed with aqueous saturated NaHCO₃ solution and aqueous saturated sodium chloride solution. The organic layer was dried over MgSO₄, filtered, and concentrated. The crude product was purified using flash column chromatography (0 to 5% MeOH-DCM) to provide the title compound. MS m/e 603.2 (M+H)⁺. (4-Chloro-2-methoxy-3-((4-(trifluoromethyl)piperidin-1-yl)methyl)quinolin-6-yl)(1-methyl-1H-1,2,3-triazol-5-yl)(1-(methylsulfonyl)azetidin-3-yl)methanol was purified by chiral SFC (Chiralcel OD-H, 5 μm, 250×20 mm, mobile phase: 0.3% isopropyl amine, 60% CO₂, 40% methanol). The first eluting enantiomer was Example 127b: ¹H NMR (600 MHz, CDCl₃) δ ppm 8.25 (d, J=2.1 Hz, 1H), 7.79 (d, J=8.7 Hz, 1H), 7.53 (s, 1H), 7.34 (dd, J=8.7, 2.1 Hz, 1H), 4.39 (s, 1H), 4.23-4.20 (m, 1H), 4.15-4.10 (m, 2H), 4.08 (s, 3H), 3.82 (s, 2H), 3.69 (s, 3H), 3.61-3.59 (m, 1H), 3.58-3.52 (m, 1H), 3.05-3.03 (m, 2H), 2.89 (s, 3H), 2.25-2.15 (m, 2H), 2.01-1.94 (m, 1H), 1.81-1.79 (m, 2H), 1.61-1.56 (m, 2H); MS m/e 603.2 (M+H)⁺ and the second eluting enantiomer was Example 127c: ¹H NMR (600 MHz, CDCl₃) δ ppm 8.24 (d, J=2.1 Hz, 1H), 7.79 (d, J=8.7 Hz, 1H), 7.54 (s, 1H), 7.34 (dd, J=8.7, 2.1 Hz, 1H), 4.24-4.21 (m, 1H), 4.14-4.09 (m, 1H), 4.08 (s, 3H), 3.82 (s, 2H), 3.69 (s, 3H), 3.63-3.60 (m, 1H), 3.58-3.52 (m, 1H), 3.05-3.03 (m, 2H), 2.88 (s, 3H), 2.25-2.16 (m, 2H), 2.02-1.95 (s, 1H), 1.81-1.79 (m, 2H), 1.61-1.55 (m, 2H); MS m/e 603.2 (M+H)⁺.

Example 128a: (4-Chloro-2-methoxy-3-((4-(trifluoromethyl)piperidin-1-yl)methyl)quinolin-6yl)(tetrahydro-2H-pyran-4-yl)(2-(trifluoromethyl)pyridin-4-yl)methanol

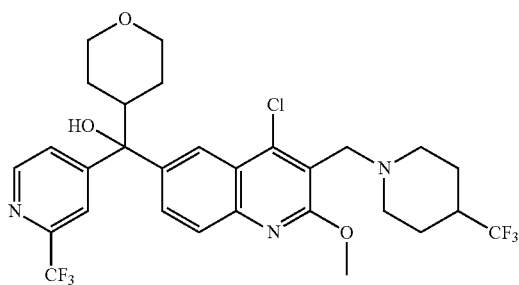 [SMILES: COc1nc2ccc(C(O)(c3ccnc(C(F)(F)F)c3)C3CCOCC3)cc2c(Cl)c1CN1CCC(C(F)(F)F)CC1]

The title compound was prepared analogously to the method described in Example 100a using (tetrahydro-2H-pyran-4-yl)(2-(trifluoromethyl)pyridin-4-yl)methanone (Intermediate 61: step b). MS m/e 618.2 (M+H)⁺.

(4-Chloro-2-methoxy-3-((4-(trifluoromethyl)piperidin-1-yl)methyl)quinolin-6yl)(tetrahydro-2H-pyran-4-yl)(2-(trifluoromethyl)pyridin-4-yl)methanol was purified by chiral SFC (Chiralcel OD-H, 5 μm, 250×20 mm, mobile phase: 0.3% isopropyl amine, 70% CO₂, 30% isopropanol). The first eluting enantiomer was Example 128b: ¹H NMR (600 MHz, CDCl₃) δ ppm 8.66 (d, J=5.2 Hz, 1H), 8.30 (d, J=2.1 Hz, 1H), 7.88 (s, 1H), 7.83 (d, J=8.8 Hz, 1H), 7.73 (dd, J=8.9, 2.2 Hz, 1H), 7.64 (dd, J=5.1, 1.7 Hz, 1H), 4.07 (s, 3H), 4.05-4.02 (dd, J=11.6, 3.5 Hz, 2H), 3.81 (s, 2H), 3.54-3.43 (m, 2H), 3.03-3.01 (m, 2H), 2.82-2.79 (m, 1H), 2.41 (s, 1H), 2.22-2.17 (m, 2H), 1.98-1.96 (m, 1H), 1.79-1.77 (m, 2H), 1.72-1.59 (m, 1H), 1.60-1.46 (m, 2H), 1.29-1.14 (m, 2H); MS m/e 618.2 (M+H)⁺ and the second eluting enantiomer was Example 128c: ¹H NMR (600 MHz, CDCl₃) δ ppm 8.66 (d, J=5.2 Hz, 1H), 8.32-8.27 (m, 1H), 7.88 (m, 1H), 7.85-7.80 (m, 1H), 7.73 (dd, J=8.8, 2.2 Hz, 1H), 7.64 (dd, J=5.3, 1.7 Hz, 1H), 4.07 (s, 3H), 4.04-4.02 (m, 2H), 3.81 (s, 2H), 3.54-3.43 (m, 2H), 3.03-3.01 (m, 2H), 2.86-2.77 (m, 1H), 2.41 (s, 1H), 2.21-2.17 (m, 2H), 1.99-1.96 (m, 1H), 1.79-1.77 (m, 2H), 1.67-1.64 (m, 1H), 1.59-1.46 (m, 2H), 1.27-1.17 (m, 2H); MS m/e 618.2 (M+H)⁺.

Example 129a: (4-Chloro-2-methoxy-3-((4-(trifluoromethyl)piperidin-1-yl)methyl)quinolin-6-yl)(1-methyl-1H-1,2,3-triazol-5-yl)(2-(trifluoromethyl)pyridin-4-yl)methanol

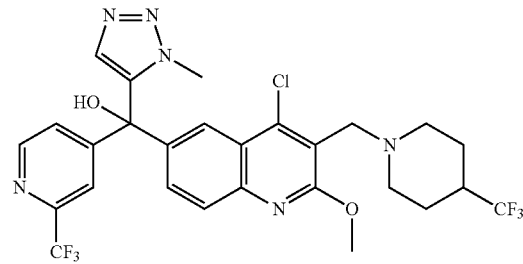

The title compound was prepared analogously to the method described in Example 100a using (1-methyl-1H-1,2,3-triazol-5-yl)(2-(trifluoromethyl)pyridin-4-yl)methanone (Intermediate 51: step b). MS m/e 615 (M+H)⁺.

(4-Chloro-2-methoxy-3-((4-(trifluoromethyl)piperidin-1-yl)methyl)quinolin-6-yl)(1-methyl-1H-1,2,3-triazol-5-yl)(2-(trifluoromethyl)pyridin-4-yl)methanol was purified by chiral SFC (Chiralcel OJ-H, 5 μm, 250×20 mm, mobile phase: 0.3% isopropyl amine, 80% CO₂, 20% isopropanol). The first eluting enantiomer was Example 129b: ¹H NMR (600 MHz, CDCl₃) δ ppm 8.77 (d, J=5.1 Hz, 1H), 8.04 (d, J=2.3 Hz, 1H), 7.87 (d, J=8.7 Hz, 1H), 7.83-7.82 (m, 1H), 7.47 (dd, J=8.7, 2.3 Hz, 1H), 7.45-7.42 (m, 1H), 7.13 (s, 1H), 4.10 (s, 3H), 3.86 (s, 3H), 3.80 (s, 2H), 3.76 (s, 1H), 3.02-3.00 (m, 2H), 2.23-2.15 (m, 2H), 1.99-1.97 (m, 1H), 1.79-1.77 (m, 2H), 1.60-1.55 (m, 2H); MS m/e 615 (M+H)⁺ and the second eluting enantiomer was Example 129c: ¹H NMR (600 MHz, CDCl₃) δ ppm 8.76 (d, J=5.1 Hz, 1H), 8.05 (d, J=2.2 Hz, 1H), 7.86 (d, J=8.8 Hz, 1H), 7.84-7.83 (m, 1H), 7.47 (dd, J=8.7, 2.2 Hz, 1H), 7.44 (dd, J=5.1, 1.7 Hz, 1H), 7.07 (s, 1H), 4.33 (s, 1H), 4.10 (s, 3H), 3.84 (s, 3H), 3.80 (s, 2H), 3.02-3.00 (m, 2H), 2.21-2.17 (m, 2H), 2.00-1.95 (s, 1H), 1.84-1.72 (m, 2H), 1.64-1.49 (m, 2H); MS m/e 615 (M+H)⁺.

Example 130a: (4-Chloro-2-methoxy-3-((4-(trifluoromethyl)piperidin-1-yl)methyl)quinolin-6-yl)(1,2-dimethyl-1H-imidazol-5-yl)(tetrahydro-2H-pyran-4-yl)methanol

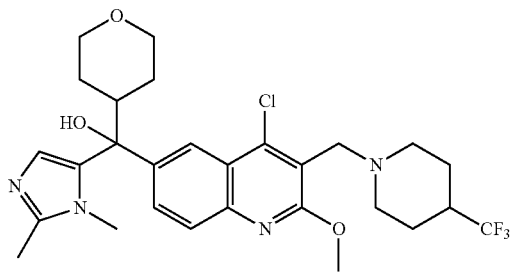 [SMILES: COc1nc2ccc(C(O)(c3cnc(C)n3C)C3CCOCC3)cc2c(Cl)c1CN1CCC(C(F)(F)F)CC1]

The title compound was prepared analogously to the method described in Example 100a using (1,2-dimethyl-1H-imidazol-5-yl)(tetrahydro-2H-pyran-4-yl)methanone (Intermediate 62). MS m/e 567.4 (M+H)+.

(4-Chloro-2-methoxy-3-((4-(trifluoromethyl)piperidin-1-yl)methyl)quinolin-6-yl)(1,2-dimethyl-1H-imidazol-5-yl)(tetrahydro-2H-pyran-4-yl)methanol was purified by chiral SFC (Chiralcel OD-H, 5 m, 250×20 mm, mobile phase: 0.3% isopropyl amine, 60% CO2, 40% isopropanol). The first eluting enantiomer was Example 130b: 1H NMR (600 MHz, CDCl3) δ ppm 8.16 (s, 1H), 7.75 (d, J=8.5 Hz, 1H), 7.42 (d, J=8.6 Hz, 1H), 7.08 (s, 1H), 4.09-4.04 (m, 4H), 3.89 (dd, J=11.6, 4.2 Hz, 1H), 3.82 (s, 2H), 3.54-3.50 (m, 1H), 3.35-3.30 (m, 1H), 3.14 (s, 3H), 3.06-3.04 (m, 2H), 2.49-2.41 (m, 1H), 2.28-2.27 (m, 4H), 2.22-2.18 (m, 2H), 2.14-2.12 (m, 1H), 2.0-1.98 (m, 1H), 1.83-1.77 (m, 2H), 1.71-1.52 (m, 3H), 1.45-1.35 (m, 1H), 1.04-1.02 (m, 1H); MS m/e 567.4 (M+H)+ and the second eluting enantiomer was Example 130c: 1H NMR (600 MHz, CDCl3) δ ppm 8.16 (s, 1H), 7.75 (d, J=8.7 Hz, 1H), 7.42 (d, J=8.5 Hz, 1H), 7.08 (s, 1H), 4.09-4.05 (m, 4H), 3.89 (dd, J=11.6, 3.9 Hz, 1H), 3.82 (s, 2H), 3.55-3.48 (m, 1H), 3.35-3.30 (m, 1H), 3.14 (s, 3H), 3.06-3.04 (m, 2H), 2.50-2.41 (m, 1H), 2.28-2.27 (m, 3H), 2.25-2.17 (m, 2H), 2.14-2.12 (m, 1H), 2.00-1.98 (m, 1H), 1.81-1.79 (m, 2H), 1.69-1.52 (m, 3H), 1.41-1.38 (m, 1H), 1.04-1.02 (m, 1H); MS m/e 567.4 (M+H)+.

Example 131a: 1-(3-((4-Chloro-2-methoxy-3-((4-(trifluoromethyl)piperidin-1-yl)methyl)quinolin-6-yl)(hydroxy)(6-(trifluoromethyl)pyridin-3-yl)methyl)azetidin-1-yl)ethanone

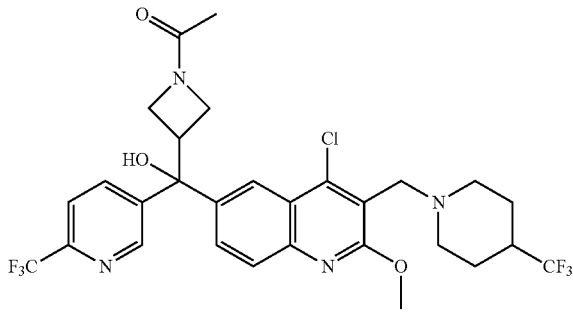 [SMILES: COc1nc2ccc(C(O)(c3ccc(C(F)(F)F)nc3)C3CN(C(C)=O)C3)cc2c(Cl)c1CN1CCC(C(F)(F)F)CC1]

The title compound was prepared analogously to the method described in Example 123a using tert-butyl-3-((4-chloro-2-methoxy-3-((4-(trifluoromethyl)piperidin-1-yl)methyl)quinolin-6-yl)(hydroxy)(6-(trifluoromethyl)pyridin-3-yl)methyl)azetidine-1-carboxylate (Example 181). MS m/e 631 (M+H)+.

1-(3-((4-Chloro-2-methoxy-3-((4-(trifluoromethyl)piperidin-1-yl)methyl)quinolin-6-yl)(hydroxy)(6-(trifluoromethyl)pyridin-3-yl)methyl)azetidin-1-yl)ethanone was purified by chiral SFC (Chiralpak AD-H, 5 rpm, 250×20 mm, mobile phase: 0.3% isopropyl amine, 80% CO2, 20% mixture of ethanol-isopropanol 50/50 v/v). The first eluting enantiomer was Example 131b: 1H NMR (600 MHz, CDCl3, mixture of rotamers) δ ppm 8.77 (d, J=2.1 Hz, 0.6H), 8.71-8.68 (m, 0.4H), 8.18 (d, J=2.1 Hz, 0.4H), 8.08 (d, J=2.1 Hz, 0.6H), 7.95-7.93 (m, 1H), 7.81-7.79 (m, 1H), 7.67-7.61 (m, 1H), 7.49-7.43 (m, 1H), 4.27-4.14 (m, 2H), 4.07 (s, 3H), 4.06-3.99 (m, 2H), 3.82-3.81 (m, 2H), 3.80-3.68 (m, 2H), 3.05-2.97 (m, 2H), 2.25-2.13 (m, 2H), 2.00-1.95 (m, 1H), 1.83 (s, 1.8H), 1.82-1.77 (m, 2H), 1.76 (s, 1.2H), 1.64-1.49 (m, 2H); MS m/e 631 (M+H)+ and the second eluting enantiomer was Example 131c: 1H NMR (600 MHz, CDCl3, mixture of rotamers) δ ppm 8.77 (d, J=2.2 Hz, 0.6H), 8.69 (d, J=2.1 Hz, 0.4H), 8.18 (d, J=2.1 Hz, 0.4H), 8.08 (d, J=2.1 Hz, 0.6H), 7.95-7.93 (m, 1H), 7.81-7.79 (m, 1H), 7.68-7.61 (m, 1H), 7.49-7.46 (m, 1H), 4.28-4.14 (m, 2H), 4.07 (s, 3H), 4.06-3.99 (m, 2H), 3.82-3.81 (m, 2H), 3.81-3.78 (m, 1H), 3.64 (s, 0.4H), 3.55 (s, 0.6H), 3.06-2.99 (m, 2H), 2.24-2.14 (m, 2H), 2.01-1.94 (m, 1H), 1.83 (s, 1.8H), 1.82-1.76 (m, 3.2H), 1.62-1.52 (m, 2H); MS m/e 631 (M+H)+.

Example 132a: (4-Chloro-3-isopropyl-2-methoxyquinolin-6-yl)(2,6-dimethylpyridin-3-yl)(1-methyl-1H-1,2,3-triazol-5-yl)methanol

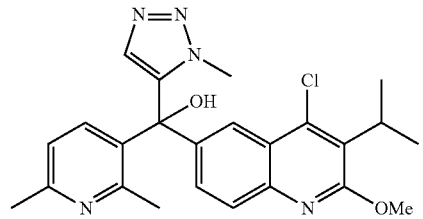 [SMILES: COc1nc2ccc(C(O)(c3ccc(C)nc3C)c3cnnn3C)cc2c(Cl)c1C(C)C]

To a flask containing 6-bromo-4-chloro-3-isopropyl-2-methoxyquinoline (1.0 g, 3.18 mmol, Intermediate 67: step b) was added THF (25 mL) and the solution was cooled to −78° C. n-BuLi (2.5 M in hexanes, 1.5 mL, 3.75 mmol) was added drop wise and the mixture was stirred for 2 minutes at −78° C., then (2,6-dimethylpyridin-3-yl)(1-methyl-1H-1,2,3-triazol-5-yl)methanone (800 mg, 3.7 mmol, Intermediate 11: step b) in 4 mL THF was introduced. After 5 minutes, the reaction mixture was transferred to a 0° C. bath. After 25 minutes, the reaction mixture was quenched with aqueous NH4Cl solution and the aqueous portion was extracted with EtOAc (3×50 mL). The combined organics were washed with brine, dried over MgSO4, filtered and concentrated. Chromatography on silica gel (2% MeOH-DCM increasing to 5% MeOH) provided the title compound as an off white solid. 1H NMR (400 MHz, CDCl3) δ ppm 8.11 (d, J=2.1 Hz, 1H), 7.75 (d, J=8.7 Hz, 1H), 7.30 (dd, J=8.7, 2.2 Hz, 1H), 6.99-6.84 (m, 2H), 4.61 (s, 1H), 4.09 (s, 3H), 3.92 (s, 3H), 3.81 (hept, J=7.1 Hz, 1H), 2.52 (s, 3H), 2.35 (s, 3H), 1.41-1.34 (d, J=7 Hz, 6H). MS (ESI): mass calcd. for Chemical Formula: $C_{24}H_{26}ClN_5O_2$, 451.2, m/z found, 452.1 $[M+H]^+$. (4-Chloro-3-isopropyl-2-methoxyquinolin-6-yl)(2,6-dimethylpyridin-3-yl)(1-methyl-1H-1,2,3-triazol-5-yl)methanol was purified by chiral SFC (Stationary phase: Chiralpak AD 5 μm 250×30 mm, Mobile phase: 80% $CO_2$, 20% MeOH) to give Example 132b as the first compound eluted from the chiral column and Example 132c as the second compound eluted from the chiral column.

Example 133a: (4-Chloro-3-isobutyl-2-methoxyquinolin-6-yl)(2,6-dimethylpyridin-3-yl)(1-methyl-1H-1,2,3-triazol-5-yl)methanol

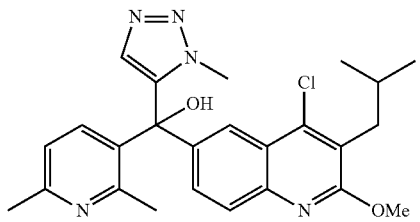 [SMILES: COc1nc2ccc(C(O)(c3ccc(C)nc3C)c3cnnn3C)cc2c(Cl)c1CC(C)C]

To a flask containing 1-methyl-1H-1,2,3-triazole (250 mg, 3.01 mmol) was added THF (20 mL) and the solution was cooled to −45° C. using a $CH_3CN$—$CO_2$ bath. n-BuLi (2.5 M in hexanes, 1.2 mL, 3 mmol) was added dropwise which produced an opaque suspension. The suspension was stirred at −45° C. for 20 minutes, then a homogeneous solution of (4-chloro-3-isobutyl-2-methoxyquinolin-6-yl)(2,6-dimethylpyridin-3-yl)methanone (848 mg, 2.21 mmol, Intermediate 66: step d) in 3 mL THF was introduced at −45° C. After 10 minutes, the reaction vessel was placed in an ice-water bath. The reaction mixture was quenched after 40 minutes with aqueous $NH_4Cl$ solution. The aqueous portion was extracted with EtOAc (4×30 mL) and EtOAc:THF (1:1, 30 mL). The combined organics were washed with brine, dried over $MgSO_4$, filtered and concentrated. Chromatography on silica gel (100% DCM increasing to 5% MeOH-DCM) provided the title compound as an off white amorphous solid. $^1$H NMR (500 MHz, $CDCl_3$) δ ppm 8.07 (d, J=2.2 Hz, 1H), 7.78 (d, J=8.7 Hz, 1H), 7.32 (dd, J=8.7, 2.2 Hz, 1H), 6.99-6.88 (m, 3H), 4.24 (s, 1H), 4.09 (s, 3H), 3.92 (s, 3H), 2.80 (d, J=7.3 Hz, 2H), 2.53 (s, 3H), 2.36 (s, 3H), 2.08 (hept, J=6.8 Hz, 1H), 0.95 (dd, J=6.7, 1.5 Hz, 6H). MS (ESI): mass calcd. for $C_{25}H_{28}ClN_5O_2$, 465.2: m/z found 466.0 $[M+H]^+$. The racemate was separated by chiral chromatography using: Chiralpack OD-H column, 80% heptane/20% ethanol, to give Example 133b as the first compound eluted from the chiral column and Example 133c as the second compound eluted from the chiral column.

Example 134a: (4-Chloro-3-isobutyl-2-methoxyquinolin-6-yl)(1,2-dimethyl-1H-imidazol-5-yl)(1-methyl-1H-1,2,3-triazol-5-yl)methanol

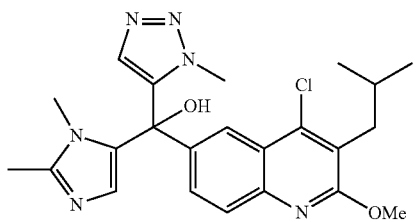 [SMILES: COc1nc2ccc(C(O)(c3cnnn3C)c3cnc(C)n3C)cc2c(Cl)c1CC(C)C]

To a flask containing 1-methyl-1H-1,2,3-triazole (275 mg, 3.31 mmol) was added THF (10 mL) and the solution was cooled to −45° C. using a $CH_3CN$—$CO_2$ bath. n-BuLi (2.5 M in hexanes, 1.4 mL, 3.5 mmol) was added dropwise which afforded an opaque white suspension. The mixture was stirred at −43° C. for 20 minutes, then a homogeneous solution of (4-chloro-3-isobutyl-2-methoxyquinolin-6-yl)(1,2-dimethyl-1H-imidazol-5-yl)methanone (550 mg, 1.48 mmol, Intermediate 65) in 3 mL THF was introduced. After 10 minutes, the reaction flask was then placed in an ice-water bath. The reaction mixture was quenched after 30 minutes with aqueous $NH_4Cl$ solution and the aqueous portion was extracted with EtOAc (4×30 mL) and EtOAc:THF (1:1, 30 mL). The combined organics were washed with brine, dried over $MgSO_4$, filtered and concentrated. Chromatography on silica gel (5% MeOH-DCM increasing to 10% MeOH-DCM) provided the title compound as a tan amorphous solid. $^1$H NMR (400 MHz, $CD_3OD$) δ 8.19 (d, J=2.1 Hz, 1H), 7.85 (d, J=8.7 Hz, 1H), 7.52 (dd, J=8.7, 2.2 Hz, 1H), 7.17 (s, 1H), 6.11 (s, 1H), 4.09 (s, 3H), 3.98 (s, 3H), 3.47 (s, 3H), 2.85 (d, J=7.3 Hz, 2H), 2.37 (s, 3H), 2.11 (hept, J=6.9 Hz, 1H), 0.96 (d, J=6.6 Hz, 6H). MS (ESI): mass calcd. for $C_{23}H_{27}ClN_6O_2$, 454.2, m/z found 455.0 $[M+H]^+$. The racemate was separated by chiral SFC (Stationary phase: CHIRALPAK AD-H 5 rpm, 250×30 mm, Mobile phase: 70% $CO_2$, 30% mixture of MeOH/iPrOH 50/50 v/v (+0.3% $iPrNH_2$)), to give Example 134b as the first compound that eluted from the chiral column and Example 134c as the second compound that eluted from the chiral column.

Example 135a: (4-Chloro-3-cyclopentyl-2-methoxyquinolin-6-yl)(1,2-dimethyl-1H-imidazol-5-yl)(1-methyl-1H-1,2,3-triazol-5-yl)methanol

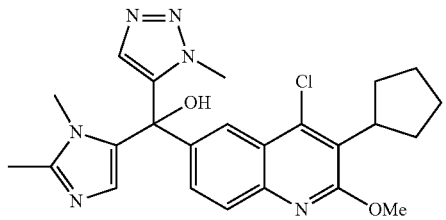 [SMILES: COc1nc2ccc(C(O)(c3cnnn3C)c3cnc(C)n3C)cc2c(Cl)c1C1CCCC1]

To a flask containing 1-methyl-1H-1,2,3-triazole (200 mg, 2.41 mmol) was added THF (15 mL) and the solution was cooled to −45° C. using a $CH_3CN$—$CO_2$ bath. n-BuLi (2.5 M in hexanes, 1.0 mL, 2.5 mmol) was added dropwise which afforded an opaque white suspension. The mixture was stirred at −45° C. for 25 minutes, then a solution of (4-chloro-3-cyclopentyl-2-methoxyquinolin-6-yl)(1,2-dimethyl-1H-imidazol-5-yl)methanone (475 mg, 1.24 mmol, Intermediate 68: step c) in THF (3 mL) was introduced. After 10 minutes, the −45° C. bath was replaced with an ice-water bath. After 30 minutes, the reaction mixture was quenched with aqueous $NH_4Cl$ solution and extracted with EtOAc:THF (2:1, 3×40 mL). The combined organics were washed with brine, dried over $MgSO_4$, filtered and concentrated. Chromatography on silica gel (3% MeOH-DCM increasing to 10% MeOH) provided the compound as a light tan solid. $^1$H NMR (500 MHz, $CDCl_3$) δ ppm 8.24 (d, J=1.9 Hz, 1H), 7.69 (d, J=8.7 Hz, 1H), 7.35 (dd, J=8.7, 2.0 Hz, 2H), 7.07 (s, 1H), 6.01 (s, 1H), 4.07 (s, 3H), 3.90-3.80 (m, 4H containing a 3H singlet at 3.86), 3.32 (s, 3H), 2.06-1.94 (m, 3H), 1.94-1.84 (m, 6H), 1.75-1.69 (m, 2H).

MS (ESI): mass calcd. for $C_{24}H_{27}ClN_6O_2$, 466.2: m/z found 467.1 [M+H]$^+$. The racemate was separated by chiral SFC (Stationary phase: Chiralpak AD-H, 5 μm 250×20 mm, Mobile phase: 70% $CO_2$: 30% EtOH (0.3% iPrNH$_2$)) to give Example 135b as the first compound that eluted from the chiral column and Example 135c as the second compound that eluted from the chiral column.

Example 136a: (4-Chloro-3-cyclopentyl-2-methoxyquinolin-6-yl)(2,6-dimethylpyridin-3-yl)(1-methyl-1H-1,2,3-triazol-5-yl)methanol

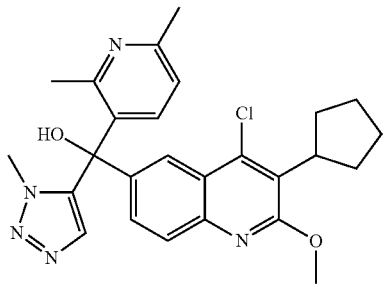 [SMILES: COc1nc2ccc(C(O)(c3ccc(C)nc3C)c3cnnn3C)cc2c(Cl)c1C1CCCC1]

To a flask containing 6-bromo-4-chloro-3-cyclopentyl-2-methoxyquinoline (Intermediate 68: step b, 500 mg, 1.47 mmol) was added THF (12 mL) and the solution was cooled to −78° C. n-BuLi (2.5 M in hexanes, 0.690 mL, 1.73 mmol) was added dropwise and the mixture was stirred for 3 minutes at −78° C. Then, (2,6-dimethylpyridin-3-yl)(1-methyl-1H-1,2,3-triazol-5-yl)methanone (370 mg, 1.71 mmol, in 3 mL THF, Intermediate 11: step b) was introduced. The temperature was raised to 0° C. after 5 minutes. After 25 minutes, the reaction mixture was quenched with aqueous NH$_4$Cl solution and the aqueous portion was extracted with EtOAc (3×50 mL). The combined organics were washed with brine, dried over MgSO$_4$, filtered and concentrated. Chromatography on silica gel (2% MeOH-DCM increasing to 5% MeOH) provided the title compound as an off white amorphous solid. $^1$H NMR (500 MHz, CDCl$_3$) δ ppm 8.09 (s, 1H), 7.77 (d, J=8.7 Hz, 1H), 7.31 (d, J=8.7 Hz, 1H), 6.94 (m, 3H), 4.08 (s, 3H), 3.92 (s, 3H), 3.86 (m, 1H), 2.53 (s, 3H), 2.36 (s, 3H), 2.02-1.84 (m, 5H), 1.74-1.68 (m, 3H). MS (ESI): mass calcd. for $C_{26}H_{28}ClN_5O_2$, 477.2, m/z found 478.1 [M+H]$^+$. The enantiomers were separated by chiral SFC (Stationary phase: Chiralpak AD 5 μm 250×30 mm), Mobile phase: 70% $CO_2$, 30% MeOH (0.3% iPrNH$_2$) to give Example 136b as the first compound eluted from the chiral column and Example 136c as the second compound eluted from the chiral column.

Example 137: (4-Chloro-2-methoxy-3-(2,2,2-trifluoroethyl)quinolin-6-yl)(1,2-dimethyl-1H-imidazol-5-yl)(1-methyl-1H-1,2,3-triazol-5-yl)methanol

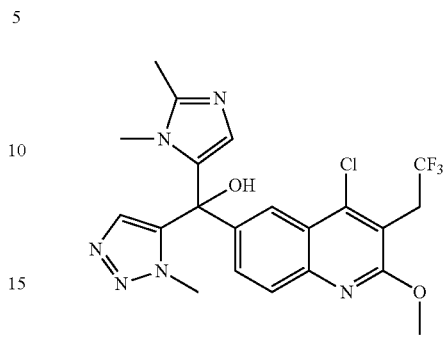

To a flask containing 2,4-dichloro-3-(2,2,2-trifluoroethyl)quinolin-6-yl)(1,2-dimethyl-1H-imidazol-5-yl)(1-methyl-1H-1,2,3-triazol-5-yl)methanol (210 mg, 0.43 mmol, Example 160) was added MeOH (10 mL) followed by solid sodium methoxide (30 mg, 0.54 mmol, 97% purity) at room temperature. The reaction mixture was heated to 50° C. for 15 hours, then cooled to room temperature and concentrated. The crude material was chromatographed directly on silica gel (2% MeOH-DCM increasing to 8% MeOH) which provided a mixture of regioisomeric products. RP-HPLC (acetonitrile/water+0.05% TFA) provided the title compound as an off white solid. $^1$H NMR (500 MHz, CD$_3$OD) δ ppm 8.32 (d, J=1.9 Hz, 1H), 7.96 (d, J=8.8 Hz, 1H), 7.60 (dd, J=8.8, 2.1 Hz, 1H), 7.44 (s, 1H), 6.87 (s, 1H), 4.14 (s, 3H), 4.02-3.89 (m, 5H), 3.69 (s, 3H), 2.65 (s, 3H). MS (ESI): mass calc. for $C_{21}H_{20}ClF_3N_6O_2$, 480.1; found, 481.1 (M+H)$^+$.

Example 138: (2-Chloro-4-methoxy-3-(2,2,2-trifluoroethyl)quinolin-6-yl)(1,2-dimethyl-1H-imidazol-5-yl)(1-methyl-1H-1,2,3-triazol-5-yl)methanol

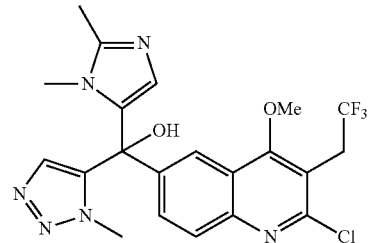 [SMILES: COc1c(CC(F)(F)F)c(Cl)nc2ccc(C(O)(c3cnnn3C)c3cnc(C)n3C)cc12]

To a flask containing 1-methyl-1H-1,2,3-triazole (160 mg, 1.93 mmol) was added THF (12 mL) and the colorless solution was cooled to −43° C. using a CH$_3$CN—CO$_2$ bath. Then, n-BuLi, (2.5 M in hexanes, 0.72 mL, 1.8 mmol) was added which afforded an opaque white suspension. The suspension was stirred at −40° C. for 20 minutes, then a homogeneous solution of (2-chloro-4-methoxy-3-(2,2,2-trifluoroethyl)quinolin-6-yl)(1,2-dimethyl-1H-imidazol-5-yl)methanone (350 mg, 0.88 mmol, Intermediate 59: step c) in 5 mL THF, was introduced at −40° C. The reaction mixture was allowed to warm gradually to 0° C. over 25 minutes, then quenched with aqueous NH$_4$Cl solution. The aqueous portion was extracted with EtOAc (3×35 mL). The combined organics were washed with brine, dried over Na$_2$SO$_4$ and MgSO₄, filtered and concentrated to give a brown solid. Chromatography on silica gel (3% MeOH-DCM increasing to 10% MeOH) provided the title compound as a tan amorphous solid. ¹H NMR (500 MHz, CD₃OD) δ ppm 8.22 (d, J=1.8 Hz, 1H), 8.05 (d, J=8.9 Hz, 1H), 7.70 (dd, J=8.9, 2.0 Hz, 1H), 7.48 (s, 1H), 6.91 (s, 1H), 4.09 (s, 3H), 4.03-3.89 (m, 5H), 3.69 (s, 3H), 2.66 (s, 3H). MS (ESI): mass calcd. for $C_{21}H_{20}ClF_3N_6O_2$, 480.1, found, 481.1 (M+H)⁺.

Example 139a: [2-Azetidin-1-yl-4-chloro-3-(2,2,2-trifluoroethyl)quinolin-6-yl](1-methyl-1H-imidazol-5-yl)[6-(trifluoromethyl)pyridin-3-yl]methanol

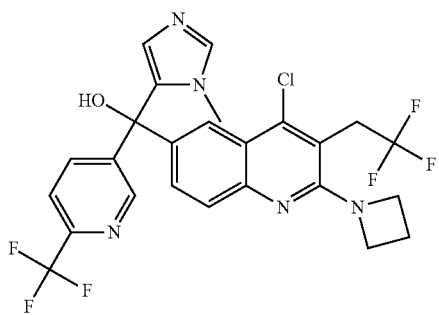 [SMILES: Cn1cncc1C(O)(c1ccc(C(F)(F)F)nc1)c1ccc2nc(N3CCC3)c(CC(F)(F)F)c(Cl)c2c1]

(2,4-Dichloro-3-(2,2,2-trifluoroethyl)quinolin-6-yl)(1-methyl-1H-imidazol-5-yl)(6-(trifluoromethyl)pyridin-3-yl) methanol (150 mg, 0.28 mmol, Example 161), azetidine (56.7 µL, 0.841 mmol), and DMF (7 mL) were combined in a reaction tube, then sealed and heated to 100° C. and maintained at that temperature overnight. The reaction vessel was then cooled to room temperature and contents were transferred to a separatory funnel with EtOAc dilution, then extracted three times with deionized water. The organic phase was separated, dried over MgSO₄, filtered and concentrated under reduced pressure. The crude material was purified via reverse phase chromatography using acetonitrile with ammonium hydroxide in water as eluent to provide the title compound. MS (ESI): mass calcd. for $C_{25}H_{20}ClF_6N_5O$, 555.1; m/z found, 556.6 [M+H]⁺. ¹H NMR (600 MHz, CDCl₃) δ ppm 8.79 (d, J=2.2 Hz, 1H), 8.06 (d, J=2.2 Hz, 1H), 7.85 (dd, J=8.3, 2.2 Hz, 1H), 7.64 (d, J=8.8 Hz, 1H), 7.60 (d, J=8.2 Hz, 1H), 7.44 (dd, J=8.8, 2.2 Hz, 1H), 7.04 (s, 1H), 6.15 (d, J=1.3 Hz, 1H), 4.38-4.29 (m, 4H), 3.86-3.75 (m, 2H), 3.28 (s, 3H), 2.42-2.33 (m, 2H).

[2-Azetidin-1-yl-4-chloro-3-(2,2,2-trifluoroethyl)quinolin-6-yl](1-methyl-1H-imidazol-5-yl)[6-(trifluoromethyl)pyridin-3-yl]methanol was purified via SFC with a Chiralpak AD-H column (5 µm 250×20 mm) using a mobile phase of 80% CO₂ and a 20% methanol to provide two enantiomers. The first eluting enantiomer was Example 139b: MS (ESI): mass calcd. for $C_{25}H_{20}ClF_6N_5O$, 555.1; m/z found, 556 [M+H]⁺; ¹H NMR (600 MHz, CDCl₃) δ ppm 8.79 (d, J=2.2 Hz, 1H), 8.05 (d, J=2.1 Hz, 1H), 7.86 (dd, J=8.3, 2.2 Hz, 1H), 7.69-7.59 (m, 2H), 7.45 (dd, J=8.8, 2.2 Hz, 1H), 7.14 (s, 1H), 6.20 (s, 1H), 4.34 (t, J=7.5 Hz, 4H), 3.81 (q, J=9.8 Hz, 2H), 3.30 (s, 3H), 2.42-2.34 (m, 2H) and the second eluting enantiomer was Example 139c: MS (ESI): mass calcd. for $C_{25}H_{20}ClF_6N_5O$, 555.1; m/z found, 556.2 [M+H]⁺; ¹H NMR (600 MHz, CDCl₃) δ ppm 8.78 (d, J=2.3 Hz, 1H), 8.06 (d, J=2.2 Hz, 1H), 7.86 (dd, J=8.2, 2.2 Hz, 1H), 7.68-7.59 (m, 2H), 7.45 (dd, J=8.8, 2.2 Hz, 1H), 7.11 (s, 1H), 6.17 (s, 1H), 4.34 (t, J=7.5 Hz, 4H), 3.80 (q, J=9.8 Hz, 2H), 3.29 (s, 3H), 2.38 (p, J=7.4 Hz, 2H).

Example 140a: [4-Azetidin-1-yl-2-chloro-3-(2,2,2-trifluoroethyl)quinolin-6-yl](1-methyl-1H-imidazol-5-yl)[6-(trifluoromethyl)pyridin-3-yl]methanol

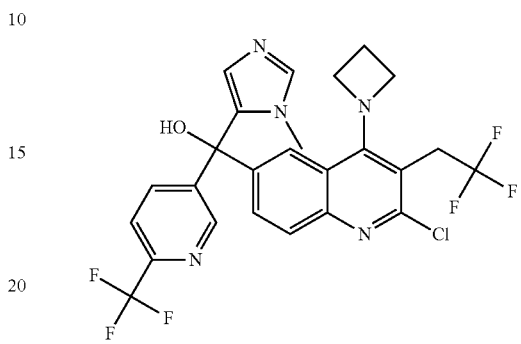

Purification of the crude reaction mixture from the synthesis of [2-azetidin-1-yl-4-chloro-3-(2,2,2-trifluoroethyl) quinolin-6-yl](1-methyl-1H-imidazol-5-yl)[6-(trifluoromethyl)pyridin-3-yl]-methanol (Example 139a) also provided the title compound as a regioisomer. MS (ESI): mass calcd. for $C_{25}H_{20}ClF_6N_5O$, 555.1; m/z found, 556.6 [M+H]⁺. ¹H NMR (600 MHz, CDCl₃) δ ppm 8.77 (d, J=2.2 Hz, 1H), 7.84 (dd, J=8.2, 2.2 Hz, 1H), 7.81-7.76 (m, 1H), 7.69 (d, J=8.8 Hz, 1H), 7.65 (d, J=8.2 Hz, 1H), 7.54 (dd, J=8.9, 2.0 Hz, 1H), 7.07 (s, 1H), 6.13 (d, J=1.3 Hz, 1H), 4.47-4.36 (m, 4H), 3.95-3.82 (m, 2H), 3.30 (s, 3H), 2.43-2.34 (m, 2H).

[4-Azetidin-1-yl-2-chloro-3-(2,2,2-trifluoroethyl)quinolin-6-yl](1-methyl-1H-imidazol-5-yl)[6-(trifluoromethyl) pyridin-3-yl]methanol was purified via SFC with a Chiralpak AD-H column (5 m 250×20 mm) using a mobile phase of 70% CO₂ and a 30% methanol to provide two enantiomers. The first eluting enantiomer was Example 140b: MS (ESI): mass calcd. for $C_{25}H_{20}ClF_6N_5O$, 555.1; m/z found, 556.2 [M+H]⁺; ¹H NMR (600 MHz, CDCl₃) δ ppm 8.79-8.74 (m, 1H), 7.84 (dd, J=8.1, 2.2 Hz, 1H), 7.80 (d, J=2.0 Hz, 1H), 7.69 (d, J=8.8 Hz, 1H), 7.66 (d, J=8.2 Hz, 1H), 7.54 (dd, J=8.8, 2.0 Hz, 1H), 7.11 (s, 1H), 6.14 (s, 1H), 4.47-4.37 (m, 4H), 3.94-3.82 (m, 2H), 3.31 (s, 3H), 2.43-2.32 (m, 2H) and the second eluting enantiomer was Example 140c: MS (ESI): mass calcd. for $C_{25}H_{20}ClF_6N_5O$, 555.1; m/z found, 556 [M+H]⁺; ¹H NMR (600 MHz, CDCl₃) δ ppm 8.77 (d, J=2.2 Hz, 1H), 7.86 (dd, J=8.2, 2.2 Hz, 1H), 7.82-7.78 (m, 1H), 7.74 (d, J=8.7 Hz, 1H), 7.67 (d, J=8.2 Hz, 1H), 7.55 (dd, J=8.9, 2.0 Hz, 1H), 7.18 (s, 1H), 6.21 (s, 1H), 4.48-4.37 (m, 4H), 3.95-3.83 (m, 2H), 3.32 (s, 3H), 2.44-2.35 (m, 2H).

Example 141: [2,4-Dichloro-3-(2,2,2-trifluoroethyl)quinolin-6-yl](2,6-dimethylpyridin-3-yl)(1-methyl-1H-1,2,3-triazol-5-yl)methanol

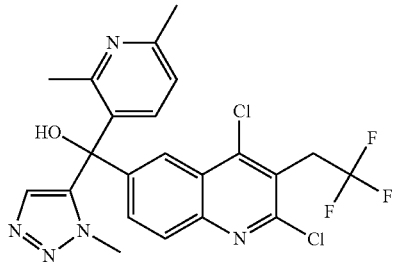 [SMILES: Cc1ccc(C(O)(c2ccc3nc(Cl)c(CC(F)(F)F)c(Cl)c3c2)c2cnnn2C)c(C)n1]

6-Bromo-2,4-dichloro-3-(2,2,2-trifluoroethyl)quinoline (1.00 g, 2.79 mmol, Intermediate 69: step d), (2,6-dimethylpyridin-3-yl)(1-methyl-1H-1,2,3-triazol-5-yl)methanone (0.602 g, 2.79 mmol, Intermediate 11: step b) were dissolved in THF (30 mL) in a dry round bottom flask under an $N_2$ atmosphere, then cooled to −40° C. in dry ice acetone bath. n-BuLi (1.6 M in hexanes, 1.74 mL, 2.79 mmol) was then added dropwise via syringe over approximately 2 minutes. The contents were stirred at −40° C. for approximately 45 minutes, then the dry ice bath was removed and replaced with an ice water bath and the reaction was stirred at that temperature for approximately 45 minutes. The reaction was quenched with a saturated, aqueous $NH_4Cl$, then transferred to a separatory funnel with EtOAc. The organic phase was separated, then the aqueous layer was back extracted twice with EtOAc, then the combined organic phases were dried over $MgSO_4$, filtered and concentrated under reduced pressure. The crude product was purified by flash column chromatography (silica gel, 0-50% DCM/(10% of a 2 M $NH_3$ MeOH in DCM)) to afford the title compound. MS (ESI): mass calcd. for $C_{22}H_{18}Cl_2F_3N_5O$, 495.1; m/z found, 496.3 [M+H]$^+$. $^1$H NMR (400 MHz, CDCl$_3$) δ ppm 8.27 (dd, J=2.1, 0.6 Hz, 1H), 8.03 (dd, J=8.8, 0.6 Hz, 1H), 7.60 (dd, J=8.9, 2.1 Hz, 1H), 6.97 (d, J=8.1 Hz, 1H), 6.93 (d, J=8.1 Hz, 1H), 6.88 (s, 1H), 4.13-4.01 (m, 2H), 3.94 (s, 3H), 2.55 (s, 3H), 2.38 (s, 3H).

Example 142a: [2-Azetidin-1-yl-4-chloro-3-(2,2,2-trifluoroethyl)quinolin-6-yl](2,6-dimethylpyridin-3-yl)(1-methyl-1H-1,2,3-triazol-5-yl)methanol

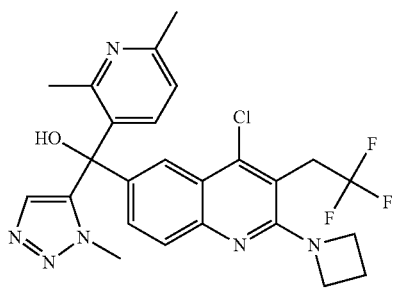 [SMILES: Cc1ccc(C(O)(c2ccc3nc(N4CCC4)c(CC(F)(F)F)c(Cl)c3c2)c2cnnn2C)c(C)n1]

[2,4-Dichloro-3-(2,2,2-trifluoroethyl)quinolin-6-yl](2,6-dimethylpyridin-3-yl)(1-methyl-1H-1,2,3-triazol-5-yl)methanol (200 mg, 0.28 mmol, Example 141), azetidine (82 μL, 1.2 mmol), and DMF (2 mL) were combined in a reaction tube, then sealed and heated to 100° C. and maintained at that temperature overnight. The reaction vessel was then cooled to room temperature and contents were transferred to a separatory funnel with EtOAc dilution, then extracted three times with deionized water. The organic phase was separated, dried over $MgSO_4$, filtered and concentrated under reduced pressure. The crude material was purified via reverse phase chromatography using acetonitrile with ammonium hydroxide in water as eluent to provide the title compound. MS (ESI): mass calcd. for $C_{25}H_{24}ClF_3N_6O$, 516.2; m/z found, 517.5 [M+H]$^+$; $^1$H NMR (600 MHz, CDCl$_3$) δ ppm 8.00 (d, J=2.2 Hz, 1H), 7.64 (d, J=8.8 Hz, 1H), 7.30 (dd, J=8.8, 2.2 Hz, 1H), 6.96 (d, J=8.1 Hz, 1H), 6.90 (d, J=8.1 Hz, 1H), 6.83 (s, 1H), 4.35 (t, J=7.5 Hz, 4H), 3.88 (s, 3H), 3.84-3.76 (m, 2H), 2.49 (s, 3H), 2.43-2.35 (m, 2H), 2.31 (s, 3H).

[2-Azetidin-1-yl-4-chloro-3-(2,2,2-trifluoroethyl)quinolin-6-yl](2,6-dimethylpyridin-3-yl)(1-methyl-1H-1,2,3-triazol-5-yl)methanol was purified via SFC with a Chiralpak AD-H column (5 m 250×20 mm) using a mobile phase of 75% $CO_2$ and a 25% methanol to provide two enantiomers. The first eluting enantiomer was Example 142b MS (ESI): mass calcd. for $C_{25}H_{24}ClF_3N_6O$, 516.2; m/z found, 517.6 [M+H]$^+$; $^1$H NMR (600 MHz, CDCl$_3$) δ ppm 7.99 (d, J=2.2 Hz, 1H), 7.64 (d, J=8.8 Hz, 1H), 7.29 (dd, J=8.8, 2.2 Hz, 1H), 6.97 (d, J=8.0 Hz, 1H), 6.91 (d, J=8.1 Hz, 1H), 6.86 (s, 1H), 4.39-4.32 (m, 4H), 3.90 (s, 3H), 3.84-3.75 (m, 2H), 2.50 (s, 3H), 2.43-2.36 (m, 2H), 2.33 (s, 3H) and the second eluting enantiomer was Example 142c: MS (ESI): mass calcd. for $C_{25}H_{24}ClF_3N_6O$, 516.2; m/z found, 517.6 [M+H]$^+$; $^1$H NMR (600 MHz, CDCl$_3$) δ ppm 7.99 (d, J=2.2 Hz, 1H), 7.64 (d, J=8.8 Hz, 1H), 7.29 (dd, J=8.8, 2.2 Hz, 1H), 6.97 (d, J=8.1 Hz, 1H), 6.92 (d, J=8.1 Hz, 1H), 6.86 (s, 1H), 4.39-4.32 (m, 4H), 3.90 (s, 3H), 3.84-3.76 (m, 2H), 2.51 (s, 3H), 2.43-2.35 (m, 2H), 2.33 (s, 3H).

Example 143a: [4-Chloro-2-methoxy-3-(2,2,2-trifluoroethyl)quinolin-6-yl](2,6-dimethylpyridin-3-yl)(1-methyl-1H-1,2,3-triazol-5-yl)methanol

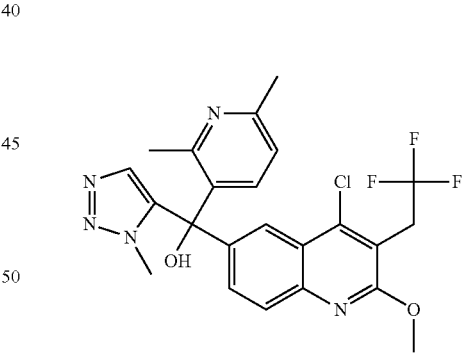

[2,4-Dichloro-3-(2,2,2-trifluoroethyl)quinolin-6-yl](2,6-dimethylpyridin-3-yl)(1-methyl-1H-1,2,3-triazol-5-yl)methanol (100 mg, 0.202 mmol, Example 141), toluene (2 mL), and sodium methoxide (109 mg, 2.02 mmol) were combined in a round bottom flask equipped with a stirbar and condenser under an $N_2$ atmosphere. The reaction solution was heated to 60° C. and maintained at that temperature for 4 hours. The reaction was cooled to room temperature and contents were transferred to a separatory funnel with EtOAc dilution and extracted with a saturated, aqueous $NH_4Cl$ solution. The aqueous layer was separated, neutralized with 10% aqueous HCl, then extracted twice with ethyl acetate. The combined organic phases were dried over MgSO₄, filtered and concentrated under reduced pressure. The crude material was purified via reverse phase chromatography using acetonitrile with ammonium hydroxide in water as eluent to afford the title compound. MS (ESI): mass calcd. for C₂₃H₂₁ClF₃N₅O₂, 491.1; m/z found, 492.5 [M+H]⁺; ¹H NMR (600 MHz, CDCl₃) δ ppm 8.19 (d, J=2.2 Hz, 1H), 7.78 (d, J=8.7 Hz, 1H), 7.39 (dd, J=8.7, 2.2 Hz, 1H), 6.96-6.89 (m, 2H), 6.74 (s, 1H), 4.11 (s, 3H), 3.91 (s, 3H), 3.83-3.74 (m, 2H), 2.47 (s, 3H), 2.29 (s, 3H). [4-Chloro-2-methoxy-3-(2,2,2-trifluoroethyl)quinolin-6-yl] (2,6-dimethylpyridin-3-yl)(1-methyl-1H-1,2,3-triazol-5-yl) methanol was purified via SFC with a Chiralpak AD-H column (5 μm 250×20 mm) using a mobile phase of 82% CO₂ and an 18% mixture of (MeOH/iPrOH 50/50 v/v (+0.3% iPrNH₂)) to provide two enantiomers. The first eluting enantiomer was Example 143b: MS (ESI): mass calcd. for C₂₃H₂₁ClF₃N₅O₂, 491.1; m/z found, 492.1 [M+H]⁺; ¹H NMR (600 MHz, CDCl₃) δ 8.19 (d, J=2.1 Hz, 1H), 7.76 (d, J=8.7 Hz, 1H), 7.36 (dd, J=8.8, 2.2 Hz, 1H), 6.94 (s, 2H), 6.76 (s, 1H), 4.11 (s, 3H), 3.95 (s, 3H), 3.83-3.71 (m, 2H), 2.51 (s, 3H), 2.32 (s, 3H) and the second eluting enantiomer was Example 143c: MS (ESI): mass calcd. for C₂₃H₂₁ClF₃N₅O₂, 491.1; m/z found, 492.1 [M+H]⁺; ¹H NMR (600 MHz, CDCl₃) δ ppm 8.19 (d, J=2.1 Hz, 1H), 7.76 (d, J=8.7 Hz, 1H), 7.36 (dd, J=8.8, 2.2 Hz, 1H), 6.94 (s, 2H), 6.76 (s, 1H), 4.11 (s, 3H), 3.95 (s, 3H), 3.83-3.71 (m, 2H), 2.51 (s, 3H), 2.32 (s, 3H).

Example 144: [2,4-Dichloro-3-(2,2,2-trifluoroethyl)quinolin-6-yl][bis(1,2-dimethyl-1H-imidazol-5-yl)]methanol

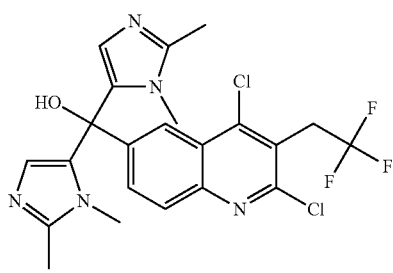 [SMILES: Cc1ncc(C(O)(c2ccc3nc(Cl)c(CC(F)(F)F)c(Cl)c3c2)c2cnc(C)n2C)n1C]

5-Bromo-1,2-dimethyl-1H-imidazole (359 mg, 1.85 mmol) and THF (10 mL) were combined in a dry round bottom flask under an N₂ atmosphere and cooled to −78° C. in a dry ice acetone bath. n-BuLi (1.6 M in hexanes, 1.74 mL, 2.79 mmol) was then added dropwise via syringe over approximately 2 minutes and the contents were allowed to stir at −78° C. for an additional 10 minutes. 2,4-Dichloro-3-(2,2,2-trifluoroethyl)quinoline-6-carboxylate (250 mg, 0.74 mmol, Intermediate 71) in THF (5 mL) was then cannulated into the reaction vessel and the reaction was stirred at −78° C. for 10 minutes. The dry ice bath was removed and replaced by an ice water bath and the reaction continued for approximately 30 minutes. The reaction was quenched with a saturated, aqueous NH₄Cl solution, then transferred to a separatory funnel with EtOAc. The organic phase was separated and the aqueous layer was back extracted with EtOAc, then the combined organic phases were dried over MgSO₄, filtered and concentrated under reduced pressure. The crude material was purified via reverse phase chromatography using acetonitrile with ammonium hydroxide in water as eluent. The fractions from the purification containing the desired product were transferred to a separatory funnel with EtOAc and extracted with a saturated, aqueous NaHCO₃ solution. The aqueous layer was separated, extracted with EtOAc, then the combined organic phases were dried over MgSO₄, filtered and concentrated under reduced pressure to afford the title compound. MS (ESI): mass calcd. for C₂₂H₂₀Cl₂F₃N₅O, 497.1; m/z found, 498.1 [M+H]⁺; ¹H NMR (400 MHz, CDCl₃) δ ppm 8.38 (s, 1H), 7.90-7.81 (m, 1H), 7.66 (d, J=9.0 Hz, 1H), 6.02 (s, 2H), 4.12-3.99 (m, 2H), 3.41 (d, J=2.6 Hz, 6H), 2.24 (d, J=2.9 Hz, 6H).

Example 145: [4-Chloro-2-methoxy-3-(2,2,2-trifluoroethyl)quinolin-6-yl][bis(1,2-dimethyl-1H-imidazol-5-yl)]methanol

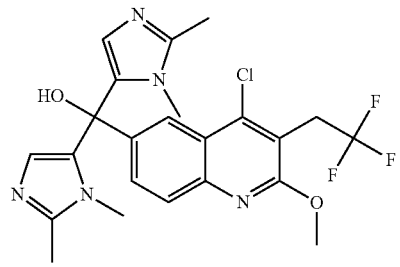

[2,4-Dichloro-3-(2,2,2-trifluoroethyl)quinolin-6-yl][bis(1,2-dimethyl-1H-imidazol-5-yl)]methanol (150 mg, 0.202 mmol, Example 144), toluene (2 mL), and sodium methoxide (163 mg, 3.01 mmol) were combined in a round bottom flask equipped with a stirbar and condenser under an N₂ atmosphere. The reaction solution was heated to 60° C. and maintained at that temperature for 4 hours. The reaction was then cooled to room temperature and the contents were transferred to a separatory funnel with EtOAc dilution, then extracted with a saturated, aqueous NH₄Cl solution. The aqueous layer was separated, neutralized then extracted twice with ethyl acetate. The combined organic layers were then dried over MgSO₄, filtered and concentrated under reduced pressure. The crude material was purified via reverse phase chromatography using acetonitrile with ammonium hydroxide in water as eluent to provide the title compound. MS (ESI): mass calcd. for C₂₃H₂₃ClF₃N₅O₂, 493.1; m/z found, 494.2 [M+H]⁺; ¹H NMR (600 MHz, CDCl₃) δ ppm 8.35-8.22 (m, 1H), 7.68 (d, J=8.7 Hz, 1H), 7.51-7.43 (m, 1H), 6.04 (s, 2H), 4.12 (s, 3H), 3.81 (q, J=10.0 Hz, 2H), 3.41 (s, 6H), 2.25 (s, 6H).

Example 146: (4-Chloro-2-methoxy-3-{[4-(trifluoromethyl)piperidin-1-yl]carbonyl}quinolin-6-yl)(1-methyl-1H-imidazol-5-yl)[6-(trifluoromethyl)pyridin-3-yl]methanol

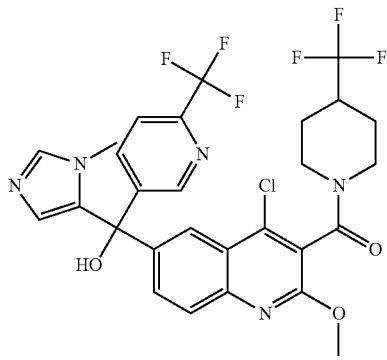 [SMILES: COc1nc2ccc(C(O)(c3ccc(C(F)(F)F)nc3)c3cncn3C)cc2c(Cl)c1C(=O)N1CCC(C(F)(F)F)CC1]

To a solution of (4-chloro-6-iodo-2-methoxyquinolin-3-yl)(4-(trifluoromethyl)piperidin-1-yl)methanone (125 mg, 0.25 mmol, Intermediate 35: step f) and (1-methyl-1H-imidazol-5-yl)(6-(trifluoromethyl)pyridin-3-yl)methanone (64 mg, 0.25 mmol, Intermediate 10: step c) in THF (6.9 mL) at −78° C. was added n-BuLi (1.85 M in hexanes, 136 µL, 0.25 mmol) dropwise. The resulting dark yellow solution was stirred at −78° C. for 15 minutes, then warmed to 0° C. and stirred for an additional 30 minutes. Saturated aqueous NH$_4$Cl (8 mL), water (20 mL) and EtOAc (20 mL) were added and the layers separated. The aqueous layer was further extracted with EtOAc (20 mL). The organics were combined, dried (Na$_2$SO$_4$), filtered and concentrated to dryness to afford a yellow oil. The crude material was purified by FCC (0.5-7.5% MeOH/DCM) followed by reverse-phase HPLC (acetonitrile/water+NH$_4$OH) to provide the title compound as a white solid. $^1$H NMR (500 MHz, CDCl$_3$) δ ppm 8.82-8.78 (m, 1H), 8.25-8.06 (m, 1H), 7.96-7.91 (m, 1H), 7.88-7.82 (m, 1H), 7.71-7.66 (m, 1H), 7.66-7.56 (m, 1H), 7.45-7.36 (m, 1H), 6.44 (s, 1H), 4.98-4.90 (m, 1H), 4.31-4.11 (m, 1H), 4.11-4.07 (m, 3H), 3.56-3.48 (m, 1H), 3.40-3.35 (m, 3H), 3.14-3.04 (m, 1H), 2.90-2.82 (m, 1H), 2.38-2.25 (m, 1H), 2.11-2.02 (m, 1H), 1.88-1.78 (m, 1H), 1.75-1.65 (m, 1H). MS (ESI): mass calcd. for C$_{28}$H$_{24}$ClF$_6$N$_5$O$_3$, 627.1; m/z found, 628.0 [M+H]$^+$.

Example 147: 4-Chloro-N-(cyclopropylmethyl)-6-[(2,6-dimethylpyridin-3-yl)(hydroxy)(1-methyl-1H-1,2,3-triazol-5-yl)methyl]-2-methoxyquinoline-3-carboxamide

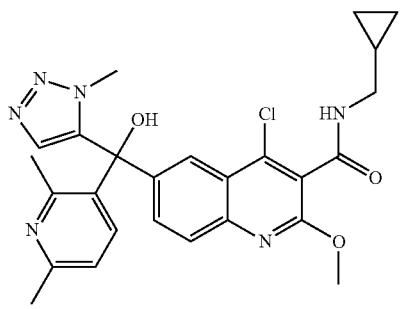 [SMILES: COc1nc2ccc(C(O)(c3ccc(C)nc3C)c3cnnn3C)cc2c(Cl)c1C(=O)NCC1CC1]

A mixture of 4-chloro-6-((2,6-dimethylpyridin-3-yl)(hydroxy)(1-methyl-1H-1,2,3-triazol-5-yl)methyl)-2-methoxyquinoline-3-carboxylic acid (177 mg, 0.35 mmol, Intermediate 37), EDCI (103 mg, 0.53 mmol) and HOBt (72 mg, 0.53 mmol) in DMF (3.9 mL) was stirred at room temperature for 15 minutes. Then, cyclopropanemethylamine (154 µL, 1.72 mmol) was added and the reaction mixture stirred at room temperature for 1 hour. The mixture was concentrated to dryness and the residue partitioned between DCM (15 mL) and saturated aqueous NaHCO$_3$ (15 mL). The layers were separated and the aqueous further extracted with DCM (25 mL). The organics were combined, dried (Na$_2$SO$_4$), filtered and concentrated to dryness to afford an orange oil. The crude material was purified by FCC (0.5-7.5% MeOH/DCM) followed by reverse phase HPLC (acetonitrile/water+NH$_4$OH) to provide the title compound as a white solid. $^1$H NMR (400 MHz, CDCl$_3$) δ ppm 8.25 (d, J=2.1 Hz, 1H), 7.69 (d, J=8.8 Hz, 1H), 7.43 (s, 1H), 7.13-7.10 (m, 1H), 6.96-6.86 (m, 2H), 6.54 (s, 1H), 5.21 (s, 1H), 4.15 (s, 3H), 3.96 (s, 3H), 3.64-3.57 (m, 1H), 3.39-3.31 (m, 1H), 2.53 (s, 3H), 2.28 (s, 3H), 1.25-1.18 (m, 1H), 0.68-0.63 (m, 2H), 0.42-0.38 (m, 2H). MS (ESI): mass calcd. for C$_{26}$H$_{27}$ClN$_6$O$_3$, 506.2; m/z found, 507.1 [M+H]$^+$.

Example 148: 4-Chloro-6-[(2,6-dimethylpyridin-3-yl)(hydroxy)(1-methyl-1H-1,2,3-triazol-5-yl)methyl]-2-methoxy-N,N-dimethylquinoline-3-carboxamide

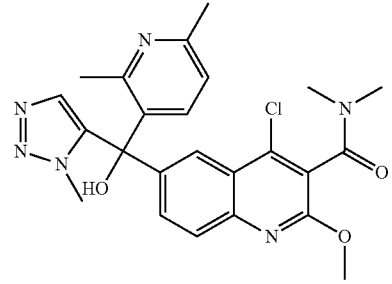 [SMILES: COc1nc2ccc(C(O)(c3ccc(C)nc3C)c3cnnn3C)cc2c(Cl)c1C(=O)N(C)C]

A mixture of 4-chloro-6-((2,6-dimethylpyridin-3-yl)(hydroxy)(1-methyl-1H-1,2,3-triazol-5-yl)methyl)-2-methoxyquinoline-3-carboxylic acid (226 mg, 0.45 mmol, Intermediate 37), EDCI (132 mg, 0.67 mmol) and HOBt (92 mg, 0.67 mmol) in DMF (4.5 mL) was stirred at room temperature for 15 minutes. Then, dimethylamine (2 M in THF, 1.1 mL, 2.2 mmol) was added and the reaction mixture stirred at room temperature for 2 hours. The mixture was concentrated to dryness and the residue partitioned between DCM (20 mL) and saturated aqueous NaHCO$_3$ (20 mL). The layers were separated and the aqueous further extracted with DCM (30 mL). The organics were combined, dried (Na$_2$SO$_4$), filtered and concentrated to dryness to afford an orange oil. The crude material was purified by FCC (0.5-7.5% MeOH/DCM) to provide the title compound as a white oil.

$^1$H NMR (500 MHz, CDCl$_3$, 1:1 mixture of isomers) δ ppm 8.15-8.03 (m, 1H), 7.88-7.83 (m, 1H), 7.51-7.37 (m, 1H), 6.97 (d, J=2.0 Hz, 1H), 6.96-6.93 (m, 2H), 4.11 (s, 3H), 3.96-3.91 (m, 3H), 3.67-3.61 (m, 1H), 3.20-3.17 (m, 3H), 2.92-2.90 (m, 3H), 2.55 (s, 3H), 2.40-2.37 (m, 3H). MS (ESI): mass calcd. for C$_{24}$H$_{25}$ClN$_6$O$_3$, 480.2; m/z found, 481.2 [M+H]$^+$.

Example 149: 4-Chloro-N-cyclopropyl-6-{hydroxy(1-methyl-1H-imidazol-5-yl)[6-(trifluoromethyl)pyridin-3-yl]methyl}-2-methoxyquinoline-3-carboxamide

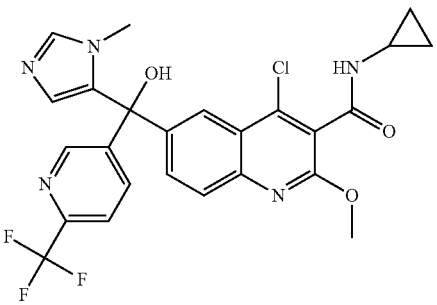 [SMILES: COc1nc2ccc(C(O)(c3ccc(C(F)(F)F)nc3)c3cncn3C)cc2c(Cl)c1C(=O)NC1CC1]

A mixture of 4-chloro-6-(hydroxy(1-methyl-1H-imidazol-5-yl)(6-(trifluoromethyl)pyridin-3-yl)methyl)-2-methoxyquinoline-3-carboxylic acid (74 mg, 0.15 mmol, Intermediate 36), EDCI (44 mg, 0.23 mmol) and HOBt (31 mg, 0.23 mmol) in DMF (1.5 mL) was stirred at room temperature for 15 minutes. Then, cyclopropylamine (52 μL, 0.74 mmol) was added and the reaction mixture stirred at room temperature for 1.5 hours. The mixture was concentrated to dryness and the residue partitioned between DCM (10 mL) and saturated aqueous NaHCO₃ (10 mL). The layers were separated and the aqueous further extracted with DCM (15 mL). The organics were combined, dried (Na₂SO₄), filtered and concentrated to dryness to afford an orange oil. The crude material was purified by FCC (0.5-7.5% MeOH/DCM) followed by reverse-phase HPLC (acetonitrile/water+NH₄OH) to provide the title compound as a white solid. $^1$H NMR (500 MHz, CDCl₃) δ ppm 8.79-8.65 (m, 1H), 8.33-8.24 (m, 1H), 7.96-7.91 (m, 1H), 7.70-7.60 (m, 2H), 7.40-7.34 (m, 1H), 7.01-6.95 (m, 1H), 6.15 (s, 1H), 5.91 (s, 1H), 4.13-4.09 (m, 3H), 3.40-3.33 (m, 3H), 3.07-3.00 (m, 1H), 0.99-0.91 (m, 2H), 0.79-0.73 (m, 2H). MS (ESI): mass calcd. for $C_{25}H_{21}ClF_3N_5O_3$, 531.1; m/z found, 532.0 [M+H]⁺.

Example 150: 4-Chloro-N-cyclopropyl-6-[(2,6-dimethylpyridin-3-yl)(hydroxy)(1-methyl-1H-1,2,3-triazol-5-yl)methyl]-2-methoxyquinoline-3-carboxamide

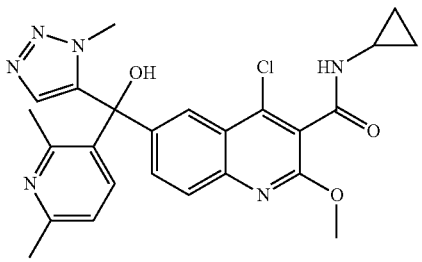 [SMILES: COc1nc2ccc(C(O)(c3ccc(C)nc3C)c3cnnn3C)cc2c(Cl)c1C(=O)NC1CC1]

A mixture of 4-chloro-6-((2,6-dimethylpyridin-3-yl)(hydroxy)(1-methyl-1H-1,2,3-triazol-5-yl)methyl)-2-methoxyquinoline-3-carboxylic acid (144 mg, 0.32 mmol, Intermediate 37), EDCI (93 mg, 0.48 mmol) and HOBt (65 mg, 0.48 mmol) in DMF (3.2 mL) was stirred at room temperature for 15 minutes. Then, cyclopropylamine (110 μL, 1.55 mmol) was added and the reaction mixture stirred at room temperature for 1 hour. The mixture was concentrated to dryness and the residue partitioned between DCM (10 mL) and saturated aqueous NaHCO₃ (10 mL). The layers were separated and the aqueous further extracted with DCM (15 mL). The organics were combined, dried (Na₂SO₄), filtered and concentrated to dryness to afford an orange oil. The crude material was purified by FCC (0.5-7.5% MeOH/DCM) followed by reverse-phase HPLC (acetonitrile/water+NH₄OH) to provide the title compound as a white solid. $^1$H NMR (500 MHz, CDCl₃) δ ppm 8.22-8.16 (m, 1H), 7.60 (d, J=8.7 Hz, 1H), 7.20-7.16 (m, 1H), 7.10 (s, 1H), 6.96-6.93 (m, 1H), 6.90-6.86 (m, 1H), 6.59 (s, 1H), 4.83 (s, 1H), 4.14-4.12 (m, 3H), 3.96-3.95 (m, 3H), 3.08-3.02 (m, 1H), 2.56-2.53 (m, 3H), 2.40-2.29 (m, 3H), 1.00-0.94 (m, 2H), 0.82-0.77 (m, 2H). MS (ESI): mass calcd. for $C_{25}H_{25}ClN_6O_3$, 492.2; m/z found, 493.2 [M+H]⁺.

Example 151: [4-Chloro-2-methoxy-3-(pyrrolidin-1-ylcarbonyl)quinolin-6-yl](2,6-dimethylpyridin-3-yl)(1-methyl-1H-1,2,3-triazol-5-yl)methanol

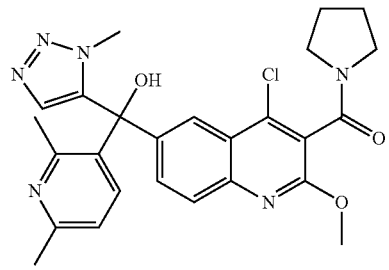 [SMILES: COc1nc2ccc(C(O)(c3ccc(C)nc3C)c3cnnn3C)cc2c(Cl)c1C(=O)N1CCCC1]

n-BuLi (1.85 M in hexanes, 316 μL, 0.58 mmol) was added dropwise to a stirred solution of (6-bromo-4-chloro-2-methoxyquinolin-3-yl)(pyrrolidin-1-yl)methanone (216 mg, 0.58 mmol, Intermediate 34: step e) in THF (7 mL) at −78° C. under nitrogen. After stirring for 5 minutes at −78° C., the mixture was treated dropwise with a solution of (2,6-dimethylpyridin-3-yl)(1-methyl-1H-1,2,3-triazol-5-yl)methanone (126 mg, 0.58 mmol, Intermediate 11: step b) in THF (5 mL). The flask was rinsed with THF (2 mL) and that THF was added to the reaction. The solution was stirred at −78° C. for 15 minutes, then warmed to 0° C. and stirred for an additional 30 minutes. Saturated aqueous NH₄Cl (7 mL), water (25 mL) and EtOAc (30 mL) were added and the layers separated. The aqueous layer was further extracted with EtOAc (30 mL). The organics were combined, dried (Na₂SO₄), filtered and concentrated to dryness to afford a light yellow oil. The crude material was purified by FCC (0.5-7.5% MeOH/DCM) followed by reverse phase HPLC (acetonitrile/water+NH₄OH) to provide the title compound as a white solid. $^1$H NMR (400 MHz, CDCl₃, 1:1 mixture of isomers) δ ppm 8.17-8.06 (m, 1H), 7.86-7.80 (m, 1H), 7.50-7.35 (m, 1H), 6.98-6.93 (m, 3H), 4.29-4.13 (m, 1H), 4.10 (s, 3H), 3.93-3.91 (m, 3H), 3.75-3.57 (m, 2H), 3.24-3.18 (m, 2H), 2.55-2.53 (m, 3H), 2.38-2.34 (m, 3H), 2.03-1.90 (m, 4H). MS (ESI): mass calcd. for $C_{26}H_{27}ClN_6O_3$, 506.2; m/z found, 507.1 [M+H]⁺.

Example 152: 4-Chloro-6-[(2,6-dimethylpyridin-3-yl)(hydroxy)(1-methyl-1H-1,2,3-triazol-5-yl)methyl]-2-methoxy-N-(2,2,2-trifluoroethyl)quinoline-3-carboxamide

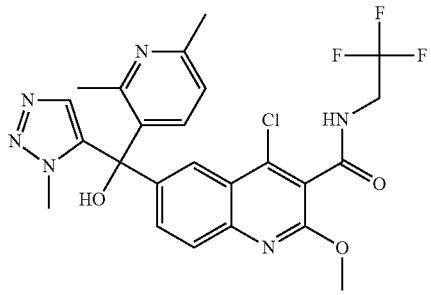 [SMILES: COc1nc2ccc(C(O)(c3ccc(C)nc3C)c3cnnn3C)cc2c(Cl)c1C(=O)NCC(F)(F)F]

To a mixture of 4-chloro-6-((2,6-dimethylpyridin-3-yl)(hydroxy)(1-methyl-1H-1,2,3-triazol-5-yl)methyl)-2-methoxyquinoline-3-carboxylic acid (158 mg, 0.31 mmol, Intermediate 37), HOBt (64 mg, 0.47 mmol) and triethylamine (213 μL, 1.54 mmol) in DMF (3.1 mL) was added 2,2,2-trifluoroethylamine-HCl (213 mg, 1.54 mmol). The resulting mixture was stirred at room temperature for 15 minutes, then EDCI (92 mg, 0.47 mmol) was added and the mixture stirred at room temperature for an additional 35 minutes. The reaction was concentrated to dryness and the residue partitioned between DCM (15 mL) and saturated aqueous NaHCO$_3$ (15 mL). The layers were separated and the aqueous extracted with DCM (25 mL). The organics were combined, dried (Na$_2$SO$_4$), filtered and concentrated to dryness to afford a yellow oil. The crude material was purified by FCC (0.5-7.5% MeOH/DCM) followed by reverse phase HPLC (acetonitrile/water+NH$_4$OH) to provide the title compound as a white solid. $^1$H NMR (400 MHz, CDCl$_3$) δ ppm 8.25 (d, J=2.2 Hz, 1H), 7.66 (d, J=8.8 Hz, 1H), 7.60 (s, 1H), 7.17 (dd, J=8.8, 2.2 Hz, 1H), 6.97-6.85 (m, 2H), 6.53 (s, 1H), 5.10 (s, 1H), 4.50-4.39 (m, 1H), 4.14 (s, 3H), 4.10-4.00 (m, 1H), 3.96 (s, 3H), 2.54 (s, 3H), 2.28 (s, 3H). MS (ESI): mass calcd. for C$_{24}$H$_{22}$ClF$_3$N$_6$O$_3$, 534.1; m/z found, 535.0 [M+H]$^+$.

Example 153: {4-Chloro-3-[(3,3-difluoroazetidin-1-yl)carbonyl]-2-methoxyquinolin-6-yl}(2,6-dimethylpyridin-3-yl)(1-methyl-1H-1,2,3-triazol-5-yl)methanol

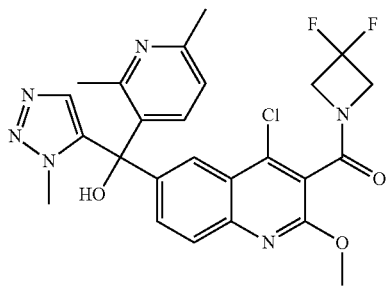 [SMILES: COc1nc2ccc(C(O)(c3ccc(C)nc3C)c3cnnn3C)cc2c(Cl)c1C(=O)N1CC(F)(F)C1]

To a mixture of 4-chloro-6-((2,6-dimethylpyridin-3-yl)(hydroxy)(1-methyl-1H-1,2,3-triazol-5-yl)methyl)-2-methoxyquinoline-3-carboxylic acid (177 mg, 0.35 mmol, Intermediate 37), HOBt (72 mg, 0.53 mmol) and triethylamine (238 μL, 1.72 mmol) in DMF (3.5 mL) was added 3,3-difluoroazetidine-HCl (235 mg, 1.72 mmol). The resulting mixture was stirred at room temperature for 15 minutes, then EDCI (103 mg, 0.53 mmol) was added and the mixture stirred at room temperature for an additional 17 hours. The reaction was concentrated to dryness and the residue partitioned between DCM (10 mL) and saturated aqueous NaHCO$_3$ (10 mL). The layers were separated and the aqueous extracted with DCM (15 mL). The organics were combined, dried (Na$_2$SO$_4$), filtered and concentrated to dryness to afford an orange oil. The crude material was purified by FCC (0.5-7.5% MeOH/DCM) followed by reverse-phase HPLC (acetonitrile/water+NH$_4$OH) to provide the title compound as a white solid. $^1$H NMR (500 MHz, CDCl$_3$) δ ppm 8.14-8.11 (m, 1H), 7.86 (d, J=8.8 Hz, 1H), 7.50-7.46 (m, 1H), 6.97-6.92 (m, 3H), 4.62-4.55 (m, 2H), 4.31-4.24 (m, 2H), 4.13 (s, 3H), 3.94 (s, 3H), 3.74 (s, 1H), 2.55 (s, 3H), 2.38 (s, 3H). MS (ESI): mass calcd. for C$_{25}$H$_{23}$ClF$_2$N$_6$O$_3$, 528.1; m/z found, 529.0 [M+H]$^+$.

Example 154a: [4-Chloro-2-methoxy-3-(tetrahydro-2H-pyran-4-ylmethoxy)quinolin-6-yl](2,6-dimethylpyridin-3-yl)(1-methyl-1H-1,2,3-triazol-5-yl)methanol

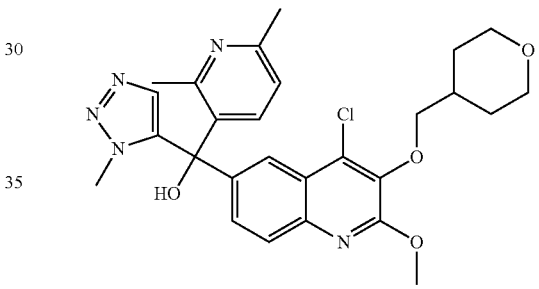

The title compound was prepared using tetrahydropyran-4-methanol in place of 3-methyl-3-oxetanemethanol using the procedure described for Example 36a. $^1$H NMR (500 MHz, CDCl$_3$) δ ppm 8.04 (d, J=2.2 Hz, 1H), 7.77 (d, J=8.7 Hz, 1H), 7.30-7.28 (m, 1H), 6.96-6.91 (m, 2H), 6.86 (s, 1H), 4.65 (s, 1H), 4.13 (s, 3H), 4.03-3.98 (m, 2H), 3.95 (d, J=6.5 Hz, 2H), 3.92 (s, 3H), 3.48-3.42 (m, 2H), 2.52 (s, 3H), 2.35 (s, 3H), 2.18-2.09 (m, 1H), 1.88-1.85 (m, 1H), 1.85-1.83 (m, 1H), 1.54-1.45 (m, 2H). MS (ESI): mass calcd. for C$_{27}$H$_{30}$ClN$_5$O$_4$, 523.2; m/z found, 524.1 [M+H]$^+$.

[4-Chloro-2-methoxy-3-(tetrahydro-2H-pyran-4-ylmethoxy)quinolin-6-yl](2,6-dimethylpyridin-3-yl)(1-methyl-1H-1,2,3-triazol-5-yl)methanol was purified by chiral SFC (Stationary phase: CHIRALPAK AD-H 5 μM 250× 20 mm, Mobile phase: 75% CO$_2$, 25% MeOH/iPrOH 50/50 v/v+(0.3% iPrNH$_2$)) to give 2 enantiomers. The first eluting enantiomer was Example 154b: $^1$H NMR (400 MHz, CDCl$_3$) δ ppm 7.99 (d, J=2.2 Hz, 1H), 7.82 (d, J=8.7 Hz, 1H), 7.33-7.30 (m, 1H), 6.98 (s, 1H), 6.95 (s, 2H), 4.14 (s, 3H), 4.06-4.01 (m, 2H), 3.96 (d, J=6.6 Hz, 2H), 3.95 (s, 3H), 3.51-3.43 (m, 2H), 3.26 (s, 1H), 2.56 (s, 3H), 2.40 (s, 3H), 2.20-2.10 (m, 1H), 1.89-1.83 (m, 2H), 1.54-1.48 (m, 2H). MS (ESI): mass calcd. for C$_{27}$H$_{30}$ClN$_5$O$_4$, 523.2; m/z found, 524.1 [M+H]$^+$ and the second eluting enantiomer was Example 154c: $^1$H NMR (400 MHz, CDCl$_3$) δ ppm 7.99 (d, J=2.2 Hz, 1H), 7.82 (d, J=8.8 Hz, 1H), 7.33-7.30 (m, 1H), 6.98 (s, 1H), 6.95 (s, 2H), 4.14 (s, 3H), 4.07-4.01 (m, 2H), 3.96 (d, J=6.5 Hz, 2H), 3.95 (s, 3H), 3.51-3.43 (m, 2H), 3.24 (s, 1H), 2.56 (s, 3H), 2.40 (s, 3H), 2.20-2.11 (m, 1H), 1.90-1.83 (m, 2H), 1.53-1.47 (m, 2H). MS (ESI): mass calcd. for $C_{27}H_{30}ClN_5O_4$, 523.2; m/z found, 524.1 [M+H]$^+$.

Example 155: (4-Chloro-3-isopropoxy-2-methoxyquinolin-6-yl)(2,6-dimethylpyridin-3-yl)methanol.TFA

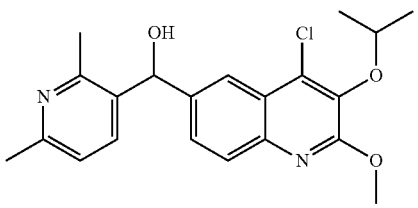 [SMILES: COc1nc2ccc(C(O)c3ccc(C)nc3C)cc2c(Cl)c1OC(C)C]

n-BuLi (1.23 M in hexanes, 369 μL, 0.45 mmol) was added dropwise to a stirred solution of 6-bromo-4-chloro-3-isopropoxy-2-methoxyquinoline (150 mg, 0.45 mmol, Intermediate 26) in THF (6 mL) at −40° C. under nitrogen. After stirring for 5 minutes, the solution was treated dropwise with a solution of 2,6-dimethyl-3-formylpyridine (63 mg, 0.45 mmol) in THF (3 mL). The flask was then rinsed with THF (2 mL), and that was added to the imidazole flask. The reaction was stirred in the dry ice/acetone bath for another 15 minutes, then the dry ice/acetone bath was removed and the mixture stirred at 0° C. for 30 minutes. Saturated aqueous NH$_4$Cl (5 mL), water (20 mL) and EtOAc (25 mL) were added and the layers separated. The aqueous layer was further extracted with EtOAc (25 mL). The organics were combined, dried (Na$_2$SO$_4$), filtered and concentrated to dryness to afford a yellow oil. The crude material was purified by reverse-phase HPLC (acetonitrile/water+0.05% TFA) to provide the title compound as a clear colorless oil. $^1$H NMR (500 MHz, CDCl$_3$) δ ppm 8.42 (d, J=8.2 Hz, 1H), 7.94 (d, J=2.0 Hz, 1H), 7.76 (d, J=8.6 Hz, 1H), 7.43 (d, J=8.1 Hz, 1H), 7.36 (dd, J=8.6, 2.0 Hz, 1H), 6.12 (s, 1H), 4.72-4.65 (m, 1H), 4.11 (s, 3H), 2.74 (s, 3H), 2.65 (s, 3H), 1.40-1.36 (m, 6H). MS (ESI): mass calcd. for $C_{21}H_{23}ClN_2O_3$, 386.1; m/z found, 387.0 [M+H]$^+$.

Example 156: [4-Chloro-2-methoxy-3-(1-methylethoxy)quinolin-6-yl](1,2-dimethyl-1H-imidazol-5-yl)methanol

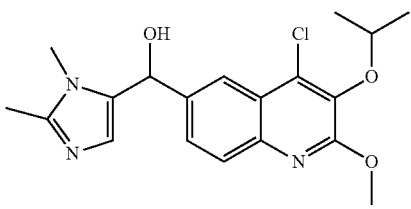 [SMILES: COc1nc2ccc(C(O)c3cnc(C)n3C)cc2c(Cl)c1OC(C)C]

The title compound was prepared using 6-bromo-4-chloro-3-isopropoxy-2-methoxyquinoline (Intermediate 26) in place of 6-bromo-2,4-dichloro-3-isopropoxyquinoline using the procedure described for Example 172. $^1$H NMR (400 MHz, CDCl$_3$) δ ppm 8.15-8.12 (m, 1H), 7.77 (d, J=8.6 Hz, 1H), 7.56-7.52 (m, 1H), 6.44 (s, 1H), 5.96 (s, 1H), 4.72-4.64 (m, 1H), 4.12 (s, 3H), 3.46 (s, 3H), 2.27 (s, 3H), 1.40-1.36 (m, 6H). MS (ESI): mass calcd. for $C_{19}H_{22}ClN_3O_3$, 375.1; m/z found, 376.0 [M+H]$^+$.

Example 157: (4-Chloro-3-isobutyl-2-methoxyquinolin-6-yl)(2,6-dimethylpyridin-3-yl)methanol

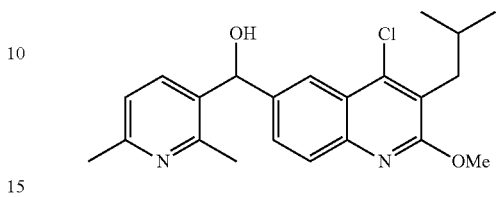

To a flask containing 6-bromo-4-chloro-3-isobutyl-2-methoxyquinoline (1.0 g, 3.04 mmol, Intermediate 66: step c) was added THF (20 mL) and the solution was cooled to −75° C. n-BuLi (2.5 M in hexanes, 1.3 mL, 3.25 mmol) was added dropwise and after 2 minutes, 2,6-dimethylnicotinaldehyde (450 mg, 3.33 mmol, in 1 mL THF) was introduced. The reaction mixture was allowed to gradually warm to 0° C. over 30 minutes at which time the contents were quenched with aqueous NH$_4$Cl solution. The aqueous portion was extracted with EtOAc (3×50 mL) and the combined organics were washed with brine, dried over MgSO$_4$, filtered and concentrated. Chromatography on silica gel (100% DCM increasing to 5% MeOH-DCM) provided the title compound. $^1$H NMR (500 MHz, CDCl$_3$) δ ppm 8.10 (d, J=2.0 Hz, 1H), 7.74 (dd, J=20.8, 8.2 Hz, 2H), 7.47 (dd, J=8.6, 2.0 Hz, 1H), 7.04 (d, J=8.0 Hz, 1H), 6.14 (d, J=3.1 Hz, 1H), 4.06 (s, 3H), 2.81 (d, J=7.3 Hz, 2H), 2.50 (d, J=17.8 Hz, 7H), 2.09 (hept, J=6.8 Hz, 1H), 0.95 (d, J=6.7 Hz, 6H). MS (ESI): mass calcd. for $C_{22}H_{25}ClN_2O_2$, 384.2, m/z found 385.0 [M+H]$^+$.

Example 158: (4-Chloro-3-isobutyl-2-methoxyquinolin-6-yl)(1,2-dimethyl-1H-imidazol-5-yl)methanol

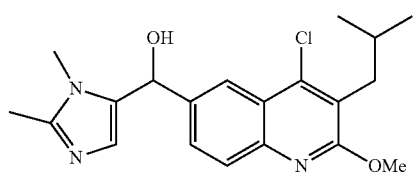 [SMILES: COc1nc2ccc(C(O)c3cnc(C)n3C)cc2c(Cl)c1CC(C)C]

To a flask containing 6-bromo-4-chloro-3-isobutyl-2-methoxyquinoline (Intermediate 66: step c, 1.0 g, 3.04 mmol) was added THF (30 mL) and the solution was cooled to −75° C. n-BuLi (2.5 M in hexanes, 1.33 mL, 3.33 mmol) was added dropwise. After 4 minutes, 1,2-dimethyl-1H-imidazole-5-carbaldehyde (400 mg, 3.22 mmol, in 4 mL THF) was introduced. After 10 minutes, the −75° C. bath was replaced with an ice-water bath which was allowed to warm gradually to room temperature. The reaction mixture was quenched with aqueous NH$_4$Cl solution after 75 minutes and the aqueous portion was extracted with EtOAc, (3×50 mL). The combined organics were washed with brine, dried over MgSO$_4$, filtered and concentrated. The resulting solid was triturated with Et$_2$O and collected by filtration to give the title compound as a bright white powder. $^1$H NMR (500 MHz, CDCl$_3$) δ ppm 8.20 (s, 1H), 7.79 (d, J=8.6 Hz, 1H), 7.58 (dd, J=8.6, 1.9 Hz, 1H), 6.49 (s, 1H), 5.98 (s, 1H), 4.08 (s, 3H), 3.71 (s, 1H), 3.47 (s, 3H), 2.82 (d, J=7.3 Hz, 2H), 2.30 (s, 3H), 2.16-1.98 (m, 1H), 0.96 (dd, J=6.7, 1.9 Hz, 7H). MS (ESI): mass calcd. for $C_{20}H_{24}ClN_3O_2$, Exact Mass: 373.2, m/z found, 374.0 [M+H]$^+$.

Example 159: (4-Chloro-3-cyclopentyl-2-methoxy-quinolin-6-yl)(1,2-dimethyl-1H-imidazol-5-yl)methanol.TFA

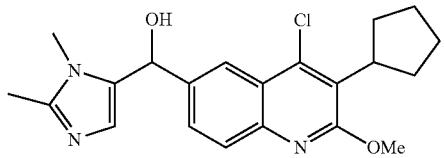 [SMILES: COc1nc2ccc(C(O)c3cnc(C)n3C)cc2c(Cl)c1C1CCCC1]

To a flask containing 6-bromo-4-chloro-3-cyclopentyl-2-methoxyquinoline (1.0 g, 2.94 mmol, Intermediate 68: step b) was added THF (25 mL) and the solution was cooled to −45° C. n-BuLi (2.5 M in hexanes, 1.3 mL, 3.25 mmol) was added dropwise and the mixture was stirred for 3 minutes at −45° C. Then 1,2-dimethyl-1H-imidazole-5-carbaldehyde (450 mg, 3.62 mmol in 3 mL THF) was introduced. After 30 minutes, the reaction mixture was quenched with aqueous NH$_4$Cl solution and the aqueous portion was extracted with EtOAc (4×50 mL). The combined organics were washed with brine, dried over MgSO$_4$, filtered and concentrated. Trituration with Et$_2$O afforded the title compound as a free flowing white solid. $^1$H NMR (400 MHz, CDCl$_3$) δ ppm 8.21 (s, 1H), 7.77 (d, J=8.6 Hz, 1H), 7.56 (dd, J=8.6, 1.8 Hz, 1H), 6.48 (s, 1H), 5.98 (s, 1H), 4.07 (s, 3H), 3.89 (p, J=8.9 Hz, 1H), 3.46 (s, 3H), 2.31 (s, 3H), 2.07-1.84 (m, 8H). MS (ESI): mass calcd. for $C_{21}H_{24}ClN_3O_2$, 385.2, m/z found 386.1 [M+H]$^+$.

Example 160: (2,4-Dichloro-3-(2,2,2-trifluoroethyl)quinolin-6-yl)(1,2-dimethyl-1H-imidazol-5-yl)(1-methyl-1H-1,2,3-triazol-5-yl)methanol

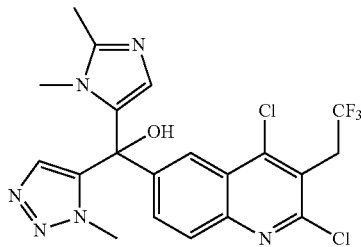 [SMILES: Cc1ncc(C(O)(c2ccc3nc(Cl)c(CC(F)(F)F)c(Cl)c3c2)c2cnnn2C)n1C]

To a flask containing 1-methyl-1H-1,2,3-triazole (111 mg, 1.34 mmol) was added THF (10 mL) and the solution was cooled to −45° C. using a CH$_3$CN—CO$_2$ bath. n-BuLi (2.5 M in hexanes, 0.5 mL, 1.25 mmol) was added dropwise to provide a white suspension. The suspension was stirred at −45° C. for 25 minutes. A pre-warmed THF solution of (2,4-dichloro-3-(2,2,2-trifluoroethyl)quinolin-6-yl)(1,2-dimethyl-1H-imidazol-5-yl)methanone (470 mg, 1.17 mmol in 7 mL THF, Intermediate 70) was introduced at −45° C. The reaction temperature was allowed to warm gradually to room temperature over 70 minutes then quenched with aqueous NH$_4$Cl solution. The aqueous portion was extracted with EtOAc (3×40 mL), and the combined organics were washed with brine, dried over MgSO$_4$, filtered and concentrated. Chromatography on silica gel (2% MeOH-DCM increasing to 8% MeOH) afforded the title compound as a tan amorphous solid. MS (ESI): mass calcd. for $C_{20}H_{17}Cl_2F_3N_6O$, 484.1, found, 485.0 (M+H)$^+$. $^1$H NMR (500 MHz, CDCl$_3$) δ ppm 8.60 (s, 1H), 8.44-8.40 (m, 2H), 7.95 (d, J=8.8 Hz, 1H), 7.62 (dd, J=8.8, 1.8 Hz, 2H), 6.95 (s, 1H), 5.89 (s, 1H), 4.05 (q, J=9.6 Hz, 2H), 3.89 (s, 3H), 3.32 (s, 3H).

Example 161: (2,4-Dichloro-3-(2,2,2-trifluoroethyl)quinolin-6-yl)(1-methyl-1H-imidazol-5-yl)(6-(trifluoromethyl)pyridin-3-yl)methanol

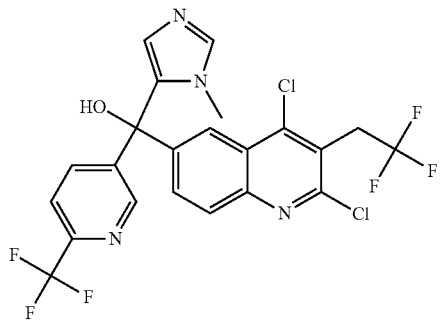 [SMILES: Cn1cncc1C(O)(c1ccc(C(F)(F)F)nc1)c1ccc2nc(Cl)c(CC(F)(F)F)c(Cl)c2c1]

6-Bromo-2,4-dichloro-3-(2,2,2-trifluoroethyl)quinoline (0.504 g, 1.40 mmol, Intermediate 69: step d), (1-methyl-1H-imidazol-5-yl)(6-(trifluoromethyl)pyridin-3-yl)methanone (0.382 g, 1.50 mmol, Intermediate 10: step c) were dissolved in THF (30 mL) under an N$_2$ atmosphere in a dry round bottom flask, then cooled to −78° C. in dry ice/acetone bath. n-BuLi (1.6 M in hexanes, 0.88 mL, 1.4 mmol) was then added dropwise via syringe over approximately 2 minutes. The contents were stirred at −78° C. for approximately 15 minutes, then the dry ice bath was removed and replaced with an ice water bath and stirred at that temperature for approximately one hour. The reaction was then quenched with saturated, aqueous NH$_4$Cl, then transferred to a separatory funnel with EtOAc. The organic phase was separated, then the aqueous layer was back extracted twice with EtOAc, then the combined organic phases were dried over MgSO$_4$, filtered and concentrated under reduced pressure. The crude product was purified by flash column chromatography (silica gel, 0-50% DCM/(10% of a 2 M NH$_3$ MeOH in DCM)) to provide the title compound. MS m/e 535.5 [M+H]$^+$.

Example 162: (2,4-Dichloro-3-(2,2,2-trifluoroethyl)quinolin-6-yl)(1,2-dimethyl-1H-imidazol-5-yl)methanol

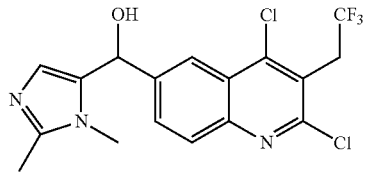 [SMILES: Cc1ncc(C(O)c2ccc3nc(Cl)c(CC(F)(F)F)c(Cl)c3c2)n1C]

To a flask containing 6-bromo-2,4-dichloro-3-(2,2,2-trifluoroethyl)quinoline (2.0 g, 5.57 mmol, Intermediate 69: step d) was added THF (40 mL) and the solution was cooled to −78° C. n-BuLi (2.5 M in hexanes, 2.8 mL, 7 mmol) was added dropwise and the resulting dark brownish mixture was stirred for 3 minutes at −78° C. Then, 1,2-dimethyl-1H-imidazole-5-carbaldehyde (830 mg, 6.69 mmol, in 2 mL THF) was introduced. The reaction temperature was allowed to rise gradually to 0° C. over 40 minutes, and then was quenched with aqueous NH$_4$Cl solution. The aqueous portion was extracted with EtOAc (3×35 mL) and the combined organics were washed with brine, dried over MgSO$_4$, filtered and concentrated. Chromatography on silica gel (10% CH$_3$CN-DCM increasing to 40% CH$_3$CN+2% MeOH) provided the title compound as a faint yellow solid. MS (ESI): mass calcd. for C$_{17}$H$_{14}$Cl$_2$F$_3$N$_3$O, 403.1; found, 404.0 (M+H)$^+$. $^1$H NMR (500 MHz, CDCl$_3$) δ ppm 8.38 (s, 1H), 8.00 (d, J=8.7 Hz, 1H), 7.77 (dd, J=8.7, 1.8 Hz, 1H), 6.49 (s, 1H), 6.04 (s, 1H), 4.07 (q, J=9.7 Hz, 2H), 3.47 (s, 3H), 2.32 (s, 3H).

Example 163

(4-Chloro-2-methoxy-3-((tetrahydro-2H-thiopyran-4-yl)methyl)quinolin-6-yl)(2,6-dimethylpyridin-3-yl)(1-methyl-1H-1,2,3-triazol-5-yl)methanol

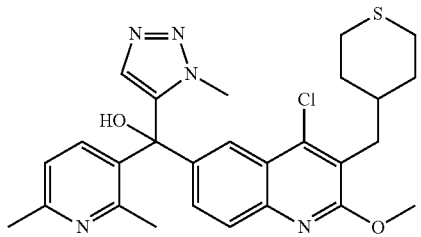 [SMILES: COc1nc2ccc(C(O)(c3ccc(C)nc3C)c3cnnn3C)cc2c(Cl)c1CC1CCSCC1]

The title compound was prepared using 6-bromo-4-chloro-2-methoxy-3-((tetrahydro-2H-thiopyran-4-yl)methyl)quinoline (Intermediate 54: step c) in place of 6-bromo-4-chloro-3-((4,4-difluorocyclohexyl)methyl)-2-methoxyquinoline (Intermediate 56: step c) using the procedure described for Example 1a. $^1$H NMR (400 MHz, CDCl$_3$) δ ppm 8.05 (d, J=2.02 Hz, 1H), 7.82 (d, J=9.09 Hz, 1H), 7.36 (dd, J=2.02, 8.59 Hz, 1H), 6.93-6.98 (m, 3H), 4.10 (s, 2H), 3.94 (s, 3H), 3.44 (s, 1H), 2.86 (d, J=7.07 Hz, 2H), 2.64 (d, J=7.07 Hz, 2H), 2.57-2.62 (m, 2H), 2.56 (s, 3H), 2.39 (s, 3H), 2.04 (s, 3H), 1.91-1.98 (m, 2H); MS m/e 524.1 [M+H]$^+$.

Example 164: tert-Butyl 4-(hydroxy(1-methyl-1H-imidazol-5-yl)(3-(piperidine-1-carbonyl)-2,4-bis(trifluoromethyl)quinolin-6-yl)methyl)piperidine-1-carboxylate

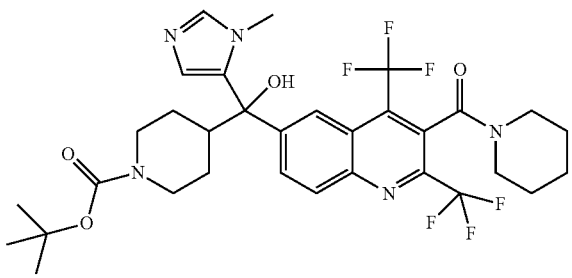 [SMILES: Cn1cncc1C(O)(c1ccc2nc(C(F)(F)F)c(C(=O)N3CCCCC3)c(C(F)(F)F)c2c1)C1CCN(C(=O)OC(C)(C)C)CC1]

5-Bromo-1-methyl-1H-imidazole (0.5 M in DCM, 1.67 mL, 0.834 mmol) was treated with ethylmagnesium chloride (2.09 M in THF, 0.399 mL, 0.834 mmol) dropwise under argon with stirring at room temperature over 1 minute, and the resulting slurry was stirred at 40° C. for 20 minutes. This was treated rapidly dropwise over 1 minute with a solution of tert-butyl 4-(3-(piperidine-1-carbonyl)-2,4-bis(trifluoromethyl)quinoline-6-carbonyl)piperidine-1-carboxylate (196 mg, 0.334 mmol, Intermediate 3: step f) in THF (1.6 mL) with stirring at room temperature, and was then stirred at 40° C. for 2 hours. The reaction was then quenched at room temperature with 5 M aqueous NH$_4$Cl (1 mL) and extracted with 1:1 THF/heptanes (2×3 mL), and the combined organic layers were dried (Na$_2$SO$_4$), filtered, and concentrated. The residue was purified by FCC (0-10% MeOH in DCM) to provide a ~1:1 mixture of the title compound and tert-butyl 4-(2-(1-methyl-1H-imidazol-5-yl)-3-(piperidine-1-carbonyl)-2,4-bis(trifluoromethyl)-1,2-dihydroquinoline-6-carbonyl)piperidine-1-carboxylate as a beige foam. MS m/e 670.3 [M+H]$^+$.

Example 165: (6-(Hydroxy(1-methyl-1H-imidazol-5-yl)(piperidin-4-yl)methyl)-2,4-bis(trifluoromethyl)quinolin-3-yl)(piperidin-1-yl)methanone

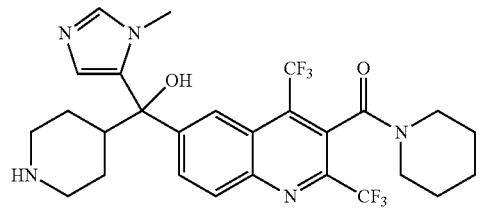 [SMILES: Cn1cncc1C(O)(c1ccc2nc(C(F)(F)F)c(C(=O)N3CCCCC3)c(C(F)(F)F)c2c1)C1CCNCC1]

A ~1:1 mixture of tert-butyl 4-(hydroxy(1-methyl-1H-imidazol-5-yl)(3-(piperidine-1-carbonyl)-2,4-bis(trifluoromethyl)quinolin-6-yl)methyl)piperidine-1-carboxylate and tert-butyl 4-(2-(1-methyl-1H-imidazol-5-yl)-3-(piperidine-1-carbonyl)-2,4-bis(trifluoromethyl)-1,2-dihydroquinoline-6-carbonyl)piperidine-1-carboxylate (120 mg total, 0.179 mmol total, Example 164) in TFA (0.274 mL, 3.58 mmol) and DCM (1 mL) was stirred at 40° C. for 1 hour, and then allowed to sit at room temperature overnight. The dark yellow solution was then diluted with DCM (8 mL) and stirred at room temperature while 10 M aqueous NaOH (0.35 mL) was added dropwise. The lower dark yellow aqueous layer was extracted with DCM (1×8 mL), and the combined organic layers were dried (Na$_2$SO$_4$), filtered, and concentrated to provide a ~1:1 mixture of the title compound and (2-(1-methyl-1H-imidazol-5-yl)-3-(piperidine-1-carbonyl)-2,4-bis(trifluoromethyl)-1,2-dihydroquinolin-6-yl)(piperidin-4-yl)methanone as a beige foam. MS (ESI): mass calcd. for C$_{27}$H$_{29}$F$_6$N$_5$O$_2$, 569.2; m/z found, 570.3 [M+H]$^+$.

Example 166a: 1-[4-Chloro-2-methoxy-3-(1-methylethoxy)quinolin-6-yl]-1-(2,6-dimethylpyridin-3-yl)ethanol

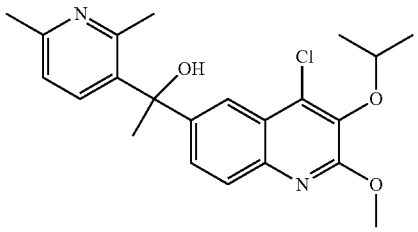 [SMILES: COc1nc2ccc(C(C)(O)c3ccc(C)nc3C)cc2c(Cl)c1OC(C)C]

MeLi (1.6 M in diethyl ether, 173 µL, 0.28 mmol) was added to a mixture of (4-chloro-3-isopropoxy-2-methoxyquinolin-6-yl)(2,6-dimethylpyridin-3-yl)methanone (91.5 mg, 0.24 mmol, Intermediate 28) in THF (7.9 mL) at −40° C. under nitrogen. The mixture was stirred at −40° C. for 50 minutes, then additional MeLi was added (1.6 M in diethyl ether, 37 µL, 0.06 mmol) and the reaction stirred at −40° C. for 30 minutes. Additional MeLi was added (1.6 M in diethyl ether, 37 µL, 0.06 mmol) and the reaction stirred at −40° C. for 1 hour. The reaction was quenched with saturated aqueous NH$_4$Cl at −40° C. then the acetonitrile/dry ice bath was removed. The mixture was diluted with water and extracted with EtOAc (2×20 mL). The organics were combined, washed with brine, dried (Na$_2$SO$_4$), filtered and concentrated to dryness to provide a light yellow oil. The crude material was purified by reverse-phase HPLC (acetonitrile/water+NH$_4$OH) to provide the title compound as a cream-colored solid. MS (ESI): mass calcd. for C$_{22}$H$_{25}$ClN$_2$O$_3$, 400.2; m/z found, 401.1 [M+H]$^+$. 1-[4-Chloro-2-methoxy-3-(1-methylethoxy)quinolin-6-yl]-1-(2,6-dimethylpyridin-3-yl)ethanol was purified by chiral SFC (Stationary phase: CHIRALPAK AD-H 5 µM 250×20 mm, Mobile phase: 85% CO$_2$, 15% MeOH+(0.3% iPrNH$_2$)) to give 2 enantiomers. The first eluting enantiomer was Example 166b: $^1$H NMR (400 MHz, CDCl$_3$) δ ppm 8.12-8.10 (m, 1H), 7.93 (d, J=8.0 Hz, 1H), 7.72 (d, J=8.7 Hz, 1H), 7.38-7.34 (m, 1H), 7.08 (d, J=8.0 Hz, 1H), 4.71-4.64 (m, 1H), 4.10 (s, 3H), 2.54 (s, 3H), 2.18 (s, 3H), 2.01 (s, 3H), 1.40-1.36 (m, 6H). MS (ESI): mass calcd. for C$_{22}$H$_{25}$ClN$_2$O$_3$, 400.2; m/z found, 401.1 [M+H]$^+$ and the second eluting enantiomer was Example 166c: $^1$H NMR (400 MHz, CDCl$_3$) δ ppm 8.11 (d, J=2.1 Hz, 1H), 7.93 (d, J=8.0 Hz, 1H), 7.72 (d, J=8.7 Hz, 1H), 7.36 (dd, J=8.7, 2.1 Hz, 1H), 7.08 (d, J=8.1 Hz, 1H), 4.71-4.64 (m, 1H), 4.10 (s, 3H), 2.54 (s, 3H), 2.18 (s, 3H), 2.01 (s, 3H), 1.40-1.36 (m, 6H). MS (ESI): mass calcd. for C$_{22}$H$_{25}$ClN$_2$O$_3$, 400.2; m/z found, 401.1 [M+H]$^+$.

Example 167: (3-(Benzyloxy)-2,4-dichloroquinolin-6-yl)(1-methyl-1H-imidazol-5-yl)(6-(trifluoromethyl)pyridin-3-yl)methanol

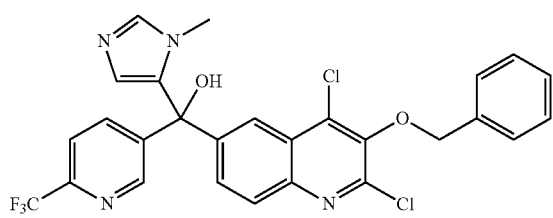 [SMILES: Cn1cncc1C(O)(c1ccc(C(F)(F)F)nc1)c1ccc2nc(Cl)c(OCc3ccccc3)c(Cl)c2c1]

A solution of 3-(benzyloxy)-6-bromo-2,4-dichloroquinoline (2.57 g, 6.71 mmol, Intermediate 29: step c) in THF (100 mL) was cooled to −78° C., during which it became a white suspension. Then, n-BuLi (1.6 M in hexanes, 5.87 mL, 9.39 mmol) was added dropwise and the resulting dark red solution was stirred for 10 minutes at −78° C. To this mixture was added a solution of (1-methyl-1H-imidazol-5-yl)(6-(trifluoromethyl)pyridin-3-yl)methanone (2.23 g, 8.72 mmol, Intermediate 10: step c) in THF (30 mL) over 4 minutes and the resulting mixture stirred at −78° C. for 2 minutes. The dry-ice/acetone bath was then replaced with an ice bath and the mixture was stirred for an additional 45 minutes. The reaction was then quenched with water and extracted with EtOAc. The organics were combined, dried (MgSO$_4$), and concentrated to dryness to afford the crude product which was purified by FCC (4% MeOH/DCM) to provide the title compound. MS (ESI): mass calcd. for C$_{27}$H$_{19}$Cl$_2$F$_3$N$_4$O$_2$, 558.1; m/z found, 559.0 [M+H]$^+$ Example 168: (3-(Benzyloxy)-4-chloro-2-methoxyquinolin-6-yl)(1-methyl-1H-imidazol-5-yl)(6-(trifluoromethyl)pyridin-3-yl)methanol

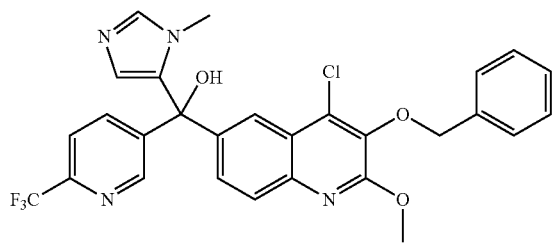 [SMILES: COc1nc2ccc(C(O)(c3ccc(C(F)(F)F)nc3)c3cncn3C)cc2c(Cl)c1OCc1ccccc1]

To a mixture of (3-(benzyloxy)-2,4-dichloroquinolin-6-yl)(1-methyl-1H-imidazol-5-yl)(6-(trifluoromethyl)pyridin-3-yl)methanol (2.46 g, 4.4 mmol, Example 167) in methanol (24.6 mL) was added NaOMe (0.5 M in MeOH, 8.8 mL, 4.4 mmol) and the resulting suspension heated to 65° C. for 8 hours. The mixture was then cooled to room temperature and concentrated to dryness. Water was added and the mixture acidified with 2 N aqueous HCl to ~pH 2. The aqueous was then extracted with EtOAc. The organics were combined and washed with water, saturated aqueous NaHCO$_3$ and brine. The organics were then dried (MgSO$_4$), filtered and concentrated to dryness to afford the title compound which was used without further purification. MS (ESI): mass calcd. for C$_{28}$H$_{22}$ClF$_3$N$_4$O$_3$, 554.1; m/z found, 555.2 [M+H]$^+$.

Example 169: (3-(Benzyloxy)-4-chloro-2-methoxyquinolin-6-yl)(2,6-dimethylpyridin-3-yl)(1-methyl-1H-1,2,3-triazol-5-yl)methanol

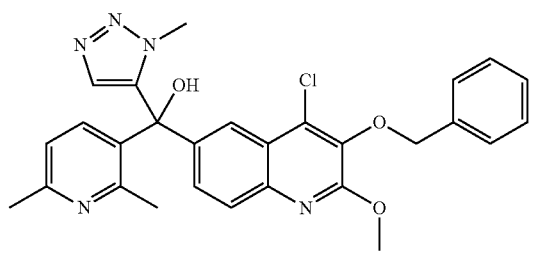 [SMILES: COc1nc2ccc(C(O)(c3ccc(C)nc3C)c3cnnn3C)cc2c(Cl)c1OCc1ccccc1]

To a solution of 3-(benzyloxy)-6-bromo-4-chloro-2-methoxyquinoline (3 g, 7.92 mmol, Intermediate 29: step d) and (2,6-dimethylpyridin-3-yl)(1-methyl-1H-1,2,3-triazol-5-yl)methanone (1.71 g, 7.92 mmol, Intermediate 11: step b) in THF (189 mL) at −78° C. was added n-BuLi (1.23 M in hexanes, 7.09 mL, 8.72 mmol) dropwise. The resulting red-orange solution was stirred at −78° C. for 30 minutes, then warmed to 0° C. and stirred for an additional 30 minutes. Saturated aqueous NH$_4$Cl (75 mL), water (150 mL) and EtOAc (200 mL) were added and the layers separated. The aqueous layer was further extracted with EtOAc (200 mL). The organics were combined, dried (Na$_2$SO$_4$), filtered and concentrated to dryness to afford a yellow foam. The crude material was purified by FCC (0-100% acetonitrile/DCM) to provide the title compound as a yellow foam. MS (ESI): mass calcd. for C$_{28}$H$_{26}$ClN$_5$O$_3$, 515.2; m/z found, 516.3 [M+H]$^+$.

Example 170: tert-Butyl 4-((4-chloro-2-methoxy-3-((tetrahydro-2H-pyran-4-yl)methyl)quinolin-6-yl)(hydroxy)(1-methyl-1H-imidazol-5-yl)methyl)piperidine-1-carboxylate

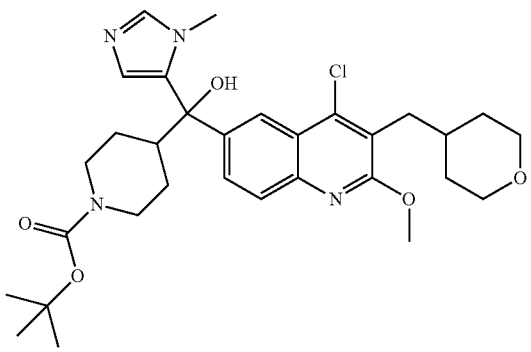 [SMILES: COc1nc2ccc(C(O)(c3cncn3C)C3CCN(C(=O)OC(C)(C)C)CC3)cc2c(Cl)c1CC1CCOCC1]

iPrMgCl (2.06 M in THF, 0.72 mL, 1.48 mmol) was added dropwise at 0° C. over 1.5 minutes to a solution of 5-bromo-1,2-dimethyl-1H-imidazole (0.257 g, 1.60 mmol) in THF (4 mL; dried over 3A molecular sieves) under argon. After stirring for 17 minutes, a solution of tert-butyl 4-(4-chloro-2-methoxy-3-((tetrahydro-2H-pyran-4-yl)methyl)quinoline-6-carbonyl)piperidine-1-carboxylate (0.452 g, 0.899 mmol, Intermediate 5) and LaCl$_3$·2LiCl (0.5 M in THF, 1.98 mL, 0.988 mmol) in THF (2 mL) was added dropwise over 2 minutes to the Grignard reagent at 0° C., and after 30 minutes the reaction was quenched with 5 M aqueous NH$_4$Cl (1 mL). The aqueous layer was extracted with DCM (1×5 mL), and the combined organic layers were dried (Na$_2$SO$_4$), filtered, and concentrated. The residue was purified by FCC (0-10% MeOH in DCM) to afford the title compound as a white foam. $^1$H NMR (400 MHz, CDCl$_3$) δ 8.10 (br. s., 1H), 7.74 (d, J=8.59 Hz, 1H), 7.34-7.41 (m, 1H), 7.29 (s, 1H), 7.18 (s, 1H), 4.25 (br. s., 1H), 4.07 (s, 3H), 3.91-3.98 (m, 2H), 3.28-3.38 (m, 2H), 3.23 (s, 3H), 2.90 (d, J=7.07 Hz, 2H), 2.55-2.85 (m, 2H), 2.31-2.42 (m, 1H), 2.18-2.26 (m, 1H), 1.91-2.04 (m, 1H), 1.66 (br. s., 3H), 1.49-1.59 (m, 3H), 1.41 (s, 9H), 1.29-1.38 (m, 1H), 1.13-1.23 (m, 2H); MS m/e 584.8 [M+H]$^+$.

Example 171: (4-Chloro-2-methoxy-3-((tetrahydro-2H-pyran-4-yl)methyl)quinolin-6-yl)(1-methyl-1H-imidazol-5-yl)(piperidin-4-yl)methanol

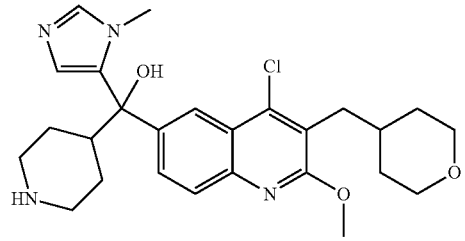 [SMILES: COc1nc2ccc(C(O)(c3cncn3C)C3CCNCC3)cc2c(Cl)c1CC1CCOCC1]

A solution of tert-butyl 4-((4-chloro-2-methoxy-3-((tetrahydro-2H-pyran-4-yl)methyl)quinolin-6-yl)(hydroxy)(1-methyl-1H-imidazol-5-yl)methyl)piperidine-1-carboxylate (405 mg, 0.692 mmol, Example 170) in DCM (1 mL) was treated with TFA (0.53 mL, 6.92 mmol) at room temperature and stirred for 50 minutes. LCMS indicated the reaction had stalled at 50+% conversion, so additional TFA (0.53 mL, 6.92 mmol) was added and the reaction stirred for an additional 40 minutes (90 minutes total). The reaction was then diluted with DCM (12 mL) and stirred in an ice bath while 10 M aqueous NaOH was added dropwise to pH~12-13 (litmus paper), and the aqueous layer was extracted with DCM (1×5 mL). The combined organic layers were dried (Na$_2$SO$_4$), filtered, and concentrated at <40° C. to provide the title compound as an off-white foam. $^1$H NMR (400 MHz, CDCl$_3$) δ 8.11 (s, 1H), 7.73 (d, J=8.59 Hz, 1H), 7.36-7.42 (m, 1H), 7.30 (s, 1H), 7.18 (s, 1H), 4.07 (s, 3H), 3.91-3.98 (m, 2H), 3.28-3.38 (m, 2H), 3.25 (s, 3H), 3.21 (d, J=12.13 Hz, 1H), 3.01 (d, J=12.13 Hz, 1H), 2.89 (d, J=7.07 Hz, 2H), 2.75 (t, J=11.37 Hz, 1H), 2.55 (td, J=3.28, 11.49 Hz, 1H), 2.36 (t, J=11.12 Hz, 1H), 2.23 (d, J=12.63 Hz, 1H), 1.92-2.04 (m, 1H), 1.79 (br. s., 3H), 1.51-1.56 (m, 3H), 1.36-1.49 (m, 1H), 1.14-1.26 (m, 2H); MS m/e 485.2 [M+H]$^+$.

Example 172: (2,4-Dichloro-3-isopropoxyquinolin-6-yl)(1,2-dimethyl-1H-imidazol-5-yl)methanol

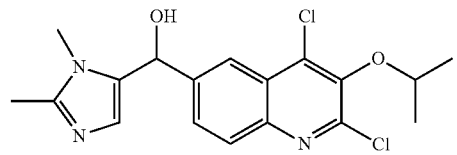 [SMILES: Cc1ncc(C(O)c2ccc3nc(Cl)c(OC(C)C)c(Cl)c3c2)n1C]

To a solution of 6-bromo-2,4-dichloro-3-isopropoxyquinoline (150 mg, 0.45 mmol, Intermediate 20: step c) and 1,2-dimethyl-1H-imidazole-5-carbaldehyde (56 mg, 0.45 mmol) in THF (11 mL) at −40° C. was added n-BuLi (1.23 M in hexanes, 364 μL, 0.45 mmol) dropwise. The resulting red-orange solution was stirred at −40° C. for 30 minutes. Additional n-BuLi (1.23 M in hexanes, 182 μL, 0.23 mmol) and 1,2-dimethyl-1H-imidazole-5-carbaldehyde (28 mg, 0.23 mmol) were added and the solution was stirred at −40° C. for 30 minutes then warmed to 0° C. and stirred for an additional 30 minutes. Saturated aqueous NH$_4$Cl (5 mL), water (20 mL) and EtOAc (25 mL) were added and the layers separated. The aqueous layer was further extracted with EtOAc (25 mL). The organics were combined, dried (Na$_2$SO$_4$), filtered and concentrated to dryness to afford the crude product as a yellow oil. The crude material was purified by FCC (0.5-10% MeOH/DCM) to provide the title compound as a clear colorless oil. MS (ESI): mass calcd. for C18H$_{19}$Cl$_2$N$_3$O$_2$, 379.1; m/z found, 380.3 [M+H]$^+$. $^1$H NMR (500 MHz, CDCl$_3$) δ 8.30-8.26 (m, 1H), 7.94 (d, J=8.7 Hz, 1H), 7.67-7.62 (m, 1H), 6.44 (s, 1H), 6.01 (s, 1H), 4.81-4.72 (m, 1H), 3.46 (s, 3H), 2.28 (s, 3H), 1.47-1.42 (m, 6H).

Example 173: tert-Butyl 4-(2-(4-chloro-6-(hydroxy (1-methyl-1H-imidazol-5-yl)(6-(trifluoromethyl) pyridin-3-yl)methyl)-2-methoxyquinolin-3-yl)ethyl) piperidine-1-carboxylate

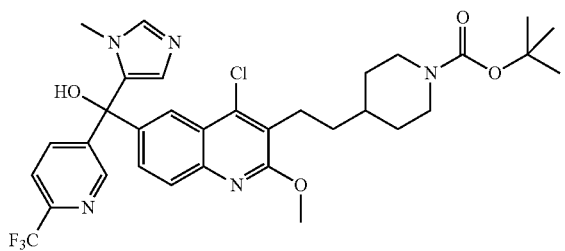 [SMILES: COc1nc2ccc(C(O)(c3ccc(C(F)(F)F)nc3)c3cncn3C)cc2c(Cl)c1CCC1CCN(C(=O)OC(C)(C)C)CC1]

A solution of tert-butyl 4-(2-(6-bromo-4-chloro-2-methoxyquinolin-3-yl)ethyl)piperidine-1-carboxylate (445 mg, 0.92 mmol, Intermediate 38: step f) in THF (15 mL) was cooled to −78° C. Then, n-BuLi (1.6 M in hexanes, 747 µL, 1.2 mmol) was added dropwise and the resulting orange-red solution was stirred for 5 minutes at −78° C. To this mixture was added a solution of (1-methyl-1H-imidazol-5-yl)(6-(trifluoromethyl)pyridin-3-yl)methanone (305 mg, 1.2 mmol, Intermediate 10: step c) in THF (3 mL) and the resulting mixture stirred at −78° C. for 3 minutes. The dry-ice/acetone bath was then replaced with an ice bath and the mixture was stirred for an additional 30 minutes. The reaction was then quenched with water and extracted with EtOAc. The organics were dried (MgSO$_4$), filtered and concentrated to dryness to afford the crude product which was purified by FCC (100% EtOAc) to provide the title compound. MS (ESI): mass calcd. for C$_{33}$H$_{37}$ClF$_3$N$_5$O$_4$, 659.3; m/z found, 660.3 [M+H]$^+$.

Example 174: (4-Chloro-2-methoxy-3-(2-(piperidin-4-yl)ethyl)quinolin-6-yl)(1-methyl-1H-imidazol-5-yl)(6-(trifluoromethyl)pyridin-3-yl)methanol

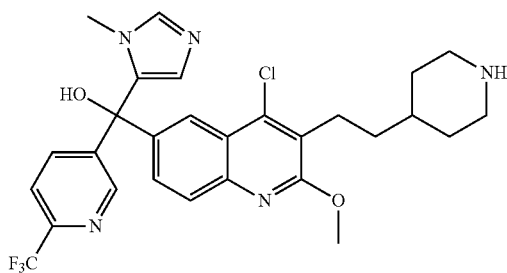 [SMILES: COc1nc2ccc(C(O)(c3ccc(C(F)(F)F)nc3)c3cncn3C)cc2c(Cl)c1CCC1CCNCC1]

To a solution of tert-butyl 4-(2-(4-chloro-6-(hydroxy(1-methyl-1H-imidazol-5-yl)(6-(trifluoromethyl)pyridin-3-yl)methyl)-2-methoxyquinolin-3-yl)ethyl)piperidine-1-carboxylate (110 mg, 0.17 mmol, Example 173) in DCM (5 mL) was added TFA (64 µL, 0.83 mmol) and the resulting solution stirred at room temperature overnight. The solution was diluted with DCM, cooled to 0° C. and the pH adjusted to ~pH 8 by the addition of 3 N aqueous NaOH dropwise. The layers were separated and the organics dried (MgSO$_4$), filtered and concentrated to dryness to afford the title compound which was used without further purification. MS (ESI): mass calcd. for C$_{28}$H$_{29}$ClF$_3$N$_5$O$_2$, 559.2; m/z found, 560.2 [M+H]$^+$.

Example 175: (3-((4-(1H-Pyrazol-1-yl)piperidin-1-yl)methyl)-4-chloro-2-methoxyquinolin-6-yl)(1,2-dimethyl-1H-imidazol-5-yl)methanol

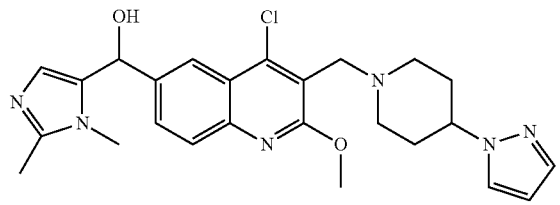 [SMILES: COc1nc2ccc(C(O)c3cnc(C)n3C)cc2c(Cl)c1CN1CCC(n2cccn2)CC1]

A solution of n-butyllithium (1.6 M in hexanes, 0.52 mL, 0.83 mmol) was added dropwise by syringe to a solution of 3-((4-(1H-pyrazol-1-yl)piperidin-1-yl)methyl)-6-bromo-4-chloro-2-methoxyquinoline (0.40 g, 0.92 mmol, Intermediate 41) in dry deoxygenated THF (26 mL) at −78° C. After 2 minutes, a solution of 1,2-dimethyl-1H-imidazole-5-carbaldehyde (0.104 g, 0.835 mmol) in dry THF (6 mL) was added dropwise by syringe. An additional 2 mL of THF was used to complete the quantitative addition. After 10 minutes, the flask was removed from the dry-ice bath and placed into an ice-water bath. After 1 hour, the reaction was quenched with saturated aqueous ammonium chloride solution and the mixture was partitioned between water and EtOAc. The layers were separated and the aqueous phase was further extracted with EtOAc and washed with saturated aqueous NaCl solution. The organic phase was dried (MgSO$_4$), filtered, and concentrated to dryness. The crude product was purified by flash column chromatography (silica gel, 0-7% MeOH-DCM) to provide the title compound. MS m/e 481.5 (M+H)$^+$. $^1$H NMR (500 MHz, CDCl$_3$) δ ppm 8.24 (s, 1H), 7.82 (d, J=8.6 Hz, 1H), 7.63 (dd, J=8.6, 2.0 Hz, 1H), 7.48 (d, J=1.9 Hz, 1H), 7.40 (d, J=2.3, Hz, 1H), 6.53 (s, 1H), 6.22 (t, J=2.1 Hz, 1H), 6.01 (s, 1H), 4.16-4.12 (m, 1H), 4.10 (s, 3H), 3.88 (s, 2H), 3.49 (s, 3H), 3.10-3.07 (m, 2H), 2.43-2.38 (m, 2H), 2.34 (s, 3H), 2.13-2.05 (m, 2H), 2.05-1.94 (m, 2H).

Example 176: (4-Chloro-2-methoxy-3-((4-(trifluoromethyl)piperidin-1-yl)methyl)quinolin-6-yl)(1,2-dimethyl-1H-imidazol-5-yl)methanol

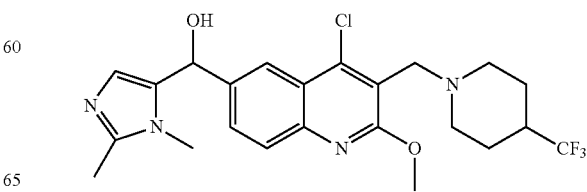

The title compound was prepared analogously to the method in Example 175 using 6-bromo-4-chloro-2-methoxy-3-((4-(trifluoromethyl)piperidin-1-yl)methyl)quinoline (Intermediate 40) in place of 3-((4-(1H-pyrazol-1-yl)piperidin-1-yl)methyl)-6-bromo-4-chloro-2-methoxyquinoline. MS m/e 483.0 (M+H)$^+$. $^1$H NMR (500 MHz, CDCl$_3$) δ ppm 8.24 (s, 1H), 7.82 (d, J=8.6 Hz, 1H), 7.62 (dd, J=8.6, 2.0 Hz, 1H), 6.53 (s, 1H), 6.01 (s, 1H), 4.09 (s, 3H), 3.83 (s, 2H), 3.49 (s, 3H), 3.06-3.04 (m, 2H), 2.34 (s, 3H), 2.23-2.14 (m, 2H), 1.99-1.96 (m, 1H), 1.80-1.78 (d, J=12.9 Hz, 2H), 1.61-1.54 (m, 2H).

Example 177: (4-Chloro-2-methoxy-3-((3-(trifluoromethyl)azetidin-1-yl)methyl)quinolin-6-yl)(1,2-dimethyl-1H-imidazol-5-yl)methanol

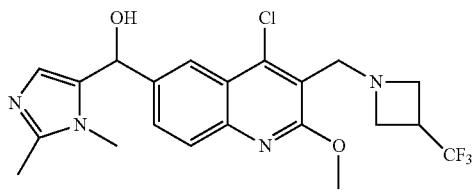 [SMILES: COc1nc2ccc(C(O)c3cnc(C)n3C)cc2c(Cl)c1CN1CC(C(F)(F)F)C1]

The title compound was prepared analogously to the method in Example 175 using 6-bromo-4-chloro-2-methoxy-3-((3-(trifluoromethyl)azetidin-1-yl)methyl)quinoline (Intermediate 49) in place of 3-((4-(1H-pyrazol-1-yl)piperidin-1-yl)methyl)-6-bromo-4-chloro-2-methoxyquinoline. MS m/e 454.9 (M+H)$^+$. $^1$H NMR (500 MHz, CDCl$_3$) δ 8.21 (s, 1H), 7.79 (d, J=8.6 Hz, 1H), 7.60 (dd, J=8.6, 2.0 Hz, 1H), 6.44 (s, 1H), 5.96 (s, 1H), 4.10 (s, 3H), 3.95 (s, 2H), 3.62-3.56 (m, 2H), 3.50-3.42 (m, 5H), 3.18-3.13 (m, 1H), 2.29 (s, 3H).

Example 178: tert-Butyl-3-((4-chloro-2-methoxy-3-((4-(trifluoromethyl)piperidin-1-yl)methyl)quinolin-6-yl)(hydroxy)(1-methyl-1H-1,2,3-triazol-5-yl)methyl)azetidine-1-carboxylate

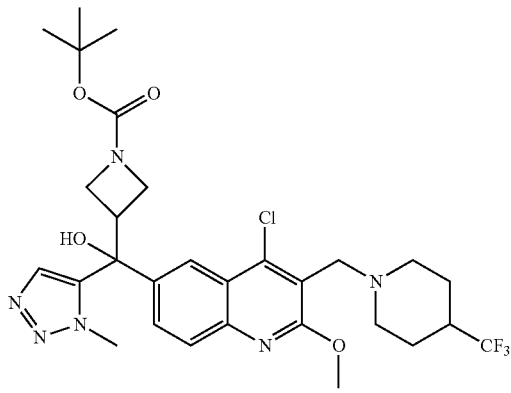 [SMILES: COc1nc2ccc(C(O)(c3cnnn3C)C3CN(C(=O)OC(C)(C)C)C3)cc2c(Cl)c1CN1CCC(C(F)(F)F)CC1]

A solution of n-butyllithium (2.5 M in hexanes, 0.8 mL, 2.0 mmol) was added dropwise by syringe to a solution of 6-bromo-4-chloro-2-methoxy-3-((4-(trifluoromethyl)piperidin-1-yl)methyl)quinoline (0.96 g, 2.2 mmol, Intermediate 40) in dry deoxygenated THF (50 mL) at −78° C. After 2 minutes, a solution of tert-butyl 3-(1-methyl-1H-1,2,3-triazole-5-carbonyl)azetidine-1-carboxylate (0.104 g, 0.835 mmol, Intermediate 55: step b) in dry THF (20 mL) was added dropwise by syringe. An additional 4 mL of THF was used to complete the quantitative addition. After 10 minutes, the flask was removed from the dry-ice bath and placed into an ice-water bath. After 1 hour, the reaction was quenched with saturated aqueous ammonium chloride solution and the mixture was partitioned between water and EtOAc. The layers were separated and the aqueous phase was further extracted with EtOAc and washed with saturated aqueous NaCl solution. The organic phase was dried (MgSO$_4$), filtered, and concentrated to dryness. The crude product was purified by flash column chromatography (silica gel, 0-6% MeOH-DCM) to provide the title compound. $^1$H NMR (400 MHz, CDCl$_3$) δ ppm 8.26 (d, J=2.1 Hz, 1H), 7.77 (d, J=8.9 Hz, 1H), 7.53 (s, 1H), 7.35 (dd, J=8.7, 2.1 Hz, 1H), 4.22-4.18 (m, 1H), 4.08 (s, 3H), 4.04-4.00 (m, 1H), 3.95-3.91 (m, 1H), 3.82 (s, 2H), 3.68 (s, 3H), 3.64-3.59 (m, 1H), 3.40-3.43 (m, 1H), 3.06-3.03 (m, 2H), 2.23-2.17 (m, 2H), 2.01-1.92 (m, 1H), 1.81-1.78 (m, 2H), 1.64-1.52 (m, 2H), 1.38 (s, 9H).

Example 179: tert-Butyl-3-((4-chloro-2-methoxy-3-((4-(trifluoromethyl)piperidin-1-yl)methyl)quinolin-6-yl)(1,2-dimethyl-1H-imidazol-5-yl)(hydroxy)methyl)azetidine-1-carboxylate

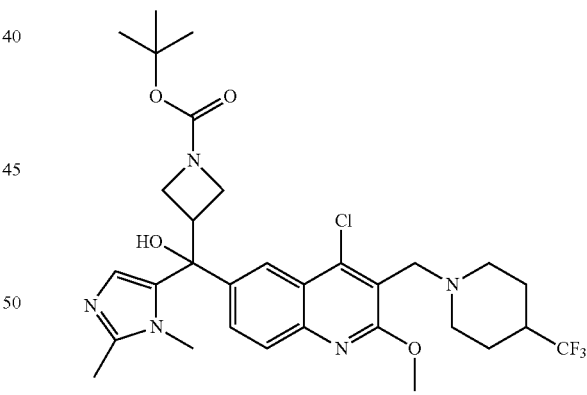

The title compound was prepared analogously to the method in Example 178 using tert-butyl 3-(1,2-dimethyl-1H-imidazole-5-carbonyl)azetidine-1-carboxylate (Intermediate 57: step b) in place of tert-butyl 3-(1-methyl-1H-1,2,3-triazole-5-carbonyl)azetidine-1-carboxylate. MS m/e 638.2 (M+H)$^+$. $^1$H NMR (500 MHz, CDCl$_3$) δ ppm 8.29 (s, 1H), 7.75 (d, J=8.7 Hz, 1H), 7.43 (d, J=8.7, 1H), 6.78-6.73 (m, 1H), 4.21-4.18 (m, 1H), 4.07 (s, 3H), 3.9-3.92 (m, 2H), 3.82 (s, 2H), 3.55-3.51 (m, 1H), 3.43-3.39 (m, 1H), 3.12 (s, 3H), 3.07-3.04 (m, 2H), 2.28 (s, 3H), 2.23-2.17 (m, 2H), 2.02-1.93 (m, 1H), 1.82-1.78 (m, 2H), 1.63-1.50 (m, 2H), 1.41 (s, 9H).

Example 180: tert-Butyl-3-((4-chloro-2-methoxy-3-((4-(trifluoromethyl)piperidin-1-yl)methyl)quinolin-6-yl)(hydroxy)(2-(trifluoromethyl)pyridin-4-yl)methyl)azetidine-1-carboxylate

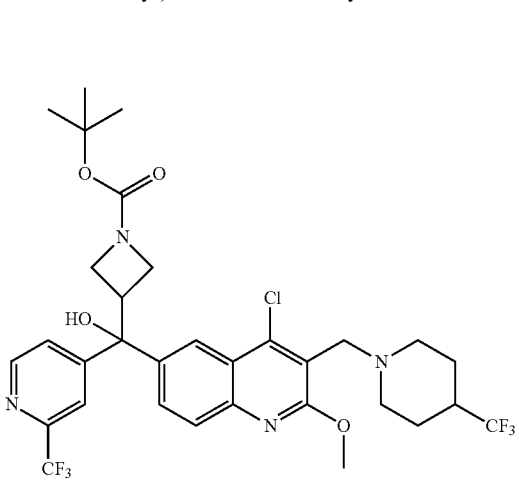

The title compound was prepared analogously to the method in Example 178 using tert-butyl 3-(2-(trifluoromethyl)isonicotinoyl)azetidine-1-carboxylate (Intermediate 58: step b) in place of tert-butyl 3-(1-methyl-1H-1,2,3-triazole-5-carbonyl)azetidine-1-carboxylate. MS m/e 689.1 (M+H)+.

Example 181: tert-Butyl-3-((4-chloro-2-methoxy-3-((4-(trifluoromethyl)piperidin-1-yl)methyl)quinolin-6-yl)(hydroxy)(6-(trifluoromethyl)pyridin-3-yl)methyl)azetidine-1-carboxylate

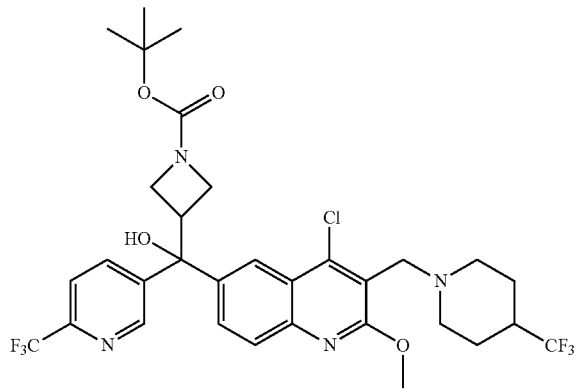 [SMILES: COc1nc2ccc(C(O)(c3ccc(C(F)(F)F)nc3)C3CN(C(=O)OC(C)(C)C)C3)cc2c(Cl)c1CN1CCC(C(F)(F)F)CC1]

The title compound was prepared analogously to the method in Example 178 using tert-butyl 3-(6-(trifluoromethyl)nicotinoyl)azetidine-1-carboxylate (Intermediate 63: step b) in place of tert-butyl 3-(1-methyl-1H-1,2,3-triazole-5-carbonyl)azetidine-1-carboxylate. MS m/e 689.1 (M+H)+.

Example 182a: 1-((4-Chloro-6-(hydroxy(1-methyl-1H-imidazol-5-yl)(2-(trifluoromethyl)pyridin-4-yl)methyl)-2-methoxyquinolin-3-yl)methyl)-4-(trifluoromethyl)piperidin-4-ol

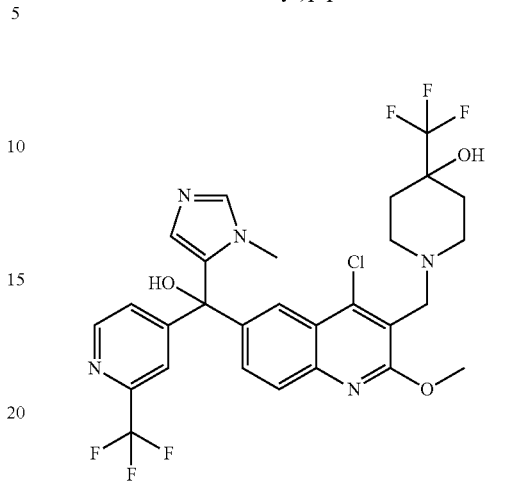

A solution of methyllithium in ether (1.6 M, 0.300 mL, 0.480 mmol) was added dropwise to a dry ice-acetone cooled, stirring solution of 1-((6-bromo-4-chloro-2-methoxyquinolin-3-yl)methyl)-4-(trifluoromethyl)piperidin-4-ol (200 mg, 0.441 mmol, Intermediate 16) in dry tetrahydrofuran (4 mL). After 1 minute, a solution of n-butyllithium in hexanes (2.5 M, 0.180 mL, 0.450 mmol) was added dropwise by syringe. After 1 minute, a solution of (1-methyl-1H-imidazol-5-yl)(2-(trifluoromethyl)pyridin-4-yl)methanone (148 mg, 0.580 mmol, Intermediate 14: step b) in dry tetrahydrofuran (1 mL) was added dropwise by syringe. After 5 minutes, the flask was removed from the cooling bath. After 5 minutes, the flask was placed into an ice-water bath. After 15 minutes, water (20 mL) and ethyl acetate (50 mL) were added sequentially. The layers were separated. The organic layer was dried with sodium sulfate and the dried solution was filtered. Celite® (7 g) was added to the filtrate and the mixture was concentrated in vacuo. The dry solid was loaded onto a silica gel column for flash column chromatography. Elution with dichloromethane initially, grading to 10% methanol-dichloromethane provided the title compound as an off-white solid. $^1$H NMR (400 MHz, CDCl$_3$) δ ppm 8.68 (d, J=5.1 Hz, 1H), 8.15 (d, J=2.1 Hz, 1H), 7.88 (d, J=1.6 Hz, 1H), 7.82 (d, J=8.8 Hz, 1H), 7.57-7.52 (m, 1H), 7.51-7.47 (m, 1H), 7.36 (s, 1H), 6.37 (s, 1H), 4.70 (s, 1H), 4.09 (s, 3H), 3.85 (s, 2H), 3.36 (s, 3H), 2.88-2.79 (m, 2H), 2.60-2.50 (m, 2H), 1.97 (s, 1H), 1.93-1.82 (m, 2H), 1.65 (d, J=13.3 Hz, 2H); MS (ESI): mass calcd. for $C_{28}H_{26}ClF_6N_5O_3$, 629.2; m/z found, 630.0 [M+H]+.

1-((4-Chloro-6-(hydroxy(1-methyl-1H-imidazol-5-yl)(2-(trifluoromethyl)pyridin-4-yl)methyl)-2-methoxyquinolin-3-yl)methyl)-4-(trifluoromethyl)piperidin-4-ol was further purified by chiral SFC (stationary phase: Chiralpak IC 5 μm, 250 mm×21 mm; mobile phase: 17% isopropanol containing 0.2% isopropylamine, 83% CO$_2$) to provide two enantiomers. The first eluting enantiomer was Example 182b: $^1$H NMR (500 MHz, CDCl$_3$) δ ppm 8.69 (d, J=5.0 Hz, 1H), 8.15 (d, J=2.1 Hz, 1H), 7.89-7.85 (m, 1H), 7.82 (d, J=8.7 Hz, 1H), 7.58-7.52 (m, 1H), 7.50 (d, J=4.9 Hz, 1H), 7.37 (s, 1H), 6.38 (s, 1H), 4.64 (s, 1H), 4.09 (s, 3H), 3.85 (s, 2H), 3.36 (s, 3H), 2.84 (d, J=11.1 Hz, 2H), 2.60-2.50 (m, 2H), 1.95 (s, 1H), 1.92-1.82 (m, 2H), 1.70-1.61 (m, 2H); MS (ESI): mass calcd. for $C_{28}H_{26}ClF_6N_5O_3$, 629.2; m/z found, 630.0 [M+H]$^+$ and the second eluting isomer was Example 182c: $^1$H NMR (500 MHz, CDCl$_3$) δ ppm 8.70 (d, J=5.0 Hz, 1H), 8.15 (d, J=2.1 Hz, 1H), 7.87 (s, 1H), 7.82 (d, J=8.7 Hz, 1H), 7.58-7.53 (m, 1H), 7.50 (d, J=5.0 Hz, 1H), 7.40 (s, 1H), 6.41 (s, 1H), 4.31 (s, 1H), 4.09 (s, 3H), 3.85 (s, 2H), 3.37 (s, 3H), 2.88-2.79 (m, 2H), 2.60-2.49 (m, 2H), 1.95-1.82 (m, 3H), 1.70-1.62 (m, 2H); MS (ESI): mass calcd. for $C_{28}H_{26}ClF_6N_5O_3$, 629.2; m/z found, 630.0 [M+H]$^+$.

Example 183: N-((6-(Bis(1,2-dimethyl-1H-imidazol-5-yl)(hydroxy)methyl)-4-chloro-2-methoxyquinolin-3-yl)methyl)-1-(trifluoromethyl)cyclobutanecarboxamide

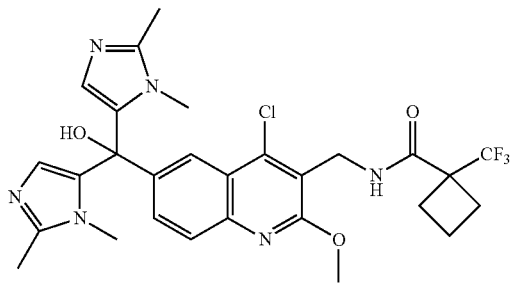 [SMILES: COc1nc2ccc(C(O)(c3cnc(C)n3C)c3cnc(C)n3C)cc2c(Cl)c1CNC(=O)C1(C(F)(F)F)CCC1]

Dichloromethane (1.9 mL, sparged with argon for 20 minutes) was added to a mixture of 1,3-dimethylpyrimidine-2,4,6(1H,3H,5H)-trione (44.9 mg, 0.288 mmol), (4-chloro-3-((diallylamino)methyl)-2-methoxyquinolin-6-yl)bis(1,2-dimethyl-1H-imidazol-5-yl)methanol (50 mg, 0.096 mmol, Intermediate 74: step b) and tetrakis(triphenylphosphine)palladium (55.5 mg, 0.048 mmol) The mixture was heated to 40° C. for 1 hour and the solvent was removed by sparging with nitrogen and then DMF (1.9 mL) was added to the reaction mixture. Then, 1-(trifluoromethyl)cyclobutanecarboxylic acid (16.1 mg, 0.096 mmol), DIPEA (0.066 mL, 0.38 mmol) and HATU (36.5 mg, 0.096 mmol) were added and the mixture was stirred for 16 hours. Water was added and the aqueous layer was extracted with ethyl acetate and the combined organic layer was washed with saturated aqueous NaHCO$_3$ solution, saturated aqueous NaCl solution, dried (MgSO$_4$), filtered and concentrated. The crude product was purified by reverse phase HPLC (30% to 70% acetonitrile/20 mmol aqueous NH$_4$OH over 12 minutes and then 100% acetonitrile for 6 minutes) to provide the title compound as a white solid. $^1$H NMR (600 MHz, CDCl$_3$) δ ppm 8.24 (s, 1H), 7.70 (d, J=8.8 Hz, 1H), 7.40 (dd, J=8.7, 2.1 Hz, 1H), 6.57 (t, J=5.6 Hz, 1H), 6.14 (s, 2H), 5.05 (s, 1H), 4.82 (d, J=5.7 Hz, 2H), 4.12 (d, J=1.1 Hz, 3H), 3.40 (s, 6H), 2.64-2.53 (m, 2H), 2.47-2.36 (m, 2H), 2.27 (s, 6H), 2.06-1.88 (m, 2H). MS (ESI): mass calcd. for $C_{28}H_{30}ClF_3N_6O_3$, 591.0; m/z found, 592.0 [M+H]$^+$.

Example 184: N-((6-(Bis(1,2-dimethyl-1H-imidazol-5-yl)(hydroxy)methyl)-4-chloro-2-methoxyquinolin-3-yl)methyl)-1-(trifluoromethyl)cyclopropanecarboxamide

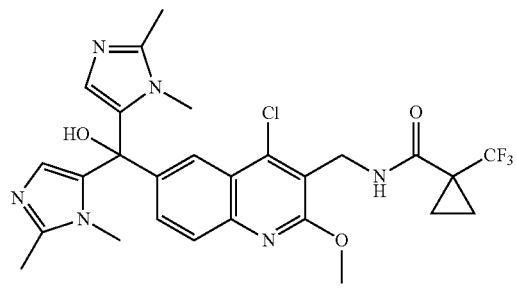 [SMILES: COc1nc2ccc(C(O)(c3cnc(C)n3C)c3cnc(C)n3C)cc2c(Cl)c1CNC(=O)C1(C(F)(F)F)CC1]

The title compound was prepared analogously to the method described in Example 183 replacing 1-(trifluoromethyl)cyclobutanecarboxylic acid with 1-(trifluoromethyl)cyclopropanecarboxylic acid. $^1$H NMR (600 MHz, CDCl$_3$) δ ppm 8.24 (s, 1H), 7.71 (d, J=8.8 Hz, 1H), 7.42 (dd, J=8.6, 2.2 Hz, 1H), 6.98-6.96 (m, 1H), 6.18 (s, 2H), 4.84 (d, J=5.8 Hz, 2H), 4.75 (s, 1H), 4.15 (s, 3H), 3.41 (s, 6H), 2.30 (s, 6H), 1.46-1.41 (m, 2H), 1.23-1.17 (m, 2H). MS (ESI): mass calcd. for $C_{27}H_{28}ClF_3N_6O_3$, 576.2; m/z found, 576.9 [M+H]$^+$.

Example 185: N-((6-(Bis(1,2-dimethyl-1H-imidazol-5-yl)(hydroxy)methyl)-4-chloro-2-methoxyquinolin-3-yl)methyl)-3,3,3-trifluoropropanamide

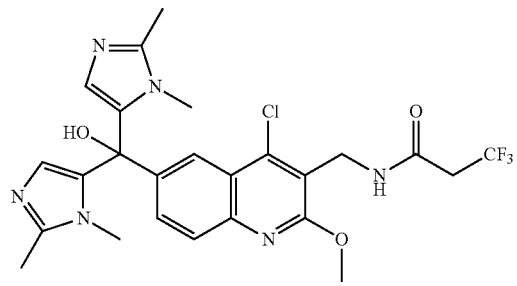 [SMILES: COc1nc2ccc(C(O)(c3cnc(C)n3C)c3cnc(C)n3C)cc2c(Cl)c1CNC(=O)CC(F)(F)F]

The title compound was prepared analogously to the method described in Example 183 replacing 1-(trifluoromethyl)cyclobutanecarboxylic acid with 3,3,3-trifluoropropanoic acid. $^1$H NMR (600 MHz, CDCl$_3$) δ ppm 8.25 (s, 1H), 7.70 (d, J=8.7 Hz, 1H), 7.38 (d, J=8.6 Hz, 1H), 6.95 (s, 1H), 6.15 (s, 2H), 4.81 (d, J=5.4 Hz, 2H), 4.66 (s, 1H), 4.13 (s, 3H), 3.40 (s, 6H), 3.10 (q, J=10.5 Hz, 2H), 2.30 (s, 6H). MS (ESI): mass calcd. for $C_{25}H_{26}ClF_3N_6O_3$, 550.2; m/z found, 550.9 [M+H]$^+$.

Example 186: N-((6-(Bis(1,2-dimethyl-1H-imidazol-5-yl)(hydroxy)methyl)-4-chloro-2-methoxyquinolin-3-yl)methyl)-4,4,4-trifluorobutanamide

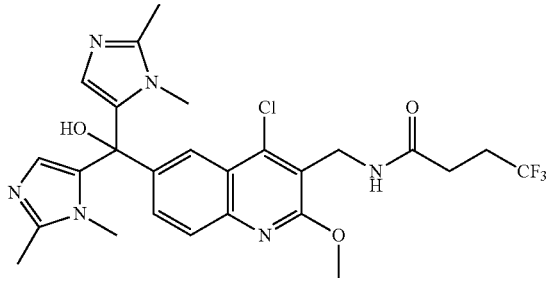 [SMILES: COc1nc2ccc(C(O)(c3cnc(C)n3C)c3cnc(C)n3C)cc2c(Cl)c1CNC(=O)CCC(F)(F)F]

The title compound was prepared analogously to the method described in Example 183 replacing 1-(trifluoromethyl)cyclobutanecarboxylic acid with 4,4,4-trifluorobutanoic acid. $^1$H NMR (600 MHz, CDCl$_3$) δ ppm 8.24 (s, 1H), 7.69 (d, J=8.6 Hz, 1H), 7.39 (d, J=8.6 Hz, 1H), 6.43 (s, 1H), 6.19 (s, 2H), 4.82-4.75 (m, 2H), 4.15 (s, 3H), 3.42 (s, 6H), 2.59-2.45 (m, 4H), 2.34 (s, 6H). MS (ESI): mass calcd. for C$_{26}$H$_{28}$ClF$_3$N$_6$O$_3$, 564.2; m/z found, 564.9 [M+H]$^+$.

Example 187: 4-((4-Chloro-2-methoxy-3-((4-(trifluoromethyl)piperidin-1-yl)methyl)quinolin-6-yl)(hydroxy)methyl)benzonitrile

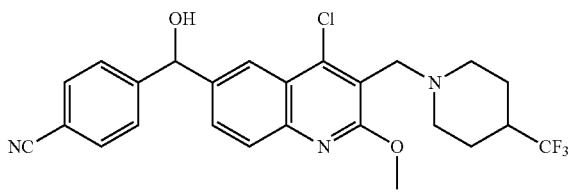 [SMILES: COc1nc2ccc(C(O)c3ccc(C#N)cc3)cc2c(Cl)c1CN1CCC(C(F)(F)F)CC1]

A solution of n-butyllithium (2.5 M in hexanes, 0.5 mL, 1.25 mmol) was added dropwise by syringe to a solution of 6-bromo-4-chloro-2-methoxy-3-((4-(trifluoromethyl)piperidin-1-yl)methyl)quinoline (0.492 g, 1.12 mmol, Intermediate 40) in dry deoxygenated THF (24 mL) at −78° C. After 2 minutes, a solution of 4-formylbenzonitrile (0.164 g, 1.25 mmol) in dry THF (4 mL) was added dropwise by syringe. An additional 2 mL of THF was used to complete the quantitative addition. After 10 minutes, the flask was removed from the dry-ice bath and placed into an ice-water bath. After 2 hours, the reaction was quenched with saturated aqueous ammonium chloride solution and the mixture was partitioned between water and EtOAc. The layers were separated and the aqueous phase was further extracted with EtOAc and the combined organic layers were washed with saturated aqueous NaCl solution. The organic phase was dried (MgSO$_4$), filtered, and concentrated to dryness. The crude product was purified by flash column chromatography (silica gel, 0-30% EtOAc/hexanes) to provide the title compound. $^1$H NMR (500 MHz, CDCl$_3$) δ ppm 8.15 (d, J=2.0 Hz, 1H), 7.80 (d, J=8.6 Hz, 1H), 7.66-7.62 (m, 2H), 7.58-7.52 (m, 3H), 6.06 (s, 1H), 4.07 (s, 3H), 3.82 (s, 2H), 3.04-3.02 (m, 2H), 2.53 (s, 1H), 2.22-2.16 (m, 2H), 1.99-1.94 (m, 1H), 1.83-1.73 (m, 2H), 1.61-1.53 (m, 2H). MS (ESI): mass calcd. for C$_{25}$H$_{23}$ClF$_3$N$_3$O$_2$, 489.2; m/z found, 490.0 [M+H]$^+$.

Example 188a: (4-Chloro-2-methoxy-3-((2-(trifluoromethyl)-5,6-dihydro-[1,2,4]triazolo[1,5-a]pyrazin-7(8H)-yl)methyl)quinolin-6-yl)(1-methyl-1H-imidazol-5-yl)(2-(trifluoromethyl)pyridin-4-yl)methanol

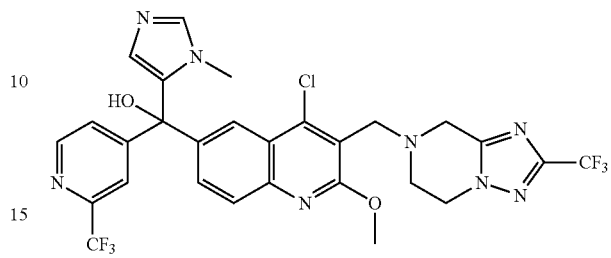

The title compound was prepared analogously to the method described in Example 100a using 6-bromo-4-chloro-2-methoxy-3-((2-(trifluoromethyl)-5,6-dihydro-[1,2,4]triazolo[1,5-a]pyrazin-7(8H)-yl)methyl)quinoline (Intermediate 75) and (1-methyl-1H-imidazol-5-yl)(2-(trifluoromethyl)pyridin-4-yl)methanone (Intermediate 14: step b) in place of 6-bromo-4-chloro-2-methoxy-3-((4-(trifluoromethyl)piperidin-1-yl)methyl)quinoline and 1-methyl-1H-imidazol-5-yl)(2-(trifluoromethyl)pyridin-4-yl)methanone respectively.

(4-Chloro-2-methoxy-3-((2-(trifluoromethyl)-5,6-dihydro-[1,2,4]triazolo[1,5-a]pyrazin-7(8H)-yl)methyl)quinolin-6-yl)(1-methyl-1H-imidazol-5-yl)(2-(trifluoromethyl)pyridin-4-yl)methanol was purified by chiral SFC (Chiralpak AD-H, 5 μm, 250×20 mm, mobile phase: 0.3% isopropyl amine, 75% CO$_2$, 25% ethanol). The first eluting enantiomer was Example 188b: $^1$H NMR (400 MHz, CDCl$_3$) δ ppm 8.72 (d, J=5.1 Hz, 1H), 8.14 (d, J=2.1 Hz, 1H), 7.90-7.82 (m, 2H), 7.61 (dd, J=8.8, 2.1 Hz, 1H), 7.55-7.48 (m, 1H), 7.43 (s, 1H), 6.43 (s, 1H), 4.23 (t, J=5.5 Hz, 2H), 4.14-4.08 (m, 5H), 3.95 (s, 2H), 3.38 (s, 3H), 3.20 (t, J=5.5 Hz, 2H); MS (ESI): mass calcd. for C$_{28}$H$_{23}$ClF$_6$N$_8$O$_2$, 652.1; m/z found, 652.9 [M+H]$^+$ and the second eluting enantiomer was Example 188c: $^1$H NMR (400 MHz, CDCl$_3$) δ ppm 8.71 (d, J=5.1 Hz, 1H), 8.15 (d, J=2.1 Hz, 1H), 7.93-7.79 (m, 2H), 7.61 (dd, J=8.8, 2.2 Hz, 1H), 7.50 (dd, J=5.4, 1.6 Hz, 1H), 7.38 (s, 1H), 6.39 (s, 1H), 4.70 (s, 1H), 4.23 (t, J=5.5 Hz, 2H), 4.17-4.01 (m, 5H), 3.95 (s, 2H), 3.36 (s, 3H), 3.20 (t, J=5.5 Hz, 2H); MS (ESI): mass calcd. for C$_{28}$H$_{23}$ClF$_6$N$_8$O$_2$, 652.1; m/z found, 652.9 [M+H]$^+$.

Example 189a: (4-Chloro-2-methoxy-3-((3-(trifluoromethyl)-5,6-dihydro-[1,2,4]triazolo[4,3-a]pyrazin-7(8H)-yl)methyl)quinolin-6-yl)(1-methyl-1H-imidazol-5-yl)(2-(trifluoromethyl)pyridin-4-yl)methanol

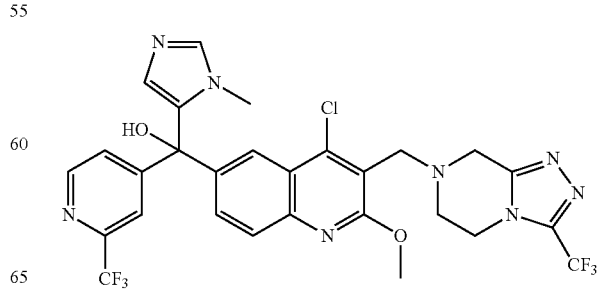

The title compound was prepared analogously to the method described in Example 100a using 6-bromo-4-chloro-2-methoxy-3-((3-(trifluoromethyl)-5,6-dihydro-[1,2,4]triazolo[4,3-a]pyrazin-7(8H)-yl)methyl)quinoline (Intermediate 76) and (1-methyl-1H-imidazol-5-yl)(2-(trifluoromethyl)pyridin-4-yl)methanone (Intermediate 14: step b) in place of 6-bromo-4-chloro-2-methoxy-3-((4-(trifluoromethyl)piperidin-1-yl)methyl)quinoline and 1-methyl-1H-imidazol-5-yl)(2-(trifluoromethyl)pyridin-4-yl)methanone respectively.

(4-Chloro-2-methoxy-3-((3-(trifluoromethyl)-5,6-dihydro-[1,2,4]triazolo[4,3-a]pyrazin-7(8H)-yl)methyl)quinolin-6-yl)(1-methyl-1H-imidazol-5-yl)(2-(trifluoromethyl)pyridin-4-yl)methanol was purified by chiral SFC (Chiralpak AD-H, 5 µm, 250×20 mm, mobile phase: 0.3% isopropyl amine, 75% $CO_2$, 25% ethanol). The first eluting enantiomer was Example 189b: $^1$H NMR (400 MHz, CDCl$_3$) δ ppm 8.70 (d, J=5.1 Hz, 1H), 8.15 (d, J=2.1 Hz, 1H), 7.91-7.82 (m, 2H), 7.61 (dd, J=8.8, 2.1 Hz, 1H), 7.54-7.48 (m, 1H), 7.41 (s, 1H), 6.42 (s, 1H), 4.56 (s, 1H), 4.13-4.10 (m, 7H), 4.00 (s, 2H), 3.38 (s, 3H), 3.12 (t, J=5.5 Hz, 2H); MS (ESI): mass calcd. for $C_{28}H_{23}ClF_6N_8O_2$, 652.1; m/z found, 652.9 [M+H]$^+$ and the second eluting enantiomer was Example 189c: $^1$H NMR (400 MHz, CDCl$_3$) δ ppm 8.69 (d, J=5.1 Hz, 1H), 8.16 (d, J=2.1 Hz, 1H), 7.91-7.81 (m, 2H), 7.61 (dd, J=8.8, 2.1 Hz, 1H), 7.51 (dd, J=5.2, 1.7 Hz, 1H), 7.38 (s, 1H), 6.39 (s, 1H), 4.93 (s, 1H), 4.13-4.10 (m, 7H), 4.00 (s, 2H), 3.37 (s, 3H), 3.12 (t, J=5.5 Hz, 2H); MS (ESI): mass calcd. for $C_{28}H_{23}ClF_6N_8O_2$, 652.1; m/z found, 652.9 [M+H]$^+$.

Example 190a: (4-Chloro-2-methoxy-3-((methyl(2,2,2-trifluoroethyl)amino)methyl)quinolin-6-yl)(1-methyl-1H-imidazol-5-yl)(2-(trifluoromethyl)pyridin-4-yl)methanol

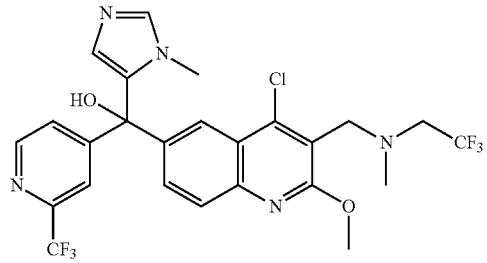 [SMILES: COc1nc2ccc(C(O)(c3ccnc(C(F)(F)F)c3)c3cncn3C)cc2c(Cl)c1CN(C)CC(F)(F)F]

The title compound was prepared analogously to the method described in Example 100a using N-((6-bromo-4-chloro-2-methoxyquinolin-3-yl)methyl)-2,2,2-trifluoro-N-methylethanamine (Intermediate 77) and (1-methyl-1H-imidazol-5-yl)(2-(trifluoromethyl)pyridin-4-yl)methanone (Intermediate 14: step b) in place of 6-bromo-4-chloro-2-methoxy-3-((4-(trifluoromethyl)piperidin-1-yl)methyl)quinoline and 1-methyl-1H-imidazol-5-yl)(2-(trifluoromethyl)pyridin-4-yl)methanone respectively.

(4-Chloro-2-methoxy-3-((methyl(2,2,2-trifluoroethyl)amino)methyl)quinolin-6-yl)(1-methyl-1H-imidazol-5-yl)(2-(trifluoromethyl)pyridin-4-yl)methanol was purified by chiral SFC (Chiralpak IC, 5 µm, 250×20 mm, mobile phase: 0.3% isopropyl amine, 70% $CO_2$, 30% ethanol). The first eluting enantiomer was Example 190b: $^1$H NMR (600 MHz, CDCl$_3$) δ ppm 8.70 (d, J=5.1 Hz, 1H), 8.16 (d, J=2.1 Hz, 1H), 7.88 (s, 1H), 7.82 (d, J=8.7 Hz, 1H), 7.56 (dd, J=8.7, 2.2 Hz, 1H), 7.49 (dd, J=5.1, 1.7 Hz, 1H), 7.33 (s, 1H), 6.35 (s, 1H), 4.84 (s, 1H), 4.10 (s, 3H), 4.05 (s, 2H), 3.35 (s, 3H), 3.21 (q, J=9.5 Hz, 2H), 2.47 (s, 3H); MS (ESI): mass calcd. for $C_{25}H_{22}ClF_6N_5O_2$, 573.1; m/z found, 574.1 [M+H]$^+$ and the second eluting enantiomer was Example 190c: $^1$H NMR (600 MHz, CDCl$_3$) δ ppm 8.71 (d, J=5.1 Hz, 1H), 8.15 (d, J=2.1 Hz, 1H), 7.87 (d, J=1.7 Hz, 1H), 7.82 (d, J=8.7 Hz, 1H), 7.56 (dd, J=8.8, 2.2 Hz, 1H), 7.50 (dd, J=5.1, 1.7 Hz, 1H), 7.38 (s, 1H), 6.39 (s, 1H), 4.44 (s, 1H), 4.10 (s, 3H), 4.05 (s, 2H), 3.36 (s, 3H), 3.21 (q, J=9.6 Hz, 2H), 2.47 (s, 3H); MS (ESI): mass calcd. for $C_{25}H_{22}ClF_6N_5O_2$, 573.1; m/z found, 574.1 [M+H]$^+$.

Example 191a: 6-(Hydroxy(1-methyl-1H-imidazol-5-yl)(6-(trifluoromethyl)pyridin-3-yl)methyl)-2-methoxy-3-((4-(trifluoromethyl)piperidin-1-yl)methyl)quinoline-4-carbonitrile

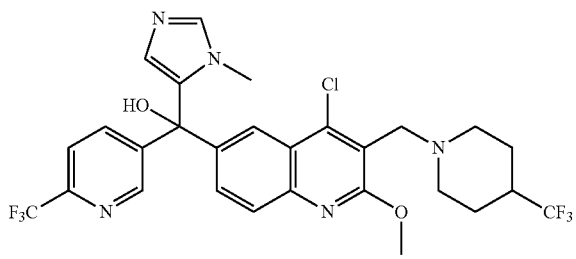

A microwave vial was charged with (4-chloro-2-methoxy-3-((4-(trifluoromethyl)piperidin-1-yl)methyl)quinolin-6-yl)(1-methyl-1H-imidazol-5-yl)(6-(trifluoromethyl)pyridin-3-yl)methanol (370 mg, 0.603 mmol, Example 112a), Zn(CN)$_2$ (230 mg, 1.96 mmol), Pd$_2$dba$_3$ (82.3 mg, 0.090 mmol), zinc dust (19.7 mg, 0.301 mmol), and dicyclohexyl(2',4',6'-triisopropyl-[1,1'-biphenyl]-2-yl)phosphine (X-Phos, 59.2 mg, 0.121 mmol). Dimethylacetamide (10 mL) was then added and the mixture was purged with nitrogen for 10 minutes and placed in a pre-heated aluminum block at 120° C. for 18 hours. The mixture was cooled to room temperature and was filtered through Celite®, and washed with EtOAc. Purification by flash column chromatography (silica gel, 5% MeOH in dichloromethane) yielded the title compound.

6-(Hydroxy(1-methyl-1H-imidazol-5-yl)(6-(trifluoromethyl)pyridin-3-yl)methyl)-2-methoxy-3-((4-(trifluoromethyl)piperidin-1-yl)methyl)quinoline-4-carbonitrile was purified by chiral SFC (Lux 5u Cellulose-4, 5 µm, 250×21 mm, mobile phase: 88% $CO_2$, 12% isopropanol containing isopropyl amine). The first eluting enantiomer was Example 191b: $^1$H NMR (600 MHz, CDCl$_3$) δ ppm 8.79 (s, 1H), 8.22 (d, J=2.1 Hz, 1H), 7.96 (dd, J=8.2, 2.2 Hz, 1H), 7.85 (d, J=8.8 Hz, 1H), 7.69 (d, J=8.3 Hz, 1H), 7.51 (dd, J=8.8, 2.1 Hz, 1H), 7.37 (s, 1H), 6.42 (s, 1H), 4.11 (s, 3H), 3.81 (d, J=1.7 Hz, 2H), 3.40 (s, 3H), 3.03-3.01 (m, 2H), 2.27-2.19 (m, 2H), 2.06-1.94 (m, 1H), 1.82-1.80 (d, J=12.9 Hz, 2H), 1.67-1.50 (m, 2H); MS (ESI): mass calcd. for $C_{29}H_{26}F_6N_6O_2$, 604.1; m/z found, 604.8 [M+H]$^+$ and the second eluting enantiomer was Example 191c: $^1$H NMR (600 MHz, CDCl$_3$) δ ppm 8.77 (s, 1H), 8.22 (d, J=2.1 Hz, 1H), 7.96-7.91 (m, 1H), 7.85 (d, J=8.8 Hz, 1H), 7.68 (d, J=8.1 Hz, 1H), 7.51 (dd, J=8.9, 2.1 Hz, 1H), 7.40 (s, 1H), 6.42 (s, 1H), 4.11 (s, 3H), 3.82 (s, 2H), 3.41 (s, 3H), 3.04-3.01 (m, 2H), 2.27-2.19 (m, 2H), 2.07-1.94 (m, 1H), 1.82-1.80 (m, 2H), 1.67-1.51 (m, 2H); MS (ESI): mass calcd. for $C_{29}H_{26}F_6N_6O_2$, 604.1; m/z found, 604.8 [M+H]$^+$.

Example 192a: 4-((4-Chloro-2-methoxy-3-((4-(trifluoromethyl)piperidin-1-yl)methyl)quinolin-6-yl)(hydroxy)(1-methyl-1H-imidazol-5-yl)methyl)benzonitrile

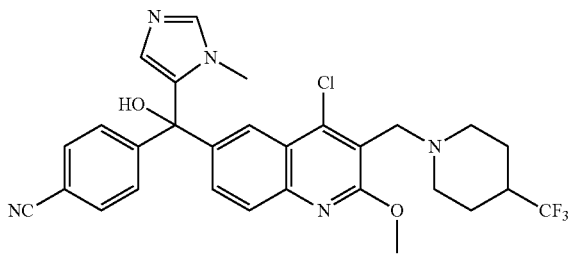 [SMILES: COc1nc2ccc(C(O)(c3ccc(C#N)cc3)c3cncn3C)cc2c(Cl)c1CN1CCC(C(F)(F)F)CC1]

A solution of iPrMgCl (0.44 mL, 0.86 mmol, 1.96 M solution in hexane) was added slowly to a solution of 5-bromo-1-methyl-1H-imidazole (150 mg, 0.932 mmol) in THF (2.5 mL) at 0° C. After addition, stirring was continued for an additional 35 minutes. Then a mixture of LaCl$_3$.2LiCl (1.07 mL, 0.643 mmol, 0.6 M in THF) and (4-(4-chloro-2-methoxy-3-((4-(trifluoromethyl)piperidin-1-yl)methyl)quinoline-6-carbonyl)benzonitrile (300 mg, 0.615 mmol, Intermediate 78: step b) in THF (2 mL) prepared in a separate flask was added slowly via syringe to the Grignard solution described above. An additional 1.5 mL of THF was used to complete the quantitative addition. The mixture was stirred at 0° C. for 30 minutes. The solution was quenched with saturated aqueous NH$_4$Cl solution. H$_2$O was added and layers were separated. The aqueous layer was extracted with EtOAc and the combined organic extracts were washed with brine, dried over MgSO$_4$, filtered, and evaporated in vacuo. The crude product was purified by trituration with DCM to provide the title compound.

4-((4-Chloro-2-methoxy-3-((4-(trifluoromethyl)piperidin-1-yl)methyl)quinolin-6-yl)(hydroxy)(1-methyl-1H-imidazol-5-yl)methyl)benzonitrile was purified by chiral SFC (Chiralpak AD-H, 5 μm, 250×30 mm, mobile phase: 0.3% isopropyl amine, 90% CO$_2$, 10% methanol). The first eluting enantiomer was Example 192b: $^1$H NMR (400 MHz, CDCl$_3$) δ ppm 8.09 (s, 1H), 7.79 (d, J=8.7 Hz, 1H), 7.66 (d, J=8.0 Hz, 2H), 7.55 (d, J=7.8 Hz, 3H), 7.41 (s, 1H), 6.40 (s, 1H), 4.08 (s, 3H), 4.00 (s, 1H), 3.80 (s, 2H), 3.38 (s, 3H), 3.05-2.99 (m, 2H), 2.22-2.16 (m, 2H), 2.00-1.95 (m, 1H), 1.81-1.75 (m, 2H), 1.65-1.52 (m, 2H); MS (ESI): mass calcd. for $C_{29}H_{27}ClF_3N_5O_2$, 569.2; m/z found, 569.9 [M+H]$^+$ and the second eluting enantiomer was Example 192c: $^1$H NMR (400 MHz, CDCl$_3$) δ ppm 8.09 (d, J=2.1 Hz, 1H), 7.80 (d, J=8.7 Hz, 1H), 7.66 (d, J=8.1 Hz, 2H), 7.58-7.51 (m, 3H), 7.41 (s, 1H), 6.40 (s, 1H), 4.08 (s, 3H), 3.90 (s, 1H), 3.80 (s, 2H), 3.38 (s, 3H), 3.03-3.01 (m, 2H), 2.20-2.16 (m, 2H), 2.00-1.95 (m, 1H), 1.79-1.77 (m, 2H), 1.63-1.53 (m, 2H); MS (ESI): mass calcd. for $C_{29}H_{27}ClF_3N_5O_2$, 569.2; m/z found, 569.9 [M+H]$^+$.

Example 193: (4-Chloro-2-methoxy-3-(((3,3,3-trifluoropropyl)amino)methyl)quinolin-6-yl)bis(1,2-dimethyl-1H-imidazol-5-yl)methanol

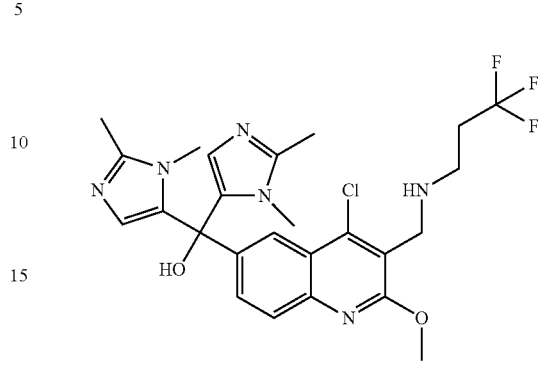

3,3,3-Trifluoropropylamine (0.13 mL, 1.321 mmol) was added to a suspension of (4-chloro-3-(chloromethyl)-2-methoxyquinolin-6-yl)bis(1,2-dimethyl-1H-imidazol-5-yl)methanol (202.7 mg, 0.44 mmol, Intermediate 79: step e) in ethanol. Triethylamine (0.13 mL, 0.935 mmol) was added and then the mixture was stirred at 85° C. overnight. The reaction was allowed to cool to ambient temperature and was concentrated to remove ethanol. Methylene chloride and water were added, the layers were separated, and the aqueous layer was extracted with additional methylene chloride. The combined organic layers were dried over sodium sulfate, filtered, and concentrated to dryness. The crude product was purified by reverse-phase HPLC (acetonitrile/20 mM ammonium hydroxide). Product fractions were lyophilized to isolate the title compound. $^1$H NMR (500 MHz, CDCl$_3$) δ ppm 8.20 (d, J=2.2 Hz, 1H), 7.72 (d, J=8.7 Hz, 1H), 7.42 (dd, J=8.7, 2.2 Hz, 1H), 6.21 (s, 2H), 4.34 (s, 1H), 4.12 (s, 2H), 4.11 (s, 3H), 3.42 (s, 6H), 2.89 (t, J=7.2 Hz, 2H), 2.39-2.34 (m, 2H), 2.33 (s, 6H); MS m/e 537.2 [M+H]$^+$.

Example 194: (4-Chloro-2-methoxy-3-(((2-(2,2,2-trifluoroethoxy)ethyl)amino)methyl)quinolin-6-yl)bis(1,2-dimethyl-1H-imidazol-5-yl)methanol

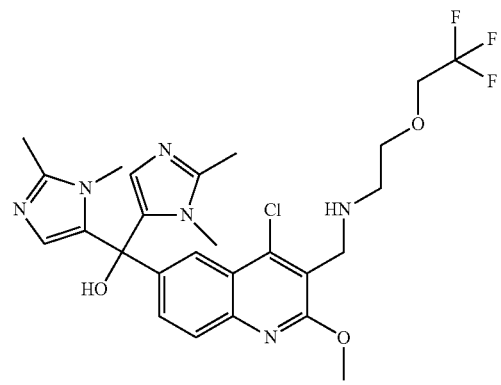 [SMILES: COc1nc2ccc(C(O)(c3cnc(C)n3C)c3cnc(C)n3C)cc2c(Cl)c1CNCCOCC(F)(F)F]

2-(2,2,2-Trifluoroethoxy)ethanamine hydrochloride (242 mg, 1.35 mmol) was added to a suspension of (4-chloro-3-(chloromethyl)-2-methoxyquinolin-6-yl)bis(1,2-dimethyl-1H-imidazol-5-yl)methanol (206.8 mg, 0.449 mmol, Intermediate 79: step e) in ethanol. Triethylamine (0.19 mL, 1.37 mmol) and potassium iodide (14.9 mg, 0.09 mmol) were added and the mixture was heated in a microwave at 85° C. for 30 minutes. The reaction was allowed to cool to ambient temperature and was concentrated to remove ethanol. Methylene chloride and water were added, the layers were separated, and the aqueous layer was extracted with additional methylene chloride. The combined organic layers were dried over sodium sulfate, filtered, and concentrated to dryness. The crude product was purified by reverse-phase HPLC (acetonitrile/20 mM ammonium hydroxide). Product fractions were lyophilized to isolate the title compound. $^1$H NMR (500 MHz, CDCl$_3$) δ ppm 8.21 (d, J=2.1 Hz, 1H), 7.68 (d, J=8.7 Hz, 1H), 7.38 (d, J=8.6 Hz, 1H), 6.14 (s, 2H), 5.63 (s, 1H), 4.12 (s, 2H), 4.11 (s, 3H), 3.82 (q, J=8.7 Hz, 2H), 3.74 (t, J=5.1 Hz, 2H), 3.39 (s, 6H), 2.86 (t, J=5.1 Hz, 2H), 2.28 (s, 6H), 2.25 (s, 1H); MS m/e 567.0 [M+H]$^+$.

Example 195: (4-Chloro-2-methoxy-3-(((4,4,4-trifluorobutyl)amino)methyl)quinolin-6-yl)bis(1,2-dimethyl-1H-imidazol-5-yl)methanol

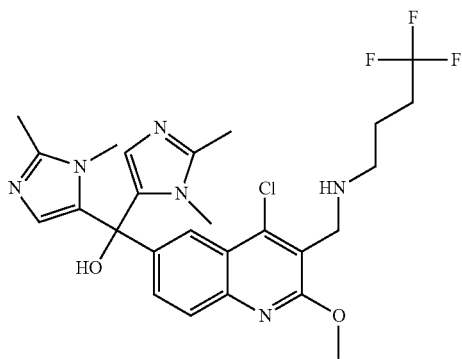 [SMILES: COc1nc2ccc(C(O)(c3cnc(C)n3C)c3cnc(C)n3C)cc2c(Cl)c1CNCCCC(F)(F)F]

The title compound was prepared analogously to the method in Example 194, using 4,4,4-trifluorobutylamine in place of 2-(2,2,2-trifluoroethoxy)ethanamine hydrochloride. $^1$H NMR (500 MHz, CDCl$_3$) δ ppm 8.21 (d, J=2.2 Hz, 1H), 7.68 (d, J=8.7 Hz, 1H), 7.39 (d, J=8.7 Hz, 1H), 6.16 (s, 2H), 4.11 (s, 3H), 4.09 (s, 2H), 3.40 (s, 6H), 2.71 (t, J=6.9 Hz, 2H), 2.30 (s, 6H), 2.22-2.15 (m, 2H), 1.80-1.75 (m, 2H); MS m/e 551.0 [M+H]$^+$.

Example 196: (4-Chloro-2-methoxy-3-((4-(3-(trifluoromethyl)-1H-pyrazol-1-yl)piperidin-1-yl)methyl)quinolin-6-yl)bis(1,2-dimethyl-1H-imidazol-5-yl)methanol

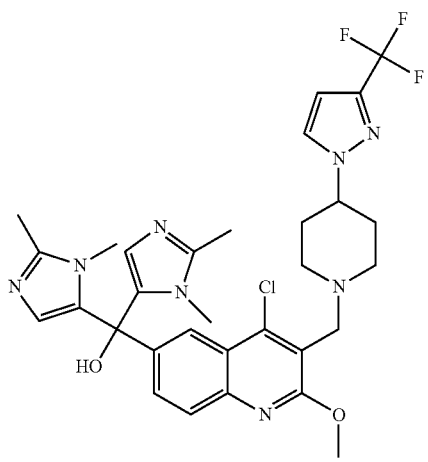 [SMILES: COc1nc2ccc(C(O)(c3cnc(C)n3C)c3cnc(C)n3C)cc2c(Cl)c1CN1CCC(n2ccc(C(F)(F)F)n2)CC1]

The title compound was prepared analogously to the method in Example 193, using 4-[3-(trifluoromethyl)pyrazol-1-yl]piperidine in place of 3,3,3-trifluoropropylamine. $^1$H NMR (500 MHz, CDCl$_3$) δ ppm 8.21 (d, J=2.2 Hz, 1H), 7.72 (d, J=8.6 Hz, 1H), 7.45-7.40 (m, 2H), 6.49 (d, J=2.3 Hz, 1H), 6.23 (s, 2H), 4.25-4.16 (m, 1H), 4.10 (s, 3H), 4.06 (s, 1H), 3.85 (s, 2H), 3.43 (s, 6H), 3.11 (d, J=11.7 Hz, 2H), 2.40 (td, J=11.9, 2.4 Hz, 2H), 2.34 (s, 6H), 2.15-2.08 (m, 2H), 2.06-1.98 (m, 2H); MS m/e 643.2 [M+H]$^+$.

Example 197: (4-Chloro-2-methoxy-3-(((1,1,1-trifluorobutan-2-yl)amino)methyl)quinolin-6-yl)bis(1,2-dimethyl-1H-imidazol-5-yl)methanol

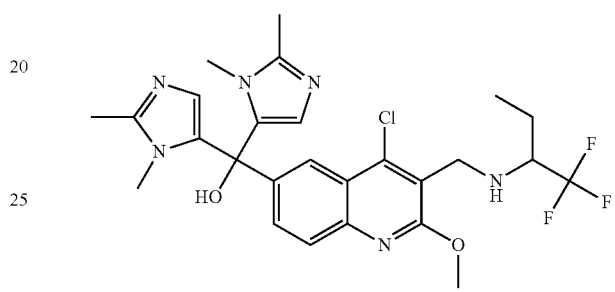

The title compound was prepared analogously to the method in Example 193, using 1,1,1-trifluoro-2-butylamine in place of 3,3,3-trifluoropropylamine. $^1$H NMR (500 MHz, CDCl$_3$) δ ppm 8.22 (d, J=2.2 Hz, 1H), 7.69 (d, J=8.7 Hz, 1H), 7.38 (dd, J=8.8, 2.2 Hz, 1H), 6.18 (d, J=7.6 Hz, 2H), 4.88 (s, 1H), 4.30-4.23 (m, 1H), 4.20-4.14 (m, 1H), 4.12 (s, 3H), 3.41 (d, J=2.4 Hz, 6H), 3.01-2.93 (m, 1H), 2.31 (d, J=1.5 Hz, 6H), 1.78-1.72 (m, 2H), 1.53-1.43 (m, 1H), 0.91 (t, J=7.4 Hz, 3H); MS m/e 551.2 [M+H]$^+$.

Example 198: (4-Chloro-2-methoxy-3-((methyl(2,2,2-trifluoroethyl)amino)methyl)quinolin-6-yl)bis(1,2-dimethyl-1H-imidazol-5-yl)methanol

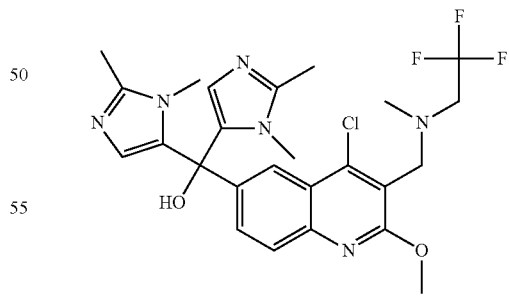

The title compound was prepared analogously to the method in Example 193, using N-methyl-N-(2,2,2-trifluoroethyl)amine in place of 3,3,3-trifluoropropylamine. $^1$H NMR (500 MHz, CDCl$_3$) δ ppm 8.21 (d, J=2.2 Hz, 1H), 7.73 (d, J=8.6 Hz, 1H), 7.43 (dd, J=8.8, 2.2 Hz, 1H), 6.24 (s, 2H), 4.11 (s, 3H), 4.06 (s, 2H), 3.43 (s, 6H), 3.23 (q, J=9.6 Hz, 2H), 2.49 (s, 3H), 2.34 (s, 6H). MS m/e 537.2 [M+H]$^+$.

Example 199: (R)-(4-Chloro-2-methoxy-3-(((1,1,1-trifluoropropan-2-yl)amino)methyl)quinolin-6-yl)bis(1,2-dimethyl-1H-imidazol-5-yl)methanol

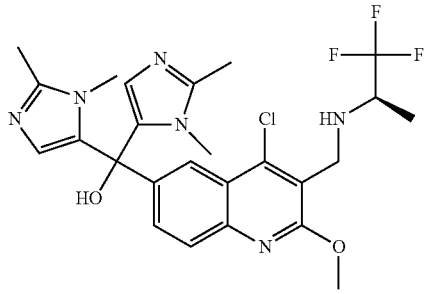 [SMILES: COc1nc2ccc(C(O)(c3cnc(C)n3C)c3cnc(C)n3C)cc2c(Cl)c1CN[C@H](C)C(F)(F)F]

The title compound was prepared analogously to the method in Example 193, using (R)-1,1,1-trifluoro-2-propylamine in place of 3,3,3-trifluoropropylamine. $^1$H NMR (500 MHz, CDCl$_3$) δ ppm 8.21 (d, J=2.2 Hz, 1H), 7.70 (d, J=8.8 Hz, 1H), 7.40 (dd, J=8.7, 2.2 Hz, 1H), 6.20 (d, J=6.8 Hz, 2H), 4.55 (s, 1H), 4.21 (s, 2H), 4.12 (s, 3H), 3.41 (s, 6H), 3.27-3.19 (m, 1H), 2.32 (s, 6H), 1.26 (d, J=6.7 Hz, 3H); MS m/e 537.2 [M+H]$^+$.

Example 200: (S)-(4-Chloro-2-methoxy-3-(((1,1,1-trifluoropropan-2-yl)amino)methyl)quinolin-6-yl)bis(1,2-dimethyl-1H-imidazol-5-yl)methanol

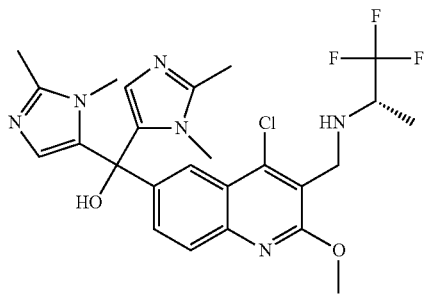 [SMILES: COc1nc2ccc(C(O)(c3cnc(C)n3C)c3cnc(C)n3C)cc2c(Cl)c1CN[C@@H](C)C(F)(F)F]

The title compound was prepared analogously to the method in Example 193, using (S)-1,1,1-trifluoro-2-propylamine in place of 3,3,3-trifluoropropylamine. $^1$H NMR (500 MHz, CDCl$_3$) δ ppm 8.21 (d, J=2.1 Hz, 1H), 7.70 (d, J=8.7 Hz, 1H), 7.39 (dd, J=8.6, 2.1 Hz, 1H), 6.19 (d, J=7.3 Hz, 2H), 4.68 (s, 1H), 4.21 (d, J=1.8 Hz, 2H), 4.12 (s, 3H), 3.44-3.39 (m, 6H), 3.29-3.20 (m, 1H), 2.32 (s, 6H), 1.26 (d, J=6.7 Hz, 3H); MS m/e 537.2 [M+H]$^+$.

Example 201: (4-Chloro-2-methoxy-3-(((3-(trifluoromethyl)cyclohexyl)amino)methyl)quinolin-6-yl)bis(1,2-dimethyl-1H-imidazol-5-yl)methanol

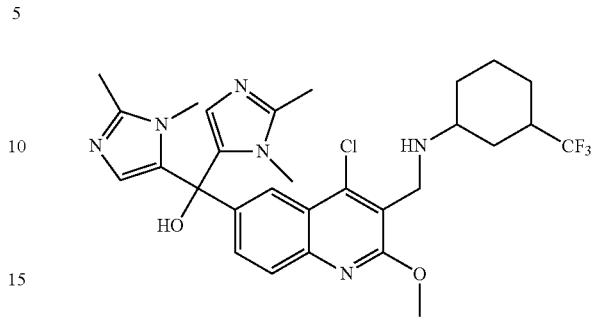

The title compound was prepared analogously to the method in Example 194, using 3-(trifluoromethyl)cyclohexanamine in place of 2-(2,2,2-trifluoroethoxy)ethanamine hydrochloride.

$^1$H NMR (500 MHz, DMSO-d$_6$) δ ppm 8.21 (s, 1H), 7.79 (d, J=8.7 Hz, 1H), 7.45 (d, J=8.4 Hz, 1H), 7.05 (s, 1H), 5.94 (d, J=1.4 Hz, 2H), 4.04 (s, 3H), 4.03-3.99 (m, 2H), 2.50 (s, 6H, two methyl peaks hidden under residual solvent peak), 2.45 (s, 1H), 2.25 (s, 6H), 2.13 (dd, J=13.2, 3.0 Hz, 1H), 1.97-1.89 (m, 2H), 1.80-1.75 (m, 2H), 1.34-1.22 (m, 1H), 1.17-1.07 (m, 1H), 1.03-0.93 (m, 2H)

Example 202: (R)-(4-Chloro-2-methoxy-3-(((1,1,1-trifluorobutan-2-yl)amino)methyl)quinolin-6-yl)bis(1,2-dimethyl-1H-imidazol-5-yl)methanol

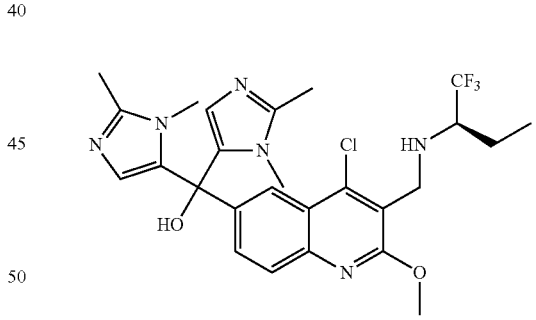

The title compound was prepared analogously to the method in Example 194, using (R)-1,1,1-trifluoro-2-butylamine in place of 2-(2,2,2-trifluoroethoxy)ethanamine hydrochloride. $^1$H NMR (500 MHz, DMSO-d$_6$) δ ppm 8.22 (s, 1H), 7.83-7.77 (m, 1H), 7.46 (d, J=7.9 Hz, 1H), 7.05 (s, 1H), 5.93 (dd, J=6.7, 2.1 Hz, 2H), 4.18-4.06 (m, 2H), 4.06-3.97 (m, 3H), 3.06 (s, 1H), 2.50 (s, 6H, two methyl peaks hidden under residual solvent peak), 2.41-2.34 (m, 1H), 2.31-2.20 (m, 6H), 1.67-1.55 (m, 1H), 1.46-1.36 (m, 1H), 0.85 (t, J=7.4 Hz, 3H)

Example 203: (4-Chloro-2-methoxy-3-((((4-(trifluoromethyl)cyclohexyl)methyl)amino)methyl)quinolin-6-yl)bis(1,2-dimethyl-1H-imidazol-5-yl)methanol

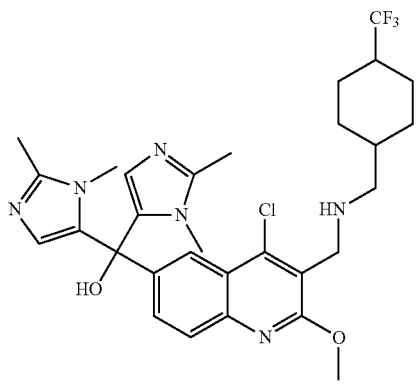 [SMILES: COc1nc2ccc(C(O)(c3cnc(C)n3C)c3cnc(C)n3C)cc2c(Cl)c1CNCC1CCC(C(F)(F)F)CC1]

The title compound was prepared analogously to the method in Example 194, using (4-(trifluoromethyl)cyclohexyl)methanamine in place of 2-(2,2,2-trifluoroethoxy)ethanamine hydrochloride. $^1$H NMR (500 MHz, DMSO-$d_6$) δ ppm 8.22 (s, 1H), 7.82 (d, J=8.7 Hz, 1H), 7.48 (d, J=8.6 Hz, 1H), 7.11 (s, 1H), 5.97 (s, 2H), 4.14-4.09 (m, 2H), 4.06 (s, 3H), 2.73-2.67 (m, 1H), 2.50 (s, 6H, two methyl peaks hidden under residual solvent peak), 2.27 (s, 6H), 1.86 (d, J=11.2 Hz, 2H), 1.65-1.56 (m, 4H), 1.55-1.46 (m, 2H), 1.45-1.35 (m, 2H), 1.26-1.17 (m, 1H), 0.97 (s, 1H)

Example 204: (4-Chloro-2-methoxy-3-(((1,1,1-trifluoro-2-methylpropan-2-yl)amino)methyl)quinolin-6-yl)bis(1,2-dimethyl-1H-imidazol-5-yl)methanol

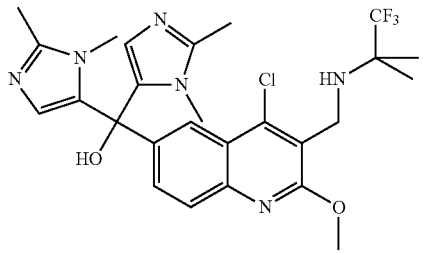 [SMILES: COc1nc2ccc(C(O)(c3cnc(C)n3C)c3cnc(C)n3C)cc2c(Cl)c1CNC(C)(C)C(F)(F)F]

The title compound was prepared analogously to the method in Example 194, using 1,1,1-trifluoro-2-methylpropan-2-amine in place of 2-(2,2,2-trifluoroethoxy)ethanamine hydrochloride. $^1$H NMR (500 MHz, DMSO-$d_6$) δ ppm 8.19 (s, 1H), 7.82-7.77 (m, 1H), 7.49-7.43 (m, 1H), 5.95-5.92 (m, 2H), 4.06-4.02 (m, 5H), 3.18-3.15 (m, 1H), 2.50 (s, 6H, two methyl peaks hidden under residual solvent peak), 2.33-2.28 (m, 1H), 2.27-2.23 (m, 6H), 1.31-1.27 (m, 6H)

Example 205a: (4-Chloro-2-cyclopropyl-3-((4-trifluoromethyl)piperidin-1-yl)methyl)quinolin-6-yl)(1-methyl-1H-imidazol-5-yl)(6-trifluoromethyl)pyridine-3-yl)methanol

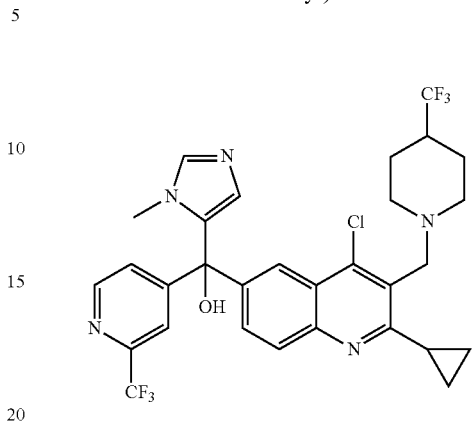

In a 2-necked, 50 mL oven dried round bottom flask containing 6-bromo-4-chloro-2-cyclopropyl-3-((4-trifluoromethyl)piperidin-1-yl)methyl)quinolone (500 mg, 1.1 mmol, Intermediate 80: step e) was added deoxygenated THF (3.5 mL, THF was deoxygenated by passing argon through the solvent with a vent for 30 minutes, to get reagent completely in solution a total of 8.5 mL of THF was necessary). The mixture was cooled to −78° C. (approximately 10 minutes was given for the reaction to reach this temperature) then n-BuLi (0.45 mL, 1.1 mmol, 2.5 M in hexanes) was added over 1 minute, maintaining the temperature at −78° C. A solution of (1-methyl-1H-imidazol-5-yl)(6-(trifluoromethyl)pyridine-3-yl)methanone (313 mg, 1.2 mmol, Intermediate 14: step b) in THF (3.5 mL) was added at −78° C. After 20 minutes at −78° C., the dry ice/acetone bath was removed and replaced with a 0° C. ice bath. The reaction was stirred for an additional 2 hours allowing the temperature to gradually warm to room temperature. The reaction was then quenched with saturated aqueous ammonium chloride solution (100 mL) and extracted with EtOAc (3×50 mL). The combined organic layers were washed with brine, dried (MgSO$_4$), filtered and concentrated. The crude material was purified using 0 to 6% MeOH in DCM (40 gram silica gel column, 15 minute ramp, 30 minute run) to afford the title compound. The pure enantiomers of (4-chloro-2-cyclopropyl-3-((4-trifluoromethyl)piperidin-1-yl)methyl)quinolin-6-yl)(1-methyl-1H-imidazol-5-yl)(6-trifluoromethyl)pyridine-3-yl)methanol were separated by SFC (Stationary phase: Chiralpak OZ-H 5 µm, 250×21 mm, Mobile phase: 10% EtOH+0.2% TEA, 90% CO$_2$, elution was monitored by following absorbance at 240 nm. The first eluting enantiomer was Example 205b: $^1$H NMR (400 MHz, CDCl$_3$) δ ppm 8.66 (d, J=5.0 Hz, 1H), 8.21 (d, J=2.0 Hz, 1H), 7.95-7.81 (m, 2H), 7.56 (dd, J=8.8, 2.1 Hz, 1H), 7.52-7.43 (m, 1H), 7.20 (s, 1H), 6.25 (s, 2H), 3.97 (s, 2H), 3.30 (s, 3H), 3.04-2.87 (m, 2H), 2.73-2.65 (m, 1H), 2.30-2.14 (m, 2H), 2.07-1.98 (m, 1H), 1.88-1.45 (m, 3H), 1.39-1.20 (m, 3H), 1.12-0.95 (m, 2H), MS (ESI): mass calcd. for C$_{30}$H$_{28}$ClF$_6$N$_5$O 623.19; found m/z=624.2 [M+H]$^+$; and the second eluting enantiomer was Example 205c: $^1$H NMR (400 MHz, CDCl$_3$) δ 8.66 (d, J=5.0 Hz, 1H), 8.21 (d, J=2.0 Hz, 1H), 7.96-7.81 (m, 2H), 7.56 (dd, J=8.9, 2.2 Hz, 1H), 7.51-7.43 (m, 1H), 7.20 (s, 1H), 6.25 (s, 2H), 3.97 (s, 2H), 3.30 (s, 3H), 3.04-2.87 (m, 2H), 2.73-2.65 (m, 1H), 2.30-2.14 (m, 2H), 2.07-1.98 (m, 1H), 1.88-1.46 (m, 3H), 1.39-1.20 (m, 3H), 1.12-0.95 (m, 2H), MS (ESI): mass calcd. for $C_{30}H_{28}ClF_6N_5O$ 623.19; found m/z=624.2 [M+H]⁺.

Example 206: 6-((1,2-Dimethyl-1H-imidazol-5-yl)(hydroxy)(1-methyl-1H-1,2,3-triazol-5-yl)methyl)-2-methoxy-3-(2,2,2-trifluoroethyl)quinoline-4-carbonitrile

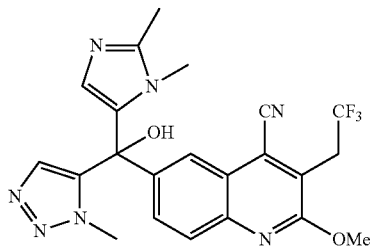 [SMILES: COc1nc2ccc(C(O)(c3cnnn3C)c3cnc(C)n3C)cc2c(C#N)c1CC(F)(F)F]

To a large microwave vial containing (4-chloro-2-methoxy-3-(2,2,2-trifluoroethyl)quinolin-6-yl)(1,2-dimethyl-1H-imidazol-5-yl)(1-methyl-1H-1,2,3-triazol-5-yl) methanol (330 mg, 0.69 mmol, Example 137) was added zinc cyanide (169 mg, 1.44 mmol), 2-dicyclohexylphosphino-2',4',6'-triisopropylbiphenylene (X-Phos, 105 mg, 0.22 mmol), tris(dibenzylideneacetone)dipalladium (95 mg, 0.10 mmol), and zinc metal (3 mg, 0.046 mmol). Then DMA (sparged with argon for 20 minutes) was added and the vial was sealed and evacuated. The mixture was placed in an aluminum heating mantle preheated to 125° C. After 3 hours, the contents were filtered through a Celite® pad and rinsed with EtOAc-MeOH (10:1) and the light brown effluent was concentrated under vacuum, affording a brown oil. The crude material was purified directly on silica gel (3% MeOH-DCM increasing to 10% MeOH-DCM) to provide both unreacted starting material and product. This material was re-submitted to the cyanation conditions for another 3 hours at 125° C., then cooled to room temperature, filtered through Celite® and rinsed with EtOAc:MeOH (10:1). The eluent was concentrated and purified on silica gel (3% MeOH-DCM increasing to 10% MeOH-DCM) which provided the product that was still impure. Thus, this material was subjected to RP-HPLC which afforded the titled racemic compound as a white solid. ¹H NMR (500 MHz, CD₃OD, racemate) δ ppm 8.24 (s, 1H), 8.04 (d, J=8.8 Hz, 1H), 7.66 (dd, J=8.8, 2.0 Hz, 1H), 7.42 (s, 1H), 6.92 (s, 1H), 4.18 (s, 3H), 4.03-3.93 (m, 5H, containing a 3H singlet at 3.98), 3.68 (s, 3H), 2.65 (s, 3H). MS (ESI): mass calc. for Chemical Formula: $C_{22}H_{20}F_3N_7O_2$; Exact Mass: 471.16, found, 472.0 (M+H)⁺. 6-((1,2-dimethyl-1H-imidazol-5-yl)(hydroxy)(1-methyl-1H-1,2,3-triazol-5-yl)methyl)-2-methoxy-3-(2,2,2-trifluoroethyl)quinoline-4-carbonitrile was purified by chiral SFC (Chiralpak AZ-H, 5 µm, 250×21 mm, mobile phase: 0.4% triethyl amine, 80% CO₂, 10% ethanol). The first eluting enantiomer was Example 206b # and the second eluting enantiomer was Example 206c.

Example 207a: 4-((4-Chloro-2-methoxy-3-(2,2,2-trifluoroethyl)quinolin-6-yl)(hydroxy)(1-methyl-1H-imidazol-5-yl)methyl)benzonitrile

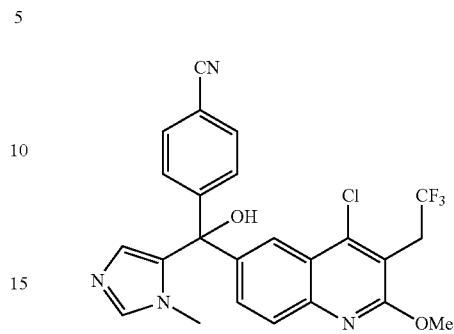

To a 50 mL 2-necked flask containing 5-bromo-1-methyl-1H-imidazole (900 mg, 5.59 mmol) was added THF (30 mL) and the solution was cooled to 0° C. Isopropyl magnesium chloride LiCl complex (1.3 M in THF, 4 mL, 5.2 mmol) was added and a thick white suspension resulted. The mixture was stirred at 0° C. for 10 minutes and then at room temperature for 10 minutes, then cooled back to 0° C. for 10 minutes. After 30 minutes total, a THF solution of 6-bromo-4-chloro-2-methoxy-3-(2,2,2-trifluoroethyl)quinoline (Intermediate 69: step e, 510 mg, 1.26 mmol in 5 mL THF) was introduced. After 10 minutes, the reaction mixture was raised to room temperature and after 4 hours, the mixture was quenched with water (25 mL). The quenched mixture was filtered through Celite® and the effluent was extracted with EtOAc (5×30 mL). The combined organics were washed with brine, dried over MgSO₄, filtered and concentrated to give a tan solid. Trituration with Et₂O afforded the title compound as a white powder. ¹H NMR (500 MHz, CDCl₃, racemate) δ ppm 8.16 (d, J=2.1 Hz, 1H), 7.79 (d, J=8.8 Hz, 1H), 7.66-7.52 (m, 5H), 7.24 (s, 1H), 6.28 (s, 1H), 5.37 (bs, 1H), 4.11 (s, 3H), 3.82 (q, J=10.1 Hz, 2H), 3.33 (s, 3H). MS (ESI): mass calc. for Chemical Formula: $C_{24}H_{18}ClF_3N_4O_2$; Exact Mass: 486.11 found, 486.90 (M+H)⁺. 4-((4-Chloro-2-methoxy-3-(2,2,2-trifluoroethyl)quinolin-6-yl)(hydroxy)(1-methyl-1H-imidazol-5-yl)methyl)benzonitrile was purified by chiral SFC (Chiralpak AD-H, 5 m, 250×20 mm, mobile phase: 0.3% i-PrNH₂ amine, 85% CO₂, 15% mixture of MeOH/i-PrOH 50/50 v/v). The first eluting enantiomer was Example 207b and the second eluting enantiomer was Example 207c.

Example 208a: 6-[Hydroxy-(3-methylimidazol-4-yl)-[6-(trifluoromethyl)-3-pyridyl]methyl]-2-methoxy-3-(2,2,2-trifluoroethoxy)quinoline-4-carbonitrile

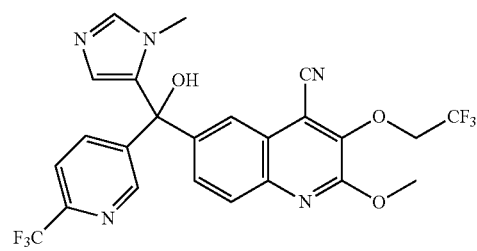 [SMILES: COc1nc2ccc(C(O)(c3ccc(C(F)(F)F)nc3)c3cncn3C)cc2c(C#N)c1OCC(F)(F)F]

[4-Chloro-2-methoxy-3-(2,2,2-trifluoroethoxy)quinolin-6-yl](1-methyl-1H-imidazol-5-yl)[6-(trifluoromethyl)pyridin-3-yl]methanol (233 mg, 0.43 mmol, Example 98), zinc cyanide (105 mg, 0.87 mmol), zinc dust (24 mg, 0.35 mmol), X-Phos (45 mg, 0.093 mmol), and $Pd_2(dba)_3$ (59 mg, 0.065 mmol) were charged to an oven-dried round-bottom flask. The flask was evacuated and back-filled with nitrogen. Dimethylacetamide (4.3 mL) was sparged with nitrogen and added to the mixture via syringe. Nitrogen was bubbled through the reaction mixture for 1 minute, then the mixture was placed in a pre-heated 120° C. heating block and stirred for 5.5 hours. The reaction was incomplete by LC/MS, therefore additional zinc cyanide (105 mg, 0.87 mmol), X-Phos (45 mg, 0.093 mmol), zinc dust (24 mg, 0.35 mmol) and $Pd_2(dba)_3$ (59 mg, 0.065 mmol) were added. The resulting mixture was stirred at 120° C. for 15 hours. The mixture was allowed to cool to room temperature, filtered through Celite®, and rinsed with dichloromethane. The filtrate was concentrated in vacuo and the residue purified by reverse-phase HPLC (acetonitrile/water+0.05% TFA) to provide the title compound as a clear colorless oil. 6-[Hydroxy-(3-methylimidazol-4-yl)-[6-(trifluoromethyl)-3-pyridyl]methyl]-2-methoxy-3-(2,2,2-trifluoroethoxy)quinoline-4-carbonitrile was purified by chiral SFC (Stationary phase: CHIRALPAK AD-H 5 µM 250×20 mm, Mobile phase: 80% $CO_2$, 20% EtOH+0.3% $iPrNH_2$) to give 2 enantiomers. The first eluting enantiomer was Example 208b: $^1$H NMR (600 MHz, $CDCl_3$) δ ppm 8.80-8.78 (m, 1H), 8.15 (d, J=2.1 Hz, 1H), 7.98-7.94 (m, 1H), 7.86 (d, J=8.8 Hz, 1H), 7.71-7.69 (m, 1H), 7.52-7.49 (m, 2H), 6.52-6.50 (m, 1H), 4.74 (q, J=8.1 Hz, 2H), 4.19 (s, 3H), 3.65 (s, 1H), 3.42 (s, 3H). MS (ESI): mass calcd. for $C_{24}H_{17}F_6N_5O_3$, 537.1; m/z found, 538.0 [M+H]$^+$ and the second eluting enantiomer was Example 208c: $^1$H NMR (600 MHz, $CDCl_3$) δ ppm 8.80-8.78 (m, 1H), 8.16-8.15 (m, 1H), 7.97-7.94 (m, 1H), 7.87-7.84 (m, 1H), 7.71-7.69 (m, 1H), 7.52-7.49 (m, 1H), 7.49-7.47 (m, 1H), 6.50-6.49 (m, 1H), 4.76-4.71 (m, 2H), 4.19 (s, 3H), 3.81 (s, 1H), 3.41 (s, 3H). MS (ESI): mass calcd. for $C_{24}H_{17}F_6N_5O_3$, 537.1; m/z found, 538.0 [M+H]$^+$.

Example 209a: 3-(Cyclopropylmethoxy)-6-[hydroxy-(3-methylimidazol-4-yl)-[2-(trifluoromethyl)-4-pyridyl]methyl]-2-methoxy-quinoline-4-carbonitrile

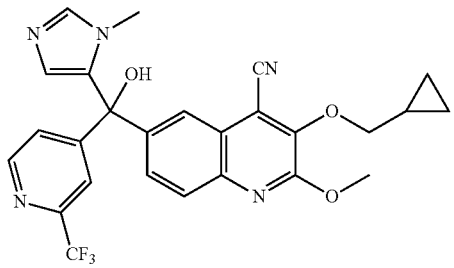

The title compound was prepared using [4-chloro-3-(cyclopropylmethoxy)-2-methoxy-6-quinolyl]-(3-methyl-imidazol-4-yl)-[2-(trifluoromethyl)-4-pyridyl]methanol (Example 217a) in place of [4-chloro-2-methoxy-3-(2,2,2-trifluoroethoxy)quinolin-6-yl](1-methyl-1H-imidazol-5-yl)[6-(trifluoromethyl)pyridin-3-yl]methanol using the procedure described for Example 208a. 3-(Cyclopropylmethoxy)-6-[hydroxy-(3-methylimidazol-4-yl)-[2-(trifluoromethyl)-4-pyridyl]methyl]-2-methoxy-quinoline-4-carbonitrile was purified by chiral SFC (Stationary phase: CHIRALPAK IC 5 µM 250×20 mm, Mobile phase: 70% $CO_2$, 30% iPrOH+0.3% $iPrNH_2$) to give 2 enantiomers. The first eluting enantiomer was Example 209b: $^1$H NMR (600 MHz, $CDCl_3$) δ 8.73 (d, J=5.1 Hz, 1H), 8.09 (d, J=2.1 Hz, 1H), 1.34-1.29 (m, 1H), 7.82 (d, J=8.8 Hz, 1H), 0.67-0.63 (m, 2H), 7.44-7.41 (m, 2H), 6.47-6.45 (m, 1H), 4.37 (s, 1H), 7.86-7.83 (m, 1H), 0.38-0.34 (m, 2H), 7.54-7.52 (m, 1H), 4.26 (d, J=7.3 Hz, 2H), 4.14 (s, 3H), 3.39 (s, 3H). MS (ESI): mass calcd. for $C_{26}H_{22}F_3N_5O_3$, 509.2; m/z found, 510.1 [M+H]$^+$ and the second eluting enantiomer was Example 209c: $^1$H NMR (600 MHz, $CD_2Cl_2$) δ ppm 7.56-7.45 (m, 2H), 7.45-7.39 (m, 2H), 7.36-7.33 (m, 1H), 5.45-5.38 (m, 1H), 4.28-4.04 (m, 1H), 3.55-3.36 (m, 1H), 2.99 (s, 2H), 1.77-1.67 (m, 5H), 1.67-1.61 (m, 2H), 1.21-1.15 (m, 3H), 1.06-0.97 (m, 2H). MS (ESI): mass calcd. for $C_{26}H_{22}F_3N_5O_3$, 509.2; m/z found, 510.1 [M+H]$^+$.

Example 210a: 6-[Hydroxy-(3-methylimidazol-4-yl)-[2-(trifluoromethyl)-4-pyridyl]methyl]-2-methoxy-3-(2,2,2-trifluoroethoxy)quinoline-4-carbonitrile

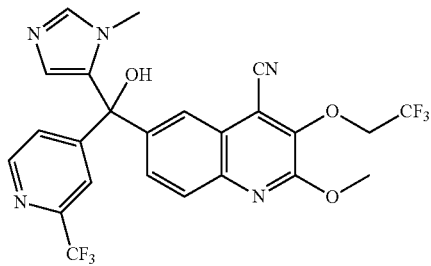 [SMILES: COc1nc2ccc(C(O)(c3ccnc(C(F)(F)F)c3)c3cncn3C)cc2c(C#N)c1OCC(F)(F)F]

The title compound was prepared using [4-chloro-2-methoxy-3-(2,2,2-trifluoroethoxy)-6-quinolyl]-(3-methyl-imidazol-4-yl)-[2-(trifluoromethyl)-4-pyridyl]methanol (Example 213a) in place of [4-chloro-2-methoxy-3-(2,2,2-trifluoroethoxy)quinolin-6-yl](1-methyl-1H-imidazol-5-yl)[6-(trifluoromethyl)pyridin-3-yl]methanol using the procedure described for Example 208a. 6-[Hydroxy-(3-methylimidazol-4-yl)-[2-(trifluoromethyl)-4-pyridyl]methyl]-2-methoxy-3-(2,2,2-trifluoroethoxy)quinoline-4-carbonitrile was purified by chiral SFC (Stationary phase: CHIRALPAK IC 5 µM 250×20 mm, Mobile phase: 75% $CO_2$, 25% iPrOH+0.3% $iPrNH_2$) to give 2 enantiomers. The first eluting enantiomer was Example 210b: $^1$H NMR (600 MHz, $CDCl_3$) δ 8.74 (d, J=5.2 Hz, 1H), 8.17-8.14 (m, 1H), 7.87-7.83 (m, 2H), 7.54 (d, J=4.9 Hz, 1H), 7.50-7.47 (m, 1H), 7.42 (s, 1H), 6.44 (s, 1H), 4.76-4.71 (m, 2H), 4.19 (s, 3H), 3.38 (s, 3H). MS (ESI): mass calcd. for $C_{24}H_{17}F_6N_5O_3$, 537.1; m/z found, 538.0 [M+H]$^+$ and the second eluting enantiomer was Example 210c: $^1$H NMR (600 MHz, $CDCl_3$) δ ppm 8.74 (d, J=5.2 Hz, 1H), 8.17-8.14 (m, 1H), 7.88-7.84 (m, 2H), 7.54 (d, J=5.0 Hz, 1H), 7.51-7.49 (m, 1H), 7.48 (s, 1H), 6.48 (s, 1H), 4.74 (q, J=8.1 Hz, 2H), 4.19 (s, 3H), 3.39 (s, 3H). MS (ESI): mass calcd. for $C_{24}H_{17}F_6N_5O_3$, 537.1; m/z found, 538.0 [M+H]$^+$.

Example 211a: 6-[(4-Cyanophenyl)-hydroxy-(3-methylimidazol-4-yl)methyl]-2-methoxy-3-(2,2,2-trifluoroethoxy)quinoline-4-carbonitrile

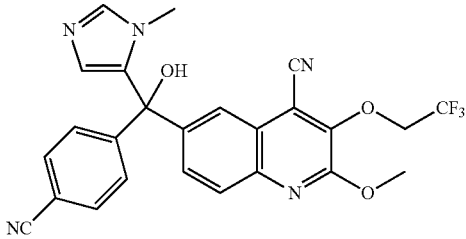 [SMILES: COc1nc2ccc(C(O)(c3ccc(C#N)cc3)c3cncn3C)cc2c(C#N)c1OCC(F)(F)F]

The title compound was prepared using 4-[[4-chloro-2-methoxy-3-(2,2,2-trifluoroethoxy)-6-quinolyl]-hydroxy-(3-methylimidazol-4-yl)methyl]benzonitrile (Example 215a) in place of [4-chloro-2-methoxy-3-(2,2,2-trifluoroethoxy)quinolin-6-yl](1-methyl-1H-imidazol-5-yl)[6-(trifluoromethyl)pyridin-3-yl]methanol using the procedure described for Example 208a. 6-[(4-Cyanophenyl)-hydroxy-(3-methylimidazol-4-yl)methyl]-2-methoxy-3-(2,2,2-trifluoroethoxy)quinoline-4-carbonitrile was purified by chiral SFC (Stationary phase: CHIRALPAK IC 5 μM 250×20 mm, Mobile phase: 60% CO$_2$, 40% iPrOH+0.3% iPrNH$_2$) to give 2 enantiomers. The first eluting enantiomer was Example 211b: $^1$H NMR (600 MHz, CDCl$_3$) δ ppm 8.10 (d, J=2.2 Hz, 1H), 7.83 (d, J=8.7 Hz, 1H), 7.68-7.65 (m, 2H), 7.56-7.53 (m, 2H), 7.52-7.49 (m, 1H), 7.45-7.42 (m, 1H), 6.43 (s, 1H), 4.75-4.70 (m, 2H), 4.18 (s, 3H), 3.86 (s, 1H), 3.39 (s, 3H). MS (ESI): mass calcd. for C$_{25}$H$_{18}$F$_3$N$_5$O$_3$, 493.1; m/z found, 494.1 [M+H]$^+$ and the second eluting enantiomer was Example 211c: $^1$H NMR (600 MHz, CDCl$_3$) δ ppm 8.10-8.06 (m, 1H), 7.84 (d, J=8.6 Hz, 1H), 7.70-7.64 (m, 3H), 7.55 (d, J=8.0 Hz, 2H), 7.53-7.49 (m, 1H), 6.49 (s, 1H), 4.75-4.70 (m, 2H), 4.19 (s, 3H), 3.44 (s, 3H). MS (ESI): mass calcd. for C$_{25}$H$_{18}$F$_3$N$_5$O$_3$, 493.1; m/z found, 494.1 [M+H]$^+$.

Example 212a: 6-[(4-Cyanophenyl)-hydroxy-(3-methylimidazol-4-yl)methyl]-3-(cyclopropylmethoxy)-2-methoxy-quinoline-4-carbonitrile

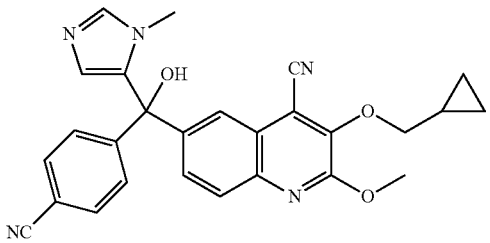 [SMILES: COc1nc2ccc(C(O)(c3ccc(C#N)cc3)c3cncn3C)cc2c(C#N)c1OCC1CC1]

The title compound was prepared using 4-[[4-chloro-3-(cyclopropylmethoxy)-2-methoxy-6-quinolyl]-hydroxy-(3-methylimidazol-4-yl)methyl]benzonitrile (Example 214a) in place of [4-chloro-2-methoxy-3-(2,2,2-trifluoroethoxy)quinolin-6-yl](1-methyl-1H-imidazol-5-yl)[6-(trifluoromethyl)pyridin-3-yl]methanol using the procedure described for Example 208a. 6-[(4-Cyanophenyl)-hydroxy-(3-methylimidazol-4-yl)methyl]-3-(cyclopropylmethoxy)-2-methoxy-quinoline-4-carbonitrile was purified by chiral SFC (Stationary phase: CHIRALPAK IC 5 μM 250×20 mm, Mobile phase: 50% CO$_2$, 50% iPrOH+0.3% iPrNH$_2$) to give 2 enantiomers. The first eluting enantiomer was Example 212b: $^1$H NMR (600 MHz, CDCl$_3$) δ ppm 8.03 (d, J=2.2 Hz, 1H), 7.80 (d, J=8.8 Hz, 1H), 7.68-7.65 (m, 2H), 7.57-7.54 (m, 2H), 7.47-7.44 (m, 2H), 6.46 (s, 1H), 4.25 (d, J=7.3 Hz, 2H), 4.13 (s, 3H), 3.59-3.55 (m, 1H), 3.39 (s, 3H), 1.33-1.28 (m, 1H), 0.66-0.62 (m, 2H), 0.38-0.34 (m, 2H). MS (ESI): mass calcd. for C$_{27}$H$_{23}$N$_5$O$_3$, 465.2; m/z found, 466.0 [M+H]$^+$ and the second eluting enantiomer was Example 212c: $^1$H NMR (600 MHz, CDCl$_3$) δ ppm 8.02-8.00 (m, 1H), 7.83-7.81 (m, 1H), 7.76-7.71 (m, 1H), 7.70-7.67 (m, 2H), 7.56-7.53 (m, 2H), 7.46-7.43 (m, 1H), 6.56-6.53 (m, 1H), 4.27-4.25 (m, 2H), 4.14 (s, 3H), 3.45 (s, 3H), 1.26-1.24 (m, 1H), 0.66-0.63 (m, 2H), 0.38-0.35 (m, 2H). MS (ESI): mass calcd. for C$_{27}$H$_{23}$N$_5$O$_3$, 465.2; m/z found, 466.0 [M+H]$^+$.

Example 213a: [4-Chloro-2-methoxy-3-(2,2,2-trifluoroethoxy)-6-quinolyl]-(3-methylimidazol-4-yl)-[2-(trifluoromethyl)-4-pyridyl]methanol

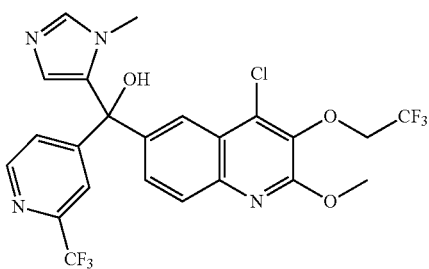 [SMILES: COc1nc2ccc(C(O)(c3ccnc(C(F)(F)F)c3)c3cncn3C)cc2c(Cl)c1OCC(F)(F)F]

To a mixture of 4-chloro-6-(hydroxy(1-methyl-1H-imidazol-5-yl)(2-(trifluoromethyl)pyridin-4-yl)methyl)-2-methoxyquinolin-3-ol (622 mg, 1.34 mmol, Intermediate 82) and Cs$_2$CO$_3$ (414 mg, 1.27 mmol) in DMF (6.7 mL) was added 2,2,2-trifluoroethyl trifluoromethanesulfonate (193 μL, 1.27 mmol) dropwise. The resulting mixture was stirred at room temperature for 1 hour. The reaction mixture was diluted with water (15 mL) and extracted with EtOAc (3×25 mL). The organic layers were combined, washed with water (30 mL), dried (Na$_2$SO$_4$), filtered and concentrated to dryness. The residue was purified by FCC (MeOH/CH$_2$Cl$_2$) to afford the title compound as a cream-colored solid.

[4-Chloro-2-methoxy-3-(2,2,2-trifluoroethoxy)-6-quinolyl]-(3-methylimidazol-4-yl)-[2-(trifluoromethyl)-4-pyridyl]methanol was purified by chiral SFC (Stationary phase: CHIRALPAK IC 5 μM 250×20 mm, Mobile phase: 80% CO$_2$, 20% iPrOH+0.3% iPrNH$_2$) to give 2 enantiomers. The first eluting enantiomer was Example 213b: $^1$H NMR (600 MHz, CDCl$_3$) δ ppm 8.72 (d, J=5.1 Hz, 1H), 8.09 (d, J=2.1 Hz, 1H), 7.86-7.84 (m, 1H), 7.83 (d, J=8.8 Hz, 1H), 7.54-7.52 (m, 1H), 7.52-7.49 (m, 1H), 7.47-7.45 (m, 1H), 6.47-6.45 (m, 1H), 4.54-4.49 (m, 2H), 4.16 (s, 3H), 3.70 (s, 1H), 3.38 (s, 3H). MS (ESI): mass calcd. for C$_{23}$H$_{17}$ClF$_6$N$_4$O$_3$, 546.1; m/z found, 547.0 [M+H]$^+$ and the second eluting enantiomer was Example 213c: $^1$H NMR (600 MHz, CDCl$_3$) δ ppm 8.71 (d, J=5.1 Hz, 1H), 8.10-8.08 (m, 1H), 7.86-7.84 (m, 1H), 7.84-7.81 (m, 1H), 7.52 (dd, J=8.8, 2.2 Hz, 1H), 7.50 (d, J=5.2, 1.7 Hz, 1H), 7.43-7.42 (m, 1H), 6.43-6.41 (m, 1H), 4.55-4.49 (m, 2H), 4.16 (s, 3H), 4.05 (s, 1H), 3.37 (s, 3H). MS (ESI): mass calcd. for C$_{23}$H$_{17}$ClF$_6$N$_4$O$_3$, 546.1; m/z found, 547.0 [M+H]$^+$.

Example 214a: 4-[[4-Chloro-3-(cyclopropyl-methoxy)-2-methoxy-6-quinolyl]-hydroxy-(3-methylimidazol-4-yl)methyl]benzonitrile

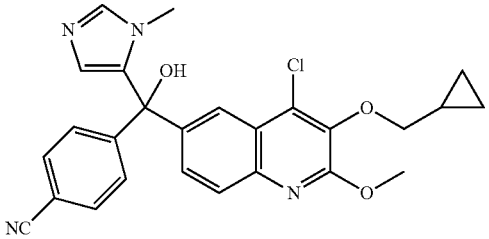 [SMILES: COc1nc2ccc(C(O)(c3ccc(C#N)cc3)c3cncn3C)cc2c(Cl)c1OCC1CC1]

The title compound was prepared using 4-((4-chloro-3-hydroxy-2-methoxyquinolin-6-yl)(hydroxy)(1-methyl-1H-imidazol-5-yl)methyl)benzonitrile (Intermediate 83: step b) in place of 4-chloro-6-((2,6-dimethylpyridin-3-yl)(hydroxy)(1-methyl-1H-1,2,3-triazol-5-yl)methyl)-2-methoxyquinolin-3-ol and cyclopropylmethanol in place of 3-methyl-3-oxetanemethanol using the procedure described for Example 36a.

4-[[4-Chloro-3-(cyclopropylmethoxy)-2-methoxy-6-quinolyl]-hydroxy-(3-methylimidazol-4-yl)methyl]benzonitrile was purified by chiral SFC (Stationary phase: CHIRALPAK AD-H 5 μM 250×20 mm, Mobile phase: 75% CO$_2$, 25% MeOH+0.3% iPrNH$_2$) followed by achiral SFC (Stationary phase: CHIRALPAK AD-H 5 μM 250×20 mm, Mobile phase: 75% CO$_2$, 25% iPrOH+0.3% iPrNH$_2$) to give 2 enantiomers. The first eluting enantiomer was Example 214b: $^1$H NMR (600 MHz, CDCl$_3$) δ ppm 8.02-7.96 (m, 1H), 7.83-7.76 (m, 1H), 7.70-7.64 (m, 2H), 7.57-7.51 (m, 2H), 7.51-7.44 (m, 2H), 6.48 (s, 1H), 4.14-4.09 (m, 3H), 4.01-3.95 (m, 2H), 3.43-3.37 (m, 3H), 3.09-3.02 (m, 1H), 1.36-1.29 (m, 1H), 0.65-0.58 (m, 2H), 0.36-0.30 (m, 2H). MS (ESI): mass calcd. for C$_{26}$H$_{23}$ClN$_4$O$_3$, 474.1; m/z found, 475.0 [M+H]$^+$ and the second eluting enantiomer was Example 214c: $^1$H NMR (600 MHz, CDCl$_3$) δ ppm 8.03-7.95 (m, 1H), 7.82-7.77 (m, 1H), 7.69-7.63 (m, 2H), 7.58-7.52 (m, 2H), 7.51-7.45 (m, 2H), 6.47 (s, 1H), 4.14-4.09 (m, 3H), 4.01-3.95 (m, 2H), 3.43-3.38 (m, 3H), 3.15-3.10 (m, 1H), 1.35-1.29 (m, 1H), 0.64-0.57 (m, 2H), 0.35-0.30 (m, 2H). MS (ESI): mass calcd. for C$_{26}$H$_{23}$ClN$_4$O$_3$, 474.1; m/z found, 475.0 [M+H]$^+$.

Example 215a: 4-[[4-Chloro-2-methoxy-3-(2,2,2-trifluoroethoxy)-6-quinolyl]-hydroxy-(3-methylimidazol-4-yl)methyl]benzonitrile

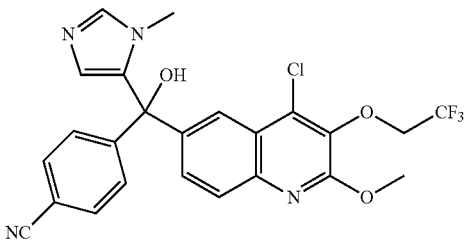 [SMILES: COc1nc2ccc(C(O)(c3ccc(C#N)cc3)c3cncn3C)cc2c(Cl)c1OCC(F)(F)F]

The title compound was prepared using 4-((4-chloro-3-hydroxy-2-methoxyquinolin-6-yl)(hydroxy)(1-methyl-1H-imidazol-5-yl)methyl)benzonitrile (Intermediate 83: step b) in place of 4-chloro-6-(hydroxy(1-methyl-1H-imidazol-5-yl)(2-(trifluoromethyl)pyridin-4-yl)methyl)-2-methoxyquinolin-3-ol using the procedure described for Example 213a.

4-[[4-Chloro-2-methoxy-3-(2,2,2-trifluoroethoxy)-6-quinolyl]-hydroxy-(3-methylimidazol-4-yl)methyl]benzonitrile was purified by chiral SFC (Stationary phase: CHIRALPAK AD-H 5 μM 250×20 mm, Mobile phase: 85% CO$_2$, 15% mixture of MeOH/iPrOH 50/50 v/v+0.3% iPrNH$_2$) to give 2 enantiomers. The first eluting enantiomer was Example 215b: $^1$H NMR (600 MHz, CDCl$_3$) δ ppm 8.05 (d, J=2.2 Hz, 1H), 7.80 (d, J=8.8 Hz, 1H), 7.68-7.65 (m, 2H), 7.56-7.53 (m, 2H), 7.53-7.51 (m, 1H), 7.47-7.46 (m, 1H), 6.45-6.44 (m, 1H), 4.54-4.49 (m, 2H), 4.15 (s, 3H), 3.39 (s, 3H), 3.33 (s, 1H). MS (ESI): mass calcd. for C$_{24}$H$_{18}$ClF$_3$N$_4$O$_3$, 502.1; m/z found, 503.1 [M+H]$^+$ and the second eluting enantiomer was Example 215c: $^1$H NMR (600 MHz, CDCl$_3$) δ ppm 8.05 (d, J=2.1 Hz, 1H), 7.81 (d, J=8.8 Hz, 1H), 7.68-7.65 (m, 2H), 7.56-7.53 (m, 2H), 7.53-7.51 (m, 1H), 7.48-7.47 (m, 1H), 6.46-6.45 (m, 1H), 4.54-4.49 (m, 2H), 4.15 (s, 3H), 3.39 (s, 3H), 3.26 (s, 1H). MS (ESI): mass calcd. for C$_{24}$H$_{18}$ClF$_3$N$_4$O$_3$, 502.1; m/z found, 503.0 [M+H]$^+$.

Example 216a: [4-Chloro-3-(cyclopropylmethoxy)-2-methoxy-6-quinolyl]-(4-chlorophenyl)-(3-methylimidazol-4-yl)methanol

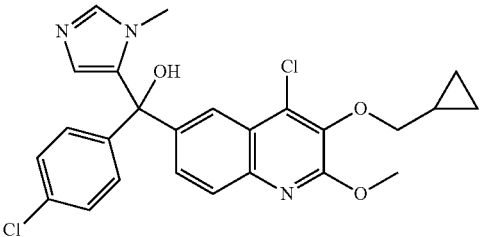 [SMILES: COc1nc2ccc(C(O)(c3ccc(Cl)cc3)c3cncn3C)cc2c(Cl)c1OCC1CC1]

The title compound was prepared using 4-chloro-6-((4-chlorophenyl)(hydroxy)(1-methyl-1H-imidazol-5-yl)methyl)-2-methoxyquinolin-3-ol (Intermediate 84) in place of 4-chloro-6-((2,6-dimethylpyridin-3-yl)(hydroxy)(1-methyl-1H-1,2,3-triazol-5-yl)methyl)-2-methoxyquinolin-3-ol and cyclopropylmethanol in place of 3-methyl-3-oxetanemethanol using the procedure described for Example 36a. $^1$H NMR (500 MHz, CDCl$_3$) δ ppm 8.03 (d, J=2.1 Hz, 1H), 7.77 (d, J=8.7 Hz, 1H), 7.49-7.45 (m, 1H), 7.43-7.42 (m, 1H), 7.34-7.29 (m, 4H), 6.44-6.41 (m, 1H), 4.12 (s, 3H), 3.97 (d, J=7.2 Hz, 2H), 3.40 (s, 3H), 3.37 (s, 1H), 1.36-1.29 (m, 1H), 0.63-0.59 (m, 2H), 0.35-0.31 (m, 2H). MS (ESI): mass calcd. for C$_{25}$H$_{23}$Cl$_2$N$_3$O$_3$, 483.1; m/z found, 484.1 [M+H]$^+$.

[4-Chloro-3-(cyclopropylmethoxy)-2-methoxy-6-quinolyl]-(4-chlorophenyl)-(3-methylimidazol-4-yl)methanol was purified by chiral SFC (Stationary phase: CHIRALPAK AD-H 5 μM 250×20 mm, Mobile phase: 65% CO$_2$, 35% iPrOH+0.3% iPrNH$_2$) to give 2 enantiomers. The first eluting enantiomer was Example 216b: $^1$H NMR (500 MHz, CDCl$_3$) δ ppm 8.04-8.02 (m, 1H), 7.77 (d, J=8.7 Hz, 1H), 7.47 (dd, J=8.8, 2.2 Hz, 1H), 7.44 (s, 1H), 7.34-7.29 (m, 4H), 6.45-6.42 (m, 1H), 4.12 (s, 3H), 3.97 (d, J=7.2 Hz, 2H), 3.40 (s, 3H), 3.27 (s, 1H), 1.35-1.30 (m, 1H), 0.63-0.59 (m, 2H), 0.35-0.32 (m, 2H). MS (ESI): mass calcd. for C$_{25}$H$_{23}$Cl$_2$N$_3$O$_3$, 483.1; m/z found, 484.0 [M+H]$^+$ and the second eluting enantiomer was Example 216c: $^1$H NMR (500 MHz, CDCl$_3$) δ ppm 8.03 (d, J=2.1 Hz, 1H), 7.77 (d, J=8.5 Hz, 1H), 7.47 (dd, J=8.8, 2.2 Hz, 1H), 7.44 (s, 1H), 7.34-7.30 (m, 4H), 6.45-6.43 (m, 1H), 4.12 (s, 3H), 3.98 (d, J=7.2 Hz, 2H), 3.40 (s, 3H), 3.20 (s, 1H), 1.36-1.30 (m, 1H), 0.63-0.59 (m, 2H), 0.35-0.31 (m, 2H). MS (ESI): mass calcd. for $C_{25}H_{23}Cl_2N_3O_3$, 483.1; m/z found, 484.0 $[M+H]^+$.

Example 217a: [4-Chloro-3-(cyclopropylmethoxy)-2-methoxy-6-quinolyl]-(3-methylimidazol-4-yl)-[2-(trifluoromethyl)-4-pyridyl]methanol

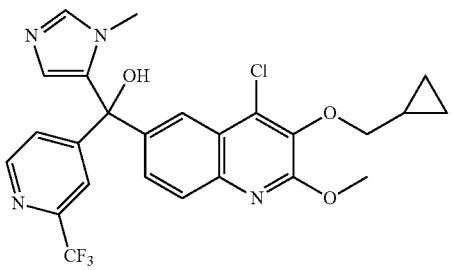 [SMILES: COc1nc2ccc(C(O)(c3ccnc(C(F)(F)F)c3)c3cncn3C)cc2c(Cl)c1OCC1CC1]

The title compound was prepared using 4-chloro-6-(hydroxy(1-methyl-1H-imidazol-5-yl)(2-(trifluoromethyl)pyridin-4-yl)methyl)-2-methoxyquinolin-3-ol (Intermediate 82) in place of 4-chloro-6-((2,6-dimethylpyridin-3-yl)(hydroxy)(1-methyl-1H-1,2,3-triazol-5-yl)methyl)-2-methoxyquinolin-3-ol and cyclopropylmethanol in place of 3-methyl-3-oxetanemethanol using the procedure described for Example 36a.

[4-Chloro-3-(cyclopropylmethoxy)-2-methoxy-6-quinolyl]-(3-methylimidazol-4-yl)-[2-(trifluoromethyl)-4-pyridyl]methanol was purified by chiral SFC (Stationary phase: CHIRALPAK IC 5 µM 250×20 mm, Mobile phase: 60% $CO_2$, 40% iPrOH+0.3% iPrNH$_2$) to give 2 enantiomers. The first eluting enantiomer was Example 217b: $^1$H NMR (500 MHz, CDCl$_3$) δ ppm 8.71 (d, J=5.1 Hz, 1H), 8.05 (d, J=2.2 Hz, 1H), 7.88-7.86 (m, 1H), 7.81 (d, J=8.7 Hz, 1H), 7.52-7.50 (m, 1H), 7.48 (dd, J=8.7, 2.2 Hz, 1H), 7.43 (s, 1H), 6.44 (s, 1H), 4.12 (s, 3H), 3.98 (d, J=7.3 Hz, 2H), 3.94 (s, 1H), 3.37 (s, 3H), 1.35-1.30 (m, 1H), 0.63-0.59 (m, 2H), 0.35-0.31 (m, 2H). MS (ESI): mass calcd. for $C_{25}H_{22}ClF_3N_4O_3$, 518.1; m/z found, 519.0 $[M+H]^+$ and the second eluting enantiomer was Example 217c: $^1$H NMR (500 MHz, CDCl$_3$) δ ppm 8.71 (d, J=5.1 Hz, 1H), 8.06 (d, J=2.1 Hz, 1H), 7.89-7.87 (m, 1H), 7.80 (d, J=8.8 Hz, 1H), 7.51-7.49 (m, 1H), 7.49-7.46 (m, 1H), 7.38 (s, 1H), 6.40 (s, 1H), 4.35 (s, 1H), 4.12 (s, 3H), 3.98 (d, J=7.3 Hz, 2H), 3.36 (s, 3H), 1.35-1.29 (m, 1H), 0.64-0.59 (m, 2H), 0.35-0.31 (m, 2H). MS (ESI): mass calcd. for $C_{25}H_{22}ClF_3N_4O_3$, 518.1; m/z found, 519.0 $[M+H]^+$.

Example 218a: 6-[Hydroxy-(3-methylimidazol-4-yl)-[2-(trifluoromethyl)-4-pyridyl]methyl]-2-methoxy-3-(2,2,2-trifluoroethyl)quinoline-4-carbonitrile

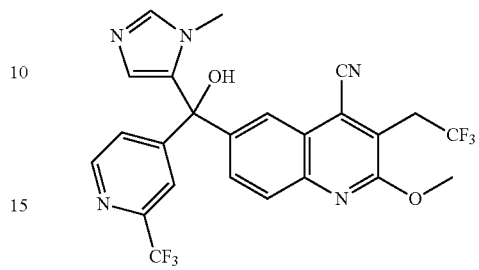

The title compound was prepared using [4-chloro-2-methoxy-3-(2,2,2-trifluoroethyl)-6-quinolyl]-(3-methylimidazol-4-yl)-[2-(trifluoromethyl)-4-pyridyl]methanol (Example 225a) in place of [4-chloro-2-methoxy-3-(2,2,2-trifluoroethoxy)quinolin-6-yl](1-methyl-1H-imidazol-5-yl)[6-(trifluoromethyl)pyridin-3-yl]methanol using the procedure described for Example 208a. 6-[Hydroxy-(3-methylimidazol-4-yl)-[2-(trifluoromethyl)-4-pyridyl]methyl]-2-methoxy-3-(2,2,2-trifluoroethyl)quinoline-4-carbonitrile was purified by chiral SFC (Stationary phase: CHIRALPAK IC 5 µM 250×20 mm, Mobile phase: 80% $CO_2$, 20% iPrOH+0.3% iPrNH$_2$) to give 2 enantiomers. The first eluting enantiomer was Example 218b: $^1$H NMR (500 MHz, CDCl$_3$) δ ppm 8.75 (d, J=5.1 Hz, 1H), 8.23 (d, J=2.1 Hz, 1H), 7.91 (d, J=8.7 Hz, 1H), 7.86-7.83 (m, 1H), 7.61 (dd, J=8.9, 2.1 Hz, 1H), 7.54 (d, J=5.2 Hz, 1H), 7.50-7.47 (m, 1H), 6.51 (s, 1H), 4.15 (s, 3H), 3.91-3.83 (m, 3H), 3.40 (s, 3H). MS (ESI): mass calcd. for $C_{24}H_{17}F_6N_5O_2$, 521.1; m/z found, 522.0 $[M+H]^+$ and the second eluting enantiomer was Example 218c: $^1$H NMR (500 MHz, CDCl$_3$) δ ppm 8.75 (d, J=5.1 Hz, 1H), 8.23-8.20 (m, 1H), 7.92 (d, J=8.8 Hz, 1H), 7.86-7.84 (m, 1H), 7.64-7.61 (m, 1H), 7.61-7.57 (m, 1H), 7.54 (d, J=5.0 Hz, 1H), 6.54 (s, 1H), 4.15 (s, 3H), 3.91-3.83 (m, 2H), 3.42 (s, 3H). MS (ESI): mass calcd. for $C_{24}H_{17}F_6N_5O_2$, 521.1; m/z found, 522.0 $[M+H]^+$.

Example 219a: 6-[(1-Acetylazetidin-3-yl)-hydroxy-(3-methyltriazol-4-yl)methyl]-3-(cyclopropylmethoxy)-2-ethyl-quinoline-4-carbonitrile

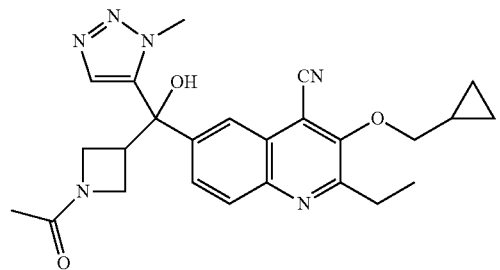

The title compound was prepared using 1-[3-[[4-chloro-3-(cyclopropylmethoxy)-2-ethyl-6-quinolyl]-hydroxy-(3-methyltriazol-4-yl)methyl]azetidin-1-yl]ethanone (Example 222) in place of [4-chloro-2-methoxy-3-(2,2,2-trifluoroethoxy)quinolin-6-yl](1-methyl-1H-imidazol-5-yl)[6-(trifluoromethyl)pyridin-3-yl]methanol using the procedure described for Example 208a. 6-[(1-Acetylazetidin-3-yl)-hydroxy-(3-methyltriazol-4-yl)methyl]-3-(cyclopropylmethoxy)-2-ethyl-quinoline-4-carbonitrile was purified by chiral SFC (Stationary phase: CHIRALCEL OD-H 5 µM 250×20 mm, Mobile phase: 60% CO$_2$, 40% MeOH) followed by chiral SFC (Stationary phase: CHIRALCEL OD-H 5 µM 250×20 mm, Mobile phase: 60% CO$_2$, 40% MeOH) to give 2 enantiomers. The first eluting enantiomer was Example 219b: $^1$H NMR (500 MHz, CDCl$_3$) δ ppm 8.34-8.21 (m, 1H), 8.01-7.97 (m, 1H), 7.63-7.60 (m, 1H), 7.33-7.29 (m, 1H), 4.41-4.34 (m, 3H), 4.29-4.22 (m, 1H), 4.16-4.11 (m, 1H), 4.09-3.96 (m, 1H), 3.80-3.74 (m, 1H), 3.73-3.70 (m, 3H), 3.63-3.49 (m, 1H), 3.12-3.04 (m, 2H), 1.87-1.81 (m, 3H), 1.40-1.36 (m, 4H), 0.75-0.70 (m, 2H), 0.47-0.42 (m, 2H). MS (ESI): mass calcd. for C$_{25}$H$_{28}$N$_6$O$_3$, 460.2; m/z found, 461.1 [M+H]$^+$ and the second eluting enantiomer was Example 219c: $^1$H NMR (500 MHz, CDCl$_3$) δ ppm 8.34-8.21 (m, 1H), 8.01-7.97 (m, 1H), 7.62-7.60 (m, 1H), 7.34-7.29 (m, 1H), 4.44-4.36 (m, 3H), 4.28-4.20 (m, 1H), 4.18-4.11 (m, 1H), 4.11-3.96 (m, 1H), 3.81-3.75 (m, 1H), 3.73-3.70 (m, 3H), 3.62-3.51 (m, 1H), 3.12-3.04 (m, 2H), 1.87-1.82 (m, 3H), 1.40-1.36 (m, 4H), 0.76-0.69 (m, 2H), 0.47-0.41 (m, 2H). MS (ESI): mass calcd. for C$_{25}$H$_{28}$N$_6$O$_3$, 460.2; m/z found, 461.2 [M+H]$^+$.

Example 220: (4-Chloro-2-methoxy-8-methyl-3-(2,2,2-trifluoroethoxy)quinolin-6-yl)(1,2-dimethyl-1H-imidazol-5-yl)(1,3,5-trimethyl-1H-pyrazol-4-yl)methanol

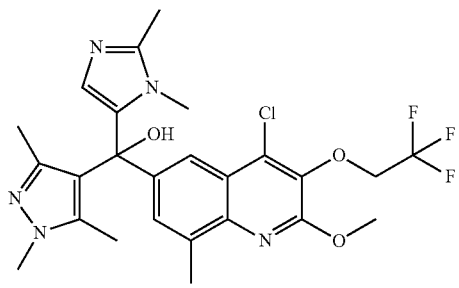 [SMILES: COc1nc2c(C)cc(C(O)(c3c(C)nn(C)c3C)c3cnc(C)n3C)cc2c(Cl)c1OCC(F)(F)F]

2,2,2-Trifluoroethyl trifluoromethanesulfonate (255 mg, 1.10 mmol) was added drop-wise to a mixture consisting of 4-chloro-6-((1,2-dimethyl-1H-imidazol-5-yl)(hydroxy)(1,3,5-trimethyl-1H-pyrazol-4-yl)methyl)-2-methoxy-8-methylquinolin-3-ol (500 mg, 1.10 mmol, Intermediate 90), Cs$_2$CO$_3$ (357 mg, 1.10 mmol) and THF (50 mL). The resultant reaction mixture was stirred at room temperature for 2 hours. The suspension was filtered through a pad of Celite® and the pad was washed with ethyl acetate (20 mL×3). The filtrate was concentrated to dryness under reduced pressure to give the crude product, which was purified by preparative HPLC (ACN/water with 0.05% NH$_3$). The pure fractions were collected and the volatiles were removed under vacuum. The residue was suspended in water (10 mL) and the resulting mixture lyophilized to dryness. $^1$H NMR (400 MHz, DMSO-d$_6$) δ ppm 7.96-7.93 (m, 1H), 7.45-7.42 (m, 1H), 6.45-6.42 (m, 1H), 5.76-5.74 (m, 1H), 4.87-4.78 (m, 2H), 4.11 (s, 3H), 3.61 (s, 3H), 3.42 (s, 3H), 2.61 (s, 3H), 2.28 (s, 3H), 1.80 (s, 3H), 1.66 (s, 3H); MS m/e 538.1 [M+H]$^+$.

Example 221: [4-Chloro-2-methoxy-3-(2,2,2-trifluoroethoxy)-6-quinolyl]-bis(2,3-dimethylimidazol-4-yl)methanol

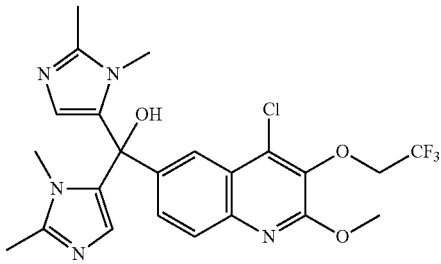 [SMILES: COc1nc2ccc(C(O)(c3cnc(C)n3C)c3cnc(C)n3C)cc2c(Cl)c1OCC(F)(F)F]

The title compound was prepared using 6-(bis(1,2-dimethyl-1H-imidazol-5-yl)(hydroxy)methyl)-4-chloro-2-methoxyquinolin-3-ol (Intermediate 33) in place of 4-chloro-6-(hydroxy(1-methyl-1H-imidazol-5-yl)(2-(trifluoromethyl)pyridin-4-yl)methyl)-2-methoxyquinolin-3-ol using the procedure described for Example 213a. $^1$H NMR (500 MHz, CDCl$_3$) δ ppm 8.19 (s, 1H), 7.86 (d, J=8.7 Hz, 1H), 7.42 (s, 1H), 6.74 (s, 2H), 4.55-4.50 (m, 2H), 4.15 (s, 3H), 3.62 (s, 6H), 2.59 (s, 6H). MS (ESI): mass calcd. for C$_{23}$H$_{23}$ClF$_3$N$_5$O$_3$, 509.1; m/z found, 510.0 [M+H]$^+$.

Example 222: 1-[3-[[4-Chloro-3-(cyclopropylmethoxy)-2-ethyl-6-quinolyl]-hydroxy-(3-methyltriazol-4-yl)methyl]azetidin-1-yl]ethanone

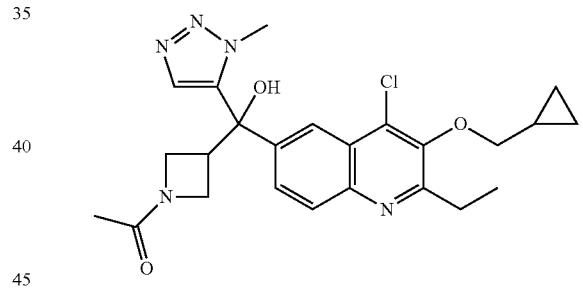

To a mixture of azetidin-3-yl(4-chloro-3-(cyclopropylmethoxy)-2-ethylquinolin-6-yl)(1-methyl-1H-1,2,3-triazol-5-yl)methanol (147 mg, 0.34 mmol, Example 234) in CH$_2$Cl$_2$ (3.4 mL) was added Et$_3$N (239 µL, 1.72 mmol) followed by acetic anhydride (131 µL, 1.37 mmol). The resulting mixture was stirred at 46° C. for 4 hours then cooled to room temperature. The mixture was diluted with CH$_2$Cl$_2$ (6 mL) and sat. aq. NaHCO$_3$ (5 mL) and stirred at room temperature for 10 minutes. The layers were separated and the aqueous further extracted with CH$_2$Cl$_2$ (2×15 mL). The organic layers were combined, dried (Na$_2$SO$_4$), filtered and concentrated to dryness. The residue was purified by FCC (silica gel, MeOH/CH$_2$Cl$_2$) to provide the title compound as a white oil. $^1$H NMR (500 MHz, CDCl$_3$) δ ppm 8.31-8.22 (m, 1H), 7.99-7.95 (m, 1H), 7.61-7.57 (m, 1H), 7.37-7.34 (m, 1H), 5.08 (s, 1H), 4.28-4.22 (m, 1H), 4.14-4.00 (m, 1H), 3.97-3.95 (m, 2H), 3.74-3.71 (m, 4H), 3.57-3.48 (m, 1H), 3.12-3.06 (m, 2H), 1.89-1.84 (m, 1H), 1.68-1.63 (m, 2H), 1.43-1.37 (m, 4H), 1.28-1.23 (m, 1H), 0.73-0.66 (m, 2H), 0.44-0.36 (m, 2H). MS (ESI): mass calcd. for C$_{24}$H$_{28}$ClN$_5$O$_3$, 469.2; m/z found, 470.1 [M+H]$^+$.

Example 223a: 1-[3-[[4-Chloro-2-methoxy-3-(2,2,2-trifluoroethyl)-6-quinolyl]-hydroxy-(3-methyltriazol-4-yl)methyl]azetidin-1-yl]ethanone

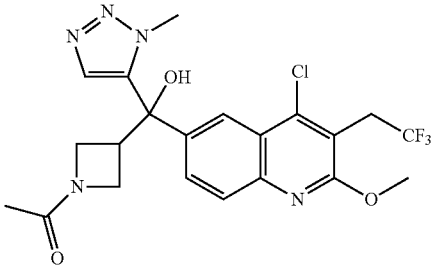 [SMILES: COc1nc2ccc(C(O)(c3cnnn3C)C3CN(C(C)=O)C3)cc2c(Cl)c1CC(F)(F)F]

The title compound was prepared using azetidin-3-yl(4-chloro-2-methoxy-3-(2,2,2-trifluoroethyl)quinolin-6-yl)(1-methyl-1H-1,2,3-triazol-5-yl)methanol (Example 237) in place of azetidin-3-yl(4-chloro-3-(cyclopropylmethoxy)-2-ethylquinolin-6-yl)(1-methyl-1H-1,2,3-triazol-5-yl)methanol using the procedure described for Example 222.

1-[3-[[4-Chloro-2-methoxy-3-(2,2,2-trifluoroethyl)-6-quinolyl]-hydroxy-(3-methyltriazol-4-yl)methyl]azetidin-1-yl]ethanone was purified by chiral SFC (Stationary phase: CHIRALPAK IC 5 μM 250×20 mm, Mobile phase: 50% $CO_2$, 50% mixture of EtOH/iPrOH 50/50 v/v) to give 2 enantiomers. The first eluting enantiomer was Example 223b: $^1$H NMR (500 MHz, $CDCl_3$) δ ppm 8.34-8.25 (m, 1H), 7.80 (d, J=8.8 Hz, 1H), 7.59 (d, J=3.6 Hz, 1H), 7.40-7.35 (m, 1H), 4.77-4.44 (m, 1H), 4.41-4.25 (m, 1H), 4.25-4.19 (m, 1H), 4.16-4.11 (m, 1H), 4.11 (s, 3H), 3.88-3.81 (m, 2H), 3.80-3.76 (m, 1H), 3.72-3.70 (m, 3H), 3.58-3.49 (m, 1H), 1.85-1.79 (m, 3H). MS (ESI): mass calcd. for $C_{21}H_{21}ClF_3N_5O_3$, 483.1; m/z found, 484.0 [M+H]$^+$ and the second eluting enantiomer was Example 223c: $^1$H NMR (500 MHz, $CDCl_3$) δ ppm 8.34-8.24 (m, 1H), 7.82-7.79 (m, 1H), 7.63-7.54 (m, 1H), 7.39-7.35 (m, 1H), 4.75-4.37 (m, 1H), 4.27-4.20 (m, 1H), 4.17-4.14 (m, 1H), 4.11 (s, 3H), 3.89-3.82 (m, 2H), 3.82-3.73 (m, 1H), 3.72-3.67 (m, 3H), 3.61-3.34 (m, 2H), 1.86-1.82 (m, 3H). MS (ESI): mass calcd. for $C_{21}H_{21}ClF_3N_5O_3$, 483.1; m/z found, 484.0 [M+H]$^+$.

Example 224a: [2,4-Diethyl-3-(2,2,2-trifluoroethyl)-6-quinolyl]-(3-methylimidazol-4-yl)-[2-(trifluoromethyl)-4-pyridyl]methanol

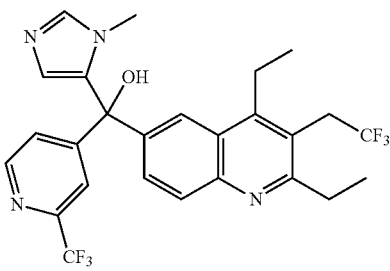

The title compound was prepared using (2,4-dichloro-3-(2,2,2-trifluoroethyl)quinolin-6-yl)(1-methyl-1H-imidazol-5-yl)(2-(trifluoromethyl)pyridin-4-yl)methanol (Example 231) in place of tert-butyl 3-((3-(benzyloxy)-2,4-dichloroquinolin-6-yl)(hydroxy)(1-methyl-1H-1,2,3-triazol-5-yl)methyl)azetidine-1-carboxylate using the procedure described for Intermediate 85.

[2,4-Diethyl-3-(2,2,2-trifluoroethyl)-6-quinolyl]-(3-methylimidazol-4-yl)-[2-(trifluoromethyl)-4-pyridyl]methanol was purified by achiral SFC (Stationary phase: $NH_2$ 5 μM 150×30 mm, Mobile phase: 82% $CO_2$, 18% MeOH+ 0.3% $iPrNH_2$) followed by chiral SFC (Stationary phase: CHIRALPAK IC 5 m 250×20 mm, Mobile phase: 75% $CO_2$, 25% iPrOH+0.3% $iPrNH_2$), to give 2 enantiomers. The first eluting enantiomer was Example 224b: $^1$H NMR (500 MHz, $CDCl_3$) δ ppm 8.73 (d, J=5.1 Hz, 1H), 8.06 (d, J=8.8 Hz, 1H), 7.91 (d, J=2.0 Hz, 1H), 7.87-7.85 (m, 1H), 7.65 (dd, J=8.8, 2.1 Hz, 1H), 7.54-7.51 (m, 2H), 6.55 (s, 1H), 3.77-3.70 (m, 2H), 3.41 (s, 3H), 3.31 (s, 1H), 3.11-3.04 (m, 4H), 1.40-1.36 (m, 3H), 1.17 (t, J=7.6 Hz, 3H). MS (ESI): mass calcd. for $C_{26}H_{24}F_6N_4O$, 522.2; m/z found, 523.3 [M+H]$^+$ and the second eluting enantiomer was Example 224c: $^1$H NMR (500 MHz, $CDCl_3$) δ ppm 8.74 (d, J=5.1 Hz, 1H), 8.06 (d, J=8.8 Hz, 1H), 7.91-7.89 (m, 1H), 7.88-7.85 (m, 1H), 7.67-7.63 (m, 1H), 7.54-7.51 (m, 2H), 6.56 (s, 1H), 3.77-3.70 (m, 2H), 3.41 (s, 3H), 3.25 (s, 1H), 3.12-3.05 (m, 4H), 1.38 (t, J=7.5 Hz, 3H), 1.18-1.15 (m, 3H). MS (ESI): mass calcd. for $C_{26}H_{24}F_6N_4O$, 522.2; m/z found, 523.3 [M+H]$^+$.

Example 225a: [4-Chloro-2-methoxy-3-(2,2,2-trifluoroethyl)-6-quinolyl]-(3-methylimidazol-4-yl)-[2-(trifluoromethyl)-4-pyridyl]methanol

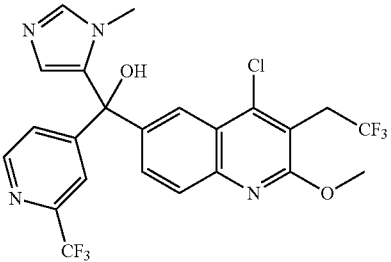

To a mixture of (2,4-dichloro-3-(2,2,2-trifluoroethyl)quinolin-6-yl)(1-methyl-1H-imidazol-5-yl)(2-(trifluoromethyl)pyridin-4-yl)methanol (208 mg, 0.39 mmol, Example 231), toluene (3.9 mL) and methanol (0.97 mL) was added sodium methoxide (107 mg, 1.94 mmol). The resulting mixture was stirred at 40° C. for 5 hours and then at room temperature for 15 hours. The mixture was diluted with EtOAc (25 mL) and washed with saturated aqueous $NH_4Cl$ (20 mL) followed by sat. aq. $NaHCO_3$ (20 mL). The organics were dried ($Na_2SO_4$), filtered and concentrated to dryness. The crude was purified by reverse-phase HPLC (acetonitrile/water+ 0.05% TFA) followed by another reverse-phase HPLC (acetonitrile/water+$NH_4OH$) to provide the title compound as a yellow amorphous solid.

[4-Chloro-2-methoxy-3-(2,2,2-trifluoroethyl)-6-quinolyl]-(3-methylimidazol-4-yl)-[2-(trifluoromethyl)-4-pyridyl]methanol was purified by chiral SFC (Stationary phase: CHIRALPAK IC 5 μM 250×20 mm, Mobile phase: 80% $CO_2$, 20% iPrOH+0.3% $iPrNH_2$) to give two enantiomers. The first eluting enantiomer was Example 225b: $^1$H NMR (500 MHz, $CDCl_3$) δ ppm 8.73 (d, J=5.2 Hz, 1H), 8.15 (d, J=2.1 Hz, 1H), 7.87-7.85 (m, 2H), 7.60 (dd, J=8.8, 2.2 Hz, 1H), 7.51 (dd, J=5.0, 1.7 Hz, 1H), 7.50-7.48 (m, 1H), 6.49 (s, 1H), 4.11 (s, 3H), 3.83 (q, J=10.0 Hz, 2H), 3.55 (s, 1H), 3.40 (s, 3H). MS (ESI): mass calcd. for C$_{23}$H$_{17}$ClF$_6$N$_4$O$_2$, 530.1; m/z found, 531.2 [M+H]$^+$ and the second eluting enantiomer was Example 225c: $^1$H NMR (500 MHz, CDCl$_3$) δ ppm 8.73 (d, J=5.2 Hz, 1H), 8.15 (d, J=2.1 Hz, 1H), 7.87-7.85 (m, 2H), 7.60 (dd, J=8.8, 2.2 Hz, 1H), 7.52-7.50 (m, 1H), 7.50-7.49 (m, 1H), 6.50 (s, 1H), 4.11 (s, 3H), 3.87-3.80 (m, 2H), 3.53 (s, 1H), 3.40 (s, 3H). MS (ESI): mass calcd. for C$_{23}$H$_{17}$ClF$_6$N$_4$O$_2$, 530.1; m/z found, 531.2 [M+H]$^+$.

Example 226a: 2-Ethyl-6-[hydroxy-(3-methylimidazol-4-yl)-[2-(trifluoromethyl)-4-pyridyl]methyl]-3-(2,2,2-trifluoroethyl)quinoline-4-carbonitrile

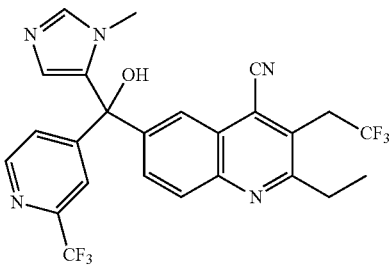

The title compound was prepared using [4-chloro-2-ethyl-3-(2,2,2-trifluoroethyl)-6-quinolyl]-(3-methylimidazol-4-yl)-[2-(trifluoromethyl)-4-pyridyl]methanol (Example 227a) in place of [4-chloro-2-methoxy-3-(2,2,2-trifluoroethoxy)quinolin-6-yl](1-methyl-1H-imidazol-5-yl)[6-(trifluoromethyl)pyridin-3-yl]methanol using the procedure described for Example 208a. 2-Ethyl-6-[hydroxy-(3-methylimidazol-4-yl)-[2-(trifluoromethyl)-4-pyridyl]methyl]-3-(2,2,2-trifluoroethyl)quinoline-4-carbonitrile was purified by chiral SFC (Stationary phase: CHIRALPAK IC 5 μM 250×20 mm, Mobile phase: 80% CO$_2$, 20% iPrOH+0.3% iPrNH$_2$) followed by Reverse phase HPLC (Stationary phase: X-Bridge-C18 5 μM 150×30 mm), Mobile phase: Gradient from 70% NH$_4$HCO$_3$, 0.5% to 30% CH$_3$CN to 0% NH$_4$HCO$_3$, 0.5% to 100% CH$_3$CN) to give two enantiomers. The first eluting enantiomer was Example 226b: $^1$H NMR (600 MHz, CDCl$_3$) δ ppm 8.75 (d, J=5.2 Hz, 1H), 8.34 (d, J=2.1 Hz, 1H), 8.12 (d, J=8.9 Hz, 1H), 7.88-7.85 (m, 1H), 7.69 (dd, J=8.9, 2.1 Hz, 1H), 7.56-7.53 (m, 1H), 7.48 (s, 1H), 6.51 (s, 1H), 4.29 (s, 1H), 3.98-3.92 (m, 2H), 3.40 (s, 3H), 3.16-3.12 (m, 2H), 1.44-1.41 (m, 3H). MS (ESI): mass calcd. for C$_{25}$H$_{19}$F$_6$N$_5$O, 519.1; m/z found, 520.0 [M+H]$^+$ and the second eluting enantiomer was Example 226c: $^1$H NMR (600 MHz, CDCl$_3$) δ ppm 8.77-8.73 (m, 1H), 8.35-8.33 (m, 1H), 8.14-8.10 (m, 1H) 7.88-7.85 (m, 1H), 7.71-7.68 (m, 1H), 7.57-7.54 (m, 1H), 7.50-7.47 (m, 1H), 6.53-6.51 (m, 1H), 4.15-4.09 (m, 1H), 3.40 (s, 3H), 3.16-3.12 (m, 2H), 3.98-3.92 (m, 2H), 1.44-1.41 (m, 3H). MS (ESI): mass calcd. for C$_{25}$H$_{19}$F$_6$N$_5$O, 519.1; m/z found, 520.0 [M+H]$^+$.

Example 227a: [4-Chloro-2-ethyl-3-(2,2,2-trifluoroethyl)-6-quinolyl]-(3-methylimidazol-4-yl)-[2-(trifluoromethyl)-4-pyridyl]methanol

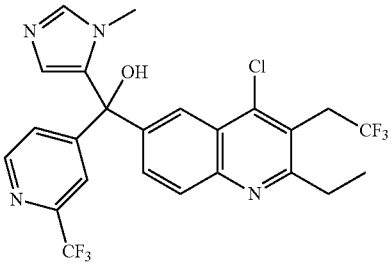

The title compound was prepared using (2,4-dichloro-3-(2,2,2-trifluoroethyl)quinolin-6-yl)(1-methyl-1H-imidazol-5-yl)(2-(trifluoromethyl)pyridin-4-yl)methanol (Example 231) in place of tert-butyl 3-((3-(benzyloxy)-2,4-dichloroquinolin-6-yl)(hydroxy)(1-methyl-1H-1,2,3-triazol-5-yl)methyl)azetidine-1-carboxylate using the procedure described for Intermediate 85.

[4-Chloro-2-ethyl-3-(2,2,2-trifluoroethyl)-6-quinolyl]-(3-methylimidazol-4-yl)-[2-(trifluoromethyl)-4-pyridyl]methanol was purified by chiral SFC (Stationary phase: CHIRALPAK IC 5 μM 250×20 mm, Mobile phase: 75% CO$_2$, 25% iPrOH+0.3% iPrNH$_2$) to give two enantiomers. The first eluting enantiomer was Example 227b: $^1$H NMR (600 MHz, CDCl$_3$) δ ppm 8.72 (d, J=5.1 Hz, 1H), 8.29-8.26 (m, 1H), 8.05 (d, J=8.8 Hz, 1H), 7.90-7.88 (m, 1H), 7.70-7.67 (m, 1H), 7.54-7.51 (m, 1H), 7.46-7.41 (m, 1H), 6.45 (s, 1H), 4.25 (s, 1H), 3.96-3.90 (m, 2H), 3.38 (s, 3H), 3.13-3.08 (m, 2H), 1.41-1.38 (m, 3H), MS (ESI): mass calcd. for C$_{24}$H$_{19}$ClF$_6$N$_4$O, 528.1; m/z found, 529.0 [M+H]$^+$ and the second eluting enantiomer was Example 227c: $^1$H NMR (600 MHz, CDCl$_3$) δ ppm 8.75-8.73 (m, 1H), 8.27-8.24 (m, 1H), 8.09-8.04 (m, 1H) 7.88-7.86 (m, 1H), 7.71-7.66 (m, 1H), 7.54-7.49 (m, 2H), 6.57-6.49 (m, 1H), 3.97-3.90 (m, 2H), 3.54-3.50 (m, 1H), 3.13-3.08 (m, 2H), 3.40 (s, 3H), 1.42-1.38 (m, 3H). MS (ESI): mass calcd. for C$_{24}$H$_{19}$ClF$_6$N$_4$O, 528.1; m/z found, 529.0 [M+H]$^+$.

Example 228: (3-(Benzyloxy)-4-chloro-2-methoxyquinolin-6-yl)(1-methyl-1H-imidazol-5-yl)(2-(trifluoromethyl)pyridin-4-yl)methanol

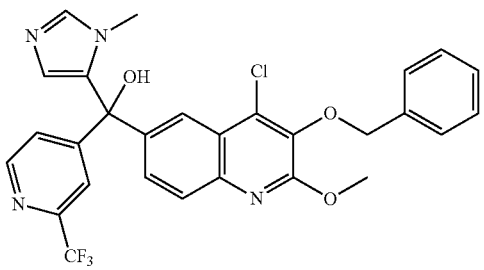 [SMILES: COc1nc2ccc(C(O)(c3ccnc(C(F)(F)F)c3)c3cncn3C)cc2c(Cl)c1OCc1ccccc1]

The title compound was prepared using (1-methyl-1H-imidazol-5-yl)(2-(trifluoromethyl)pyridin-4-yl)methanone (Intermediate 14: step b) in place of (2,6-dimethylpyridin-3-yl)(1-methyl-1H-1,2,3-triazol-5-yl)methanone using the procedure described for Example 169. $^1$H NMR (500 MHz, CDCl$_3$) δ ppm 8.65 (d, J=5.1 Hz, 1H), 8.10 (d, J=2.1 Hz, 1H), 7.94-7.90 (m, 1H), 7.79 (d, J=8.8 Hz, 1H), 7.55-7.51 (m, 2H), 7.50-7.44 (m, 2H), 7.40-7.36 (m, 2H), 7.36-7.31 (m, 1H), 7.17-7.15 (m, 1H), 6.62 (s, 1H), 6.22-6.19 (m, 1H), 5.16 (s, 2H), 4.15 (s, 3H), 3.29 (s, 3H). MS (ESI): mass calcd. for C$_{28}$H$_{22}$ClF$_3$N$_4$O$_3$, 554.1; m/z found, 555.0 [M+H]$^+$.

Example 229: 4-((3-(Benzyloxy)-4-chloro-2-methoxyquinolin-6-yl)(hydroxy)(1-methyl-1H-imidazol-5-yl)methyl)benzonitrile

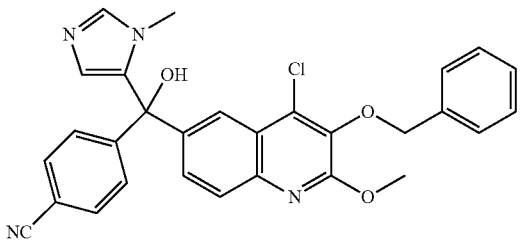 [SMILES: COc1nc2ccc(C(O)(c3ccc(C#N)cc3)c3cncn3C)cc2c(Cl)c1OCc1ccccc1]

To a mixture of 5-bromo-1-methyl-1H-imidazole (569 mg, 3.417 mmol) in THF (14 mL) at 0° C. was added iPrMgCl—LiCl (1.3 M in THF, 2.48 mL, 3.22 mmol) to provide a white suspension. This mixture was stirred at 0° C. for 10 minutes, then the ice-water bath was removed and the mixture stirred at room temperature for 10 minutes. The reaction was then cooled to 0° C. in an ice-water bath and stirred at 0° C. for an additional 10 minutes. Then, a solution of 4-(3-(benzyloxy)-4-chloro-2-methoxyquinoline-6-carbonyl)benzonitrile (335 mg, 0.78 mmol, Intermediate 83: step a) in THF (8 mL) was added. The flask was rinsed with THF (1.5 mL), which was also added to the reaction. The resulting mixture was stirred at 0° C. for 10 minutes, then the ice-water bath was removed and the reaction was allowed to stir at room temperature for 4 hours. The reaction was quenched by the addition of water (15 mL). The aqueous was then extracted with EtOAc (3×20 mL). The organic layers were combined, washed with brine, dried (Na$_2$SO$_4$), filtered and concentrated to dryness. The residue was triturated with Et$_2$O, filtered and dried under air to provide the title compound as a white solid. $^1$H NMR (500 MHz, CDCl$_3$) δ ppm 8.01-7.99 (m, 1H), 7.80 (d, J=8.7 Hz, 1H), 7.68-7.65 (m, 2H), 7.56-7.53 (m, 3H), 7.53-7.52 (m, 1H), 7.50-7.46 (m, 2H), 7.41-7.34 (m, 3H), 6.45-6.44 (m, 1H), 5.16 (s, 2H), 4.15 (s, 3H), 3.39 (s, 3H). MS (ESI): mass calcd. for C$_{29}$H$_{23}$ClN$_4$O$_3$, 510.2; m/z found, 511.0 [M+H]$^+$.

Example 230: (3-(Benzyloxy)-4-chloro-2-methoxyquinolin-6-yl)(4-chlorophenyl)(1-methyl-1H-imidazol-5-yl)methanol

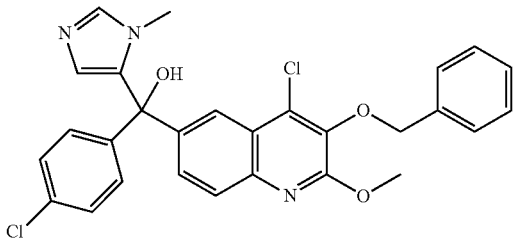 [SMILES: COc1nc2ccc(C(O)(c3ccc(Cl)cc3)c3cncn3C)cc2c(Cl)c1OCc1ccccc1]

The title compound was prepared using (4-chlorophenyl)(1-methyl-1H-imidazol-5-yl)methanone (Intermediate 22: step b) in place of (2,6-dimethylpyridin-3-yl)(1-methyl-1H-1,2,3-triazol-5-yl)methanone using the procedure described for Example 169. $^1$H NMR (600 MHz, CDCl$_3$) δ ppm 8.03-8.02 (m, 1H), 7.79-7.77 (m, 1H), 7.55-7.52 (m, 2H), 7.48 (dd, J=8.7, 2.2 Hz, 1H), 7.46-7.45 (m, 1H), 7.40-7.37 (m, 2H), 7.36-7.33 (m, 2H), 7.33-7.30 (m, 3H), 6.45 (d, J=1.1 Hz, 1H), 5.16 (s, 2H), 4.15 (s, 3H), 3.41-3.40 (m, 3H), 3.08 (s, 1H). MS (ESI): mass calcd. for C$_{28}$H$_{23}$Cl$_2$N$_3$O$_3$, 519.1; m/z found, 520.0 [M+H]$^+$.

Example 231: (2,4-Dichloro-3-(2,2,2-trifluoroethyl)quinolin-6-yl)(1-methyl-1H-imidazol-5-yl)(2-(trifluoromethyl)pyridin-4-yl)methanol

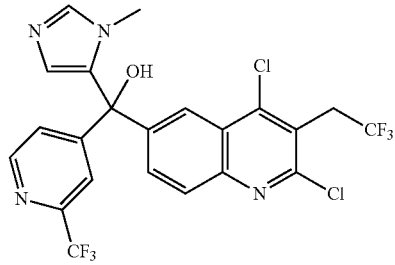 [SMILES: Cn1cncc1C(O)(c1ccnc(C(F)(F)F)c1)c1ccc2nc(Cl)c(CC(F)(F)F)c(Cl)c2c1]

The title compound was prepared using (1-methyl-1H-imidazol-5-yl)(2-(trifluoromethyl)pyridin-4-yl)methanone (Intermediate 14: step b) in place of (1-methyl-1H-imidazol-5-yl)(6-(trifluoromethyl)pyridin-3-yl)methanone using the procedure described for Example 161. $^1$H NMR (500 MHz, CDCl$_3$) δ ppm 8.66 (d, J=5.1 Hz, 1H), 8.35 (d, J=2.0 Hz, 1H), 8.01 (d, J=8.9 Hz, 1H), 7.96-7.94 (m, 1H), 7.79-7.74 (m, 1H), 7.48-7.44 (m, 1H), 7.38 (s, 1H), 7.13-7.10 (m, 1H), 6.18-6.16 (m, 1H), 4.10-4.03 (m, 2H), 3.30 (s, 3H). MS (ESI): mass calcd. for C$_{22}$H$_{14}$Cl$_2$F$_6$N$_4$O, 534.0; m/z found, 534.9 [M+H]$^+$.

Example 232: tert-Butyl 3-((3-(benzyloxy)-2,4-dichloroquinolin-6-yl)(hydroxy)(1-methyl-1H-1,2,3-triazol-5-yl)methyl)azetidine-1-carboxylate

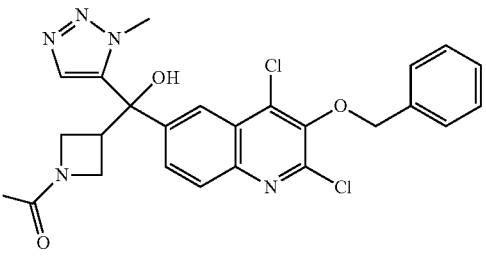

The title compound was prepared using 3-(benzyloxy)-6-bromo-2,4-dichloroquinoline (Intermediate 29: step c) in place of 3-(benzyloxy)-6-bromo-4-chloro-2-methoxyquinoline and tert-butyl 3-(1-methyl-1H-1,2,3-triazole-5-carbonyl)azetidine-1-carboxylate (Intermediate 55: step b) in place of (2,6-dimethylpyridin-3-yl)(1-methyl-1H-1,2,3-triazol-5-yl)methanone using the procedure described for Example 169. $^1$H NMR (500 MHz, CDCl$_3$) δ ppm 8.31 (d, J=2.1 Hz, 1H), 7.98 (d, J=8.8 Hz, 1H), 7.62-7.61 (m, 1H), 7.61-7.59 (m, 2H), 7.47-7.40 (m, 4H), 5.19 (s, 2H), 4.31-4.26 (m, 1H), 3.97-3.88 (m, 2H), 3.71 (s, 3H), 3.70-3.65 (m, 1H), 3.52-3.46 (m, 1H), 3.24 (s, 1H), 1.42 (s, 9H). MS (ESI): mass calcd. for $C_{28}H_{29}Cl_2N_5O_4$, 569.2; m/z found, 570.1 $[M+H]^+$.

Example 233: tert-Butyl 3-((4-chloro-3-(cyclopropylmethoxy)-2-ethylquinolin-6-yl)(hydroxy)(1-methyl-1H-1,2,3-triazol-5-yl)methyl)azetidine-1-carboxylate

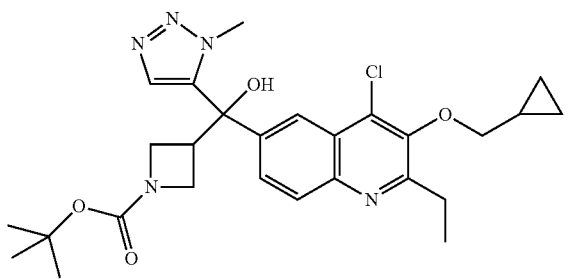 [SMILES: CCc1nc2ccc(C(O)(c3cnnn3C)C3CN(C(=O)OC(C)(C)C)C3)cc2c(Cl)c1OCC1CC1]

The title compound was prepared using tert-butyl 3-((4-chloro-2-ethyl-3-hydroxyquinolin-6-yl)(hydroxy)(1-methyl-1H-1,2,3-triazol-5-yl)methyl)azetidine-1-carboxylate (Intermediate 85) in place of 4-chloro-6-((2,6-dimethylpyridin-3-yl)(hydroxy)(1-methyl-1H-1,2,3-triazol-5-yl)methyl)-2-methoxyquinolin-3-ol and cyclopropylmethanol in place of 3-methyl-3-oxetanemethanol using the procedure described for Example 36a. $^1$H NMR (500 MHz, CDCl$_3$) δ ppm 8.34 (d, J=2.0 Hz, 1H), 8.23 (d, J=8.9 Hz, 1H), 7.63 (s, 1H), 7.51 (d, J=8.8 Hz, 1H), 4.30-4.24 (m, 1H), 4.09-4.01 (m, 3H), 3.99-3.95 (m, 1H), 3.88 (dd, J=9.0, 5.4 Hz, 1H), 3.71 (s, 3H), 3.68-3.63 (m, 1H), 3.50-3.45 (m, 1H), 3.27-3.21 (m, 2H), 1.44 (s, 3H), 0.74-0.71 (m, 2H), 1.42-1.41 (m, 9H), 0.42-0.39 (m, 2H). MS (ESI): mass calcd. for $C_{27}H_{34}ClN_5O_4$, 527.2; m/z found, 528.2 $[M+H]^+$.

Example 234: Azetidin-3-yl(4-chloro-3-(cyclopropylmethoxy)-2-ethylquinolin-6-yl)(1-methyl-1H-1,2,3-triazol-5-yl)methanol

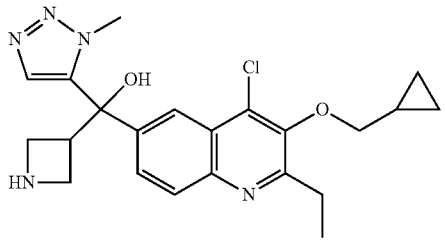 [SMILES: CCc1nc2ccc(C(O)(c3cnnn3C)C3CNC3)cc2c(Cl)c1OCC1CC1]

To a mixture of tert-butyl 3-((4-chloro-3-(cyclopropylmethoxy)-2-ethylquinolin-6-yl)(hydroxy)(1-methyl-1H-1,2,3-triazol-5-yl)methyl)azetidine-1-carboxylate (218 mg, 0.34 mmol, Example 233) in CH$_2$Cl$_2$ (1.7 mL) was added TFA (0.26 mL, 3.4 mmol) and the resulting solution was stirred at room temperature for 18 hours. The reaction was then diluted with CH$_2$Cl$_2$ (10 mL) and partitioned with saturated aqueous NaHCO$_3$ (7 mL). The layers were separated and the aqueous further extracted with CH$_2$Cl$_2$ (2×15 mL). The organics were combined, dried (Na$_2$SO$_4$), filtered and concentrated to dryness to afford the title compound as a cream-colored solid. $^1$H NMR (500 MHz, CDCl$_3$) δ ppm 8.37-8.35 (m, 1H), 7.93 (d, J=8.8 Hz, 1H), 7.52 (s, 1H), 7.40-7.37 (m, 1H), 4.22-4.17 (m, 1H), 3.94 (d, J=7.2 Hz, 2H), 3.77 (s, 3H), 3.74-3.69 (m, 1H), 3.53-3.49 (m, 1H), 3.31-3.26 (m, 2H), 3.07 (q, J=7.5 Hz, 2H), 1.38 (t, J=7.5 Hz, 4H), 1.28-1.24 (m, 2H), 0.71-0.67 (m, 2H), 0.41-0.38 (m, 2H). MS (ESI): mass calcd. for $C_{22}H_{26}ClN_5O_2$, 427.2; m/z found, 428.1 $[M+H]^+$.

Example 235: tert-Butyl 3-((2,4-dichloro-3-(2,2,2-trifluoroethyl)quinolin-6-yl)(hydroxy)(1-methyl-1H-1,2,3-triazol-5-yl)methyl)azetidine-1-carboxylate

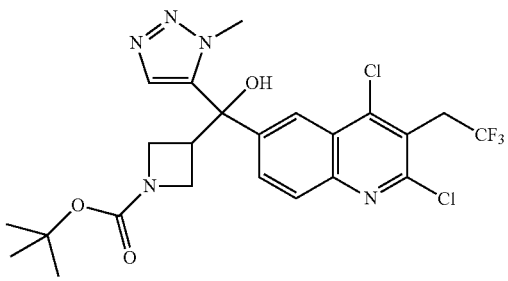 [SMILES: Cn1nncc1C(O)(c1ccc2nc(Cl)c(CC(F)(F)F)c(Cl)c2c1)C1CN(C(=O)OC(C)(C)C)C1]

The title compound was prepared using tert-butyl 3-(1-methyl-1H-1,2,3-triazole-5-carbonyl)azetidine-1-carboxylate (Intermediate 55: step b) in place of (2,6-dimethylpyridin-3-yl)(1-methyl-1H-1,2,3-triazol-5-yl)methanone using the procedure described for Example 141. $^1$H NMR (500 MHz, CDCl$_3$) δ ppm 8.44 (d, J=2.0 Hz, 1H), 7.99 (d, J=8.7 Hz, 1H), 7.54 (s, 1H), 7.53-7.49 (m, 1H), 4.25-4.20 (m, 1H), 4.11-4.05 (m, 2H), 4.05-4.00 (m, 1H), 3.92-3.88 (m, 1H), 3.70 (s, 3H), 3.64-3.59 (m, 1H), 3.51-3.44 (m, 1H), 1.69-1.65 (m, 1H), 1.38 (s, 9H). MS (ESI): mass calcd. for $C_{23}H_{24}Cl_2F_3N_5O_3$, 545.1; m/z found, 546.1 $[M+H]^+$.

Example 236: tert-Butyl 3-((4-chloro-2-methoxy-3-(2,2,2-trifluoroethyl)quinolin-6-yl)(hydroxy)(1-methyl-1H-1,2,3-triazol-5-yl)methyl)azetidine-1-carboxylate

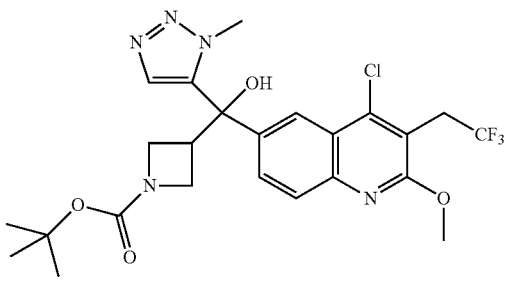 [SMILES: COc1nc2ccc(C(O)(c3cnnn3C)C3CN(C(=O)OC(C)(C)C)C3)cc2c(Cl)c1CC(F)(F)F]

To a mixture of tert-butyl 3-((2,4-dichloro-3-(2,2,2-trifluoroethyl)quinolin-6-yl)(hydroxy)(1-methyl-1H-1,2,3-triazol-5-yl)methyl)azetidine-1-carboxylate (393 mg, 0.72 mmol, Example 235) in toluene (7.2 mL) and MeOH (1.8 mL) was added NaOMe (198 mg, 3.6 mmol) and the resulting mixture heated to 40° C. for 6.5 hours. The mixture was then cooled to room temperature and allowed to stir at that temperature for 15.5 hours. The mixture was then diluted with EtOAc (50 mL) and washed with saturated aqueous NH$_4$Cl (35 mL) followed by saturated aqueous NaHCO$_3$ (35 mL). The organics were dried (Na$_2$SO$_4$), filtered and concentrated to dryness. The residue was purified by reverse-phase HPLC (acetonitrile+water/NH$_4$OH) to afford the title compound as a white solid. $^1$H NMR (500 MHz, CDCl$_3$) δ ppm 8.28 (d, J=2.1 Hz, 1H), 7.81-7.78 (m, 1H), 7.56 (s, 1H), 7.38-7.35 (m, 1H), 4.26-4.20 (m, 1H), 4.10 (s, 3H), 4.00-3.96 (m, 1H), 3.93-3.89 (m, 1H), 3.88-3.81 (m, 2H), 3.69 (s, 3H), 3.67-3.62 (m, 1H), 3.50-3.45 (m, 1H), 1.40 (s, 9H). MS (ESI): mass calcd. for C$_{24}$H$_{27}$ClF$_3$N$_5$O$_4$, 541.2; m/z found, 542.1 [M+H]$^+$.

Example 237: Azetidin-3-yl(4-chloro-2-methoxy-3-(2,2,2-trifluoroethyl)quinolin-6-yl)(1-methyl-1H-1,2,3-triazol-5-yl)methanol

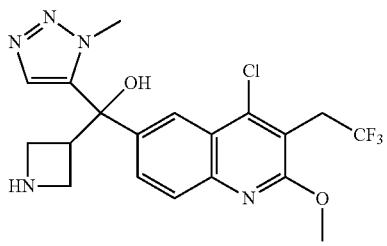 [SMILES: COc1nc2ccc(C(O)(c3cnnn3C)C3CNC3)cc2c(Cl)c1CC(F)(F)F]

The title compound was prepared using tert-butyl 3-((4-chloro-2-methoxy-3-(2,2,2-trifluoroethyl)quinolin-6-yl)(hydroxy)(1-methyl-1H-1,2,3-triazol-5-yl)methyl)azetidine-1-carboxylate (Example 236) in place of tert-butyl 3-((4-chloro-3-(cyclopropylmethoxy)-2-ethylquinolin-6-yl)(hydroxy)(1-methyl-1H-1,2,3-triazol-5-yl)methyl)azetidine-1-carboxylate using the procedure described for Example 234. $^1$H NMR (400 MHz, CDCl$_3$) δ ppm 8.39 (d, J=2.0 Hz, 1H), 7.77 (d, J=8.8 Hz, 1H), 7.51 (s, 1H), 7.44-7.40 (m, 1H), 4.22-4.17 (m, 1H), 4.09 (s, 3H), 3.87-3.81 (m, 2H), 3.77 (s, 3H), 3.73-3.68 (m, 1H), 3.53-3.48 (m, 1H), 3.30-3.24 (m, 2H). MS (ESI): mass calcd. for C$_{19}$H$_{19}$ClF$_3$N$_5$O$_2$, 441.1; m/z found, 442.0 [M+H]$^+$.

Example 238a: [4-(Azetidin-1-yl)-2-chloro-3-(2,2,2-trifluoroethyl)-6-quinolyl]-(2,6-dimethyl-3-pyridyl)-(3-methyltriazol-4-yl)methanol

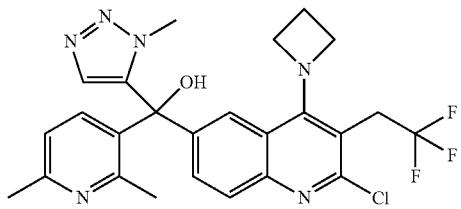 [SMILES: Cc1ccc(C(O)(c2ccc3nc(Cl)c(CC(F)(F)F)c(N4CCC4)c3c2)c2cnnn2C)c(C)n1]

[2,4-Dichloro-3-(2,2,2-trifluoroethyl)quinolin-6-yl](2,6-dimethylpyridin-3-yl)(1-methyl-1H-1,2,3-triazol-5-yl)methanol (200 mg, 0.28 mmol, Example 141), azetidine (82 μL, 1.2 mmol), and DMF (2 mL) were combined in a reaction tube, then sealed and heated to 100° C. and maintained at that temperature overnight. The reaction vessel was then cooled to room temperature and the contents were transferred to a separatory funnel with EtOAc dilution, then extracted three times with deionized water. The organic phase was separated, dried over MgSO$_4$, filtered and concentrated under reduced pressure. The crude material was purified via reverse phase chromatography using acetonitrile with ammonium hydroxide in water as eluent to afford the title compound. $^1$H NMR (600 MHz, CDCl$_3$) δ ppm 7.80 (d, J=8.8 Hz, 1H), 7.61 (s, 1H), 7.54 (dd, J=8.9, 2.0 Hz, 1H), 6.94 (d, J=8.1 Hz, 1H), 6.91 (d, J=8.1 Hz, 1H), 6.81 (s, 1H), 4.40-4.29 (m, 4H), 3.98-3.80 (m, 5H), 2.52 (s, 3H), 2.38 (s, 3H), 2.37-2.30 (m, 2H). MS (ESI): mass calcd. for C$_{25}$H$_{24}$ClF$_3$N$_6$O, 516.2; m/z found, 517.5 [M+H]$^+$. Racemic [4-(azetidin-1-yl)-2-chloro-3-(2,2,2-trifluoroethyl)-6-quinolyl]-(2,6-dimethyl-3-pyridyl)-(3-methyltriazol-4-yl)methanol was purified via SFC with a Chiralpak AD-H column (5 m 250×20 mm) using a mobile phase of 75% CO$_2$ and a 25% methanol to provide one enantiomer: Example 238b: $^1$H NMR (600 MHz, CDCl$_3$) δ ppm 7.75 (d, J=8.8 Hz, 1H), 7.60-7.55 (m, 1H), 7.55-7.49 (m, 1H), 6.92 (d, J=8.0 Hz, 1H), 6.87 (d, J=8.1 Hz, 1H), 6.67 (s, 1H), 4.38-4.21 (m, 4H), 4.00-3.77 (m, 5H), 2.51 (s, 3H), 2.36 (s, 3H), 2.32-2.19 (m, 2H). MS (ESI): mass calcd. for C$_{25}$H$_{24}$ClF$_3$N$_6$O, 516.2; m/z found, 517.6 [M+H]$^+$.

Example 239: [4-(Azetidin-1-yl)-2-chloro-3-(2,2,2-trifluoroethyl)-6-quinolyl]-bis(2,3-dimethylimidazol-4-yl)methanol

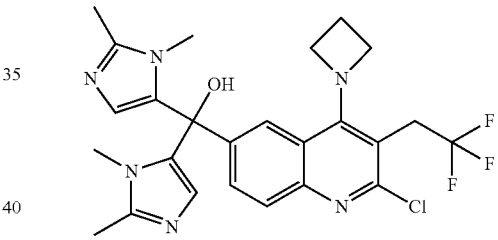

[2,4-Dichloro-3-(2,2,2-trifluoroethyl)quinolin-6-yl][bis(1,2-dimethyl-1H-imidazol-5-yl)]methanol (101 mg, 0.20 mmol, Example 144), azetidine (27 μL, 0.41 mmol), and DMF (10 mL) were combined in a reaction tube, then sealed and heated to 100° C. and maintained at that temperature overnight. The reaction vessel was then cooled to room temperature and the contents were transferred to a separatory funnel with EtOAc dilution, then extracted three times with deionized water. The organic phase was separated, dried over MgSO$_4$, filtered and concentrated under reduced pressure. The crude material was purified via reverse phase chromatography using acetonitrile with ammonium hydroxide in water as eluent to provide the title compound. $^1$H NMR (600 MHz, CDCl$_3$) δ ppm 7.88-7.76 (m, 1H), 7.67 (d, J=8.7 Hz, 1H), 7.63-7.53 (m, 1H), 5.97 (s, 2H), 4.43 (t, J=7.8 Hz, 4H), 4.00-3.86 (m, 2H), 3.39 (s, 6H), 2.38 (p, J=7.6 Hz, 2H), 2.23 (s, 6H). MS (ESI): mass calcd. for C$_{25}$H$_{26}$ClF$_3$N$_6$O, 518.2; m/z found, 519.2 [M+H]$^+$.

Example 240a: [4-Chloro-2-methoxy-3-(2,2,2-trifluoroethyl)-6-quinolyl]-(3-methylimidazol-4-yl)-[6-(trifluoromethyl)-3-pyridyl]methanol

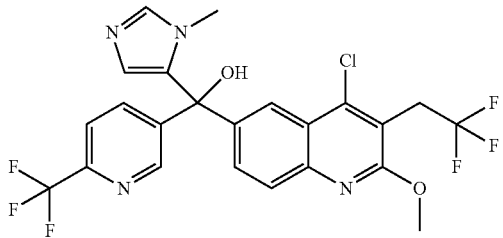 [SMILES: COc1nc2ccc(C(O)(c3ccc(C(F)(F)F)nc3)c3cncn3C)cc2c(Cl)c1CC(F)(F)F]

6-Bromo-4-chloro-2-methoxy-3-(2,2,2-trifluoroethyl)quinoline (508 mg, 1.43 mmol, Intermediate 69: step e) and THF (30 mL) were combined in a dry round bottom flask under an $N_2$ atmosphere and cooled to −78° C. in a dry ice acetone bath. n-BuLi (1.6 M in hexanes, 0.99 mL, 1.58 mmol) was then added dropwise via syringe over approximately 2 minutes and the contents were allowed to stir at −78° C. for an additional 5 minutes. (1-Methyl-1H-imidazol-5-yl)(6-(trifluoromethyl)pyridin-3-yl)methanone (0.410 g, 1.61 mmol, Intermediate 10: step c) in THF (5 mL) was then cannulated into the reaction vessel and the reaction was stirred at −78° C. for two and a half hours. The dry ice bath was removed and replaced by an ice water bath and the reaction continued for approximately 45 minutes. The reaction was quenched with a saturated, aqueous $NH_4Cl$ solution, then transferred to a separatory funnel with EtOAc. The organic phase was separated and the aqueous layer was back extracted with EtOAc, then the combined organic phases were dried over $MgSO_4$, filtered and concentrated under reduced pressure. The crude product was purified by flash column chromatography (silica gel, 0-10% DCM/(10% of a 2 M $NH_3$/MeOH in DCM)) to afford the title compound. $^1$H NMR (600 MHz, $CDCl_3$) δ 8.82 (d, J=2.2 Hz, 1H), 8.20 (d, J=2.1 Hz, 1H), 7.89 (dd, J=8.2, 2.2 Hz, 1H), 7.82 (d, J=8.8 Hz, 1H), 7.63 (dd, J=8.3, 0.8 Hz, 1H), 7.58 (dd, J=8.7, 2.1 Hz, 1H), 7.21 (d, J=1.1 Hz, 1H), 6.24 (d, J=1.1 Hz, 1H), 4.11 (s, 3H), 3.87-3.78 (m, 2H), 3.33 (s, 3H). MS (ESI): mass calcd. for $C_{23}H_{17}ClF_6N_4O_2$, 530.1; m/z found, 531.1 [M+H]$^+$. Racemic [4-chloro-2-methoxy-3-(2,2,2-trifluoroethyl)-6-quinolyl]-(3-methylimidazol-4-yl)-[6-(trifluoromethyl)-3-pyridyl]methanol was purified via SFC with a Chiralpak AD-H column (5 μm 250×20 mm) using a mobile phase of 80% $CO_2$ and a 20% MeOH/i-PrOH 50/50 v/v (+0.3% i-PrNH$_2$)) to provide two enantiomers: Example 240b: $^1$H NMR (400 MHz, $CDCl_3$) δ 8.81 (d, J=2.3 Hz, 1H), 8.21 (d, J=2.1 Hz, 1H), 7.89 (dd, J=8.3, 2.2 Hz, 1H), 7.85-7.78 (m, 1H), 7.65 (dd, J=8.3, 0.8 Hz, 1H), 7.57 (dd, J=8.8, 2.2 Hz, 1H), 7.20 (s, 1H), 6.33 (s, 1H), 6.25 (s, 1H), 4.11 (d, J=2.4 Hz, 3H), 3.89-3.75 (m, 2H), 3.33 (d, J=2.2 Hz, 3H); MS (ESI): mass calcd. for $C_{23}H_{17}ClF_6N_4O_2$, 530.1; m/z found, 531.1 [M+H]$^+$; and Example 240c: $^1$H NMR (400 MHz, $CDCl_3$) δ 8.81 (d, J=2.3 Hz, 1H), 8.21 (d, J=2.1 Hz, 1H), 7.89 (dd, J=8.3, 2.2 Hz, 1H), 7.81 (d, J=8.8 Hz, 1H), 7.64 (d, J=8.3 Hz, 1H), 7.57 (dd, J=8.8, 2.2 Hz, 1H), 7.17 (s, 1H), 6.64 (s, 1H), 6.22 (s, 1H), 4.11 (s, 3H), 3.87-3.75 (m, 2H), 3.32 (d, J=2.2 Hz, 3H); MS (ESI): mass calcd. for $C_{23}H_{17}ClF_6N_4O_2$, 530.1; m/z found, 531.1 [M+H]$^+$.

Example 241a: (6-[Hydroxy-(3-methylimidazol-4-yl)-[6-(trifluoromethyl)-3-pyridyl]methyl]-2-methoxy-3-(2,2,2-trifluoroethyl)quinoline-4-carbonitrile

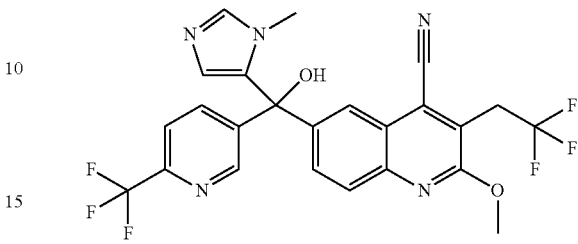

To a dry tube equipped with a stirbar under a nitrogen atmosphere was added [4-chloro-2-methoxy-3-(2,2,2-trifluoroethyl)-6-quinolyl]-(3-methylimidazol-4-yl)-[6-(trifluoromethyl)-3-pyridyl]methanol (205 mg, 0.39 mmol, Example 240a), zinc cyanide (98 mg, 0.82 mmol), X-Phos (41 mg, 0.085 mmol), Zn powder (26 mg, 0.39 mmol), $Pd_2(dba)_3$ (55 mg, 0.060 mmol) then DMA (2 mL), which was previously degassed with a stream of nitrogen. The vessel and contents were briefly degassed with nitrogen, then sealed and placed in a pre-equilibrated 120° C. reaction block for approximately 20 hours. The contents were cooled to room temperature then transferred to a separatory funnel with EtOAc dilution and extracted with saturated, aqueous ammonium chloride solution then dionized water. The organic phase was then separated, dried over $MgSO_4$, filtered and concentrated under reduced pressure. The compound was purified via reverse phase chromatography using acetonitrile with ammonium hydroxide in water as eluent. The fractions from the purification containing the desired product were transferred to a separatory funnel with EtOAc and extracted with deionized water. The organic phase was then dried over magnesium sulfate, filtered and concentrated under reduced pressure to provide the title compound. $^1$H NMR (600 MHz, $CDCl_3$) δ ppm $^1$H NMR (600 MHz, $CDCl_3$) δ ppm 8.81 (s, 1H), 8.20 (s, 1H), 8.03 (s, 1H), 7.98-7.87 (m, 2H), 7.71-7.60 (m, 2H), 7.44-7.36 (m, 1H), 6.50 (s, 1H), 4.14 (s, 3H), 3.90-3.80 (m, 2H), 3.51 (s, 3H). MS (ESI): mass calcd. for $C_{24}H_{17}F_6N_5O_2$, 521.1; m/z found, 522.1 [M+H]$^+$. Racemic 6-[hydroxy-(3-methylimidazol-4-yl)-[6-(trifluoromethyl)-3-pyridyl]methyl]-2-methoxy-3-(2,2,2-trifluoroethyl)quinoline-4-carbonitrile was purified by chiral SFC (Stationary phase: CHIRALCEL OJ-H 5 μm 250×20 mm) using mobile phase: 90% $CO_2$ and a 10% mixture of MeOH/i-PrOH 50/50 v/v (+0.3% i-PrNH$_2$)) to provide two enantiomers: Example 241b: $^1$H NMR (600 MHz, $CDCl_3$) δ ppm 8.77 (d, J=2.2 Hz, 1H), 8.26 (d, J=2.1 Hz, 1H), 7.92 (dd, J=8.3, 2.2 Hz, 1H), 7.86 (d, J=8.8 Hz, 1H), 7.66 (d, J=8.3 Hz, 1H), 7.54 (dd, J=8.8, 2.1 Hz, 1H), 7.19 (s, 1H), 6.24 (s, 1H), 4.14 (s, 3H), 3.89-3.80 (m, 2H), 3.36 (s, 3H); MS (ESI): mass calcd. for $C_{24}H_{17}F_6N_5O_2$, 521.1; m/z found, 522.1 [M+H]$^+$; and Example 241c: $^1$H NMR (600 MHz, $CDCl_3$) δ ppm 8.77 (d, J=2.2 Hz, 1H), 8.26 (d, J=2.1 Hz, 1H), 7.92 (dd, J=8.2, 2.2 Hz, 1H), 7.86 (d, J=8.8 Hz, 1H), 7.66 (d, J=8.2 Hz, 1H), 7.54 (dd, J=8.8, 2.1 Hz, 1H), 7.20 (s, 1H), 6.25 (s, 1H), 4.14 (s, 3H), 3.85 (q, J=9.8 Hz, 2H), 3.36 (s, 3H); MS (ESI): mass calcd. for $C_{24}H_{17}F_6N_5O_2$, 521.1; m/z found, 522.1 [M+H]$^+$.

Example 242a: [4-Chloro-2-methoxy-3-(2,2,2-trifluoroethyl)-6-quinolyl]-(4-chlorophenyl)-(3-methylimidazol-4-yl)methanol

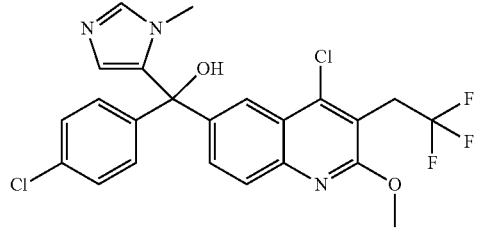 [SMILES: COc1nc2ccc(C(O)(c3ccc(Cl)cc3)c3cncn3C)cc2c(Cl)c1CC(F)(F)F]

6-Bromo-4-chloro-2-methoxy-3-(2,2,2-trifluoroethyl) quinoline (500 mg, 1.41 mmol, Intermediate 69: step e) and THF (30 mL) were combined in a dry round bottom flask under an N₂ atmosphere and cooled to −78° C. in a dry ice acetone bath. n-BuLi (1.6 M in hexanes, 1.00 mL, 1.55 mmol) was then added dropwise via syringe over approximately 2 minutes and the contents were allowed to stir at −78° C. for an additional 2 minutes. (4-Chlorophenyl)-(3-methylimidazol-4-yl)methanone (0.34 g, 1.6 mmol, Intermediate 22: step b) in THF (5 mL) was then cannulated into the reaction vessel and the reaction was stirred at −78° C. and gradually allowed to warm to room temperature overnight. The reaction was quenched with a saturated, aqueous NH₄Cl solution, then transferred to a separatory funnel with EtOAc. The organic phase was separated and the aqueous layer was back extracted with EtOAc, then the combined organic phases were dried over MgSO₄, filtered and concentrated under reduced pressure. The crude product was purified by flash column chromatography (silica gel, 0-10% DCM/(10% 2 M NH₃/MeOH in DCM)) to afford the title compound. $^1$H NMR (400 MHz, CDCl₃) δ ppm 8.18 (d, J=2.1 Hz, 1H), 7.76 (d, J=8.8 Hz, 1H), 7.55 (dd, J=8.8, 2.1 Hz, 1H), 7.32-7.24 (m, 4H), 7.11-7.05 (m, 1H), 6.18 (d, J=1.2 Hz, 1H), 4.10 (s, 3H), 3.86-3.75 (m, 2H), 3.30 (s, 3H). MS (ESI): mass calcd. for C₂₃H₁₈Cl₂F₃N₃O₂, 495.1; m/z found, 496.1 [M+H]⁺. Racemic [4-chloro-2-methoxy-3-(2,2,2-trifluoroethyl)-6-quinolyl]-(4-chlorophenyl)-(3-methylimidazol-4-yl)methanol was purified on a chiral SFC (Stationary phase: CHIRALPAK AD-H 5 m 250×20 mm, Mobile phase: 70% CO₂, 30% EtOH (0.3% i-PrNH₂)) to provide two enantiomers: Example 242b: $^1$H NMR (600 MHz, CDCl₃) δ 8.15 (d, J=2.2 Hz, 1H), 7.78 (d, J=8.8 Hz, 1H), 7.57 (dd, J=8.8, 2.1 Hz, 1H), 7.32-7.30 (m, 4H), 7.27 (s, 1H), 6.31 (s, 1H), 4.10 (s, 3H), 3.87-3.76 (m, 2H), 3.35 (s, 3H); MS (ESI): mass calcd. for C₂₃H₁₈Cl₂F₃N₃O₂, 495.1; m/z found, 496.1 [M+H]⁺; and Example 242c: $^1$H NMR (600 MHz, CDCl₃) δ ppm 8.15 (d, J=2.1 Hz, 1H), 7.78 (d, J=8.8 Hz, 1H), 7.57 (dd, J=8.8, 2.1 Hz, 1H), 7.33-7.29 (m, 4H), 7.27 (s, 1H), 6.31 (s, 1H), 4.10 (s, 3H), 3.87-3.77 (m, 2H), 3.35 (s, 3H); MS (ESI): mass calcd. for C₂₃H₁₈Cl₂F₃N₃O₂, 495.1; m/z found, 496.1 [M+H]⁺.

Example 243a: [4-Chloro-2-methoxy-3-(3,3,3-trifluoropropyl)-6-quinolyl]-(3-methylimidazol-4-yl)-[6-(trifluoromethyl)-3-pyridyl]methanol

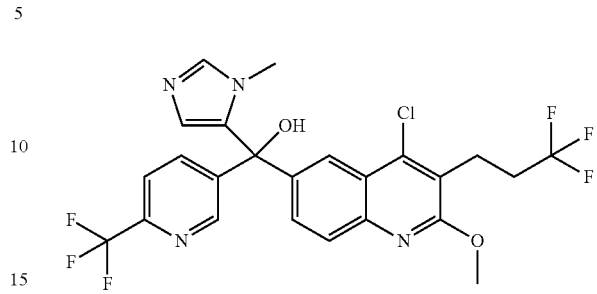

4-Chloro-6-iodo-2-methoxy-3-(3,3,3-trifluoropropyl)quinoline (500 mg, 1.203 mmol, Intermediate 86: step c) was dissolved in THF under a nitrogen atmosphere in a dry round bottom flask, then cooled to −78° C. in dry ice acetone bath. The contents were maintained at −78° C. for approximately 5 minutes then n-BuLi (530 μL, 1.6 M in hexane, 1.32 mmol) was added dropwise via syringe over approximately 2 minutes and allowed to stir at −78° C. for approximately 2 minutes. (1-Methyl-1H-imidazol-5-yl)(6-(trifluoromethyl)pyridin-3-yl)methanone (0.338 g, 1.32 mmol, Intermediate 10: step c) in THF (10 mL) was added via cannula over 2 minutes and the reaction was stirred at −78° C. for 5 minutes, then the dry ice acetone bath was removed and replaced with an ice water bath. The contents were stirred at 0° C. for 1 hour, then quenched with a saturated aqueous ammonium chloride solution then warmed to room temperature. The contents were transferred to a separatory funnel with EtOAc dilution. The aqueous layer was separated and extracted twice with EtOAc. The combined organic layers were then dried over MgSO₄, filtered and concentrated under reduced pressure. The crude product was purified by flash column chromatography (silica gel, 0-70% DCM/(10% 2 M NH₃/MeOH in DCM)) to afford the title compound. $^1$H NMR (600 MHz, CDCl₃) δ ppm 8.80 (d, J=2.3 Hz, 1H), 8.15 (d, J=2.1 Hz, 1H), 7.88 (dd, J=8.1, 2.2 Hz, 1H), 7.80 (d, J=8.7 Hz, 1H), 7.63 (dd, J=8.2, 0.8 Hz, 1H), 7.53 (dd, J=8.8, 2.2 Hz, 1H), 7.22 (s, 1H), 6.24 (s, 1H), 4.11 (s, 3H), 3.33 (s, 3H), 3.23-3.15 (m, 2H), 2.43-2.32 (m, 2H). MS (ESI): mass calcd. for C₂₄H₁₉ClF₆N₄O₂, 544.1; m/z found, 545.1 [M+H]⁺. Racemic [4-chloro-2-methoxy-3-(3,3,3-trifluoropropyl)-6-quinolyl]-(3-methylimidazol-4-yl)-[6-(trifluoromethyl)-3-pyridyl]methanol was purified via chiral SFC (Stationary phase: Chiralpak AD-H 5 m 250×30 mm, Mobile phase: 85% CO₂, 15% mixture of MeOH/i-PrOH 50/50 v/v (+0.3% i-PrNH₂)) to provide two enantiomers: Example 243b: $^1$H NMR (600 MHz, CDCl₃) δ ppm 8.82-8.77 (m, 1H), 8.18 (d, J=2.0 Hz, 1H), 7.86 (dd, J=8.4, 2.2 Hz, 1H), 7.77 (d, J=8.7 Hz, 1H), 7.62 (dd, J=8.3 Hz, 1H), 7.54 (s, 1H), 7.52-7.50 (m, 1H), 7.09 (s, 1H), 6.17-6.12 (m, 1H), 4.10 (d, J=1.1 Hz, 3H), 3.31 (s, 3H), 3.22-3.14 (m, 2H), 2.43-2.31 (m, 2H); MS (ESI): mass calcd. for C₂₄H₁₉ClF₆N₄O₂, 544.1; m/z found, 545.1 [M+H]⁺; and Example 243c: $^1$H NMR (600 MHz, CDCl₃) δ ppm 8.80 (d, J=2.2 Hz, 1H), 8.20-8.16 (m, 1H), 7.87 (dd, J=8.2, 2.2 Hz, 1H), 7.78 (dd, J=8.8, 1.3 Hz, 1H), 7.63 (d, J=8.3 Hz, 1H), 7.54-7.49 (m, 1H), 7.12 (s, 1H), 6.15 (s, 1H), 4.10 (s, 3H), 3.31 (s, 3H), 3.21-3.14 (m, 2H), 2.43-2.32 (m, 2H); MS (ESI): mass calcd. for C₂₄H₁₉ClF₆N₄O₂, 544.1; m/z found, 545.1 [M+H]⁺.

Example 244a: [4-Chloro-2-methoxy-3-(3,3,3-trifluoropropyl)-6-quinolyl]-(3-methylimidazol-4-yl)-[2-(trifluoromethyl)-4-pyridyl]methanol

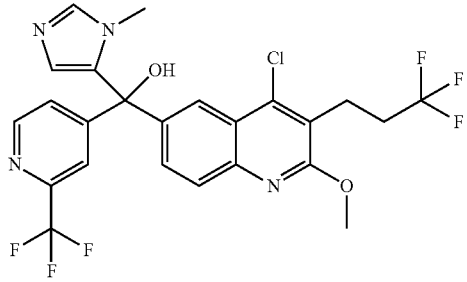 [SMILES: COc1nc2ccc(C(O)(c3ccnc(C(F)(F)F)c3)c3cncn3C)cc2c(Cl)c1CCC(F)(F)F]

4-Chloro-6-iodo-2-methoxy-3-(3,3,3-trifluoropropyl)quinoline (500 mg, 1.203 mmol, Intermediate 86: step c) was dissolved in THF under a nitrogen atmosphere in a dry round bottom flask, then cooled to −78° C. in dry ice acetone bath. The contents were maintained at −78° C. for approximately 5 minutes then n-BuLi (530 μL, 1.6 M in hexane, 1.32 mmol) was added dropwise via syringe over approximately 2 minutes and allowed to stir at −78° C. for approximately 2 minutes. (1-Methyl-1H-imidazol-5-yl)(2-(trifluoromethyl)pyridin-4-yl)methanone (0.338 g, 1.32 mmol, Intermediate 14: step b) in THF (10 mL) was added via cannula over 2 minutes and the reaction was stirred at −78° C. for 5 minutes, then the dry ice acetone bath was removed and replaced with an ice water bath. The contents were stirred at 0° C. for 1 hour, then quenched with a saturated aqueous ammonium chloride solution then warmed to room temperature. The contents were transferred to a separatory funnel with EtOAc dilution. The aqueous layer was separated and extracted twice with EtOAc. The combined organic layers were then dried over MgSO$_4$, filtered and concentrated under reduced pressure. The crude product was purified by flash column chromatography (silica gel, 30-70% DCM/(10% 2 M NH$_3$/MeOH in DCM)) to provide the title compound. $^1$H NMR (600 MHz, CDCl$_3$) δ 8.65 (d, J=5.1 Hz, 1H), 8.16 (d, J=2.1 Hz, 1H), 7.91 (dd, J=1.7, 0.8 Hz, 1H), 7.80 (d, J=8.8 Hz, 1H), 7.54 (dd, J=8.8, 2.2 Hz, 1H), 7.47 (dd, J=5.3, 1.7 Hz, 1H), 7.17 (s, 1H), 6.21 (d, J=1.1 Hz, 1H), 4.11 (s, 3H), 3.31 (s, 3H), 3.22-3.16 (m, 2H), 2.43-2.32 (m, 2H). MS (ESI): mass calcd. for C$_{24}$H$_{19}$ClF$_6$N$_4$O$_2$, 544.1; m/z found, 545.1 [M+H]$^+$. Racemic [4-chloro-2-methoxy-3-(3,3,3-trifluoropropyl)-6-quinolyl]-(3-methylimidazol-4-yl)-[2-(trifluoromethyl)-4-pyridyl]methanol was purified on a chiral SFC (Stationary phase: Chiralpak IC 5 μm 250×30 mm, Mobile phase: 80% CO$_2$, 20% mixture of i-PrOH (+0.3% i-PrNH$_2$)) to provide two enantiomers: Example 244b: $^1$H NMR (400 MHz, CDCl$_3$) δ 8.70 (d, J=5.1 Hz, 1H), 8.15 (d, J=2.1 Hz, 1H), 7.88 (dd, J=1.7, 0.8 Hz, 1H), 7.81 (d, J=8.8 Hz, 1H), 7.54 (dd, J=8.8, 2.2 Hz, 1H), 7.50 (dd, J=5.1, 1.7 Hz, 1H), 7.31 (s, 1H), 6.32 (d, J=1.1 Hz, 1H), 5.20 (s, 1H), 4.11 (s, 3H), 3.34 (s, 3H), 3.25-3.14 (m, 2H), 2.47-2.29 (m, 2H); MS (ESI): mass calcd. for C$_{24}$H$_{19}$ClF$_6$N$_4$O$_2$, 544.1; m/z found, 545.1 [M+H]$^+$; and Example 244c: $^1$H NMR (400 MHz, CDCl$_3$) δ ppm 8.69 (d, J=5.1 Hz, 1H), 8.15 (d, J=2.1 Hz, 1H), 7.88 (dd, J=1.8, 0.8 Hz, 1H), 7.81 (d, J=8.7 Hz, 1H), 7.54 (dd, J=8.8, 2.2 Hz, 1H), 7.49 (dd, J=5.2, 1.7 Hz, 1H), 7.29 (s, 1H), 6.30 (d, J=1.1 Hz, 1H), 5.37 (s, 1H), 4.11 (s, 3H), 3.33 (s, 3H), 3.23-3.14 (m, 2H), 2.46-2.29 (m, 2H); MS (ESI): mass calcd. for C$_{24}$H$_{19}$ClF$_6$N$_4$O$_2$, 544.1; m/z found, 545.1 [M+H]$^+$.

Example 245a: [4-Chloro-2-methoxy-3-(3,3,3-trifluoropropyl)-6-quinolyl]-(4-chlorophenyl)-(3-methylimidazol-4-yl)methanol

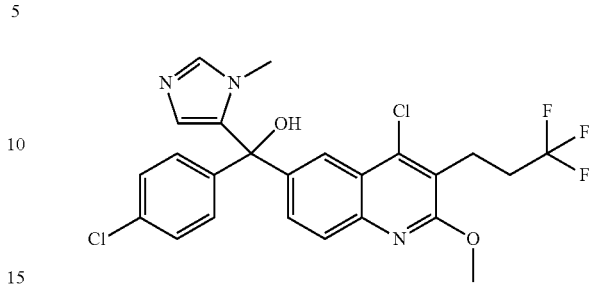

4-Chloro-6-iodo-2-methoxy-3-(3,3,3-trifluoropropyl)quinoline (500 mg, 1.203 mmol, Intermediate 86: step c) was dissolved in THF under a nitrogen atmosphere in a dry round bottom flask, then cooled to −78° C. in dry ice acetone bath. The contents were maintained at −78° C. for approximately 5 minutes then n-BuLi (530 μL, 1.6 M in hexane, 1.32 mmol) was added dropwise via syringe over approximately 2 minutes and the mixture was allowed to stir at −78° C. for approximately 2 minutes. (4-Chlorophenyl)(1-methyl-1H-imidazol-5-yl)methanone (0.292 g, 1.32 mmol, Intermediate 22: step b) in THF (10 mL) was added via cannula over 2 minutes and the reaction was stirred at −78° C. for 5 minutes, then the dry ice acetone bath was removed and replaced with an ice water bath. The contents were stirred at 0° C. for 1 hour, then quenched with a saturated aqueous ammonium chloride solution then warmed to room temperature. The contents were transferred to a separatory funnel with EtOAc dilution. The aqueous layer was separated and extracted twice with EtOAc. The combined organic layers were then dried over MgSO$_4$, filtered and concentrated under reduced pressure. The crude product was purified by flash column chromatography (silica gel, 30-70% DCM/(10% 2 M NH$_3$/MeOH in DCM)) to afford the title compound. $^1$H NMR (600 MHz, CDCl$_3$) δ ppm 8.12 (d, J=2.1 Hz, 1H), 7.76 (d, J=8.8 Hz, 1H), 7.52 (dd, J=8.7, 2.2 Hz, 1H), 7.33-7.27 (m, 3H), 7.25 (d, J=12.3 Hz, 2H), 6.28 (s, 1H), 4.10 (s, 3H), 3.34 (s, 3H), 3.23-3.15 (m, 2H), 2.43-2.31 (m, 2H). MS (ESI): mass calcd. for C$_{24}$H$_{20}$Cl$_2$F$_3$N$_3$O$_2$, 509.1; m/z found, 510.1 [M+H]$^+$. Racemic [4-chloro-2-methoxy-3-(3,3,3-trifluoropropyl)-6-quinolyl]-(4-chlorophenyl)-(3-methylimidazol-4-yl)methanol was purified via chiral SFC (Stationary phase: Chiralpak AD-H 5 μm 250×30 mm, Mobile phase: 80% CO$_2$, 20% mixture of MeOH/i-PrOH 50/50 v/v (+0.3% i-PrNH$_2$)) to provide two enantiomers: Example 245b: $^1$H NMR (600 MHz, CDCl$_3$) δ ppm 8.13 (d, J=2.1 Hz, 1H), 7.72 (d, J=8.8 Hz, 1H), 7.49 (dd, J=8.8, 2.2 Hz, 1H), 7.32-7.25 (m, 4H), 7.06 (s, 1H), 6.57 (s, 1H), 6.20-6.16 (m, 1H), 4.10 (s, 3H), 3.30 (s, 3H), 3.20-3.13 (m, 2H), 2.41-2.31 (m, 2H); MS (ESI): mass calcd. for C$_{24}$H$_{20}$Cl$_2$F$_3$N$_3$O$_2$, 509.1; m/z found, 510.1 [M+H]$^+$; and Example 245c: $^1$H NMR (600 MHz, CDCl$_3$) δ ppm 8.13 (d, J=2.1 Hz, 1H), 7.72 (d, J=8.7 Hz, 1H), 7.49 (dd, J=8.8, 2.1 Hz, 1H), 7.33-7.25 (m, 4H), 7.07 (s, 1H), 6.54 (s, 1H), 6.18 (s, 1H), 4.10 (s, 3H), 3.30 (s, 3H), 3.21-3.13 (m, 2H), 2.42-2.31 (m, 2H); MS (ESI): mass calcd. for C$_{24}$H$_{20}$Cl$_2$F$_3$N$_3$O$_2$, 509.1; m/z found, 510.1 [M+H]$^+$.

Example 246: (3-(Benzyloxy)-4-chloro-2-methoxyquinolin-6-yl)(1,2-dimethyl-1H-imidazol-5-yl)(1,3,5-trimethyl-1H-pyrazol-4-yl)methanol

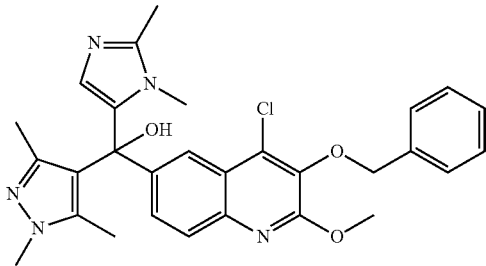 [SMILES: COc1nc2ccc(C(O)(c3c(C)nn(C)c3C)c3cnc(C)n3C)cc2c(Cl)c1OCc1ccccc1]

n-BuLi (1.5 mL, 2.5 M in hexanes, 3.7 mmol) was added dropwise to a −65° C. solution consisting of 5-bromo-1,2-dimethyl-1H-imidazole (642 mg, 3.67 mmol) and THF (25 mL). The resultant reaction mixture was stirred at −65° C. for 20 minutes and then treated with a solution of (3-(benzyloxy)-4-chloro-2-methoxyquinolin-6-yl)(1,3,5-trimethyl-1H-pyrazol-4-yl)methanone (800 mg, 1.83 mmol, Intermediate 87: step b) and THF (10 mL) at −65° C. The resulting mixture was stirred at room temperature for 20 minutes before quenching with saturated aqueous NH$_4$Cl (20 mL) and extracting with dichloromethane:methanol (5:1, 50 mL×10). The combined organic extracts were dried over Na$_2$SO$_4$, filtered and concentrated to dryness under reduced pressure to give the crude product, which was purified by FCC (silica gel, eluent: petroleum ether:ethyl acetate=1:1) to afford the title compound. MS m/e 532.1 [M+H]$^+$.

Example 247: (3-(Benzyloxy)-4-chloro-2-methoxy-8-methylquinolin-6-yl)(1,2-dimethyl-1H-imidazol-5-yl)(1,3,5-trimethyl-1H-pyrazol-4-yl)methanol

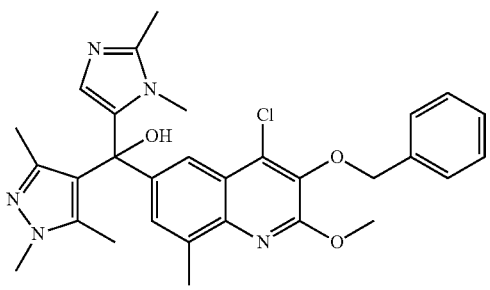 [SMILES: COc1nc2c(C)cc(C(O)(c3c(C)nn(C)c3C)c3cnc(C)n3C)cc2c(Cl)c1OCc1ccccc1]

n-BuLi (0.5 mL, 2.5 M in hexane, 1.25 mmol) was added drop-wise to a −70° C. solution consisting of 5-bromo-1,2-dimethyl-1H-imidazole (600 mg, 1.33 mmol) and THF (50 mL). The resultant reaction mixture was stirred at −70° C. for 20 minutes and then treated with a solution of (3-(benzyloxy)-4-chloro-2-methoxy-8-methylquinolin-6-yl)(1,3,5-trimethyl-1H-pyrazol-4-yl)methanone (600 mg, 1.33 mmol, Intermediate 89: step h) and THF (15 mL) at −70° C. The resulting mixture was stirred at room temperature for 20 minutes before quenching with saturated aqueous NH$_4$Cl (20 mL) and extracting with dichloromethane:methanol (5:1, 50 mL×10). The combined organic extracts were dried over Na$_2$SO$_4$, filtered and concentrated to dryness under reduced pressure to give the crude product, which was purified by FCC (silica gel, eluent: petroleum ether:ethyl acetate=50:1 to 20:1) to afford the title compound. MS m/e 546.2 [M+H]$^+$.

Example 248: (4-Chloro-2-methoxy-3-(2,2,2-trifluoroethoxy)quinolin-6-yl)(1,2-dimethyl-1H-imidazol-5-yl)(1,3,5-trimethyl-1H-pyrazol-4-yl)methanol

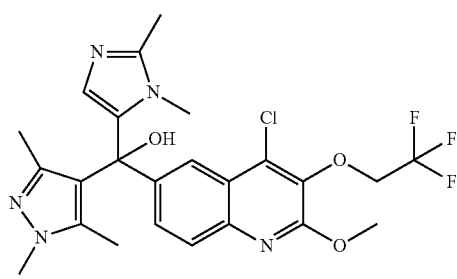 [SMILES: COc1nc2ccc(C(O)(c3c(C)nn(C)c3C)c3cnc(C)n3C)cc2c(Cl)c1OCC(F)(F)F]

2,2,2-Trifluoroethyl trifluoromethanesulfonate (157 mg, 0.679 mmol) was added drop-wise to a mixture consisting of 4-chloro-6-((1,2-dimethyl-1H-imidazol-5-yl)(hydroxy)(1,3,5-trimethyl-1H-pyrazol-4-yl)methyl)-2-methoxyquinolin-3-ol (300 mg, 0.679 mmol, Intermediate 88), Cs$_2$CO$_3$ (221 mg, 0.678 mmol) and THF (50 mL). The resultant reaction mixture was stirred at room temperature for 2 hours. The suspension was filtered through a pad of Celite® and the pad was washed with ethyl acetate (20 mL×3). The filtrate was concentrated to dryness under reduced pressure to give the crude product, which was purified by reverse phase preparative HPLC (ACN/water with 0.05% NH$_3$). The pure fractions were collected and the volatiles were removed under vacuum. The residue was suspended in water (10 mL) and the resulting mixture lyophilized to dryness. $^1$H NMR (400 MHz, DMSO-d$_6$) δ ppm 8.19-8.13 (m, 1H), 7.77 (d, J=9.2 Hz, 1H), 7.52-7.44 (m, 1H), 6.51 (br. s., 1H), 5.71 (s, 1H), 4.88-4.77 (m, 2H), 4.08 (s, 3H), 3.61 (s, 3H), 3.43 (s, 3H), 2.28 (s, 3H), 1.79 (s, 3H), 1.65 (s, 3H); MS m/e 524.2 [M+H]$^+$.

In Vitro Biological Data

ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants (K$_D$).

In a ThermoFluor® experiment where protein stability is monitored as the temperature is steadily increased, an equilibrium binding ligand causes the midpoint of an unfolding transition (T$_m$) to occur at a higher temperature. The shift in the melting point described as a ΔT$_m$ is proportional to the concentration and affinity of the ligand. The compound potency may be compared as a rank order of either ΔT$_m$ values at a single compound concentration or in terms of $K_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM_001001523.1 (SEQ ID NO:1). Nucleotides 850-1635 (SEQ ID NO:2) coding for the wild type human RORγt ligand binding domain (RORγt LBD) were cloned into the pHIS1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor® assay is shown as SEQ ID NO:4.

ThermoFluor® experiments were carried out using instruments owned by Janssen Research and Discovery, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 μL, Fluka, type DC 200) to prevent evaporation.

Bar-coded assay plates are robotically loaded onto a thermostatically controlled PCR-type thermal block and then heated at a typical ramp-rate of 1° C./min for all experiments. Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
60 M 1,8-ANS
100 mM Hepes, pH 7.0
10 mM NaCl
2.5 mM GSH
0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound). The compounds were robotically dispensed directly into assay plates (1x=46 nL) using a Hummingbird capillary liquid handling instrument (Digilab). Following compound dispense, protein and dye in buffer was added to achieve the final assay volume of 3 μL, followed by 1 μL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. *Biochemistry* 44, 5258-66) using the following thermodynamic parameters of protein unfolding:
Reference RORγt $T_m$: 47.8° C.
$\Delta H_{(Tm)}$=115 kcal/mol
$\Delta C_{p(Tm)}$=3 kcal/mol Cell Based Biological Data Compounds were assessed for RORgt functional modulation using either the RORgt ligand binding domain (LBD) reporter assay, or the RORgt full-length (FL) reporter assay. Data from either assay can be used to demonstrate functional modulation of RORgt activity by compounds RORγt (LBD) Reporter Assay A reporter assay was used to test functional activity of RORγt modulatory compounds on transcriptional activation driven by the RORγt LBD. Cells used in the assay were co-transfected with two constructs. The first construct, pBIND-RORγt LBD, contained the wild type human RORγt LBD fused to the DNA binding domain of the GAL4 protein. The second construct, pGL4.31 (Promega Cat no. $C_{935}A$), contained multiple GAL4 responsive DNA elements upstream of firefly luciferase. To generate a background control, cells were similarly co-transfected with two constructs, but in the first construct the AF2 amino acid motif in the RORγt LBD was changed from LYKELF (SEQ ID NO:5) to LFKELF (SEQ ID NO:6). The AF2 mutation has been shown to prevent co-activator binding to the RORγt LBD, thus preventing transcription of firefly luciferase. The mutant construct was called pBIND-RORγt-AF2.

For the RORγt constructs used in the reporter assay, numbering for the nucleotide sequences was also based on the reference sequence for human RORγt, transcript variant 2, NCBI Accession: NM_001001523.1 (SEQ ID NO:1). For the wild type human RORγt LBD construct, pBIND-RORγt LBD, nucleotides 850-1635 (SEQ ID NO:2) coding for the wild type human RORγt LBD were cloned into EcoRI and NotI sites in the pBIND vector (Promega cat. No E245A). The pBIND vector contains the GAL4 DNA Binding Domain (GAL4 DBD) and the renilla luciferase gene under control of the SV40 promoter. Renilla luciferase expression serves as a control for transfection efficiency and cell viability. For the background control construct, pBIND-RORγt-AF2, the AF2 domain of RORγt LBD was mutated using the Quik Change II Site Directed Mutagenesis System (Stratagene Cat. No. 200519). The nucleotide sequence coding for the RORγt LBD sequence with the mutated AF2 domain is shown as SEQ ID NO:7. The amino acid sequences for the wild type RORγt LBD and RORγt LBD with the mutated AF2 domain are shown as SEQ ID NO:8 and SEQ ID NO:9, respectively.

The reporter assay was performed by transiently transfecting HEK293T cells with 5 μg of pBIND-RORγt LBD or pBIND-RORγt LBD-AF2 and 5 μg pGL4.31 (Promega Cat no. $C_{935}A$) using Fugene 6 (Invitrogen Cat no. E2691) at a 1:6 ratio of DNA:Fugene 6 in a T-75 flask in which cells were at least 80% confluent. Twenty four hours after bulk transfection, cells were plated into 96-well plates at 50,000 cells/well in phenol-red free DMEM containing 5% Lipid Reduced FCS and Pen/Strep. Six hours after plating, cells were treated with compounds for 24 hours. Media was removed and cells were lysed with 50 μL 1x Glo Lysis Buffer (Promega). Dual Glo Luciferase Reagent (50 μL/well) was then added and firefly luciferase luminescence was read on an Envision after a ten minute incubation. Finally, Stop and Glo reagent (50 L/well) was added and renilla luciferase luminescence was read on an Envision after a ten minute incubation. To calculate the effect of compounds on RORγt activity, the ratio of firefly to renilla luciferase was determined and plotted against compound concentration. Agonist compounds increase RORγt-driven luciferase expression, and antagonist or inverse agonist compounds decrease luciferase expression.

RORγt (Full-Length Human) Reporter Assay

A reporter assay was used to test functional activity of RORγt modulatory compounds on transcriptional activation driven by full-length human RORγt. Cells used in this assay were transiently co-transfected with three different plasmids, one expressing the GAL4-DNA binding domain (DBD)-RORγt fusion protein under control of a CMV promoter (NH$_2$-Gal4-DBD:RORC—COOH in pCMV-BD, Stratagene #211342), and two reporter plasmids—the firefly luciferase reporter under control of a GAL4 promoter (pFR-Luc 2×GAL4) and Renilla luciferase reporter under control of CMV promoter (pRL-CMV, Promega #E2261). The full-length coding sequence was used for human RORγt, i.e., nucleotides 142-1635 of human RORγt, transcript variant 2, NCBI Accession: NM_001001523.1 (SEQ ID NO:1). HEK293T cells were plated at 35000 per well in 96-well plate in medium of MEM with 8.6% FBS. After 18-22 hours incubation, the transfection was carried out by using a PEI solution with 170.5 ng total DNA/well (50 ng pCMV-BD-ROR plus 20 ng of pFR-Luc reporter and 0.5 ng of pRL-CMV reporter plus 100 ng Carrier DNA (Clontech #630440) for each well). 4-6 hours after transfection, cells were treated with compounds for overnight in the medium with final concentration of FBS 1.1% and DMSO 0.1%. After overnight (16 to 20 hours) incubation, media were removed and cells were lysed with 20 μL 1× Passive Lysis Buffer (Promega) for 10-15 minutes. Luminescence was measured using a BMG LUMIstar OPTIMA plate reader, after addition of 75 μL/well firefly luciferase buffer, followed by 75 μL/well Renilla luciferase buffer. To calculate the effect of compounds on RORγt activity, firefly values were normalized against values of DMSO only and values of reference compound at saturating concentration, then further normalized against Renilla signals. IC50s were generated by plotting final Renilla normalized data against compound concentration and percent inhibition was calculated against DMSO control.

Human Th17 Assay

The human Th17 assay tests the effect of RORγt modulatory compounds on IL-17 production by CD4 T cells under conditions which favor Th17 differentiation. Total CD4$^+$ T cells were isolated from the peripheral blood mononuclear cells (PBMC) of healthy donors using a CD4$^+$ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at 1.5×105 per 100 μL per well. 50 μL of compound at titrated concentrations in DMSO were added into each well at final DMSO concentration at 0.2%. Cells were incubated for 1 hour, then 50 μL of Th17 cell differentiation medium was added to each well. The final concentrations of antibodies and cytokines (R&D Systems) in differentiation medium were: 3×10$^6$/mL anti-CD3/CD28 beads (prepared using human T cell activation/expansion kit, Miltenyi Biotec), 10 μg/mL anti-IL4, 10 μg/mL anti-IFNγ, 10 ng/mL IL1β, 10 ng/mL IL23, 50 ng/mL IL6, 3 ng/mL TGFβ and 20 U/mL IL2. Cells were cultured at 37° C. and 5% CO$_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

TABLE 1

| Example Number | ThermoFluor® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 6 μM | Human Th17 Assay, IC$_{50}$ (μM) |
|---|---|---|---|---|---|---|
| 1a | ND | ND | ND | ND | ND | ND |
| 1b | 0.22 | 1.8 | 78 | ND | ND | ND |
| 1c | 0.0001 | ~2 | 66 | ND | ND | ND |
| 2a | ND | ND | ND | ND | ND | ND |
| 2b | ND | ND | ND | ND | ND | ND |
| 2c | 0.11 | ND | ND | ND | ND | ND |
| 3 | 0.1 | 1.8 | 81 | ND | ND | ND |
| 4a | 0.016 | >6 | 24 | ND | ND | ND |
| 4b | 0.009 | >6 | 42 | ND | ND | >6 |
| 4c | 0.053 | >6 | −6 | ND | ND | ND |
| 5a | 0.25 | >6 | 45 | ND | ND | ND |
| 5b | 0.35 | >6 | 33 | ND | ND | ND |
| 5c | 0.13 | >6 | 36 | ND | ND | ND |
| 6a | 0.22 | >6 | 26 | ND | ND | ND |
| 6b | 0.24 | >6 | 17 | ND | ND | ND |
| 6c | 0.13 | >6 | 26 | ND | ND | ND |
| 7a | 0.22 | 0.71 | 80 | ND | ND | ND |
| 7b | 0.06 | 0.45 | 84 | ND | ND | 0.21 |
| 7c | 0.49 | >6 | 47 | ND | ND | ND |
| 8 | 0.031 | 0.11 | 93 | ND | ND | 0.2 |
| 9 | 8.2 | >6 | 16 | ND | ND | ND |
| 10 | 0.52 | ~6 | 55 | ND | ND | ND |
| 11a | 0.39 | 1.5 | 86 | ND | ND | ND |
| 11b | 0.14 | 0.56 | 93 | ND | ND | ND |
| 11c | 3.6 | 5 | 52 | ND | ND | ND |
| 12a | 0.29 | 1.1 | 93 | ND | ND | ND |
| 12b | 9.6 | >6 | 23 | ND | ND | ND |
| 12c | 0.063 | 0.33 | 93 | ND | ND | ND |
| 13a | 0.025 | 0.25 | 100 | ND | ND | ND |
| 13b | 1.1 | ~4 | 70 | ND | ND | ND |
| 13c | 0.029 | 0.042 | 100 | ND | ND | 0.065 |
| 14a | 0.0025 | 0.023 | 99 | ND | ND | ND |
| 14b | 1.4 | 4.5 | 72 | ND | ND | ND |
| 14c | 0.0013 | 0.03 | 98 | ND | ND | ND |

TABLE 1-continued

| Example Number | ThermoFluor® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 6 μM | Human Th17 Assay, IC$_{50}$ (μM) |
|---|---|---|---|---|---|---|
| 15a | 0.029 | 0.08 | 94 | ND | ND | ND |
| 15b | 0.0051 | ~0.04 | 97 | ND | ND | ND |
| 15c | 0.15 | 0.7 | 86 | ND | ND | ND |
| 16 | 0.029 | ND | ND | 0.12 | 101 | ND |
| 17a | ND | ND | ND | ND | ND | ND |
| 17b | 0.0059 | ND | ND | 0.071 | 105 | ND |
| 17c | 0.017 | ND | ND | 0.095 | 107 | ND |
| 18 | 0.35 | 1.7 | 80 | ND | ND | ND |
| 19 | 0.45 | 0.37 | 95 | ND | ND | 1.3 |
| 20 | 3.8 | 1.3 | 87 | ND | ND | ND |
| 21 | 1.1 | 1.1 | 93 | ND | ND | ND |
| 22 | 3.1 | ~6 | 50 | ND | ND | ND |
| 23 | 4.3 | ~6 | 55 | ND | ND | ND |
| 24 | 2 | >6 | 29 | ND | ND | ND |
| 25 | 7.4 | ~4 | 73 | ND | ND | ND |
| 26 | 0.48 | ~1 | 100 | ND | ND | ND |
| 27 | 6.6 | 0.42 | 100 | ND | ND | ~3 |
| 28 | 4.8 | ~6 | 54 | ND | ND | ND |
| 29 | 0.026 | ~0.4 | 66 | ND | ND | ND |
| 30 | 0.1 | 0.23 | 92 | ND | ND | ND |
| 31 | 0.027 | >6 | −32 | ND | ND | ND |
| 32 | 0.039 | >6 | 32 | ND | ND | ND |
| 33 | 4.8 | >6 | −32 | ND | ND | ND |
| 34a | 0.084 | >6 | 10 | ND | ND | ND |
| 34b | 0.03 | ND | ND | 0.72 | 39 | ND |
| 34c | 0.089 | ND | ND | 0.81 | 50 | ND |
| 35 | 1.3 | 1.8 | 77 | ND | ND | ND |
| 36a | 0.1 | 0.56 | 68 | ND | ND | ND |
| 36b | 6.9 | >6 | 24 | ND | ND | ND |
| 36c | 0.026 | 0.77 | 77 | ND | ND | ND |
| 37a | 0.37 | ~6 | 47 | ND | ND | ND |
| 37c | 0.16 | 1 | 54 | ND | ND | ND |
| 38a | 0.0088 | 0.064 | 99 | ND | ND | ND |
| 38b | 4.7 | ~6 | 60 | ND | ND | ND |
| 38c | 0.02 | 0.026 | 100 | ND | ND | ND |
| 39 | 0.2 | 1.1 | 90 | ND | ND | ND |
| 40 | 0.3 | ~0.9 | 79 | ND | ND | ND |
| 41 | 0.091 | 0.095 | 97 | ND | ND | ND |
| 42 | 0.088 | 0.19 | 98 | ND | ND | ND |
| 43 | 0.022 | 0.024 | 98 | ND | ND | ND |
| 44 | 0.19 | 0.37 | 93 | ND | ND | ND |
| 45 | 0.25 | ~2 | 83 | ND | ND | ND |
| 46 | 0.38 | 1.7 | 85 | ND | ND | ND |
| 47 | 0.75 | ~3 | 75 | ND | ND | ND |
| 48 | 0.19 | 1 | 96 | ND | ND | ND |
| 49a | 0.48 | 1.2 | 93 | ND | ND | ND |
| 49b | 0.25 | 0.71 | 94 | ND | ND | ND |
| 49c | 2.5 | >6 | 48 | ND | ND | ND |
| 50a | 0.17 | 0.74 | 68 | ND | ND | ND |
| 50b | 6.1 | ND | ND | 1.8 | 55 | ND |
| 50c | 0.24 | ND | ND | 0.35 | 90 | ND |
| 51a | ND | ND | ND | ND | ND | ND |
| 51b | 3 | ND | ND | >6 | 4 | ND |
| 51c | 5 | >6 | −4 | >6 | 13 | ND |
| 52 | 2.9 | ND | ND | >6 | 10 | ND |
| 53a | 0.19 | 0.83 | 57 | ND | ND | ND |
| 53b | 0.14 | ND | ND | 0.64 | 49 | ND |
| 53c | 0.07 | ND | ND | 0.45 | 74 | ND |
| 54 | 0.86 | ~6 | 53 | 2.3 | 73 | ND |
| 55a | 0.83 | ~3 | 68 | ND | ND | ND |
| 55b | 0.48 | ~5 | 57 | 1.6 | 62 | ND |
| 55c | 0.4 | 1 | 52 | 1.8 | 69 | ND |
| 56a | 0.037 | 0.21 | 94 | ND | ND | ND |
| 56b | 0.0099 | 0.19 | 86 | 0.12 | 99 | 0.012 |
| 56c | 0.02 | 0.42 | 92 | 0.18 | 89 | ND |
| 57a | 0.014 | 0.11 | 98 | ND | ND | ND |
| 57b | 0.0082 | 0.17 | 99 | 0.12 | 97 | ND |
| 57c | 0.0063 | 0.34 | 97 | 0.088 | 96 | ND |
| 58 | 0.72 | 2.1 | 89 | 1.3 | 85 | ND |
| 59 | 0.071 | 0.91 | 81 | 0.62 | 75 | ND |
| 60 | 0.47 | ~1 | 78 | ND | ND | ND |
| 61 | 0.0088 | 0.32 | 93 | ND | ND | ND |
| 62 | 1.1 | 2.2 | 83 | ND | ND | ND |

TABLE 1-continued

| Example Number | ThermoFluor ® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 6 μM | Human Th17 Assay, IC$_{50}$ (μM) |
|---|---|---|---|---|---|---|
| 63 | 0.46 | 1.5 | 81 | ND | ND | ND |
| 64 | 0.025 | 0.18 | 95 | ND | ND | ND |
| 65a | ND | ND | ND | ND | ND | ND |
| 65b | 5.3 | >6 | 39 | ND | ND | ND |
| 66a | 0.63 | >6 | −112 | ND | ND | ND |
| 66b | 0.26 | 0.32 | −129 | ND | ND | ND |
| 67a | ND | ND | ND | ND | ND | ND |
| 67b | 1 | >6 | −37 | ND | ND | ND |
| 68a | 0.011 | 0.087 | 83 | ND | ND | ND |
| 68b | 1.2 | 5 | 54 | ND | ND | ND |
| 68c | 0.0038 | 0.02 | 87 | ND | ND | ND |
| 69a | 0.058 | ~6 | 57 | ND | ND | ND |
| 69b | 4.6 | >6 | 37 | ND | ND | ND |
| 69c | 0.014 | 0.19 | 61 | ND | ND | ND |
| 70a | 3.3 | >6 | 36 | ND | ND | ND |
| 70b | 2.2 | >6 | 28 | ND | ND | ND |
| 71a | 0.48 | ~0.2 | 86 | ND | ND | ND |
| 71c | 0.11 | 0.23 | 87 | ND | ND | ND |
| 72a | 0.041 | 0.057 | 85 | ND | ND | ND |
| 72b | 3.3 | ~6 | 53 | ND | ND | ND |
| 72c | 0.0082 | 0.033 | 86 | ND | ND | ND |
| 73a | ND | ND | ND | ND | ND | ND |
| 73b | 8.5 | >6 | −15 | ND | ND | ND |
| 73c | 0.031 | >6 | −80 | ND | ND | ND |
| 74a | ND | ND | ND | ND | ND | ND |
| 74b | 4.9 | >6 | −9 | ND | ND | ND |
| 75 | 0.009 | >6 | −1 | ND | ND | ND |
| 76a | ND | ND | ND | ND | ND | ND |
| 76b | 1.2 | >6 | −17 | ND | ND | ND |
| 76c | 0.11 | >6 | −35 | ND | ND | ND |
| 77a | ND | ND | ND | ND | ND | ND |
| 77b | 0.084 | 0.073 | 100 | ND | ND | ND |
| 78a | ND | ND | ND | ND | ND | ND |
| 78b | 0.19 | 3.4 | 56 | ND | ND | ND |
| 78c | 1.9 | ~4 | 59 | ND | ND | ND |
| 79a | ND | ND | ND | ND | ND | ND |
| 79b | 1.2 | >6 | 30 | ND | ND | ND |
| 79c | 0.2 | >6 | −2.5 | ND | ND | ND |
| 80a | 0.016 | 0.026 | 99 | ND | ND | ND |
| 80b | 0.019 | 0.041 | 100 | 0.021 | 104 | 0.019 |
| 80c | 0.048 | 0.099 | 99 | ND | ND | ND |
| 81a | ND | ND | ND | ND | ND | ND |
| 81b | 2.2 | 3.2 | 57 | ND | ND | ND |
| 81c | 0.0061 | 0.029 | 102 | ND | ND | 0.01 |
| 82a | 0.0058 | 0.019 | 101 | ND | ND | ND |
| 82b | 0.52 | 3.7 | 91 | ND | ND | ND |
| 82c | 0.0021 | 0.014 | 104 | ND | ND | 0.0012 |
| 83 | 0.36 | ND | ND | ND | ND | ND |
| 84a | 0.016 | 0.047 | 94 | ND | ND | ND |
| 84b | 0.011 | 0.096 | 97 | ND | ND | 0.0054 |
| 84c | 0.19 | 0.97 | 87 | ND | ND | ND |
| 85a | ND | ND | ND | ND | ND | ND |
| 85b | 0.22 | ~0.8 | 88 | ND | ND | ND |
| 85c | 0.0013 | 0.00099, ~0.008 | 99 | ND | ND | 0.0016 |
| 86a | ND | ND | ND | ND | ND | ND |
| 86b | 0.95 | ~2 | 83 | ND | ND | ND |
| 86c | 0.025 | 0.13 | 97 | ND | ND | 0.021 |
| 87a | ND | ND | ND | ND | ND | ND |
| 87b | 0.22 | 1 | 92 | ND | ND | ND |
| 87c | 0.016 | 0.23 | 87 | ND | ND | 0.12 |
| 88a | ND | ND | ND | ND | ND | ND |
| 88b | 0.21 | 1 | 82 | ND | ND | ND |
| 88c | 0.027 | 0.42 | 75 | ND | ND | 0.31 |
| 89a | ND | ND | ND | ND | ND | ND |
| 89b | 0.43 | 0.6 | 95 | ND | ND | ND |
| 89c | 0.022 | 0.051 | 99 | ND | ND | 0.079 |
| 90a | 0.2 | 0.46 | 101 | ND | ND | ND |
| 90b | 1.7 | 2.8 | 70 | ND | ND | ND |
| 90c | 0.043 | 0.2 | 96 | ND | ND | 0.2 |
| 91a | ND | ND | ND | ND | ND | ND |
| 91b | 1.6 | 1.8 | 82 | ND | ND | ND |
| 91c | 0.13 | 0.44 | 100 | ND | ND | 0.52 |
| 92a | 0.35 | 0.78 | 87 | ND | ND | ND |

TABLE 1-continued

| Example Number | ThermoFluor ® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 6 μM | Human Th17 Assay, IC$_{50}$ (μM) |
|---|---|---|---|---|---|---|
| 92b | 4 | 1.8 | 50 | ND | ND | ND |
| 92c | 0.2 | 0.64 | 96 | ND | ND | ND |
| 93a | ND | ND | ND | ND | ND | ND |
| 93b | 1.2 | ~6 | 48 | ND | ND | ND |
| 93c | 0.064 | 0.45 | 100 | ND | ND | ND |
| 94a | ND | ND | ND | ND | ND | ND |
| 94b | 3.7 | 4.5 | 68 | ND | ND | ND |
| 94c | 0.08 | 0.22 | 97 | ND | ND | 0.38 |
| 95a | ND | ND | ND | ND | ND | ND |
| 95b | 0.023 | 0.19 | 97 | ND | ND | 0.061 |
| 95c | 0.18 | 0.9 | 93 | ND | ND | ND |
| 96 | 0.69 | 1.4 | 80 | ND | ND | ND |
| 97 | 0.75 | 1.6 | 68 | ND | ND | ND |
| 98 | 0.036 | 0.22 | 97 | ND | ND | ND |
| 99a | ND | ND | ND | ND | ND | ND |
| 99b | 0.065 | 0.19 | 96 | ND | ND | 1.2 |
| 99c | 1.8 | ~4 | 67 | ND | ND | ND |
| 100a | ND | ND | ND | ND | ND | ND |
| 100b | 0.5 | 0.75 | 90 | ND | ND | ND |
| 100c | 0.00031 | 0.012 | 100 | ND | ND | 0.0076 |
| 101a | 0.27 | 0.73 | 84 | ND | ND | ND |
| 101b | 1.6 | ~4 | 73 | ND | ND | ND |
| 101c | 0.038 | 0.29 | 89 | ND | ND | 0.36 |
| 102a | 0.23 | 0.62 | 78 | ND | ND | ND |
| 102b | 1.7 | ~1 | 70 | ND | ND | ND |
| 102c | 0.24 | 0.22 | 90 | ND | ND | ND |
| 103a | 0.0011 | 0.0093 | 101 | ND | ND | ND |
| 103b | 0.51 | 0.89 | 90 | ND | ND | ND |
| 103c | 0.0015 | 0.022 | 99 | ND | ND | ND |
| 104a | ND | ND | ND | ND | ND | ND |
| 104b | 0.087 | 0.69 | 85 | ND | ND | ND |
| 104c | 0.25 | 0.96 | 84 | ND | ND | ND |
| 105a | ND | ND | ND | ND | ND | ND |
| 105b | 17 | >6 | 33 | ND | ND | ND |
| 105c | 0.047 | 0.12 | 87 | ND | ND | ND |
| 106a | ND | ND | ND | ND | ND | ND |
| 106b | 0.0023 | 0.017 | 103 | 0.018 | 103 | 0.012 |
| 106c | 0.0053 | 0.017 | 100 | ND | ND | 0.0014 |
| 107a | 0.0057 | 0.019 | 54 | ND | ND | ND |
| 107b | 2 | >6 | 38 | ND | ND | ND |
| 107c | 0.0057 | 0.019 | 54 | ND | ND | ND |
| 108a | ND | ND | ND | ND | ND | ND |
| 108b | 20 | >6 | 6 | ND | ND | ND |
| 108c | 0.046 | >6 | 14 | ND | ND | ND |
| 109a | ND | ND | ND | ND | ND | ND |
| 109b | 6.9 | >6 | 28 | ND | ND | ND |
| 109c | 0.02 | 0.018 | 79 | ND | ND | ND |
| 110a | ND | ND | ND | ND | ND | ND |
| 110b | 11 | >6 | 4 | ND | ND | ND |
| 110c | 0.048 | 0.3 | 76 | ND | ND | ND |
| 111 | 0.0024 | 0.12 | 97 | ND | ND | 0.017 |
| 112a | ND | ND | ND | ND | ND | ND |
| 112b | 0.054 | 0.17 | 97 | ND | ND | ND |
| 112c | 0.003 | 0.061 | 96 | ND | ND | 0.017 |
| 113a | ND | ND | ND | ND | ND | ND |
| 113b | 0.88 | 0.72 | 77 | ND | ND | ND |
| 114a | ND | ND | ND | ND | ND | ND |
| 114b | 1.4 | ~2 | 60 | ND | ND | ND |
| 114c | 0.0039 | 0.041 | 72 | ND | ND | ND |
| 115 | 1 | 1.7 | 69 | ND | ND | ND |
| 116a | 0.11 | 0.21 | 97 | 0.091 | 87* | 0.21 |
| 116b | 0.0085 | 0.047 | 98 | 0.037 | 95* | 0.03 |
| 116c | 0.11 | 0.21 | 97 | 0.091 | 87* | 0.21 |
| 117a | ND | ND | ND | ND | ND | ND |
| 117b | 0.4 | ND | ND | ND | ND | ND |
| 117c | 0.00002 | ND | ND | ND | ND | ND |
| 118 | 0.004 | ND | ND | 0.33 | 86 | 0.22 |
| 119a | ND | ND | ND | ND | ND | ND |
| 119b | 0.0022 | ND | ND | 0.039 | 86 | ND |
| 119c | 0.0063 | ND | ND | 0.065 | 93 | ND |
| 120a | ND | ND | ND | ND | ND | ND |
| 120b | 0.13 | ND | ND | ND | ND | ND |
| 120c | 0.014 | ND | ND | ND | ND | ND |

TABLE 1-continued

| Example Number | ThermoFluor ® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 6 μM | Human Th17 Assay, IC$_{50}$ (μM) |
|---|---|---|---|---|---|---|
| 121a | ND | ND | ND | ND | ND | ND |
| 121b | 0.93 | ND | ND | ND | ND | ND |
| 121c | 0.0017 | ND | ND | ND | ND | ND |
| 122a | ND | ND | ND | ND | ND | ND |
| 122b | 0.0008 | ND | ND | 0.023 | 98 | ND |
| 122c | 0.0083 | ND | ND | 0.038 | 100 | ND |
| 123a | ND | ND | ND | ND | ND | ND |
| 123b | 0.018 | ND | ND | 0.13 | 95 | ND |
| 123c | 0.019 | ND | ND | 0.17 | 95 | ND |
| 124a | ND | ND | ND | ND | ND | ND |
| 124b | 0.0024 | ND | ND | 0.12 | 87 | >6 |
| 124c | 0.0048 | ND | ND | 0.31 | 87 | 0.035 |
| 125a | ND | ND | ND | ND | ND | ND |
| 125b | 0.032 | ND | ND | 0.084 | 86* | ND |
| 125c | 0.00031 | ND | ND | 0.026 | 94 | ND |
| 126a | ND | ND | ND | ND | ND | ND |
| 126b | 0.00047 | ND | ND | 0.014 | 101* | ND |
| 126c | 0.63 | ND | ND | 0.37 | 78* | ND |
| 127a | ND | ND | ND | ND | ND | ND |
| 127b | 0.01 | ND | ND | 0.032 | 100 | ND |
| 127c | 0.14 | ND | ND | 0.28 | 91 | ND |
| 128a | ND | ND | ND | ND | ND | ND |
| 128b | 0.24 | ND | ND | 0.23 | 89* | ND |
| 128c | 0.022 | ND | ND | 0.053 | 87* | ND |
| 129a | ND | ND | ND | ND | ND | ND |
| 129b | 0.84 | ND | ND | 0.9 | 88 | ND |
| 129c | 0.0013 | ND | ND | 0.012 | 100* | ND |
| 130a | ND | ND | ND | ND | ND | ND |
| 130b | 0.15 | ND | ND | 0.35 | 82* | ND |
| 130c | 0.00059 | ND | ND | 0.025 | 87 | ND |
| 131a | ND | ND | ND | ND | ND | ND |
| 131b | 0.087 | ND | ND | 0.14 | 81* | ND |
| 131c | 0.0033 | ND | ND | 0.05 | 94* | ND |
| 132a | 0.027 | 0.12 | 101 | ND | ND | ND |
| 132b | 1.4 | ~5 | 70 | ND | ND | ND |
| 132c | 0.0041 | 0.058 | 99 | ND | ND | ND |
| 133a | 0.0012 | 0.011 | 98 | ND | ND | ND |
| 133b | 0.41 | 0.84 | 90 | ND | ND | ND |
| 133c | 0.0011 | 0.0064 | 98 | ND | ND | ND |
| 134a | 0.00058 | 0.015 | 101 | ND | ND | ND |
| 134b | 0.00054 | 0.0024 | 101 | ND | ND | ND |
| 134c | 0.0014 | 0.0031 | 99 | ND | ND | ND |
| 135a | 0.00066 | 0.0082 | 100 | ND | ND | ND |
| 135b | 0.00075 | ND | ND | ND | ND | ND |
| 135c | 0.0012 | ND | ND | ND | ND | ND |
| 136a | 0.00095 | 0.06 | 97 | ND | ND | ND |
| 136b | 0.71 | 2.3 | 76 | 0.95 | 79 | ND |
| 136c | 0.0014 | 0.014 | 98 | 0.011 | 95* | ND |
| 137 | 0.0013 | ND | ND | 0.011 | 105 | ND |
| 138 | 0.38 | ND | ND | 0.75 | 96 | ND |
| 139a | 0.079 | 0.3 | 101 | ND | ND | ND |
| 139b | 0.48 | 0.96 | 99 | ND | ND | ND |
| 139c | 0.043 | 0.17 | 101 | ND | ND | ND |
| 140a | 1.7 | ~6 | 48 | ND | ND | ND |
| 140b | 16 | >6 | 48 | ND | ND | ND |
| 140c | 5.5 | ~6 | 56 | ND | ND | ND |
| 141 | 0.038 | 0.21 | 99 | ND | ND | ND |
| 142a | 0.13 | 0.14 | 100 | ND | ND | ND |
| 142b | 2.4 | ~6 | 53 | ND | ND | ND |
| 142c | 0.018 | 0.061 | 101 | ND | ND | ND |
| 143a | ND | ND | ND | ND | ND | ND |
| 143b | 1.2 | 3 | 77 | ND | ND | ND |
| 143c | 0.0029 | 0.045 | 100 | ND | ND | 0.37 |
| 144 | 0.012 | 0.21 | 101 | ND | ND | ND |
| 145 | 0.0009 | ND | ND | 0.074 | 103 | ND |
| 146 | 0.85 | ND | ND | 1.4 | 79 | ND |
| 147 | 0.93 | ND | ND | ND | ND | ND |
| 148 | 1.7 | ND | ND | ND | ND | ND |
| 149 | 6.8 | ND | ND | 2.5 | 42 | ND |
| 150 | 3.4 | ND | ND | 2.5 | 57 | ND |
| 151 | 5.1 | ND | ND | >6 | 45 | ND |
| 152 | 0.6 | ND | ND | ND | ND | ND |
| 153 | 3 | ND | ND | ND | ND | ND |

TABLE 1-continued

| Example Number | ThermoFluor ® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 6 μM | Human Th17 Assay, IC$_{50}$ (μM) |
|---|---|---|---|---|---|---|
| 154a | 0.075 | >6 | 35 | ND | ND | ND |
| 154b | 4.2 | >6 | 30 | ND | ND | ND |
| 154c | 0.019 | 3.6 | 45 | ND | ND | ND |
| 155 | 1.4 | 5.4 | 64 | ND | ND | ND |
| 156 | 3.4 | >6 | 34 | ND | ND | ND |
| 157 | 0.28 | 1.3 | 68 | ND | ND | ND |
| 158 | 0.17 | 1.7 | 81 | ND | ND | ND |
| 159 | 0.16 | 1 | 86 | ND | ND | ND |
| 160 | ND | ND | ND | ND | ND | ND |
| 161 | ND | ND | ND | ND | ND | ND |
| 162 | ND | ND | ND | ND | ND | ND |
| 163 | ND | ND | ND | ND | ND | ND |
| 164 | ND | ND | ND | ND | ND | ND |
| 165 | ND | ND | ND | ND | ND | ND |
| 166a | ND | ND | ND | ND | ND | ND |
| 166b | 0.61 | 0.36 | 96 | ND | ND | ND |
| 166c | 1.5 | 2.2 | 84 | ND | ND | ND |
| 167 | ND | ND | ND | ND | ND | ND |
| 168 | ND | ND | ND | ND | ND | ND |
| 169 | ND | ND | ND | ND | ND | ND |
| 170 | ND | ND | ND | ND | ND | ND |
| 171 | ND | ND | ND | ND | ND | ND |
| 172 | 12 | >6 | 12 | ND | ND | ND |
| 173 | ND | ND | ND | ND | ND | ND |
| 174 | ND | ND | ND | ND | ND | ND |
| 175 | ND | ND | ND | ND | ND | ND |
| 176 | ND | ND | ND | ND | ND | ND |
| 177 | ND | ND | ND | ND | ND | ND |
| 178 | ND | ND | ND | ND | ND | ND |
| 179 | ND | ND | ND | ND | ND | ND |
| 180 | ND | ND | ND | ND | ND | ND |
| 181 | ND | ND | ND | ND | ND | ND |
| 182a | 0.029 | ND | ND | 0.12 | 101 | ND |
| 182b | 2.5 | ND | ND | 1.5 | 79 | ND |
| 182c | 0.012 | ND | ND | 0.081 | 100 | ND |
| 183 | 0.015 | ND | ND | 0.95 | 33 | ND |
| 184 | 0.017 | ND | ND | 1 | 53 | ND |
| 185 | 0.77 | ND | ND | >6 | 6 | ND |
| 186 | 0.59 | ND | ND | >6 | 5 | ND |
| 187 | 0.54 | ND | ND | 0.64 | 72* | ND |
| 188a | ND | ND | ND | ND | ND | ND |
| 188b | 0.0036 | ND | ND | 0.041 | 98* | ND |
| 188c | 3.4 | ND | ND | 0.84 | 42* | ND |
| 189a | ND | ND | ND | ND | ND | ND |
| 189b | 0.051 | ND | ND | 0.17 | 102 | ND |
| 189c | 49 | ND | ND | >6 | 16 | ND |
| 190a | ND | ND | ND | ND | ND | ND |
| 190b | 0.58 | ND | ND | 0.75 | 38* | ND |
| 190c | 0.0012 | ND | ND | 0.021 | 84* | ND |
| 191a | ND | ND | ND | ND | ND | ND |
| 191b | 0.098 | ND | ND | 0.096 | 93* | ND |
| 191c | 0.0031 | ND | ND | 0.033 | 95 | ND |
| 192a | ND | ND | ND | ND | ND | ND |
| 192b | 0.27 | ND | ND | 0.36 | 97 | ND |
| 192c | 0.004 | ND | ND | 0.022 | 99* | ND |
| 193 | 0.042 | ND | ND | 1.1 | 82 | ND |
| 194 | 0.11 | ND | ND | 2 | 61 | ND |
| 195 | 0.026 | ND | ND | 1.4 | 79 | ND |
| 196 | 0.0012 | ND | ND | 0.28 | 104 | ND |
| 197 | 0.0027 | ND | ND | 0.23 | 75 | ND |
| 198 | 0.0012 | ND | ND | 0.12 | 96 | ND |
| 199 | 0.0096 | ND | ND | 0.19 | 86 | ND |
| 200 | 0.01 | ND | ND | 0.17 | 79 | ND |
| 201 | 0.0025 | ND | ND | 0.91 | 94 | 0.27 |
| 202 | ND | ND | ND | 0.13 | 68* | ND |
| 203 | 0.0078 | ND | ND | 0.62 | 86* | ND |
| 204 | ND | ND | ND | 0.35 | 83 | ND |
| 205a | ND | ND | ND | ND | ND | ND |
| 205b | 0.41 | ND | ND | 0.56 | 58* | ND |
| 205c | 0.00048 | ND | ND | 0.021 | 99* | ND |
| 206a | 0.0044 | ND | ND | 0.041 | 103 | ND |
| 206b | 0.0046 | ND | ND | 0.018 | 102 | ND |
| 206c | 0.01 | ND | ND | 0.047 | 100 | ND |

TABLE 1-continued

| Example Number | ThermoFluor ® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 6 μM | Human Th17 Assay, IC$_{50}$ (μM) |
|---|---|---|---|---|---|---|
| 207a | 0.076 | ND | ND | 0.058 | 92 | ND |
| 207b | 0.076 | ND | ND | 0.44 | 67** | ND |
| 207c | 0.015 | ND | ND | 0.05 | 97* | ND |
| 208a | ND | ND | ND | ND | ND | ND |
| 208b | 0.014 | ND | ND | 0.071 | 88* | ND |
| 208c | 0.27 | ND | ND | 0.28 | 84* | ND |
| 209a | ND | ND | ND | ND | ND | ND |
| 209b | 2.8 | ND | ND | 1.1 | 25* | ND |
| 209c | 0.0086 | ND | ND | 0.045 | 96* | ND |
| 210a | ND | ND | ND | ND | ND | ND |
| 210b | 3.6 | ND | ND | 0.97 | 33* | ND |
| 210c | 0.0076 | ND | ND | 0.059 | 101* | ND |
| 211a | ND | ND | ND | ND | ND | ND |
| 211b | 0.72 | ND | ND | 0.68 | 56* | ND |
| 211c | 0.13 | ND | ND | 0.28 | 87* | ND |
| 212a | ND | ND | ND | ND | ND | ND |
| 212b | 0.38 | ND | ND | 0.69 | 53* | ND |
| 212c | 0.065 | ND | ND | 0.37 | 77* | ND |
| 213a | ND | ND | ND | ND | ND | ND |
| 213b | 1.2 | ND | ND | 1 | 31* | ND |
| 213c | 0.003 | ND | ND | 0.013 | 95* | ND |
| 214a | ND | ND | ND | ND | ND | ND |
| 214b | 0.23 | ND | ND | 0.62 | 48* | ND |
| 214c | 0.021 | ND | ND | 0.11 | 55* | ND |
| 215a | ND | ND | ND | ND | ND | ND |
| 215b | 0.26 | ND | ND | 0.51 | 65* | ND |
| 215c | 0.059 | ND | ND | 0.046 | 90* | ND |
| 216a | 0.23 | ND | ND | 0.41 | 77* | ND |
| 216b | 2.5 | ND | ND | 0.92 | 27* | ND |
| 216c | 0.11 | ND | ND | 0.12 | 82* | ND |
| 217a | ND | ND | ND | ND | ND | ND |
| 217b | 1.3 | ND | ND | >2 | 13* | ND |
| 217c | 0.0096 | ND | ND | 0.026 | 63* | ND |
| 218a | ND | ND | ND | ND | ND | ND |
| 218b | 0.73 | ND | ND | 0.86 | 53* | ND |
| 218c | 0.0032 | ND | ND | 0.018 | 104* | ND |
| 219a | ND | ND | ND | ND | ND | ND |
| 219b | 1 | ND | ND | 1.3 | 55 | ND |
| 219c | 1.2 | ND | ND | 1.8 | 47 | ND |
| 220 | 0.00006 | ND | ND | 0.014 | 103* | ND |
| 221 | 0.0033 | ND | ND | 0.12 | 104 | ND |
| 222 | 0.31 | ND | ND | 0.46 | 50 | ND |
| 223a | ND | ND | ND | ND | ND | ND |
| 223b | 0.048 | ND | ND | 0.14 | 95 | ND |
| 223c | 0.05 | ND | ND | 0.22 | 96 | 0.19 |
| 224a | ND | ND | ND | ND | ND | ND |
| 224b | 0.67 | ND | ND | 0.58 | 64* | ND |
| 224c | 0.046 | ND | ND | 0.13 | 97* | ND |
| 225a | ND | ND | ND | ND | ND | ND |
| 225b | 0.18 | ND | ND | 0.67 | 66* | ND |
| 225c | 0.002 | ND | ND | 0.008 | 99* | ND |
| 226a | ND | ND | ND | ND | ND | ND |
| 226b | 0.69 | ND | ND | 0.56 | 58* | ND |
| 226c | 0.0033 | ND | ND | 0.018 | 102* | ND |
| 227a | ND | ND | ND | ND | ND | ND |
| 227b | 0.075 | ND | ND | 0.42 | 79* | 0.052 |
| 227c | 0.0024 | ND | ND | 0.015 | 100* | ND |
| 228 | ND | ND | ND | ND | ND | ND |
| 229 | ND | ND | ND | ND | ND | ND |
| 230 | ND | ND | ND | ND | ND | ND |
| 231 | ND | ND | ND | ND | ND | ND |
| 232 | ND | ND | ND | ND | ND | ND |
| 233 | ND | ND | ND | ND | ND | ND |
| 234 | ND | ND | ND | ND | ND | ND |
| 235 | ND | ND | ND | ND | ND | ND |
| 236 | ND | ND | ND | ND | ND | ND |
| 237 | ND | ND | ND | ND | ND | ND |
| 238a | >24 | >6 | −8 | ND | ND | ND |
| 238b | 13 | >6 | 9 | ND | ND | ND |
| 239 | >62 | ND | ND | 2.1 | 24 | ND |
| 240a | 0.036 | ND | ND | 0.11 | 91* | ND |
| 240b | 0.15 | ND | ND | 0.32 | 88* | ND |
| 240c | 0.024 | ND | ND | 0.045 | 93* | ND |

TABLE 1-continued

| Example Number | ThermoFluor® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 6 μM | Human Th17 Assay, IC50 (μM) |
|---|---|---|---|---|---|---|
| 241a | ND | ND | ND | ND | ND | ND |
| 241b | 0.024 | ND | ND | 0.07 | 94* | ND |
| 241c | 0.44 | ND | ND | 0.52 | 74* | ND |
| 242a | ND | ND | ND | ND | ND | ND |
| 242b | 0.43 | ND | ND | 0.9 | 48* | ND |
| 242c | 0.052 | ND | ND | 0.095 | 99* | ND |
| 243a | 0.01 | ND | ND | 0.074 | 69* | ND |
| 243b | 0.055 | ND | ND | 0.17 | 66*** | ND |
| 243c | 0.0031 | ND | ND | 0.061 | 76* | ND |
| 244a | 0.0024 | ND | ND | 0.018 | 83* | ND |
| 244b | 9.3 | ND | ND | 0.78 | 42* | ND |
| 244c | 0.0035 | ND | ND | 0.012 | 86* | ND |
| 245a | 0.028 | ND | ND | 0.073 | 90* | ND |
| 245b | 0.85 | ND | ND | 0.66 | 39* | ND |
| 245c | 0.013 | ND | ND | 0.045 | 93* | ND |
| 246 | ND | ND | ND | ND | ND | ND |
| 247 | ND | ND | ND | ND | ND | ND |
| 248 | 0.00046 | ND | ND | 0.024 | 106 | ND |

All data shown in Table 1 is either the value of one data point or the average of more than one data point. In cases where more than one value is shown in a table cell, values with qualifiers such as ~, > or < could not be included in the averaging calculation for the value shown on the left side of the table cell.
*% inhibition is shown at 2 μM compound concentration,
**% inhibition is shown at 1 μM compound concentration,
***% inhibition is shown at 0.67 μM compound concentration.
Compounds marked "ND" were not tested.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

What is claimed is:

1. A method for treating or ameliorating a RORγt mediated inflammatory syndrome, disorder or disease selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus, comprising administering to a subject in need thereof an effective amount of a compound of Formula I, wherein:

Formula I

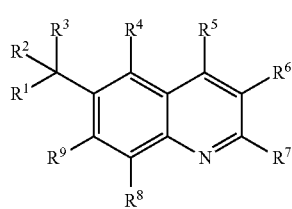

$R^1$ is imidazolyl, pyrimidinyl, triazolyl, tetrahydropyranyl, thiazolyl, pyridyl, piperidinyl, phenyl, or oxazolyl; wherein said piperidinyl, pyridyl, imidazolyl, and phenyl are optionally substituted with $SO_2CH_3$, $C(O)CH_3$, $CH_3$, $CF_3$, Cl, F, —CN, $OCH_3$, or $N(CH_3)_2$; and optionally substituted with up to one additional group independently selected from the group consisting of Cl, $OCH_3$, and $CH_3$; and wherein said triazolyl, oxazolyl, and thiazolyl are optionally substituted with one or two $CH_3$ groups;

$R^2$ is H, $CH_3$, —C≡CH, 1-methyl-1,2,3-triazol-5-yl, pyrid-3-yl, 2-trifluoromethyl-pyrid-4-yl, 1-methyl-pyrazol-4-yl, 1,3,5-trimethyl-pyrazol-4-yl, thiazol-5-yl, N-acetyl-azetidin-3-yl, N-methylsulfonyl-azetidin-3-yl, N-Boc-azetidin-3-yl, N-acetyl-piperidin-4-yl, N-Boc-piperidin-4-yl, 1-H-piperidin-4-yl, N-methylsulfonyl-piperidin-4-yl, 1,2-dimethyl imidazol-5-yl, or 1-methyl imidazol-5-yl, provided that $R^2$ is not H when $R^5$ is H;

$R^3$ is OH;

R⁴ is H;

R⁵ is H, Cl, —CN, CF₃, C₍₁₋₂₎alkyl, OH, N(CH₃)OCH₃, OCH₃, azetidin-1-yl, or fur-2-yl; provided that R⁵ is not H if R⁷ is OCH₃;

R⁶ is C₍₁₋₄₎alkylene-Q, OC₍₁₋₄₎alkylene-Q, C(O)NA³A⁴, C(O)OC₍₁₋₄₎alkyl, O-tetrahydropyranyl, —O—(N-methyl)piperidinyl, cyclopentyl, cyclohexyl, 1-methyl-1,2,3,6-tetrahydropyridin-4-yl, or tetrahydropyran-4-yl; provided that R⁶ is not CH₂-phenyl, CH₂-pyridinyl, nor CH₂-pyrimidinyl;

Q is H, CF₃, OH, SO₂CH₃, NA³A⁴, OC₍₁₋₄₎alkyl, cyclopropyl, 1-methyl-cyclopropyl, oxetanyl, 3-methyl-oxetanyl, tetrahydrofuranyl, 1,3-dimethyl-pyrazol-5-yl, 3,5-dimethyl-isoxazol-4-yl, thiazol-2-yl, N-methyl-pyrrolidin-2-yl, cyclohexyl, N-acetyl-piperidin-4-yl, N-Boc-piperidin-4-yl, 1-H-piperidin-4-yl, tetrahydropyran-4-yl, 1,1-dioxo-tetrahydrothiopyran-4-yl, tetrahydrothiopyran-4-yl, phenyl, pyridin-3-yl, or pyrimidin-2-yl; wherein said cyclopropyl, and said cyclohexyl are optionally substituted with up to two fluorine atoms;

wherein

A³ is H, or CH₃;

A⁴ is CH₃, CH₂-cyclopropyl, cyclopropyl, C₍₁₋₃₎alkylCF₃, CH₂CH₂OCH₂CF₃, C(O)C₍₁₋₂₎alkylCF₃,

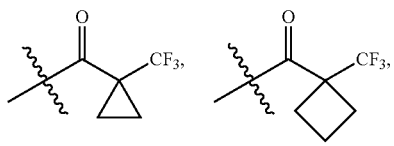 [SMILES: *C(=O)C1(C(F)(F)F)CC1 ; *C(=O)C1(C(F)(F)F)CCC1]

or C₍₀₋₁₎alkyl-trifluoromethyl-cyclohexyl, or A³ and A⁴ may be taken together with their attached nitrogen to form a ring selected from the group consisting of:

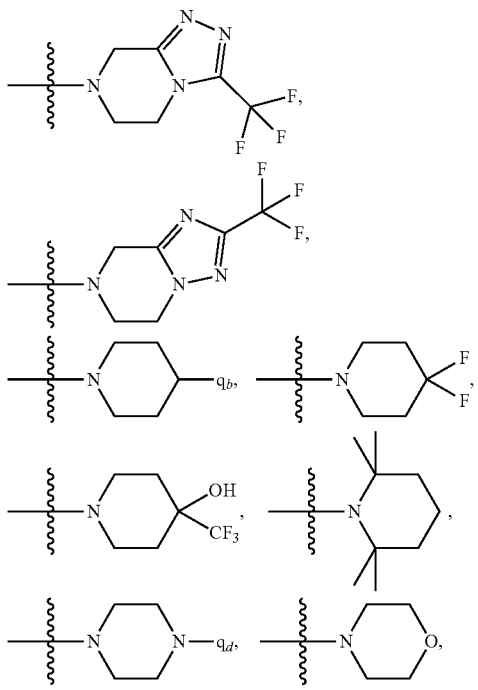

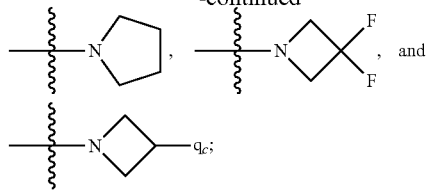

wherein q_b is H, F, CF₃, SO₂CH₃, pyrazol-1-yl, or 3-trifluoromethyl-pyrazol-1-yl;

q_c is H, F, or CF₃;

q_d is CH₂CF₃;

provided that if R⁶ is OCH₂-Q, then Q may not be OH, nor NA³A⁴;

R⁷ is Cl, —CN, CF₃, C₍₁₋₄₎alkyl, cyclopropyl, NA¹A², C(O)NHCH₃, OCH₂CH₂OCH₃, 1-methyl imidazol-2-yl, 1-methyl pyrazol-4-yl, OC₍₁₋₂₎alkyl, pyrimidin-5-yl, thiophen-3-yl, 1-methyl-indazol-5-yl, 1-methyl-indazol-6-yl, fur-2-yl, phenyl, or

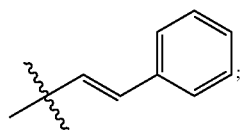

A¹ is C₍₁₋₂₎alkyl;

A² is C₍₁₋₂₎alkyl, CH₂CH₂OCH₃, or OCH₃; or A¹ and A² may be taken together with their attached nitrogen to form a ring which is:

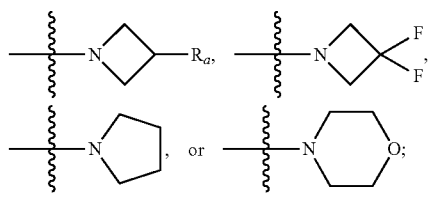

R_a is H, OH, OCH₃, F;

R⁸ is H, CH₃, OCH₃, or F;

R⁹ is H;

and pharmaceutically acceptable salts thereof.

2. The method of claim 1, wherein in said compound:

R¹ is imidazolyl, triazolyl, tetrahydropyranyl, thiazolyl, pyridyl, or phenyl; wherein said pyridyl, imidazolyl, and phenyl are optionally substituted with one substituent selected from the group consisting of CH₃, CF₃, Cl, and —CN; and optionally substituted with up to one additional CH₃; and wherein said triazolyl, and thiazolyl are optionally substituted with one or two CH₃ groups;

R² is H, CH₃, 1-methyl-1,2,3-triazol-5-yl, pyrid-3-yl, 2-trifluoromethyl-pyrid-4-yl, 1,3,5-trimethyl-pyrazol-4-yl, N-acetyl-azetidin-3-yl, N-methylsulfonyl-azetidin-3-yl, N-Boc-azetidin-3-yl, N-acetyl-piperidin-4-yl, N-methylsulfonyl-piperidin-4-yl, N-Boc-piperidin-4-yl, 1-H-piperidin-4-yl, 1,2-dimethyl-imidazol-5-yl, or 1-methyl-imidazol-5-yl, provided that R² is not H when R⁵ is H;

$R^5$ is H, Cl, —CN, CF$_3$, C$_{(1-2)}$alkyl, OCH$_3$, azetidin-1-yl, or fur-2-yl; provided that $R^5$ is not H if $R^7$ is OCH$_3$;

$R^7$ is Cl, CF$_3$, CH$_2$CH$_3$, cyclopropyl, OCH$_3$, pyrimidin-5-yl, thiophen-3-yl, 1-methyl-indazol-5-yl, 1-methyl-indazol-6-yl, fur-2-yl, azetidin-1-yl, phenyl, or

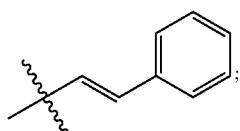 [SMILES: */C=C/c1ccccc1]

$R^8$ is H or CH$_3$;

and pharmaceutically acceptable salts thereof.

3. A method of claim 1, wherein the compound is selected from the group consisting of:

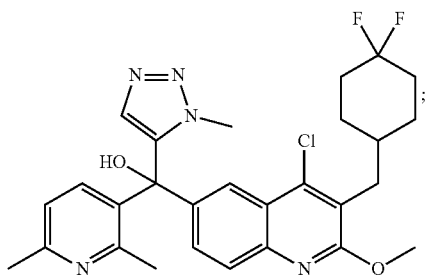

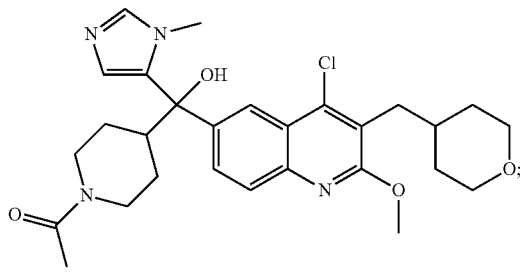

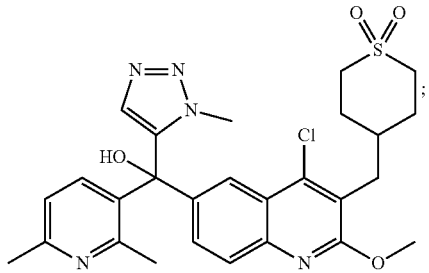

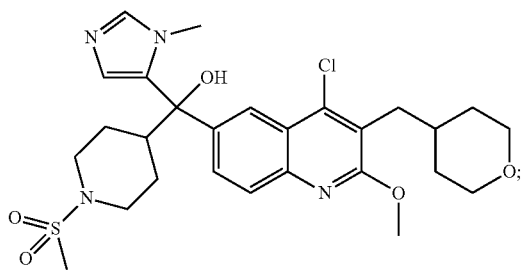

-continued

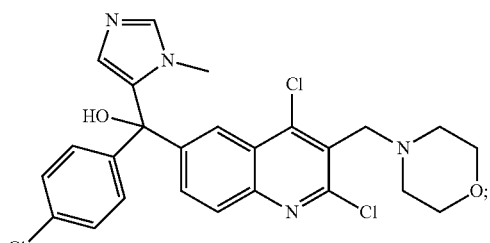

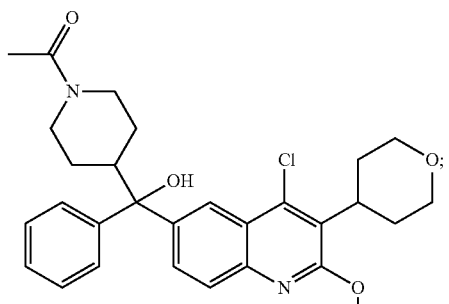

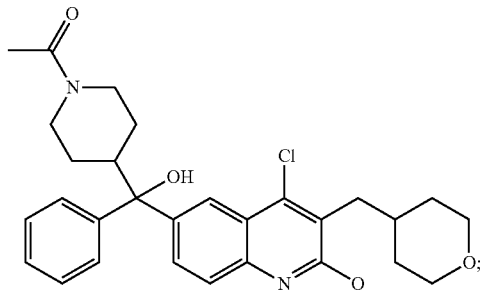

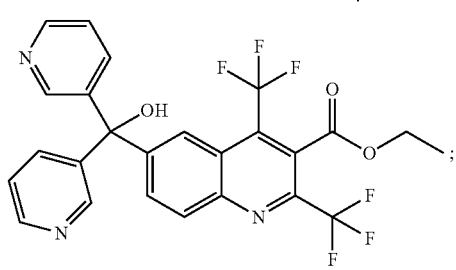

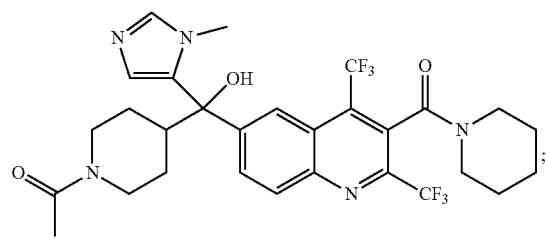

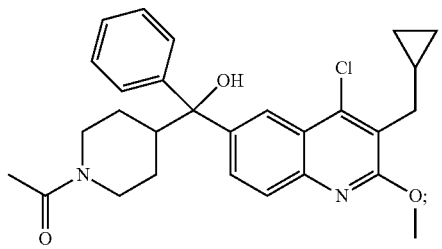

403
-continued
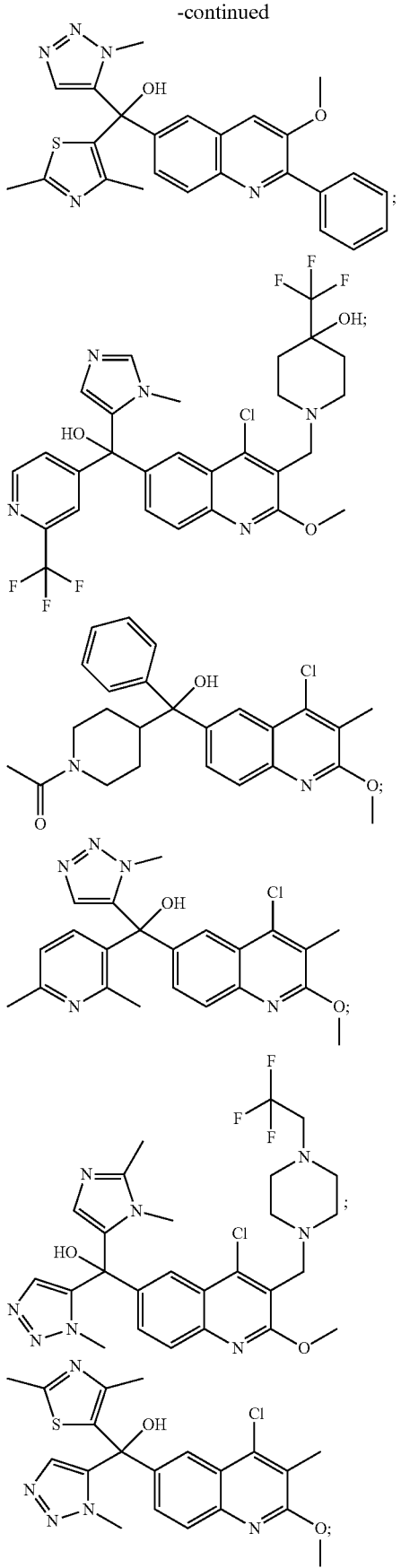
404
-continued
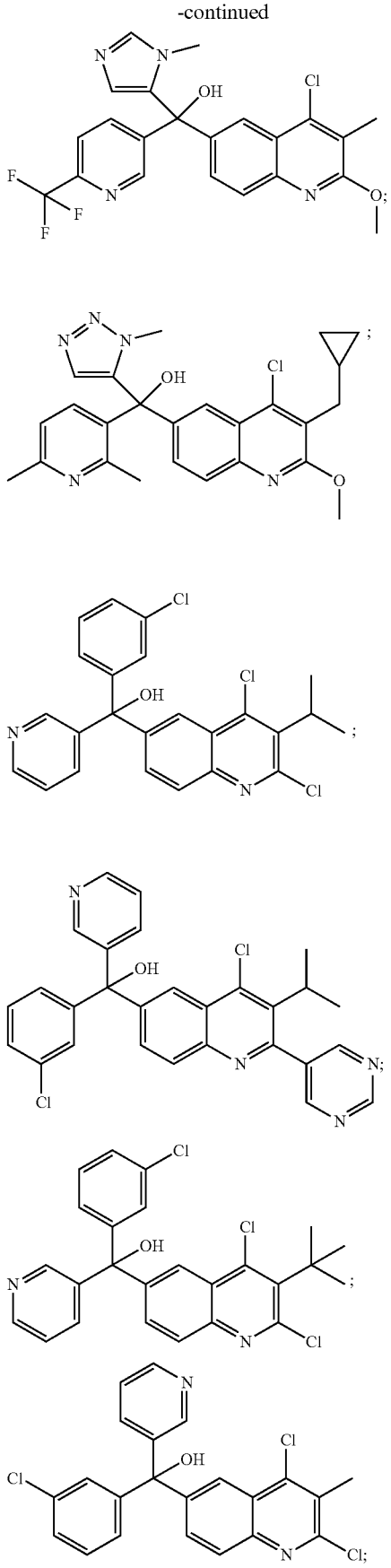

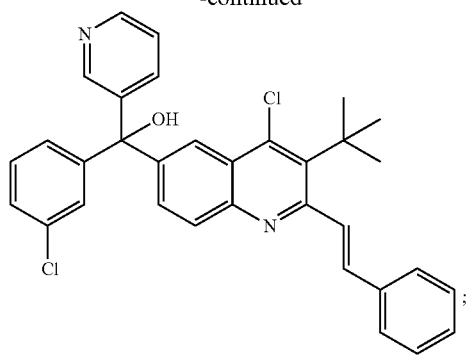
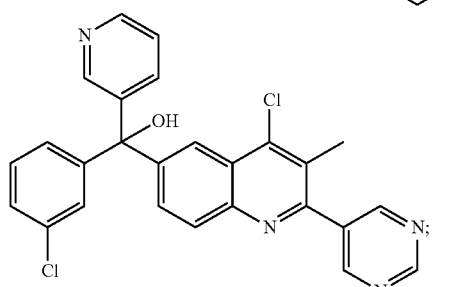
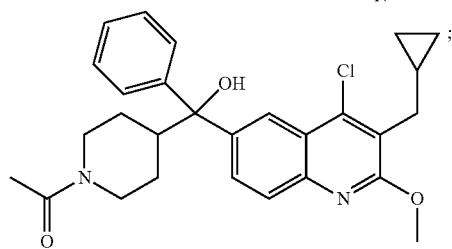
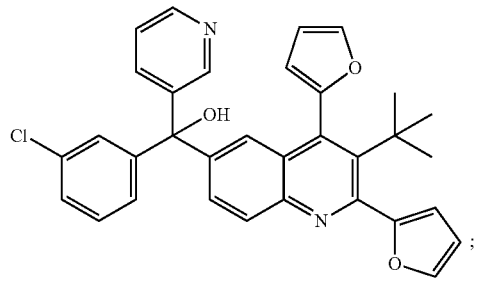
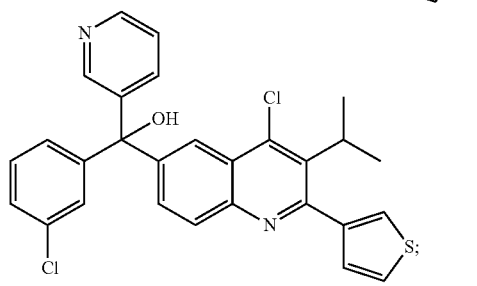
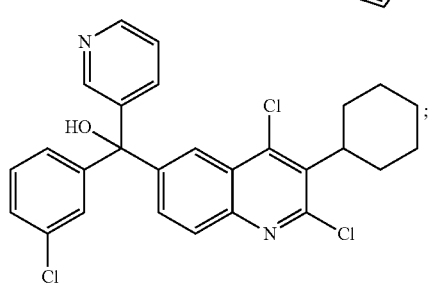
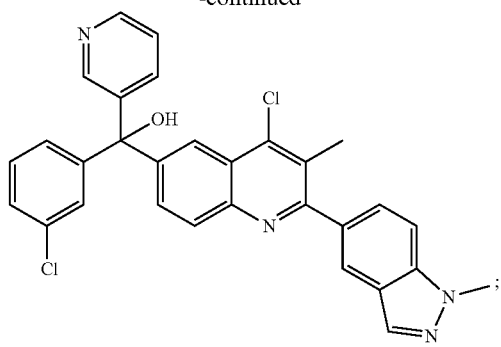
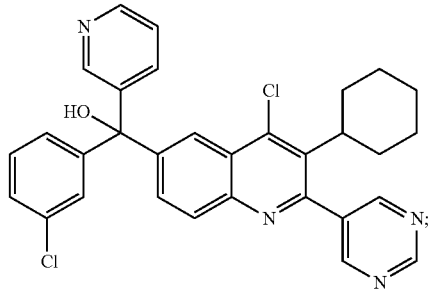
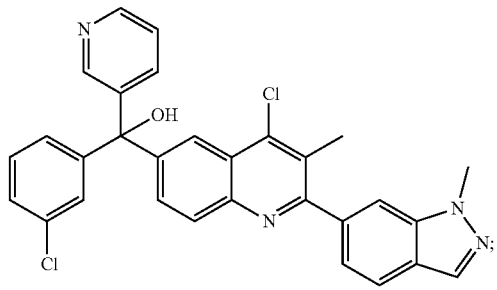
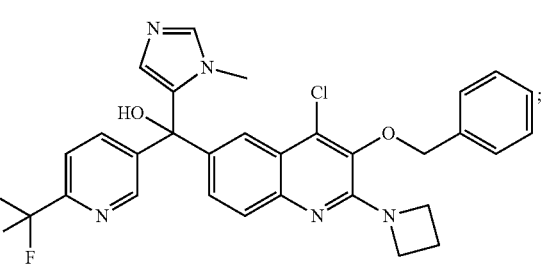
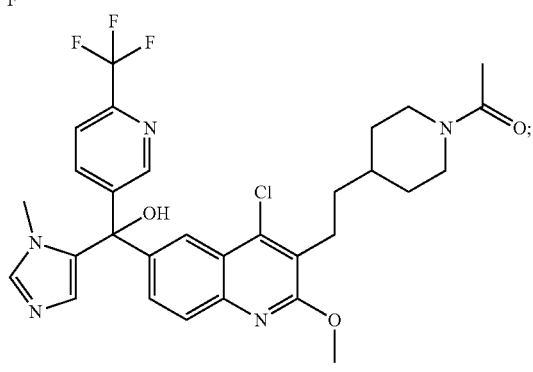

407
-continued
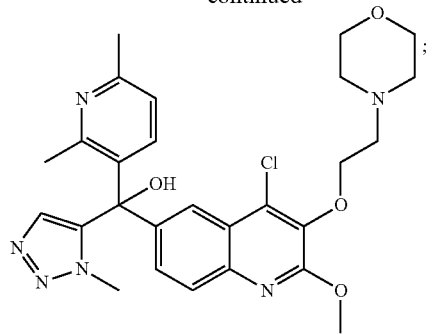
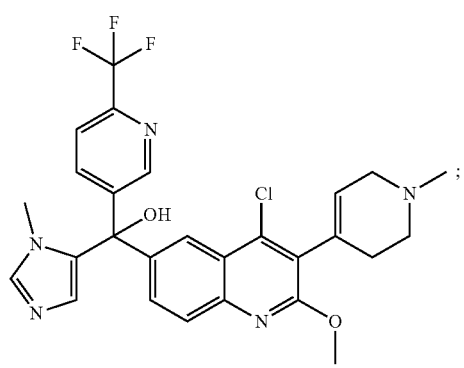
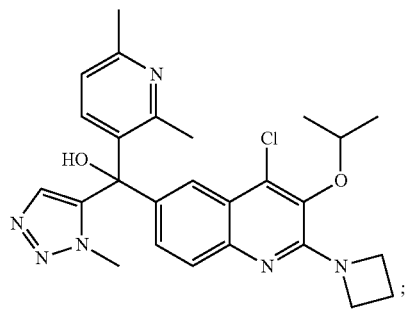
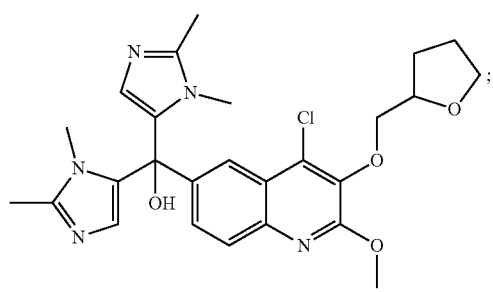
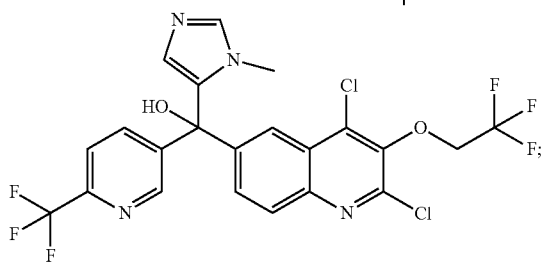
408
-continued
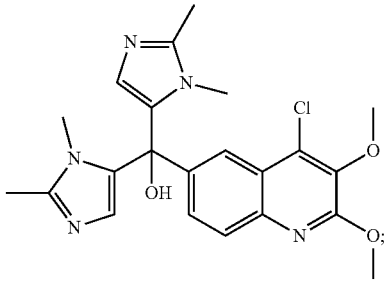
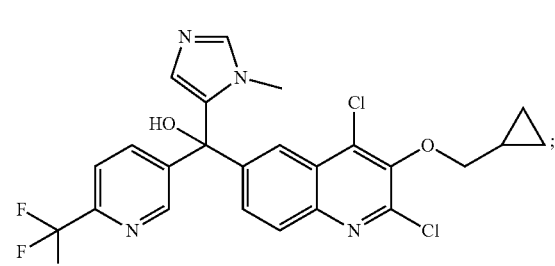
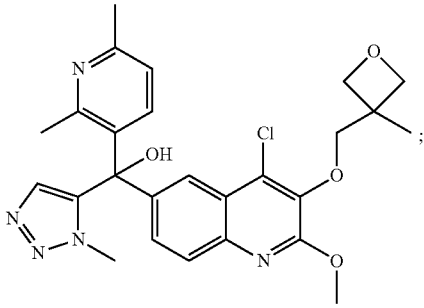
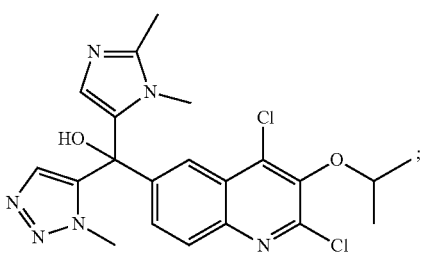
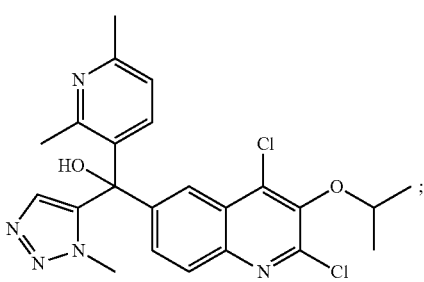
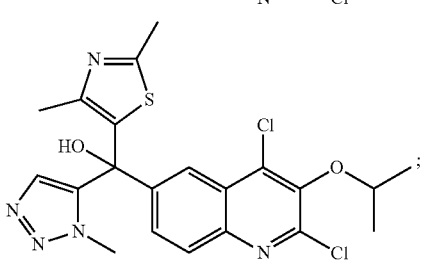

409
-continued
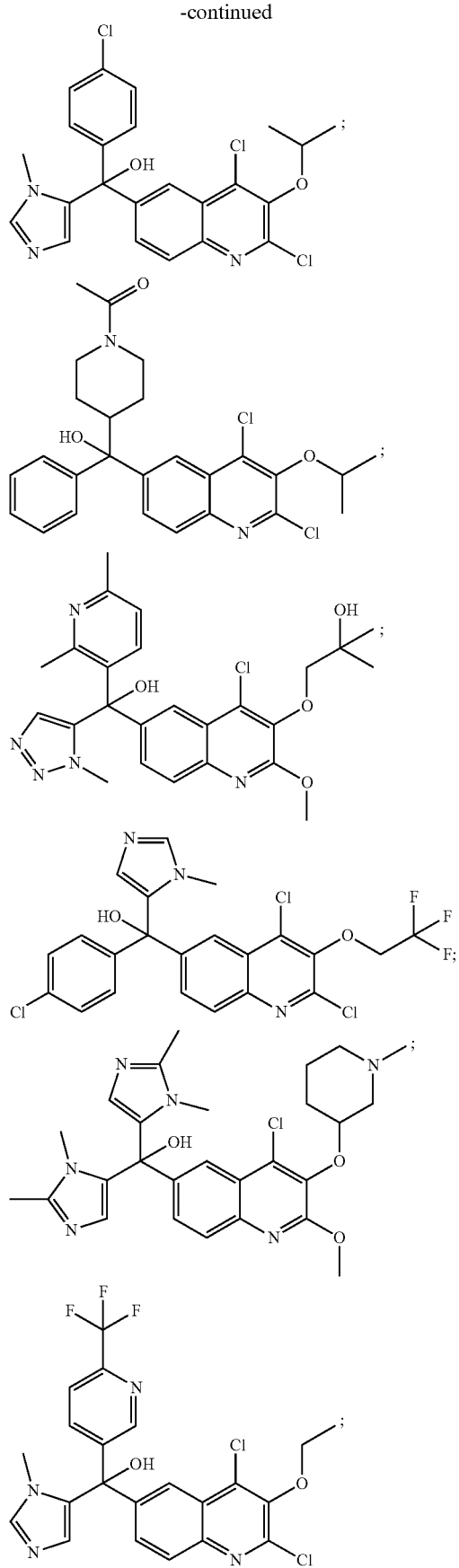
410
-continued
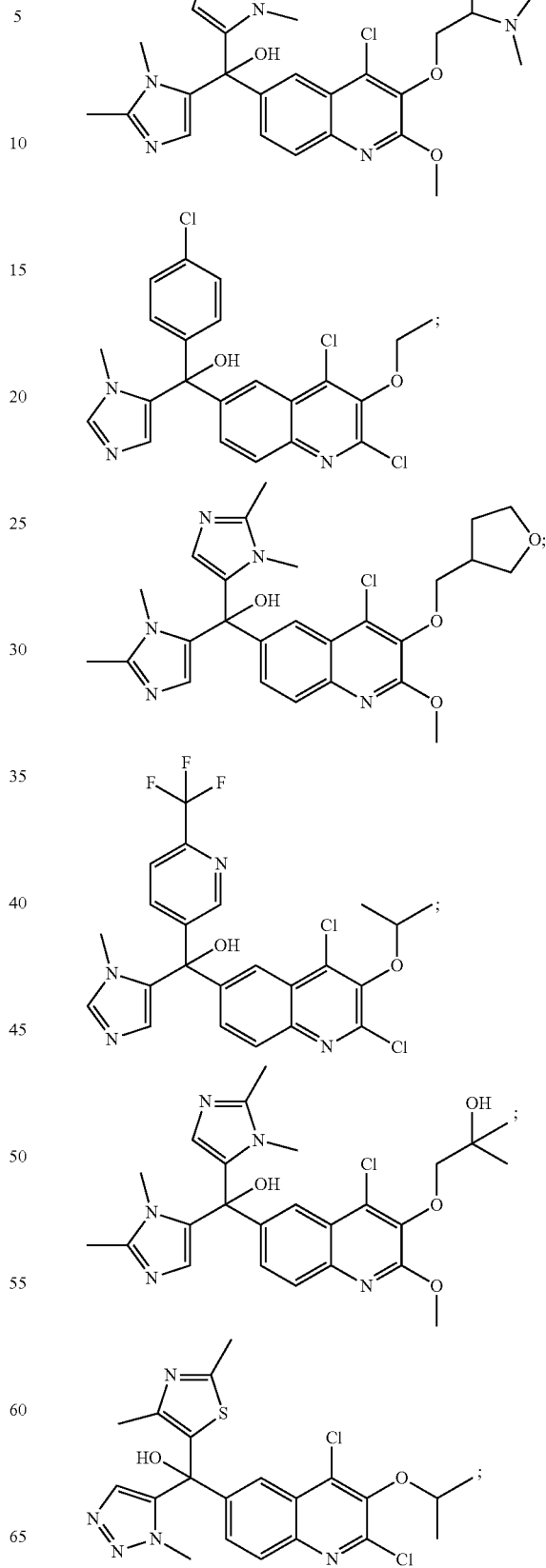

411
-continued
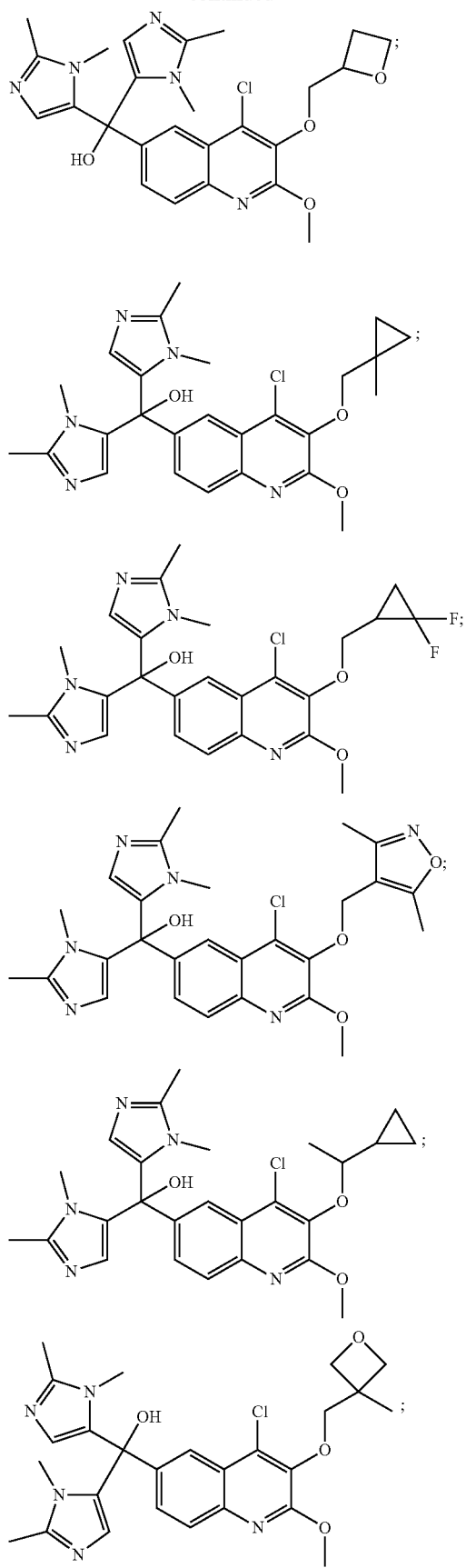
412
-continued
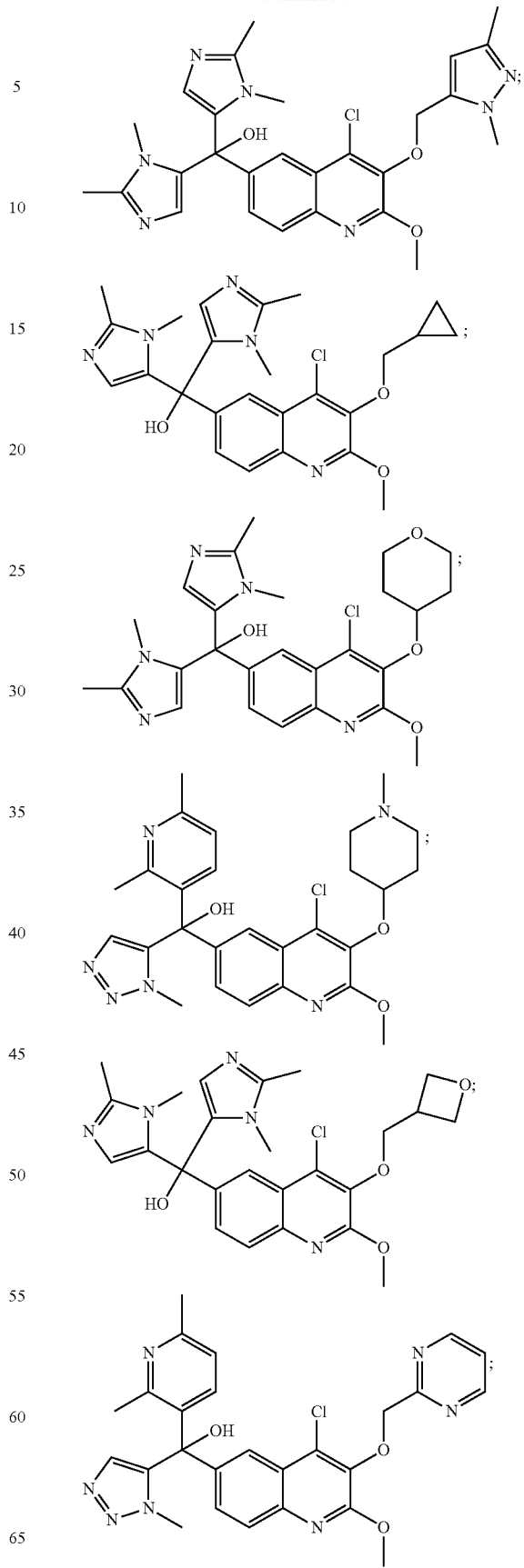

413
-continued
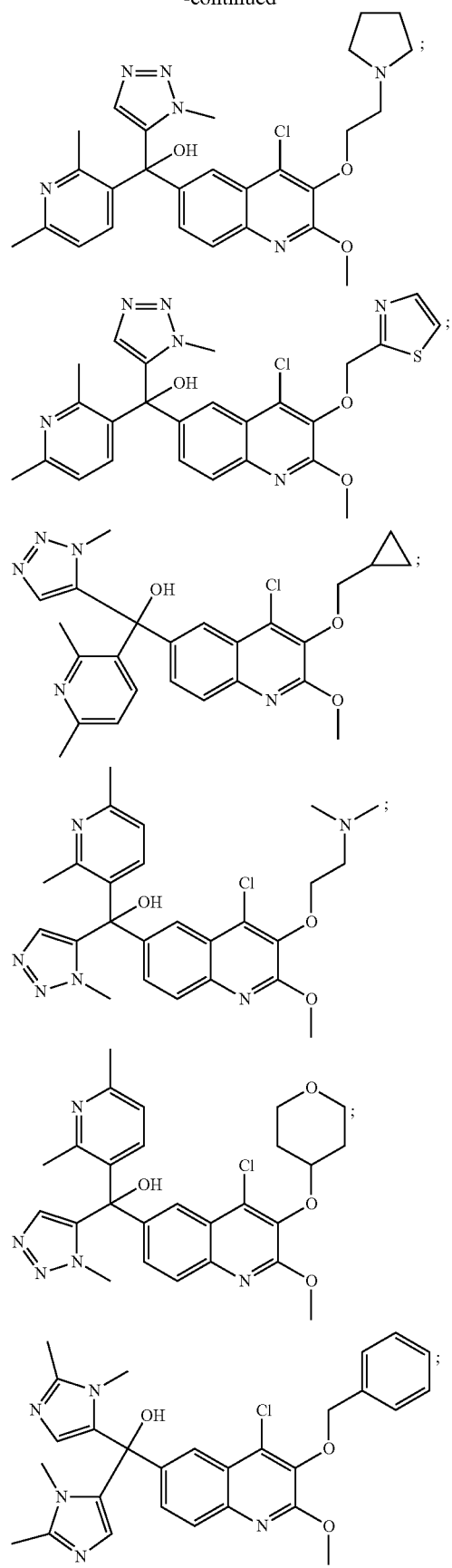
414
-continued
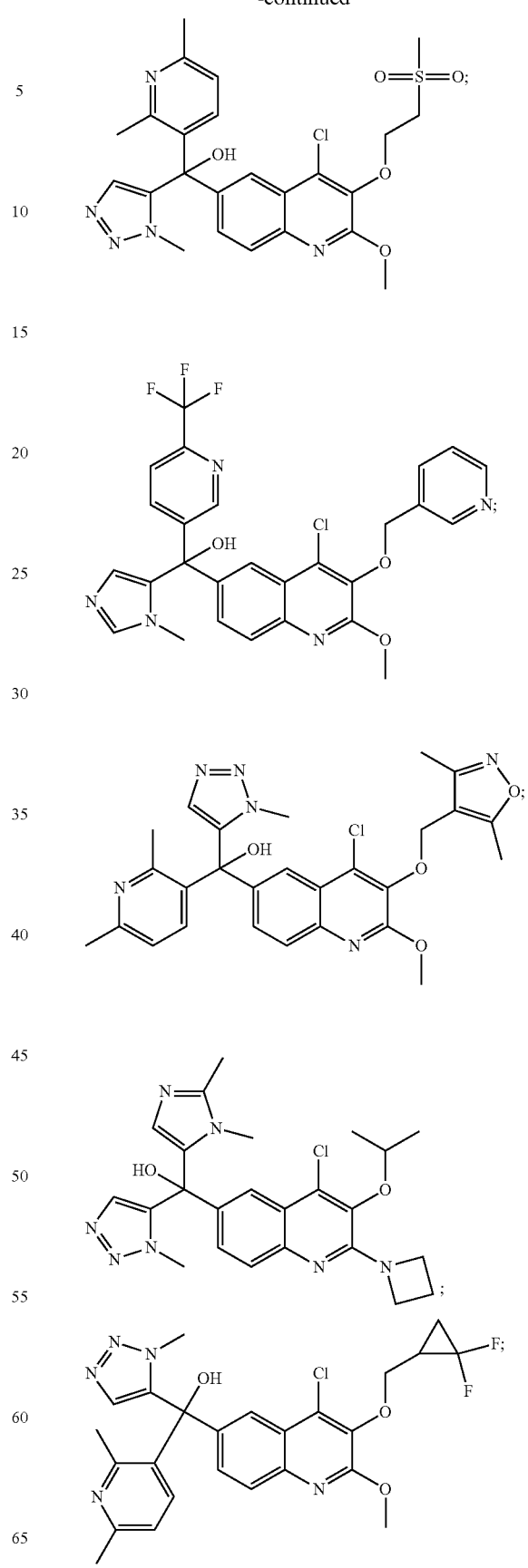

415
-continued
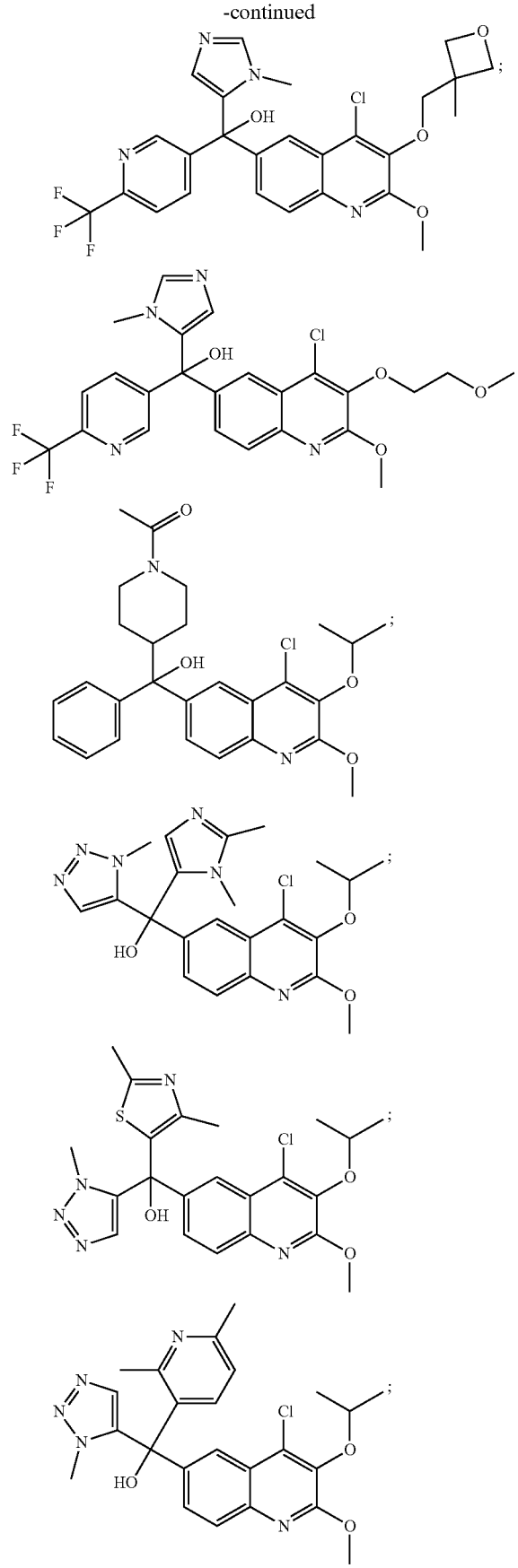
416
-continued
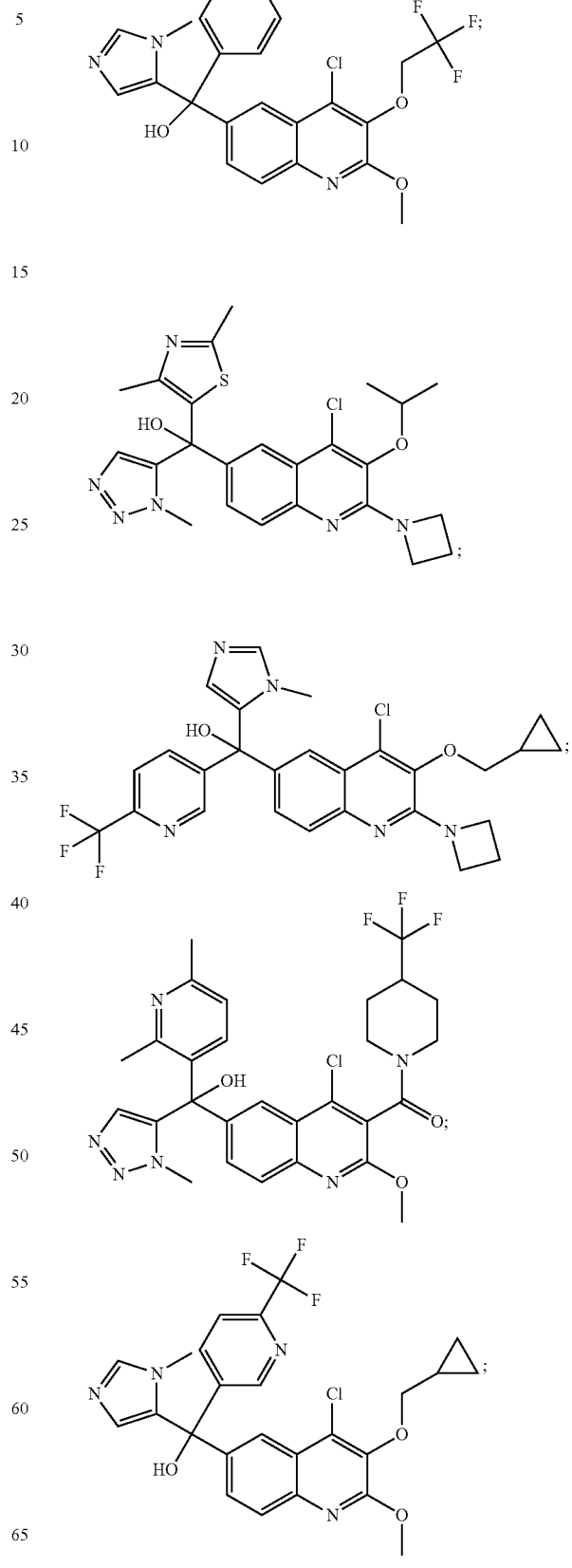

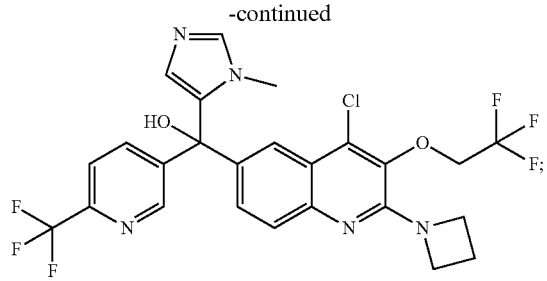
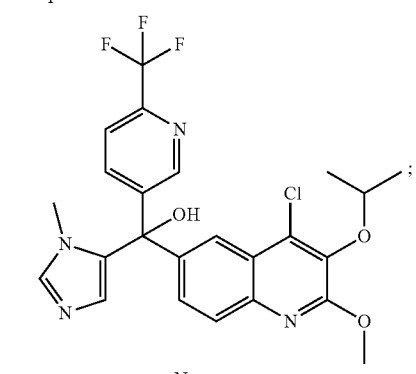
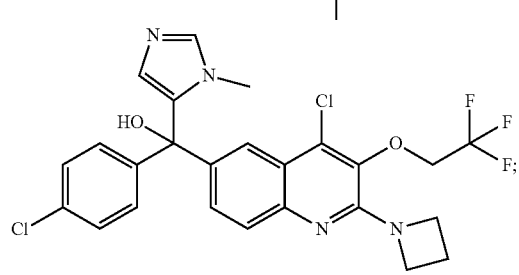
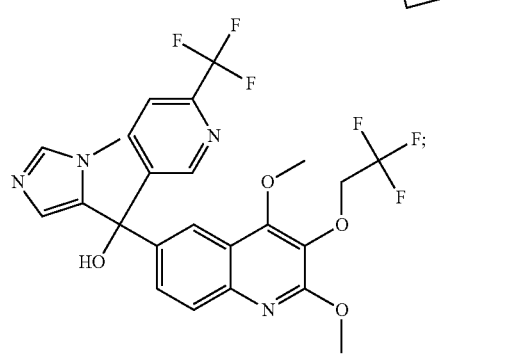
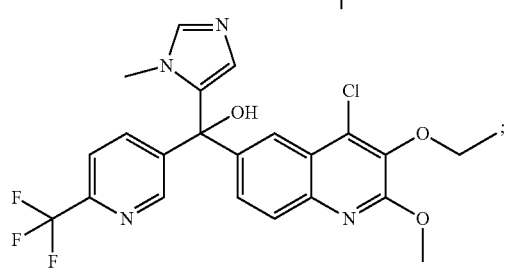
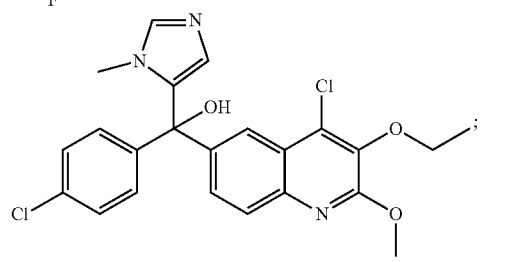
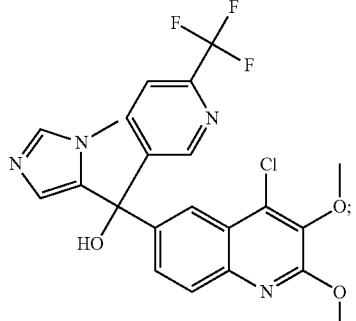
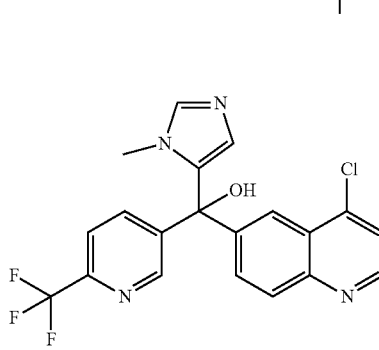
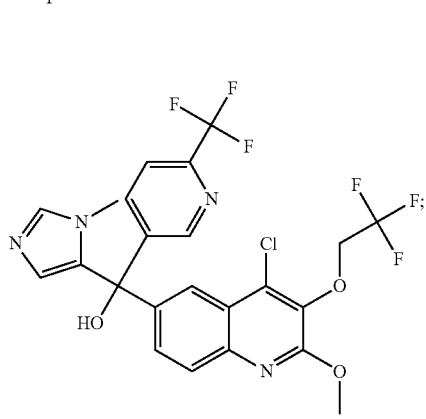
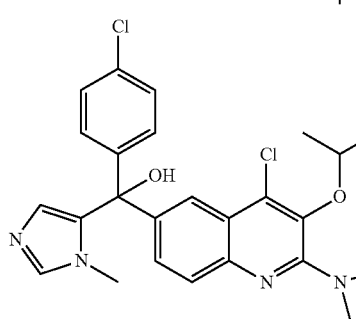
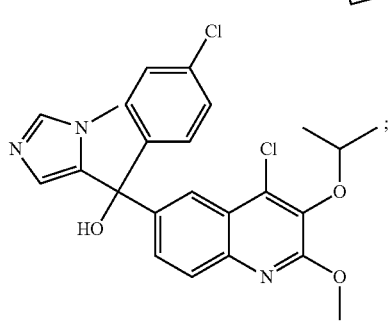

419
-continued
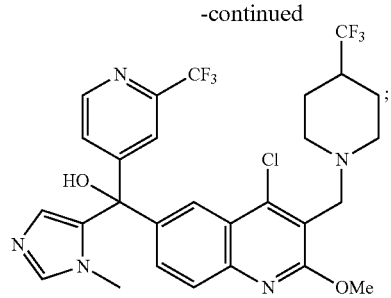
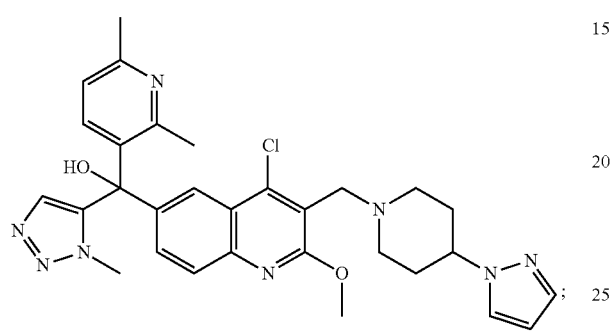
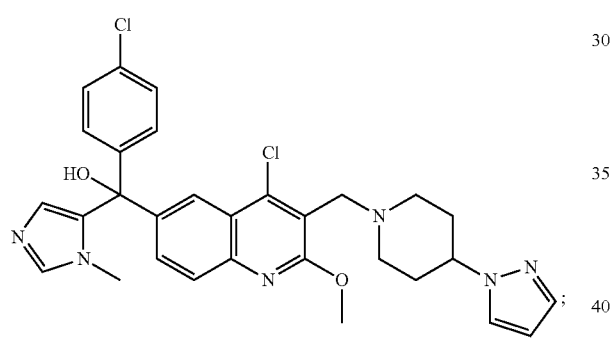
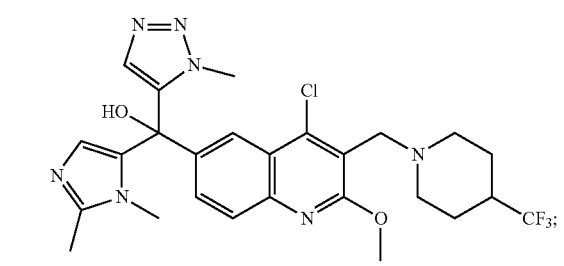
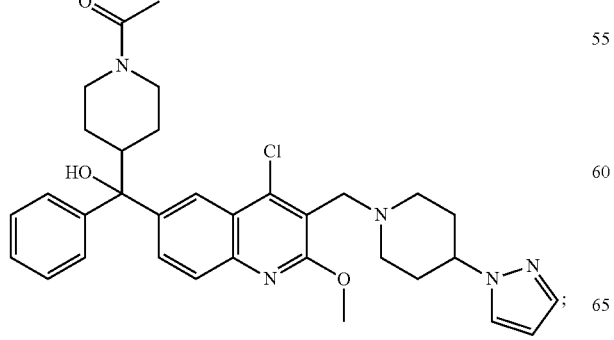
420
-continued
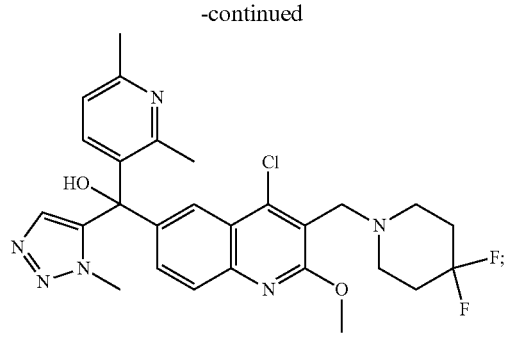
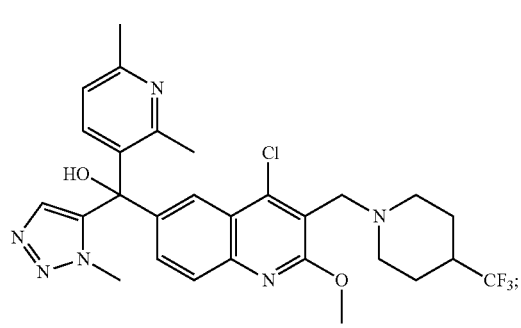
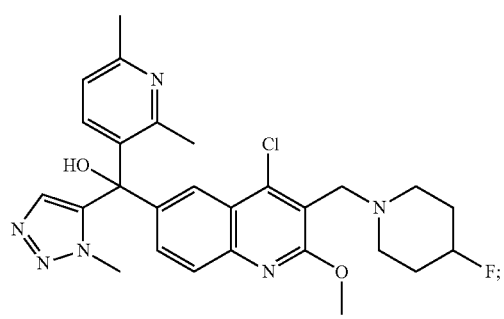
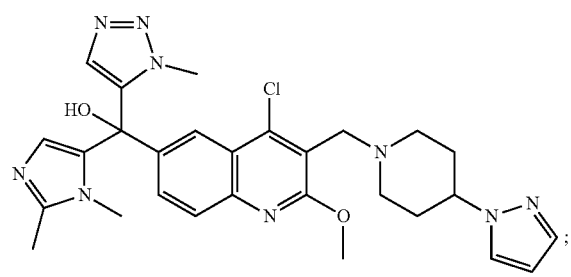
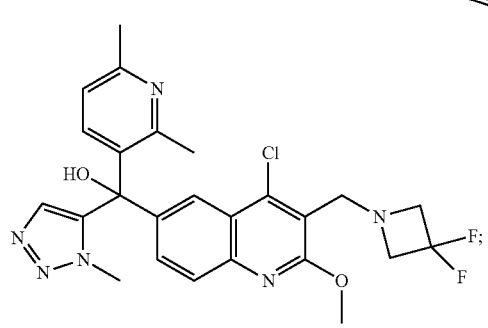

-continued
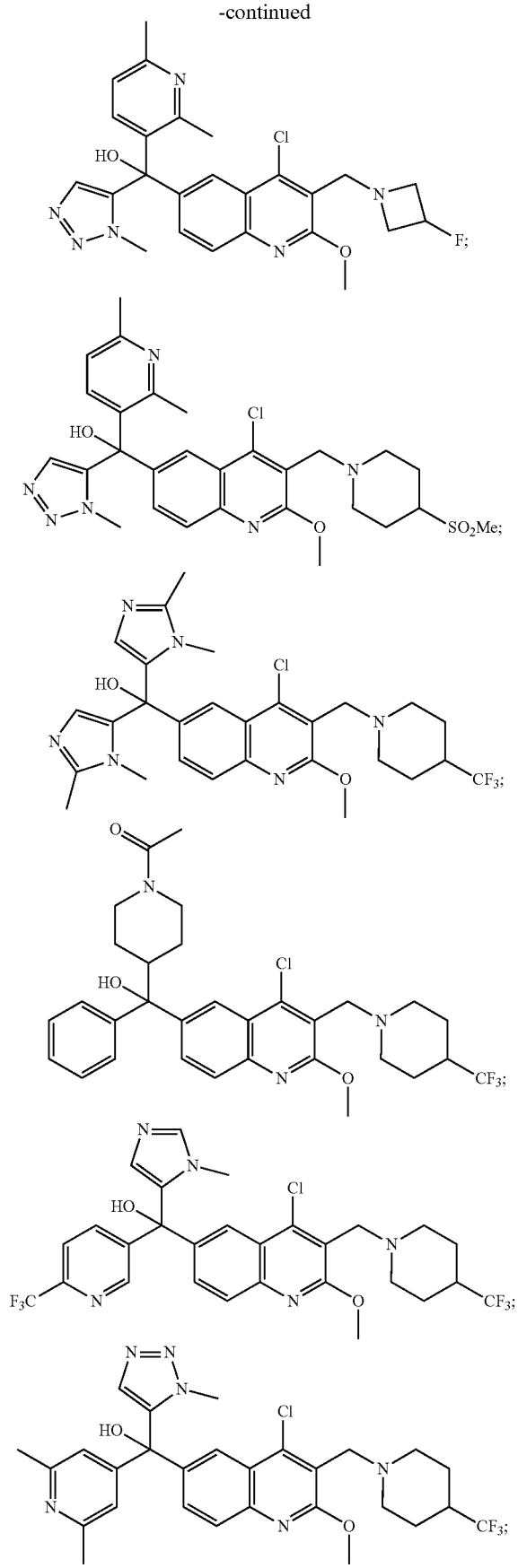
-continued
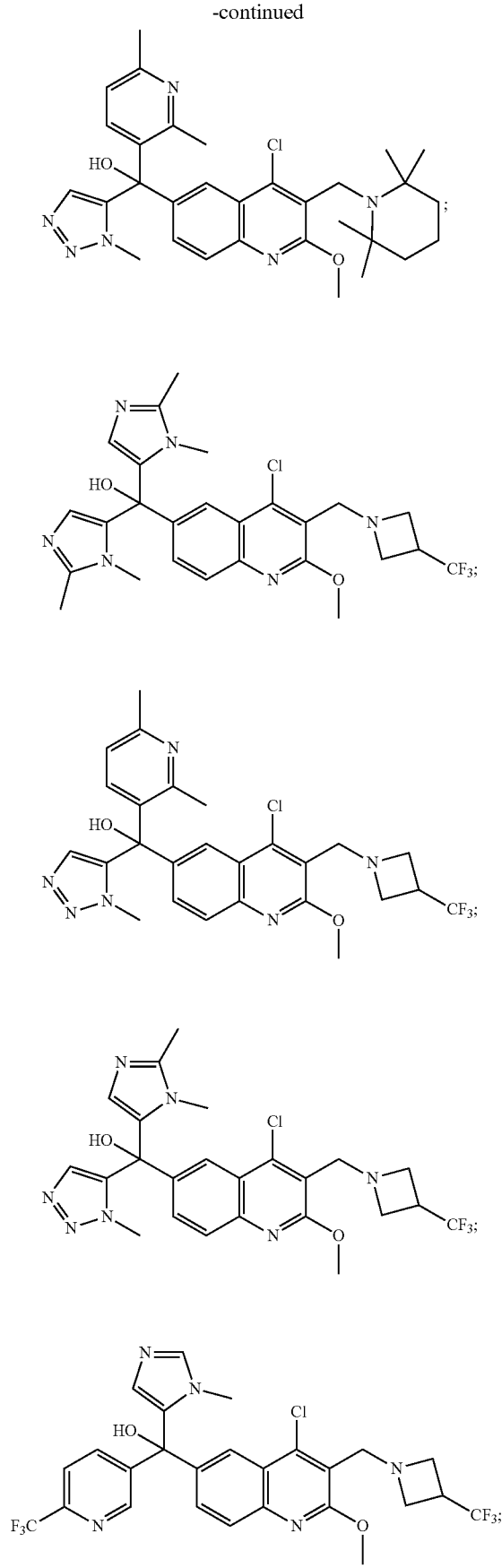

-continued
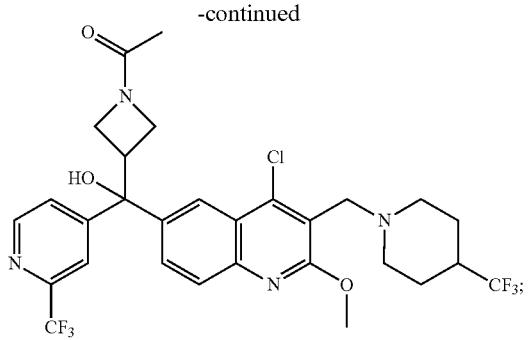
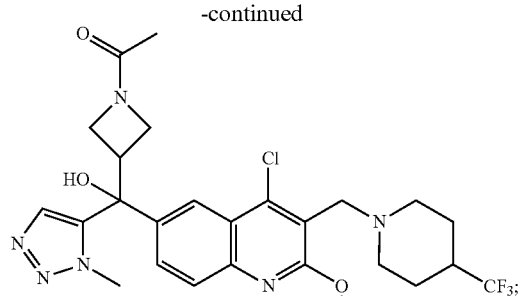
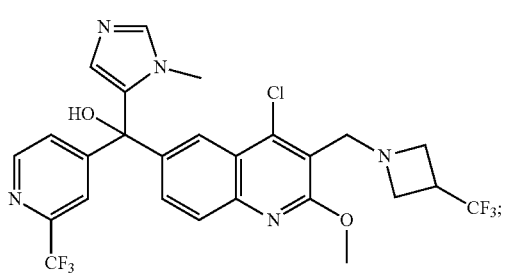
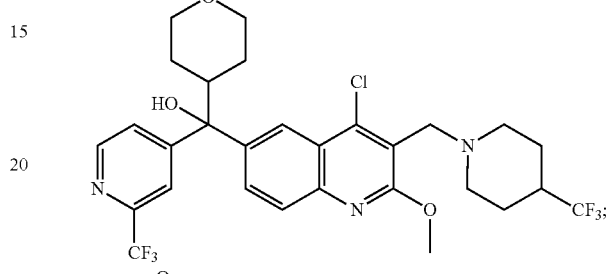
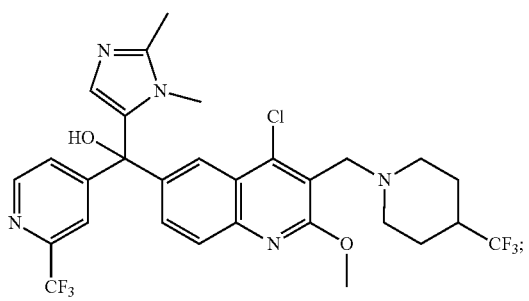
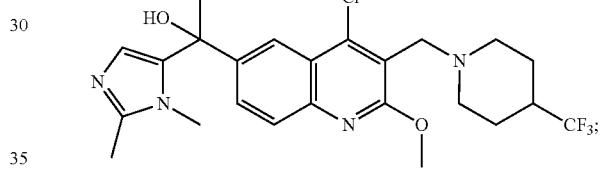
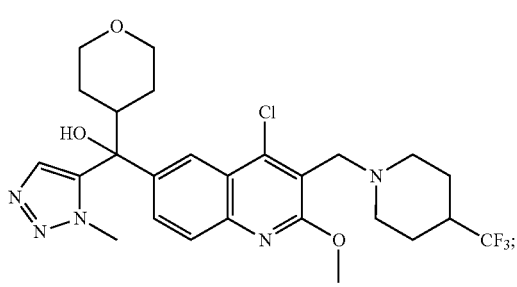
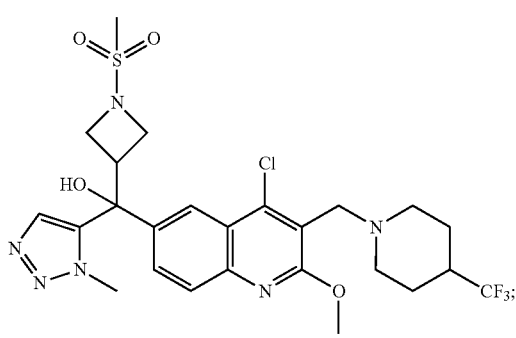
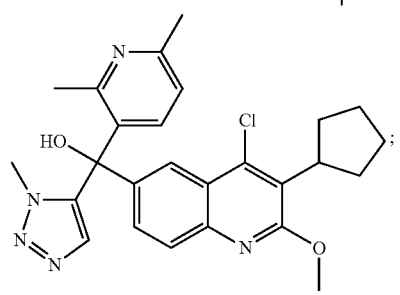

425
-continued
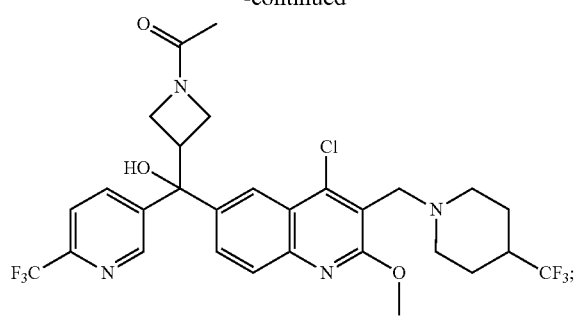
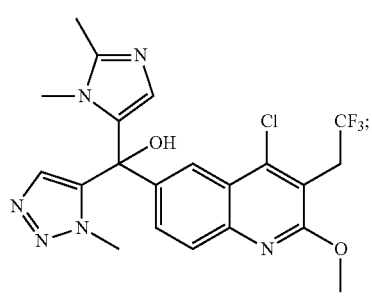
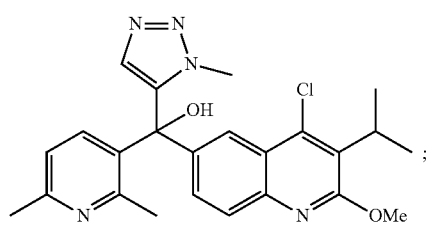
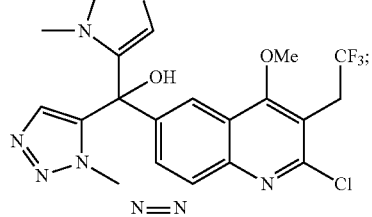
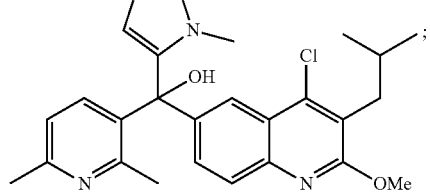
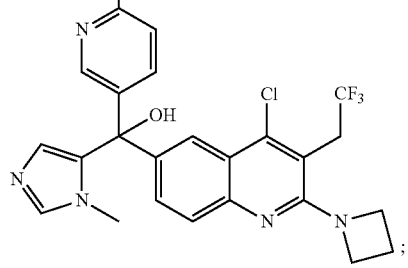
426
-continued
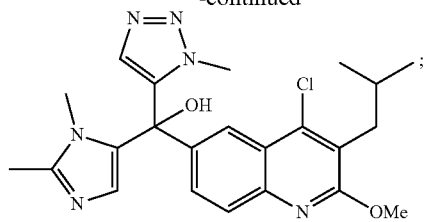
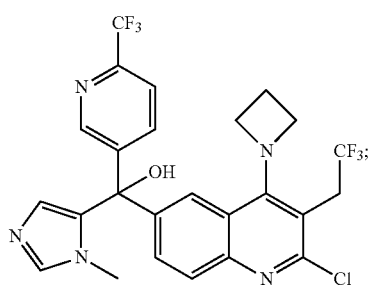
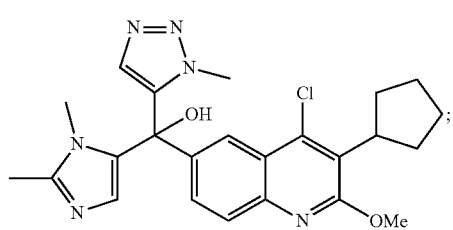
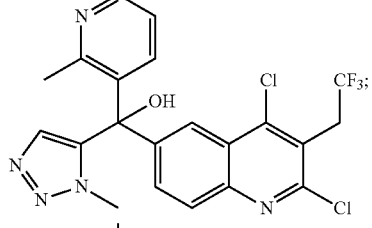
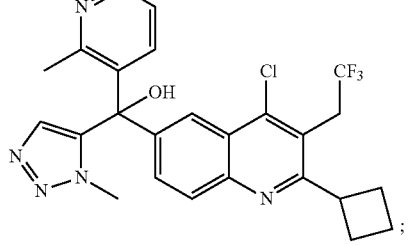
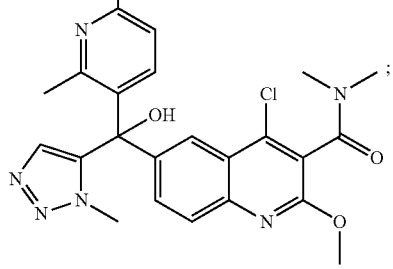

427
-continued
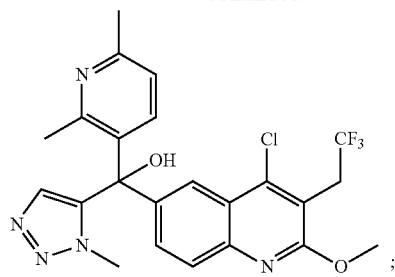
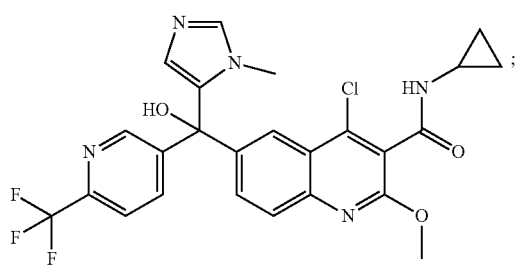
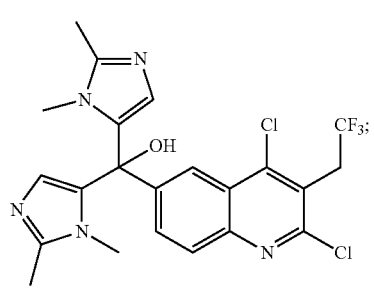
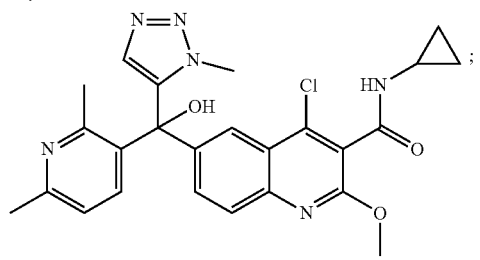
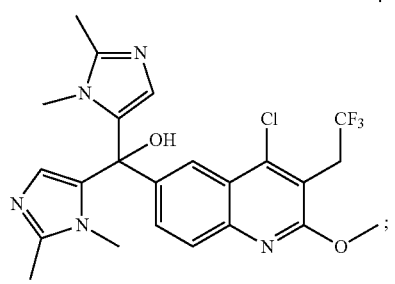
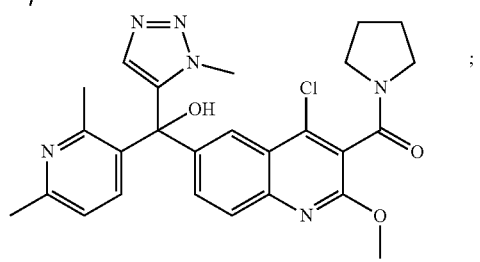
428
-continued
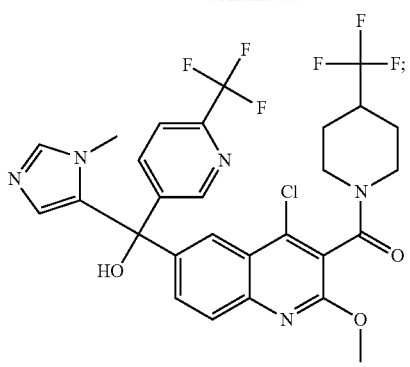
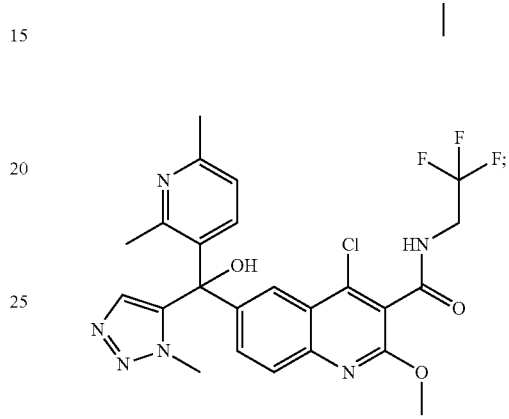
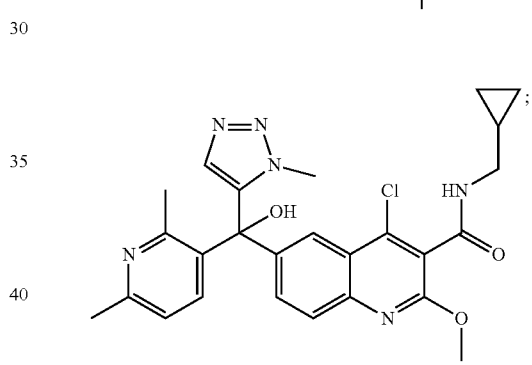
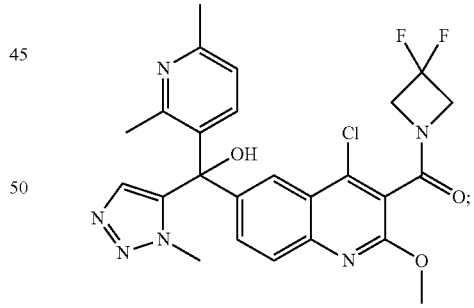
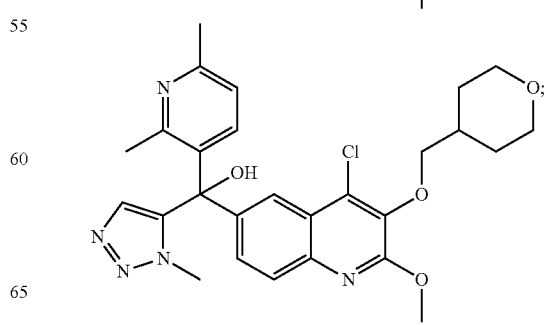

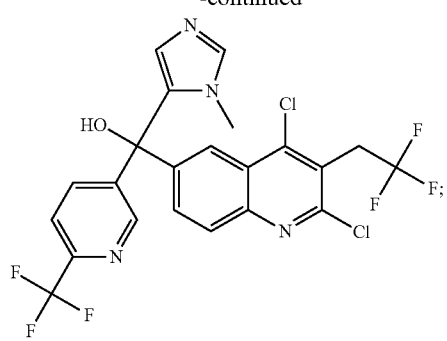
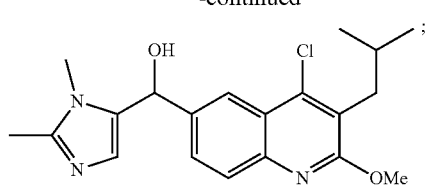
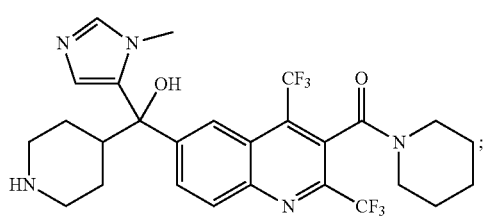
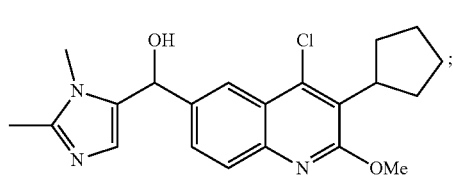
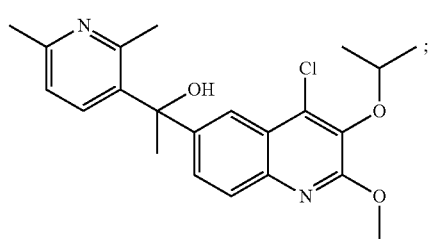
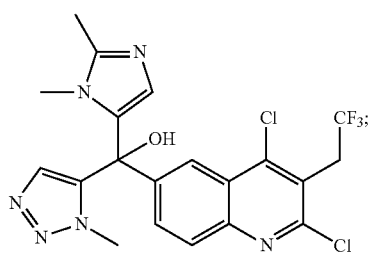
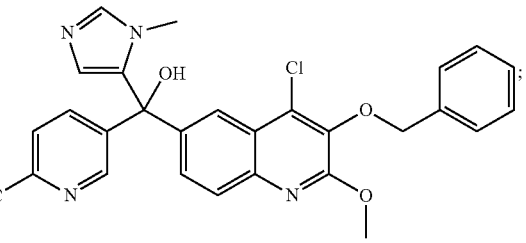
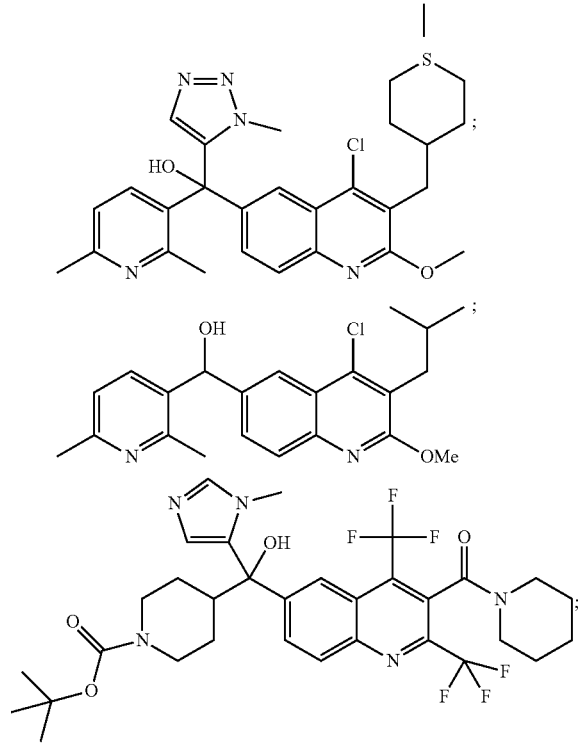

431
-continued
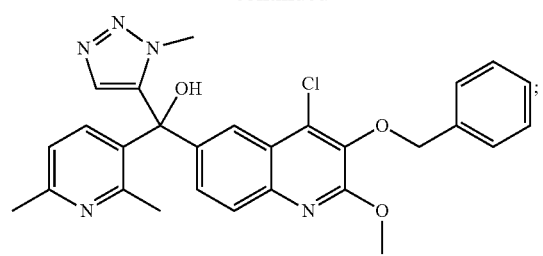
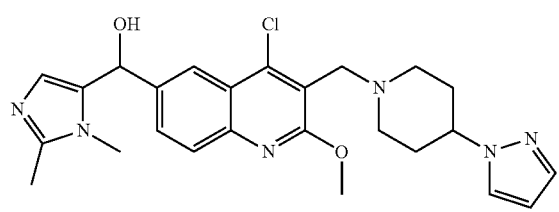
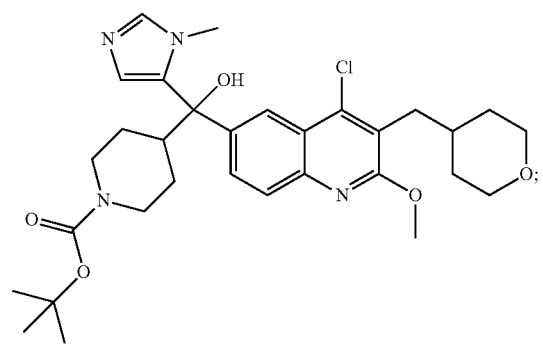
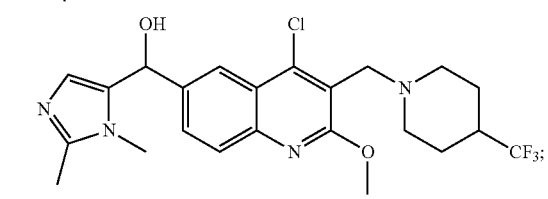
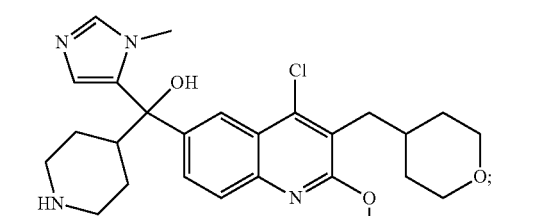
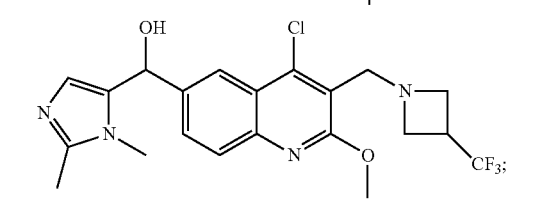
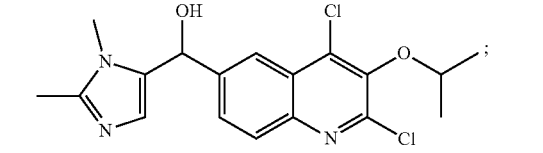
432
-continued
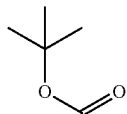
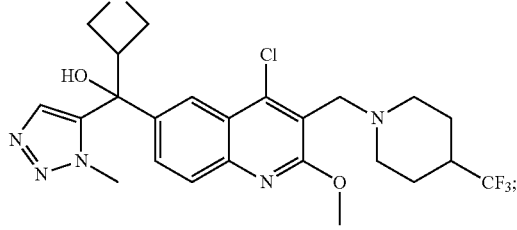
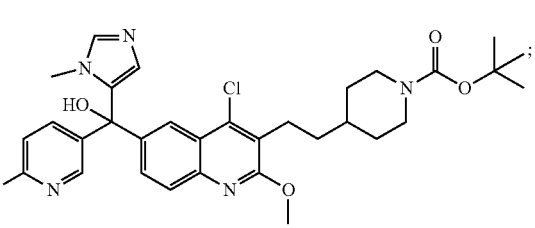
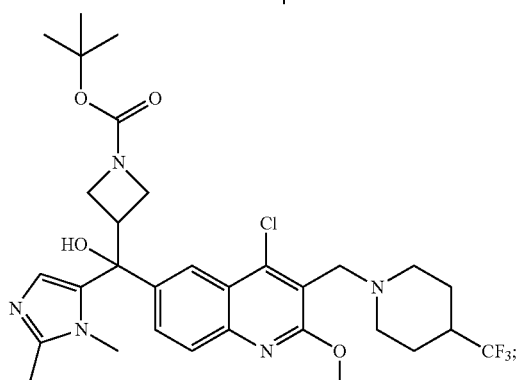
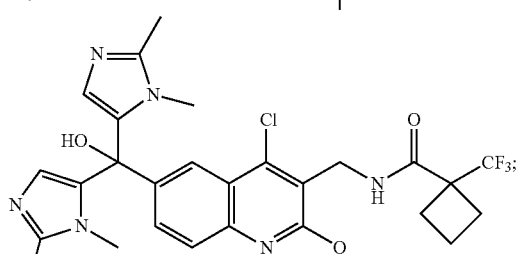
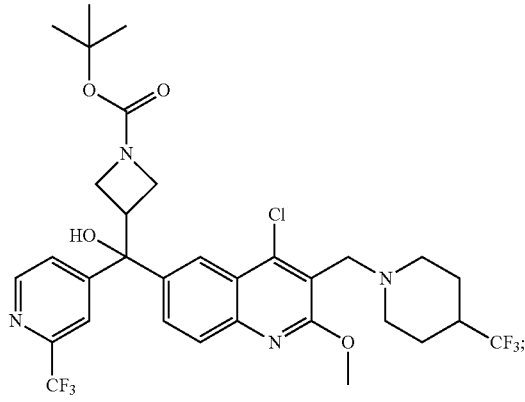

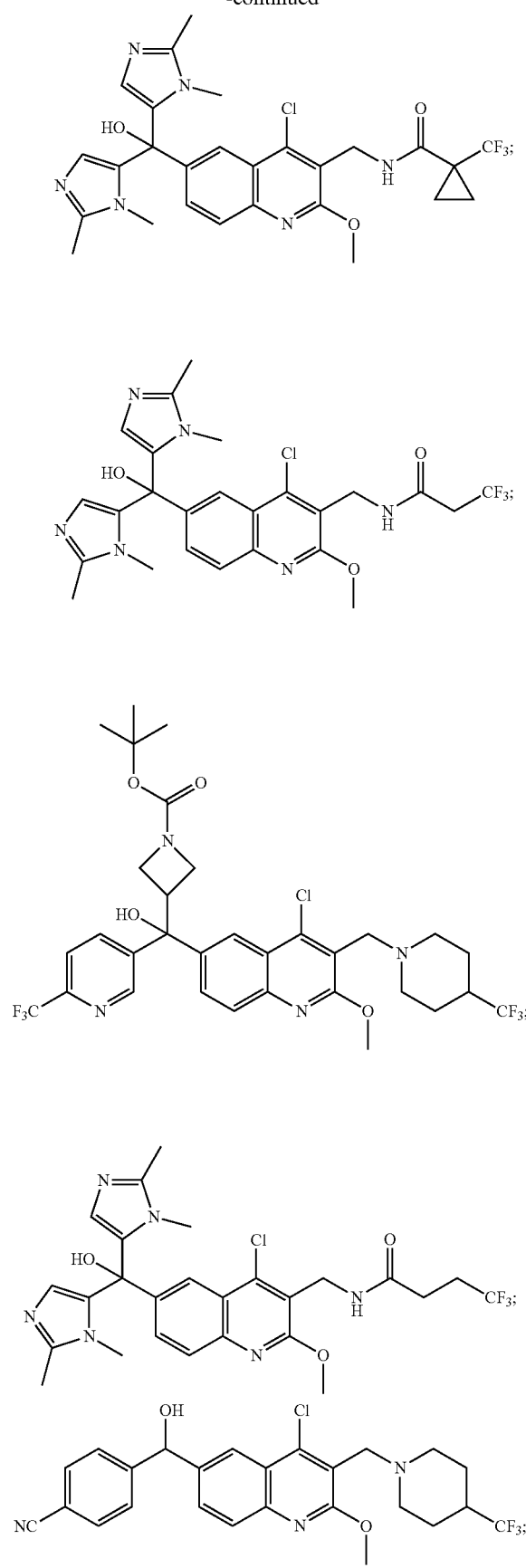
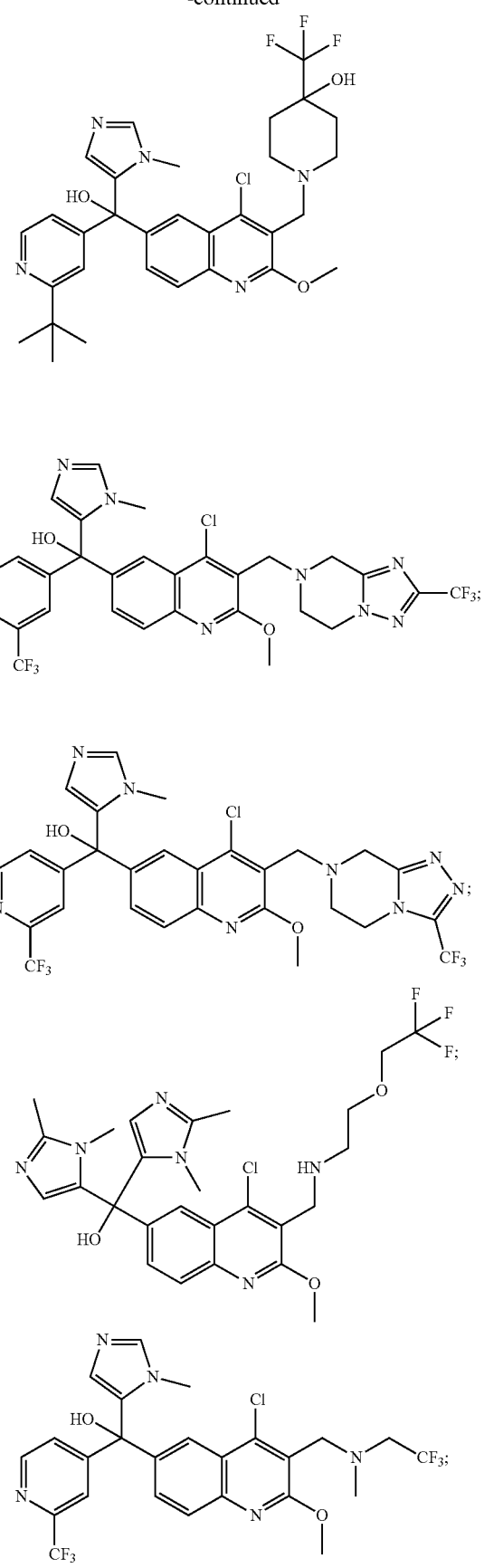

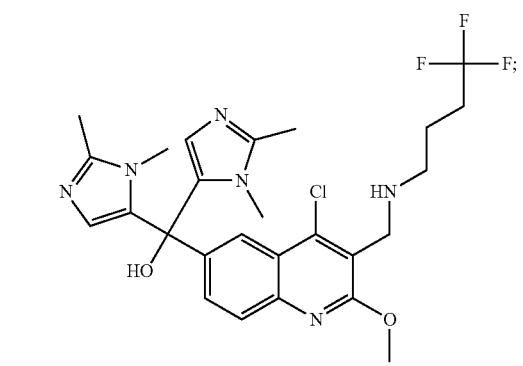
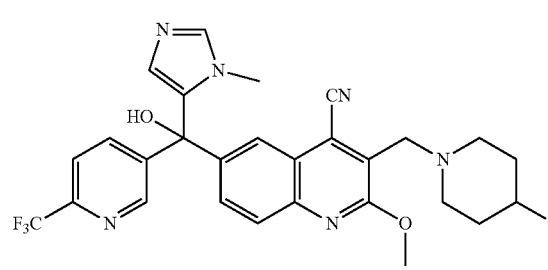
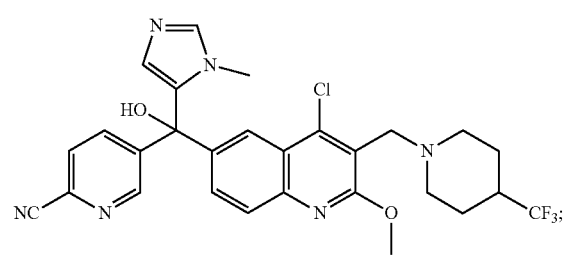
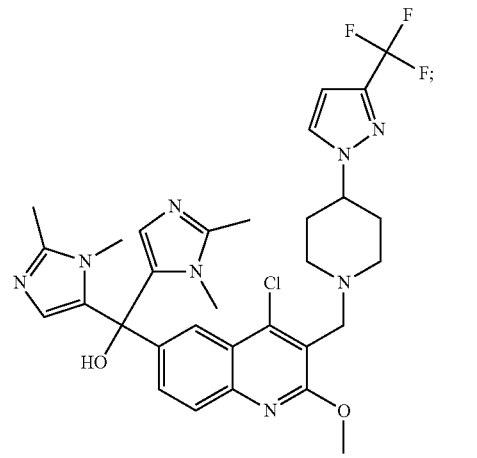
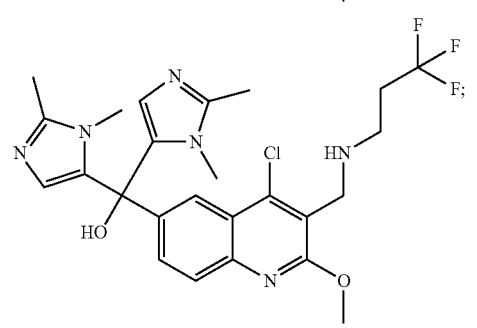
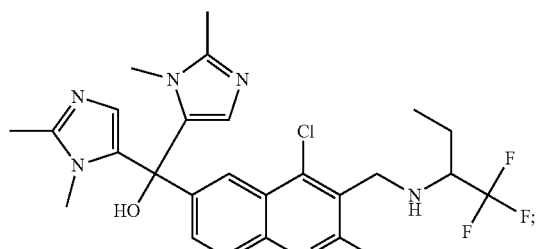
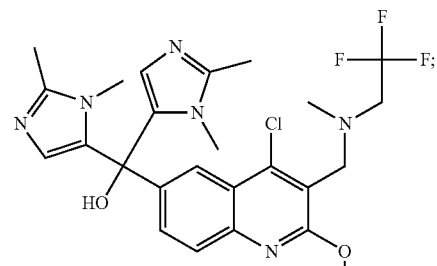
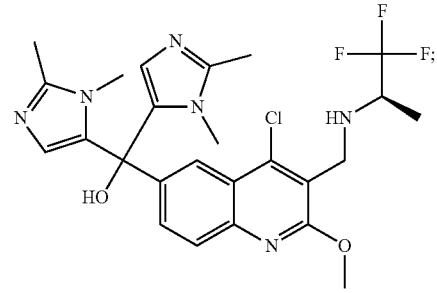
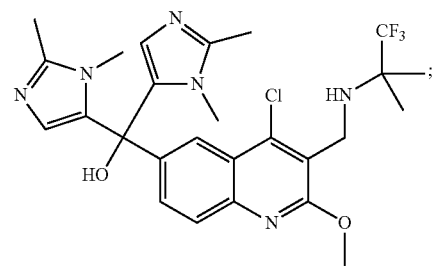
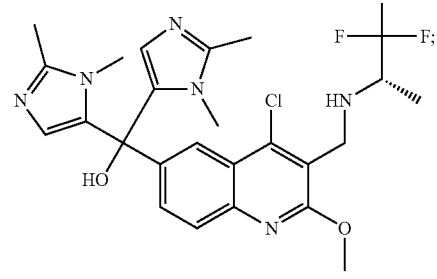
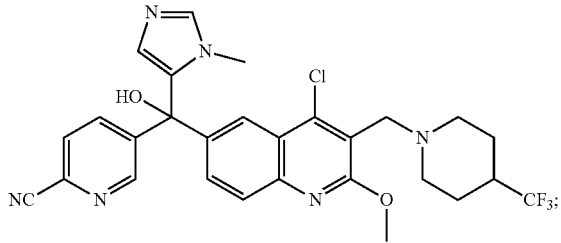

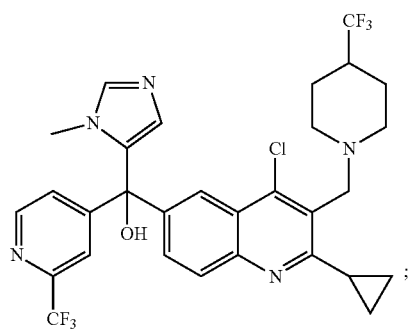
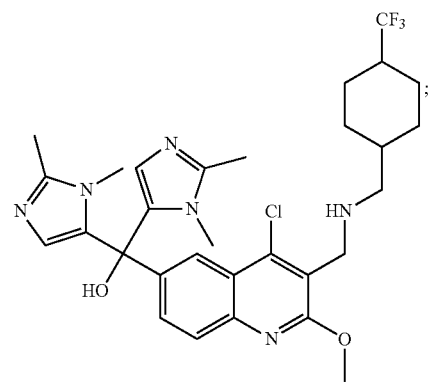
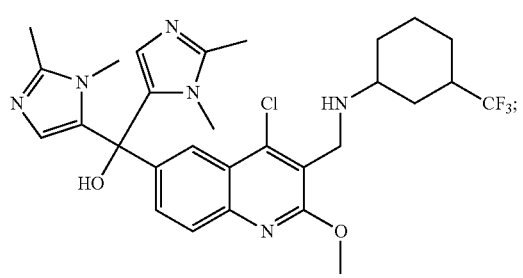
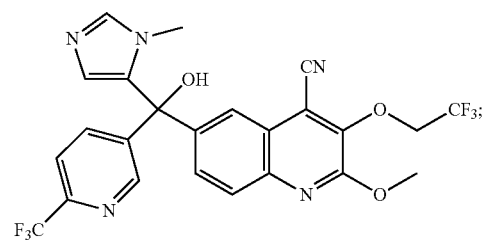
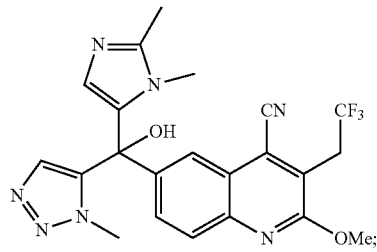
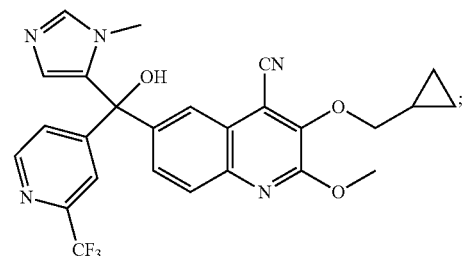
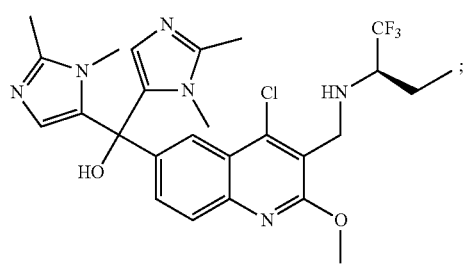
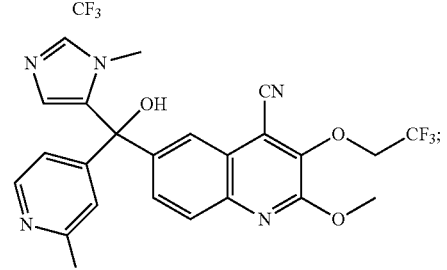
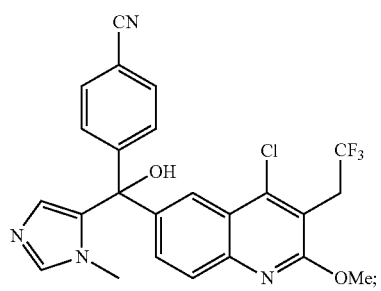
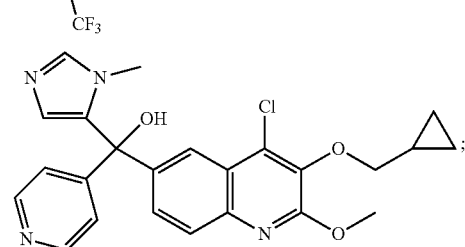
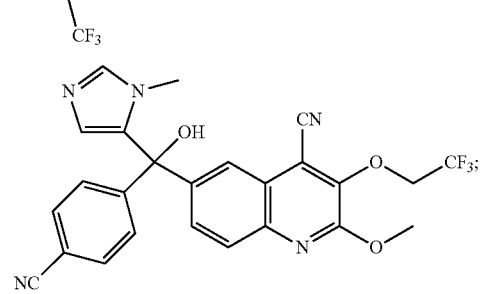

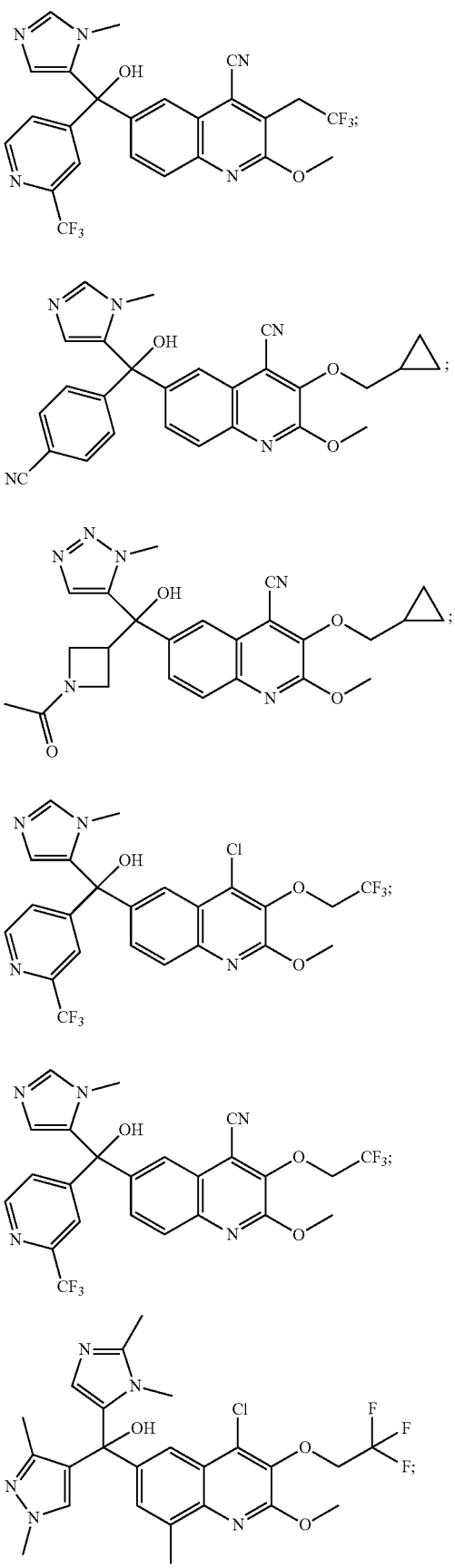
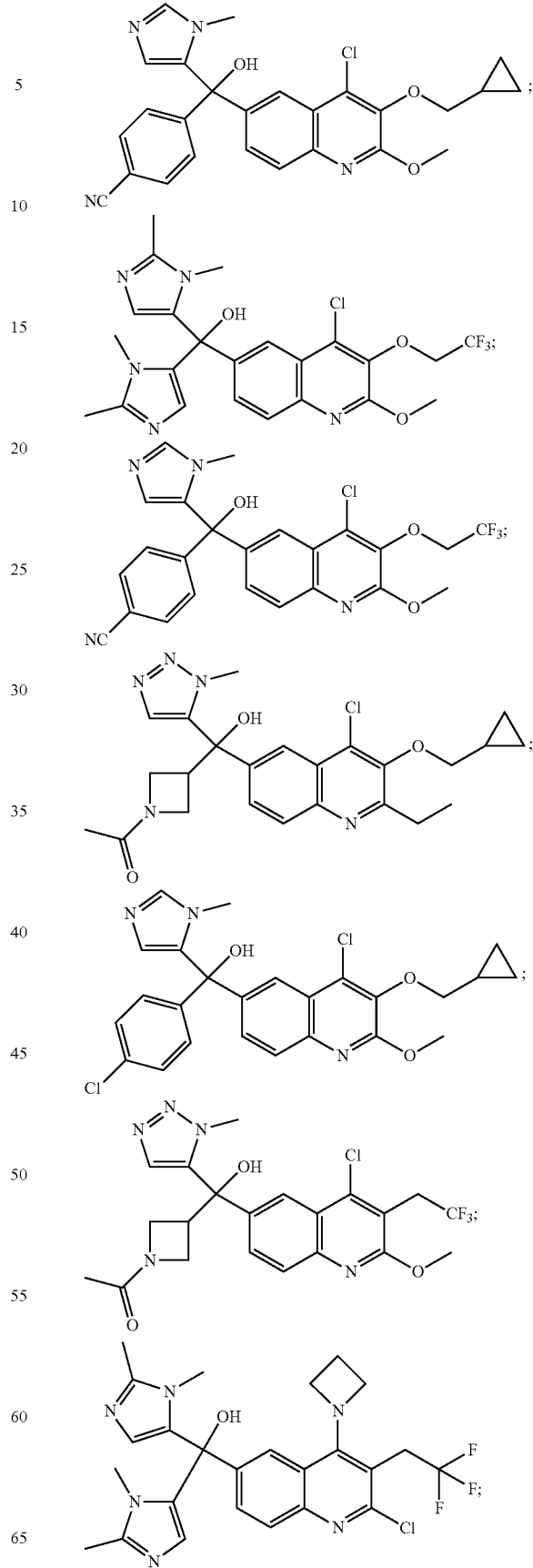

-continued

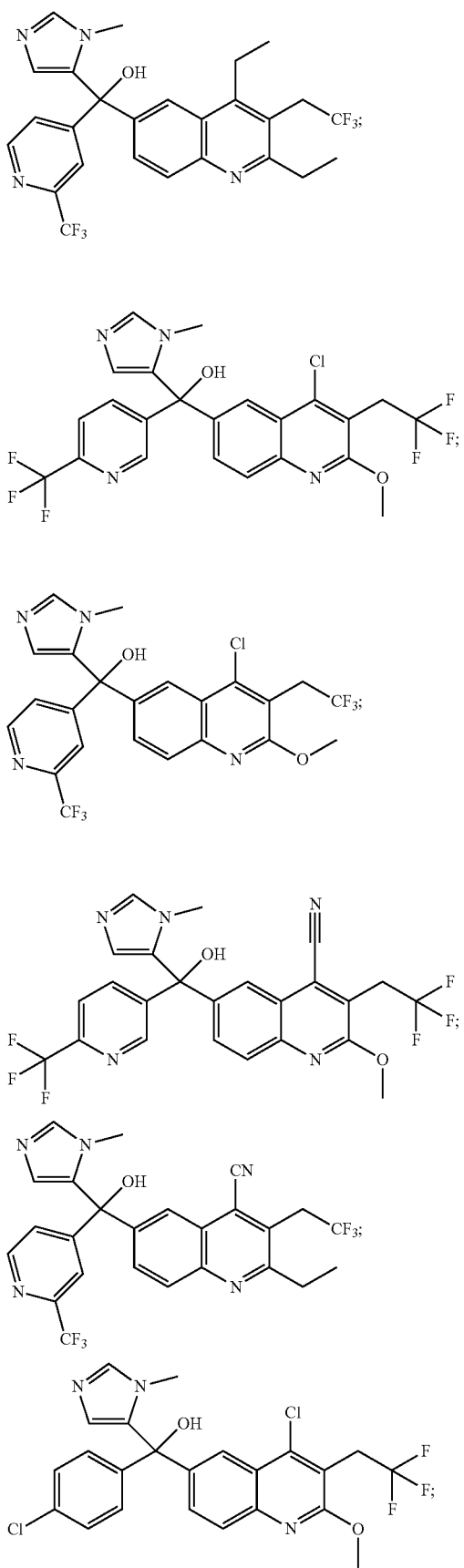

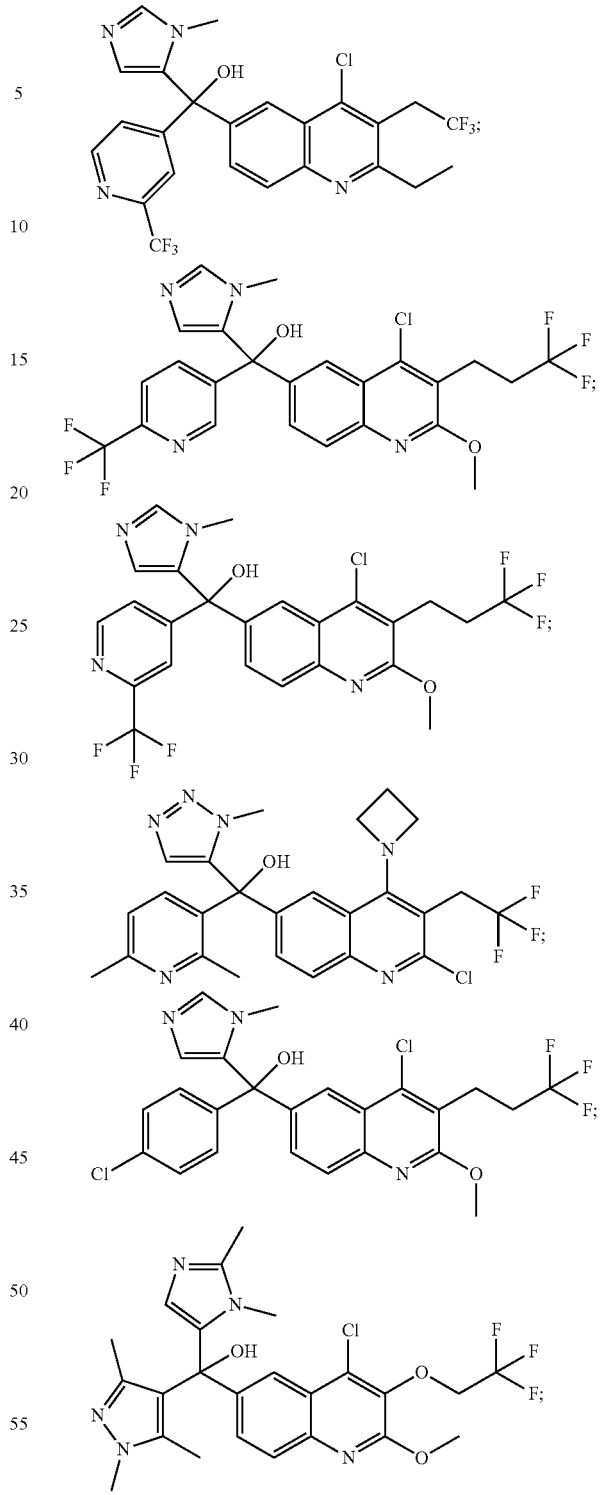

and pharmaceutically acceptable salts thereof.

4. A method of claim 1, wherein in the compound:

R[1] is imidazolyl, triazolyl, tetrahydropyranyl, thiazolyl, pyridyl, or phenyl; wherein said pyridyl, imidazolyl, and phenyl are optionally substituted with one substituent selected from the group consisting of $CH_3$, $CF_3$, Cl, and —CN; and optionally substituted with up to one additional CH₃; and wherein said triazolyl, and thiazolyl are optionally substituted with one or two CH₃ groups;

$R^2$ is 1-methyl-1,2,3-triazol-5-yl, pyrid-3-yl, 2-trifluoromethyl-pyrid-4-yl, 1,3,5-trimethyl-pyrazol-4-yl, N-acetyl-azetidin-3-yl, N-methylsulfonyl-azetidin-3-yl, N-Boc-azetidin-3-yl, N-acetyl-piperidin-4-yl, N-methylsulfonyl-piperidin-4-yl, N-Boc-piperidin-4-yl, 1-H-piperidin-4-yl, 1,2-dimethyl-imidazol-5-yl, or 1-methyl-imidazol-5-yl;

$R^3$ is OH;

$R^4$ is H;

$R^5$ is Cl, —CN, CF₃, $C_{(1-2)}$alkyl, OCH₃, azetidin-1-yl, or fur-2-yl;

$R^6$ is $C_{(1-4)}$alkylene-Q, $OC_{(1-4)}$alkylene-Q, $C(O)NA^3A^4$, $C(O)OC_{(1-4)}$alkyl, O-tetrahydropyranyl, —O—(N-methyl)piperidinyl, cyclopentyl, cyclohexyl, 1-methyl-1,2,3,6-tetrahydropyridin-4-yl, or tetrahydropyran-4-yl; provided that $R^6$ is not CH₂-phenyl, CH₂-pyridinyl, nor CH₂-pyrimidinyl;

Q is H, CF₃, OH, SO₂CH₃, $NA^3A^4$, $OC_{(1-4)}$alkyl, cyclopropyl, 1-methyl-cyclopropyl, oxetanyl, 3-methyl-oxetanyl, tetrahydrofuranyl, 1,3-dimethyl-pyrazol-5-yl, 3,5-dimethyl-isoxazol-4-yl, thiazol-2-yl, N-methyl-pyrrolidin-2-yl, cyclohexyl, N-acetyl-piperidin-4-yl, N-Boc-piperidin-4-yl, 1-H-piperidin-4-yl, tetrahydropyran-4-yl, 1,1-dioxo-tetrahydrothiopyran-4-yl, tetrahydrothiopyran-4-yl, phenyl, pyridin-3-yl, or pyrimidin-2-yl; wherein said cyclopropyl, and said cyclohexyl are optionally substituted with up to two fluorine atoms;

wherein $A^3$ is H, or CH₃;

$A^4$ is CH₃, CH₂-cyclopropyl, cyclopropyl, $C_{(1-3)}$alkylCF₃, CH₂CH₂OCH₂CF₃, $C(O)C_{(1-2)}$alkylCF₃,

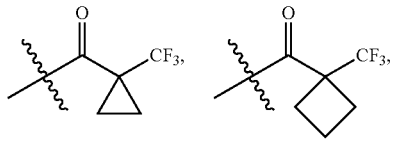 [SMILES: *C(=O)C1(C(F)(F)F)CC1 ; *C(=O)C1(C(F)(F)F)CCC1]

or $C_{(0-1)}$alkyl-trifluoromethyl-cyclohexyl, or $A^3$ and $A^4$ may be taken together with their attached nitrogen to form a ring selected from the group consisting of:

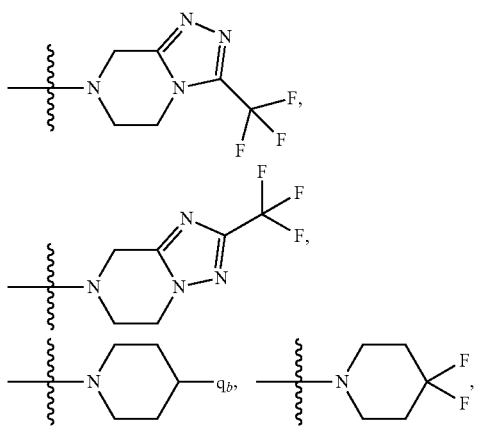

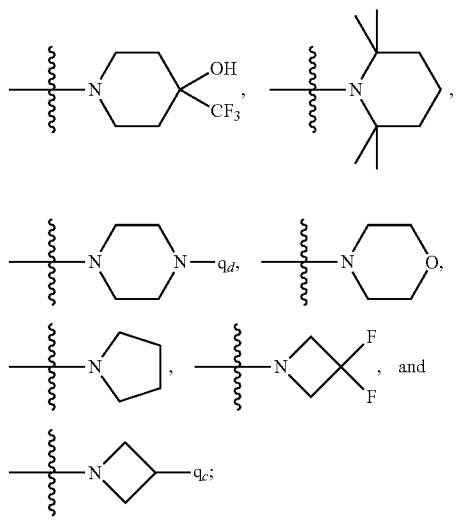

wherein $q_b$ is H, F, CF₃, SO₂CH₃, pyrazol-1-yl, or 3-trifluoromethyl-pyrazol-1-yl;

$q_c$ is H, F, or CF₃, $q_d$ is CH₂CF₃;

provided that if $R^6$ is OCH₂-Q, then Q may not be OH, nor $NA^3A^4$;

$R^7$ is Cl, CF₃, CH₂CH₃, cyclopropyl, OCH₃, pyrimidin-5-yl, thiophen-3-yl, 1-methyl-indazol-5-yl, 1-methyl-indazol-6-yl, fur-2-yl, azetidin-1-yl, phenyl, or

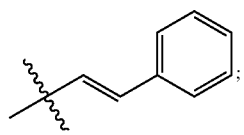 [SMILES: */C=C/c1ccccc1]

$A^1$ is $C_{(1-2)}$alkyl;

$A^2$ is $C_{(1-2)}$alkyl, CH₂CH₂OCH₃, or OCH₃; or $A^1$ and $A^2$ may be taken together with their attached nitrogen to form a ring which is:

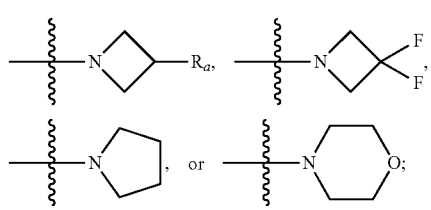

$R_a$ is H, OH, OCH₃, F;

$R^8$ is H or CH₃;

$R^9$ is H;

and pharmaceutically acceptable salts thereof.

5. A method of claim 4, wherein the compound is selected from the group consisting of:

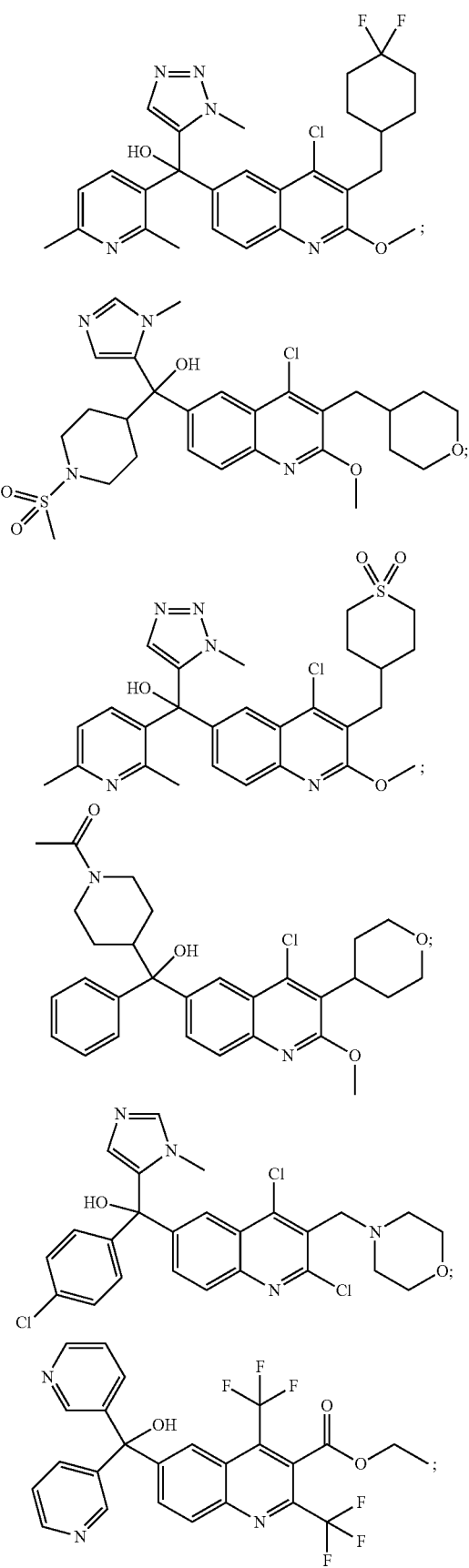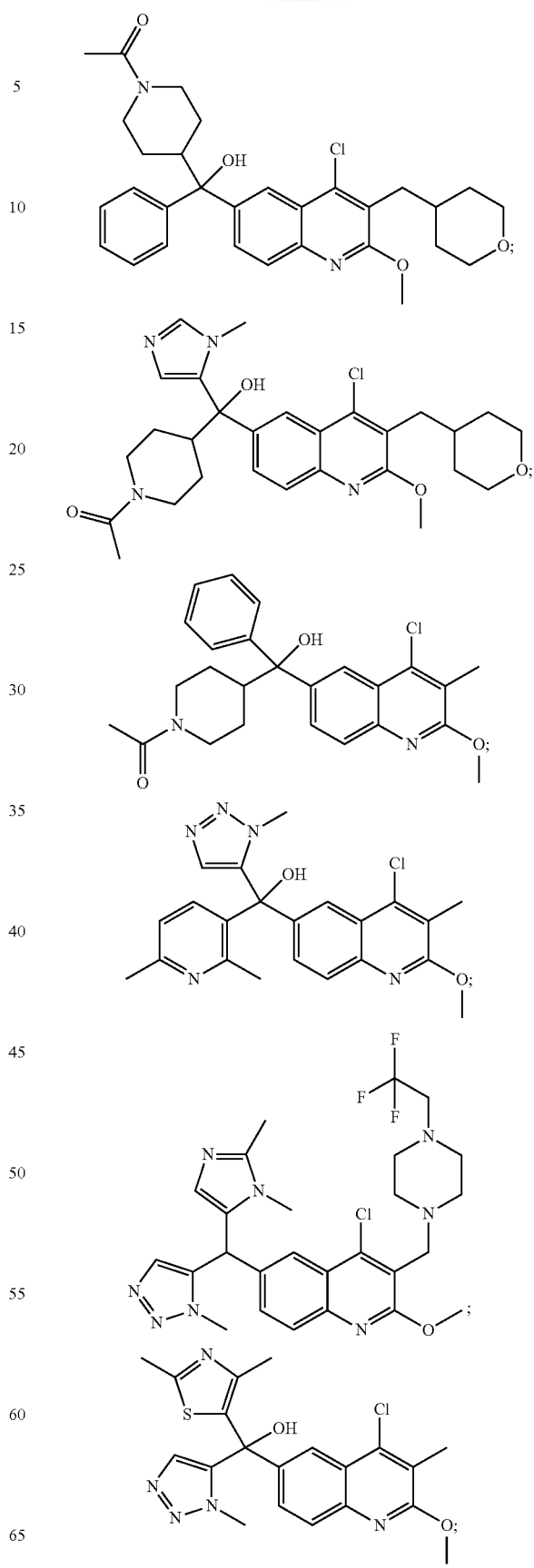

447
-continued
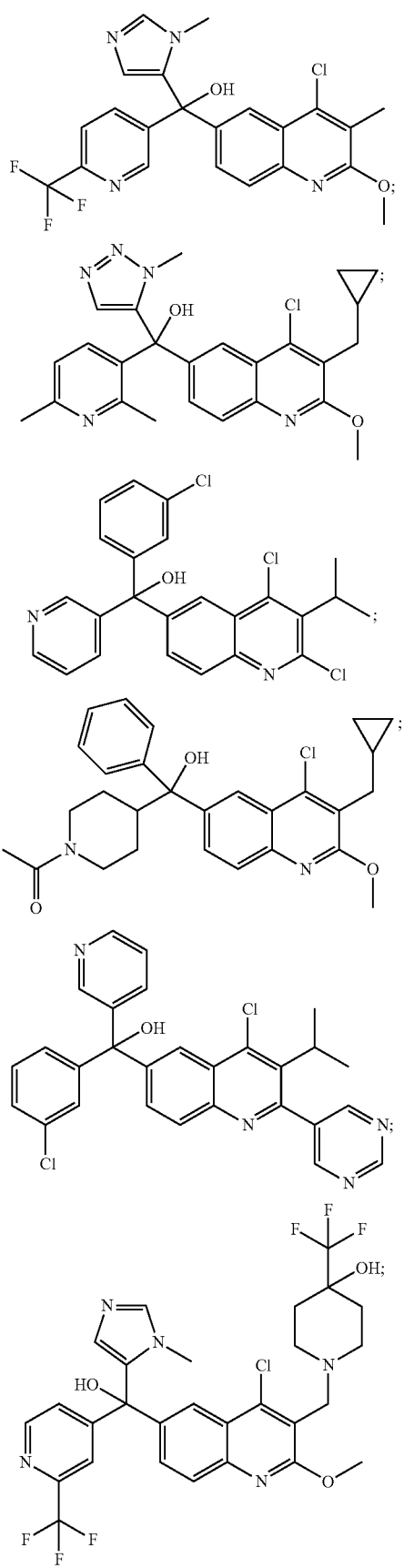
448
-continued
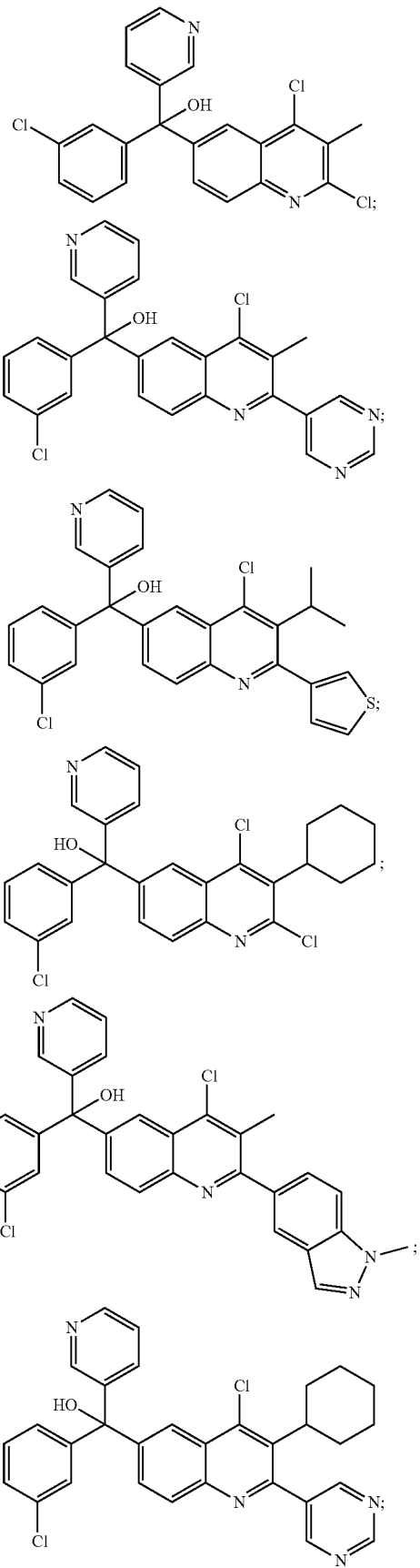

449
-continued
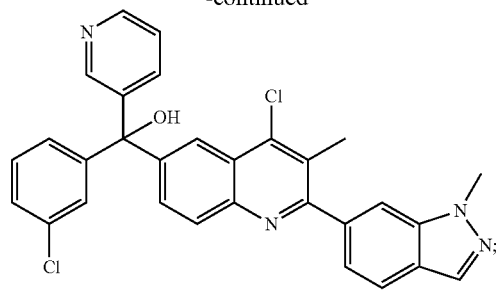
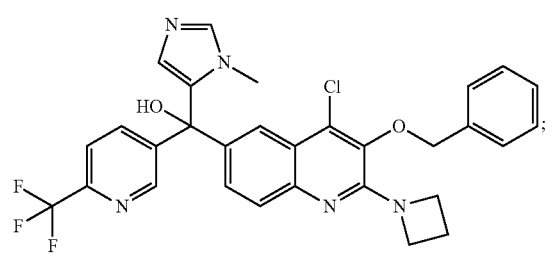
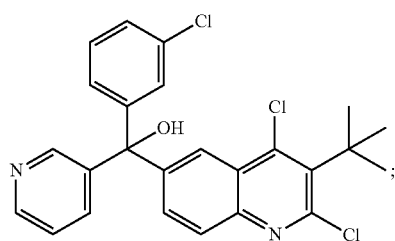
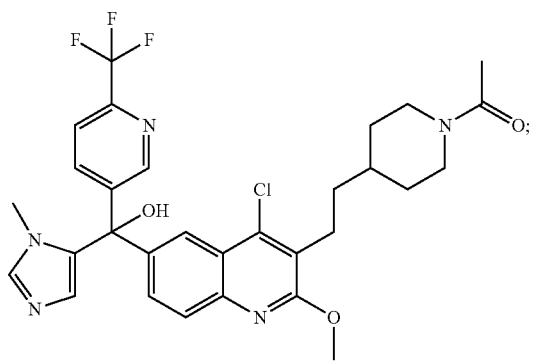
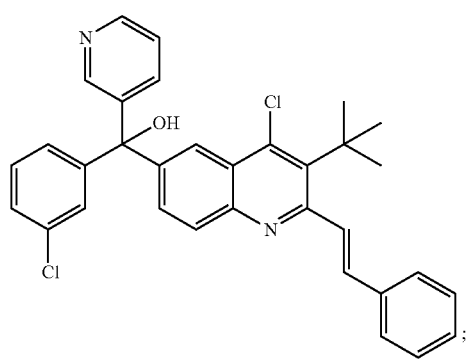
450
-continued
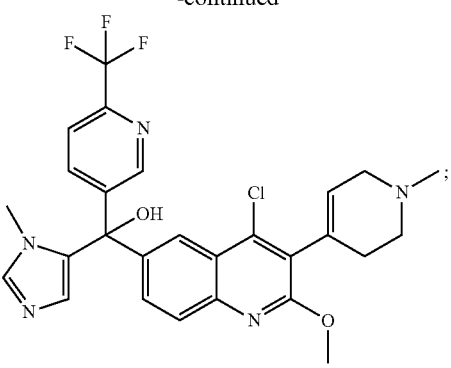
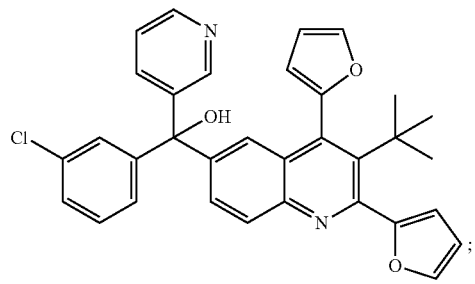
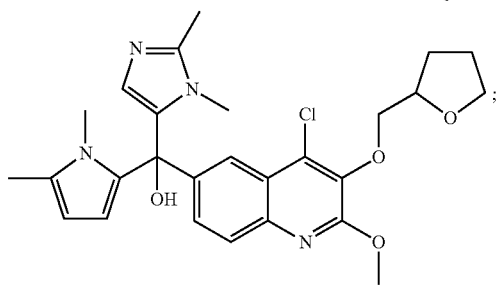
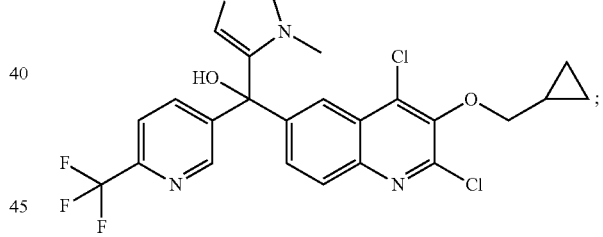
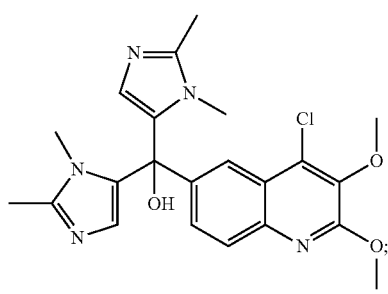
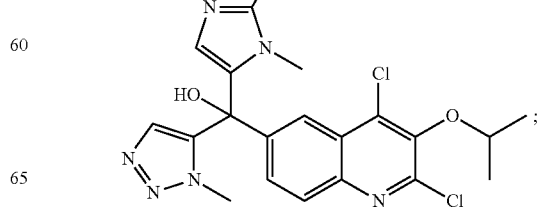

451
-continued
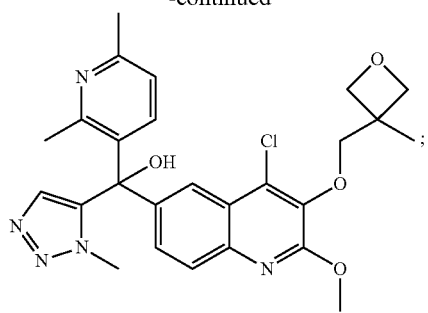
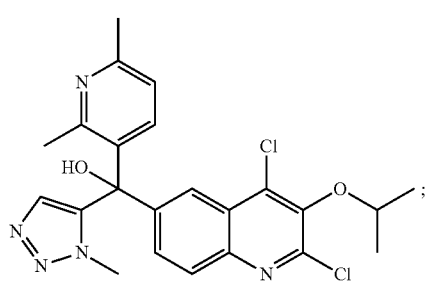
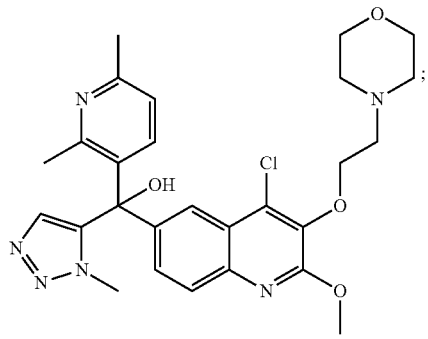
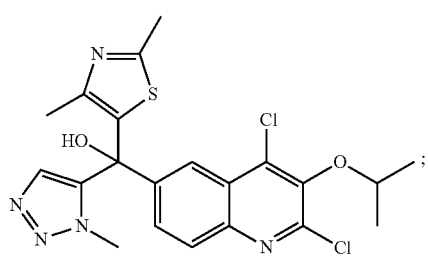
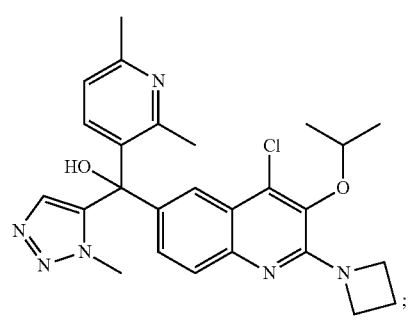
452
-continued
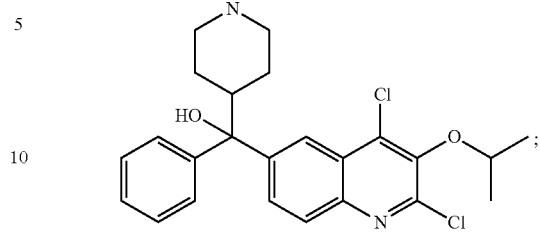
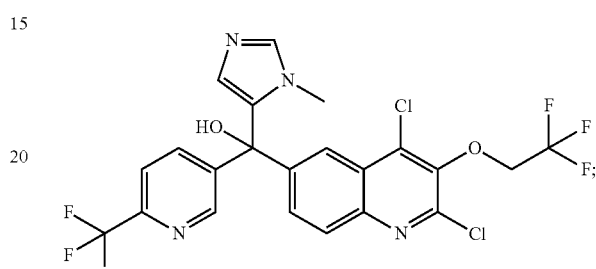
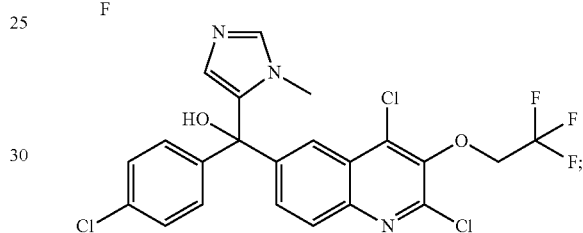
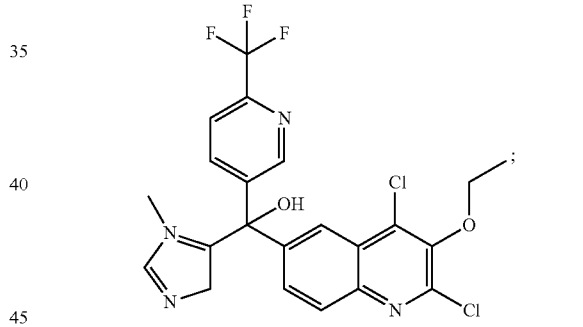
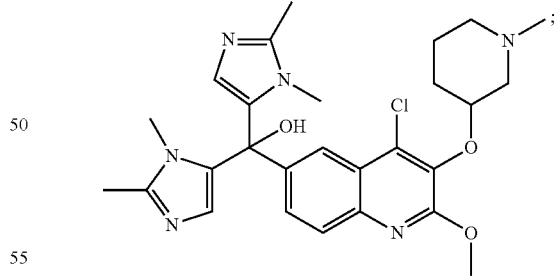
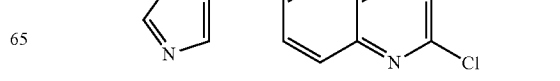

453
-continued
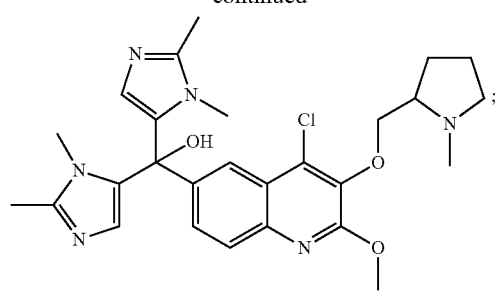
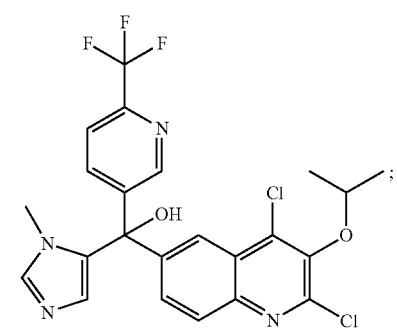
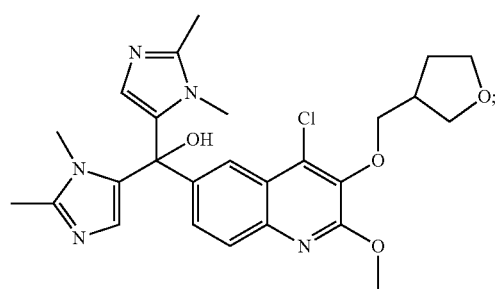
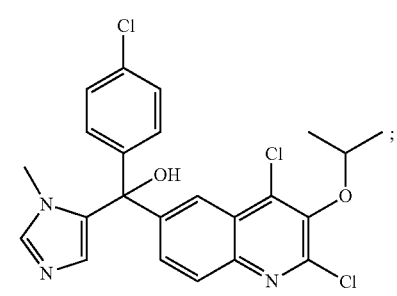
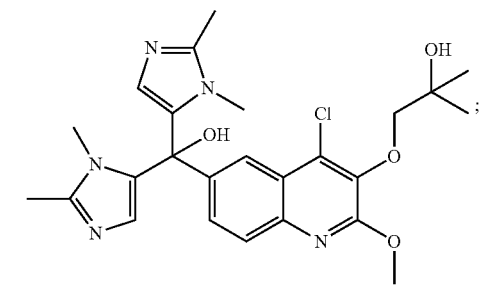
454
-continued
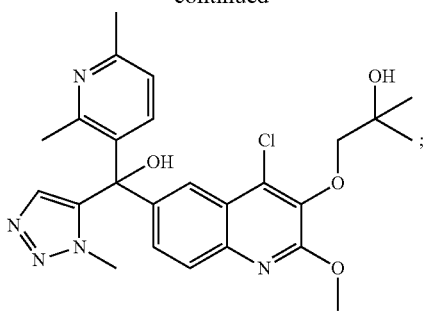
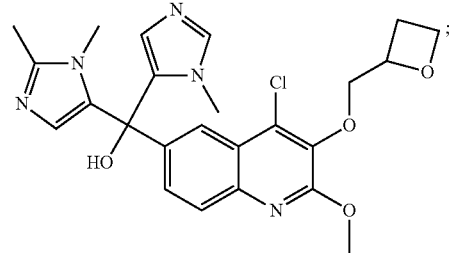
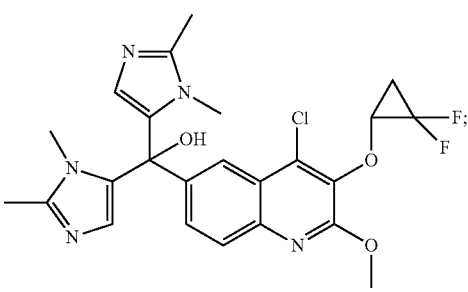
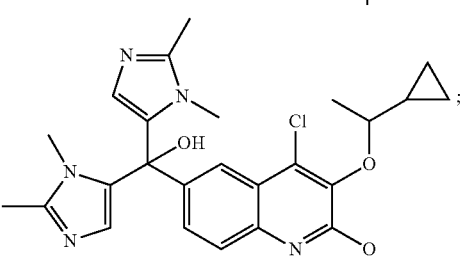
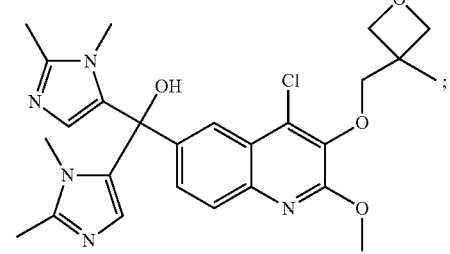
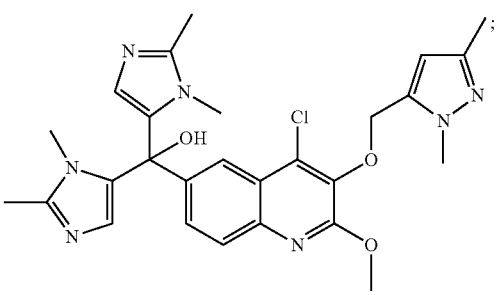

455
-continued
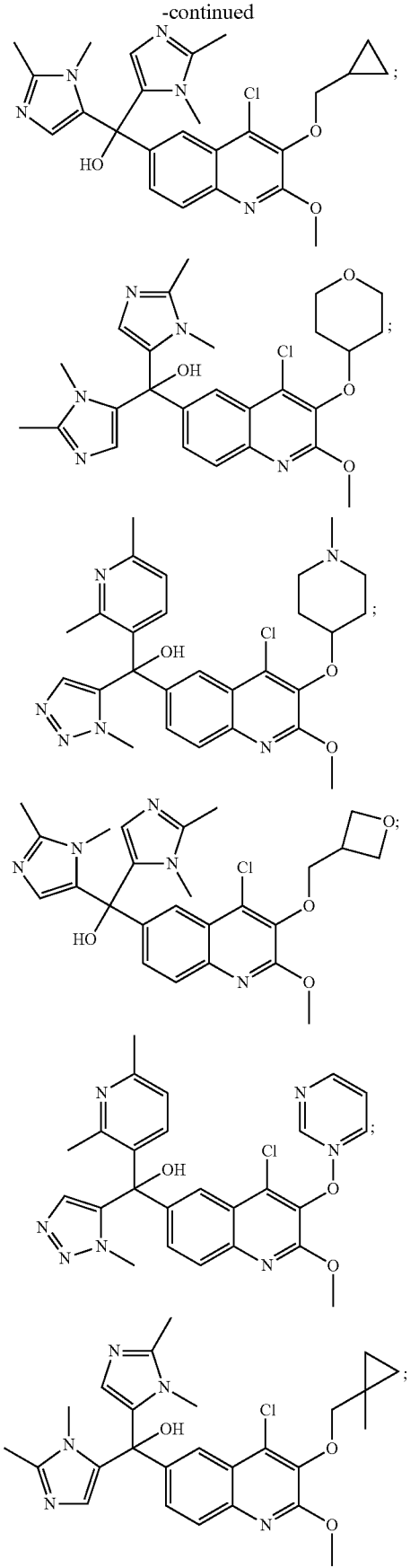
456
-continued
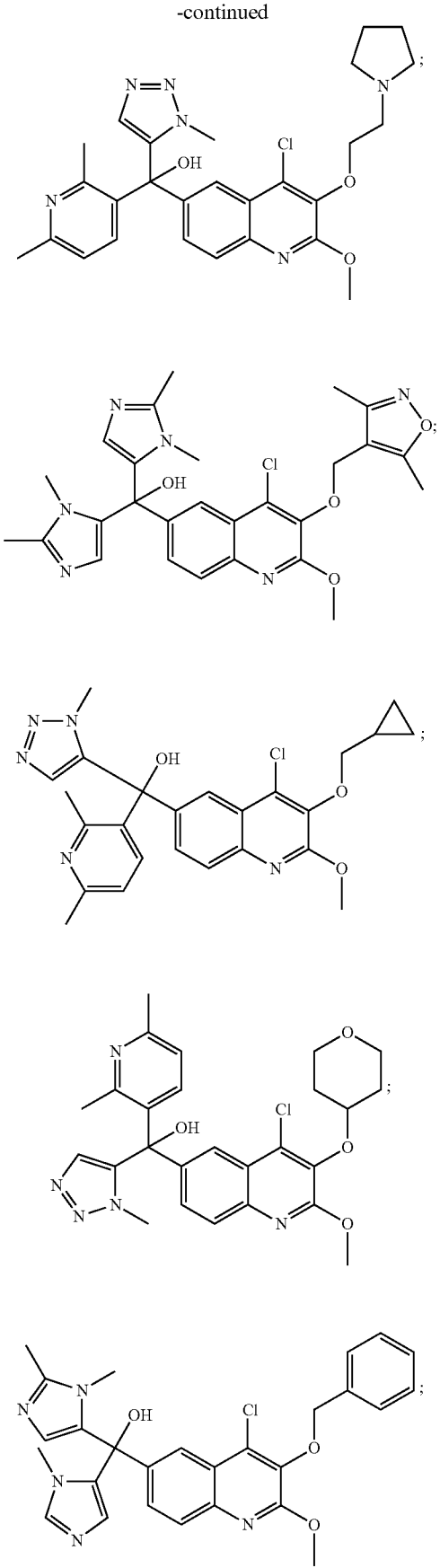

457
-continued
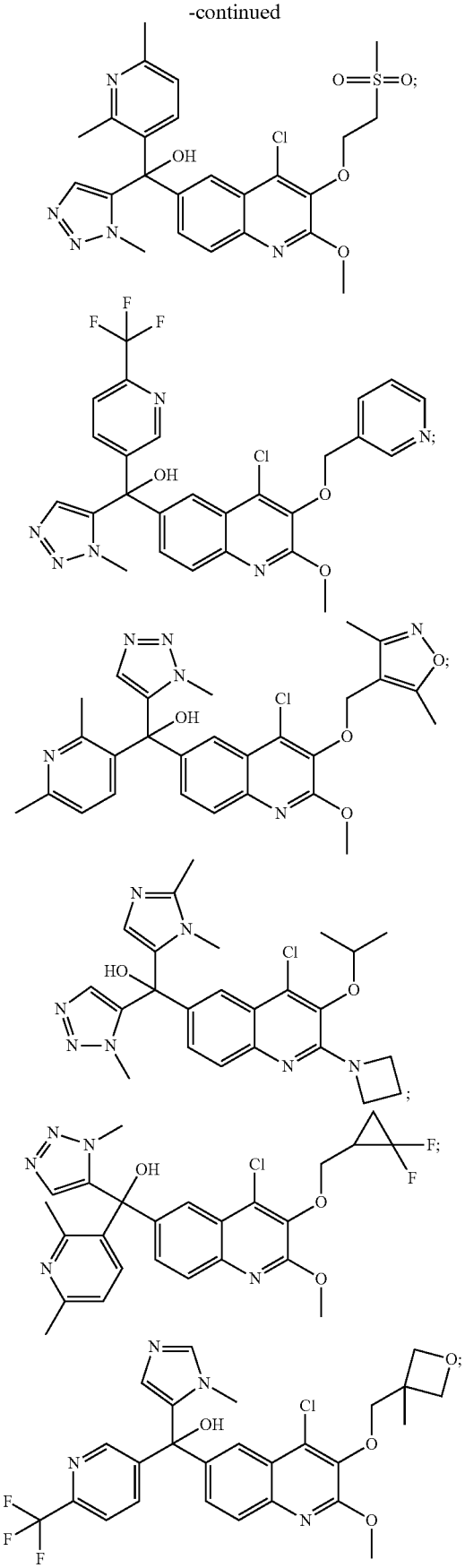
458
-continued
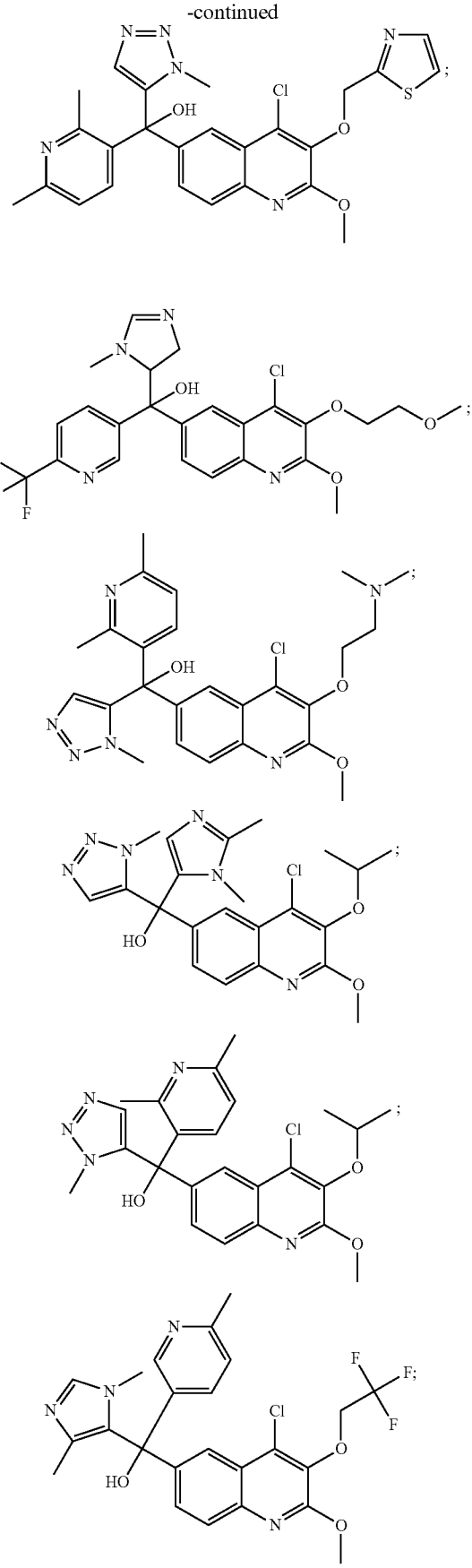

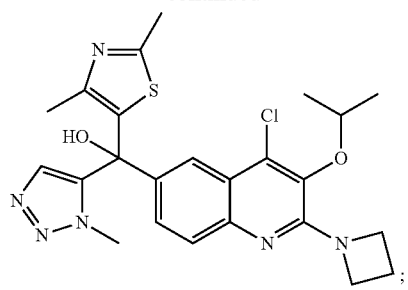
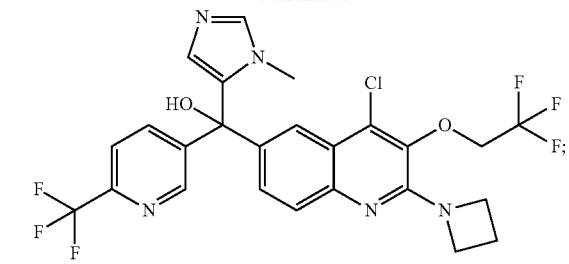
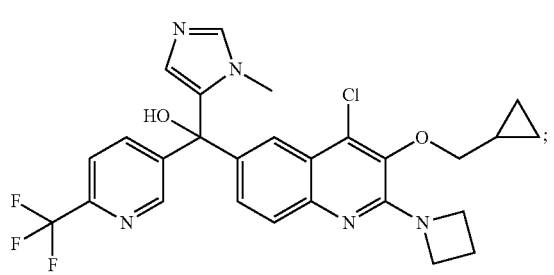
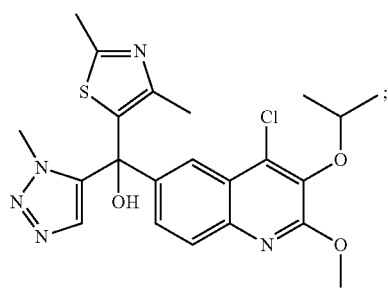
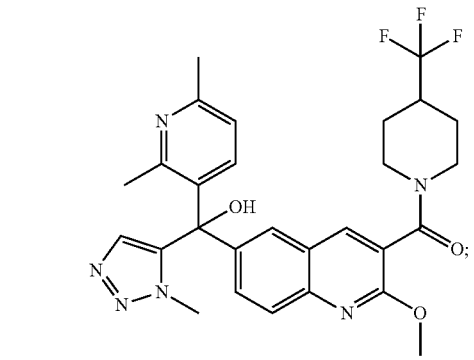
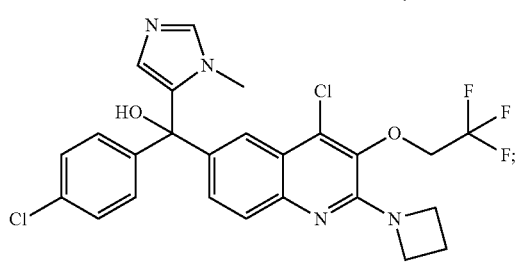
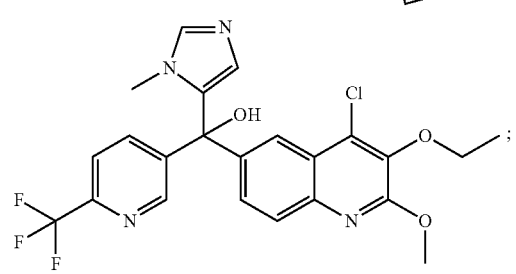
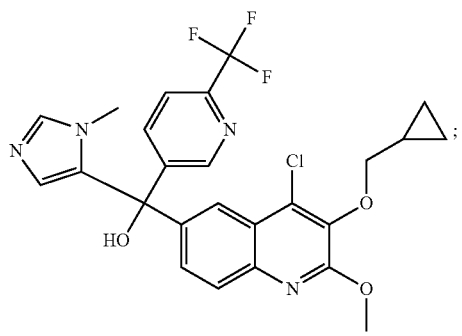
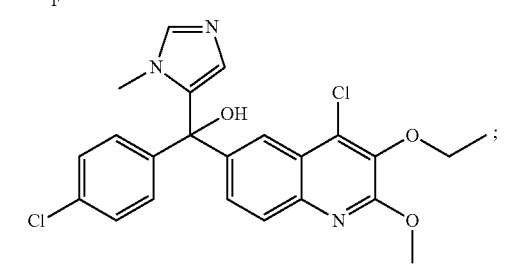
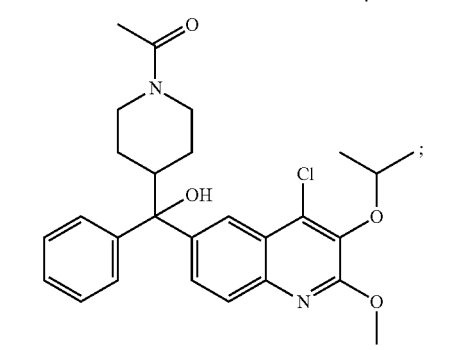
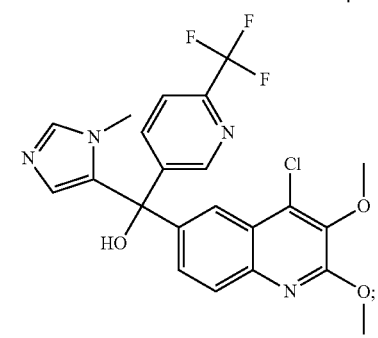

461
-continued
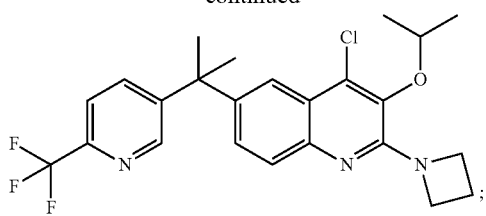
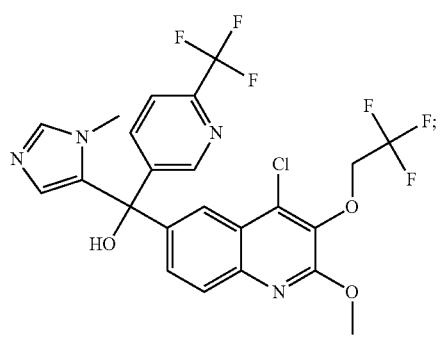
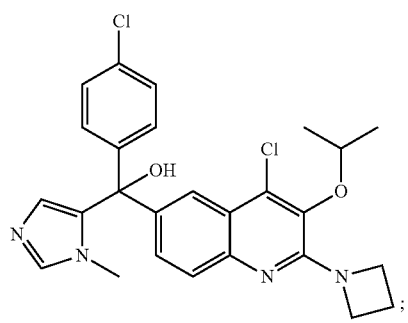
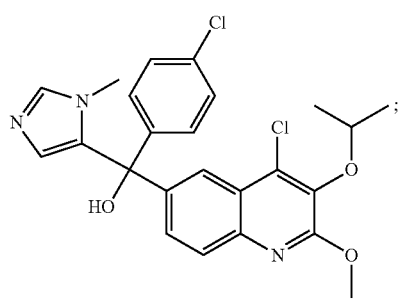
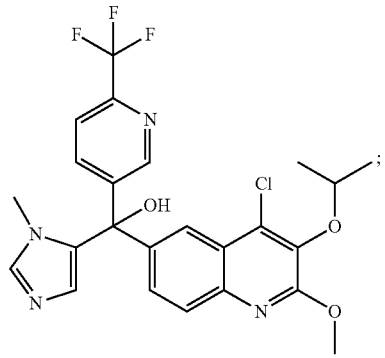
462
-continued
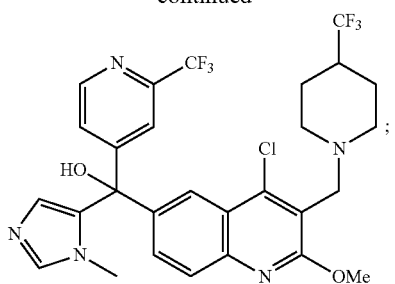
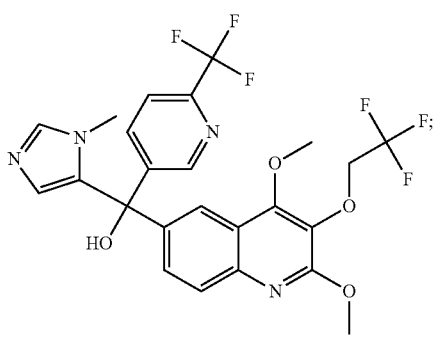
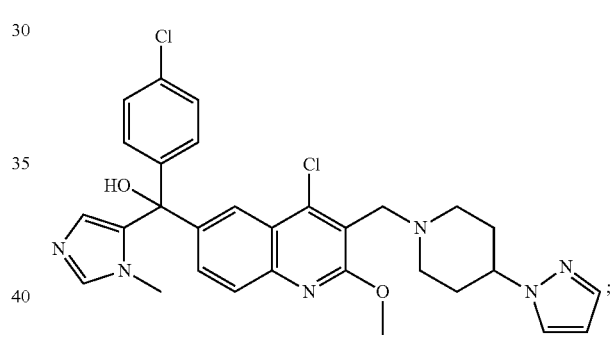
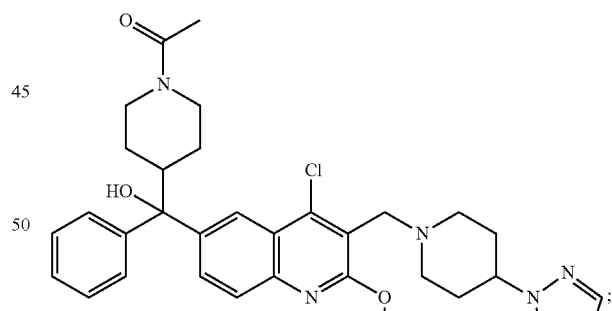
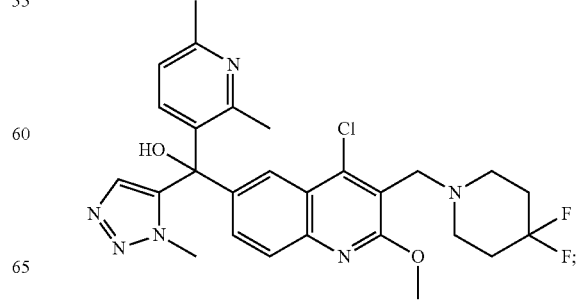

463
-continued
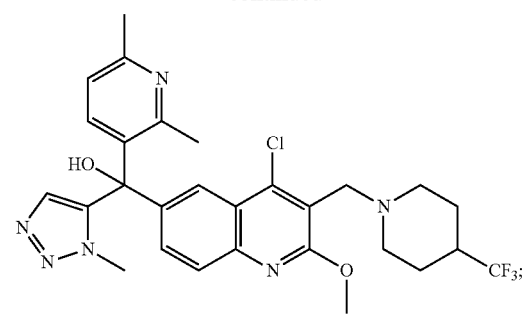
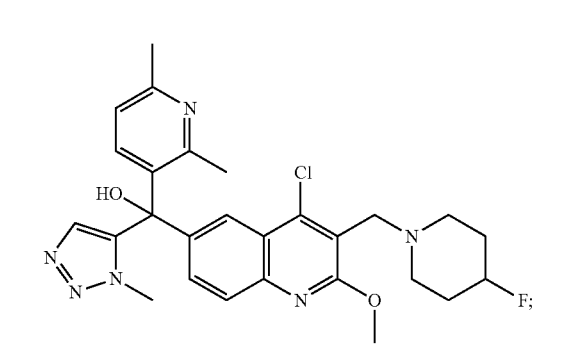
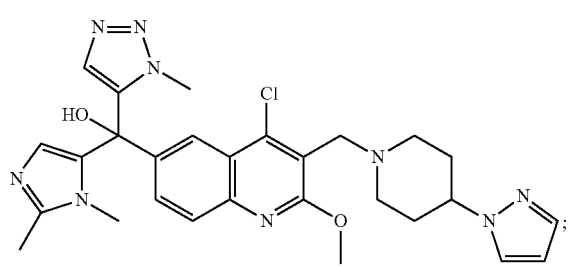
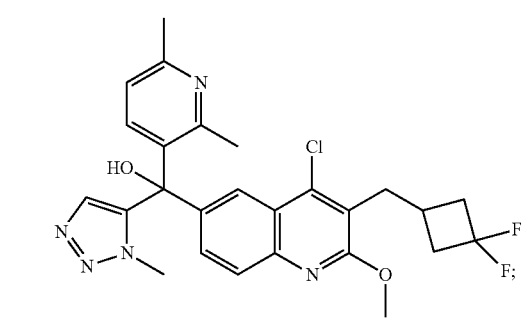
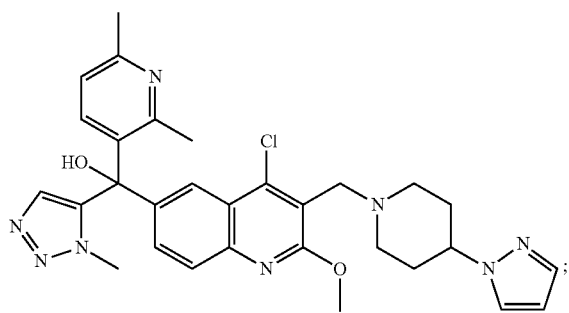
464
-continued
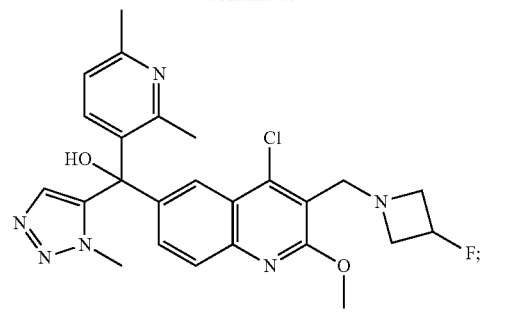
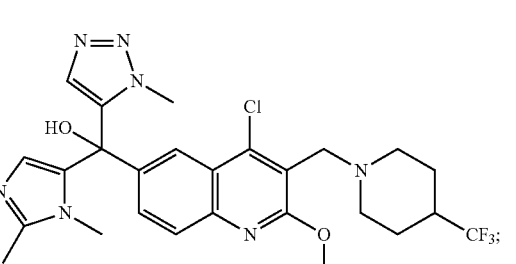
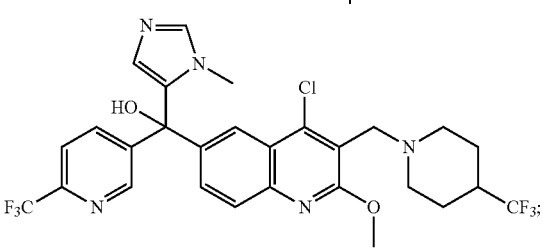
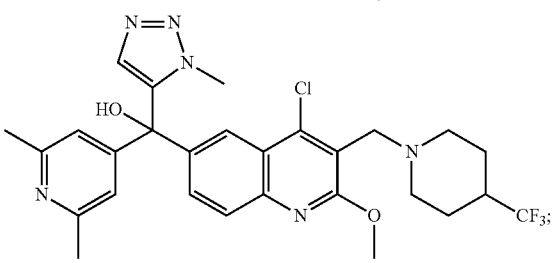
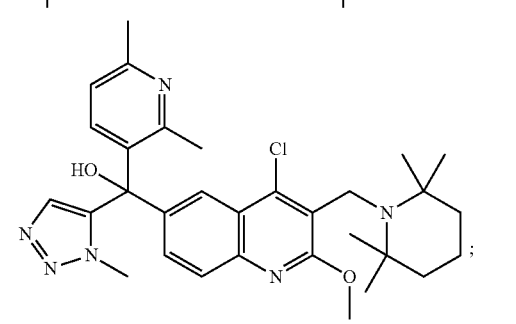

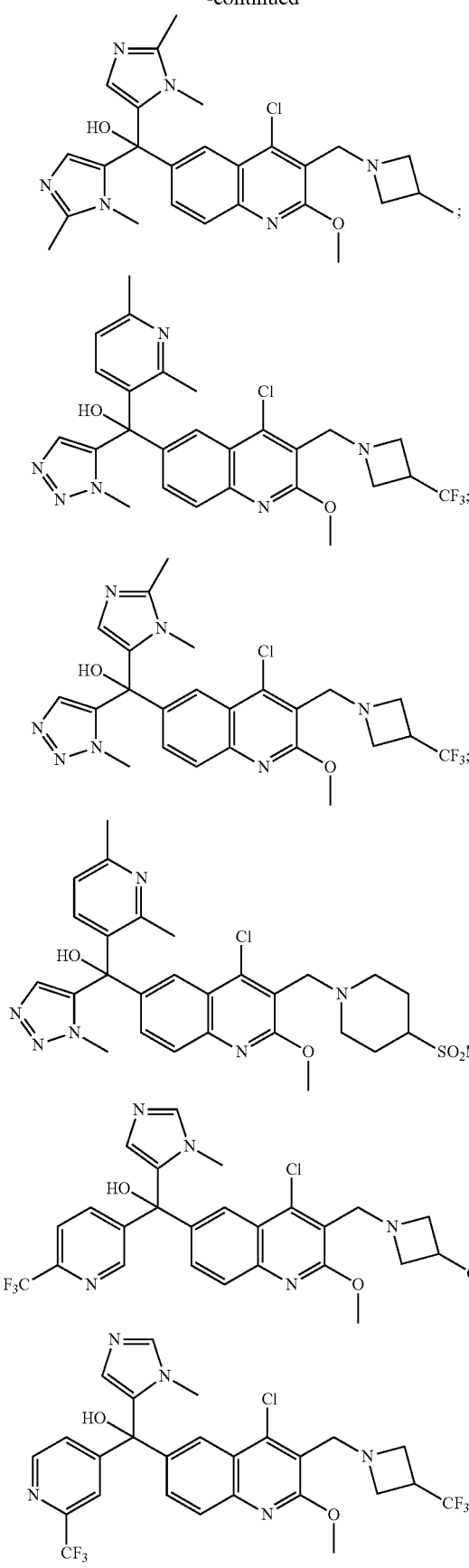
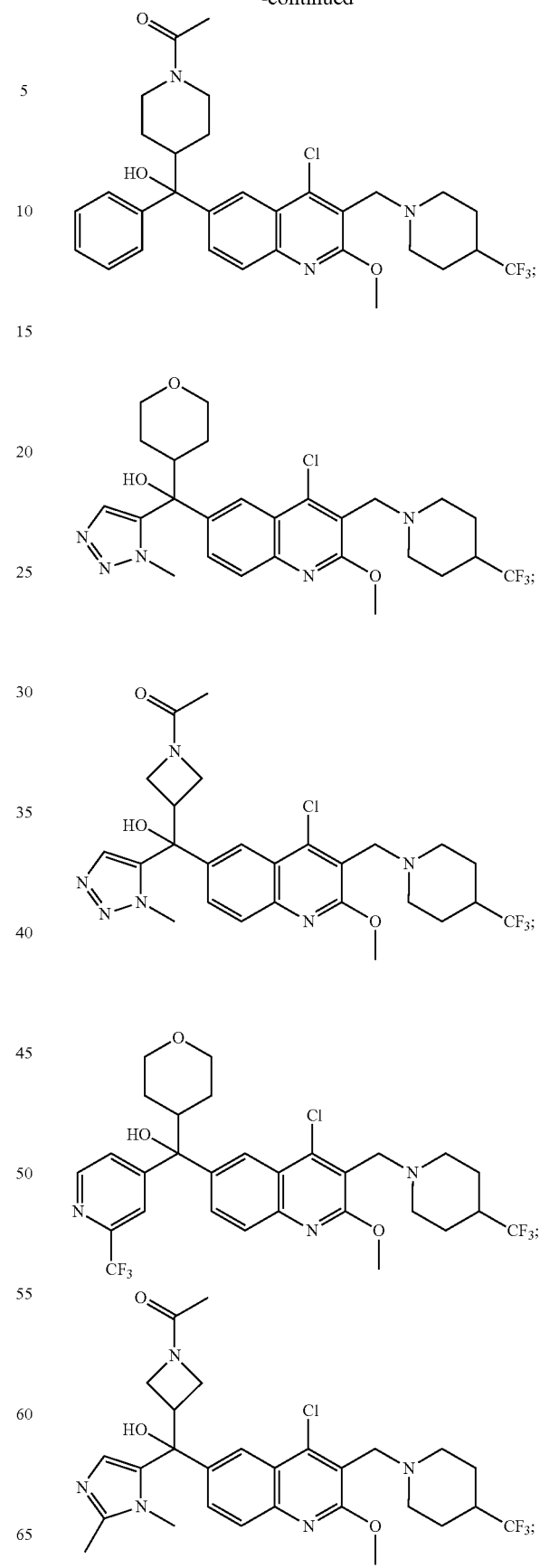

US 10,201,546 B2
467
-continued
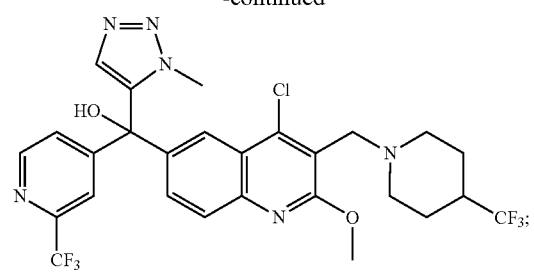
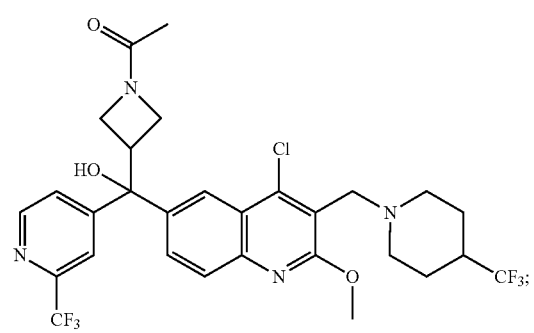
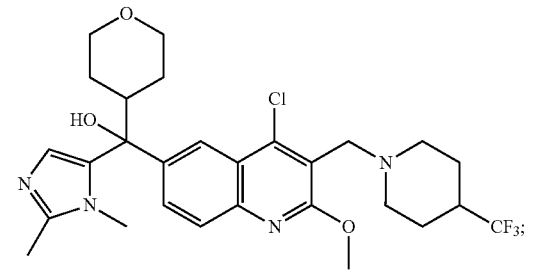
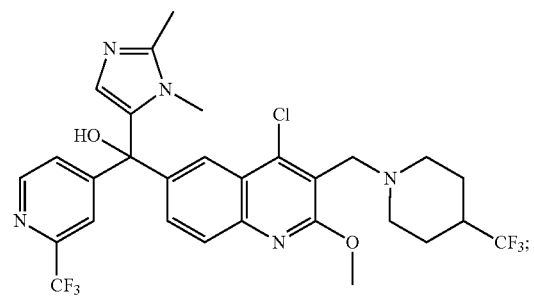
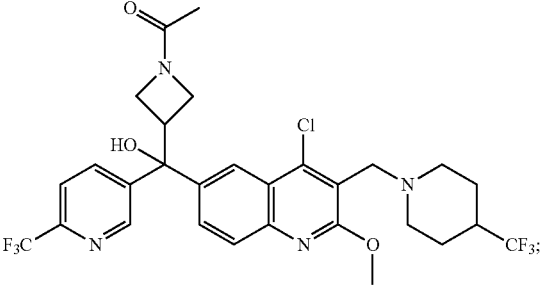
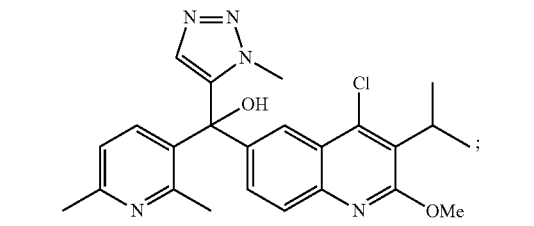
468
-continued
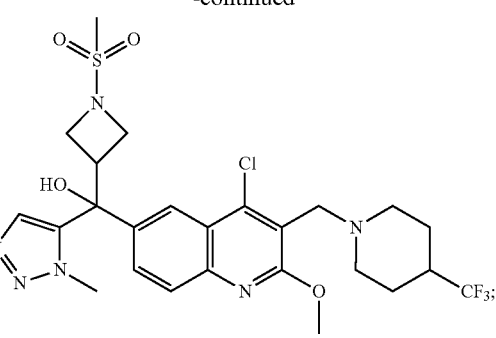
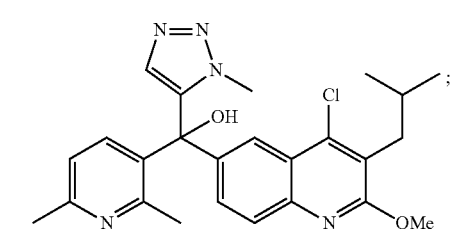
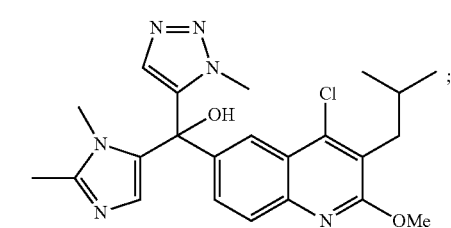
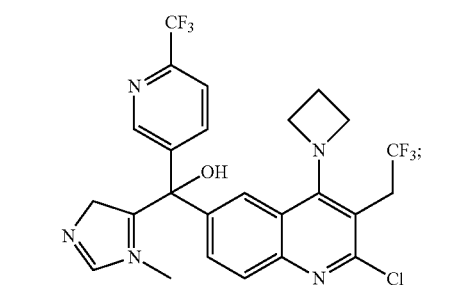
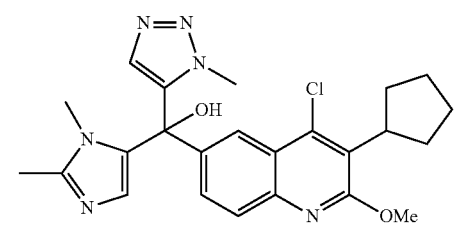
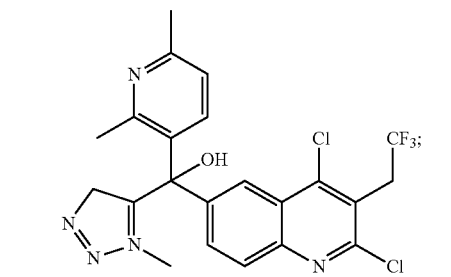

469
-continued
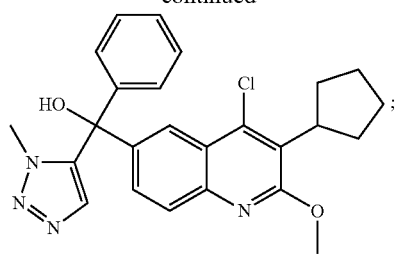
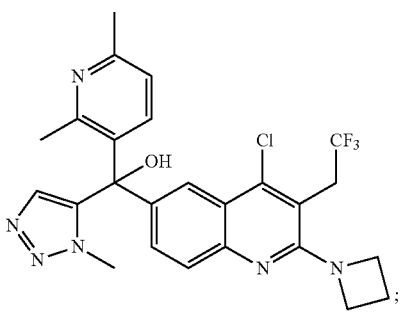
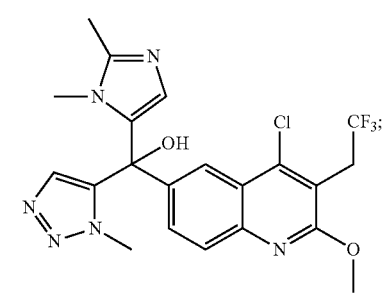
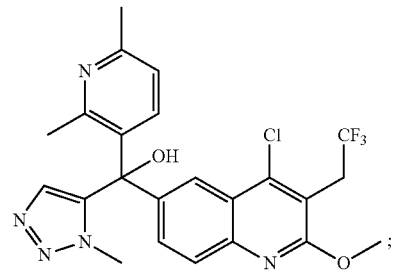
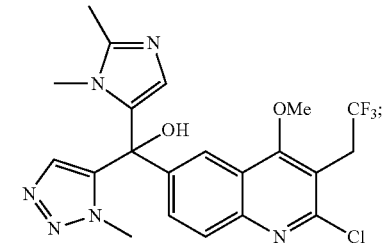
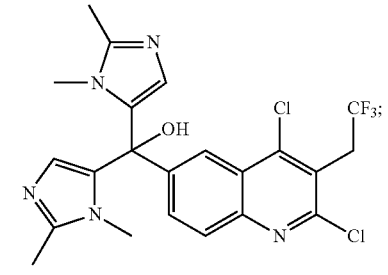
470
-continued
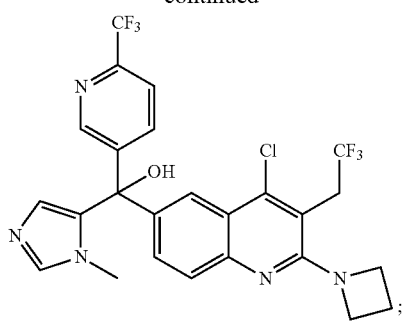
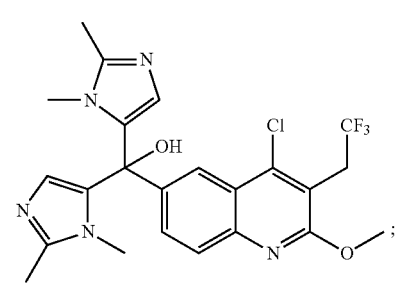
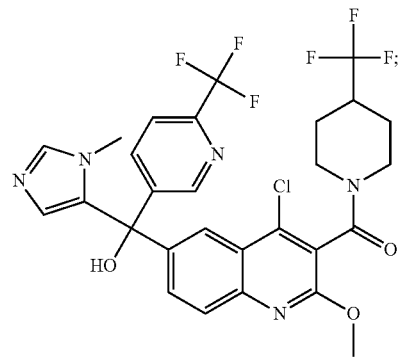
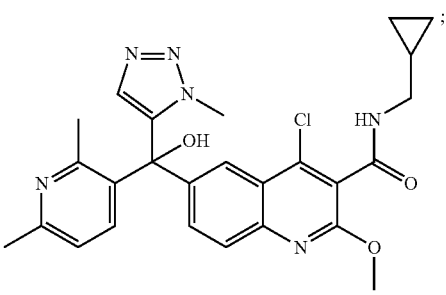
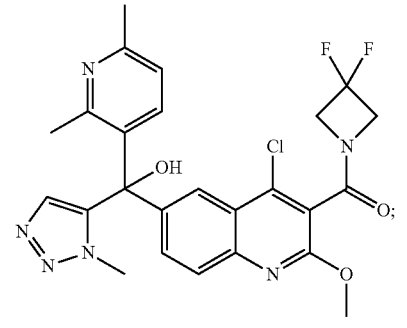

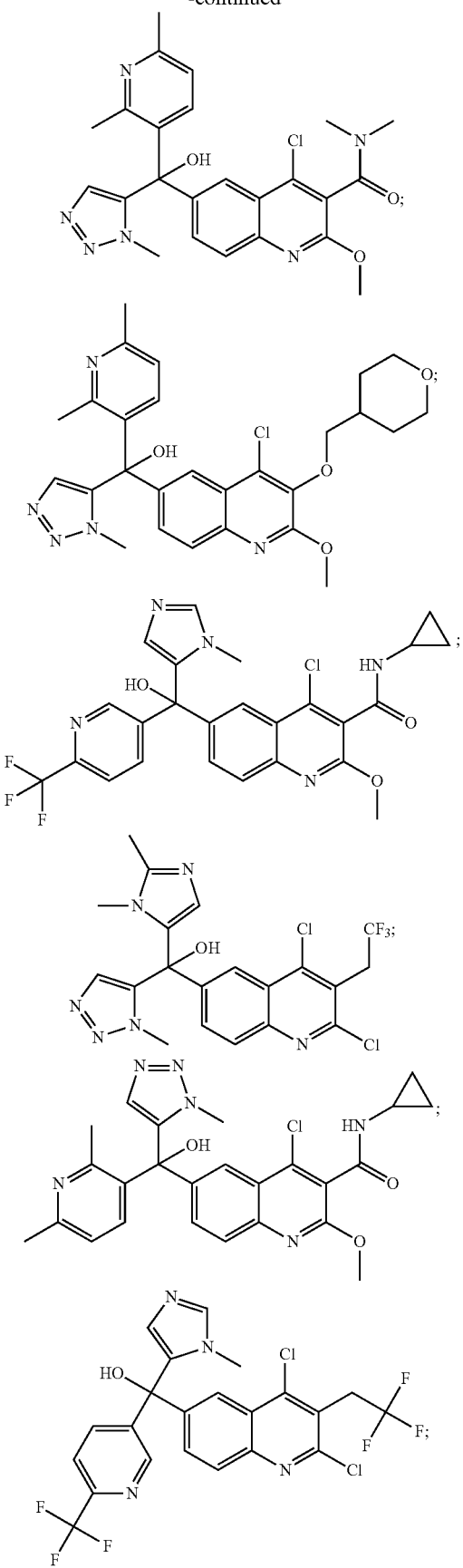
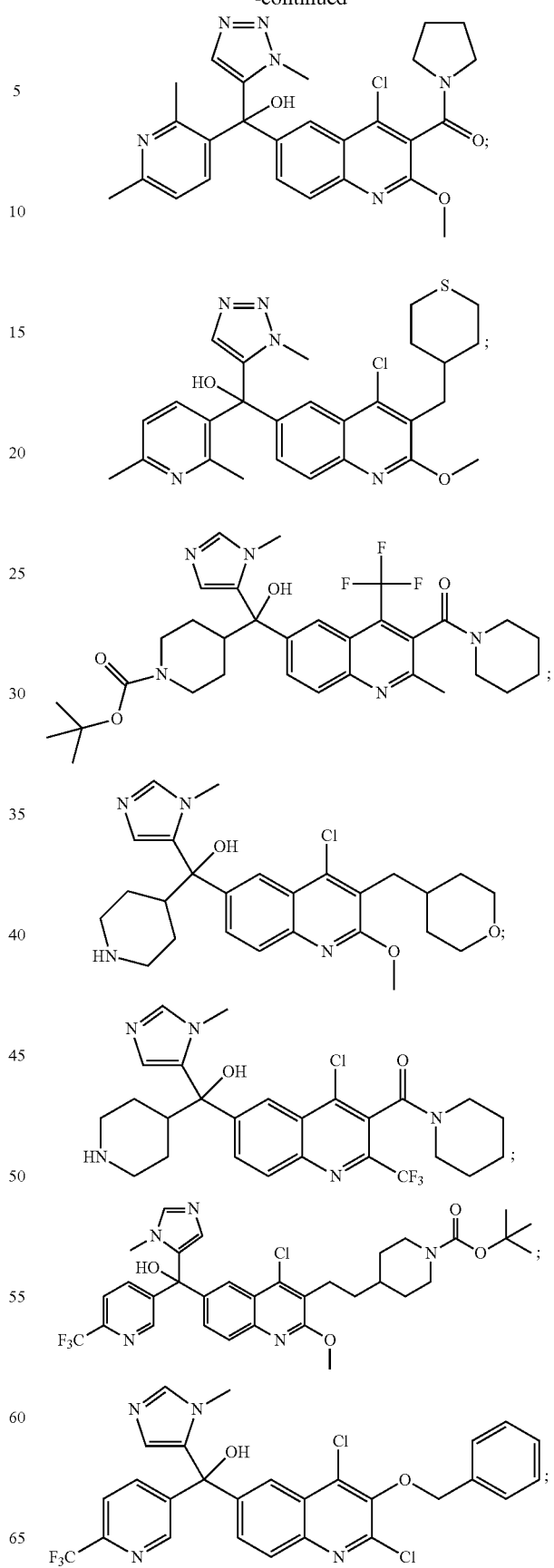

473
-continued
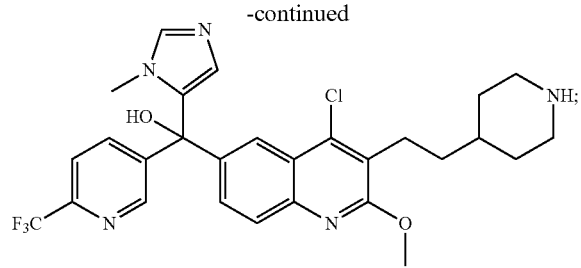
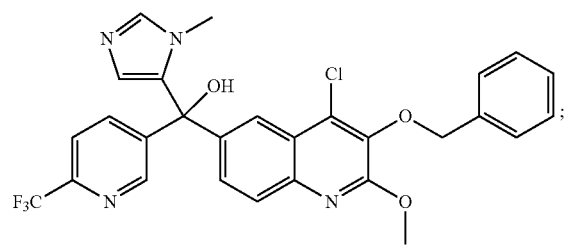
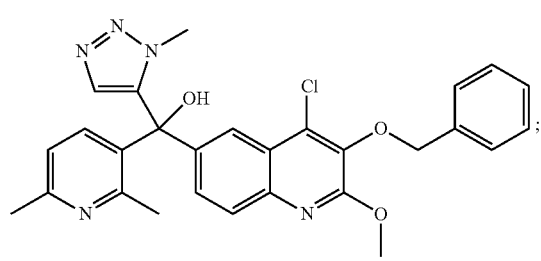
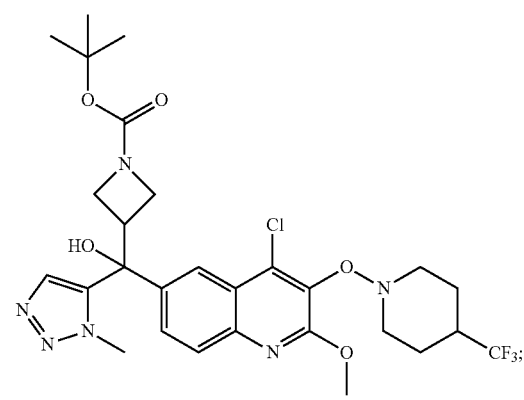
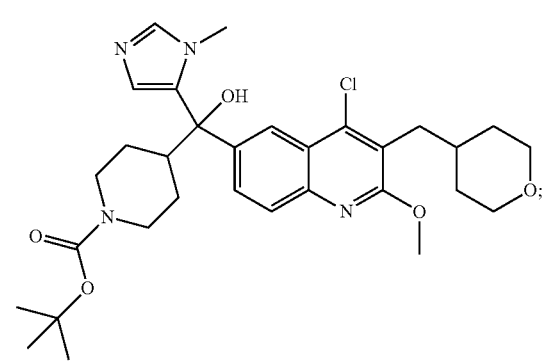
474
-continued
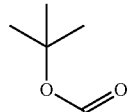
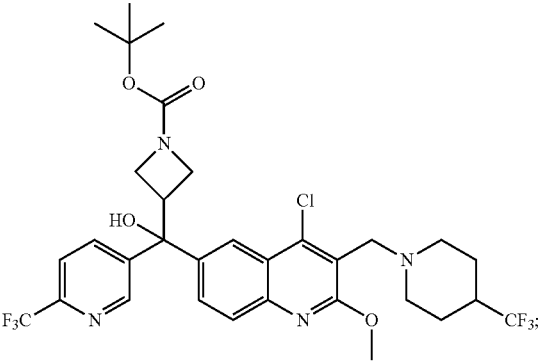

475
-continued
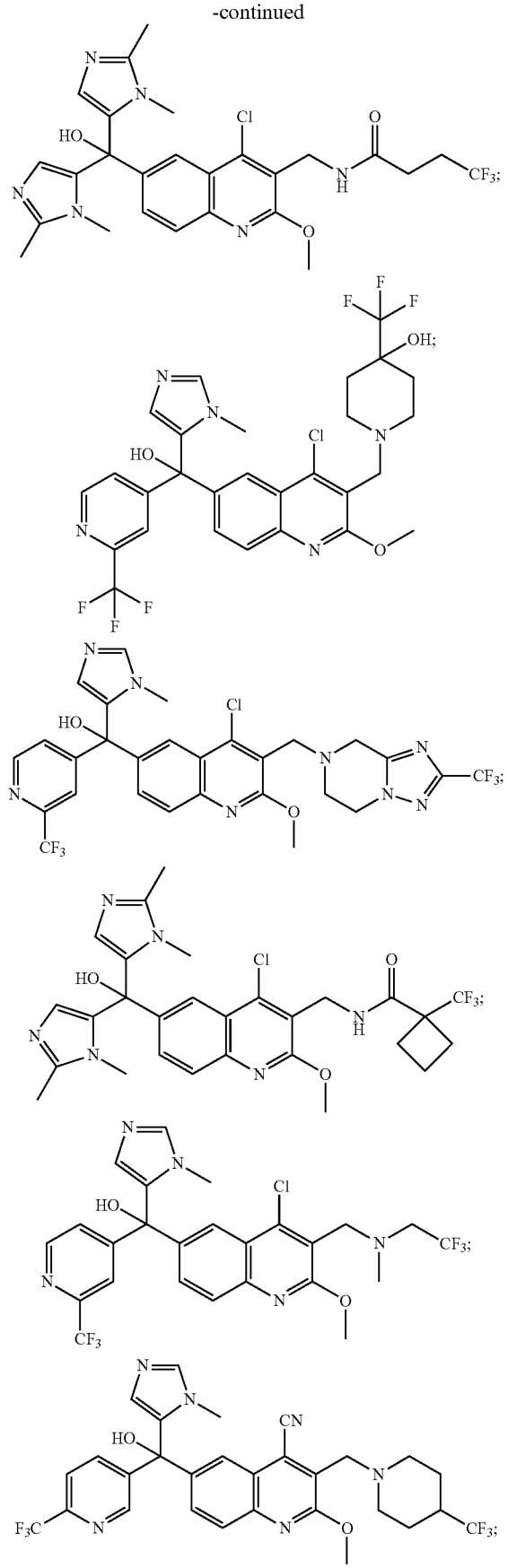
476
-continued
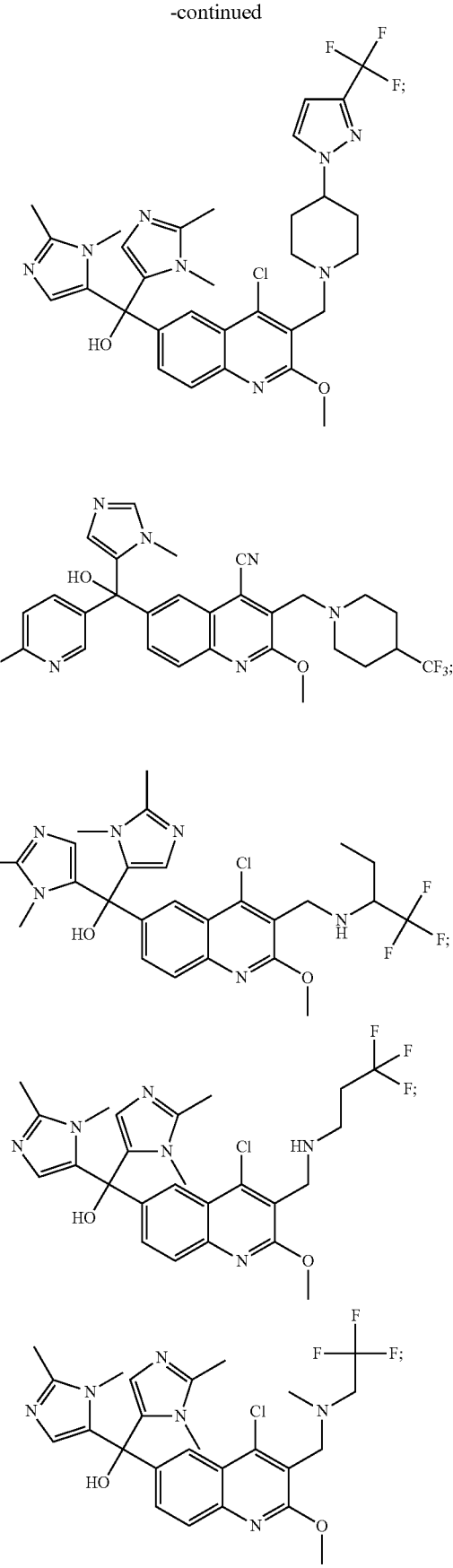

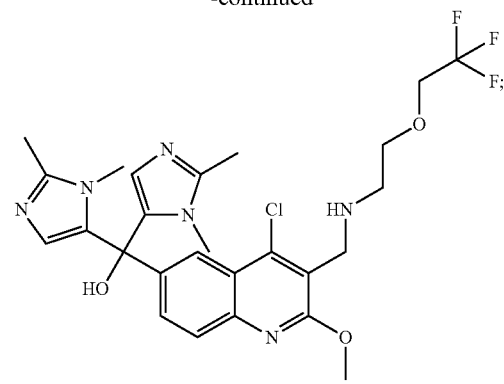
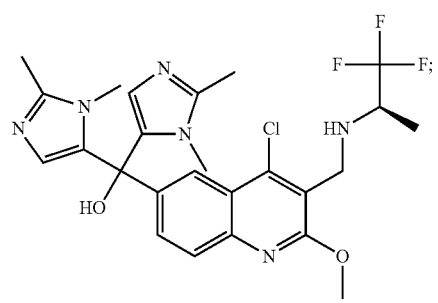
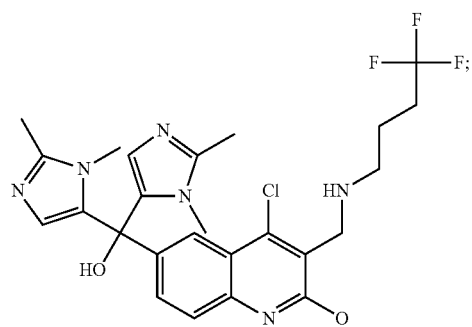
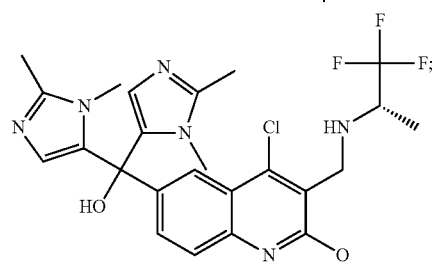
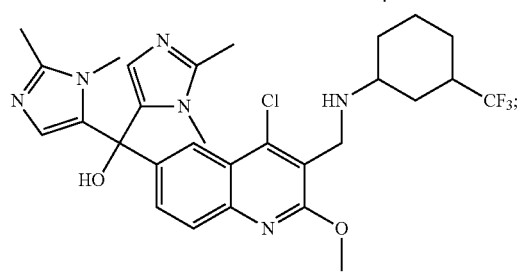
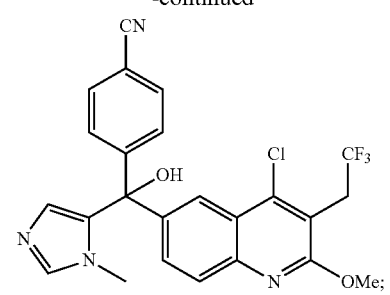
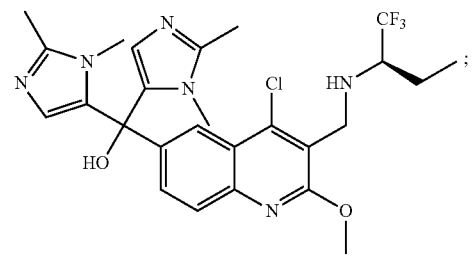
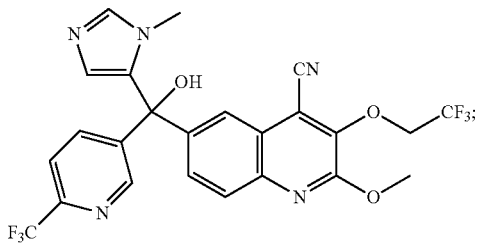
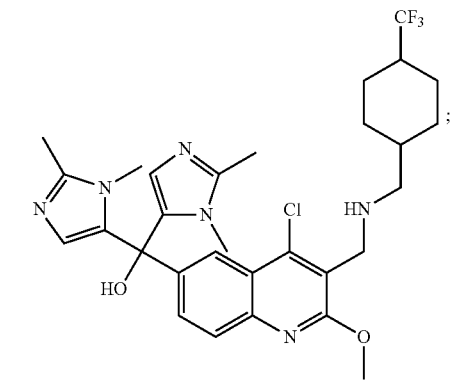
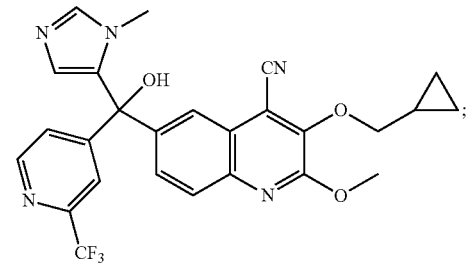
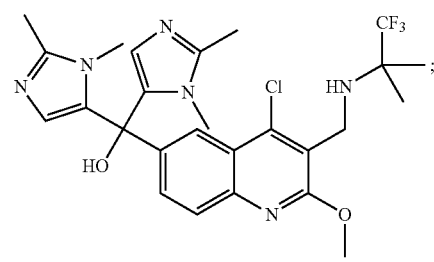

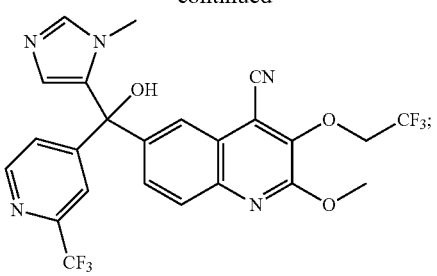
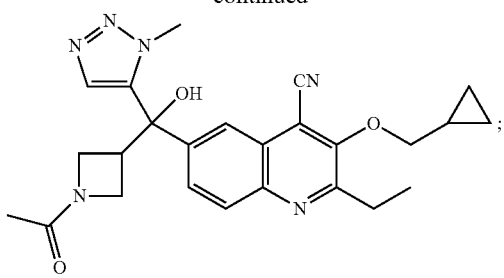
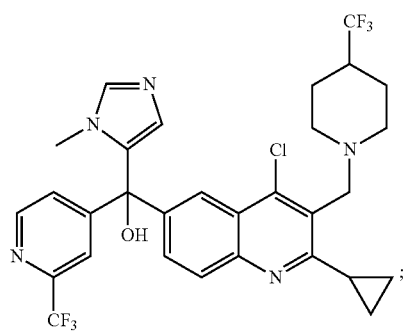
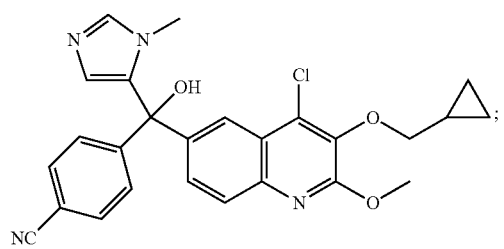
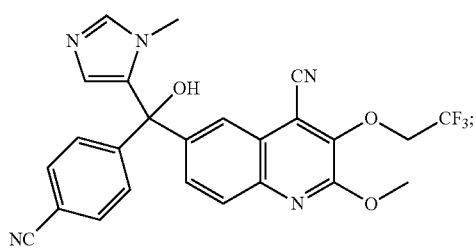
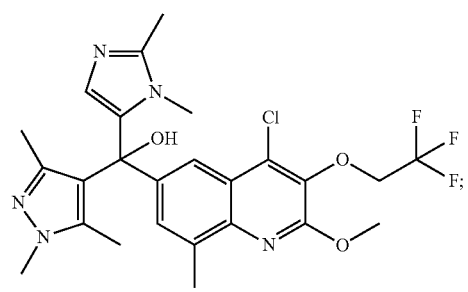
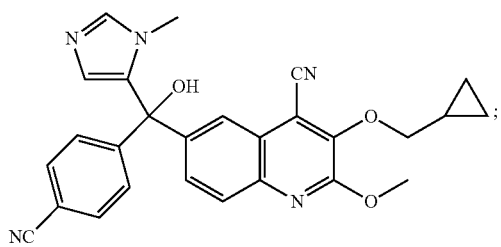
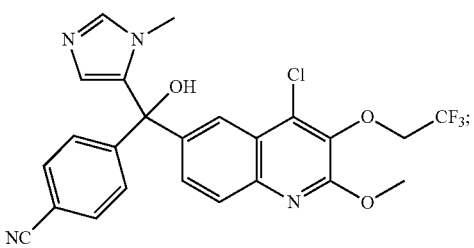
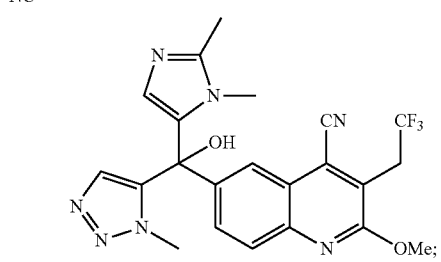
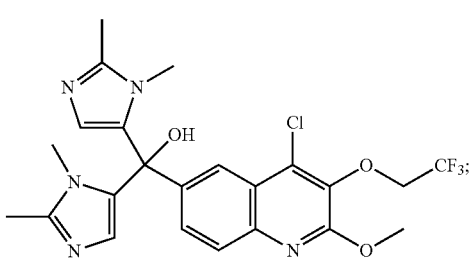
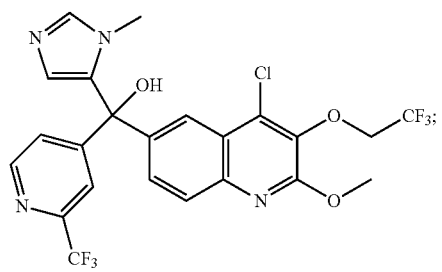
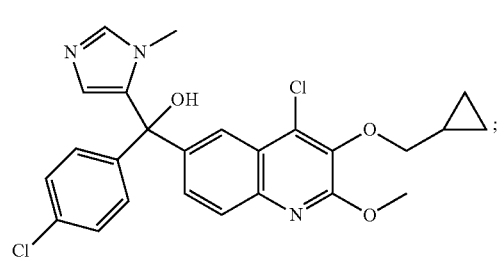

481
-continued
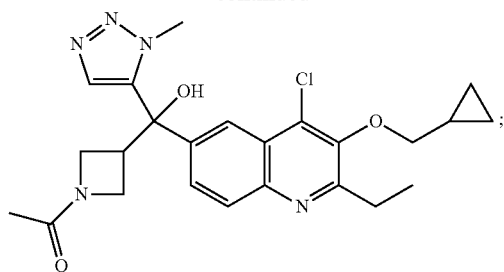;
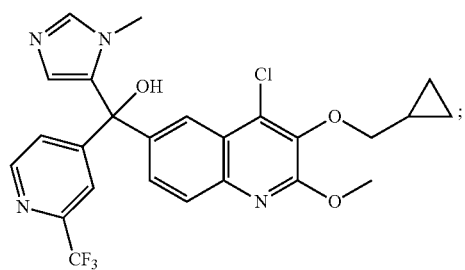;
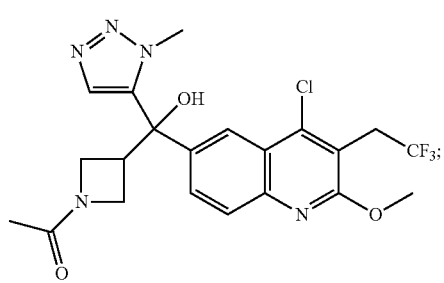;
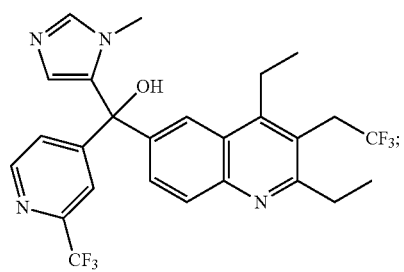;
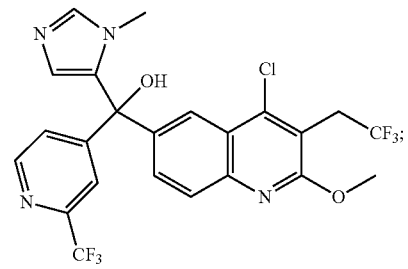;
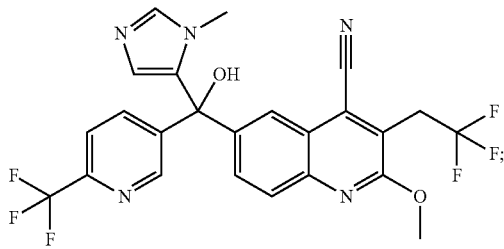;
482
-continued
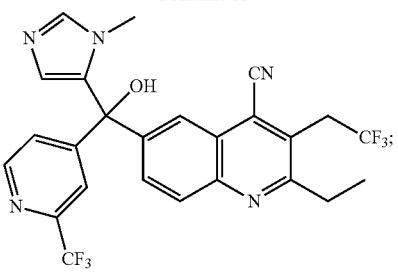;
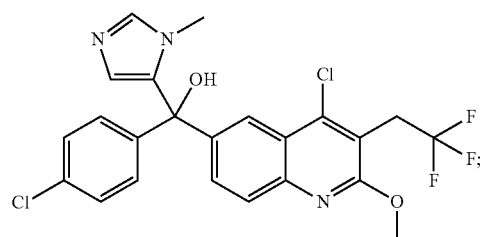;
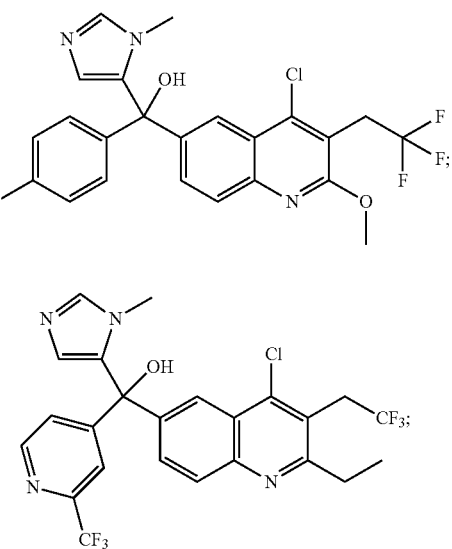;
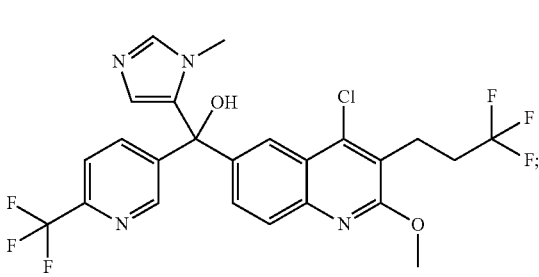;
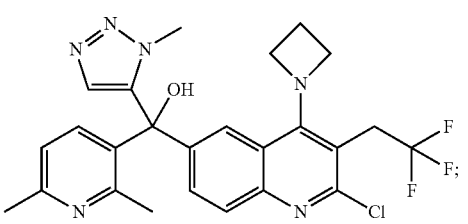;
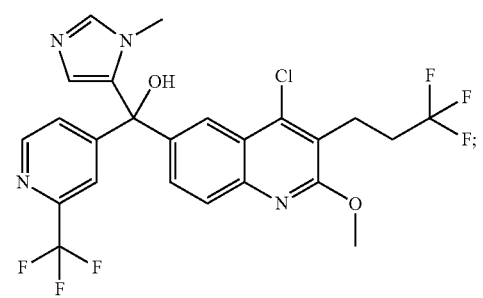;

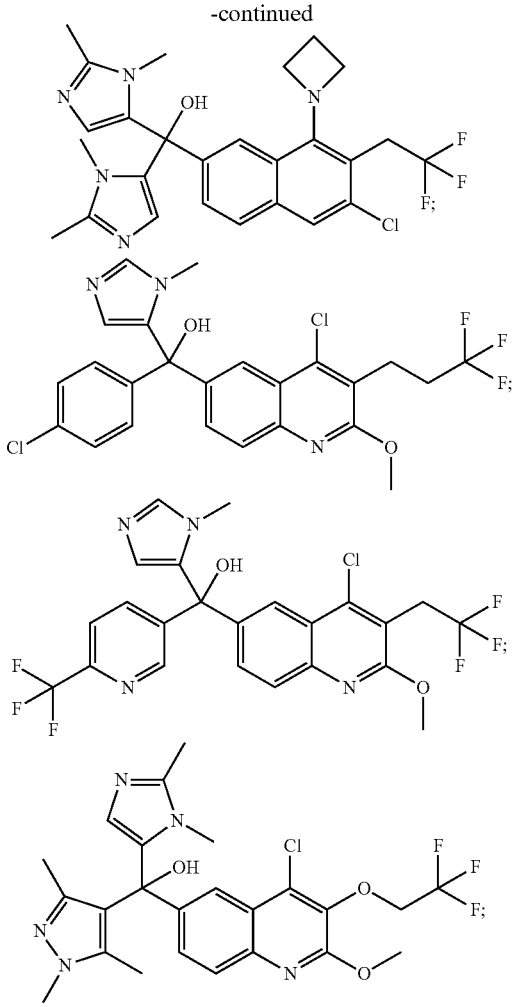

and pharmaceutically acceptable salts thereof.

6. A method of claim 4, wherein in the compound, $R^8$ is H.

7. The method of claim 1, wherein the disease is psoriasis.

8. The method of claim 1, wherein the disease is rheumatoid arthritis.

9. The method of claim 1, wherein the inflammatory bowel disease is ulcerative colitis.

10. The method of claim 1, wherein the inflammatory bowel disease is Crohn's disease.

11. The method of claim 1, wherein the disease is multiple sclerosis.

12. The method of claim 1, wherein the disease is neutrophilic asthma.

13. The method of claim 1, wherein the disease is steroid resistant asthma.

14. The method of claim 1, wherein the disease is psoriatic arthritis.

15. The method of claim 1, wherein the disease is ankylosing spondylitis.

16. The method of claim 1, wherein the disease is systemic lupus erythematosus.

17. The method of claim 1, wherein the disease is chronic obstructive pulmonary disorder.

18. A method of treating or ameliorating a syndrome, disorder or disease, in a subject in need thereof, comprising administering to the subject an effective amount of a compound of Formula I, wherein:

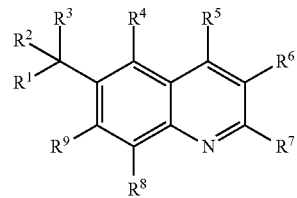

Formula I $R^1$ is imidazolyl, pyrimidinyl, triazolyl, tetrahydropyranyl, thiazolyl, pyridyl, piperidinyl, phenyl, or oxazolyl; wherein said piperidinyl, pyridyl, imidazolyl, and phenyl are optionally substituted with $SO_2CH_3$, $C(O)CH_3$, $CH_3$, $CF_3$, Cl, F, —CN, $OCH_3$, or $N(CH_3)_2$; and optionally substituted with up to one additional group independently selected from the group consisting of Cl, $OCH_3$, and $CH_3$; and wherein said triazolyl, oxazolyl, and thiazolyl are optionally substituted with one or two $CH_3$ groups;

$R^2$ is H, $CH_3$, —C≡CH, 1-methyl-1,2,3-triazol-5-yl, pyrid-3-yl, 2-trifluoromethyl-pyrid-4-yl, 1-methyl-pyrazol-4-yl, 1,3,5-trimethyl-pyrazol-4-yl, thiazol-5-yl, N-acetyl-azetidin-3-yl, N-methylsulfonyl-azetidin-3-yl, N-Boc-azetidin-3-yl, N-acetyl-piperidin-4-yl, N-Boc-piperidin-4-yl, 1-H-piperidin-4-yl, N-methylsulfonyl-piperidin-4-yl, 1,2-dimethyl imidazol-5-yl, or 1-methyl imidazol-5-yl, provided that $R^2$ is not H when $R^5$ is H;

$R^3$ is OH;

$R^4$ is H;

$R^5$ is H, Cl, —CN, $CF_3$, $C_{(1-2)}$alkyl, OH, $N(CH_3)OCH_3$, $OCH_3$, azetidin-1-yl, or fur-2-yl;

provided that $R^5$ is not H if $R^7$ is $OCH_3$;

$R^6$ is $C_{(1-4)}$alkylene-Q, $OC_{(1-4)}$alkylene-Q, $C(O)NA^3A^4$, $C(O)OC_{(1-4)}$alkyl, O-tetrahydropyranyl, —O—(N-methyl)piperidinyl, cyclopentyl, cyclohexyl, 1-methyl-1,2,3,6-tetrahydropyridin-4-yl, or tetrahydropyran-4-yl; provided that $R^6$ is not $CH_2$-phenyl, $CH_2$-pyridinyl, nor $CH_2$-pyrimidinyl;

Q is H, $CF_3$, OH, $SO_2CH_3$, $NA^3A^4$, $OC_{(1-4)}$alkyl, cyclopropyl, 1-methyl-cyclopropyl, oxetanyl, 3-methyl-oxetanyl, tetrahydrofuranyl, 1,3-dimethyl-pyrazol-5-yl, 3,5-dimethyl-isoxazol-4-yl, thiazol-2-yl, N-methyl-pyrrolidin-2-yl, cyclohexyl, N-acetyl-piperidin-4-yl, N-Boc-piperidin-4-yl, 1-H-piperidin-4-yl, tetrahydropyran-4-yl, 1,1-dioxo-tetrahydrothiopyran-4-yl, tetrahydrothiopyran-4-yl, phenyl, pyridin-3-yl, or pyrimidin-2-yl; wherein said cyclopropyl, and said cyclohexyl are optionally substituted with up to two fluorine atoms;

wherein $A^3$ is H, or $CH_3$;

$A^4$ is $CH_3$, $CH_2$-cyclopropyl, cyclopropyl, $C_{(1-3)}$alkylCF_3$, $CH_2CH_2OCH_2CF_3$, $C(O)C_{(1-2)}$alkylCF_3$,

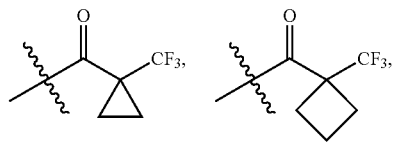

or $C_{(0-1)}$alkyl-trifluoromethyl-cyclohexyl, or $A^3$ and $A^4$ may be taken together with their attached nitrogen to form a ring selected from the group consisting of:

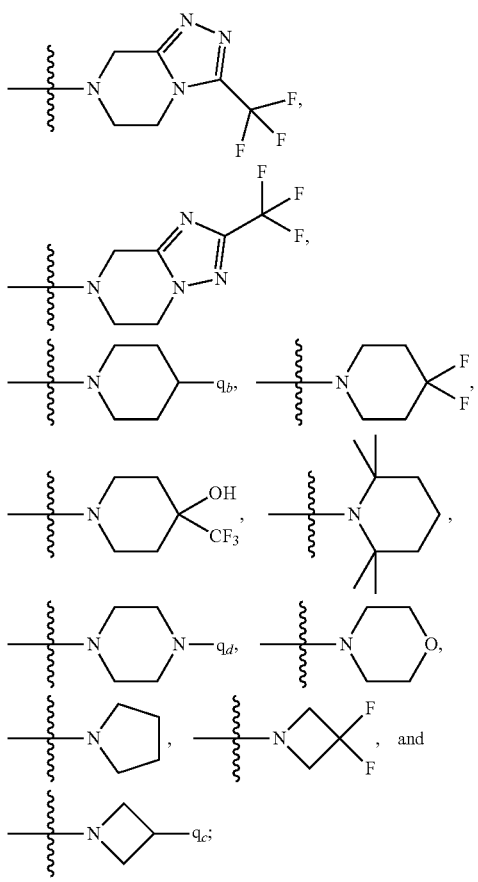

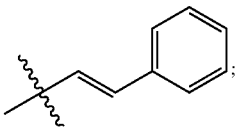

wherein
$q_b$ is H, F, CF$_3$, SO$_2$CH$_3$, pyrazol-1-yl, or 3-trifluoromethyl-pyrazol-1-yl;
$q_c$ is H, F, or CF$_3$,
$q_d$ is CH$_2$CF$_3$;

provided that if R$^6$ is OCH$_2$-Q, then Q may not be OH, nor NA$^3$A$^4$;

R$^7$ is Cl, —CN, CF$_3$, C$_{(1-4)}$alkyl, cyclopropyl, NA$^1$A$^2$, C(O)NHCH$_3$, OCH$_2$CH$_2$OCH$_3$, 1-methyl imidazol-2-yl, 1-methyl pyrazol-4-yl, OC$_{(1-2)}$alkyl, pyrimidin-5-yl, thiophen-3-yl, 1-methyl-indazol-5-yl, 1-methyl-indazol-6-yl, fur-2-yl, phenyl, or

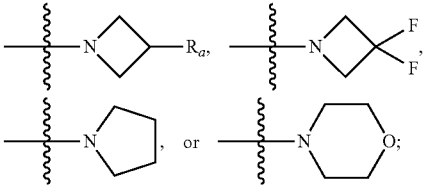

A$^1$ is C$_{(1-2)}$alkyl;
A$^2$ is C$_{(1-2)}$alkyl, CH$_2$CH$_2$OCH$_3$, or OCH$_3$; or A$^1$ and A$^2$ may be taken together with their attached nitrogen to form a ring which is:

R$_a$ is H, OH, OCH$_3$, F;
R$^8$ is H, CH$_3$, OCH$_3$, or F;
R$^9$ is H;
and pharmaceutically acceptable salts thereof; or composition or medicament thereof in a combination therapy with one or more anti-inflammatory agents, or immunosuppressive agents, wherein said syndrome, disorder or disease is selected from the group consisting of: rheumatoid arthritis, and psoriasis.

* * * * *

SEQUENCE LISTING

<160> NUMBER OF SEQ ID NOS: 9

<210> SEQ ID NO 1
<211> LENGTH: 3054
<212> TYPE: DNA
<213> ORGANISM: Homo sapiens

<400> SEQUENCE: 1

```
agagagctag gtgcagagct tcaggctgag gcgctgctga gagggcctcg ccccgcctct    60
gccgccagct gcaccccact cctggaccac cccctgctga gaaggacagg gagccaaggc   120
cggcagagcc aaggctcagt catgagaaca caaattgaag tgatcccttg caaaatctgt   180
ggggacaagt cgtctgggat ccactacggg gttatcacct gtgaggggtg caagggcttc   240
ttccgccgga gccagcgctg taacgcggcc tactcctgca cccgtcagca gaactgcccc   300
atcgaccgca ccagccgaaa ccgatgccag cactgccgcc tgcagaaatg cctggcgctg   360
ggcatgtccc gagatgctgt caagttcggc cgcatgtcca agaagcagag ggacagcctg   420
catgcagaag tgcagaaaca gctgcagcag cggcaacagc agcaacagga accagtggtc   480
aagacccctc cagcagggc ccaaggagca gataccctca cctacacctt ggggctccca   540
gacgggcagc tgcccctggg ctcctcgcct gacctgcctg aggcttctgc ctgtccccct   600
ggcctcctga aagcctcagg ctctgggccc tcatattcca caaacttggc caaggcaggg   660
ctcaatgggg cctcatgcca ccttgaatac agccctgagc ggggcaaggc tgagggcaga   720
gagagcttct atagcacagg cagccagctg accctgacc gatgtggact tcgttttgag   780
gaacacaggc atcctgggct tggggaactg ggacagggcc cagacagcta cggcagcccc   840
```

```
agtttccgca gcacaccgga ggcaccctat gcctccctga cagagataga gcacctggtg      900
cagagcgtct gcaagtccta cagggagaca tgccagctgc ggctggagga cctgctgcgg      960
cagcgctcca acatcttctc ccgggaggaa gtgactggct accagaggaa gtccatgtgg     1020
gagatgtggg aacggtgtgc ccaccacctc accgaggcca ttcagtacgt ggtggagttc     1080
gccaagaggc tctcaggctt tatggagctc tgccagaatg accagattgt gcttctcaaa     1140
gcaggagcaa tggaagtggt gctggttagg atgtgccggg cctacaatgc tgacaaccgc     1200
acggtctttt ttgaaggcaa atacggtggc atggagctgt ccgagccttg ggctgcagc      1260
gagctcatca gctccatctt tgacttctcc cactccctaa gtgccttgca ctttccgag      1320
gatgagattg ccctctacac agcccttgtt ctcatcaatg cccatcggcc agggctccaa     1380
gagaaaagga agtagaaaca gctgcagtac aatctggagc tggcctttca tcatcatctc     1440
tgcaagactc atcgccaaag catcctggca aagctgccac ccaaggggaa gcttcggagc     1500
ctgtgtagcc agcatgtgga aaggctgcag atcttccagc acctccaccc catcgtggtc     1560
caagccgctt tccctccact ctacaaggag ctcttcagca ctgaaaccga gtcacctgtg     1620
gggctgtcca gtgacctgg aagagggact ccttgcctct ccctatggcc tgctggccca     1680
cctccctgga ccccgttcca ccctcaccct tttccttcc catgaaccct ggagggtggt      1740
ccccaccagc tctttggaag tgagcagatg ctgcggctgg ctttctgtca gcaggccggc     1800
ctggcagtgg gacaatcgcc agagggtggg gctggcagaa caccatctcc agcctcagct     1860
ttgacctgtc tcatttccca tattccttca cacccagctt ctggaaggca tggggtggct     1920
gggatttaag gacttctggg ggaccaagac atcctcaaga aaacaggggc atccagggct     1980
ccctggatga atagaatgca attcattcag aagctcagaa gctaagaata agcctttgaa     2040
atacctcatt gcatttccct ttgggcttcg gcttggggag atggatcaag ctcagagact     2100
ggcagtgaga gcccagaagg acctgtataa aatgaatctg gagctttaca ttttctgcct     2160
ctgccttcct cccagctcag caaggaagta tttgggcacc ctacccttta cctggggtct     2220
aaccaaaaat ggatgggatg aggatgagag gctggagata attgttttat gggatttggg     2280
tgtgggacta gggtacaatg aaggccaaga gcatctcaga catagagtta aaactcaaac     2340
ctcttatgtg cactttaaag atagacttta ggggctggca caaatctgat cagagacaca     2400
tatccataca caggtgaaac acatacagac tcaacagcaa tcatgcagtt ccagagacac     2460
atgaacctga cacaatctct cttatccttg aggccacagc ttggaggagc ctagaggcct     2520
caggggaaag tccaatcct gagggaccct cccaaacatt tccatggtgc tccagtccac     2580
tgatcttggg tctggggtga tccaaatacc accccagctc cagctgtctt ctaccactag     2640
aagacccaag agaagcagaa gtcgctcgca ctggtcagtc ggaaggcaag atcagatcct     2700
ggaggacttt cctggcctgc ccgccagccc tgctcttgtt gtggagaagg aagcagatgt     2760
gatcacatca ccccgtcatt gggcaccgct gactccagca tggaggacac cagggagcag     2820
ggcctgggcc tgtttcccca gctgtgatct tgcccagaac ctctcttggc ttcataaaca     2880
gctgtgaacc ctcccctgag ggattaacag caatgatggg cagtcgtgga gttgggggg      2940
ttgggggtgg gattgtgtcc tctaagggga cgggttcatc tgagtaaaca taaaccccaa     3000
cttgtgccat tctttataaa atgatttaa aggcaaaaaa aaaaaaaaaa aaaa           3054

<210> SEQ ID NO 2
<211> LENGTH: 786
<212> TYPE: DNA
```

<213> ORGANISM: Homo sapiens

<400> SEQUENCE: 2

```
agcacaccgg aggcacccta tgcctccctg acagagatag agcacctggt gcagagcgtc    60
tgcaagtcct acagggagac atgccagctg cggctggagg acctgctgcg gcagcgctcc   120
aacatcttct cccggggagga agtgactggc taccagagga agtccatgtg ggagatgtgg   180
gaacggtgtg cccaccacct caccgaggcc attcagtacg tggtggagtt cgccaagagg   240
ctctcaggct ttatggagct ctgccagaat gaccagattg tgcttctcaa agcaggagca   300
atggaagtgg tgctggttag gatgtgccgg gcctacaatg ctgacaaccg cacggtcttt   360
tttgaaggca aatacggtgg catggagctg ttccgagcct gggctgcag cgagctcatc    420
agctccatct ttgacttctc ccactcccta agtgccttgc acttttccga ggatgagatt   480
gccctctaca cagcccttgt tctcatcaat gcccatcggc agggctcca agagaaaagg    540
aaagtagaac agctgcagta caatctggag ctggcctttc atcatcatct ctgcaagact   600
catcgccaaa gcatcctggc aaagctgcca cccaagggga agcttcggag cctgtgtagc   660
cagcatgtgg aaaggctgca gatcttccag cacctccacc ccatcgtggt ccaagccgct   720
ttccctccac tctacaagga gctcttcagc actgaaaccg agtcacctgt ggggctgtcc   780
aagtga                                                              786
```

<210> SEQ ID NO 3
<211> LENGTH: 7
<212> TYPE: PRT
<213> ORGANISM: Artificial Sequence
<220> FEATURE:
<223> OTHER INFORMATION: TurboTEV protease cleavage site

<400> SEQUENCE: 3

```
Glu Asn Leu Tyr Phe Gln Gly
1               5
```

<210> SEQ ID NO 4
<211> LENGTH: 283
<212> TYPE: PRT
<213> ORGANISM: Artificial Sequence
<220> FEATURE:
<223> OTHER INFORMATION: Construct used in the Thermofluor assay

<400> SEQUENCE: 4

```
Met Ala His His His His His His Ala Gly Gly Ala Glu Asn Leu Tyr
1               5                   10                  15

Phe Gln Gly Ala Met Asp Ser Thr Pro Glu Ala Pro Tyr Ala Ser Leu
            20                  25                  30

Thr Glu Ile Glu His Leu Val Gln Ser Val Cys Lys Ser Tyr Arg Glu
        35                  40                  45

Thr Cys Gln Leu Arg Leu Glu Asp Leu Leu Arg Gln Arg Ser Asn Ile
    50                  55                  60

Phe Ser Arg Glu Glu Val Thr Gly Tyr Gln Arg Lys Ser Met Trp Glu
65                  70                  75                  80

Met Trp Glu Arg Cys Ala His His Leu Thr Glu Ala Ile Gln Tyr Val
                85                  90                  95

Val Glu Phe Ala Lys Arg Leu Ser Gly Phe Met Glu Leu Cys Gln Asn
            100                 105                 110

Asp Gln Ile Val Leu Leu Lys Ala Gly Ala Met Glu Val Val Leu Val
        115                 120                 125
```

```
Arg Met Cys Arg Ala Tyr Asn Ala Asp Asn Arg Thr Val Phe Phe Glu
            130                 135                 140
Gly Lys Tyr Gly Gly Met Glu Leu Phe Arg Ala Leu Gly Cys Ser Glu
145                 150                 155                 160
Leu Ile Ser Ser Ile Phe Asp Phe Ser His Ser Leu Ser Ala Leu His
                165                 170                 175
Phe Ser Glu Asp Glu Ile Ala Leu Tyr Thr Ala Leu Val Leu Ile Asn
            180                 185                 190
Ala His Arg Pro Gly Leu Gln Glu Lys Arg Lys Val Glu Gln Leu Gln
        195                 200                 205
Tyr Asn Leu Glu Leu Ala Phe His His Leu Cys Lys Thr His Arg
    210                 215                 220
Gln Ser Ile Leu Ala Lys Leu Pro Pro Lys Gly Lys Leu Arg Ser Leu
225                 230                 235                 240
Cys Ser Gln His Val Glu Arg Leu Gln Ile Phe Gln His Leu His Pro
                245                 250                 255
Ile Val Val Gln Ala Ala Phe Pro Pro Leu Tyr Lys Glu Leu Phe Ser
            260                 265                 270
Thr Glu Thr Glu Ser Pro Val Gly Leu Ser Lys
            275                 280

<210> SEQ ID NO 5
<211> LENGTH: 6
<212> TYPE: PRT
<213> ORGANISM: Homo sapiens

<400> SEQUENCE: 5

Leu Tyr Lys Glu Leu Phe
1               5

<210> SEQ ID NO 6
<211> LENGTH: 6
<212> TYPE: PRT
<213> ORGANISM: Artificial Sequence
<220> FEATURE:
<223> OTHER INFORMATION: mutated AF2 domain

<400> SEQUENCE: 6

Leu Phe Lys Glu Leu Phe
1               5

<210> SEQ ID NO 7
<211> LENGTH: 786
<212> TYPE: DNA
<213> ORGANISM: Artificial Sequence
<220> FEATURE:
<223> OTHER INFORMATION: LBD with mutated AF2 domain

<400> SEQUENCE: 7
agcacaccgg aggcacccta tgcctccctg acagagatag agcacctggt gcagagcgtc      60
tgcaagtcct acaggagac atgccagctg cggctggagg acctgctgcg gcagcgctcc     120
aacatcttct cccggggagga agtgactggc taccagagga gtccatgtg ggagatgtgg     180 gaacggtgtg cccaccacct caccgaggcc attcagtacg tggtggagtt cgccaagagg     240
ctctcaggct ttatggagct ctgccagaat gaccagattg tgcttctcaa agcaggagca     300
atggaagtgg tgctggttag gatgtgccgg gcctacaatg ctgacaaccg cacggtcttt     360
tttgaaggca atacggtgg catggagctg ttccgagcct gggctgcag cgagctcatc     420 agctccatct ttgacttctc ccactcccta agtgccttgc acttttccga ggatgagatt     480
```

-continued

```
gccctctaca cagcccttgt tctcatcaat gcccatcggc cagggctcca agagaaaagg    540
aaagtagaac agctgcagta caatctggag ctggcctttc atcatcatct ctgcaagact    600
catcgccaaa gcatcctggc aaagctgcca cccaaggggga agcttcggag cctgtgtagc    660
cagcatgtgg aaaggctgca gatcttccag cacctccacc ccatcgtggt ccaagccgct    720
ttccctccac tcttcaagga gctcttcagc actgaaaccg agtcacctgt ggggctgtcc    780
aagtga                                                               786
```

<210> SEQ ID NO 8
<211> LENGTH: 261
<212> TYPE: PRT
<213> ORGANISM: Homo sapiens

<400> SEQUENCE: 8

Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
            20                  25                  30

Glu Asp Leu Leu Arg Gln Arg Ser Asn Ile Phe Ser Arg Glu Glu Val
        35                  40                  45

Thr Gly Tyr Gln Arg Lys Ser Met Trp Glu Met Trp Glu Arg Cys Ala
    50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
                85                  90                  95

Lys Ala Gly Ala Met Glu Val Val Leu Val Arg Met Cys Arg Ala Tyr
            100                 105                 110

Asn Ala Asp Asn Arg Thr Val Phe Phe Glu Gly Lys Tyr Gly Gly Met
        115                 120                 125

Glu Leu Phe Arg Ala Leu Gly Cys Ser Glu Leu Ile Ser Ser Ile Phe
    130                 135                 140

Asp Phe Ser His Ser Leu Ser Ala Leu His Phe Ser Glu Asp Glu Ile
145                 150                 155                 160

Ala Leu Tyr Thr Ala Leu Val Leu Ile Asn Ala His Arg Pro Gly Leu
                165                 170                 175

Gln Glu Lys Arg Lys Val Glu Gln Leu Gln Tyr Asn Leu Glu Leu Ala
            180                 185                 190

Phe His His His Leu Cys Lys Thr His Arg Gln Ser Ile Leu Ala Lys
        195                 200                 205

Leu Pro Pro Lys Gly Lys Leu Arg Ser Leu Cys Ser Gln His Val Glu
    210                 215                 220

Arg Leu Gln Ile Phe Gln His Leu His Pro Ile Val Val Gln Ala Ala
225                 230                 235                 240

Phe Pro Pro Leu Tyr Lys Glu Leu Phe Ser Thr Glu Thr Glu Ser Pro
                245                 250                 255

Val Gly Leu Ser Lys
            260

<210> SEQ ID NO 9
<211> LENGTH: 261
<212> TYPE: PRT
<213> ORGANISM: Artificial Sequence
<220> FEATURE:
<223> OTHER INFORMATION: LBD with mutated AF2 domain

```
<400> SEQUENCE: 9

Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
            20                  25                  30

Glu Asp Leu Leu Arg Gln Arg Ser Asn Ile Phe Ser Arg Glu Glu Val
        35                  40                  45

Thr Gly Tyr Gln Arg Lys Ser Met Trp Glu Met Trp Glu Arg Cys Ala
    50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
                85                  90                  95

Lys Ala Gly Ala Met Glu Val Val Leu Val Arg Met Cys Arg Ala Tyr
            100                 105                 110

Asn Ala Asp Asn Arg Thr Val Phe Phe Glu Gly Lys Tyr Gly Gly Met
        115                 120                 125

Glu Leu Phe Arg Ala Leu Gly Cys Ser Glu Leu Ile Ser Ser Ile Phe
    130                 135                 140

Asp Phe Ser His Ser Leu Ser Ala Leu His Phe Ser Glu Asp Glu Ile
145                 150                 155                 160

Ala Leu Tyr Thr Ala Leu Val Leu Ile Asn Ala His Arg Pro Gly Leu
                165                 170                 175

Gln Glu Lys Arg Lys Val Glu Gln Leu Gln Tyr Asn Leu Glu Leu Ala
            180                 185                 190

Phe His His His Leu Cys Lys Thr His Arg Gln Ser Ile Leu Ala Lys
        195                 200                 205

Leu Pro Pro Lys Gly Lys Leu Arg Ser Leu Cys Ser Gln His Val Glu
    210                 215                 220

Arg Leu Gln Ile Phe Gln His Leu His Pro Ile Val Val Gln Ala Ala
225                 230                 235                 240

Phe Pro Pro Leu Phe Lys Glu Leu Phe Ser Thr Glu Thr Glu Ser Pro
                245                 250                 255

Val Gly Leu Ser Lys
                260
```